(12) United States Patent
Mattner et al.

(10) Patent No.: US 7,528,223 B2
(45) Date of Patent: May 5, 2009

(54) ANTIGENS ENCODED BY ALTERNATIVE READING FRAMES FROM PATHOGENIC VIRUSES

(75) Inventors: Frank Mattner, Vienna (AT); Walter Schmidt, Vienna (AT); Andre Habel, Vienna (AT)

(73) Assignee: Intercell AG, Vienna (AT)

( * ) Notice: Subject to any disclaimer, the term of this patent is extended or adjusted under 35 U.S.C. 154(b) by 384 days.

(21) Appl. No.: 10/512,790

(22) PCT Filed: Jul. 24, 2003

(86) PCT No.: PCT/EP03/08112

§ 371 (c)(1),
(2), (4) Date: Oct. 27, 2004

(87) PCT Pub. No.: WO2004/011650

PCT Pub. Date: Feb. 5, 2004

(65) Prior Publication Data

US 2007/0134262 A1    Jun. 14, 2007

(30) Foreign Application Priority Data

Jul. 24, 2002   (AT)   .............................. A 1124/2002
Jul. 11, 2003   (EP)   .................................. 03450171

(51) Int. Cl.
  *C07K 5/00*    (2006.01)
  *A61K 39/145*  (2006.01)
  *A61K 39/00*   (2006.01)
(52) U.S. Cl. .................. 530/300; 424/209.1; 424/184.1
(58) Field of Classification Search ........................ None
See application file for complete search history.

(56) References Cited

U.S. PATENT DOCUMENTS

| 5,663,153 | A | 9/1997 | Hutcherson et al. ............ 514/44 |
| 5,723,335 | A | 3/1998 | Hutcherson et al. ........ 435/7.24 |
| 6,037,135 | A | 3/2000 | Kubo et al. ................ 435/7.24 |
| 6,083,703 | A | * 7/2000 | Wang et al. .................... 435/6 |
| 6,150,087 | A | 11/2000 | Chien ............................. 435/5 |
| 6,413,517 | B1 | 7/2002 | Sette et al. ................ 424/185.1 |
| 2003/0162738 | A1 | 8/2003 | Egyed et al. .................... 514/44 |

FOREIGN PATENT DOCUMENTS

| AT | A 1973/2000 | 11/2000 |
| AT | A 805/2001 | 5/2001 |
| EP | 0 468 520 | 7/1991 |
| WO | WO 92/03458 | 3/1992 |
| WO | WO 93/00365 | 1/1993 |
| WO | WO 94/20127 | 9/1994 |
| WO | WO 94/25601 | 11/1994 |
| WO | WO 95/12766 | 5/1995 |
| WO | WO 95/22317 | 8/1995 |
| WO | WO 95/25122 | 9/1995 |
| WO | WO 95/27733 | 10/1995 |
| WO | WO 95/27901 | 10/1995 |
| WO | WO 96/02555 | 2/1996 |
| WO | WO 97/30721 | 8/1997 |
| WO | WO 98/15287 | 4/1998 |
| WO | WO 98/16247 | 4/1998 |
| WO | WO 98/18810 | 5/1998 |
| WO | WO 98/37919 | 9/1998 |
| WO | WO 98/40100 | 9/1998 |
| WO | WO 98/52581 | 11/1998 |
| WO | WO 98/52962 | 11/1998 |
| WO | WO 99/15259 | 4/1999 |
| WO | WO 99/33488 | 6/1999 |
| WO | WO 99/38528 | 8/1999 |
| WO | WO 99/51259 | 10/1999 |
| WO | WO 99/56755 | 11/1999 |
| WO | WO 99/63941 | 12/1999 |
| WO | WO 00/11186 | 3/2000 |
| WO | WO 00/23105 | 4/2000 |
| WO | WO 00/31542 | 6/2000 |
| WO | WO 00/44775 | 8/2000 |
| WO | WO 01/17551 | 3/2001 |
| WO | WO 01/21189 | 3/2001 |
| WO | WO 01/24822 | 4/2001 |
| WO | WO 01/54719 | 8/2001 |
| WO | WO 01/72782 | 10/2001 |
| WO | WO 01/78767 | 10/2001 |
| WO | WO 01/24822 | * 12/2001 |
| WO | WO 01/93903 | 12/2001 |
| WO | WO 01/93905 | 12/2001 |
| WO | WO 02/13857 | * 2/2002 |
| WO | WO 02/32451 | 4/2002 |
| WO | WO 02/33127 | 4/2002 |
| WO | WO 02/053185 | 7/2002 |
| WO | WO 02/095027 | * 11/2002 |
| WO | WO 03/047602 | 6/2003 |
| WO | WO 03/073097 | 9/2003 |
| WO | WO 2004/014936 | 2/2004 |
| WO | WO 2004/024182 | 3/2004 |

OTHER PUBLICATIONS

Walewski et al, RNA, 2001, vol. 7, p. 710-721.*
Bullock et al., Journal of Experimental Medicine, 1997, vol. 186, p. 1051-1058, in IDS of Oct. 16, 2006.*
Parker et al. Journal of Immunology, 1992, vol. 149, p. 2580-3587 in IDS of Oct. 16, 2006.*
Mayrand et al., Journal of Immunology, 1998, vol. 160, p. 39-50, in IDS of Oct. 16, 2006.*
van Rompuy et al., 1981, NCBI Accession No. NP_040982, 1981, p. 1-2.*

(Continued)

*Primary Examiner*—Bruce Campell
*Assistant Examiner*—Agnieszka Boesen
(74) *Attorney, Agent, or Firm*—Fulbright & Jaworski LLP

(57) ABSTRACT

The invention discloses polypeptides encoded by an alternative reading frame of a pathogenic virus, which polypeptides—start with a methionine amino acid residue,—comprise an antigenic determinant and—comprise more than 7 amino acid residues and fragments of said polypeptides comprising more than 7 amino acids.

41 Claims, 4 Drawing Sheets

OTHER PUBLICATIONS

Parker, Background on the HLA Peptide Motif Searches, 2007, p. 1-5, website: bimas.cit.nih.gov/molbio/hla_bind/.*

Boesen et al. Clinical and Diagnostic Laboratory Immunology, 2005, vol. 12, p. 1223-1230.*

Sidney et al. Human Immunology, 2001, vol. 62, p. 1200-1216.*

Southwood et al. Journal of Immunology, 1998, vol. 160, p. 3363-3373.*

Machuca et al. Intervirology 1998, vol. 42, p. 37-42.*

Vaccine Concepts/Designs, NIAID Division of AIDS, 2003, p. 1-6.*

Potter et al. PSTT, 1999, vol. 2, p. 402-408.*

Price et al. J. Exp. Med. 2008, vol. 191, p. 1853-1867.*

Anthony et al., "Comprehensive determinant mapping of the hepatitis C-specific CD8 cell repertoire reveals unpredicted immune hierarchy," *Clinical Immunology*, 103(3):264-276, 2002.

Bitmansour et al., "Clonotypic structure of the human CD4+ memory T cell response to cytomegalovirus," *J Immunol*, 167:1151-1163, 2001.

Britt and Alford, "Cytomegalovirus," In: *Fields Virology* by Fields et al. eds., Livincott-Raven, 2493-2523 1999.

Bullock et al. "Initiation codon scanthrough verses termination codon readthrough demonstrates strong potential for MHC class I restricted cryptic epitope expression," *Journal of Experimental Medicine*, 186:1051-1058, 1997.

Chen et al., A novel influenza A virus mitochondrial protein that induces cell death,: *Nature Medicine*, 7:1306-1312, 2001.

Chen et al., "Efficient class II major histocompatibility complex presentation of endogenously synthesized hepatitis C virus core protein by Epstein-Bar virus-transformed B-lymphoblastoid cell lines to CD4+ T cells," *Journal of Virology*, 72(10):8301-8308, 1998.

Cox et al., "Identification of a peptide recognized by five melanoma-specific human cytotoxic t cell lines," *Science*, 264:716-719, 1994.

Di Bisceglie et al., "New therapeutic strategies for hepatitis C," *Hepatology*, 35:224-231, 2002.

Drew and Lalezari, "Cytomegalovirus: disease syndromes and treatment," *Curr Clin Top Infect Dis*, 19:16-29, 1999.

Elliot et al. "Recognition of out-of-frame major histocompatibility complex class I-restricted epitopes in vivo," *European Journal of Immunology*, 26:1175-1179, 1996.

Fleckenstein et al., "New ligands binding to the human leukocyte antigen class II molecule DRB+0101 based on the activity pattern of an undecappeptide library," *European Journal of Biochemistry*, 240:71-77, 1996.

Greten et al., "Development and use of multimeric major histocompatibility complex molecules," *Clinical and Diagnostic Laboratory Immunology*, 9(2):216-220, 2002.

Hammer et al., "Promiscuous and allel-specific anchors in HLA-DR-binding peptides," *Cell*, 74:197-203, 1993.

Heemels et al., "Generation, translocation and presentation of mhc class I-restricted peptides," *Annu Rev Biochem*, 64:463-491, 1995.

Hunziker et al., "In vitro studies of core peptide-bearing immunopotentiating reconstituted influenza virosomes as a non-live prototype vaccine against hepatitis C virus," *International Immunology*, 14(6):615-626, 2002.

Kern et al., "Analysis of cd8 t cell reactivity to cytomegalovirus using protein-spanning pools of overlapping pentadecapeptides," *Eur J Immun*, 30:1676-1682, 2000.

Kern et al., "Target structures of the cd8+-t-cell response to human cytomegalovirus: the 72-kilodalton major immediate-early protein revisited," *J Virol*, 73:8179-8184, 1999.

Klein, *Natural History of the MHC*, John Wiley and Sons, 1986.

Komanduri et al., "Restoration of cytomegalovirus-specific cd4+ t-lymphocyte responses after ganciclovir and highly active antiretroviral therapy in individuals infected with HIV-1," *Nat Med*, 4:953-956, 1998.

Kwok et al., "Rapid epitope identification from complex class-II-restricted T-cell antigens," *Trends in Immunology*, 22(11):583-588, 2001.

Lauer et al., "Comprehensive analysis of CD8+-T-cell responces against hepatitis C virus reveals multiple unpredicted specificities," *Journal of Virology*, 76(12):6104-6113, 2002.

Maecker, "Use of overlapping peptide mixtures as antigens for cytokine flow cytometry," *J Immunol Methods*, 255:27-40, 2001.

Malarkannan et al., "Presentation of out-of-frame peptide/MHC class I complexes by a novel translation initiation mechanism," *Immunity*, 10:681-690, 1999.

Maynard et al. "An alternative translation reading frame encodes an immunodominant retroviral CTL determinant expressed by an immunodeficiency-causing retrovirus," *J. of Immunology*, 160:39-50, 1998.

Maynard et al. "Non-traditionally derived CTL epitopes: exceptions that prove the rules?" *Immunology Today*, 19:551-556, 1998.

Morgan et al., "The influence of exogenous peptide on beta2-microglobulin exchange in the HLA complex: analysis in real time," *Immunogenetics*, 48:98-107, 1998.

Novak et al., "Tetramer-guided epitope mapping: rapid identification and characterization of immunodominant CD4+ T cell eiptopes from complex antigens," *The Journal of Immunology*, 166:6665-6670, 2001.

Parker et al., "Scheme for ranking potential HLA-A2 binding peptides based on independent binding of individual peptide sidechains," *J. Immunol.*, 152:163, 1994.

Plotkin et al., "Vaccination against cytomegalovirus, the changeling demon," *Pediatr Infect Dis J*, 18:313-325, 1999.

Reddehase, "The immunogenicity of human and murine cytomegaloviruses," *Curr Opin Immunol*, 12:390-396, 2000.

Shastri et al., "Major histocompatibility class I molecules can present cryptic translation products to T-cells.," *J. Biol. Chem.* 270:1088-1091, 1995.

Smith et al., "Peptide sequences binding to MHC class II proteins," *Molecular Immunology*, 31:1431-1437, 1994.

Stern and Wiley, "Antigenic peptide binding by class I and class II histocompatibility proteins," *Structure*, 2:245-251, 1994.

Stevens et al., "Efficient generation of major histocompatibility complex class I-peptide complexes using synthetic peptide libraries," *Journal of Biological Chemistry*, 273:2874-2884, 1998.

Tana et al., "An HLA-binding-motif-aided peptide epitope library: a novel library design for the screening of HLA-DR4-restricted antigenic peptides recognized by CD4+ T cells," *J Hum Genet*, 43:14-21, 1998.

Tobery, "A simple and efficient method for the monitoring of antigen-specific T cell responses using peptide pool arrays in a modified elispot assay," *J Immunol Methods*, 254:59-66, 2001.

Tourdot et al., "A general strategy to enhance immunogenicity of low-affinity HLA-A2.1-associated peptides: implication in the identification of cryptic tumor epitopes," *Eur. J. Immunol.* 30:3411-3421, 2000.

Van den Eynde and van der Bruggen, "T cell defined tumor antigens," *Curr Opin Immunol*, 5:684-693, 1997.

Varaklioti et al., "Alternative translation occurs within the core coding region of the hepatitis C viral menome," *The Journal of Biological Chemistry*, 227:17713-17721, 2002.

Villadangos, "Proteolysis in mhc class II antigen presentation: who's in charge," *Immunity*, 12:233-239, 2000.

Waldrop et al., "Normal human cd4+ memory t cells display broad heterogeneity in their activation threshold for cytokine synthesis," *J Immunol*, 161:5284, 1998.

Walewski et al., "Evidence for a new hepatitis C virus antigen encoded in an overlapping reading frame," *RNA*, 7:710-721, 2001.

Wang et al., "Sequence variation in the gene encoding the nonstructural 3 protein of hepatitis C virus: evidence for immune selection," *J. Mol. Evol.*, 54:456-473, 2002.

Weekes et al., "Human CD28-CD28+ T cells contain greatly expanded functional virus-specific memory CTL clones," *J. Immunol*, 162:7569-7577, 1999.

Weekes et al., "The memory cytotoxic T-lymphocyte (CTL) response to human cytomegalovirus infection contains individual peptide-specific CTL clones that have undergone extensive expansion in vivo," *J. Virol.*, 73(3):2099-2108, 1999.

Wolfel et al., "Isolation of naturally processed peptides recognized by cytolytic t lymphocytes(ctl) on human emlanoma cells in association with hla-a2.1," *Int. J. Cancer*, 57:413-419, 1994.

Wong et al., "Detection of diverse hepatitis C virus (HCV)-specific cytotoxic T lymphocytes in peripheral blood of infected persons by screening for responses to all tranlated proteins of HCV," *Journal of Virology*, 75(3):1229-1235, 2001.

Xu et al., "Synthesis of a novel hepatitis C virus protein by ribosomal frameshift," *The EMBO Journal*, 20:3840-3848, 2001.

Zaia et al., "Cytomegalovirus prevention and treatment in 2000," *Hematology*, 339-355, 2000.

"Aluminiumhydroxide," Röempp, 10th Ed., pp. 139-140, 2006 (in German).

Battegay et al., "Patients with chronic hepatitis C have circulating cytotoxic T cells which recognize hepatitis C virus-encoded peptides binding to HLA-A2.1 molecules," *J. Virol.*, 69(4):2462-2470, 1995.

Bellentani et al., "Epidemiology of hepatitis C virus infection in Italy: the slowly unraveling mystery," *Microbes Infect.*, 2(14):1757-63, 2000.

Blake et al., "Use of combinatorial peptide libraries to construct functional mimics of tumor epitopes recognized by MHC class I-restricted cytolytic T lymphocytes," *J. Exp. Med.*, 184:121-130, 1996.

Chang et al., "Identification of HLA-A3 and -B7-restricted CTL response to hepatitis C virus in patients with acute and chronic hepatitis C," *J. Immunol.*, 162:1156-1164, 1999.

Cho et al., "Activation of human neutrophils by a synthetic antimicrobial peptide, KLKLLLLLK-NH2, via cell surface calreticulin," *Eur. J. Biochem.*, 266:878-885, 1999.

Diepolder et al., "Immunodominant CD4+ T-cell epitope within nonstructural protein 3 in acute hepatitis C virus infection," *J. Virol.*, 71(8):6011-6019, 1997.

Duenas-Carrera et al., "Enhancement of the immune response generated against hepatitis C virus envelope proteins after DNA vaccination with polyprotein-encoding plasmids," *Biotechnol. Appl. Biochem.*, 35:205-212, 2002.

Farci and Purcell, "Clinical significance of hepatitis C virus genotypes and quasispecies," *Semin Liver Dis.*, 20(1):103-26, 2000.

Gruener et al., "Sustained dysfunction of antiviral CD8+ T lymphocytes after infection with hepatitis C virus," *J. Virol.*, 75:5550-5558, 2001.

Heile et al., "Evaluation of hepatitis C virus glycoprotein E2 for vaccine design: an endoplasmic reticulum-retained recombinant protein is superior to secreted recombinant protein and DNA-based vaccine candidates," *J. Virol.*, 74(15):6885-6892, 2000.

Hemmer et al., "Predictable TCR antigen recognition based on peptide scans leads to the identification of agonist ligands with no sequence homology," *J. Immunol.*, 160:3631-3636, 1998.

Hemmer et al., "The use of soluble synthetic peptide combinatorial libraries to determine antigen recognition of T cells," *J. Peptide Res.*, 52:338-345, 1998.

HLA-prevalence studies, In: HLA 1998, (Gjertson and Terasaki, eds.) American Society for Histocompatibility and Immunogenetics, Lenexa, Kansas, pp. 103-263, 1998.

Hoffmann et al., "Mapping of Immunodominant CD4+ T Lymphocyte Epitopes of Hepatitis C Virus Antigens and Their Relevance During the Course if Chronic Infection," *Hepatology*, 21(3):632-638, 1995.

Ibe et al., "Identification and characterization of a cytotoxic T cell epitope of hepatitis C virus presented by HLA-B*3501 in acute hepatitis," *J. Gen. Virol.*, 79:1735-1744, 1998.

Inchauspe and Feinstone, "Development of a hepatitis C virus vaccine," *Clinics in Liver Disease*, 7:243-259, 2003.

Keilholz et al., "Immunologic monitoring of cancer vaccine therapy: results of a workshop sponsored by the Society for Biological Therapy," *J Immunother.*, 25(2):97-138, 2002.

Koziel et al., "Hepatitis C virus (HCV)-specific cytotoxic T lymphocytes recognize epitopes in the core and envelope proteins of HCV," *J. Virol.*, 67:7522-7532, 1993.

Koziel et al., "HLA class I-restricted cytotoxic T lymphocytes specific for hepatitis C virus. Identification of multiple epitopes and characterization of patterns of cytokine release," *J. Clin. Invest.*, 96:2311-2321, 1995.

Kurokohchi et al., "A novel cytotoxic T-cell epitope presented by HLA-A24 molecule in hepatitis C virus infection," *J. Hepatology*, 34:930-935, 2001.

Lamonaca et al., "Conserved Hepatitis C Virus Sequences Are Highly Immunogenic for CD4+ T Cells: Implications for Vaccine Development," *Hepatology*, 30(4):1088-1098, 1999.

Lechmann and Liang, "Vaccine development for hepatitis C," *Seminars in Liver Disease*, 20:211-226, 2000.

Leroux-Roels et al., "Lymphoproliferative Responses to Hepatitis C Virus Coes, E1, E2, and NS3 in Patients With Chronic Hepatitis C Infection Treated With Interferon Alfa," *Hepatology*, 23(1):8-16, 1996.

Liang et al., "Pathogeneis, Natural History, Treatment, and Prevention of Hepatitis C," *Ann Intern Med.*, 132(4):296-305, 2000.

McCluskie et al., "Parenteral and mucosal prime-boost immunization strategies in mice with hepatitis B surface antigen and CpG DNA," *Fems Immunol and Medical Microbiol*, 32:179-185, 2002.

Nakajima et al., "Chemotherapeutic activity of synthetic antimicrobial peptides: correlation between chemotherapeutic activity and neutrophil-activating activity," *FEBS Lett.*, 415:64-66, 1997.

Rammensee et al., "SYFPEITHI: database for MHC ligands and peptide motifs," *Immunogenetics*, 50:213-219, 1999.

Rehermann et al., "Differential cytotoxic T-lymphocyte responsiveness to the hepatitis B and C viruses in chronically infected patients," *J. Virol.*, 70(10):7092-7102, 1996.

Rollier et al., "Control of heterologous hepatitis C virus infection in chimpanzees is associated with the quality of vaccine-induced peripheral T-helper immune response," *J. Virol.*, 78(1):187-196, 2004.

Sarobe et al., "Enhanced in vitro potency and in vivo immunogenicity of a CTL epitope from hepatitis C virus core protein following amino acid replacement at secondary HLA-A2.1 binding positions," *J. Clin. Invest.*, 102(6):1239-1248, 1998.

Shirai et al., "An epitope in hepatitis C virus core region recognized by cytotoxic T cells in mice and humans," *J. Virol.*, 68(5):3334-3342, 1994.

Sturniolo et al., "Generation of tissue-specific and promiscuous HLA ligand databases using DNA microarrays and virtual HLA class II matrices," *Nature Biotechnology*, 17:555-562, 1999.

Thursz et al., "Influence of MHC class II genotype on outcome of infection with hepatitis C virus. The HENCORE group. Hepatitis C European Network for Cooperative Research," *Lancet*, 354(9196):2119-24, 1999.

Vernacchio et al., "Effect of monophosphoryl lipid A (MPL) on T-helper cells when administered as an adjuvant with pneumococcal-CRM197 conjugate vaccine in healthy toddlers," *Vaccine*, 20(31-32):3658-67, 2002.

Ward et al., "Cellular immune responses against hepatitis C virus: the evidence base 2002," *Clin Exp Immunol.*, 128(2):195-203, 2002.

Weiner et al, "Persistent hepatitis C virus infection in a chimpanzee is associated with emergence of a cytotoxic T lymphocyte escape variant," *Proc Natl Acad Sci U S A.*, 92(7):2755-9, 1995.

Wentworth et al., "Identification of A2-restricted hepatitis C virus-specific cytotoxic T lymphocyte epitopes from conserved regions of the viral genome," *Int. Immunol.*, 8(5):651-659, 1996.

Wilson et al., "Immunogenicity. I. Use of peptide libraries to identify epitopes that activate clonotypic CD4+ T cells and induce T cell responses to native peptide ligands," *J. Immunol.*, 163:6424-6434, 1999.

Wong et al., "Liver-derived CTL in hepatitis C virus infection: breadth and specificity of responses in a cohort of persons with chronic infection," *J. Immunol.*, 160:1479-1488, 1998.

Aichinger et al., "Major histocompatibility complex class II-dependent unfolding, transport, and degradation of endogenous proteins," *J. Biol. Chem.*, 272:29127-29136, 1997.

Bihl et al., "Impact of HLA-B alleles, epitope binding affinity, functional avidity, and viral coinfection on the immunodominance of virus-specific CTL responses," *J. Immunol.*, 176:4094-4101, 2006.

Brooks et al., "HLA-B27 subtype polymorphism and CTL epitope choice: studies with EBV peptides link immunogenicity with stability of the B27:peptide complex," *J. Immunol.*, 161:5252-5259, 1998.

Field, "Human cytomegalovirus: challenges, opportunities and new drug development," *Antiviral Chem. Chemotherapy*, 10:219-232, 1999.

Fowler et al., "The outcome of congenital cytomegalovirus infection in relation to maternal antibody status," *New Engl. J. Med.*, 326:663-673, 1992.

Gallot et al., "Purification of Ag-specific T lymphocytes after direct peripheral blood mononuclear cell stimulation followed by CD25 selection. I. Application to CD4(+) or CD8(+) cytomegalovirus phosphoprotein pp65 epitope determination," *J. Immunol.*, 167:4196-4206, 2001.

Gavin et al., "Alkali hydrolysis of recombinant proteins allows for the rapid identification of class I MHC-restricted CTL epitopes," *J. Immunol.*, 151:3971-3980, 1993.

Gorga et al., "Purification and characterization of class II histocompatibility antigens from a homozygous human B cell line," *J. Biol. Chem.*, 262:16087-16094, 1987.

Greenberg and Riddell, "Deficient Cellular Immunity-Finding and Fixing the Defects," *Science*, 285:546-551, 1999.

Khattab et al., "Three T-cell epitopes within the C-terminal 265 amino acids of the matrix protein pp65 of human cytomegalovirus recognized by human lymphocytes," *J. Med. Virol.*, 52:68-76, 1997.

Kronenberg et al., "Conserved lipid and peptide presentation functions of nonclassical class I molecules," *Immunol. Today*, 20:515-521, 1999.

Kuzushima et al., "Efficient Identification of HLA-A*2402-restricted cytomegalovirus-specific CD8+ T-cell epitopes by a computer algorithm and an enzyme-linked immunospot assay," *Blood*, 98:1872-1880, 2001.

Lalvani et al., "Rapid effector function in CD8+ memory T cells," *J. Exp. Med.*, 186:859-865, 1997.

Lamas et al., "Relationship between peptide binding and T cell epitope selection: a study with subtypes of HLA-B27," *Int. Immunol.*, 10:259-266, 1998.

Levitsky et al., "Supermotif Peptide Binding and Degeneracy of MHC: Peptide Recognition in an EBV Peptide-Specific CTL Response with Highly Restricted TCR Usage," *Human Immunol.*, 61:972-984, 2000.

Masuoka et al., "Identification of the HLA-A24 peptide epitope within cytomegalovirus protein pp65 recognized by CMV-specific cytotoxic T lymphocytes," *Viral Immunology*, 14:369-377, 2001.

McLaughlin-Taylor et al., "Identification of the major late human cytomegalovirus matrix protein pp65 as a target antigen for CD8+ virus-specific cytotoxic T lymphocytes," *J. Med. Virol.*, 43:103-110, 1994.

Nichols and Boeckh, "Recent advances in the therapy and prevention of CMV infections," *J. Clin. Virol.*, 16:25-40, 2000.

Nijman et al., "Identification of peptide sequences that potentially trigger HLA-A2.1-restricted cytotoxic T lymphocytes," *Eur. J. Immunol.*, 6:1215-1219, 1993.

Retriere et al., "Generation of cytomegalovirus-specific human T-lymphocyte clones by using autologous B-lymphoblastoid cells with stable expression of pp65 of IE1 proteins: a tool to study the fine specificity of the antiviral response," *J. Virol.*, 74:3948-3952, 2000.

Saulquin et al., "A global appraisal of immunodominant CD8 T cell responses to Epstein-Barr virus and cytomegalovirus by bulk screening," *Eur. J. Immunol.*, 30:2531-2539, 2000.

Sia and Patel, "New strategies for prevention and therapy of cytomegalovirus infection and disease in solid-organ transplant recipients," *Clin. Microbiol. Rev.*, 13:83-121, 2000.

Solache et al., "Identification of three HLA-A*0201-restricted cytotoxic T cell epitopes in the cytomegalovirus protein pp65 that are conserved between eight strains of the virus," *J. Immunol.*, 163:5512-5518, 1999.

Tynan et al., "The immunogenicity of a viral cytotoxic T cell epitope is controlled by its MHC-bound conformation," *J. Exp. Med.*, 202:1249-1260, 2005.

Udaka et al., "Decrypting the structure of major histocompatibility complex class I-restricted cytotoxic T lymphocyte epitopes with complex peptide libraries," *J. Exp. Med.*, 181:2097-2108, 1995.

Valli et al., "Binding of myelin basic protein peptides to human histocompatibility leukocyte antigen class II molecules and their recognition by T cells from multiple sclerosis patients," *J. Clin. Invest.*, 91:616-628, 1993.

Von Son et al., "Overcoming the problem of cytomegalovirus infection after organ transplantation: calling for Heracles?," *Intervirology*, 42:285-290, 1999.

\* cited by examiner

Fig. 5a: Vaccination of mice with ncORF derived peptides from influenza A virus in combination with KLK/o-d(IC)$_{13}$ IFN-γ ELIspot

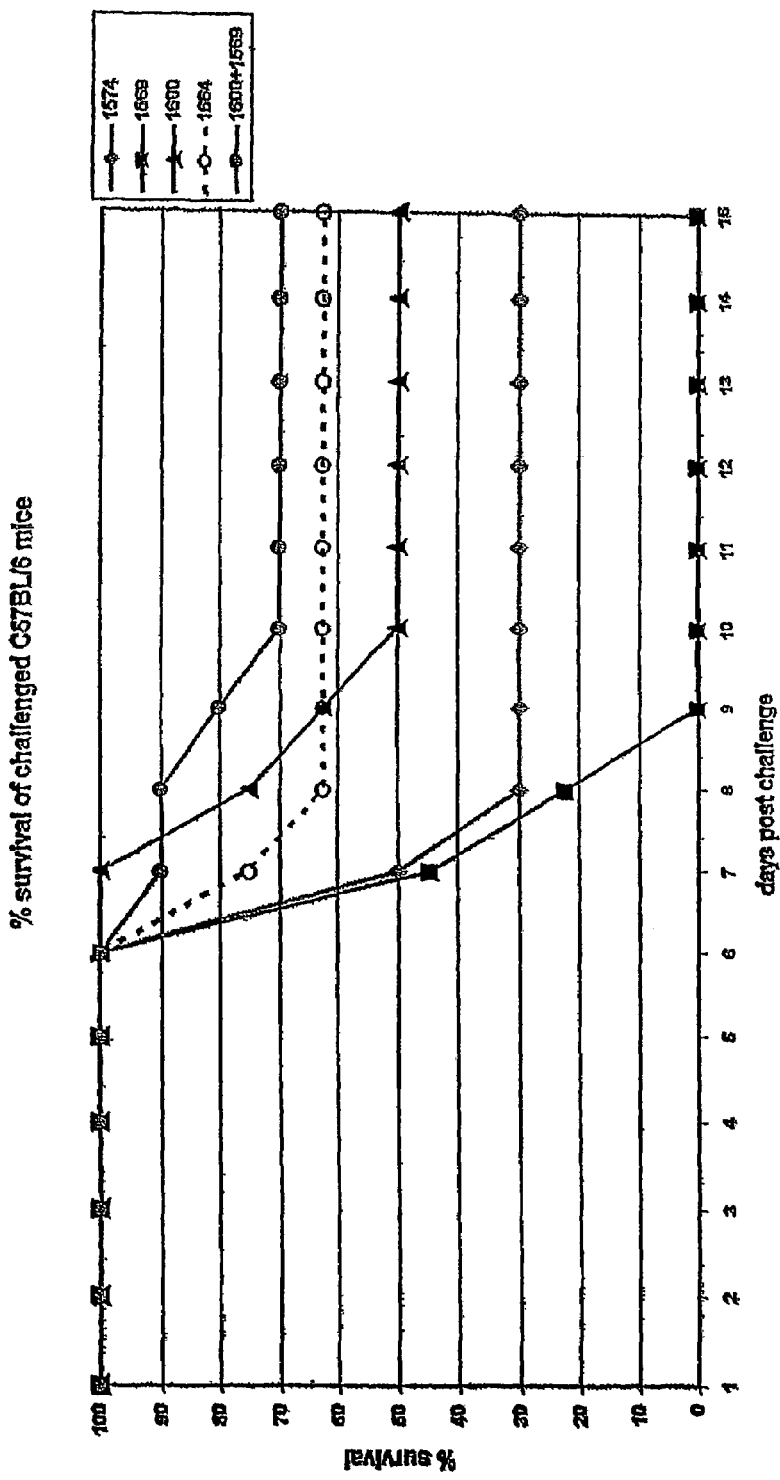
Fig. 5b: Vaccination of mice with ncORF derived peptides from influenza A virus in combination with KLK/o-d(I

ANTIGENS ENCODED BY ALTERNATIVE READING FRAMES FROM PATHOGENIC VIRUSES

This application is a national phase application under 35 U.S.C. § 317 of International Application No. PCT/EP2003/008112 filed 24 Jul. 2003, which claims priority to Austrian Application No. A 1124/2002 filed 24 Jul. 2002 and European Patent Application No. 03450171.8 filed 11 Jul. 2003.

The Sequence Listing is submitted on one compact disc (Copy 1), together with a duplicate thereof (Copy 2), each created on Jul. 21, 2005, and each containing one 2,190 kb file entitled "SONN060SEQ.txt." The material contained on the compact disc is specifically incorporated herein by reference.

The invention relates to peptides derived from pathogenic viruses.

For several viral infections it has become more and more clear that an early effective and strong CTL response to most encoded viral proteins is critical to overcome or clear a viral infection from the host.

Selection for mutations within CTL epitopes of HIV demonstrates that CTL exert pressure on virus replication in vivo, and studies in macaques have provided compelling in vivo data for the role of CD8+ T cells in controlling viremia in both acute and chronic simian immunodeficiency virus (SIV) infection. HIV-infected individuals who are treated during acute infection show enhancement of both CTL and T helper cell responses against HIV associated with subsequent viral control after treatment interruption.

Therefore the identification of precise epitopes from most (if not all) viral proteins is a major goal in view of understanding the hosts immune response and most important for the design of new and effective vaccines against those pathogens.

As up to now, most research for the identification of those epitopes has focused mainly on those proteins of the viruses which are encoded in the actually transcribed open reading frames (ORF's), i.e. the structural proteins and the proteins which have a certain function for the virus, e.g. for its regulation, replication or reproduction.

Although some research has been performed in investigating in potential alternative reading frames of pathogens, the topic of such alternative reading frames has up to now only been regarded as relevant for tumor antigens, but not for viral pathogens, despite some reports about overlapping reading frames in HCV (see Walewski et al. (RNA 7 (2001) 710-721) and WO99/63941) and other viruses or antigens (Bullock et al. (J. Exp. Med. 186(7) (1997), 1051-1058), Malarkannan et al. (Immunity 10(1999) 681-690) and Shastri et al. (J. Biol. Chem. 270(3) (1995) 1088-1091). All these reported viral polypeptides have starting codons other than AUG or ATG leading to peptides starting with e.g. Ala, Leu, Pro or Gly. Moreover these viral peptides according to the prior art were no T cell epitopes, but—at best—were able to elicit an antibody response.

It is an object of the present invention to provide further means for combating viral infections. It is a further object to provide means for replacing or improving existing or proposed vaccines against viral pathogens, especially human pathogens. A specific aim is to provide effective T cell epitopes against viral pathogens.

Therefore, the present invention provides a polypeptide encoded by an alternative reading frame of a pathogenic virus, characterized in that said polypeptide starts with a methionine amino acid residue, comprises an antigenic determinant and comprises more than 7 amino acid residues and fragments of said polypeptide comprising more than 7 amino acids.

Surprisingly, such epitopes (antigenic determinants) proved to be highly relevant in infections with pathogenic viruses. Indeed, T cell responses against such alternatively encoded epitopes are detectable in patients suffering such infections. It seems that upon infection of a virus into a host cell, not only those ORFs of the viral genome, which give rise to the viral proteins, are transcribed, but also some of those proteins or fragments which are encoded by other frames of the genome.

Such a polypeptide according to the present invention may be defined as an antigenic sequence within an ORF of the genome but outside the primarily (main) transcribed ORF of a given pathogenic virus.

Alternative reading frame as used in the context of the present invention is defined as a reading frame which is different from the open reading frames (=main frames) which encode utilized codons of an organism or virus for the expression of e.g. structural proteins or non structural proteins.

Typically but not exclusively a main frame starts with the first coding start codon, e.g. AUG or GUG of a nucleic acid eg. of a messenger RNA or an RNA from a positive/negative stranded RNA virus. Alternative frames described in this invention do not use these start codons or any other codon used by the main frames, respectively.

The present invention considers 5 such alternative reading frames which by a second name are also called non-coding open reading frames (ncORFs), to be distinctive from the main frames as described above. One such alternative reading frame is the +1 frame, which uses codons that start with the next nucleotide 3' prime of the 5' prime nucleotide of a main frame codon. A second such frame is the +2 frame which uses codons of which the 5' prime nucleotide is identical with a 3' prime nucleotide of a codon of the main coding frame. Alternative reading frames 4, 5 and six are encoded by a nucleic acid which is complementary to a nucleic acid, encoding alternative reading frames 1 and 2 respectively. The 5' prime nucleotide of a frame 4 codon is complementary to a middle nucleotide of a codon of a +1 frame. The 5' prime nucleotide of a frame 5 codon is complementary to the 5' prime nucleotide of a +1 frame codon and the 5' prime nucleotide of a frame 6 codon is complementary to a 3' prime nucleotide of a +2 frame codon.

Furthermore, alternative reading frames might be located in regions of the genome which are not involved in main frame translations, eg. so called non translated 5' prime or 3' prime regions.

Although these "ncOrfs" ("non coding ORFs") do not display a (yet) known function for the pathogen, they encode for antigenic determinants (B- or T-cell epitopes)

In contrast to all enabling reports about alternatively encoded ORFs in HCV (see Walewski et al., WO99/63941) and other viruses or antigens (Bullock et al., Malarkannan et al., Shastri et al.) the polypeptides according to the present invention have all an AUG or ATG (encoding Methionin) as start codon. Moreover the peptides provided with the present invention contain T cell epitopes as antigenic determinants and are not intended to exclusively elicit an antibody response.

The principle provided with the present invention seems to be a general one in viral infections. It is therefore not restricted to certain viruses or certain groups of viruses. Regarding this, preferred polypeptide or fragments according to the present invention are those from major and prominent (human) pathogenic viruses or pathogenic virus for which currently no proper treatment or active immunisation protocol exists, such as Hepatitis A virus (HAV), Hepatitis B virus (HBV), Hepatitis C virus (HCV), Hepatitis D virus (HDV), Hepatitis E virus (HEV), Hepatitis F virus (HFV) Hepatitis G virus (HGV) Human Immunodeficiency viruses (e.g HIV-1 and HIV-2), Influenza virus, Foot and Mouth Disease virus (FMDV), Ebola virus, HTLV I, HTLV II, SIV, Parvovirus, Papilloma virus, Rotavirus, Adenovirus, Cytomegalovirus, Feline Immunodeficiency virus (FIV), Epstein-Barr virus (EBV), Herpes simplex virus (HSV), Herpes zoster virus (HZV), Measles virus and oncogenic viruses.

With the present invention, a completely new generation of immunogenic epitopes are provided which according to a preferred embodiment are characterized in that the polypeptides and fragments according to the present invention comprise at least one cytotoxic T lymphocyte (CTL-) epitope.

Preferably the polypeptide or fragments according to the present invention comprise a cytotoxic T lymphocyte (CTL-) epitope for a HLA allele selected from the group consisting of A0201, A1, A24, A3, A31, B3501, B4403, B7, B8, especially A0201, or mixtures thereof.

According to a preferred embodiment, the polypeptide or fragments according to the present invention comprise at least one T helper cell epitope.

Preferably, the polypeptide or fragments according to the present invention comprise a T helper cell epitope for a HLA allele selected from the group consisting of DP, DQ, DR or mixtures thereof.

Preferred epitopes according to the present invention are selected from the group listed in table 2a)-n) (Seq.ID No.1-822) or a fragment of said polypeptide comprising more than 7 amino acids and/or epitopes comprising or consisting of a fragment selected from the group listed in table 4a)-n), preferable fragments with a score of 50 or more, more preferred with a score of more than 200, especially fragments with a score of more than 500 (according to the scores given in the table which were determined according to the algorithm reported by Parker et al. (J. Immunol. 152 (1994) 163)).

Further preferred epitopes according to the present invention are the polypeptides selected from the group listed in table 6 and comprising more than 7 amino acid residues (Seq.ID No.823-874) or a fragment of said polypeptide comprising more than 7 amino acid residues.

The polypeptides or fragments according to the present invention may be conjugated to a carrier, especially to an immunomodulating substance. For certain applications, such conjugations result in an improved action of these peptides. It may also be preferred to couple selected hydrophobic (F, I, L, A, Y, W, C) or acidic amino (D or E) acid residues N- and/or C-terminally to the peptides as described in WO 01/78767.

Preferred polypeptides or fragments therefore comprise a tail consisting of two to seven amino acids, said amino acids being selected from F, I, L, A, Y, W or C, at least one of its N- or C-terminus; or a tail consisting of two to seven amino acids, said amino acids being selected from E or D, at least one of its N- or C-terminus.

In specifically preferred conjugates, the polypeptides or fragments according to the present invention are conjugated to an immunomodulating substance selected from the group comprising polycationic substances, especially polycationic polypeptides, and immunomodulating nucleic acids, especially deoxyinosine- and/or deoxyuridine containing oligodeoxynucleotides.

Preferably the polycationic substance is a polymer, preferably a polycationic peptide, especially polyarginine, polylysine or an antimicrobial peptide.

The polycationic compound(s) to be used according to the present invention may be any polycationic compound which shows the characteristic effect according to the WO 97/30721. Preferred polycationic compounds are selected from basic polypeptides, organic polycations, basic polyaminoacids or mixtures thereof. These polyaminoacids should have a chain length of at least 4 amino acid residues. Especially preferred are substances containing peptidic bonds, like polylysine, polyarginine and polypeptides containing more than 20%, especially more than 50% of basic amino acids in a range of more than 8, especially more than 20, amino acid residues or mixtures thereof. Other preferred polycations and their pharmaceutical compositions are described in WO 97/30721 (e.g. polyethyleneimine) and WO 99/38528. Preferably these polypeptides contain between 20 and 500 amino acid residues, especially between 30 and 200 residues.

These polycationic compounds may be produced chemically or recombinantly or may be derived from natural sources.

Cationic (poly)peptides may also be polycationic anti-bacterial microbial peptides. These (poly)peptides may be of prokaryotic or animal or plant origin or may be produced chemically or recombinantly. Peptides may also belong to the class of defensines. Such host defense peptides or defensines are also a preferred form of the polycationic polymer according to the present invention. Generally, a compound allowing as an end product activation (or down-regulation) of the adaptive immune system, preferably mediated by APCs (including dendritic cells) is used as polycationic polymer.

Especially preferred for use as polycationic substance in the present invention are cathelicidin derived antimicrobial peptides or derivatives thereof (WO 02/13857, incorporated herein by reference), especially antimicrobial peptides derived from mammal cathelicidin, preferably from human, bovine or mouse, or neuroactive compounds, such as (human) growth hormone (as described e.g. in WO01/24822).

Polycationic compounds derived from natural sources include HIV-REV or HIV-TAT (derived cationic peptides, antennapedia peptides, chitosan or other derivatives of chitin) or other peptides derived from these peptides or proteins by biochemical or recombinant production. Other preferred polycationic compounds are cathelin or related or derived substances from cathelin, especially mouse, bovine or especially human cathelins and/or cathelicidins. Related or derived cathelin substances contain the whole or parts of the cathelin sequence with at least 15-20 amino acid residues. Derivations may include the substitution or modification of the natural amino acids by amino acids which are not among the 20 standard amino acids. Moreover, further cationic residues may be introduced into such cathelin molecules. These cathelin molecules are preferred to be combined with the antigen/vaccine composition according to the present invention. However, these cathelin molecules surprisingly have turned out to be also effective as an adjuvant for a antigen without the addition of further adjuvants. It is therefore possible to use such cathelin molecules as efficient adjuvants in vaccine formulations with or without further immunactivating substances.

Another preferred polycationic substance to be used according to the present invention is a synthetic peptide containing at least 2 KLK-motifs separated by a linker of 3 to 7 hydrophobic amino acids, especially L (WO 02/32451, incorporated herein by reference).

The immunomodulating nucleic acids to be used according to the present invention can be of synthetic, prokaryotic and eukaryotic origin. In the case of eukaryotic origin, DNA should be derived from, based on the phylogenetic tree, less developed species (e.g. insects, but also others). In a preferred embodiment of the invention the immunogenic oligodeoxynucleotide (ODN) is a synthetically produced DNA-molecule or mixtures of such molecules. Derivates or modifications of ODNs such as thiophosphate substituted analogues (thiophosphate residues substitute for phosphate) as for example described in US patents U.S. Pat. Nos. 5,723,335 and 5,663,153, and other derivatives and modifications, which preferably stabilize the immunostimulatory composition(s) but do not change their immunological properties, are also included. A preferred sequence motif is a six base DNA motif containing an (unmethylated) CpG dinucleotide flanked by two 5' purines and two 3' pyrimidines (5'-Pur-Pur-C-G-Pyr-Pyr-3'). The CpG motifs contained in the ODNs according to the present invention are more common in microbial than higher vertebrate DNA and display differences in the pattern of methylation. Surprisingly, sequences stimulating mouse APCs are not very efficient for human cells. Preferred palindromic or non-palindromic ODNs to be used according to the present invention are disclosed e.g. in Austrian Patent applications A 1973/2000, A 805/2001, EP 0 468 520 A2, WO 96/02555, WO 98/16247, WO 98/18810, WO 98/37919, WO 98/40100, WO 98/52581, WO 98/52962, WO 99/51259 and WO 99/56755 all incorporated herein by reference. Apart from stimulating the immune system certain ODNs are neutralizing some immune responses. These sequences are also included in the current invention, for example for applications for the treatment of autoimmune diseases. ODNs/DNAs may be produced chemically or recombinantly or may be derived from natural sources. Preferred natural sources are insects.

Alternatively, also nucleic acids based on hypoxanthine and cytosine (as e.g. described in the WO 01/93905) or deoxynucleic acids containing deoxyinosine and/or deoxyuridine residues (described in the PCT/EP02/05448, incorporated herein by reference) may preferably be used as immunostimulatory nucleic acids for the present invention.

Of course, also mixtures of different immunogenic nucleic acids may be used according to the present invention.

The above mentioned substances may be used as conjugates with the present peptides or fragments or as mixtures. The mixtures may either be provided in a form already mixed or as a kit of single components intended to be mixed before application.

The preferred polypeptides or fragments according to the present invention comprise a T cell epitope.

Surprisingly, with the present invention not only polypeptides or fragments having a shifted reading frame (i.e. reading frame 2 and 3) are provided as clinically relevant peptides, but also such peptides and fragments being encoded by an alternative reading frame which reads on the complementary strand as the functional reading frame of said pathogenic virus, i.e. generally referred to as reading frame 4 to 6 in the present specification. This means that also such reading frames proved to be of importance which are located at the opposite end of the known (functional or structural) gene or e.g. its regulating elements.

Therefore, one further aspect of the present invention consists in all antigens being encoded by alternative reading frames of pathological viruses which read on the complementary strand as the functional reading frame of said pathogenic virus, i.e. generally referred to as reading frame 4 to 6.

Preferred polypeptides or fragments according to the present invention comprise at least one peptide selected from the group of peptides listed in table 4a, 4c, 4e, 4g, 4i, 4k and 4m having a score of 50 or more, more preferred with a score of more than 200, especially with a score of more than 500.

According to a preferred aspect of the present invention the present polypeptides or fragments are used as a therapeutic agent. It is known that especially T cell epitopes may be used as vaccines for prophylactic uses. However, with the peptides and fragments according to the present invention, especially with the HCV derived peptides i.a. in reading frames 2 and 3, also a therapeutic tool for combatting (chronic) infections with such pathogenic viruses, such as HCV, is provided.

The peptides and fragments according to the present invention also include modified epitopes wherein preferably one or two of the amino acids of a given epitope are modified or replaced according to the rules disclosed in e.g. Tourdot et al. (Eur. J. Immunol. 30 (2000), 3411-3421), as well as the nucleic acid sequences encoding such modified epitopes.

According to a preferred aspect, the present invention also relates to a pharmaceutical composition comprising one or more polypeptides or fragments according to the present invention. This pharmaceutical composition may be used for both, prophylactic as well as therapeutic purposes.

As stated above, the present pharmaceutical compositions preferably further comprise an immunomodulating substance, preferably selected from the group comprising polycationic substances, especially polycationic polypeptides, and immunomodulating nucleic acids, especially deoxyinosine- and/or deoxyuridine containing oligodeoxynucleotides.

In the present pharmaceutical compositions, the peptides or fragments according to the present invention may be used alone or in combination with "normal" polypeptides (epitopes, antigenic determinants) of a given pathogenic virus (or combinations of antigens of different pathogens). A preferred embodiment therefore further comprises structural or functional polypeptides of a pathogenic virus or fragments thereof, especially structural or functional polypeptides or fragments thereof comprising an antigenic determinant.

The administration of the pharmaceutical compositions according to the present invention may be performed according to the administration of other known polypeptide vaccines. Preferably, the composition contains per administrable dose 1 ng to 1 g, preferably 100 ng to 10 mg, especially 10 μg to 1 mg, of one or more polypeptides or fragments according to the present invention.

Preferably, the pharmaceutical composition is formulated as a vaccine.

It is preferred that the pharmaceutical composition according to the present invention comprises further active ingredients, especially immunopotentiating cytokines, anti-inflammatory substances, antimicrobial substances or combinations thereof.

It is further preferred that the present pharmaceutical composition further comprises a polycationic polymer selected from the group consisting of a polycationic peptide, especially polyarginine, polylysine or an antimicrobial peptide, especially a cathelicidin-derived antimicrobial peptide, or a growth hormone, especially a human growth hormone.

Additionally, auxiliary substances, especially a pharmaceutically acceptable carrier, buffer substances, stabilizers or combinations thereof are provided with the pharmaceutical composition.

According to another aspect, the present invention also relates to the use of a polypeptide or fragments according to the present invention for the manufacture of a medicament for treating or preventing an infection with said pathogenic virus.

It was not foreseeable within the prior art that upon infection of a virus into a host cell, not only those ORF's of the viral genome, which give rise to the viral proteins, are transcribed, but also some of those proteins or fragments which are encoded by other frames of the genome. This was even more surprising for reading frames 4 to 6.

The invention will hereinafter be described in a more detailed way in the following examples and the figures, yet without being restricted thereto.

FIG. 5 shows that vaccination with ncORF derived peptides from influenza A virus in combination with KLK/o-d (IC)$_{13}$ induces potent IFN-γ producing T cells and protection against viral challenge.

EXAMPLES

Example 1

HCV

Figure 1:
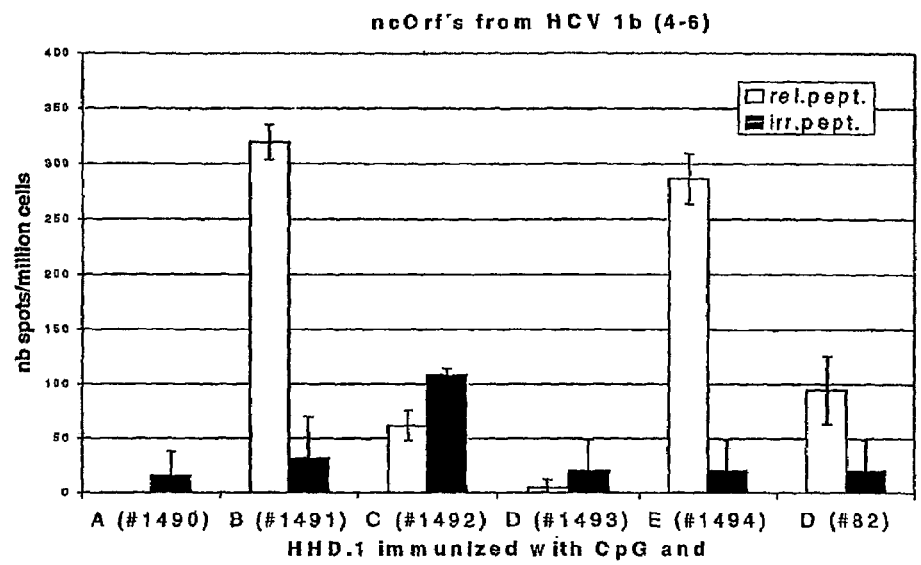
FIG. 1 shows the Elispot assay from the experiment with HLA-A*0201 tg mice+HCV-H77 ncORF 11, 13, 27-derived peptides.

HCV was used as a model virus for the present invention. The principles described in the present example, however, may be applied to any virus.

The entire genomes of 7 clinically relevant strains (1a, 1b, 2a, 2b, 3a, 3b and H77) of HCV were analysed in order to determine all ORF's being longer than 7 amino acid residues and starting with an AUG (Met) codon in all reading frames other than the reading frame for the HCV polyprotein. The HCV genome sequences were taken from the Genbank data base (Accession Nos.: AF387806 (1a), D11355 (1b), AF238485 (2a), AB030907 (2b), AF046866 (3a), D49374 (D26556) (3b), AF011751 (H77)). Altogether, 822 novel ORFs were identified in this study (see summary in table 1).

TABLE 1

Number of ORF's in six different HCV strains

| Strain | Frames | No. of frames* | Seq. ID Nos. | Full sequence listed in table 2 |
|---|---|---|---|---|
| 1a | 1-3 | 42 | 1-42 | Table 2a |
|    | 4-6 | 68 | 43-110 | Table 2b |
| 1b | 1-3 | 56 | 111-166 | Table 2c |
|    | 4-6 | 75 | 167-241 | Table 2d |
| 2a | 1-3 | 47 | 242-288 | Table 2e |
|    | 4-6 | 71 | 289-359 | Table 2f |
| 2b | 1-3 | 45 | 360-404 | Table 2g |
|    | 4-6 | 75 | 405-479 | Table 2h |
| 3a | 1-3 | 38 | 480-517 | Table 2i |
|    | 4-6 | 70 | 518-587 | Table 2j |
| 3b | 1-3 | 53 | 588-640 | Table 2k |
|    | 4-6 | 72 | 641-712 | Table 2l |
| H77 | 1-3 | 40 | 713-752 | Table 2m |
|     | 4-6 | 70 | 753-822 | Table 2n |

(*more than 7 AA long)

The following table 2 contains the full sequences of the polypeptides.

Other HCV subtypes which may also be preferably adapted for the present example include subtypes 1c, 2c, 2d, 3c-f, 4a-j, 5a or 6a.

TABLE 2a (Seq. ID Nos. 1-42)

HCV 1a ncOrf's 1-3
Genbank Accession No.: AF387806

| SEQ ID No. | Sequence | AA |
|---|---|---|
| 1 | MGATLHHESLPCEELLSSRRKRLAMALV | 28 |
| 2 | MAMRAAGGRDGSCLPVALGLAGAPQTPGVGRAIWVRSSIPLRAA SPTSWGTYRSSAPLLEALPGPWRMASGFWKTA | 76 |
| 3 | MQQGTFLVALSLSSFWPCSLA | 21 |
| 4 | MIALTRVLCTRRPMPSCTLRGASLAFARATPRGVGWR | 37 |
| 5 | MANSPRRSFDVTSICLSGAPPSVRPSTWGTCAGLSFLSANCLPS LPGATGRRKVAIALSIPAI | 63 |
| 6 | MIASTPAGWQGFSITTSSTLQAVLRG | 26 |
| 7 | MPTEAAPTSAPTAGTTPQNLAVLCPRRVCVVRYIASLPAPWWWE RPTGRARPPTAGVKMIRTSSSLTIPGHRWAIGSVVPG | 81 |
| 8 | MQHPWPGRTVLYPSSCSSALHGI | 23 |
| 9 | MFITISLLFGTGRTTACEIWPWL | 23 |
| 10 | MEWSPRVGGCWRPSRRTPSRQGAS | 24 |
| 11 | MGCAGLSTTGPERGPSRHPRVLSSRCIPM | 29 |
| 12 | MSFPCAGGVIAGAACCRPGPFPT | 23 |
| 13 | MLPQAAAKAPRSRLHMQLRAIRC | 23 |
| 14 | MGSILTSGPG | 10 |
| 15 | MPHPSWASALSLTKQRLRGRDWLCSPPPPLRAPSLCPIPTSRRL LCPPPERSLFTARLSPSK | 62 |
| 16 | MPWPTTAVLTCPSSRPAAMLSSWQPMPS | 28 |
| 17 | MLSPALNVGAGLAGGSQASTDLWHRGSAPPACSTRPSSVSAMTQ AVLGMSSRPPRLQLGYERT | 63 |
| 18 | MPTFYPRQSRVGRTFLTW | 18 |
| 19 | MGQHPCYTDWALFRMKSP | 18 |
| 20 | MRWKSALSTYRTSSKG | 16 |
| 21 | MARAWRELLWHSRS | 14 |
| 22 | MFPPRTTCRRAMQLPASLPYSAASL | 25 |
| 23 | MPTPRAPVPPFLRRTTRSRYGGCLQRNTWR | 30 |
| 24 | MTPLMLSS | 8 |
| 25 | MAARFHLQSPLLCLRLGRSGRWSSLNQPYLLPWPSSPPEALAAP QLPALRATIRQHPLSPPLLAAPPTPTLSPIPPCPPWRGSLGIRI LATGHGQRSVVRPTRRMSCAAQCLTLGQAHSSPRAPRKNRNCPS MH | 134 |
| 26 | MGQKTSVAMPERP | 13 |
| 27 | MIPAALTPQSLRATSVRRRQSTNVVTSTPKPAWPSSPSPRGFML GALLPIQGGRTAAIAGAARAAY | 66 |
| 28 | MASAHFHSTVTLQVKSIGWPHASENLGYRPCELGDTGPGASALG FWPEEAGLPYVASTSSTGQ | 63 |
| 29 | MPGPAGSGFAYSCLLQG | 17 |
| 30 | MNHSPVRNYCLHAESV | 16 |
| 31 | MPGDLGVPPQDC | 12 |

TABLE 2a-continued
(Seq. ID Nos. 1-42)
HCV 1a ncOrf's 1-3
Genbank Accession No.: AF387806

| SEQ ID No. | Sequence | AA |
|---|---|---|
| 32 | MAPVSPWLSA | 10 |
| 33 | MGYDDELVPYDGVGNGSAAPDPTSHLGHDRWCSLGSPGGHSVFL HGGELGEGPGSAAAICRRRGNPRHRGKCRPHCVWIC | 81 |
| 34 | MHVGRPGGRHEHLGARWRRPGCFGRVLPVNRLRGHSGQGRLVRE AGNHT | 49 |
| 35 | MLRFLAKGHLGLDMRGVERL | 20 |
| 36 | MEGVCRGIRGDKAGGGLPLRDGYDY | 25 |
| 37 | MPVPGPIARIFHRIGRGAPT | 20 |
| 38 | MEAGDGRQHHQG | 12 |
| 39 | MLLQRVSRPRRRWKEGLLPHP | 21 |
| 40 | MPQKTWGTALASLETPGPERPR | 22 |
| 41 | MWQVPLQLGSKNKAQTHSNSGRWPAGLVRLVHGWLQRGRHLSQR VSCPAPLDLVLPTPACCRGRHLPPPQPVKVGVNTPAS | 81 |
| 42 | MSVVQPPGPPLPGEP | 15 |
| | HCV polyprotein | 15 |

TABLE 2b
(Seq. ID Nos. 43-110)
HCV 1a ncOrf's 4-6

| SEQ ID No. | Sequence | AA |
|---|---|---|
| 43 | MIPPPAARACRGAQTYVGAPRPIL | 24 |
| 44 | MEWYTPSLSTGAVASGAGLQ | 20 |
| 45 | MPQELPPRPRHLQGCL | 17 |
| 46 | MKQWRGYQAALTSPPSIVSH | 20 |
| 47 | MRPALRRVRRTSSLNDRR | 18 |
| 48 | MWHPWSGTRHKLLCHKRPPSTRRRQGTCRRWST | 33 |
| 49 | MQPGPWCFCRCLWEHGGEPPGSSGALLVERSYP | 33 |
| 50 | MSGYLAERASPQGLDLHWYTSG | 22 |
| 51 | MVTELAPSTRREQHRHTTRPPPCPARTPAGATPTGAGGEATSRR RCRPLRAPTYPSDTMQSRRTRGRIQDRASRPGMLH | 79 |
| 52 | MWRPDACGSNQWGSAGCCCPPLR | 23 |
| 53 | MPCGDPLYGRDR | 12 |
| 54 | MALPGGGVLEAARHSY | 16 |
| 55 | MRLTDLSQLAVTRAKMEPPLKKEGKERKKEGKKKKKKKKEKKKK KEKKKKKKKKKKKKKKKTGNGLRGRSVYPNLHRLGRR | 82 |
| 56 | MPTPAASRSRQNQIQRGR A | 20 |
| 57 | MAALPPLARSLARTLRARCLQARKGGTPSFLRHAATLLISPGE | 43 |
| 58 | MIGGRSSGSME | 11 |

TABLE 2b-continued
(Seq. ID Nos. 43-110)
HCV 1a ncOrf's 4-6

| SEQ ID No. | Sequence | AA |
|---|---|---|
| 59 | MIMLPSQELTGVCLAVSHAALARGVVGSRVR | 31 |
| 60 | MSSKSYSGCGGSPGGAEYLVIASVKALRLAASSWTPALSQITTK SSPHTSMVQSWSPAARQAARALM | 67 |
| 61 | MATRAWGSRSQHW | 13 |
| 62 | MSLSVTVESKQRVSYENPIGVFLDFHACTRNSTRCPGEYWNP | 42 |
| 63 | MRRAGLRPPFSG | 12 |
| 64 | MMVVSIGVTLSSRRSFHTELMWVTAFLAWQRTSFAP | 36 |
| 65 | MGSFCSSAAHGVTSAPVQE | 20 |
| 66 | MPEVEELPKLLVASSAKAVDRVDSVRTTVRFFRGGGTGGDFGGG SGQPWTTGGS | 54 |
| 67 | MLPPISCLHRRLASMSSASGESWLAVQVALRDGADSWLAEELAT EGGDPLANLRPAASAVIWEGSVSMDVNTATSGSGSQGNCDPTGY SWSPTLNDTSSRSKGLQGGANLCRRTPSNSVKNSGDGTWHGHLR LSVVIPVT | 140 |
| 68 | MGKVPLHNFLQVLGPTILIVPFLTCPVISAPQWQRVCMMPSPRQ TPLYPRWQDTKGIPGSCGMSLAFSQVLKSLNTSHIQSQMSLSQE PEHGVVHSELIHWCSRLRSWVTVRLLSMAVTRAAASLSGT | 128 |
| 69 | MAGSRLTRSSVEGTSPLMILNATRAPATPAPYPARMSMRTFPSP TLPMAAPAKPAPTKAVAAPGAASWAATHPPNMLKRRVWLVVSGL VTAAVKAINEAMAGLPGSVDKPAKYCIPLMKFHICFAQKVSSFC QLVWTAGAITSA | 144 |
| 70 | MIAGFPDKTTLPTMTTQPVDRQYAAKAARTPPTSTQVLVTTSRS ADMHVMMYLVTGCVRVISF | 63 |
| 71 | MYARSLTVVSAGVSSYQAQPAS | 22 |
| 72 | MPEGRSPGATNL | 12 |
| 73 | MPGFPLPVLPRR | 12 |
| 74 | MVKVGSRLKSTVWVTHVLQSITESKSPV | 28 |
| 75 | MRASVATTTTSPLVGMTDTSRPR | 23 |
| 76 | MPNATSFAASSSHFFFE | 17 |
| 77 | MRCLPPLITSRGIALP | 16 |
| 78 | MLGWGTVTEPGGVAVASTTSLAPAVSAWSRTVPMPKMDVASVEW HSSQIIMS | 52 |
| 79 | MGLPVVIVLTPVLMLGSIP | 19 |
| 80 | MVVSRFSTGIKSTALATPRVHTAALNMPTACPAGHNSGPPEEPF K | 45 |
| 81 | MGRGDSRLPLLSPRRRTGMTSACLVTR | 27 |
| 82 | MTGPLGDAMVLVPAPW | 16 |
| 83 | MHVARKVWAAVDTIWTSPSTWFLSRPVRLVIHMPRRPLVCWAYA VMGASNLQPLETIPSAGPSSISRPLRAETGKPLMMSPHAAVSAP HVMSLVSIWEKTTGSTATARSRKPLCAQSRRGVRWL | 124 |

TABLE 2b-continued

(Seq. ID Nos. 43-110)

HCV 1a ncOrf's 4-6

| SEQ ID No. | Sequence | AA |
|---|---|---|
| 84 | MSNTRVGCTAHMSKMTASRPPRTLRGGIHTCSCASTLVRKY | 41 |
| 85 | MSSIIHKQEQTRASASRRNRRTTYSHLMAQDAMLDPTPYKYCTS TMFWWRWMRPVDKAGRVVKEHGRTCHCVVVSSNGLSSDLSLSSR SQRSPRVQLQAASSLCSTPPTYILILNIV | 117 |
| 86 | MTQGGAPHTLVNPVEFIQVQPNQLPSGGLVLLRTKTSVSFSPQL | 44 |
| 87 | MEKYAMPARTPQ | 12 |
| 88 | MSKMACGIRSS | 11 |
| 89 | MASAASYTILELGQSLVTW | 19 |
| 90 | MYPMRSAKPHVRVSMTLPKLRDLRRGSVGPQLGREPRGDRSHPA HPQPSLP | 51 |
| 91 | MVHGLRDLPGHSQAPYQAVPQGLSRPNTTRLAVLRGHAQISRH | 43 |
| 92 | MICREASISTLCSHAAHGPFTASRD | 25 |
| 93 | MRHAVINVSPAVASREPAGQVQLASGRYWSEFELCSYCPVEEVL ATYGSPASSGQKPSADAPGPVSPSSQGRYPKFSEACGHPIDFTW RVTVE | 93 |
| 94 | MESLNDWR | 8 |
| 95 | MGHQYHPRPQCGGKHDYVA | 19 |
| 96 | MATDVFCPITKLGFG | 15 |
| 97 | MAVQNLQSVKCDFLLPLASTA | 21 |
| 98 | MDHRWFVVGLFPRLH | 15 |
| 99 | MVSGASCLERWSG | 13 |
| 100 | MGGISEHGRQHGHVRFGLAR | 20 |
| 101 | MSSDLSSTVAASVHDAVPSPDPLIPALAGHKGDPRQLWHELSF | 43 |
| 102 | MVPPGGEGYQPVHPLHCPLARANVPAQYCCTDHADYEGSGREDG GQ | 46 |
| 103 | MLRPEGLEFLPVGLDSRGDNLCLTGRGLQEAEGLLLELLGEHHP LLDR | 49 |
| 104 | MEGGLEANQTLPHLVPRWGRGLSPSAHGGLVRYQVRKVLPTLLC LG | 46 |
| 105 | MSEACEDALPKFKVVLAHGKPRGVHVRS | 28 |
| 106 | MTEDEMSPPLDYFEGDSLAVKRDLSGGGQSNLLDVGMGHSDGAR RGGGGEHNQSRPRSLCLVKDSADAQDGCGIRGVALVTNYYVISA PRAPAVGKELAVGGVRDGAASGNCSHPGPDVRIDPMSLGHVSTK AQCCSNRGVEY | 143 |
| 107 | MEVSHLEALGHYWWRGVIREHRGPHGCL | 28 |
| 108 | MVINIGASKRP | 11 |
| 109 | MASDHLPR | 8 |
| 110 | MPKPIRVVDQAPGCDPGTGAAPRVCGVRMLAEAISGAVQGVVAR PSDDTRRRSAHFGESS | 60 |

TABLE 2c

(Seq. ID Nos. 111-166)

HCV 1b ncOrf's 1-3
Genbank Accession No.: AF

| SEQ ID No. | Sequence | AA |
|---|---|---|
| 111 | MATRVWGGQDGSCHPVALGLVGAPQTPGVGRVIWVRSSIPLHAA SPTSWGTFRLSAPP | 58 |
| 112 | MASGFWRTA | 9 |
| 113 | MQQGICPVALSLSSS | 15 |
| 114 | MSRTTAPTQVLCMRQRT | 17 |
| 115 | MRRYKIAIAQSIPATYQVTAWLGI | 24 |
| 116 | MTPSKLGSLLRCSTHTGSTRPDVQSAWPAAAPSTSSLRGGVPSL TLCLTSRTRGLIAGTMHPNRAVLYPRRRCVAQCIASPRVLLWWG RPTVPESPRIAGGRMRQTCCYSTTRGRRKATGSAVHG | 125 |
| 117 | MFCCSSFSWRTRASVPACG | 19 |
| 118 | FL | 69 |
| 119 | MFGEAAMPSSSLHARSIQS | 19 |
| 120 | MWTRTSSAGRRPPGRVP | 17 |
| 121 | MLTSFRCAGGATVGGACSPPGLSPT | 25 |
| 122 | MQPKGTRCSSSIRPLPLP | 18 |
| 123 | MASFLPMVVALGALMTS | 17 |
| 124 | MSAIQLTRLQSWASAQSWTKRRRLERGLSCSPPLRLRDRSPCHT QTSRRWPCLILERSPSMAKPSPLKPSGGEGISFSVIPRRSATSS PQSCQASESTLWRITGGSMCPSYQLSETSLSWQQTL | 124 |
| 125 | MTRAVLGTSSPPPRPRLGCGPT | 22 |
| 126 | MHTSCPRPSRQETTSPTW | 18 |
| 127 | MRSPSPTP | 8 |
| 128 | MKWKSAPRTSLTLSRECSSPSSSSRKRSGYCKQPPNKRRLLLPW WSPSGEPLRHSGRSTCGISSAGYST | 69 |
| 129 | MEQEWPARSWPLRS | 14 |
| 130 | MCLRATPQRVLLRSSPALPSLSC | 23 |
| 131 | MRTAPHRVPARG | 12 |
| 132 | MFGTGYARC | 9 |
| 133 | MEHSPSTHTPRAPAHPLQRQTILGRCGGWPLRSTWRSRGWGIST T | 45 |
| 134 | MSLRTLTSSRPTSCGGRRWAGTSPAWSRRTRW | 32 |
| 135 | MRGKYPFRRRSCGNPRSSPQRCPSGRARITTLHC | 34 |
| 136 | MSSAAQCPTHGQAP | 14 |
| 137 | MPQHLAAQACGRRRSPLTDCKSWTTTTGTCSRR | 33 |
| 138 | MGQRTSGTYPARPLTTSTPCGRTCWKTL | 28 |
| 139 | MRFSVSNQRKEAVSQPALSYSQIWESVYARRWPSMMWSPPFLRS | 44 |
| 140 | MTLAVSTQRSPRTTSVLRSQFTNVVTWPPKPDRP | 34 |
| 141 | MCRSPTMHQAKGCTTSPVIPPPPSHGLRGKQLDTLQLTPG | 40 |
| 142 | MRPLCGQG | 8 |

TABLE 2c-continued

(Seq. ID Nos. 111-166)

HCV 1b ncOrf's 1-3
Genbank Accession No.: AF

| SEQ ID No. | Sequence | AA |
|---|---|---|
| 143 | MALAHFHSIVTLQVRSIGWLHASGNLGYHPCESGDIGPGASALG YCPRGGGPPLVASTSSTGQ | 63 |
| 144 | MPGDLGVPPRDC | 12 |
| 145 | MAPVTPWLSA | 10 |
| 146 | MRLRRPHGVHSACRRPPRRRCQGPGAWRPGSGGRRELCNRESAR LLFLYLPLSFAVLFDHPSFRLRGAQRVRDIPCHERLLQLKYCV | 87 |
| 147 | MSRAHGQLPPHRQVRSGVGSHHSRCA | 26 |
| 148 | MRLGSLVDT | 9 |
| 149 | MGVCSAALPSPGGRARLCLLVDDAADSPG | 29 |
| 150 | MAVAPALAGFTTTSLCHGPRDGCIVRRRGFCRSGTLDLVTIL | 42 |
| 151 | MRGPSRANL | 21 |
| 152 | MRGPSRANL | 9 |
| 153 | MHVSAEGRWGSLCPNGLHEAGRADRHVHLQPSYPATGLGPRGPT RPCGGSGARRLLRHGDQDHHLGSRHRGVWGHHLGSARLRPKGKG DTPGPGR | 95 |
| 154 | MHLWQLRPLLGHETC | 15 |
| 155 | MHPGGCEGGGLCARRVHGNYYAVSGLHGQLIPPGRTAVISSGPP TRSHWQRQEY | 54 |
| 156 | MCHPDSRLQLGSHLHH | 16 |
| 157 | MGSNVEVSHTAETYAARANTLAVQAGSRPK | 30 |
| 158 | MWSTDHRTCQKRFHEDRRA | 19 |
| 159 | MRARTGCSSAHFHAHRPLPHHSRNG | 25 |
| 160 | MHYPPCLSGR | 10 |
| 161 | MDRRLDHAMRCGGKQAAHQRVEQLFAAPP | 29 |
| 162 | MLLEGLCSLSSCEAPGLHDARERRRPCRYL | 30 |
| 163 | MFLQCVGRPRCIRQKGVLPHP | 21 |
| 164 | MPQETWGTTLASLETSGQERPR | 22 |
| 165 | MNGELNTPGQ | 10 |
| 166 | MSVVQPPGPPLPGEP | 15 |

HCV polyprotein

TABLE 2d

(Seq. ID Nos. 167-241)

HCV 1b ncOrf's 4-6

| SEQ ID No. | Sequence | AA |
|---|---|---|
| 167 | MICREASISTLCSHAAHGPFTASRD | 25 |
| 168 | MAYWPGVFSSPFIGWGAGRCLPLQKVGVGTA | 31 |
| 169 | MHRGRPTHWRNMMLSAPSRILVGAGPRGGQST | 32 |
| 170 | MKSPWGFSLISRYSPGTRLAAQESTGIRMRSPSRPEEGWRPHHR GPSSRIHGLPDLGIR | 59 |
| 171 | MLWHKPCYGGAAKSCSTR | 18 |
| 172 | MCRTLSSRRHPH | 12 |
| 173 | MIRSCRRS | 8 |
| 174 | MSPSRKAQTTG | 11 |
| 175 | MVAVTQPGIG | 10 |
| 176 | MGTLRCQWSCPSRSGNPPPA | 20 |
| 177 | MFHATCCCRS | 10 |
| 178 | MPSMMLLRGSQAEWISLLSTVSR | 23 |
| 179 | MSQGLATWTPPREQQPPLVWWLFAVTRALSA | 31 |
| 180 | MMEVGPEPWRTPWLGMLPGRGSCLLPAWSGTRSVHLCG | 38 |
| 181 | MCYSRSLSQSRPYSPSSERLLPRQRRLR | 28 |
| 182 | MTAVRPGGMSCP | 12 |
| 183 | MVSRNAPRGAPASRRGPGPH | 20 |
| 184 | MVTRSRVPDLQKPRLRTMQPSLGPWHKLVVVKPARAGATAIRHR EHMPPQGPACL | 55 |
| 185 | MYSRTSCLAAAACC | 14 |
| 186 | MALVRARTRGSGCWRLPFPLSRGCARQRQQRVASQSRP | 38 |
| 187 | MALPGGGVLEAARHSY | 16 |
| 188 | MPTPTESRSRHSMNQRGRARDRL | 23 |
| 189 | MIMLPSQELTGVCLAVSHAARARGVVGSRVR | 31 |
| 190 | MACLASGAKSQHW | 13 |
| 191 | MSFSVTVESKQRVSYEKPMGFFFDFQVFTRNSTRCPGEYWNPYE EPITT | 49 |
| 192 | MMVVSIGVTVSSSKSFHTEWMWLTALLDRFRTSFAP | 36 |
| 193 | MLWWRSKELLNALMGSLLSSAAHGVIKAPVHV | 32 |
| 194 | MEEYDSTSDPLSPSSEAWSGRAVAVPLSTADDSELPKVLVASSA KAEDTEDSVRTTVLFLRGGGIGGALIGGNGHPCTTGGT | 82 |
| 195 | MGIAAGNFLDFRRISAGTDTSLSSSSARSGSKESRTTTLFSDST RVMFPPISCRHRRLASMRSASGETWWVVHVAFKEGADNWLAEEL AKEGGDPLANLRLAVSAVMWEGSVSMEVSTATSGSGSHGSCDPT RYWLSPTWNVTSSRRRGLHAGAYLGNRTPSTSEKNSGAGTWHGH ETLSV VMPVT | 187 |
| 196 | MGNVPCHVLLQVLGPTILMEPPLTCPVICAPHGQVVCMMPSPRQ TPLYPRWHEKKGTPGSCGRSLDWSQVLKSVNTVHIQSQTSLSHE PEHGVEQSSLIHWWSLFSS | 107 |
| 197 | GSRLTRSSVEGISPLMTLKATSAPATPAP | 31 |
| 198 | MSTSTFPRPMLPTAAPAMPAPTKAEAALGGASWAATHPPKMLNR RVLWVVSGLVIEAVNAINDAIAGFPGRVDKPAKYCIPLMKFHMC FAQNVSRAHLDSTTGAAASACLVAVCSNPSAFCLNCSASCIPC SM | |

TABLE 2d-continued

(Seq. ID Nos. 167-241)

HCV 1b ncOrf's 4-6

| SEQ ID No. | Sequence | AA |
|---|---|---|
| 199 | TTLPVVRQYAARAARTPPTSTQVLVTTSRSADMHAMMYLVMGWVRVTSFWTAPSLYSKGVGPCSVGFSRMRHFHI | 76 |
| 200 | MWVRPVKTLSQNSRWSWQTGNPGVFR | 26 |
| 201 | MPEGRSPGVTNL | 12 |
| 202 | MPLLPLPVLPRRCERDTAS | 19 |
| 203 | MVKVGSKLKSTVWVTHVLQSITESKSPV | 28 |
| 204 | MTDTSSPR | 8 |
| 205 | MRCLPPLMASMGMALP | 16 |
| 206 | MFGCGTVTDPGGVAVASTTSRAPAVSAWSRTVPMPKIVVESVEWHSSHIMMS | 52 |
| 207 | MVLTPVLMLGSIPCALDIYAPNPKVAATDGLRTSTLYPWAAYAAGTLVLLPLPVGACRWAT | 61 |
| 208 | MDSTGTKSTAFATPRVHTAARKMPTACPEGQSSGPPEEPFK | 41 |
| 209 | MTSACLVTK | 9 |
| 210 | MMQPSRPRVCWE | 12 |
| 211 | GARSRHPRPSRLSAGPRSISFPLRAETGRPKMMSPHAAVSAPQVMILVSMSEKTTGSTATARSRRPWAQSRSGVRWL | 79 |
| 212 | MYVPVSAPSFMKAIWT | 16 |
| 213 | MPAWSTMSGPSMASRSLVMSKISSGWTAHVRRMMASRPPRTLRGGTHTCKCASALVIKYCNHHMSLARNTL | 71 |
| 214 | MYQAAQKNTRKERRPCAPATDAALRTTRFSKVASAWAISSIIHKQAQTRASARRKSSRTYSHLITTETTTDPTPYRYCTSTIF | 84 |
| 215 | MVKLIVQG | 8 |
| 216 | MLHGGPPHVLVNPVLFIHVQPNQLPCGGRVLLSSSTSVSFSPQLYVGTPERSVVPTTTGLGVKQYTGPHTCDAGTIPHGWGA | 82 |
| 217 | MGRQLAMRSGHPDALNLCA | 19 |
| 218 | MNPVWRESLQFRAVLLMCQLPLVFTSWIF | 29 |
| 219 | MSTTACGIRSSCDTTRAVVGDQFIIISQAMR | 31 |
| 220 | MLLFLAASVGVSATQQREKLLSRTQGTHPGVCMIMSAASYTILELEQSFVTWYIPDTLRTS | 61 |
| 221 | MVKQDSKAKRKIEKEQPGRFPVA | 23 |
| 222 | MYPMRSAKPHVRVSMTLPKLRDLRRGSVGPQLGREPRGDRSHPAHPTPSLP | 51 |
| 223 | MMHGLRDLPGHSQAPYQAVPQGLSRPNTTRLAVSRGHAQISRH | 43 |
| 224 | MRLTDLSQLAVTRAKMEPPLKKEERKREKEGKEKKKKKKKKKNRKWPIGLECLAPRSSVGEQVDAYPYRK | 71 |
| 225 | MSPDSQGWYPKFPEA | 15 |
| 226 | MESFNDLR | 8 |
| 227 | MWGRQLAGFLYG | 12 |
| 228 | MVAQQRVAQRVDGQLAFLRSAWRDQGACPCVGH | 33 |
| 229 | MVGSACRLQGRRRQLAS | 17 |
| 230 | MPRVAAGLRPDDPHGTVFDMSGDLCSTWAGGLHDAVSPPDSLVPALAREKRDSR | 54 |
| 231 | MTENEMPSPPDGFNGDGFAIEGDLSSIRQGHLLDVWVWHGDRSRRRSGGEHDKPRSSRLRLVQDCADQDCSRVS | 75 |
| 232 | MALITYYDVISAPRATTIGKKLAIGRVCDGGACGNGPYPSSDVGVNTVCLRHIRPKP | 57 |
| 233 | MSRDQVKV | 8 |
| 234 | MVNGPTHAVDAGRQEGLCCGGNHLNLSLDLVLVPACKASDDATK | 44 |
| 235 | MVVNVRACQRAQLHEGHLDIMTPSDLPH | 28 |
| 236 | MNEPLSAHEVRHSGYASLEHHERTEYGEQEFGDVKD | 36 |
| 237 | MDRACKEDDGIAASPNIKRGDPHLQVRLGPGDKIL | 35 |
| 238 | MRSGHRRRTEDHQVL | 15 |
| 239 | MEVDQSSGQSR | 11 |
| 240 | MVYPGHVAHLVSGSWDGQTRQQS | 23 |
| 241 | MRQGPGSAS | 9 |

TABLE 2e

(Seq. ID Nos. 242-288)

HCV 2a ncOrf's 1-3
Genbank Accession No.: AF238485

| SEQ ID No. | Sequence | AA |
|---|---|---|
| 242 | MTPGIGRVTWVRSSIP | 16 |
| 243 | MTVPMTASPGSFRRRSSTSPGASRAREWEIHHGAGYRSHQMWLCSSAAPSRRACGRTSTWS | 61 |
| 244 | MAVGTSTAPP | 10 |
| 245 | MPARTFCAPRTVLGSILTPLTSNVVLGPGSRRGAWSTTLTGSGTTPAQLTIPSSR | 55 |
| 246 | MACHLPLQNMSFDGSG | 16 |
| 247 | MASYILSSFSWLLGTSKVGWSPWPPIPSPAYGPFAYCSSHCPNRLMPMMHLCKGS | 55 |
| 248 | MALYGLPPYSARVWCLT | 17 |
| 249 | MTTSPLCRIGLPTACGTWRSL | 21 |
| 250 | MDSPCPPDSVGRFSLAQLTATPPRGGSFSPPSPLTPSRHEVSWAP | 45 |
| 251 | MLRPAVEKAPKSLSRTLPRGIKC | 23 |
| 252 | MASIPTLGLESEL | 13 |
| 253 | MANSSPMGAARAAPMTSSYATNATPWTLPPSSASEQFLTKQRQPESG | 47 |
| 254 | MGERFPCLTSREGDT | 15 |

TABLE 2e-continued

(Seq. ID Nos. 242-288)

HCV 2a ncOrf's 1-3
Genbank Accession No.: AF238485

| SEQ ID No. | Sequence | AA |
|---|---|---|
| 255 | MSSRRPFGAWAMLWHTTEGWTSP | 23 |
| 256 | MFPLVSEPQGCLIAWCSVSATTQGLRGMSLRQRRLP | 36 |
| 257 | MPTSFPKQSNRGRISHT | 17 |
| 258 | MRLLMKWRNVPLKRLSLKRGSGWPRC | 26 |
| 259 | MARAFRGPSSHSRSTLARSPPWRTSSICCLGFCLRVPWWWESSARAFCAATWGREKARSNG | 61 |
| 260 | MCGTGFAPS | 9 |
| 261 | MRSRLPLGSIHL | 12 |
| 262 | MMWTWWMPTCSWGAM | 15 |
| 263 | MPSSSWPSKPSASPLQAAIQASLQGRTPPTPAVGRPLMSWPFRRQVLPPPCPPSRGSLGIQTWSPTR | 67 |
| 264 | MTPSCAAPCHTPGPGP | 16 |
| 265 | MDMGPRRFAACPGGPLTTSSPCGRTSWKTHKHQFLRPSWPKMRCSAWTPPRGVRKQLALSFTLTSVLGSARRWPFMMSHKSFLRQ | 85 |
| 266 | MDSSTPPPSGWSFS | 14 |
| 267 | MTPDALTLPSLRETLELRRPYTRLAPCLRRPVLPYTR | 37 |
| 268 | MTWLSSQKARGLRRTSGT | 18 |
| 269 | MCLWHSAYRAAADTT | 15 |
| 270 | MLQLYGSAWS | 10 |
| 271 | MPGHLGVPPQDG | 12 |
| 272 | MAPVPPRFSSLLGPQ | 15 |
| 273 | MQLLHLPGYHHWASYGVGHDDELVTHYHHDPGLRDARPRGHHRHH | 45 |
| 274 | MGHFAIRG | 8 |
| 275 | MWHSPREVRVRPSVLFHPQPSRGGHDR | 27 |
| 276 | MVRLHVDELHWEHQDLWRATLPH | 23 |
| 277 | MWFWALAHAEFPGRLPLQALALPLHS | 26 |
| 278 | MGHLALLFLRLARFVDWSTPPPPKYRGRTIHVWPVTCPYKICRSMGVGSALIPSPSGRQGLRLRVDAYLAGPGRGSTREAGRLARCERS | 89 |
| 279 | MALLPTAPRTAPTGLCL | 17 |
| 280 | MGYHHILPGCGV | 12 |
| 281 | MRGHLTWTPRVRPTRSGDSPWPS | 23 |
| 282 | MDRLPRSWQ | 9 |
| 283 | MRRMPRRGRYHHPRHRNSS | 19 |
| 284 | MAQSGAILGQTHVELH | 16 |
| 285 | MDEQAHSLCFQRKPRRPYPLRDGVGCVAACDPTAWLPYYN | 40 |
| 286 | MLCEGPSGLQSCGDSCAHNAGMRR | 24 |
| 287 | MVGKHHPVCSNYMGPHGPDDTFFLHPYGPRHSGPGP | 36 |

TABLE 2e-continued

(Seq. ID Nos. 242-288)

HCV 2a ncOrf's 1-3
Genbank Accession No.: AF238485

| SEQ ID No. | Sequence | AA |
|---|---|---|
| 288 | MSVVQPPGPPLPGEP | 15 |

HCV polyprotein

TABLE 2f

(Seq. ID Nos. 289-359)

HCV 2a ncOrf's 4-6

| SEQ ID NO. | Sequence | AA |
|---|---|---|
| 289 | MCHQDHADPYSWSILDDVSQP | 21 |
| 290 | MGWSQLARLLQGEELCADLGGR | 22 |
| 291 | MDLHSVHPGEKLWRG | 15 |
| 292 | MGRGDVVSSGSKGYEPVHPLDRAFSRPHVAAQNARADDSHHQGTRRQNPRQQIDDVLHGGLLARHDLECDEGPRNARAIPRQDIHQHLAQAYAAYSSPH | 99 |
| 293 | MCESDLVGNRAQTV | 14 |
| 294 | MVLAHGQARRVEIRSKPYGSLRWRKLIPRSPCVVALTEHHAIKHP | 45 |
| 295 | MAEDQVSPSLDVRQGKRSPIEGDLTLLPEGHLLYIGMGGRHRPRGSGRGQYS | 52 |
| 296 | MCLGQIRPKPQGGSHRGIKH | 20 |
| 297 | MQVPDLVGLGHSWWCAVVTKGGRPDDVECENGDEVYGLSHAPRAHSCPEDPDSVAPGAKHRSPRGPLQSRKRSRGE | 77 |
| 298 | MLPKTVRGAQKVRAGIEVGSNAARWRATSLGETSGVHPRAAEP | 43 |
| 299 | MRDSTPNSGGSRVHSSGHQKDDNDLGPRSLHREVGQAEHNAPMSSTNDVYDDLGDAHHVSQDHGGSG | 67 |
| 300 | MPSDGTQVDGAIAFLHKPVVLRRDNEHLGCQHYPAAEVPHVESRAERSGHHDHVDVRPQALREGAALLHSHIW | 73 |
| 301 | MRESSGNATKRGAYDGDVPHEVGEAAR | 27 |
| 302 | MPGVIGAPRGTRTSGGQEPSCPAESLVPV | 29 |
| 303 | MCAEGRRQARVTFQLWLGGPEDSRSTPIRTFQN | 33 |
| 304 | MLSAPGHIPVWGGHQEGRNTWS | 22 |
| 305 | MLSRETPPAGRGSTGIHKMPPSLPEEAFV | 29 |
| 306 | MTWSSTRRSHPPRSK | 15 |
| 307 | MVLRARGRSFLRPSGRESPERPLWTQTLSGSHRPP | 35 |
| 308 | MAPIAGSPRSLPQMGVTPALSAALQPPP | 28 |
| 309 | MDLLAWTSIHQYRAQGHKEAETRLQMN | 27 |
| 310 | MRRGPPKCPRHTPPGYPPAPCPGLCCLQQPPLGH | 34 |
| 311 | MPSWKPQQDSLVVLTVLRGTECR | 23 |
| 312 | MKPPQRVVCPGPV | 13 |

TABLE 2f-continued

(Seq. ID Nos. 289-359)

HCV 2a ncOrf's 4-6

| SEQ ID NO. | Sequence | AA |
|---|---|---|
| 313 | MRRRLPRPPQLGPTCWS | 17 |
| 314 | MWRCILSQDV | 10 |
| 315 | MRNSPPIALFGKGSGHLCV | 19 |
| 316 | MPQHSSPCPEGPPRAHHTFSLNGRRSSVSLP | 31 |
| 317 | MWSTLWPPRSSQF | 13 |
| 318 | MRPSPPPRR | 9 |
| 319 | MHHRHKPVGAVRGAVGKRAIGR | 22 |
| 320 | MTPAVVGCCSTGKHLSHSPPTCKWALQVYRSCPPRLGWG | 39 |
| 321 | MASYLLDW | 8 |
| 322 | MYFPLSRTGRTRGRGGPPPEAAR | |
| 323 | MALPGGGGLEAVRHSY | 16 |
| 324 | MYPMRSAKPHVRVSMTLPTLRDLCRGSLGPQEGREPRGDRSHPAQPSPSFPYRGQGYPGFPQDLPVERRSLGMGWRLPRGWDRSEVFLVVRTPNLGPLRGNKYTPPTIWPPPGNLTSCGRRLVFLLVFL | 129 |
| 325 | MSPPPAPTVNQLDKSRRRASGNGVSLSLVFTAQLKRYRPQTAALPPREMRDALTARARLFHALRGGAPSFLRAEATRVSSWGVYVCRRKASSPCNLSIMAGRSRGLTEYTDPYISKLRSWSRVSWAIRMEKKCVIRTMRTHIVGAYWMMFPNHELTGECLTVSQAARAIGVVGSLVR | 177 |
| 326 | MTTKSSPHTSIVGATIPAALQAARAFT | 27 |
| 327 | MVFPMLVVSTPLARQRLYPQVWPLLLNIGPPT | 32 |
| 328 | MAVRASSGKEQAWYMASSVLMSLSVTVSSKHRVSYEKPIGSFLSAHAFKRNSTRWAGEYWNP | 62 |
| 329 | MMVVGIGVCESSRRSFHTDLMWLTALPDKLRTSLAPYPYLDLAEWGGVNWHASSKVRSFALTLEAASLMSFKTES | 75 |
| 330 | MEQHTTESSSSEQVDQDPESEPGAASPPWEGGRSSTWSGSRSGSPGSPSRGGMEEVEPVSERANSSGGVRPPESAASAPVERPESPLGGGWPKVLMASCWRASPMVLSLRPTVRRLLGGGVGVFLGGGRAQPATVGGW | 138 |
| 331 | MNRLASTMSTS | 11 |
| 332 | MDINTSVSGSGSQGS | 16 |
| 333 | MAVLKFGAGFGMHWPSV | 17 |
| 334 | MLAPQGHRVVMMPVPAHTPL | 20 |
| 335 | MVQTQSHTSRSHEPAHGMGQSSVIQLWSLLSRLVIVREPSSWVTRCDASDSVT | 53 |
| 336 | MSLFIHWTAPSPGPTWRRRMPAQMTPTTRAPGDKIPGSRLMTSSMEGFSPDMILNATRAPEMPAPYPARISTSTLPRPMLPTAAPTRPLTTKPVAPAGGAIWDASQPPRMLRRIVVLVDNGLVRAALNAIMEATAGFPGSVDSPARY | 148 |
| 337 | MPLMKFHMCLAQNCSTLGHEASTAGCMSWACLEACCNKPWILDFSISAIRCPSSMRAALEAHSSISSKAS | 70 |
| 338 | MCKRPMMETHPVAKQYAATAAKTPPARTHVLVMTSRSACMHVAMYFVTGCVKVTSLVTEPKRYRRGVGPTRVGLSRVRHEHMTSQDGGGALALAHTVA | 98 |
| 339 | MCVRPVKTASQNSRWSWHTGKPGVLKYALSLTVVSAGVSSYHAAPAS | 47 |

TABLE 2f-continued

(Seq. ID Nos. 289-359)

HCV 2a ncOrf's 4-6

| SEQ ID NO. | Sequence | AA |
|---|---|---|
| 340 | MRASVATTTTSP | 12 |
| 341 | MPRRAAASSSHFFFEWQKIKCLPPLM | 26 |
| 342 | MPRMVVASTAWHSSHMMMS | 19 |
| 343 | MAAPVVTVLTPVLMLGLMPCALDKYAPNPRVAATEGLSTSTLYPWAAYATGTLVLFPLPVGACKYRTW | 68 |
| 344 | MSSASTGMKSMDLATPREHTAARKIPTAWPLGQSTGPPEDPFKVERGLGESNAPRLSPRLRAGMTSAFRVTRYRSTAPHEHGSKDLVPGGLGHPTKSPSALEYICVTGPREPARVLLPAPW | 121 |
| 345 | MDVPRKDWVTVDRTWISPACSVLSRPVMLTTMAPKRPRVCWA | 42 |
| 346 | MGARSFHPLEV | 11 |
| 347 | MSPHAAVSAPQTMTFFSIGLKMIGSTATAKSRRPLAAQSDIGARWS | 46 |
| 348 | MSNTTPGQNMVVAHIMPSRPPRACMGGTHS | 30 |
| 349 | MASPRVRR | 8 |
| 350 | MYQAATKKMTKYRKPLQLAALAACKTTSFSSAASAWPSKISIHTQAQTLASARRRNKSTTHSHRTTYFVRAGDRPYMYCTSTIFWWRWSRPVDKAGKSEKEQGKMAHSVVECNRGDSWLLSLSSKSQRSPRVKLHAAVSLCSIPPTYILILKME | 154 |
| 351 | MRQGGAPQVLVKPVEFIHVQPNHDPRGGRVLFNRKTSVSPSPHV | 44 |
| 352 | MCQLPLVLISWMFCLEPGERRPAKLSVL | 28 |
| 353 | MTTTLAHAPCIEK | 13 |
| 354 | MMSMMTSGTRIT | 12 |
| 355 | MVVVGDQFIIMSHAIRCPVMVPRMEQLHSCTNQWCSGEIMNIWAASITPPQRSPT | 55 |
| 356 | MSMCVRKPCVRAPRCCTATFGETGIQHRDVFPTLSHGTHPGTWRTAA | 47 |
| 357 | MLSLEQSLVTM | 11 |
| 358 | MVIQDSRASKKIEKEQPGRFPVA | 23 |
| 359 | MYPMRSAKPHVRVSMTLPTLRDLCRGSLGPQEGREPRGDRSHPAQPSPSFPYRGQGYPGFPQDLPVERRSLGMGWRLPRGWDRSEVFLVVRTPNLGPLRGNKYTPPTIWPPPGNLTSCGRRLVFLLVFL | 129 |

TABLE 2g

(Seq. ID Nos. 360-404)

HCV 2b ncOrf's 1-3
Genbank Accession No.: AB030907

| SEQ ID NO. | Sequence | AA |
|---|---|---|
| 360 | MGATLRHESLPCEELLSSRRKRLAMALV | 28 |
| 361 | METRVAVGQVGSCPLAGLVLLGAPATPGIDHAIWAGSSTPSRVVLPISWGTSLSLAPLSEASPELWHTVLGSWKTG | 76 |
| 362 | MQRGIYPVALFLSSYLLFCRALQCQCLQWKSGTSALATTPLMIARTTASPGSSLTQFSIFLDVSHARMTMVPCAAGYK | 78 |

TABLE 2g-continued (Seq. ID Nos. 360-404)

HCV 2b ncOrf's 1-3
Genbank Accession No.: AB030907

| SEQ ID NO. | Sequence | AA |
|---|---|---|
| 363 | MRPPIPPARQWAGPLGALLASLSLVPNRTSN | 31 |
| 364 | MTACTRVSWPPCFMPTNSTALAAPSVCLPAVGWMIFVSGGEPWNTRPTSPMLKT | 54 |
| 365 | MLPMLSVEQGPG | 12 |
| 366 | MDFLQLLRNTS | 11 |
| 367 | MGRCGSSSFLRRPGT | 15 |
| 368 | MTTSPPCQLGRPRVCGTWRLPWSLSCSAQWRRRSSCGGLRQWHVETSCMASREPRG | 56 |
| 369 | MATPPRGGSS | 10 |
| 370 | MSRPGRSRFCPPSHNPSWGHLERGFSGRYITGLVTRPWLAPEDQSPRCTPAQRGTSWDGLVPPGLSH | 67 |
| 371 | MIDGVHCCRQGLSQPSKDHPEDPCSALGDTPWACSERPCAPGVWPNLLTSSRLNLSTSLDGRPVFLTTARHQLCPKLTRWATCTHRQVAGRAPRSLPHIPVRGIKCSC | 108 |
| 372 | MASFSRMEAAQPAPMISSSATSAIQWTLPPSLASEQSLTRLRPQVLGWWF | 50 |
| 373 | MRARSLFMARLSL | 13 |
| 374 | MSSQQPFGAWASMPSPTTGVSTSPLYQLKGT | 31 |
| 375 | MSHQAKGRLGCSTA | 14 |
| 376 | MMPGQLGTSLRLLRLR | 16 |
| 377 | MPTSSPRRSKEEITLRI | 17 |
| 378 | MIRWLWPLTRKSYMRPLMRWKNAPPKPPSLRKGSGWRRCLNLRY | 44 |
| 379 | MLPLLTTWRSLTPRCA | 16 |
| 380 | MIVTWWMPTFSWEAM | 15 |
| 381 | MIVSLLYHQST | 11 |
| 382 | MWRGSLGRWQTKCSALSKTPMTPVTPLGRIPEETASSSPLARLPLQMRDHCPPCLPLRGSRGTLTWSLSQRDPLPLPRGSVRSSTRTLSRGLQSPIKRILLSAAPCHTPGQEPS | 114 |
| 383 | MTQSCRTLSGLPLRLVRGSSQ | 21 |
| 384 | MRCSVLIPPRAEKSQLASSYTLTLGSGCAKRWPFMTLHKSFPRQ | 44 |
| 385 | MGSNTLLQNGSIFSSKLGEVRRTQWGSHMTPAASTQPSRRGT | 42 |
| 386 | MGLTPSHCTHTLPTNSHGWQRLSGNLERLPLERGRVGRVL | 40 |
| 387 | MPDPAYYSPAYSYLA | 15 |
| 388 | MNHSPVRNYCLHAESV | 16 |
| 389 | MSGHLGVPPQDC | 12 |
| 390 | MGHDAELVTNSYHDPRLRCSCSRVGPGNCLRRPLGCGIWLGLFLHAGSVGQGHCHPPSCCGSGCDHLFHRRDSGPDRWELCWPL | 84 |
| 391 | MRYRPSSVGLRAGLLLYS | 18 |
| 392 | MRSTTLPH | 8 |
| 393 | MHRKFHHLQGADVCRGGGA | 19 |

TABLE 2g-continued (Seq. ID Nos. 360-404)

HCV 2b ncOrf's 1-3
Genbank Accession No.: AB030907

| SEQ ID NO. | Sequence | AA |
|---|---|---|
| 394 | MQFHTRRPLQIGR | 13 |
| 395 | MLLLRPTGTIYWPVAPSPKHRGRAVPLWTFSSCYEIHRKVGMGGPPFPVAGRRQDLCMPLDAHHTGPS | 68 |
| 396 | MGSPPGGPRGA | 11 |
| 397 | MWRHPAWPPGFREAR | 15 |
| 398 | MGPGWGGASRRGSLLPGDRLHLHHWPHTPE | 30 |
| 399 | MRLQSRPH | 8 |
| 400 | MAQDRTILGQTHVELHQWHTVPGGTLHLTGKSRSGINDGFQRRIN | 45 |
| 401 | MFGVLAPGHLGVGMFHSHRL | 20 |
| 402 | MRSKHLGPRPLGHHENNRPEDLPKHVAGNLPHQLLHRRALCAKTPS | 46 |
| 403 | MWARGGEVANQPSE | 14 |
| 404 | MSVVQPPGPPLPGEP | 15 |
| | HCV polyprotein | 15 |

TABLE 2h (Seq. ID Nos. 405-479)

HCV 2b ncOrf's 4-6

| SEQ ID No. | Sequence | AA |
|---|---|---|
| 405 | MRLTDLSQLAVTRAKMEPPRKEEKKKIRKKRKKKKNKKKKKKKEN | 46 |
| 406 | MCAMRRRQAHVAFQLWPAGLVD | 22 |
| 407 | MSWCSPCW | 8 |
| 408 | MRTPLGPSYFPKL | 13 |
| 409 | MSRSQEGCSLDGPREVVPVGTFSSWSSTLMVQKAHDHPLPQSWNRGSQERSPWSRTQFGSHRLP | 64 |
| 410 | MPFYGWYR | 8 |
| 411 | MPLRDFPVRWRVPPGTVCH | 19 |
| 412 | MMTAWLAVCPGPVLWPVVGGLVS | 23 |
| 413 | MRHTCKCPIAPSQFSLYVDYGRQRPEGQSEW | 31 |
| 414 | MRQGPWCSSRYLSVRAGSPPGKFGAQLVACCCQKNWASV | 39 |
| 415 | MHPVYHLSSGPE | 12 |
| 416 | MPLSQPPTR | 9 |
| 417 | MAPVVETL | 8 |
| 418 | MWPRGPLCPLSTRPP | 15 |

TABLE 2h-continued
(Seq. ID Nos. 405-479)

HCV 2b ncOrf's 4-6

| SEQ ID No. | Sequence | AA |
|---|---|---|
| 419 | MHRSWRLPATGKGGPPIPTLRCIS | 24 |
| 420 | MATPPTQWWSAAVDSADPYPYLPICSGLRV | 30 |
| 421 | MLQRIYAPPPLHTSAP | 16 |
| 422 | MDNATVCKGSLSGTWGSTRALLHT | 24 |
| 423 | MALGGNASSTASCLQHW | 17 |
| 424 | MGHIQEDGELR | 11 |
| 425 | MALPGGGGLEAVRHSY | 16 |
| 426 | MICRETSYGTLCSHAAHGPFTASRD | 25 |
| 427 | MPTPTLSRSRQRSNRRGRACDTL | 23 |
| 428 | MSPPPAPTVNHPDKSRRLASGNGVSLSFVFTAQLKR | 36 |
| 429 | MMSEALTAPARLFHALRGGAPSFLRVAIATRESSWGEYVCNEKASSPCSLSIMAGRSSGLTEYTAPYISKLRFWFRVSWASSMEKKWVIMTIRTQIVGAYWMMLPSQELTGECLTVSQAARVIGVVGSLVKKYRRRPRESSATDTFEEQDVISSKSYSGLGRSPGGAEYLVIASVKALRFRSSSSLPWLSEMTTRSSPHTSIVGSTIPAALHAARALM | 217 |
| 430 | MVFPMLVVKTPLARQRL | 17 |
| 431 | MDSSVLMSLSVTVESKQRVSYENPIGSFLLPQALRRKSTRSAGEYWNP | 48 |
| 432 | MRRAGFFPPLAGSIQNTSFLAMAVVSIGVCWSSRRSSHTDRMWLTAPLDKLRTSFAPNPYRDLAEWGGVNAQASSTERSLALTLEAARLTSCKTES | 96 |
| 433 | MRAPVQEYDMEQQITESS | 18 |
| 434 | MTSHSPSEGGADLAGSNSRSGSPGSPSRGGMEDSDPASEAAVSPEGCWTLSPPVSAPVE | 59 |
| 435 | MESRESRTITLESDSIRVTSPPMKRLASTMSQSYAVLWVVQVAFKDGADSWLAEELACEGGDPLASRLAAVSAVMWDGSVNMEANTSVSGSGSQGS | 96 |
| 436 | MGKVPCHMFRQVFGPVIFMVPKRTWPEMFAPHEHRVVMTPVPAHTPLYPFWQEMKGRPGILGSNFADSQFLKSVRMEHTHSQMSRSQDPEHGTGQSSVIQACSLLSKLVIVSELNTCVTRSEASDSAT | 128 |
| 437 | MTPTTKAPGDKIAGRRFTTSSTEGFSPLMILKATRAPEMPAPYPARTSTNILPRPILPTAAPTRPLTTKPVAPAGGAIWEANHPPMMFKRMVVLVGSGLVNAALKAIIDATAGFPGKVESPARYCMPLMKFHMCLAQNCSILGHDDCMAGCMSWACFVACCRRPSILDLSISAIRCPSSMRAALEAHSSISSKASYKISLSGATTT | 206 |
| 438 | MRPMMEMQPVARQ | 13 |
| 439 | MTSRSACMHVAIYFVTGWVRVISLVTAPKRYRRGVGPVSVGFSLVRHFHITSHEGGGAFALAHTVA | 66 |
| 440 | MCVRPVKTASQNSRWS | 16 |
| 441 | MVKVGSRLKSTI | 12 |
| 442 | MTESKSPVYPVIRASVATTTTSP | 23 |
| 443 | MPRRAAASSSHFFFEWQNIRCLPPLMEARGIALP | 34 |
| 444 | MLAWGVVTVPGGVAVARTTSLTPAVSAWSRTVPMPRMVVASTEWHSSQMMIS | 52 |
| 445 | MLGLIPWALDM | 11 |
| 446 | MSRDSTGMKSIDLATPLAHTAALNKPTACPLGQSTGPPDDPLRVERGLGDSNAPRLSSFLRTGMTSAFRVTR | 72 |
| 447 | MAPRRPRVC | 9 |
| 448 | MGAKSFHPLEV | 11 |
| 449 | MSPHATVSAPHTMTFFSIGLNTTGSTATARSRKPWAAQVDKGERWS | 46 |
| 450 | MVINSIWIYLAPARCLTRVHTRSRA | 25 |
| 451 | MTATQMIPSRPPRASRGGTHC | 21 |
| 452 | MDMTINMTSPSSPCSAASKA | 20 |
| 453 | MKNHSGPLALAALAECKMMSFSSAASAWPSMMSIQRHAQILASASNRKRRTTHSHFTMYFVTAGESP | 67 |
| 454 | MVKFTVHG | 8 |
| 455 | MRQGGAPHVLVNPVPFIQVQPNQAPRGGLVLFSRKTSVSLSPQL | 44 |
| 456 | MSSTLVTLVSYSKVPHPIRKSSSPRQEDKRSGQPELLNLLA | 41 |
| 457 | MKPVCKLSLQLRAVRFMCQLPLVLINWTECWAPSLKRPAKLPTVRPTVAPVE | 52 |
| 458 | MAMTLAHAPCMEK | 13 |
| 459 | MVRVGDQFSIMSHAMRWPVI | 20 |
| 460 | MEQLHSWVKLWRSGDTIRACDTIITAPHTSPTYRAEQTVAAITITSTCARRL | 52 |
| 461 | MLLFEQSLVA | 10 |
| 462 | MFLISTEDTGTVTHDRRASKKIEKEQPGKFLVA | 33 |
| 463 | MYPMRSAKPHVMVSMTLPKLRDLCRGSLGPQVGRDPRGDRSQPAQPQPSEPYRGQGYPGFPQDLPVERRSFGMGWRLPRGWDRSEVFLVARTPNLGPLRGSK | 102 |
| 464 | MRHAVKDVAPAGAHGEPPG | 19 |
| 465 | MLVFQEVLPHGPDVVNGPPG | 20 |
| 466 | MEPHKRVTQRADWQLLLLGPTWCYEGSCPGV | 31 |
| 467 | MGGTGSLQGRGGQLAR | 16 |
| 468 | MLRDLNVLRRCHPPNSGLIIRRGFWHTRPFCVTIDGEGSLPHV | 43 |
| 469 | MVSPRGKGDQSVHPLDRPLSLADVAAQDCCANDSHYQGARGQNSR | 45 |
| 470 | MGQGNLVGHGTQAV | 14 |
| 471 | MTKGHLLYVSVGSCHRTGGRGCG | 23 |
| 472 | MALVADDDIIGAG | 13 |
| 473 | MQDVSTCHCLSPPHDDLLLHWAEHDRLHGNRQVPQTLGRPS | 41 |
| 474 | MSHQGTHS | 8 |
| 475 | MLHPPYIHPHLEDGEIYGAWIMPQSVRVVYQAPGGQPGPCSTLNIGSIWVLPKTVCRAQ | 59 |
| 476 | MPAVRPHVFNIGDVGLVFQGSPPDTKIIQPTAGRQTLGAARAVEFVGIKQGGHETRVQAVIAVEGGPVYVPAAVGID | 77 |

TABLE 2h-continued

(Seq. ID Nos. 405-479)

HCV 2b ncOrf's 4-6

| SEQ ID No. | Sequence | AA |
|---|---|---|
| 477 | MAAEDNFQDQLGNTSSVGEDHGKSW | 25 |
| 478 | MTLVDGTVALLGKVVAFWRYYKSLRHDHHGPTHISHVQSRADRS CHYDHIDVCSQVVSECTAVFYSHIRCYLYPAAQGTIVILAWDTS RKMENCVSELPGDAVVRAIISGVVASADVPDFH | 122 |
| 479 | MPGVAGAPSRTRPARGQEPTCPTATLVSIQRPRISWLSPGLAGG APIFRDGLASPTRLGSLGSLPCRAHTQPGAPARQQVNSANDLAA TRELDVLWAAVCVSFGFSLRFRICAHGARSTRPPGALASTLSGS TTRPFATQRYSASSLAGARPNDRT | 156 |

TABLE 2i

(Seq. ID Nos. 480-517)

HCV 3a ncOrf's 1-3
Genbank Accession No.: AF046866

| SEQ ID No. | Sequence | AA |
|---|---|---|
| 480 | MALVRVSCSLQAPPSRESHSGLRNR | 25 |
| 481 | MVMRAAGGQGGSCPRAAPVHLGAQMTPGGGPAIWVKSSIPLRVD SPTSWGTSRSSAPPWEASQEPSRMA | 69 |
| 482 | MRPMTSFCTHPAAYLVFRTTIYPRAGPQ | 28 |
| 483 | MPPEGLLAFLVWAPNRNCSWLTPMARGTSTALP | 33 |
| 484 | MLTSPVLLMTNRTAGTTHLDLVKLSRHQVSAVLYTASHHRQWS | 43 |
| 485 | MPRACQPTPGVRMIPMCSCWSPCGLPVVGGLGARG | 35 |
| 486 | MGVGGIPEMSQTSSAPPTASGNTLRPHTAGVVRGPG | 36 |
| 487 | MSNTFMALDLAWWDGR | 16 |
| 488 | MRGRVKTALLSALGSWPSSASLPYHPGTSIGSAALYGGTSTPYV DASPPSKCGSPPYLHAGVGTVSSC | 68 |
| 489 | MTIGRWVGDCWPRSQHTPSKLGAFLGLL | 28 |
| 490 | MVQVRERSRAPNIPRSKCTQM | 21 |
| 491 | MPMSSLLGAGGTPQRACSVLDLSPVSKVPLEVLLCALRGMLQGS LGLLCAPEV | 53 |
| 492 | MPRPAAVKAQRSRPLTWHKDILFSC | 25 |
| 493 | MGSTPTSALGTAPLQLVPN | 19 |
| 494 | MNVMPKTLLAYWVSARS | 17 |
| 495 | MCPSYQQQETS | 11 |
| 496 | MRFPAANVVAVRAEVDSVHTDMSPPVKDRLECLTRLFSVSAMTR AARGTISSPLRPQSD | 59 |
| 497 | MPTFCHRLSSRDLTSRT | 17 |
| 498 | MDLRPFYTGWGLSKMKSACHTPSQNTSWHACQLIWK | 36 |
| 499 | MRWRSAHKPPRTSSKLRQ | 18 |
| 500 | MELVSQAPWWLLRSWEENSPPLRTWSTCCPPYYLRVLSSSV | 41 |
| 501 | MFPRAMLQRGSPHC | 14 |

TABLE 2i-continued

(Seq. ID Nos. 480-517)

HCV 3a ncOrf's 1-3
Genbank Accession No.: AF046866

| SEQ ID No. | Sequence | AA |
|---|---|---|
| 502 | MKZTQALVVTTGCVSSGTGFVRCCPTSSHGSLLRLCQRSPGCPS FPVKRDTRACGGGTA | 59 |
| 503 | MGPCGLQGRVHVLTCGTVLSPSMSTPPDPVHLVHHPTTLARYGA WLPTATLKCAEWGTSIILRGPQKMSSSVRAKYRLLSSSLKWMG | 87 |
| 504 | MTPSSRWLQSVSRNLPSILQPELSGLGQTTILHCWTAGKLRIMY HQLSMDVPYHHGALRRSLLLGGKEQESWTVPMCPRRYVR | 83 |
| 505 | MTPAALTQLSLNRTSGWKRRYTNAATLNRRPGK | 33 |
| 506 | MIWSWWPRVTASMRMGQP | 18 |
| 507 | MLHSPPTTLSSSHLAPPTSPWHGTTRGGGTITSPVMPPLP | 40 |
| 508 | MDHSPVRNFCLHAESA | 16 |
| 509 | MPSKAQQLQAHHELQAGVGSLDRC | 24 |
| 510 | MYSQFHIVQGEDVRGWVRAPVYRRLQLDQGGALRYRRS | 38 |
| 511 | MGAEMGVRHPHFTPPSGPTRVRCPLADADDNTSRSSLGEPCHAE RRRCWDTRYRLVPGGLLCGVVRAGQTCPGGDLQPDGPLAPSFA RPHAPPTGVCVVG | 101 |
| 512 | MVEPVHHM | 8 |
| 513 | MRVRPPSVGPPLTCTRE | 17 |
| 514 | MRCHTTPTRRTWGGGGTVDEQAHRIRIPGQPRPTNALCSRERCC SEGHRIAEFSNCHKPAPAVTPVDQ | 68 |
| 515 | MARGCQQLR | 9 |
| 516 | MCLTTTGRSAGPSSSEEKNNSAGRFQCVRGVTCASGKIISVLET AGRE | 48 |
| 517 | MLIHASSRGRTGRSGLELRLLVHR | 24 |
| | HCV polyprotein | 15 |

TABLE 2j

(Seq. ID Nos. 518-587)

HCV 3a ncOrf's 4-6

| SEQ ID No. | Sequence | AA |
|---|---|---|
| 518 | MESFNDCW | 8 |
| 519 | MVVEHLQSVEGNLPLTLRSASRRR | 24 |
| 520 | MMSQQGVAEWADGQFLLLSTTRCYQGAGPRVRHRAADHALLLAV TNGGPRVATQVRIARFSLERRHG | 67 |
| 521 | MDSWWYIIRSFPAVQQWRIVVWPSPDRKGWRILGRFLETLCSHR ELGVISFGPQRFE | 57 |
| 522 | MRPMRLASGLQRRS | 14 |
| 523 | MRRVSQHRGQHRNIWFWLTGELRSYRVGIQPYRESDLLS | 39 |
| 524 | MEVPHSAHFNVAGGSHAP | 18 |
| 525 | MTGYCCPARTACRHHAVPPPHALVSLLTGNEGQPGERWHNLSRE P | 45 |

TABLE 2j-continued (Seq. ID Nos. 518-587)

HCV 3a ncOrf's 4-6

| SEQ ID No. | Sequence | AA |
|---|---|---|
| 526 | MGGNPPPEYVEKHSLVGRQGTGD | 23 |
| 527 | MLVPEGLKLLPVGSYYGLNDSLLLGGSLQQSKDFFLELVGYCLSLLDVRGGL | 52 |
| 528 | MTHNHNAAD | 9 |
| 529 | MAKDKVPPPLEQGYRYSLTVEGDLTFRAQGHFFDVRMWHSDAAWGSSCR | 49 |
| 530 | MTFITDNHIVCPPGATPVREKLTVGGIGQFGTSCNGAVPSADVGVDPIGTRHERAKA | 57 |
| 531 | MKVSYLIALWNSRRS | 15 |
| 532 | MPRPAHNRTSRGTFETGERSRTEQARCGVPPAPSRDDIGIAGNQV | 45 |
| 533 | MFGARERSRTCTMVNSPRNPPHCCT | 25 |
| 534 | MQQWMLLAAVTIFDIAALPPGPVASGGKPVLEPTHEHPHLEQCEIDCTWVMPKPVWIVDHAAGCQPGPRTTPAVCGLRMFPEAVGGAEEV | 90 |
| 535 | MIIKQPSYEPGVYGLITVQGSAVDVPRAIGVNQLQFLLGAHTKKASKPSGGMSCRATGGICYGIDP | 66 |
| 536 | MGPGYYVEQGLGHPQDVRHRHTQSGEPIHHHIPSHSMS | 38 |
| 537 | MTTYRSGGCSDVPDCHCRCHWGPARGYIVVLNTRYAAGCVQNDVIGLIHNTAIGTVVGEDVEARRIPPL | 69 |
| 538 | MREGSCDASHGGADERDVPHEVGESTRKGIDDFTQIAGPPPGVIWAPRWTGAARGQEPPCPPAALITIEGPRVPGLSPGPASALTRLGDRLSSSAGL | 97 |
| 539 | MARRFPREDRSSSQGSDPWWSVAS | 24 |
| 540 | MSMTLSRTPLPGRGAPWK | 18 |
| 541 | MIFPLAHVTPRTHWNRPAELFFSSEEEGPAERPVVRHIHGQLVVHNPELSSGPTVEDCSLA | 62 |
| 542 | MNQESQPLFQTPPV | 14 |
| 543 | MEGTHAQGGALPSRR | 15 |
| 544 | MEGRNGGVSPHPLQ | 14 |
| 545 | MDKVYWVRWCTH | 12 |
| 546 | MYAALQAAWTHSSHDRLLLPRKDSVSTSRRPPATRPCIPFDRK | 43 |
| 547 | MYRVYLCPYGHDVGCGKPHLGEQCGSRWKRWGPG | 34 |
| 548 | MPPRSNPRPRETYRRWNRSVWHQL | 24 |
| 549 | MDSAREQYILVPRKRPGPLCFYRCRSGHEGILPDSSVEQQEELNCQRKMGT | 51 |
| 550 | MMDKAGLLAG | 10 |
| 551 | MGNAKAGMDSRPCSGVSTRAPHHTGCMWPQDVS | 33 |
| 552 | MPGQLYKV | 8 |
| 553 | MLRHRPLKT | 9 |
| 554 | MDGSRAGTGATLPTRSPHYRGAKGTRAEPRTGLRSDAPWG | 41 |
| 555 | MALPGGGGLEAARHSY | 16 |
| 556 | MPTPTVSRSRQSSK | 14 |
| 557 | MSFPPTPTVNQMDKSNWPARGSGVSLVLVRTAQLKR | 36 |
| 558 | MIAGKSSGVTE | 11 |
| 559 | MEKKCVIITMRTQMVGAYMMMLPNQELTGV | 30 |
| 560 | MSCSVTVESKQRVSYENPKGVFFEVHILSRRSTRC | 35 |
| 561 | MMVVGIGVVVSSSKKSSQTERIWLMALLDKERTSFALYPNFDRAE | 44 |
| 562 | MVSMRAFTLDARSFTSFNTVL | 21 |
| 563 | MGSFSSSALHGVIRAPVQEYDIEQQTTLCSSLSLTVDQESQLKSGSPGSPSRGGMDEHDSESDSPPGEGGTLEVVLDCVSTPEEELFSSCGFKDGNDFSASARNAADTLEPSS | 113 |
| 564 | MLLPISCRHNKLAFTSSASG | 20 |
| 555 | MGKVPCHMLAHVRGPASRMDPFFT | 24 |
| 565 | MKGSPGSAGIILAESHDLKSDSTEQTQSQMIRSQSSLQGLG | 41 |
| 567 | MSLFIHCTAPSPGPTCRRSMAAHITPTTRAPGDSMAGNRLTMSSAVGSSPPMILKATKAPETPAPYPARMSSKTLPRPIPPMAAPAKPLTTNAEELWGPAKWVATHPPSMLKNIVWLVVRGLVTEAVNAIRDATGLPGRVERPARYWIPLTKFHICLCQKASSFCQLVATMGSMTACCWVARCSNPRTFSLNWWAIA | 198 |
| 568 | MYGAACEHSSISSYC | 15 |
| 569 | MHAMTYFVMGCDKQISFWTGPNRYKRGVGPCSVGLSRTRHFHVSSQLGGGACAPAHTVAW | 60 |
| 570 | MEKVGSRLKSTYCSTATLQSMTESKSPVYPVMRASVAQTTTSPVVGMTDTSRPL | 54 |
| 571 | MLECGTVMLPGGVRVAKTVSLTPAVSA | 27 |
| 572 | MKEPKPSVAATDGFSTRTVYPCAT | 24 |
| 573 | MNCRAFATPLVHTAALKIPATCPEGHITGPPEEPLRQARGLGLSKLAVESPLRRAGMTSASRVTKYKSAEPQAHGSRDLAPGGAGHPTRS | 90 |
| 574 | MTLISMGLNITGSVATARSLRPAAAQCCIGARW SYR | 37 |
| 575 | MLSMIIWKYFPPITERTSMQRRTSTCARTK | 30 |
| 576 | MTPSLLPRASKGGTHTWRADSHLHMVYWFHHIRRPIQCLYQGDKVKKPKRAKTPAPRVALSSPDHAYARWGSMRTSKARGQRPVRL | 86 |
| 577 | MRMTNSHFSAHPTMPDPTP | 19 |
| 578 | MFWWRCIRPVDSAGMGVKEQGSMASSVVECNSGCGSLRSRSSISQRSPLVQLQAAVNRCSNPPTNILTLNNVKLTVHG | 78 |
| 579 | MQRGVNQGPAPHRLYVASGCFLKQSVGQKRSDSFPEFPPPP | 41 |
| 580 | MSQGEAPHVLTNPVEFIHVHPNHRPPGGRRDSSRNTSVSFAPQV | 44 |
| 581 | MLASVKGPHPCLKKVMGLQLLSL | 23 |
| 582 | MNPVFMDSLQFRAVLLMCHEPLVLTSCSFCWAPTLKRLVSPLVA | 44 |
| 583 | MMIATLAQLPCME | 13 |
| 584 | MPQWAPAIMSNKVWGTRRTCATAIPRAGNQFIIISQATRCPERWPGYSEQLQVWTVWWRRGLNVKACPTRKTAPHISPT | 79 |

TABLE 2j-continued

(Seq. ID Nos. 518-587)

HCV 3a ncOrf's 4-6

| SEQ ID No. | Sequence | AA |
|---|---|---|
| 585 | MTSSASYTILLLEQSLVRT | 19 |
| 586 | MYPMRSANPHVRVSMTLPKLRDLRRGSFGPQDGREPRGDRSHPA HPQPSLP | 51 |
| 587 | MVFLLVFLCGLGSVLMLHGLRDLPGHSQAPYQAVPQGLSRPNTT RLVISRGHAQISGY | 58 |

TABLE 2k

(Seq. ID Nos. 588-640)

HCV 3b ncOrf's 1-3
Genbank Accession No.: D49374, D26556

| SEQ ID No. | Sequence | AA |
|---|---|---|
| 588 | MALVRVSCSLQAPPFRESHSGLRNR | 25 |
| 589 | MSCRVGAHNWVGAKQVRLPSDHNLADGVSLPPRHARARAGPGPS PGTLGPSTGMRAVVGQDGSCPPAVLAPAGAKMTPGVDPATWVRS SIP | 91 |
| 590 | MRLAYICLPTTAPTGALCMRPTT | 23 |
| 591 | MSQDIVWLGI | 10 |
| 592 | MGHGTLTALP | 10 |
| 593 | MVPVRTDHIAGTIHPDPVT | 19 |
| 594 | MSVGPSTALHPHRWWWAPLILKACQLIGLV | 30 |
| 595 | MMPRLPAAGPGPGLRQGVW | 19 |
| 596 | MNIDSQPPATGRGESAVILKIVTAVSNNHCSIQRLTR | 37 |
| 597 | MPPSGPGCSCSSGSLPYHHGISTGLAVLSGGTSMPYAGVRPPCK YGSPPCLFEVVGTV | 58 |
| 598 | MTTCPPYRTGLPRVSKDWRWPRSPSSLVLWRLRLSPGVQTQQPA ETSCAGCPFRRGWAASCCWVRLTITRRWDGAYCPRSQHTPSKLG DYLELLSPA | 97 |
| 599 | MVLGRGLLLVTNGPRFKCTPMWTRTW | 26 |
| 600 | MLHRDILS | 8 |
| 601 | MGLTPTSVRGHAPSQPVPNSPTPHTASSSPMGVVLEAPNT | 40 |
| 602 | MNVTRKTLPPYWV | 13 |
| 603 | MAKPSHWQ | 8 |
| 604 | MTQVVPGMTYNLLRPQCD | 18 |
| 605 | MTPSCHRQNSRA | 12 |
| 606 | MRCGNVSYA | 9 |
| 607 | MMRWKNVPSLLLTSSKHRLSLSNSRTKSSACCKGRANKKLKFDP | 44 |
| 608 | MGLGSPAP | 8 |
| 609 | MYHQHTMSPRATRQQK | 16 |
| 610 | MTSGTGSVSYLVTLRPGFRPRSCPRCQAYPFSHVKRGTREYGEG MG | 46 |

TABLE 2k-continued

(Seq. ID Nos. 588-640)

HCV 3b ncOrf's 1-3
Genbank Accession No.: D49374, D26556

| SEQ ID No. | Sequence | AA |
|---|---|---|
| 611 | MAPSPSMNTPLGRVHPSPRTITRVPCGA | 28 |
| 612 | MSRCVGWGILITWWGPRTTA | 20 |
| 613 | MLLLVSPF | 8 |
| 614 | MQMGPSPHANPSRTSQC | 17 |
| 615 | MGRMCPRHSLPWQRDLSRRRNRKGQAHPPQE | 31 |
| 616 | MLTLGPPSVTPKSRAWFAVLCHTPGLAP | 28 |
| 617 | MTITKMYSRR | 10 |
| 618 | MFVPCPAKP | 9 |
| 619 | MTSGRRRGYTNVVTLNQRLGRQSALSQSTGTSGVPCITAKDSNA VIAAAALAASCLPALATQ | 62 |
| 620 | MNHSPVRNFCLHAESV | 16 |
| 621 | MTGSFLGTTRSMPGNLGVPPRDH | 23 |
| 622 | MALAPPRFSPQLGPK | 15 |
| 623 | MRALRRNRQQQHIVLDTDFTDGGRQAPWCDHRVDPKSCEYVGGP ANAVLSTIRRRRLRGRVPCGTSVHL | 69 |
| 624 | MCVDEQYRVCKDLWGSPLQHLWGDEGH | 27 |
| 625 | MPYRLFQEAP | 10 |
| 626 | MLIYTYAPPVNRAHTPPPEHRGRAIPLWCWFCRSGLGSQVGVRR PRLPPSGGRTRVCGPLDDVTDFSGGSSNGELGDAERPQRSGTTG LRLVPGCILRRMAHPGEARSADNLWFDRPVAPSPARPPAPSACL RLDGRRRCHHRGRGAPAPRVLYLITMV | 159 |
| 627 | MGPPPACSR | 9 |
| 628 | MAPTVPDLSIRPANSGTIWNYCHQPDR | 27 |
| 629 | MSPARRYLHTGYRHGAGSSRDSRGEADGTGNRDPSRQHHGAAS | 43 |
| 630 | MSHTPEADSARPYSSPV | 17 |
| 631 | MFPVCSLHRASTGYRSAIQGQSPRLAAKGEPTRS | 34 |
| 632 | MAESGGVLATAHVELCERDPVPGRSLHTARQPCRGFPYGLRRLC NQPPHNQPDYVL | 56 |
| 633 | MCCSVAPACRPWGRSSAVDEQTHSVRISGEPCITNTLCPRERRG SKSNSIAELSNRHPIASPVTPVDQRGLS | 72 |
| 634 | MSKGVQGSMARGWGDDNALPLWGRLYRTRKEWVHEDSRIRPLR | 43 |
| 635 | MPGASARVLHRVRRSEAPPLCSSL | 24 |
| 636 | MRTRAGRRSVNLDVARSCSHHRRHSGPAPCARFTSIGS | 38 |
| 637 | MEGPNLRAARSSRVCLATNSSRTSASPPQKEDNQARWVECVRGT PCPGREIFPVDETGRDRHILLRSRYRIHR | 73 |
| 638 | MQRRGKTTYQSTQQLVAETPQSCLLYVISKRRRTSEEGYLRQT ASAR | 48 |
| 639 | MLSCPPPLRPVEVRV | 15 |
| 640 | MRLSPLPR | 8 |
| | HCV polyprotein | 15 |

TABLE 21

(Seq. ID Nos. 641-712)

HCV 3b ncOrf's 4-6

| SEQ ID No. | Sequence | AA |
|---|---|---|
| 641 | MGSGTRHAVINVVPADTDRKPTRKI | 26 |
| 642 | MESFNDSW | 8 |
| 643 | MFGDSRVKATSVV | 13 |
| 644 | MLHSLFGRVLEPVGRPHRCN | 20 |
| 645 | MVIEHLQSVEGNLLLTCGGASR | 22 |
| 646 | MRPVRLTSGFQ | 11 |
| 647 | MQSYTEGDLVPQKGLTRRSIAVEPHSV | 27 |
| 648 | MSIPHPTHLDITVGGHAPQGTRVIVRGDGCTRPSGVFIDGEGAMPHVSAEA | 51 |
| 649 | MVPPRCERYESVHPLHCSFPRAYMPAQHCSTYHANNQRSRG | 41 |
| 650 | MPHDDDTTY | 9 |
| 651 | MSQSGKHSLPEV | 12 |
| 652 | MAEYKVSSSLDHCQWEGFAIKGDFSVTGEAHLLDIRMRHRDAAGRGRGCQYRQPHPGCLCLIQHRAYTQYGGSVLRVTFIADDHVIGASRTTPIGEELAVCGVGEFGTGCDGACPRTDVGVNPIGF | 126 |
| 653 | MVNSPHDPPYCRTQEGLGGRGQHLHLTSHHVLIPTCQAGDNSSK | 44 |
| 654 | MEQWLLLTAVTIEKITALSPRPVAGG | 26 |
| 655 | MFMSSYEHSDLEYREVHSARIMPQSVRVVYQTPWRKPGPGPAAGKRGIMVLPETIGRAFKVGLICFNVLHPPIDVARGSPTSLYKPCTVHPHTSKPPALGGSQRGQQEDI | 110 |
| 656 | MISDRRGGHTRVLDGHRR | 18 |
| 657 | MSEGSCDAPYRGADERNVPHEVGKSAR | 27 |
| 658 | MPRRRLRSKMKSAPSRRWAVGRLQGEQNIWSWPP | 34 |
| 659 | MKTLRGSSSTSTS | 13 |
| 660 | MLPRKRAGDPSPQMLAPSPP | 20 |
| 661 | MVLLWRQSRSMT | 12 |
| 662 | MTPRPILRQFRASHRTQRWILYLLLRRMCLSLPVSSTGKISLPGQGVPRTHSTHRA | 56 |
| 663 | MKGAKEGCSPVWPR | 14 |
| 664 | MEVNRAQGAGPLWRR | 15 |
| 665 | MKAGTHLHMNAILH | 14 |
| 666 | MGFLGRRSWPPPRNEYPPPYAPRHNCRRSRATGHASNCARGRVYSAQWCIH | 51 |
| 667 | MRERVCLAPWA | 11 |
| 668 | MLLLLLPRRSRGHSVLVIHGSPEMRTL | 27 |
| 669 | MLQVPLGVWLPNLQGG | 16 |
| 670 | MVGSPLHERRQWLDMPPSMQSLGPAVLPVTRSGHLYESVR | 40 |
| 671 | MLSVALWSQQVVGHTRNNLRHSTHIAPPSQTCRTAAPLE | 39 |
| 672 | MDLALGQNIPVQHKRRGLWCFCRFQWGREGILLGRTPGRQGGWNCH | 46 |
| 673 | MLRSGTVGAIPSSCNRQPDPATTRGPTAPKRATRTRCLRRLLCLHPR | 47 |
| 674 | MRRRMQPGTRRNPVVPLR | 18 |
| 675 | MSMAILASQSLNGAVVVAHCGHDLQDHSALPSSSCRRLRIDVHVLLRTF | 49 |
| 676 | MVCPHWDHLC | 10 |
| 677 | MCCCCRFRRRARIRVSARSRRRPHTQCSCWSSRW | 34 |
| 678 | MALPEGGGLEAARHSY | 16 |
| 679 | MPTPTVSRSRQSSKWRVRARDTL | 23 |
| 680 | MSFPPTPTVNQLERSSWPAVGNGVSLVLVRTAQLKRYRPHILAFPPWAMSLARTARARCLHARRGGIPSELRAPATLLSSVGE | 83 |
| 681 | MIAGKSSGVTE | 11 |
| 682 | MEKKWVINTMRTQMVGANMMIFPNQELTGVWRAVSQAARAKGVSGSRVR | 49 |
| 683 | MASVKARRAVLSSSTPQLSDITTKSSPQTRKDGFLRPAALLAAVALM | 47 |
| 684 | MGPPMYSRSVRALIAFRASGSRSQHWYIPSSVLMSCSVTVESKQRVSYENPKGVPFDVHILRRCSTRCLGEYWNP | 75 |
| 685 | MRRAGLRPPFAGFTLNTSFFAIMVVGIGVLLSSNKSSQTERIWFMALLDKERTSFALYPYFDRPEWGGTREHASSKESRRPFTPDARSFTSLSTEL | 96 |
| 686 | MAPVQEYDIEQQTTLCSSESLTVDQSSASRSGSPGSPSRGGMDEYDSTSDSSPVSGESPDSAVDSVPTPEEDVPVPSGFVDGKDLSARARSAADTFDPSSLIVLFLRGGGTGAGRVGGKAHP | 122 |
| 687 | MGKVPCHMLAQRPDPAILMDPPLTCPVKSSPQGQRVVITPSPRHTPLYPF | 50 |
| 688 | MPGTLGMILAESQVLKSLSTIQTQSQMSCNQSPLQGLG | 38 |
| 689 | MSLFIHCTAPSPGPTCRRNTAAHITPTTNAPGDKMAGRRLTMSSVVGSSPPMILKATPAPETPAPYPASTSSNTLPMPMPPTAAPAKPLTTNAEDAAGPARCVATQPPRMLKNIVWLVVRGLVTEAVKAIREATAGLPGSVERPARYWIPLTKFHMCCCQNASAF CHCDCTMGRISASCWLALCSKPRTLSLNC | 195 |
| 690 | MTTQPTDKQ | 9 |
| 691 | MQAMMYLVIGCVMQMSF | 17 |
| 692 | MRHFHISSQHGGLAFARAQTVA | 22 |
| 693 | MPDGRSPGVTNRYIPGLPRPVRPLR | 25 |
| 694 | MEKVGSRLKSTYCSTATLQSITVSKSPVYPVMRASVAHTTTSPDTGIITDTSRPL | 54 |
| 695 | MLPGGVAVASTVSLTPAVSA | 20 |
| 696 | MVRVPVRMLGSIP | 13 |
| 697 | MYVPKPRVAATDGFSTRTEYPCAT | 24 |
| 698 | MNCRAFATPLVHTAALKIPTTCPEGHMTGPPEEPLRQDSGLVLSKLAVESPLRRAGRTSASRVTRYRSEEPHVQGSRDLVPAGAGQPTRSWSTLVYI | 97 |
| 699 | MTPPTVVPKKVWVAVDSTCTSPVTTFLSLPVRLVTIVPNSPRVCWAYAEIGDSRRHPIFL | 60 |

TABLE 21-continued

(Seq. ID Nos. 641-712)

HCV 3b ncOrf's 4-6

| SEQ ID No. | Sequence | AA |
|---|---|---|
| 700 | MSPQAAVSAPQVITLISTGLKMTGSVATASPLRPSAAQSGMGDRWSYR | 48 |
| 701 | MQIRINTWARTK | 12 |
| 702 | MSKIREGYSRLASKITLSRLPRTSRGGTHTCKAASPLHMAYWFHQIRRPTQCLYHGDKVKNPRSRSTPAPMVASSSPVQA | 80 |
| 703 | MCHAAQNATRYQT | 13 |
| 704 | MFWWRCMSPVDRRRIGVNEHGNTSESVVEWSSGCCSLRSRSSRSQRSPLVQLQAAENRCSCPPTNILTLNIEKFTVQG | 78 |
| 705 | MLQGGAPQVETNPVLFIHTHPNHRPWGGLKEVNKKTSDSFTPNL | 44 |
| 706 | MLASVNGPHP | 10 |
| 707 | MGLQLDIRSGHPEELNL | 17 |
| 708 | MCHDPFELTNCKF | 13 |
| 709 | MISTMTTLAQLPCMEK | 16 |
| 710 | MLLLEQSLVSKYRPDAFLYSRLDAGQVKQEKRARRKIEKEQPGRFPVA | 48 |
| 711 | MSGMYPMRSANPHVRVSMTLPKLRDLRRGSFWPQLGREPRGGKSHPAQPQPSFP | 54 |
| 712 | MLHGLRDLPGHSQAPYQAVPQGLSRPNTTRLVISRGHAQISGH | 43 |

TABLE 2m

(Seq. ID Nos. 713-752)

HCV H77 ncOrf's 1-3
Genbank Accession No.: AF011751

| SEQ ID No. | Sequence | AA |
|---|---|---|
| 713 | MGATLHHESLPCEELLSSRRKRLAMALV | 28 |
| 714 | MAMRVAGGRDGSCLPVALGLAGAPQTPGVGRAIWVRSSIPLRAASPTSWGTYRSSAPLLEALPGPWRMASGFWKTA | 76 |
| 715 | MQQGTFLVALSLSSFWPCSLA | 21 |
| 716 | MSPMIALTRVLCTRRPMPSCTLRGVSLAFARVTPRGVGWR | 40 |
| 717 | MPAAPRLGLLVSLHQAPSRTSN | 22 |
| 718 | MKALTPAG | 8 |
| 719 | MPTEAASTNAPTAGTTLQDLVALCPQRACVARYIASLPAPWWWERPTGRARLPTAGVQMIRMSSSLTTPGHRWAIGSVVPG | 81 |
| 720 | MQHPWPGRTVLCPSSCSSALRGI | 23 |
| 721 | MPSSYSCV | 8 |
| 722 | MCITISPLFETGRTTACEIWPLWNQSSSPEWRPSSSRGGQIPPRAVTSSTACPSLPVGARRYCLGQPTEWSPRGGGCWRPSRRTPSREAS | 91 |
| 723 | MGYAGLSTTGPERGPSHHPRVLSSRCIPMWTKTLWAGPLLKVPAH | 45 |
| 724 | MSFPCAGEVIAGVACFRPGPFPT | 23 |
| 725 | MLPPAAVRAPRSRLRTQPRATRCWCSTPLLLQRWALVLTCPRPMGLILISGPG | 53 |

TABLE 2m-continued

(Seq. ID Nos. 713-752)

HCV H77 ncOrf's 1-3
Genbank Accession No.: AF011751

| SEQ ID No. | Sequence | AA |
|---|---|---|
| 726 | MPHPSWASALSLTKQRLRGRDWLCSPLLPLRAPSLCPILTSRRLLCPPPERSPFTARLSPSR | 62 |
| 727 | MPWPTTAVLTCLSSRPAAMLSSCRPMLS | 28 |
| 728 | MLSPGLNAGAGLAGGSQASIDLWHRGSAPPACSTRPSSVSAMTRAVLGMSSRPPRLQLGYERT | 63 |
| 729 | MPTFYPRQSRVGRTFLTW | 18 |
| 730 | MGQHPCYTDWALFRMKSP | 18 |
| 731 | MRWKSALSTYRTSSKG | 16 |
| 732 | MQRLSPLLSRPTGRNSRSFGRSTCGISSVGYNTWRACQRCLVTPPLLH | 48 |
| 733 | MARAWRELL | 9 |
| 734 | MFPPRTTCRRAMQPPASLPYSAASL | 25 |
| 735 | MTPLTPSS | 8 |
| 736 | MSGRSPYLQKECGSLGDSPGPCPSGRGRTTTPR | 33 |
| 737 | MAARYHLHGPLLCLRLGKSVRWSSPNQPYLLPWPSLPPKVLAAPQLPALRATIRQHPLSPPLLAAPPTPTLSPTLPCPPWRGSLGIRISATGHGRRSVVGPTRKMSCAAQCLIPGQAHSSPRALRKNKNCPSTH | 134 |
| 738 | MGQKTSVAMPERP | 13 |
| 739 | MIPAVLTPQSLRATSVRRRQFTNVVTWTPKPAWPSSPSLRGEMLGALLPIQGGKTAATAGAARAAY | 66 |
| 740 | MASAHFHSTVTLQVKSIGWPHASENLGSRPCELGDTGPGASALGFCPEEAGLPYVASTSSTGQ | 63 |
| 741 | MPGPAGSGFAYSCSLQG | 17 |
| 742 | MNHSPVRNYCLHAESV | 16 |
| 743 | MPGDLGVPPQDC | 12 |
| 744 | MAPVSPWLSA | 10 |
| 745 | MGYDDELVPYGSVGGSSAAPDPTSHHGHDRWCSLGSPGGHSVFLHGGELGEGPGSAAAICRRRRGNPRHRGKCRPHHGWACWSPYTRRQAEHPTDQHQRQLAHQ | 104 |
| 746 | MLDCLPRGRNEDHRITQGSCHPDVYQCGPRPCGLARSSRFPLIDTLYLRLLGPLPGHEARRCHSRAPAR | 69 |
| 747 | MHVGRPGGRHEHLGARWRRPGCSGRVLPVNRLRGHSGQDRLVREAGNYT | 49 |
| 748 | MDEPANSLRLPGEPCFPHALRAGERCSRPRHCHTQQPHCNPAPEATASVDKLGVYHSMLRFLAKGHLGLDMRGAERL | 77 |
| 749 | MPVPDPIARIFHRIGRGAPTQVCAPLQALAAGGGIIQSRTPRVPGGVAITLRARTGRSRVDVHAH | 65 |
| 750 | MLLQRVSRPRRRWKEGLLPYP | 21 |
| 751 | MPQKTWGPALASLETPGPERPR | 22 |
| 752 | MWQVPLQLGSKNKAQTHSNSGRWPAGLVRLVHGWLQRGRHLSQRVSCPAPLVLVLPTPARCRGRHLPPPQPMKVGVNTPAS | 81 |

TABLE 2n
(Seq. ID Nos. 753-822)

HCV H77 ncOrf's 4-6

| SEQ ID No. | Sequence | AA |
|---|---|---|
| 753 | MICREASISTLCSHAAHGPFTASRD | 25 |
| 754 | MIPPPAARACKGAQTCVGAPRPIL | 24 |
| 755 | MEWYTPSLSTDAVASGAGLQ | 20 |
| 756 | MLQELPPRPRHTLQECPRGPSPVQRCWRRQLGQHPQRQ | 39 |
| 757 | MKQWRGYQAALTGPPSIVSH | 20 |
| 758 | MRPASRRARRTSSLSGRR | 18 |
| 759 | MWHPWSGTRHKLLCHKHLLSTRRRQGTCRRWST | 33 |
| 760 | MSGNLEERASPQGLGPHWYTSG | 22 |
| 761 | MRWSSFRPRGRQSSIPH | 17 |
| 762 | MATESAPLTRQEQRRTTRPPPCPVRMPAEATPAGAGGEATSRRGRRPLRAPTYPSDTTQSRRTRGRTQDRASRPGMLH | 79 |
| 763 | MWLPDVCGSNQWGRARCCCPPLR | 23 |
| 764 | MPCDDPLYGRDR | 12 |
| 765 | MALPGGGVLEAARHSY | 16 |
| 766 | MPTPAASRSRQNQNQRGRA | 19 |
| 767 | MAALPPLDRSLARTLRARCLQARKGGTPSFLRHAATLLISPGE | 43 |
| 768 | MIGGRSSGSME | 11 |
| 769 | MRTLKKWVISIILAHSVGANMIMLPSQELTGVCLAVSHAALA R GVVGSRVR | 52 |
| 770 | MVQSWSPAARQAARALM | 17 |
| 771 | MATRAWGSRSQHW | 13 |
| 772 | MSLSVTVESKQRVSYENPIGVFLDFHACTRNSTRCPGEYWNP | 42 |
| 773 | MRRAGLRPPFSC3 | 12 |
| 774 | MMVVSIGVTLSSRRSFHTELMWATAFLAWQRTSFAP | 36 |
| 775 | MGSFCSSAAHGVTSAPVQE | 19 |
| 776 | MPEVEELPKLLVASSAKAVDRVDSVRTTVRFFRGGGTGGDRGGGSGQPWTTGGS | 54 |
| 777 | MLPPISCLHRRLASMSSASGESWLAVQVALRDGADSWLAEELAIEGGDPLANLLPAASAVIWEGSVSMDVNTATSGSGSQGNCDPTGYSWSPTLNDTSSRSKGLQGGANLCRRTPSNSVKNSGDGIWHGHLRLSVVIPDT | 140 |
| 778 | MGNVPLHMFLQVLGPTILIVPFLTCPVISAPQWQRVCIMPSPRQTPLYPRWQDTKGIPGSCGMSLAFSQVLKSLSTSHIQSQMSLSQEPEHGVVHSELIH | 100 |
| 779 | MAVTRAAASLSGT | 13 |
| 780 | MAGSRLTRSSVEGTSPLMILNATRAPATPAPYPARMSTRTFPSPTLPMAAPARPAPTKAVAAPGAASWAATHPPNMLKRRVWPVVSGLVTAAVKAINEAMAGLPGSVDRPAKYCIPLMKFHMCFAQKTSSFCQLVWTAGVITSAWRDAVCRRPRAFCLNCSASIIPCSMYGKC | 173 |
| 781 | MTTQPVDRQYAARAARTPPTSTQVLVTTSRSADMHVMMYLVIGCVRVTSF | 50 |
| 782 | MYARSLTVVSAGVSSYQAQPAS | 22 |
| 783 | MPEGRSPGATNL | 12 |
| 784 | MPGFPLPVLPRR | 12 |
| 785 | MVKVGSRLKSTV | 12 |
| 786 | MRASVDTTTTSPLVGMTDTSRPR | 23 |
| 787 | MPNATSFAASSSHFTFEWQKMRCLPPLITSRGIALP | 36 |
| 788 | MLGWDTVTEPGGVAVASTTSLAPAVSAWSRTVPMPKMDVASVEWHSSQTIMS | 52 |
| 789 | MGLPVVIVLTPVLILGSTPWALDM | 24 |
| 790 | MVVPRFSTGIKSTALATPRVHTAALNRPTACPAGHNSGPPEEPFK | 45 |
| 791 | MGRGESRLPLLSPRRRTGMTSACLVTR | 27 |
| 792 | MTGPLGDAMVLVPAPW | 16 |
| 793 | MHVARKVWVAVDTTWTSPSTWFLSRPVRLVIIHPRRPLVCWAYAVMGASNLHPLETIPSAGPSSISWPLRAETGKPLMMSPHAAVSAPHVMSLVSIREKTTGSTATARSRRPLCAQSRRGVRWLYT | 126 |
| 794 | MARSSLVMSNTRVGCTTHMSKMTASRPPRTLRGGTHTCSCASTLVRKY | 48 |
| 795 | MSNIIHKQEQTRASASRRNRRTTYSHLMAQDAMLDPTPYKYCTSTMFWWRWMRPVDKAGRVVKEHGRTCHCVVDSSNGLSSDLSLSSRSQRSPRVQLQAASSLCSTPPTYILTLNMV | 117 |
| 796 | MHLGVIQGPEPHREYVASGCLRKQSVGQSKVLLPTPPMTQGGAPHTLVNPVEFIQVQPNQLPSGGLVLLRTKTSVSFAPQL | 81 |
| 797 | MCQLPLVLISWMFCLAPGVRRPTSPAVVRPAFPPVTWVSASTPANSSSTTRTFAQFPTMEKYAMPARTPQ | 70 |
| 798 | MSMMACGIRSS | 11 |
| 799 | MASAASYTILELGQSLVTW | 19 |
| 800 | MYPMRSAKPHVRVSMTLPKLRDLRRGSVGPQLGREPRGDRSHPAHPQPSLP | 51 |
| 801 | MVHGLRDLPGHSQAPYQAVPQGLSRPNTTRLAVLRGHAQISRH | 43 |
| 802 | MRLTDLSQLAVTRAKMEPPLKKGKRKEKKKERKEKKKEKKKKKKKKNRKWLKRPECLPQPSSVGEEVDAYPCSEQE | 76 |
| 803 | MRHAVINVSPAVASREPTGQVQPASGRYWSEFELCSYCPVEEVLATYGSPASSGQKPSADAPGPVSPSSQGRDPKFSEACGHPTDFTWRVTVE | 93 |
| 804 | MESLNDWR | 8 |
| 805 | MGHQYHPRPQCGGKHDYVA | 19 |
| 806 | MATDVFCPIAKLGFG | 15 |
| 807 | MWGRQAASFLYG | 12 |
| 808 | MAVQNLQSVKCDFLLPLASTA | 21 |
| 809 | MDHRWFVVRLFPRLY | 15 |
| 810 | MVGGASCLERWSGQLASRGAGHRRG | 25 |
| 811 | MGGISEHGRQHGYVRFGLAR | 20 |

TABLE 2n-continued (Seq. ID Nos. 753-822)

HCV H77 ncOrf's 4-6

| SEQ ID No. | Sequence | AA |
|---|---|---|
| 812 | MSSDLSSTVAASVHNAVSSPDPPIPALAGHKGNPRQLWHELGFQPGLKVAQHLAYPVPDVP | 61 |
| 813 | MQSPQELGYSEAAEYGSDAGGCIALRHVVRGGNMVPPGGEGY | 42 |
| 814 | MAGRGLQEAEGLLLELLSEHHPLLDVR | 27 |
| 815 | MEGGFKADQTLPHLVPRWGRGLSPSAHGGLVRYQVRKVLPTLLCLG | 46 |
| 816 | MSEARKDALPKFKMVLAHGKPRGVHVRS | 28 |
| 817 | MSSPLDHLEGDSLAVKGDLSGGGQSNLLDVRMGHSDGARRGSSGEHNQSRPRSLCLVKDSADAQDGCGIRGVALVTNYYVISTS | 84 |
| 818 | MGLGHVSTKAQRCSNRGVEHQHLVALGCVRSRDLGALTAAGGSMQVGHLEALGHCWWRGVVREHRGSHGCP | 71 |
| 819 | MVIHIGASKRP | 11 |
| 820 | MTSGYLPR | 8 |
| 821 | MFAEAISGAEQGVVAHPSDDTRGRSAHFGESS | 32 |
| 822 | MTRYMAGIDRTIAVLRRPVAPGREGKQLTNKKDRPAQVPHVEGRAEGGAPDKQIDMTSKLRCGEFAVPGGHRGGHRHPTPRGVTLANARDTPRSVQDGIGRLVHNTRVRAIIGDMVKPRGIAHLVG | 126 |

Using Web-based computer software for the prediction of possible CTL epitopes for different HLA-alleles, every single ORF was analyzed for the existence of (possibly) encoded epitopes resulting in a (relative) cut-off value of 10 or more (according to Parker et al, mentioned above).

TABLE 3

| Strain | Frames | Number of epitopes No. of epitopes** | Epitope sequence listed in table 4 |
|---|---|---|---|
| 1a | 1-3 | 232 | Table 4a |
|  | 4-6 | 511 | Table 4b |
| 1b | 1-3 | 238 | Table 4c |
|  | 4-6 | 512 | Table 4d |
| 2a | 1-3 | 238 | Table 4e |
|  | 4-6 | 626 | Table 4f |
| 2b | 1-3 | 268 | Table 4g |
|  | 4-6 | 561 | Table 4h |
| 3a | 1-3 | 219 | Table 4i |
|  | 4-6 | 528 | Table 4j |
| 3b | 1-3 | 231 | Table 4k |
|  | 4-6 | 507 | Table 4l |
| H77 | 1-3 | 293 | Table 4m |
|  | 4-6 | 711 | Table 4n |

(**for eight different HLA-alleles)

In the following table 4, the exact (minimum) sequence of the eptiopes found with respect to the HLA alleles tested are given together with a (relative) score identifying the ability of the given epitope to be efficient in binding the given HLA type.

TABLE 4a 1a (1-3)

| No. | Strain | ORF | Start | AA | HLA | Peptide sequence | Seq ID NO. | Score |
|---|---|---|---|---|---|---|---|---|
| 1 | HCV-1a | 1 | 14 | 10 | B8 | ELLSSRRKRL | 2922 | 16.000 |
| 2 | HCV-1a | 1 | 17 | 9 | B8 | SSRRKRLAM | 2923 | 20.000 |
| 3 | HCV-1a | 1 | 16 | 10 | B3501 | LSSRRKRLAM | 2924 | 10.000 |
| 4 | HCV-1a | 1 | 17 | 9 | B3501 | SSRRKRLAM | 2925 | 30.000 |
| 5 | HCV-1a | 1 | 17 | 9 | B7 | SSRRKRLAM | 2926 | 15.000 |
| 6 | HCV-1a | 1 | 2 | 9 | B7 | GATLHHESL | 2927 | 12.000 |
| 7 | HCV-1a | 1 | 15 | 9 | A0201 | LLSSRRKRL | 2928 | 36.316 |
| 8 | HCV-1a | 2 | 43 | 10 | B4403 | AASPTSWGTY | 2929 | 12.000 |
| 9 | HCV-1a | 2 | 53 | 10 | B3501 | RSSAPLLEAL | 2930 | 10.000 |
| 10 | HCV-1a | 2 | 64 | 10 | B3501 | GPWRMASGFW | 2931 | 10.000 |
| 11 | HCV-1a | 2 | 64 | 9 | B3501 | GPWRMASGF | 2932 | 20.000 |
| 12 | HCV-1a | 2 | 44 | 9 | B3501 | ASPTSWGTY | 2933 | 10.000 |
| 13 | HCV-1a | 2 | 26 | 9 | B3501 | TPGVGRAIW | 2934 | 10.000 |
| 14 | HCV-1a | 2 | 5 | 10 | B7 | AAGGRDGSCL | 2935 | 36.000 |
| 15 | HCV-1a | 2 | 32 | 10 | B7 | AIWVRSSIPL | 2936 | 12.000 |
| 16 | HCV-1a | 2 | 6 | 9 | B7 | AGGRDGSCL | 2937 | 12.000 |
| 17 | HCV-1a | 2 | 51 | 9 | A24 | TYRSSAPLL | 2938 | 200.000 |
| 18 | HCV-1a | 2 | 12 | 9 | A24 | SCLPVALGL | 2939 | 10.080 |
| 19 | HCV-1a | 2 | 32 | 10 | A0201 | AIWVRSSIPL | 2940 | 24.380 |
| 20 | HCV-1a | 2 | 67 | 10 | A0201 | RMASGFWKTA | 2941 | 23.178 |
| 21 | HCV-1a | 2 | 67 | 9 | A0201 | RMASGFWKT | 2942 | 76.694 |
| 22 | HCV-1a | 2 | 58 | 10 | A1 | LLEALPGPWR | 2943 | 18.000 |
| 23 | HCV-1a | 3 | 9 | 10 | A0201 | ALSLSSFWPC | 2944 | 70.794 |
| 24 | HCV-1a | 3 | 1 | 10 | A0201 | MQQGTFLVAL | 2945 | 32.181 |
| 25 | HCV-1a | 3 | 11 | 10 | A0201 | SLSSFWPCSL | 2946 | 21.362 |
| 26 | HCV-1a | 3 | 2 | 9 | A0201 | QQGTFLVAL | 2947 | 18.930 |
| 27 | HCV-1a | 4 | 16 | 9 | B8 | SCTLRGASL | 2948 | 16.000 |
| 28 | HCV-1a | 5 | 7 | 10 | B3501 | RSFDVTSICL | 2949 | 20.000 |
| 29 | HCV-1a | 5 | 19 | 10 | B3501 | APPSVRFSTW | 2950 | 10.000 |
| 30 | HCV-1a | 5 | 49 | 10 | B7 | TGRRKVAIAL | 2951 | 40.000 |
| 31 | HCV-1a | 5 | 4 | 9 | B7 | SPRRSFDVT | 2952 | 20.000 |
| 32 | HCV-1a | 5 | 8 | 9 | A24 | SFDVTSICL | 2953 | 20.000 |
| 33 | HCV-1a | 5 | 36 | 10 | A0201 | FLSANCLPSL | 2954 | 226.014 |
| 34 | HCV-1a | 5 | 33 | 10 | A0201 | GLSFLSANCL | 2955 | 21.362 |

TABLE 4a-continued 1a (1-3)

| No. | Strain | ORF | Start | AA | HLA | Peptide sequence | Seq ID NO. | Score |
|---|---|---|---|---|---|---|---|---|
| 35 | HCV-1a | 5 | 15 | 9 | A0201 | CLSGAPPSV | 2956 | 69.552 |
| 36 | HCV-1a | 6 | 11 | 10 | A24 | GFSITTSSTL | 2957 | 20.000 |
| 37 | HCV-1a | 7 | 24 | 10 | B3501 | CPRRVCVVRY | 2958 | 120.000 |
| 38 | HCV-1a | 7 | 51 | 10 | B3501 | RPPTAGVKMI | 2959 | 16.000 |
| 39 | HCV-1a | 7 | 51 | 9 | B3501 | RPPTAGVKM | 2960 | 80.000 |
| 40 | HCV-1a | 7 | 29 | 9 | B7 | CVVRYIASL | 2961 | 20.000 |
| 41 | HCV-1a | 7 | 51 | 9 | B7 | RPPTAGVKM | 2962 | 20.000 |
| 42 | HCV-1a | 7 | 12 | 9 | B7 | TAGTTPQNL | 2963 | 12.000 |
| 43 | HCV-1a | 7 | 36 | 10 | A3 | SLPAPWWWER | 2964 | 36.000 |
| 44 | HCV-1a | 7 | 32 | 10 | A24 | RYIASLPAPW | 2965 | 18.000 |
| 45 | HCV-1a | 7 | 58 | 9 | A24 | KMIRTSSSL | 2966 | 12.000 |
| 46 | HCV-1a | 7 | 22 | 10 | A0201 | VLCPRRVCVV | 2967 | 111.499 |
| 47 | HCV-1a | 7 | 21 | 10 | A0201 | AVCLPRRVCV | 2968 | 22.517 |
| 48 | HCV-1a | 7 | 58 | 10 | A0201 | KMIRTSSSLT | 2969 | 18.837 |
| 49 | HCV-1a | 7 | 19 | 10 | A0201 | NLAVLCPRRV | 2970 | 13.910 |
| 50 | HCV-1a | 7 | 22 | 9 | A0201 | VLCPRRVCV | 2971 | 118.238 |
| 51 | HCV-1a | 7 | 58 | 9 | A0201 | KMIRTSSSL | 2972 | 53.999 |
| 52 | HCV-1a | 7 | 67 | 9 | A0201 | TIPGHRWAI | 2973 | 10.759 |
| 53 | HCV-1a | 8 | 10 | 10 | A0201 | VLPSSCSSA | 2974 | 27.026 |
| 54 | HCV-1a | 8 | 11 | 10 | A24 | LYPSSCSSAL | 2975 | 300.000 |
| 55 | HCV-1a | 8 | 3 | 9 | B7 | HPWPGRTVL | 2976 | 120.000 |
| 56 | HCV-1a | 8 | 12 | 9 | B7 | YPSSCSSAL | 2977 | 80.000 |
| 57 | HCV-1a | 9 | 15 | 9 | B7 | TACEIWPWL | 2978 | 12.000 |
| 58 | HCV-1a | 9 | 1 | 9 | A24 | MFITISLLF | 2979 | 21.000 |
| 59 | HCV-1a | 9 | 15 | 9 | A0201 | TACEIWPWL | 2980 | 11.374 |
| 60 | HCV-1a | 9 | 2 | 10 | A0201 | FITISLLFGT | 2981 | 62.877 |
| 61 | HCV-1a | 9 | 7 | 10 | A0201 | LLFGTGRTTA | 2982 | 31.249 |
| 62 | HCV-1a | 10 | 1 | 10 | B4403 | MEWSPRVGGC | 2983 | 12.000 |
| 63 | HCV-1a | 11 | 13 | 10 | A24 | RGPSRHPRVL | 2984 | 27.000 |
| 64 | HCV-1a | 11 | 5 | 9 | A3 | GLSTTGPER | 2985 | 12.000 |
| 65 | HCV-1a | 11 | 14 | 9 | B7 | GPSRHPRVL | 2986 | 80.000 |
| 66 | HCV-1a | 11 | 18 | 9 | B7 | HPRVLSSCR | 2987 | 20.000 |
| 67 | HCV-1a | 11 | 18 | 10 | B7 | HPRVLSSCRI | 2988 | 80.000 |
| 68 | HCV-1a | 11 | 14 | 9 | B3501 | GPSRHPRVL | 2989 | 20.000 |
| 69 | HCV-1a | 11 | 18 | 10 | B3501 | HPRVLSSRCI | 2990 | 24.000 |
| 70 | HCV-1a | 13 | 9 | 10 | B3501 | APRSRLHMQL | 2991 | 60.000 |
| 71 | HCV-1a | 13 | 8 | 9 | B3501 | KAPRSRLHM | 2992 | 12.000 |
| 72 | HCV-1a | 13 | 9 | 10 | B8 | APRSRLHMQL | 2993 | 16.000 |
| 73 | HCV-1a | 13 | 6 | 9 | B8 | AAKAPRSRL | 2994 | 16.000 |
| 74 | HCV-1a | 13 | 9 | 10 | B7 | APRSRLHMQL | 2995 | 2.400.000 |
| 75 | HCV-1a | 13 | 5 | 10 | B7 | AAAKAPRSRL | 2996 | 81.000 |
| 76 | HCV-1a | 13 | 6 | 9 | B7 | AAKAPRSRL | 2997 | 81.000 |
| 77 | HCV-1a | 15 | 1 | 10 | B3501 | MPHPSWASAL | 2998 | 20.000 |
| 78 | HCV-1a | 15 | 36 | 10 | B3501 | CPIPTSRRLL | 2999 | 20.000 |
| 79 | HCV-1a | 15 | 3 | 10 | B3501 | HPSWASALSL | 3000 | 20.000 |
| 80 | HCV-1a | 15 | 46 | 9 | B3501 | CPPPERSLF | 3001 | 30.000 |
| 81 | HCV-1a | 15 | 36 | 9 | B3501 | CPIPTSRRL | 3002 | 20.000 |
| 82 | HCV-1a | 15 | 36 | 10 | B7 | CPIPTSRRLL | 3003 | 120.000 |
| 83 | HCV-1a | 15 | 1 | 10 | B7 | MPHPSWASAL | 3004 | 80.000 |
| 84 | HCV-1a | 15 | 3 | 10 | B7 | HPSWASALSL | 3005 | 80.000 |
| 85 | HCV-1a | 15 | 14 | 10 | B7 | KQRLRGRDWL | 3006 | 60.000 |
| 86 | HCV-1a | 15 | 8 | 10 | B7 | SALSLTKQRL | 3007 | 12.000 |
| 87 | HCV-1a | 15 | 36 | 9 | B7 | CPIPTSRRL | 3008 | 80.000 |
| 88 | HCV-1a | 15 | 9 | 9 | B7 | ALSLTKQRL | 3009 | 12.000 |
| 89 | HCV-1a | 15 | 22 | 9 | A0201 | WLCSPPPPL | 3010 | 98.267 |
| 90 | HCV-1a | 15 | 9 | 9 | A0201 | ALSLTKQRL | 3011 | 21.362 |
| 91 | HCV-1a | 16 | 11 | 10 | B3501 | CPSSRPAAML | 3012 | 20.000 |
| 92 | HCV-1a | 16 | 11 | 9 | B3501 | CPSSRPAAM | 3013 | 40.000 |
| 93 | HCV-1a | 16 | 11 | 9 | B3501 | MPWPTTAVL | 3014 | 20.000 |
| 94 | HCV-1a | 16 | 11 | 9 | B3501 | RPAAMLSSW | 3015 | 20.000 |
| 95 | HCV-1a | 16 | 11 | 10 | B7 | CPSSRPAAML | 3016 | 120.000 |
| 96 | HCV-1a | 16 | 17 | 10 | B7 | AAMLSSWQPM | 3017 | 27.000 |
| 97 | HCV-1a | 16 | 1 | 9 | B7 | MPWPTTAVL | 3018 | 80.000 |
| 98 | HCV-1a | 16 | 11 | 9 | B7 | CPSSRPAAM | 3019 | 20.000 |
| 99 | HCV-1a | 16 | 18 | 9 | A0201 | AMLSSWQPM | 3020 | 22.569 |
| 100 | HCV-1a | 17 | 52 | 9 | B3501 | RPPRLQLGY | 3021 | 80.000 |
| 101 | HCV-1a | 17 | 50 | 9 | B3501 | SSRPPRLQL | 3022 | 15.000 |
| 102 | HCV-1a | 17 | 3 | 10 | B7 | SPALNVGAGL | 3023 | 80.000 |
| 103 | HCV-1a | 17 | 38 | 10 | B7 | SVSAMTQAVL | 3024 | 20.000 |
| 104 | HCV-1a | 17 | 13 | 10 | B7 | AGGSQASTDL | 3025 | 12.000 |
| 105 | HCV-1a | 17 | 47 | 10 | B7 | LGMSSRPPRL | 3026 | 12.000 |
| 106 | HCV-1a | 17 | 33 | 10 | B7 | STRPSSVSAM | 3027 | 10.000 |
| 107 | HCV-1a | 17 | 50 | 9 | B7 | SSRPPRLQL | 3028 | 90.000 |
| 108 | HCV-1a | 17 | 48 | 9 | A0201 | GMSSRPPRL | 3029 | 15.428 |
| 109 | HCV-1a | 18 | 7 | 10 | A0201 | RQSRVGRTFL | 3030 | 11.913 |

TABLE 4a-continued 1a (1-3)

| No. Strain | ORF | Start | AA | HLA | Peptide sequence | Seq ID NO. | Score |
|---|---|---|---|---|---|---|---|
| 110 HCV-1a | 18 | 8 | 9 | A0201 | QSRVGRTFL | 3031 | 60.000 |
| 111 HCV-1a | 18 | 5 | 10 | B7 | YPRQSRVGRT | 3032 | 20.000 |
| 112 HCV-1a | 18 | 5 | 10 | B8 | YPRQSRVGRT | 3033 | 16.000 |
| 113 HCV-1a | 18 | 8 | 9 | B3501 | QSRVGRTFL | 3034 | 15.000 |
| 114 HCV-1a | 18 | 3 | 10 | B3501 | SPALNVGAGL | 3035 | 20.000 |
| 115 HCV-1a | 19 | 7 | 10 | A1 | YTDWALFRMK | 3036 | 25.000 |
| 116 HCV-1a | 19 | 6 | 10 | A24 | CYTDWALFRM | 3037 | 30.000 |
| 117 HCV-1a | 19 | 4 | 9 | B7 | HPCYTDWAL | 3038 | 80.000 |
| 118 HCV-1a | 19 | 4 | 9 | B3501 | HPCYTDWAL | 3039 | 20.000 |
| 119 HCV-1a | 19 | 4 | 10 | B3501 | HPCYTDWALF | 3040 | 30.000 |
| 120 HCV-1a | 20 | 6 | 10 | A3 | ALSTYRTSSK | 3041 | 20.000 |
| 121 HCV-1a | 21 | 1 | 9 | B7 | MARAWRELL | 3042 | 180.000 |
| 122 HCV-1a | 21 | 1 | 9 | B8 | MARAWRELL | 3043 | 16.000 |
| 123 HCV-1a | 22 | 3 | 10 | B3501 | PPRTTCRRAM | 3044 | 12.000 |
| 124 HCV-1a | 22 | 3 | 10 | B7 | PPRTTCRRAM | 3045 | 30.000 |
| 125 HCV-1a | 22 | 16 | 10 | B7 | ASLPYSAASL | 3046 | 12.000 |
| 126 HCV-1a | 22 | 10 | 9 | B7 | RAMQLPASL | 3047 | 36.000 |
| 127 HCV-1a | 22 | 10 | 9 | A24 | RAMQLPASL | 3048 | 14.400 |
| 128 HCV-1a | 22 | 17 | 9 | A0201 | SLPYSAASL | 3049 | 21.362 |
| 129 HCV-1a | 23 | 19 | 9 | A24 | RYGGCLQRN | 3050 | 12.000 |
| 130 HCV-1a | 23 | 19 | 10 | A24 | RYGGCLQRNT | 3051 | 12.000 |
| 131 HCV-1a | 23 | 3 | 10 | B8 | TPRAPVPPFL | 3052 | 16.000 |
| 132 HCV-1a | 23 | 3 | 9 | B8 | TPRAPVPPF | 3053 | 60.000 |
| 133 HCV-1a | 23 | 3 | 10 | B3501 | TPRAPVPPFL | 3054 | 60.000 |
| 134 HCV-1a | 23 | 15 | 10 | B7 | TTRSRYGGCL | 3055 | 40.000 |
| 135 HCV-1a | 23 | 3 | 10 | B7 | TPRAPVPPFL | 3056 | 800.000 |
| 136 HCV-1a | 25 | 33 | 9 | B3501 | WPSSPPEAL | 3057 | 20.000 |
| 137 HCV-1a | 25 | 72 | 9 | B3501 | SPIPPCPPW | 3058 | 10.000 |
| 138 HCV-1a | 25 | 96 | 10 | B3501 | RSVVRPTRRM | 3059 | 20.000 |
| 139 HCV-1a | 25 | 16 | 10 | B8 | LGRSGRWSSL | 3060 | 16.000 |
| 140 HCV-1a | 25 | 2 | 10 | B8 | AARFHLQSPL | 3061 | 16.000 |
| 141 HCV-1a | 25 | 2 | 10 | B7 | AARFHLQSPL | 3062 | 360.000 |
| 142 HCV-1a | 25 | 16 | 10 | B7 | LGRSGRWSSL | 3063 | 40.000 |
| 143 HCV-1a | 25 | 65 | 10 | B7 | APPTPTLSPI | 3064 | 24.000 |
| 144 HCV-1a | 25 | 123 | 10 | B7 | APRKNRNCPS | 3065 | 12.000 |
| 145 HCV-1a | 25 | 40 | 10 | B7 | ALAAPQLPAL | 3066 | 12.000 |
| 146 HCV-1a | 25 | 75 | 10 | B7 | PPCPPWRGSL | 3067 | 12.000 |
| 147 HCV-1a | 25 | 33 | 9 | B7 | WPSSPPEAL | 3068 | 120.000 |
| 148 HCV-1a | 25 | 63 | 9 | B7 | LAAPPTPTL | 3069 | 18.000 |
| 149 HCV-1a | 25 | 41 | 9 | B7 | LAAPQLPAL | 3070 | 12.000 |
| 150 HCV-1a | 25 | 50 | 9 | B7 | RATIRQHPL | 3071 | 12.000 |
| 151 HCV-1a | 25 | 4 | 9 | A24 | RFHLQSPLL | 3072 | 40.000 |
| 152 HCV-1a | 25 | 54 | 9 | A24 | RQHPLSPPL | 3073 | 11.520 |
| 153 HCV-1a | 25 | 83 | 9 | A24 | SLGIRILAT | 3074 | 17.140 |
| 154 HCV-1a | 25 | 104 | 9 | A24 | RMSCAAQCL | 3075 | 15.428 |
| 155 HCV-1a | 25 | 62 | 9 | A24 | LLAAPPTPT | 3076 | 12.668 |
| 156 HCV-1a | 25 | 45 | 9 | A24 | QLPALRATI | 3077 | 10.433 |
| 157 HCV-1a | 25 | 40 | 10 | A0201 | ALAAPQLPAL | 3078 | 49.134 |
| 158 HCV-1a | 25 | 62 | 10 | A0201 | LLAAPPTPTL | 3079 | 36.316 |
| 159 HCV-1a | 27 | 33 | 10 | B3501 | WPSSPSPRGF | 3080 | 20.000 |
| 160 HCV-1a | 27 | 2 | 10 | B3501 | IPAALTPQSL | 3081 | 20.000 |
| 161 HCV-1a | 27 | 38 | 10 | B3501 | SPRGFMLGAL | 3082 | 60.000 |
| 162 HCV-1a | 27 | 36 | 9 | B3501 | SPSPRGFML | 3083 | 20.000 |
| 163 HCV-1a | 27 | 35 | 9 | B3501 | SSPSPRGFM | 3084 | 10.000 |
| 164 HCV-1a | 27 | 38 | 10 | B8 | SPRGFMLGAL | 3085 | 16.000 |
| 165 HCV-1a | 27 | 36 | 10 | B8 | SPSPRGFML | 3086 | 16.000 |
| 166 HCV-1a | 27 | 38 | 10 | B7 | SPRGFMLGAL | 3087 | 800.000 |
| 167 HCV-1a | 27 | 2 | 10 | B7 | IPAALTPQSL | 3088 | 80.000 |
| 168 HCV-1a | 27 | 15 | 10 | B7 | SVRRQSTNV | 3089 | 10.000 |
| 169 HCV-1a | 27 | 36 | 9 | B7 | SPSPRGFML | 3090 | 80.000 |
| 170 HCV-1a | 27 | 38 | 9 | B7 | SPRGFMLGA | 3091 | 20.000 |
| 171 HCV-1a | 27 | 42 | 9 | A0201 | FMLGALLPI | 3092 | 294.957 |
| 172 HCV-1a | 28 | 48 | 9 | B4403 | EEAGLPYVA | 3093 | 12.000 |
| 173 HCV-1a | 28 | 48 | 10 | B4403 | EEAGLPYVAS | 3094 | 12.000 |
| 174 HCV-1a | 28 | 31 | 10 | B4403 | CELGDTGPGA | 3095 | 12.000 |
| 175 HCV-1a | 28 | 37 | 10 | B3501 | GPGASALGFW | 3096 | 10.000 |
| 176 HCV-1a | 28 | 19 | 10 | B3501 | WPHASENLGY | 3097 | 60.000 |
| 177 HCV-1a | 28 | 3 | 10 | B7 | SAHFHSTVTL | 3098 | 12.000 |
| 178 HCV-1a | 28 | 44 | 9 | A24 | GFWPEEAGL | 3099 | 24.000 |
| 179 HCV-1a | 28 | 25 | 9 | A0201 | NLGYRPCEL | 3100 | 21.362 |
| 180 HCV-1a | 28 | 46 | 9 | A1 | WPEEAGLPY | 3101 | 56.250 |
| 181 HCV-1a | 29 | 3 | 9 | B4403 | GPAGSGFAY | 3102 | 13.500 |
| 182 HCV-1a | 29 | 1 | 9 | B3501 | MPGPAGSGF | 3103 | 20.000 |
| 183 HCV-1a | 29 | 3 | 9 | B3501 | GPAGSGFAY | 3104 | 40.000 |
| 184 HCV-1a | 29 | 5 | 10 | B7 | AGSGFAYSCL | 3105 | 12.000 |

TABLE 4a-continued

1a (1-3)

| No. | Strain | ORF | Start | AA | HLA | Peptide sequence | Seq ID NO. | Score |
|---|---|---|---|---|---|---|---|---|
| 185 | HCV-1a | 33 | 50 | 10 | B4403 | GEGPGSAAAI | 3106 | 12.000 |
| 186 | HCV-1a | 33 | 47 | 10 | B4403 | GELGEGPGSA | 3107 | 12.000 |
| 187 | HCV-1a | 33 | 47 | 9 | B4403 | GELGEGPGS | 3108 | 12.000 |
| 188 | HCV-1a | 33 | 5 | 9 | B4403 | DELVPYDGV | 3109 | 24.000 |
| 189 | HCV-1a | 33 | 36 | 9 | B3501 | SPGGHSVFL | 3110 | 20.000 |
| 190 | HCV-1a | 33 | 17 | 10 | B7 | SAAPDPTSHL | 3111 | 18.000 |
| 191 | HCV-1a | 33 | 36 | 9 | B7 | SPGGHSVFL | 3112 | 80.000 |
| 192 | HCV-1a | 33 | 18 | 9 | B7 | AAPDPTSHL | 3113 | 54.000 |
| 193 | HCV-1a | 33 | 41 | 9 | B7 | SVFLHGGEL | 3114 | 20.000 |
| 194 | HCV-1a | 33 | 33 | 10 | A0201 | SLGSPGGHSV | 3115 | 69.552 |
| 195 | HCV-1a | 34 | 14 | 9 | B8 | GARWRRPGC | 3116 | 16.000 |
| 196 | HCV-1a | 34 | 23 | 10 | B7 | FGRVLPVNRL | 3117 | 60.000 |
| 197 | HCV-1a | 34 | 19 | 9 | B7 | PRGCFGRVL | 3118 | 80.000 |
| 198 | HCV-1a | 34 | 5 | 9 | B7 | RPGGRHEHL | 3119 | 80.000 |
| 199 | HCV-1a | 35 | 5 | 10 | B3501 | LAKGHLGLDM | 3120 | 18.000 |
| 200 | HCV-1a | 35 | 1 | 10 | B7 | MLRFLAKGHL | 3121 | 40.000 |
| 201 | HCV-1a | 35 | 11 | 9 | A3 | GLDMRGVER | 3122 | 12.000 |
| 202 | HCV-1a | 35 | 3 | 10 | A24 | RFLAKGHLGL | 3123 | 60.000 |
| 203 | HCV-1a | 35 | 4 | 9 | A0201 | FLAKGHLGL | 3124 | 98.000 |
| 204 | HCV-1a | 35 | 11 | 9 | A1 | GLDMRGVER | 3125 | 10.000 |
| 205 | HCV-1a | 35 | 19 | 9 | B3501 | RPGCFGRVL | 3126 | 40.000 |
| 206 | HCV-1a | 35 | 5 | 9 | B3501 | RPGGRHEHL | 3127 | 40.000 |
| 207 | HCV-1a | 36 | 15 | 9 | B4403 | GGLPLRDGY | 3128 | 12.000 |
| 208 | HCV-1a | 36 | 17 | 9 | B3501 | LPLRDGYDY | 3129 | 60.000 |
| 209 | HCV-1a | 36 | 4 | 10 | B8 | VCRGIRGDKA | 3130 | 16.000 |
| 210 | HCV-1a | 36 | 16 | 10 | A3 | GLPLRDGYDY | 3131 | 36.000 |
| 211 | HCV-1a | 37 | 3 | 9 | B3501 | VPGPIARIF | 3132 | 20.000 |
| 212 | HCV-1a | 37 | 1 | 10 | B7 | MPVPGPIARI | 3133 | 12.000 |
| 213 | HCV-1a | 39 | 8 | 10 | B3501 | RPRRRWKEGL | 3134 | 120.000 |
| 214 | HCV-1a | 39 | 8 | 10 | B7 | RPRRRWKEGL | 3135 | 800.000 |
| 215 | HCV-1a | 40 | 1 | 10 | B3501 | MPQKTWGTAL | 3136 | 20.000 |
| 216 | HCV-1a | 40 | 1 | 10 | B7 | MPQKTWGTAL | 3137 | 80.000 |
| 217 | HCV-1a | 40 | 4 | 10 | A0201 | KTWGTALASL | 3138 | 19.824 |
| 218 | HCV-1a | 40 | 12 | 9 | A1 | SLETPGPER | 3139 | 18.000 |
| 219 | HCV-1a | 41 | 26 | 10 | A0201 | GLVRLVHGWL | 3140 | 15.274 |
| 220 | HCV-1a | 41 | 22 | 9 | A24 | RWPAGLVRL | 3141 | 12.000 |
| 221 | HCV-1a | 41 | 65 | 9 | A3 | HLPPPQPVK | 3142 | 45.000 |
| 222 | HCV-1a | 41 | 29 | 9 | A3 | RLVHGWLQR | 3143 | 12.000 |
| 223 | HCV-1a | 41 | 27 | 9 | B7 | LVRLVHGWL | 3144 | 200.000 |
| 224 | HCV-1a | 41 | 47 | 9 | B7 | CPAPLDLVL | 3145 | 80.000 |
| 225 | HCV-1a | 41 | 57 | 10 | B7 | TPACCRGRHL | 3146 | 80.000 |
| 226 | HCV-1a | 41 | 42 | 10 | B7 | SQRVSCPAPL | 3147 | 40.000 |
| 227 | HCV-1a | 41 | 44 | 10 | B7 | RVSCPAPLDL | 3148 | 20.000 |
| 228 | HCV-1a | 41 | 57 | 10 | B8 | TPACCRGRHL | 3149 | 16.000 |
| 229 | HCV-1a | 41 | 47 | 9 | B3501 | CPAPLDLVL | 3150 | 20.000 |
| 230 | HCV-1a | 41 | 57 | 10 | B3501 | TPACCRGRHL | 3151 | 20.000 |
| 231 | HCV-1a | 42 | 3 | 9 | B7 | VVQQPPGPPL | 3152 | 30.000 |
| 232 | HCV-1a | 42 | 2 | 10 | B7 | SVVQPPGPPL | 3153 | 30.000 |

TABLE 4b

1a (4-6)

| No. | Strain | ORF | Start | AA | HLA | Peptide sequence | SEQ ID NO | Score |
|---|---|---|---|---|---|---|---|---|
| 1 | HCV-1a | 1 | 15 | 9 | A24 | TYVGAPRPI | 3154 | 75.000 |
| 2 | HCV-1a | 1 | 16 | 9 | B7 | YVGAPRPIL | 3155 | 45.000 |
| 3 | HCV-1a | 1 | 8 | 9 | B_3501 | RACRGAQTY | 3156 | 12.000 |
| 4 | HCV-1a | 1 | 15 | 10 | A24 | TYVGAPRPIL | 3157 | 300.000 |
| 5 | HCV-1a | 1 | 6 | 10 | B8 | AARACRGAQT | 3158 | 16.000 |
| 6 | HCV-1a | 2 | 11 | 9 | B7 | GAVASGAGL | 3159 | 12.000 |
| 7 | HCV-1a | 3 | 5 | 9 | B7 | LPPRPRHTL | 3160 | 180.000 |
| 8 | HCV-1a | 3 | 8 | 9 | B7 | RPRHTLQGC | 3161 | 20.000 |
| 9 | HCV-1a | 3 | 5 | 9 | B_3501 | LPPRPRHTL | 3162 | 20.000 |
| 10 | HCV-1a | 3 | 8 | 9 | B_3501 | RPRHTLQGC | 3163 | 12.000 |
| 11 | HCV-1a | 3 | 8 | 10 | B7 | RPRHTLQGCL | 3164 | 800.000 |
| 12 | HCV-1a | 3 | 8 | 10 | B_3501 | RPRHTLQGCL | 3164 | 120.000 |
| 13 | HCV-1a | 3 | 3 | 10 | B_4403 | QELPPRPRHT | 3165 | 16.000 |
| 14 | HCV-1a | 4 | 10 | 9 | A_0201 | ALTSPPSIV | 3166 | 28.516 |
| 15 | HCV-1a | 4 | 2 | 9 | A_0201 | KQWRGYQAA | 3167 | 21.949 |
| 16 | HCV-1a | 4 | 2 | 10 | A_0201 | KQWRGYQAAL | 3168 | 62.920 |
| 17 | HCV-1a | 5 |  |  |  | NO HITS |  |  |

TABLE 4b-continued 1a (4-6)

| No. | Strain | ORF | Start | AA | HLA | Peptide sequence | SEQ ID NO | Score |
|---|---|---|---|---|---|---|---|---|
| 18 | HCV-1a | 6 | 12 | 10 | A_0201 | LLCHKRPPST | 3170 | 12.668 |
| 19 | HCV-1a | 6 | 3 | 10 | B7 | HPWSGTRHKL | 3171 | 120.000 |
| 20 | HCV-1a | 6 | 3 | 10 | B_3501 | HPWSGTRHKL | 3172 | 20.000 |
| 21 | HCV-1a | 7 | 4 | 9 | B7 | GPWCFCRCL | 3173 | 80.000 |
| 22 | HCV-1a | 7 | 18 | 9 | B7 | EPPGSSGAL | 3174 | 80.000 |
| 23 | HCV-1a | 7 | 4 | 9 | B_3501 | GPWCFCRCL | 3175 | 20.000 |
| 24 | HCV-1a | 7 | 18 | 9 | B_3501 | EPPGSSGAL | 3176 | 20.000 |
| 25 | HCV-1a | 7 | 18 | 10 | B7 | EPPGSSGALL | 3177 | 80.000 |
| 26 | HCV-1a | 7 | 18 | 10 | B_3501 | EPPGSSGALL | 3178 | 20.000 |
| 27 | HCV-1a | 7 | 4 | 10 | B_3501 | GPWCFCRCLW | 3179 | 10.000 |
| 28 | HCV-1a | 7 | 23 | 10 | B_4403 | SGALLVERSY | 3180 | 18.000 |
| 29 | HCV-1a | 8 | 12 | 9 | A_0201 | QGLDLHWYT | 3181 | 30.440 |
| 30 | HCV-1a | 8 | 6 | 9 | B7 | AERASPQGL | 3182 | 12.000 |
| 31 | HCV-1a | 8 | 8 | 9 | B7 | RASPQGLDL | 3183 | 12.000 |
| 32 | HCV-1a | 8 | 10 | 9 | B_3501 | SPQGLDLHW | 3184 | 10.000 |
| 33 | HCV-1a | 8 | 10 | 10 | B_3501 | SPQGLDLHWY | 3185 | 60.000 |
| 34 | HCV-1a | 8 | 10 | 10 | B_4403 | SPQGLDLHWY | 3186 | 13.500 |
| 35 | HCV-1a | 9 | 2 | 9 | A1 | VTELAPSTR | 3187 | 22.500 |
| 36 | HCV-1a | 9 | 51 | 9 | B7 | APTYPSDTM | 3188 | 90.000 |
| 37 | HCV-1a | 9 | 41 | 9 | B7 | TSRRRCRPL | 3189 | 40.000 |
| 38 | HCV-1a | 9 | 41 | 9 | B8 | TSRRRCRPL | 3190 | 80.000 |
| 39 | HCV-1a | 9 | 51 | 9 | B_3501 | APTYPSDTM | 3191 | 40.000 |
| 40 | HCV-1a | 9 | 41 | 9 | B_3501 | TSRRRCRPL | 3192 | 15.000 |
| 41 | HCV-1a | 9 | 2 | 10 | A1 | VTELAPSTRR | 3193 | 22.500 |
| 42 | HCV-1a | 9 | 40 | 10 | B7 | ATSRRRCRPL | 3194 | 12.000 |
| 43 | HCV-1a | 9 | 45 | 10 | B_3501 | RCRPLRAPTY | 3195 | 12.000 |
| 44 | HCV-1a | 9 | 50 | 10 | B_3501 | RAPTYPSDTM | 3196 | 12.000 |
| 45 | HCV-1a | 10 | 14 | 9 | B7 | SAGCCCPPL | 3197 | 12.000 |
| 46 | HCV-1a | 11 | 3 | 10 | A1 | CGDPLYGRDR | 3198 | 12.500 |
| 47 | HCV-1a | 12 | 8 | 9 | A1 | VLEAARHSY | 3199 | 45.000 |
| 48 | HCV-1a | 12 | 1 | 9 | B7 | MALPGGGVL | 3200 | 12.000 |
| 49 | HCV-1a | 12 | 2 | 10 | A_0201 | ALPGGGVLEA | 3201 | 11.426 |
| 50 | HCV-1a | 13 | 2 | 9 | A_0201 | RLTDLSQLA | 3202 | 20.369 |
| 51 | HCV-1a | 13 | 71 | 9 | A_0201 | SVYPNLHRL | 3203 | 13.757 |
| 52 | HCV-1a | 13 | 68 | 9 | A24 | RGRSVYPNL | 3204 | 11.200 |
| 53 | HCV-1a | 13 | 68 | 9 | B7 | RGRSVYPNL | 3205 | 40.000 |
| 54 | HCV-1a | 13 | 71 | 9 | B7 | SVYPNLHRL | 3206 | 20.000 |
| 55 | HCV-1a | 13 | 2 | 10 | A_0201 | RLTDLSQLAV | 3207 | 285.163 |
| 56 | HCV-1a | 13 | 70 | 10 | A24 | RSVYPNLHRL | 3208 | 12.000 |
| 57 | HCV-1a | 13 | 11 | 10 | B7 | VTRAKMEPPL | 3209 | 40.000 |
| 58 | HCV-1a | 13 | 70 | 10 | B_3501 | RSVYPNLHRL | 3210 | 10.000 |
| 59 | HCV-1a | 14 | 6 | 9 | B7 | ASRSRQNQI | 3211 | 12.000 |
| 60 | HCV-1a | 14 | 6 | 9 | B8 | ASRSRQNQI | 3212 | 20.000 |
| 61 | HCV-1a | 15 | 29 | 9 | A24 | SFLRHAATL | 3213 | 30.000 |
| 62 | HCV-1a | 15 | 7 | 9 | B7 | FLRHAATLL | 3214 | 120.000 |
| 63 | HCV-1a | 15 | 30 | 9 | B7 | FLRHAATLL | 3215 | 40.000 |
| 64 | HCV-1a | 15 | 3 | 9 | B7 | ALPPLARSL | 3216 | 12.000 |
| 65 | HCV-1a | 15 | 7 | 9 | B8 | LARSLARTL | 3217 | 16.000 |
| 66 | HCV-1a | 15 | 29 | 10 | A24 | SFLRHAATLL | 3218 | 30.000 |
| 67 | HCV-1a | 15 | 11 | 10 | B7 | LARTLRARCL | 3219 | 120.000 |
| 68 | HCV-1a | 15 | 2 | 10 | B7 | AALPPLARSL | 3220 | 36.000 |
| 69 | HCV-1a | 15 | 11 | 10 | B8 | LARTLRARCL | 3221 | 320.000 |
| 70 | HCV-1a | 16 | | | | No hits | | |
| 71 | HCV-1a | 17 | 13 | 9 | A_0201 | CLAVSHAAL | 3222 | 21.362 |
| 72 | HCV-1a | 17 | 1 | 9 | A_0201 | MIMLPSQEL | 3223 | 18.476 |
| 73 | HCV-1a | 17 | 2 | 9 | A_0201 | IMLPSQELT | 3224 | 16.588 |
| 74 | HCV-1a | 17 | 1 | 9 | B7 | MIMLPSQEL | 3225 | 18.000 |
| 75 | HCV-1a | 17 | 7 | 9 | B_4403 | QELTGVCLA | 3226 | 24.000 |
| 76 | HCV-1a | 17 | 3 | 10 | A_0201 | MLPSQELTGV | 3227 | 271.948 |
| 77 | HCV-1a | 17 | 7 | 10 | B_4403 | QELTGVCLAV | 3228 | 12.000 |
| 78 | HCV-1a | 18 | 18 | 9 | A_0201 | YLVIASVKA | 3229 | 22.853 |
| 79 | HCV-1a | 18 | 58 | 9 | B7 | AARQAARAL | 3230 | 360.000 |
| 80 | HCV-1a | 18 | 30 | 9 | B7 | AASSWTPAL | 3231 | 36.000 |
| 81 | HCV-1a | 18 | 19 | 9 | B7 | LVIASVKAL | 3232 | 20.000 |
| 82 | HCV-1a | 18 | 21 | 9 | B7 | IASVKALRL | 3233 | 12.000 |
| 83 | HCV-1a | 18 | 58 | 9 | B8 | AARQAARAL | 3234 | 16.000 |
| 84 | HCV-1a | 18 | 21 | 9 | B8 | IASVKALRL | 3235 | 16.000 |
| 85 | HCV-1a | 18 | 16 | 9 | B_4403 | AEYLVIASV | 3236 | 12.000 |
| 86 | HCV-1a | 18 | 18 | 10 | A_0201 | YLVIASVKAL | 3237 | 226.014 |
| 87 | HCV-1a | 18 | 58 | 10 | B7 | AARQAARALM | 3238 | 135.000 |
| 88 | HCV-1a | 18 | 29 | 10 | B7 | LAASSWTPAL | 3239 | 12.000 |
| 89 | HCV-1a | 18 | 58 | 10 | B_3501 | AARQAARALM | 3240 | 18.000 |
| 90 | HCV-1a | 18 | 12 | 10 | B_3501 | SPGGAEYLVI | 3241 | 12.000 |
| 91 | HCV-1a | 18 | 46 | 10 | B_3501 | SPHTSMVQSW | 3242 | 10.000 |
| 92 | HCV-1a | 19 | | | | NO HITS | | |

TABLE 4b-continued 1a (4-6)

| No. | Strain | ORF | Start | AA | HLA | Peptide sequence | SEQ ID NO | Score |
|---|---|---|---|---|---|---|---|---|
| 93 | HCV-1a | 20 | 15 | 9 | A_0201 | YENPIGVFL | 3243 | 10.509 |
| 94 | HCV-1a | 20 | 13 | 9 | A_0201 | VSYENPIGV | 3244 | 10.126 |
| 95 | HCV-1a | 20 | 14 | 9 | A24 | SYENPIGVF | 3245 | 150.000 |
| 96 | HCV-1a | 20 | 2 | 9 | A3 | SLSVTVESK | 3246 | 60.000 |
| 97 | HCV-1a | 20 | 17 | 9 | B_3501 | NPIGVFLDF | 3247 | 20.000 |
| 98 | HCV-1a | 20 | 31 | 9 | B_3501 | NSTRCPGEY | 3248 | 10.000 |
| 99 | HCV-1a | 20 | 7 | 9 | B_4403 | VESKQRVSY | 3249 | 120.000 |
| 100 | HCV-1a | 20 | 17 | 9 | B_4403 | NPIGVFLDF | 3250 | 11.250 |
| 101 | HCV-1a | 20 | 6 | 10 | A1 | TVESKQRVSY | 3251 | 90.000 |
| 102 | HCV-1a | 20 | 14 | 10 | A24 | SYENPIGVFL | 3252 | 420.000 |
| 103 | HCV-1a | 20 | 13 | 10 | B_3501 | VSYENPIGVF | 3253 | 10.000 |
| 104 | HCV-1a | 21 | | | | NO HITS | | |
| 105 | HCV-1a | 22 | | | | NO HITS | | |
| 106 | HCV-1a | 23 | | | | NO HITS | | |
| 107 | HCV-1a | 24 | 1 | 9 | A1 | MPEVEELPK | 3254 | 22.500 |
| 108 | HCV-1a | 24 | 17 | 9 | A_0201 | KAVDRVDSV | 3255 | 15.623 |
| 109 | HCV-1a | 24 | 11 | 9 | A_0201 | LVASSAKAV | 3256 | 10.346 |
| 110 | HCV-1a | 24 | 9 | 9 | A3 | KLLVASSAK | 3257 | 90.000 |
| 111 | HCV-1a | 24 | 5 | 9 | B_4403 | EELPKLLVA | 3258 | 36.000 |
| 112 | HCV-1a | 24 | 10 | 10 | A_0201 | LLVASSAKAV | 3259 | 118.238 |
| 113 | HCV-1a | 24 | 9 | 10 | A_0201 | KLLVASSAKA | 3260 | 64.336 |
| 114 | HCV-1a | 24 | 1 | 10 | B7 | MPEVEELPKL | 3261 | 24.000 |
| 115 | HCV-1a | 24 | 5 | 10 | B_4403 | EELPKLLVAS | 3262 | 24.000 |
| 116 | HCV-1a | 24 | 23 | 10 | B_4403 | DSVRTTVRFF | 3263 | 18.000 |
| 117 | HCV-1a | 25 | 46 | 9 | A1 | GGDPLANLR | 3264 | 12.500 |
| 118 | HCV-1a | 25 | 82 | 9 | A1 | NCDPTGYSW | 3265 | 10.000 |
| 119 | HCV-1a | 25 | 60 | 9 | A_0201 | VIWEGSVSM | 3266 | 39.518 |
| 120 | HCV-1a | 25 | 7 | 9 | A_0201 | CLHRRLASM | 3267 | 11.426 |
| 121 | HCV-1a | 25 | 102 | 9 | A24 | KGLQGGANL | 3268 | 12.000 |
| 122 | HCV-1a | 25 | 23 | 9 | A3 | WLAVQVALR | 3269 | 12.000 |
| 123 | HCV-1a | 25 | 42 | 9 | B7 | LATEGGDPL | 3270 | 12.000 |
| 124 | HCV-1a | 25 | 54 | 9 | B_3501 | RPAASAVIW | 3271 | 20.000 |
| 125 | HCV-1a | 25 | 43 | 10 | A1 | ATEGGDPLAN | 3272 | 11.250 |
| 126 | HCV-1a | 25 | 29 | 10 | A_0201 | ALRDGADSWL | 3273 | 36.611 |
| 127 | HCV-1a | 25 | 103 | 10 | A3 | GLQGGANLCR | 3274 | 36.000 |
| 128 | HCV-1a | 25 | 1 | 10 | A3 | MLPPISCLHR | 3275 | 12.000 |
| 129 | HCV-1a | 25 | 29 | 10 | B7 | ALRDGADSWL | 3276 | 120.000 |
| 130 | HCV-1a | 25 | 59 | 10 | B7 | AVIWEGSVSM | 3277 | 15.000 |
| 131 | HCV-1a | 25 | 29 | 10 | B8 | ALRDGADSWL | 3278 | 12.000 |
| 132 | HCV-1a | 25 | 20 | 10 | B_4403 | GESWLAVQVA | 3279 | 18.000 |
| 133 | HCV-1a | 26 | 12 | 9 | A_0201 | VLGPTILIV | 3280 | 111.499 |
| 134 | HCV-1a | 26 | 62 | 9 | A_0201 | GMSLAFSQV | 3281 | 95.441 |
| 135 | HCV-1a | 26 | 22 | 9 | A_0201 | FLTCPVISA | 3282 | 52.561 |
| 136 | HCV-1a | 26 | 9 | 9 | A_0201 | FLQVLGPTI | 3283 | 47.991 |
| 137 | HCV-1a | 26 | 16 | 9 | A_0201 | TILIVPFLT | 3284 | 21.989 |
| 138 | HCV-1a | 26 | 113 | 9 | A_0201 | LLSMAVTRA | 3285 | 19.425 |
| 139 | HCV-1a | 26 | 17 | 9 | A_0201 | ILIVPFLTC | 3286 | 16.047 |
| 140 | HCV-1a | 26 | 101 | 9 | A_0201 | WCSRLRSWV | 3287 | 11.487 |
| 141 | HCV-1a | 26 | 19 | 9 | A_0201 | IVPFLTCPV | 3288 | 10.346 |
| 142 | HCV-1a | 26 | 66 | 9 | A24 | AFSQVLKSL | 3289 | 28.000 |
| 143 | HCV-1a | 26 | 104 | 9 | A3 | RLRSWVTVR | 3290 | 36.000 |
| 144 | HCV-1a | 26 | 64 | 9 | A3 | SLAFSQVLK | 3291 | 20.000 |
| 145 | HCV-1a | 26 | 30 | 9 | B7 | APQWQRVCM | 3292 | 90.000 |
| 146 | HCV-1a | 26 | 39 | 9 | B7 | MPSPRQTPL | 3293 | 80.000 |
| 147 | HCV-1a | 26 | 57 | 9 | B7 | IPGSCGMSL | 3294 | 80.000 |
| 148 | HCV-1a | 26 | 117 | 9 | B7 | AVTRAAASL | 3295 | 60.000 |
| 149 | HCV-1a | 26 | 110 | 9 | B7 | TVRLLSMAV | 3296 | 10.000 |
| 150 | HCV-1a | 26 | 39 | 9 | B8 | MPSPRQTPL | 3297 | 16.000 |
| 151 | HCV-1a | 26 | 30 | 9 | B_3501 | APQWQRVCM | 3298 | 40.000 |
| 152 | HCV-1a | 26 | 39 | 9 | B_3501 | MPSPRQTPL | 3299 | 20.000 |
| 153 | HCV-1a | 26 | 14 | 9 | B_3501 | GPTILIVPF | 3300 | 20.000 |
| 154 | HCV-1a | 26 | 57 | 9 | B_3501 | IPGSCGMSL | 3301 | 20.000 |
| 155 | HCV-1a | 26 | 25 | 9 | B_3501 | CPVISAPQW | 3302 | 10.000 |
| 156 | HCV-1a | 26 | 106 | 9 | B_3501 | RSWVTVRLL | 3303 | 10.000 |
| 157 | HCV-1a | 26 | 95 | 10 | A1 | HSELIHWCSR | 3304 | 13.500 |
| 158 | HCV-1a | 26 | 84 | 10 | A_0201 | SLSQEPEHGV | 3305 | 69.552 |
| 159 | HCV-1a | 26 | 112 | 10 | A_0201 | RLLSMAVTRA | 3306 | 42.278 |
| 160 | HCV-1a | 26 | 3 | 10 | A_0201 | KVPLHMFLQV | 3307 | 40.471 |
| 161 | HCV-1a | 26 | 9 | 10 | A_0201 | FLQVLGPTIL | 3308 | 40.289 |
| 162 | HCV-1a | 26 | 27 | 10 | A_0201 | VISAPQWRV | 3309 | 27.638 |
| 163 | HCV-1a | 26 | 38 | 10 | A_0201 | MMPSPRQTPL | 3310 | 26.228 |
| 164 | HCV-1a | 26 | 62 | 10 | A_0201 | GMSLAFSQVL | 3311 | 24.037 |
| 165 | HCV-1a | 26 | 11 | 10 | A_0201 | QVLGPTILIV | 3312 | 21.234 |
| 166 | HCV-1a | 26 | 104 | 10 | A24 | RLRSWVTVRL | 3313 | 11.200 |
| 167 | HCV-1a | 26 | 46 | 10 | A3 | PLYPRWQDTK | 3314 | 45.000 |

TABLE 4b-continued 1a (4-6)

| No. | Strain | ORF | Start | AA | HLA | Peptide sequence | SEQ ID NO | Score |
|---|---|---|---|---|---|---|---|---|
| 168 | HCV-1a | 26 | 14 | 10 | B7 | GPTILIVPFL | 3315 | 80.000 |
| 169 | HCV-1a | 26 | 4 | 10 | B7 | VPLHMFLQVL | 3316 | 80.000 |
| 170 | HCV-1a | 26 | 48 | 10 | B7 | YPRWQDTKGI | 3317 | 80.000 |
| 171 | HCV-1a | 26 | 30 | 10 | B7 | APQWQRVCMM | 3318 | 60.000 |
| 172 | HCV-1a | 26 | 104 | 10 | B7 | RLRSWVTVRL | 3319 | 40.000 |
| 173 | HCV-1a | 26 | 65 | 10 | B7 | LAFSQVLKSL | 3320 | 12.000 |
| 174 | HCV-1a | 26 | 116 | 10 | B7 | MAVTRAAASL | 3321 | 12.000 |
| 175 | HCV-1a | 26 | 30 | 10 | B_3501 | APQWQRVCMM | 3322 | 40.000 |
| 176 | HCV-1a | 26 | 39 | 10 | B_3501 | MPSPRQTPLY | 3323 | 40.000 |
| 177 | HCV-1a | 26 | 48 | 10 | B_3501 | YPRWQDTKGI | 3324 | 36.000 |
| 178 | HCV-1a | 26 | 4 | 10 | B_3501 | VPLHMFLQVL | 3325 | 20.000 |
| 179 | HCV-1a | 26 | 14 | 10 | B_3501 | GPTILIVPFL | 3326 | 20.000 |
| 180 | HCV-1a | 26 | 96 | 10 | B_4403 | SELIHWCSRL | 3327 | 24.000 |
| 181 | HCV-1a | 26 | 87 | 10 | B_4403 | QEPEHGVVHS | 3328 | 12.000 |
| 182 | HCV-1a | 27 | 70 | 9 | A1 | ATHPPNMLK | 3329 | 25.000 |
| 183 | HCV-1a | 27 | 75 | 9 | A_0201 | NMLKRRVWL | 3330 | 313.968 |
| 184 | HCV-1a | 27 | 127 | 9 | A_0201 | KVSSFCQLV | 3331 | 80.941 |
| 185 | HCV-1a | 27 | 76 | 9 | A_0201 | MLKRRVWLV | 3332 | 71.386 |
| 186 | HCV-1a | 27 | 80 | 9 | A_0201 | RVWLVVSGL | 3333 | 35.683 |
| 187 | HCV-1a | 27 | 95 | 9 | A_0201 | AINEAMAGL | 3334 | 27.699 |
| 188 | HCV-1a | 27 | 82 | 9 | A_0201 | WLVVSGLVT | 3335 | 14.054 |
| 189 | HCV-1a | 27 | 112 | 9 | A24 | KYCIPLMKF | 3336 | 220.000 |
| 190 | HCV-1a | 27 | 80 | 9 | A24 | RVWLVVSGL | 3337 | 11.200 |
| 191 | HCV-1a | 27 | 123 | 9 | A24 | CFAQKVSSF | 3338 | 10.000 |
| 192 | HCV-1a | 27 | 45 | 9 | A3 | TLPMAAPAK | 3339 | 20.000 |
| 193 | HCV-1a | 27 | 30 | 9 | B7 | APYPARMSM | 3340 | 90.000 |
| 194 | HCV-1a | 27 | 109 | 9 | B7 | KPAKYCIPL | 3341 | 80.000 |
| 195 | HCV-1a | 27 | 69 | 9 | B7 | AATHPPNML | 3342 | 54.000 |
| 196 | HCV-1a | 27 | 80 | 9 | B7 | RVWLVVSGL | 3343 | 20.000 |
| 197 | HCV-1a | 27 | 28 | 9 | B7 | TPAPYPARM | 3344 | 20.000 |
| 198 | HCV-1a | 27 | 92 | 9 | B7 | AVKAINEAM | 3345 | 15.000 |
| 199 | HCV-1a | 27 | 95 | 9 | B7 | AINEAMAGL | 3346 | 12.000 |
| 200 | HCV-1a | 27 | 76 | 9 | B8 | MLKRRVWLV | 3347 | 24.000 |
| 201 | HCV-1a | 27 | 30 | 9 | B_3501 | APYPARMSM | 3348 | 40.000 |
| 202 | HCV-1a | 27 | 28 | 9 | B_3501 | TPAPYPARM | 3349 | 40.000 |
| 203 | HCV-1a | 27 | 109 | 9 | B_3501 | KPAKYCIPL | 3350 | 40.000 |
| 204 | HCV-1a | 27 | 105 | 9 | B_3501 | GSVDKPAKY | 3351 | 20.000 |
| 205 | HCV-1a | 27 | 24 | 9 | B_3501 | RAPATPAPY | 3352 | 12.000 |
| 206 | HCV-1a | 27 | 9 | 9 | B_3501 | SSVEGTSPL | 3353 | 10.000 |
| 207 | HCV-1a | 27 | 105 | 9 | B_4403 | GSVDKPAKY | 3354 | 13.500 |
| 208 | HCV-1a | 27 | 70 | 10 | A1 | ATHPPNMLKR | 3355 | 12.500 |
| 209 | HCV-1a | 27 | 75 | 10 | A_0201 | NMLKRRVWLV | 3356 | 3.206.057 |
| 210 | HCV-1a | 27 | 82 | 10 | A_0201 | WLVVSGLVTA | 3357 | 52.561 |
| 211 | HCV-1a | 27 | 87 | 10 | A_0201 | GLVTAAVKAI | 3358 | 23.995 |
| 212 | HCV-1a | 27 | 19 | 10 | A_0201 | ILNATRAPAT | 3359 | 12.668 |
| 213 | HCV-1a | 27 | 84 | 10 | A_0201 | VVSGLVTAAV | 3360 | 10.346 |
| 214 | HCV-1a | 27 | 94 | 10 | A24 | KAINEAMAGL | 3361 | 12.000 |
| 215 | HCV-1a | 27 | 37 | 10 | B7 | SMRTFPSPTL | 3362 | 60.000 |
| 216 | HCV-1a | 27 | 109 | 10 | B7 | KPAKYCIPLM | 3363 | 20.000 |
| 217 | HCV-1a | 27 | 68 | 10 | B7 | WAATHPPNML | 3364 | 18.000 |
| 218 | HCV-1a | 27 | 94 | 10 | B7 | KAINEAMAGL | 3365 | 12.000 |
| 219 | HCV-1a | 27 | 125 | 10 | B7 | AQKVSSFCQL | 3366 | 12.000 |
| 220 | HCV-1a | 27 | 109 | 10 | B_3501 | KPAKYCIPLM | 3367 | 80.000 |
| 221 | HCV-1a | 27 | 115 | 10 | B_3501 | IPLMKFHICF | 3368 | 20.000 |
| 222 | HCV-1a | 27 | 32 | 10 | B_3501 | YPARMSMRTF | 3369 | 20.000 |
| 223 | HCV-1a | 27 | 9 | 10 | B_3501 | SSVEGTSPLM | 3370 | 20.000 |
| 224 | HCV-1a | 27 | 8 | 10 | B_3501 | RSSVEGTSPL | 3371 | 10.000 |
| 225 | HCV-1a | 27 | 97 | 10 | B_4403 | NEAMAGLPGS | 3372 | 12.000 |
| 226 | HCV-1a | 28 | 44 | 9 | A1 | SADMHVMMY | 3373 | 125.000 |
| 227 | HCV-1a | 28 | 15 | 9 | A1 | TTQPVDRQY | 3374 | 12.500 |
| 228 | HCV-1a | 28 | 52 | 9 | A_0201 | YLVTGCVRV | 3375 | 319.939 |
| 229 | HCV-1a | 28 | 49 | 9 | A_0201 | VMMYLVTGC | 3376 | 51.908 |
| 230 | HCV-1a | 28 | 50 | 9 | A_0201 | MMYLVTGCV | 3377 | 35.524 |
| 231 | HCV-1a | 28 | 30 | 9 | B7 | TPPTSTQVL | 3378 | 80.000 |
| 232 | HCV-1a | 28 | 27 | 9 | B7 | AARTPPTST | 3379 | 13.500 |
| 233 | HCV-1a | 28 | 3 | 9 | B7 | AGFPDKTTL | 3380 | 12.000 |
| 234 | HCV-1a | 28 | 43 | 9 | B_3501 | RSADMHVMM | 3381 | 40.000 |
| 235 | HCV-1a | 28 | 30 | 9 | B_3501 | TPPTSTQVL | 3382 | 20.000 |
| 236 | HCV-1a | 28 | 44 | 9 | B_4403 | SADMHVMMY | 3383 | 18.000 |
| 237 | HCV-1a | 28 | 10 | 10 | A_0201 | TLPTMTTQPV | 3384 | 69.552 |
| 238 | HCV-1a | 28 | 49 | 10 | A_0201 | VMMYLVTGCV | 3385 | 41.075 |
| 239 | HCV-1a | 28 | 29 | 10 | A24 | RTPPTSTQVL | 3386 | 17.280 |
| 240 | HCV-1a | 28 | 50 | 10 | A3 | MMYLVTGCVR | 3387 | 20.000 |
| 241 | HCV-1a | 28 | 2 | 10 | B7 | IAGFPDKTTL | 3388 | 12.000 |
| 242 | HCV-1a | 28 | 41 | 10 | B7 | TSRSADMHVM | 3389 | 10.000 |

TABLE 4b-continued 1a (4-6)

| No. | Strain | ORF | Start | AA | HLA | Peptide sequence | SEQ ID NO | Score |
|---|---|---|---|---|---|---|---|---|
| 243 | HCV-1a | 28 | 24 | 10 | B8 | AAKAARTPPT | 3390 | 16.000 |
| 244 | HCV-1a | 28 | 41 | 10 | B_3501 | TSRSADMHVM | 3391 | 45.000 |
| 245 | HCV-1a | 28 | 43 | 10 | B_3501 | RSADMHVMMY | 3392 | 40.000 |
| 246 | HCV-1a | 28 | 5 | 10 | B_3501 | FPDKTTLPTM | 3393 | 12.000 |
| 247 | HCV-1a | 28 | 43 | 10 | B_4403 | RSADMHVMMY | 3394 | 18.000 |
| 248 | HCV-1a | 29 | 5 | 9 | A_0201 | SLTVVSAGV | 3395 | 69.552 |
| 249 | HCV-1a | 30 | 3 | 10 | B7 | EGRSPGATNL | 3396 | 40.000 |
| 250 | HCV-1a | 31 | 1 | 9 | B7 | MPGFPLPVL | 3397 | 120.000 |
| 251 | HCV-1a | 31 | 1 | 9 | B_3501 | MPGFPLPVL | 3398 | 20.000 |
| 252 | HCV-1a | 32 | 20 | 9 | A_0201 | SITESKSPV | 3399 | 39.210 |
| 253 | HCV-1a | 32 | 17 | 9 | A3 | VLQSITESK | 3400 | 30.000 |
| 254 | HCV-1a | 32 | 3 | 10 | A_0201 | KVGSRLKSTV | 3401 | 21.300 |
| 255 | HCV-1a | 32 | 9 | 10 | A24 | KSTVWVTHVL | 3402 | 11.200 |
| 256 | HCV-1a | 32 | 9 | 10 | B_3501 | KSTVWVTHVL | 3403 | 10.000 |
| 257 | HCV-1a | 33 | 5 | 9 | B7 | VATTTTSPL | 3404 | 12.000 |
| 258 | HCV-1a | 33 | 4 | 10 | B7 | SVATTTTSPL | 3405 | 20.000 |
| 259 | HCV-1a | 34 | 6 | 9 | A24 | SFAASSSHF | 3406 | 10.000 |
| 260 | HCV-1a | 34 | 6 | 10 | A24 | SFAASSSHFF | 3407 | 10.000 |
| 261 | HCV-1a | 35 | | | | NO HITS | | |
| 262 | HCV-1a | 36 | 7 | 9 | A1 | VTEPGGVAV | 3408 | 45.000 |
| 263 | HCV-1a | 36 | 13 | 9 | B7 | VAVASTTSL | 3409 | 12.000 |
| 264 | HCV-1a | 36 | 34 | 9 | B_3501 | MPKMDVASV | 3410 | 18.000 |
| 265 | HCV-1a | 36 | 8 | 9 | B_4403 | TEPGGVAVA | 3411 | 18.000 |
| 266 | HCV-1a | 36 | 7 | 10 | A1 | VTEPGGVAVA | 3412 | 45.000 |
| 267 | HCV-1a | 36 | 6 | 10 | A_0201 | TVTEPGGVAV | 3413 | 24.952 |
| 268 | HCV-1a | 36 | 12 | 10 | B7 | GVAVASTTSL | 3414 | 20.000 |
| 269 | HCV-1a | 36 | 28 | 10 | B7 | WSRTVPMPKM | 3415 | 15.000 |
| 270 | HCV-1a | 36 | 28 | 10 | B_3501 | WSRTVPMPKM | 3416 | 30.000 |
| 271 | HCV-1a | 36 | 25 | 10 | B_3501 | VSAWSRTVPM | 3417 | 10.000 |
| 272 | HCV-1a | 36 | 8 | 10 | B_4403 | TEPGGVAVAS | 3418 | 13.500 |
| 273 | HCV-1a | 37 | 7 | 9 | A_0201 | IVLTPVLML | 3419 | 27.042 |
| 274 | HCV-1a | 37 | 2 | 9 | A_0201 | GLPVVIVLT | 3420 | 17.140 |
| 275 | HCV-1a | 37 | 1 | 9 | A24 | MGLPVVIVL | 3421 | 10.080 |
| 276 | HCV-1a | 37 | 7 | 9 | B7 | IVLTPVLML | 3422 | 30.000 |
| 277 | HCV-1a | 37 | 5 | 9 | B7 | VVIVLTPVL | 3423 | 20.000 |
| 278 | HCV-1a | 37 | 6 | 10 | A_0201 | VIVLTPVLML | 3424 | 11.485 |
| 279 | HCV-1a | 38 | 17 | 9 | B7 | TPRVHTAAL | 3425 | 800.000 |
| 280 | HCV-1a | 38 | 17 | 9 | B8 | TPRVHTAAL | 3426 | 16.000 |
| 281 | HCV-1a | 38 | 17 | 9 | B_3501 | TPRVHTAAL | 3427 | 60.000 |
| 282 | HCV-1a | 38 | 14 | 10 | A_0201 | ALATPRVHTA | 3428 | 11.426 |
| 283 | HCV-1a | 38 | 16 | 10 | B7 | ATPRVHTAAL | 3429 | 12.000 |
| 284 | HCV-1a | 39 | 12 | 9 | B7 | SPRRRTGMT | 3430 | 20.000 |
| 285 | HCV-1a | 39 | 12 | 9 | B8 | SPRRRTGMT | 3431 | 16.000 |
| 286 | HCV-1a | 39 | 11 | 9 | B_3501 | LSPRRRTGM | 3432 | 10.000 |
| 287 | HCV-1a | 39 | 18 | 10 | A3 | GMTSACLVTR | 3433 | 18.000 |
| 288 | HCV-1a | 39 | 1 | 10 | B7 | MGRGDSRLPL | 3434 | 60.000 |
| 289 | HCV-1a | 40 | 4 | 9 | A_0201 | PLGDAMVLV | 3435 | 14.429 |
| 290 | HCV-1a | 40 | 3 | 9 | B7 | GPLGDAMVL | 3436 | 80.000 |
| 291 | HCV-1a | 40 | 3 | 9 | B_3501 | GPLGDAMVL | 3437 | 30.000 |
| 292 | HCV-1a | 41 | 77 | 9 | A_0201 | LMMSPHAAV | 3438 | 315.959 |
| 293 | HCV-1a | 41 | 22 | 9 | A_0201 | FLSRPVRLV | 3439 | 147.172 |
| 294 | HCV-1a | 41 | 31 | 9 | A_0201 | IMHPRRPLV | 3440 | 85.394 |
| 295 | HCV-1a | 41 | 15 | 9 | A_0201 | WTSPSTWFL | 3441 | 56.299 |
| 296 | HCV-1a | 41 | 6 | 9 | A_0201 | KVWAAVDTI | 3442 | 29.887 |
| 297 | HCV-1a | 41 | 21 | 9 | A24 | WFLSRPVRL | 3443 | 30.000 |
| 298 | HCV-1a | 41 | 61 | 9 | B7 | GPSSISRPL | 3444 | 80.000 |
| 299 | HCV-1a | 41 | 116 | 9 | B7 | QSRRGVRWL | 3445 | 40.000 |
| 300 | HCV-1a | 41 | 30 | 9 | B7 | VIMHPRRPL | 3446 | 27.000 |
| 301 | HCV-1a | 41 | 105 | 9 | B7 | ATARSRKPL | 3447 | 18.000 |
| 302 | HCV-1a | 41 | 43 | 9 | B7 | YAVMGASNL | 3448 | 12.000 |
| 303 | HCV-1a | 41 | 106 | 9 | B8 | TARSRKPLC | 3449 | 16.000 |
| 304 | HCV-1a | 41 | 33 | 9 | B_3501 | HPRRPLVCW | 3450 | 30.000 |
| 305 | HCV-1a | 41 | 61 | 9 | B_3501 | GPSSISRPL | 3451 | 20.000 |
| 306 | HCV-1a | 41 | 116 | 9 | B_3501 | QSRRGVRWL | 3452 | 15.000 |
| 307 | HCV-1a | 41 | 71 | 9 | B_4403 | AETGKPLMM | 3453 | 18.000 |
| 308 | HCV-1a | 41 | 45 | 10 | A_0201 | VMGASNLQPL | 3454 | 60.325 |
| 309 | HCV-1a | 41 | 30 | 10 | A_0201 | VIMHPRRPLV | 3455 | 60.154 |
| 310 | HCV-1a | 41 | 22 | 10 | A_0201 | FLSRPVRLVI | 3456 | 19.676 |
| 311 | HCV-1a | 41 | 42 | 10 | A24 | AYAVMGASNL | 3457 | 200.000 |
| 312 | HCV-1a | 41 | 90 | 10 | A3 | VMSLVSIWEK | 3458 | 90.000 |
| 313 | HCV-1a | 41 | 84 | 10 | B7 | AVSAPHVMSL | 3459 | 60.000 |
| 314 | HCV-1a | 41 | 29 | 10 | B7 | LVIMHPRRPL | 3460 | 45.000 |
| 315 | HCV-1a | 41 | 87 | 10 | B7 | APHVMSLVSI | 3461 | 24.000 |
| 316 | HCV-1a | 41 | 33 | 10 | B7 | HPRRPLVCWA | 3462 | 20.000 |
| 317 | HCV-1a | 41 | 104 | 10 | B7 | TATARSRKPL | 3463 | 18.000 |

TABLE 4b-continued 1a (4-6)

| No. | Strain | ORF | Start | AA | HLA | Peptide sequence | SEQ ID NO | Score |
|---|---|---|---|---|---|---|---|---|
| 318 | HCV-1a | 41 | 115 | 10 | B7 | AQSRRGVRWL | 3464 | 12.000 |
| 319 | HCV-1a | 41 | 60 | 10 | B7 | AGPSSISRPL | 3465 | 12.000 |
| 320 | HCV-1a | 41 | 23 | 10 | B7 | LSRPVRLVIM | 3466 | 10.000 |
| 321 | HCV-1a | 41 | 23 | 10 | B8 | LSRPVRLVIM | 3467 | 20.000 |
| 322 | HCV-1a | 41 | 106 | 10 | B8 | TARSRKPLCA | 3468 | 16.000 |
| 323 | HCV-1a | 41 | 23 | 10 | B_3501 | LSRPVRLVIM | 3469 | 30.000 |
| 324 | HCV-1a | 41 | 71 | 10 | B_4403 | AETGKPLMMS | 3470 | 18.000 |
| 325 | HCV-1a | 42 | 14 | 9 | A3 | KMTASRPPR | 3471 | 12.000 |
| 326 | HCV-1a | 42 | 33 | 9 | B_4403 | CASTLVRKY | 3472 | 13.500 |
| 327 | HCV-1a | 42 | 14 | 10 | A_0201 | KMTASRPPRT | 3473 | 18.837 |
| 328 | HCV-1a | 42 | 19 | 10 | B7 | RPPRTLRGGI | 3474 | 12.000 |
| 329 | HCV-1a | 42 | 3 | 10 | B7 | NTRVGCTAHM | 3475 | 10.000 |
| 330 | HCV-1a | 42 | 19 | 10 | B_3501 | RPPRTLRGGI | 3476 | 16.000 |
| 331 | HCV-1a | 42 | 32 | 10 | B_4403 | SCASTLVRKY | 3477 | 54.000 |
| 332 | HCV-1a | 43 | 33 | 9 | A1 | MLDPTPYKY | 3478 | 500.000 |
| 333 | HCV-1a | 43 | 95 | 9 | A_0201 | VQLQAASSL | 3479 | 13.624 |
| 334 | HCV-1a | 43 | 109 | 9 | A24 | TYILILNIV | 3480 | 12.600 |
| 335 | HCV-1a | 43 | 40 | 9 | A24 | KYCTSTMFW | 3481 | 10.000 |
| 336 | HCV-1a | 43 | 45 | 9 | A3 | TMFWWRWMR | 3482 | 180.000 |
| 337 | HCV-1a | 43 | 32 | 9 | A3 | AMLDPTPYK | 3483 | 45.000 |
| 338 | HCV-1a | 43 | 33 | 9 | A3 | MLDPTPYKY | 3484 | 18.000 |
| 339 | HCV-1a | 43 | 89 | 9 | B7 | SQRSPRVQL | 3485 | 90.000 |
| 340 | HCV-1a | 43 | 106 | 9 | B7 | TPPTYILIL | 3486 | 80.000 |
| 341 | HCV-1a | 43 | 92 | 9 | B7 | SPRVQLQAA | 3487 | 20.000 |
| 342 | HCV-1a | 43 | 71 | 9 | B7 | CVVVSSNGL | 3488 | 20.000 |
| 343 | HCV-1a | 43 | 26 | 9 | B7 | HLMAQDAML | 3489 | 12.000 |
| 344 | HCV-1a | 43 | 106 | 9 | B_3501 | TPPTYILIL | 3490 | 20.000 |
| 345 | HCV-1a | 43 | 53 | 9 | B_3501 | RPVDKAGRV | 3491 | 16.000 |
| 346 | HCV-1a | 43 | 31 | 9 | B_4403 | DAMLDPTPY | 3492 | 27.000 |
| 347 | HCV-1a | 43 | 102 | 10 | A_0201 | SLCSTPPTYI | 3493 | 57.380 |
| 348 | HCV-1a | 43 | 33 | 10 | A_0201 | MLDPTPYKYC | 3494 | 27.870 |
| 349 | HCV-1a | 43 | 94 | 10 | A24 | RVQLQAASSL | 3495 | 12.000 |
| 350 | HCV-1a | 43 | 88 | 10 | A24 | RSQRSPRVQL | 3496 | 12.000 |
| 351 | HCV-1a | 43 | 40 | 10 | A24 | KYCTSTMFWW | 3497 | 10.000 |
| 352 | HCV-1a | 43 | 38 | 10 | A24 | PYKYCTSTMF | 3498 | 10.000 |
| 353 | HCV-1a | 43 | 32 | 10 | A3 | AMLDPTPYKY | 3499 | 18.000 |
| 354 | HCV-1a | 43 | 18 | 10 | B7 | RNRRTTYSHL | 3500 | 40.000 |
| 355 | HCV-1a | 43 | 94 | 10 | B7 | RVQLQAASSL | 3501 | 20.000 |
| 356 | HCV-1a | 43 | 37 | 10 | B7 | TPYKYCTSTM | 3502 | 20.000 |
| 357 | HCV-1a | 43 | 86 | 10 | B8 | SSRSQRSPRV | 3503 | 12.000 |
| 358 | HCV-1a | 43 | 37 | 10 | B_3501 | TPYKYCTSTM | 3504 | 40.000 |
| 359 | HCV-1a | 43 | 15 | 10 | B_3501 | ASRRNRRTTY | 3505 | 30.000 |
| 360 | HCV-1a | 43 | 53 | 10 | B_3501 | RPVDKAGRVV | 3506 | 16.000 |
| 361 | HCV-1a | 43 | 88 | 10 | B_3501 | RSQRSPRVQL | 3507 | 10.000 |
| 362 | HCV-1a | 43 | 101 | 10 | B_3501 | SSLCSTPPTY | 3508 | 10.000 |
| 363 | HCV-1a | 43 | 24 | 10 | B_3501 | YSHLMAQDAM | 3509 | 10.000 |
| 364 | HCV-1a | 43 | 43 | 10 | B_3501 | TSTMFWWRWM | 3510 | 10.000 |
| 365 | HCV-1a | 43 | 30 | 10 | B_4403 | QDAMLDPTPY | 3511 | 45.000 |
| 366 | HCV-1a | 43 | 101 | 10 | B_4403 | SSLCSTPPTY | 3512 | 12.000 |
| 367 | HCV-1a | 44 | 30 | 9 | A_0201 | VLLRTKTSV | 3513 | 437.482 |
| 368 | HCV-1a | 44 | 9 | 9 | A_0201 | TLVNPVEFI | 3514 | 64.668 |
| 369 | HCV-1a | 44 | 16 | 9 | A_0201 | FIQVQPNQL | 3515 | 13.512 |
| 370 | HCV-1a | 44 | 24 | 9 | B7 | LPSGGLVLL | 3516 | 80.000 |
| 371 | HCV-1a | 44 | 6 | 9 | B7 | APHTLVNPV | 3517 | 12.000 |
| 372 | HCV-1a | 44 | 24 | 9 | B_3501 | LPSGGLVLL | 3518 | 20.000 |
| 373 | HCV-1a | 44 | 23 | 10 | A_0201 | QLPSGGLVLL | 3519 | 49.134 |
| 374 | HCV-1a | 44 | 29 | 10 | A_0201 | LVLLRTKTSV | 3520 | 38.280 |
| 375 | HCV-1a | 44 | 10 | 10 | A_0201 | LVNPVEFIQV | 3521 | 19.657 |
| 376 | HCV-1a | 44 | 15 | 10 | A24 | EFIQVQPNQL | 3522 | 36.000 |
| 377 | HCV-1a | 44 | 20 | 10 | B7 | QPNQLPSGGL | 3523 | 120.000 |
| 378 | HCV-1a | 44 | 20 | 10 | B_3501 | QPNQLPSGGL | 3524 | 20.000 |
| 379 | HCV-1a | 45 | | | | NO HITS | | |
| 380 | HCV-1a | 46 | | | | NO HITS | | |
| 381 | HCV-1a | 47 | 8 | 9 | A_0201 | TILELGQSL | 3525 | 44.559 |
| 382 | HCV-1a | 47 | 8 | 9 | A24 | TILELGQSL | 3526 | 10.368 |
| 383 | HCV-1a | 47 | 4 | 9 | B7 | AASYTILEL | 3527 | 36.000 |
| 384 | HCV-1a | 47 | 2 | 9 | B7 | ASAASYTIL | 3528 | 12.000 |
| 385 | HCV-1a | 47 | 10 | 9 | B_4403 | LELGQSLVT | 3529 | 12.000 |
| 386 | HCV-1a | 47 | 8 | 10 | A_0201 | TILELGQSLV | 3530 | 145.077 |
| 387 | HCV-1a | 47 | 1 | 10 | B7 | MASAASYTIL | 3531 | 12.000 |
| 388 | HCV-1a | 47 | 3 | 10 | B7 | SAASYTILEL | 3532 | 12.000 |
| 389 | HCV-1a | 47 | 10 | 10 | B_4403 | LELGQSLVTW | 3533 | 54.000 |
| 390 | HCV-1a | 48 | 42 | 9 | B7 | HPAHPQPSL | 3534 | 120.000 |
| 391 | HCV-1a | 48 | 12 | 9 | B7 | RVSMTLPKL | 3535 | 20.000 |
| 392 | HCV-1a | 48 | 42 | 9 | B_3501 | HPAHPQPSL | 3536 | 20.000 |

TABLE 4b-continued 1a (4-6)

| No. | Strain | ORF | Start | AA | HLA | Peptide sequence | SEQ ID NO | Score |
|---|---|---|---|---|---|---|---|---|
| 393 | HCV-1a | 48 | 8 | 10 | A24 | KPHVRVSMTL | 3537 | 11.200 |
| 394 | HCV-1a | 48 | 8 | 10 | B7 | KPHVRVSMTL | 3538 | 80.000 |
| 395 | HCV-1a | 48 | 35 | 10 | B7 | EPRGDRSHPA | 3539 | 20.000 |
| 396 | HCV-1a | 48 | 2 | 10 | B7 | YPMRSAKPHV | 3540 | 12.000 |
| 397 | HCV-1a | 48 | 35 | 10 | B8 | EPRGDRSHPA | 3541 | 32.000 |
| 398 | HCV-1a | 48 | 19 | 10 | B8 | KLRDLRRGSV | 3542 | 18.000 |
| 399 | HCV-1a | 48 | 8 | 10 | B_3501 | KPHVRVSMTL | 3543 | 40.000 |
| 400 | HCV-1a | 48 | 6 | 10 | B_3501 | SAKPHVRVSM | 3544 | 18.000 |
| 401 | HCV-1a | 49 | 15 | 9 | A24 | PYQAVPQGL | 3545 | 50.400 |
| 402 | HCV-1a | 49 | 22 | 9 | A3 | GLSRPNTTR | 3546 | 18.000 |
| 403 | HCV-1a | 49 | 23 | 9 | B7 | LSRPNTTRL | 3547 | 40.000 |
| 404 | HCV-1a | 49 | 8 | 9 | B_3501 | LPGHSQAPY | 3548 | 40.000 |
| 405 | HCV-1a | 49 | 23 | 9 | B_3501 | LSRPNTTRL | 3549 | 15.000 |
| 406 | HCV-1a | 49 | 22 | 10 | A_0201 | GLSRPNTTRL | 3550 | 21.362 |
| 407 | HCV-1a | 49 | 25 | 10 | A24 | RPNTTRLAVL | 3551 | 12.000 |
| 408 | HCV-1a | 49 | 33 | 10 | A3 | VLRGHAQISR | 3552 | 12.000 |
| 409 | HCV-1a | 49 | 14 | 10 | B7 | APYQAVPQGL | 3553 | 240.000 |
| 410 | HCV-1a | 49 | 25 | 10 | B7 | RPNTTRLAVL | 3554 | 80.000 |
| 411 | HCV-1a | 49 | 25 | 10 | B_3501 | RPNTTRLAVL | 3555 | 40.000 |
| 412 | HCV-1a | 49 | 14 | 10 | B_3501 | APYQAVPQGL | 3556 | 20.000 |
| 413 | HCV-1a | 50 | 4 | 9 | B_4403 | REASISTLC | 3557 | 12.000 |
| 414 | HCV-1a | 50 | 2 | 10 | B7 | ICREASISTL | 3558 | 40.000 |
| 415 | HCV-1a | 50 | 2 | 10 | B8 | ICREASISTL | 3559 | 24.000 |
| 416 | HCV-1a | 50 | 4 | 10 | B_4403 | REASISTLCS | 3560 | 12.000 |
| 417 | HCV-1a | 51 | 29 | 9 | A1 | WSEFELCSY | 3561 | 67.500 |
| 418 | HCV-1a | 51 | 32 | 9 | A_0201 | FELCSYCPV | 3562 | 34.527 |
| 419 | HCV-1a | 51 | 36 | 9 | A24 | SYCPVEEVL | 3563 | 336.000 |
| 420 | HCV-1a | 51 | 72 | 9 | A24 | RYPKFSEAC | 3564 | 15.000 |
| 421 | HCV-1a | 51 | 27 | 9 | A24 | RYWSEFELC | 3565 | 12.000 |
| 422 | HCV-1a | 51 | 65 | 9 | B_3501 | VSPSSQGRY | 3566 | 10.000 |
| 423 | HCV-1a | 51 | 41 | 9 | B_4403 | EEVLATYGS | 3567 | 18.000 |
| 424 | HCV-1a | 51 | 75 | 10 | A24 | KFSEACGHPI | 3568 | 12.000 |
| 425 | HCV-1a | 51 | 27 | 10 | A24 | RYWSEFELCS | 3569 | 10.000 |
| 426 | HCV-1a | 51 | 25 | 10 | B7 | SGRYWSEFEL | 3570 | 40.000 |
| 427 | HCV-1a | 51 | 38 | 10 | B_3501 | CPVEEVLATY | 3571 | 80.000 |
| 428 | HCV-1a | 51 | 77 | 10 | B_4403 | SEACGHPIDF | 3572 | 160.000 |
| 429 | HCV-1a | 51 | 38 | 10 | B_4403 | CPVEEVLATY | 3573 | 13.500 |
| 430 | HCV-1a | 51 | 15 | 10 | B_4403 | REPAGQVQLA | 3574 | 12.000 |
| 431 | HCV-1a | 51 | 59 | 10 | B_4403 | ADAPGPVSPS | 3575 | 12.000 |
| 432 | HCV-1a | 52 | | | | NO HITS | | |
| 433 | HCV-1a | 53 | 8 | 10 | B_3501 | RPQCGGKHDY | 3576 | 80.000 |
| 434 | HCV-1a | 54 | 4 | 9 | B7 | DVFCPITKL | 3577 | 30.000 |
| 435 | HCV-1a | 54 | 2 | 10 | A1 | ATDVFCPITK | 3578 | 125.000 |
| 436 | HCV-1a | 54 | 5 | 10 | A24 | VFCPITKLGF | 3579 | 12.000 |
| 437 | HCV-1a | 55 | 13 | 9 | A_0201 | FLLPLASTA | 3580 | 84.555 |
| 438 | HCV-1a | 55 | 5 | 10 | A_0201 | NLQSVKCDFL | 3581 | 57.572 |
| 439 | HCV-1a | 55 | 6 | 10 | A_0201 | LQSVKCDFLL | 3582 | 21.356 |
| 440 | HCV-1a | 55 | 8 | 10 | B7 | SVKCDFLLPL | 3583 | 20.000 |
| 441 | HCV-1a | 56 | 6 | 9 | A_0201 | FVVGLFPRL | 3584 | 16.337 |
| 442 | HCV-1a | 56 | 6 | 9 | B7 | FVVGLFPRL | 3585 | 20.000 |
| 443 | HCV-1a | 56 | 5 | 10 | A24 | WFVVGLFPRL | 3586 | 43.200 |
| 444 | HCV-1a | 57 | | | | NO HITS | | |
| 445 | HCV-1a | 58 | 9 | 10 | A_0201 | RQHGHVRFGL | 3587 | 12.562 |
| 446 | HCV-1a | 58 | 9 | 10 | A24 | RQHGHVRFGL | 3588 | 11.200 |
| 447 | HCV-1a | 58 | 5 | 10 | B_4403 | SEHGRQHGHV | 3589 | 12.000 |
| 448 | HCV-1a | 59 | 33 | 9 | B7 | DPRQLWHEL | 3590 | 800.000 |
| 449 | HCV-1a | 59 | 19 | 9 | B7 | SPDPLIPAL | 3591 | 24.000 |
| 450 | HCV-1a | 59 | 15 | 9 | B7 | DAVPSPDPL | 3592 | 12.000 |
| 451 | HCV-1a | 59 | 33 | 9 | B8 | DPRQLWHEL | 3593 | 32.000 |
| 452 | HCV-1a | 59 | 33 | 9 | B_3501 | DPRQLWHEL | 3594 | 60.000 |
| 453 | HCV-1a | 59 | 28 | 10 | B7 | AGHKGDPRQL | 3595 | 12.000 |
| 454 | HCV-1a | 60 | 10 | 10 | B7 | QPVHPLHCPL | 3596 | 80.000 |
| 455 | HCV-1a | 60 | 10 | 10 | B_3501 | QPVHPLHCPL | 3597 | 20.000 |
| 456 | HCV-1a | 60 | 19 | 10 | B_3501 | LARANVPAQY | 3598 | 18.000 |
| 457 | HCV-1a | 60 | 6 | 10 | B_4403 | GEGYQPVHPL | 3599 | 12.000 |
| 458 | HCV-1a | 61 | 38 | 9 | A_0201 | LLGEHHPLL | 3600 | 148.896 |
| 459 | HCV-1a | 61 | 27 | 9 | A_0201 | GLQEAEGLL | 3601 | 11.386 |
| 460 | HCV-1a | 61 | 26 | 9 | A24 | RGLQEAEGL | 3602 | 12.000 |
| 461 | HCV-1a | 61 | 15 | 9 | B7 | DSRGDNLCL | 3603 | 40.000 |
| 462 | HCV-1a | 61 | 15 | 9 | B_3501 | DSRGDNLCL | 3604 | 22.500 |
| 463 | HCV-1a | 61 | 31 | 9 | B_4403 | AEGLLLELL | 3605 | 12.000 |
| 464 | HCV-1a | 61 | 27 | 10 | A_0201 | GLQEAEGLLL | 3606 | 87.586 |
| 465 | HCV-1a | 61 | 1 | 10 | A_0201 | MLRPEGLEFL | 3607 | 17.108 |
| 466 | HCV-1a | 61 | 22 | 10 | A_0201 | CLTGRGLQEA | 3608 | 11.426 |
| 467 | HCV-1a | 61 | 26 | 10 | A24 | RGLQEAEGLL | 3609 | 12.000 |

TABLE 4b-continued 1a (4-6)

| No. | Strain | ORF | Start | AA | HLA | Peptide sequence | SEQ ID NO | Score |
|---|---|---|---|---|---|---|---|---|
| 468 | HCV-1a | 61 | 1 | 10 | B7 | MLRPEGLEFL | 3610 | 40.000 |
| 469 | HCV-1a | 61 | 29 | 10 | B_4403 | QEAEGLLLEL | 3611 | 12.000 |
| 470 | HCV-1a | 62 | 37 | 9 | A_0201 | KVLPTLLCL | 3612 | 55.674 |
| 471 | HCV-1a | 62 | 37 | 9 | A24 | KVLPTLLCL | 3613 | 14.400 |
| 472 | HCV-1a | 62 | 29 | 9 | A3 | GLVRYQVRK | 3614 | 270.000 |
| 473 | HCV-1a | 62 | 34 | 9 | B7 | QVRKVLPTL | 3615 | 200.000 |
| 474 | HCV-1a | 62 | 14 | 9 | B7 | LVPRWGRGL | 3616 | 20.000 |
| 475 | HCV-1a | 62 | 37 | 9 | B7 | KVLPTLLCL | 3617 | 20.000 |
| 476 | HCV-1a | 62 | 6 | 9 | B7 | EANQTLPHL | 3618 | 12.000 |
| 477 | HCV-1a | 62 | 30 | 9 | B7 | LVRYQVRKV | 3619 | 10.000 |
| 478 | HCV-1a | 62 | 25 | 9 | B_4403 | SAHGGLVRY | 3620 | 13.500 |
| 479 | HCV-1a | 62 | 29 | 10 | A_0201 | GLVRYQVRKV | 3621 | 31.994 |
| 480 | HCV-1a | 62 | 33 | 10 | A_0201 | YQVRKVLPTL | 3622 | 22.915 |
| 481 | HCV-1a | 62 | 32 | 10 | A24 | RYQVRKVLPT | 3623 | 15.000 |
| 482 | HCV-1a | 62 | 30 | 10 | B7 | LVRYQVRKVL | 3624 | 300.000 |
| 483 | HCV-1a | 62 | 34 | 10 | B7 | QVRKVLPTLL | 3625 | 200.000 |
| 484 | HCV-1a | 62 | 5 | 10 | B_4403 | LEANQTLPHL | 3626 | 12.000 |
| 485 | HCV-1a | 63 | | | | NO HITS | | |
| 486 | HCV-1a | 64 | 3 | 10 | A1 | EDEMSPPLDY | 3627 | 11.250 |
| 487 | HCV-1a | 64 | 76 | 10 | A_0201 | GVALVTNYYV | 3628 | 33.472 |
| 488 | HCV-1a | 64 | 85 | 10 | A_0201 | VISAPRAPAV | 3629 | 16.258 |
| 489 | HCV-1a | 64 | 36 | 10 | A3 | GMGHSDGARR | 3630 | 12.000 |
| 490 | HCV-1a | 64 | 91 | 10 | B7 | APAVGKELAV | 3631 | 12.000 |
| 491 | HCV-1a | 64 | 4 | 10 | B_4403 | DEMSPPLDYF | 3632 | 360.000 |
| 492 | HCV-1a | 64 | 3 | 10 | B_4403 | EDEMSPPLDY | 3633 | 15.000 |
| 493 | HCV-1a | 64 | 75 | 10 | B_4403 | RGVALVTNYY | 3634 | 13.500 |
| 494 | HCV-1a | 64 | 120 | 9 | A1 | RIDPMSLGH | 3635 | 25.000 |
| 495 | HCV-1a | 64 | 77 | 9 | A_0201 | VALVTNYYV | 3636 | 33.419 |
| 496 | HCV-1a | 64 | 90 | 9 | A24 | RAPAVGKEL | 3637 | 18.480 |
| 497 | HCV-1a | 64 | 118 | 9 | B7 | DVRIDPMSL | 3638 | 200.000 |
| 498 | HCV-1a | 64 | 53 | 9 | B7 | QSRPRSLCL | 3639 | 40.000 |
| 499 | HCV-1a | 64 | 90 | 9 | B7 | RAPAVGKEL | 3640 | 12.000 |
| 500 | HCV-1a | 64 | 53 | 9 | B8 | QSRPRSLCL | 3641 | 80.000 |
| 501 | HCV-1a | 64 | 71 | 9 | B8 | GCGIRGVAL | 3642 | 16.000 |
| 502 | HCV-1a | 64 | 53 | 9 | B_3501 | QSRPRSLCL | 3643 | 15.000 |
| 503 | HCV-1a | 64 | 116 | 9 | B_3501 | GPDVRIDPM | 3644 | 12.000 |
| 504 | HCV-1a | 64 | 29 | 9 | B_3501 | QSNLLDVGM | 3645 | 10.000 |
| 505 | HCV-1a | 64 | 4 | 9 | B_4403 | DEMSPPLDY | 3646 | 720.000 |
| 506 | HCV-1a | 64 | 75 | 9 | B_4403 | RGVALVTNY | 3647 | 27.000 |
| 507 | HCV-1a | 65 | 6 | 9 | B_4403 | LEALGHYWW | 3648 | 24.000 |
| 508 | HCV-1a | 65 | 1 | 9 | B_4403 | MEVSHLEAL | 3649 | 12.000 |
| 509 | HCV-1a | 65 | 8 | 10 | A_0201 | ALGHYWWRGV | 3650 | 23.648 |
| 510 | HCV-1a | 65 | 3 | 10 | B_3501 | VSHLEALGHY | 3651 | 10.000 |
| 511 | HCV-1a | 66 | | | | NO HITS | | |
| 512 | HCV-1a | 67 | | | | NO HITS | | |
| 513 | HCV-1a | 68 | 29 | 9 | A_0201 | MLAEAISGA | 3652 | 79.642 |
| 514 | HCV-1a | 68 | 33 | 9 | A_0201 | AISGAVQGV | 3653 | 21.996 |
| 515 | HCV-1a | 68 | 21 | 9 | B7 | APRVCGVRM | 3654 | 600.000 |
| 516 | HCV-1a | 68 | 26 | 9 | B7 | GVRMLAEAI | 3655 | 20.000 |
| 517 | HCV-1a | 68 | 21 | 9 | B_3501 | APRVCGVRM | 3656 | 120.000 |
| 518 | HCV-1a | 68 | 29 | 10 | A_0201 | MLAEAISGAV | 3657 | 63.021 |
| 519 | HCV-1a | 68 | 28 | 10 | A_0201 | RMLAEAISGA | 3658 | 30.534 |
| 520 | HCV-1a | 68 | 21 | 10 | B7 | APRVCGVRML | 3659 | 2.400.000 |
| 521 | HCV-1a | 68 | 21 | 10 | B8 | APRVCGVRML | 3660 | 16.000 |
| 522 | HCV-1a | 68 | 21 | 10 | B_3501 | APRVCGVRML | 3661 | 60.000 |
| 523 | HCV-1a | 68 | 47 | 10 | B_4403 | DDTRRRSAHF | 3662 | 15.000 |

TABLE 4c 1b (1-3)

| No. | Strain | ORF | Start | AA | HLA | Peptide sequence | SEQ ID NO: | Score |
|---|---|---|---|---|---|---|---|---|
| 1 | HCV-1b | 4 | 3 | 9 | A24 | RTTAPTQVL | 3663 | 9.600 |
| 2 | HCV-1b | 5 | 3 | 9 | A24 | RYKIAIAQS | 3664 | 10.000 |
| 3 | HCV-1b | 5 | 3 | 10 | A24 | RYKIAIAQSI | 3665 | 186.000 |
| 4 | HCV-1b | 5 | 15 | 10 | A24 | TYQVTAWLGI | 3666 | 75.000 |
| 5 | HCV-1b | 13 | 3 | 9 | A24 | SFLPMVVAL | 3667 | 36.000 |
| 6 | HCV-1b | 14 | 110 | 9 | A24 | SYQLSETSL | 3668 | 300.000 |
| 7 | HCV-1b | 14 | 26 | 9 | A24 | RGLSCSPPL | 3669 | 12.000 |
| 8 | HCV-1b | 18 | 32 | 9 | A24 | KQPPNKRRL | 3670 | 14.400 |
| 9 | HCV-1b | 18 | 32 | 10 | A24 | KQPPNKRRLL | 3671 | 14.400 |

TABLE 4c-continued 1b (1-3)

| No. | Strain | ORF | Start | AA | HLA | Peptide sequence | SEQ ID NO: | Score |
|---|---|---|---|---|---|---|---|---|
| 10 | HCV-1b | 20 | 13 | 9 | A24 | RSSPALPSL | 3672 | 9.600 |
| 11 | HCV-1b | 20 | 4 | 9 | A24 | RATPQRVLL | 3673 | 9.600 |
| 12 | HCV-1b | 20 | 9 | 10 | A24 | RVLLRSSPAL | 3674 | 12.000 |
| 13 | HCV-1b | 25 | 4 | 9 | A24 | KYPFRRRSC | 3675 | 15.000 |
| 14 | HCV-1b | 29 | 27 | 9 | A24 | VYARRWPSM | 3676 | 25.000 |
| 15 | HCV-1b | 29 | 27 | 10 | A24 | VYARRWPSMM | 3677 | 25.000 |
| 16 | HCV-1b | 30 | 9 | 9 | A24 | RSPRTTSVL | 3678 | 12.000 |
| 17 | HCV-1b | 33 | 27 | 10 | A24 | GYHPCESGDI | 3679 | 60.000 |
| 18 | HCV-1b | 36 | 57 | 9 | A24 | LFDHPSFRL | 3680 | 20.000 |
| 19 | HCV-1b | 36 | 46 | 9 | A24 | LFLYLPLSF | 3681 | 18.000 |
| 20 | HCV-1b | 36 | 44 | 9 | A24 | RLLFLYLPL | 3682 | 14.400 |
| 21 | HCV-1b | 36 | 48 | 9 | A24 | LYLPLSFAV | 3683 | 10.800 |
| 22 | HCV-1b | 36 | 48 | 10 | A24 | LYLPLSFAVL | 3684 | 432.000 |
| 23 | HCV-1b | 40 | 29 | 10 | A24 | GFCRSGTLDL | 3685 | 20.000 |
| 24 | HCV-1b | 41 | 6 | 9 | A24 | FYHQGRGAL | 3686 | 200.000 |
| 25 | HCV-1b | 41 | 5 | 10 | A24 | IFYHQGRGAL | 3687 | 20.000 |
| 26 | HCV-1b | 47 | 13 | 9 | A24 | TYAARANTL | 3688 | 240.000 |
| 27 | HCV-1b | 53 | 10 | 9 | A24 | RCIRQKGVL | 3689 | 12.000 |
| 28 | HCV-1b | 8 | 3 | 9 | A3 | RLWPERMAF | 3690 | 30.000 |
| 29 | HCV-1b | 8 | 33 | 9 | A3 | HMLSMAYGR | 3691 | 18.000 |
| 30 | HCV-1b | 14 | 60 | 9 | A3 | SMAKPSPLK | 3692 | 30.000 |
| 31 | HCV-1b | 14 | 27 | 9 | A3 | GLSCSPPLR | 3693 | 12.000 |
| 32 | HCV-1b | 14 | 54 | 10 | A3 | ILERSPSMAK | 3694 | 60.000 |
| 33 | HCV-1b | 29 | 35 | 9 | A3 | MMWSPPFLR | 3695 | 90.000 |
| 34 | HCV-1b | 29 | 22 | 9 | A3 | QIWESVYAR | 3696 | 27.000 |
| 35 | HCV-1b | 29 | 34 | 10 | A3 | SMMWSPPFLR | 3697 | 27.000 |
| 36 | HCV-1b | 36 | 56 | 9 | A3 | VLFDHPSFR | 3698 | 20.000 |
| 37 | HCV-1b | 36 | 45 | 10 | A3 | LLFLYLPLSF | 3699 | 20.000 |
| 38 | HCV-1b | 36 | 56 | 10 | A3 | VLFDHPSFRL | 3700 | 13.500 |
| 39 | HCV-1b | 43 | 37 | 9 | A3 | GLGPRGPTR | 3701 | 18.000 |
| 40 | HCV-1b | 43 | 16 | 10 | A3 | GLHEAGRADR | 3702 | 18.000 |
| 41 | HCV-1b | 47 | 16 | 9 | A3 | GLHDARERR | 3703 | 12.000 |
| 42 | HCV-1b | 1 | 32 | 10 | A0201 | VIWVRSSIPL | 3704 | 41.446 |
| 43 | HCV-1b | 1 | 20 | 10 | A0201 | LVGAPQTPGV | 3705 | 10.346 |
| 44 | HCV-1b | 6 | 84 | 9 | A0201 | LLWWGRPTV | 3706 | 981.379 |
| 45 | HCV-1b | 6 | 66 | 9 | A0201 | VLYPRRRCV | 3707 | 75.673 |
| 46 | HCV-1b | 6 | 8 | 9 | A0201 | SLLRCSTHT | 3708 | 27.527 |
| 47 | HCV-1b | 6 | 83 | 10 | A0201 | VLLWWGRPTV | 3709 | 437.482 |
| 48 | HCV-1b | 6 | 5 | 10 | A0201 | KLGSLLRCST | 3710 | 26.082 |
| 49 | HCV-1b | 6 | 66 | 10 | A0201 | VLYPRRRCVA | 3711 | 11.081 |
| 50 | HCV-1b | 7 | 7 | 9 | A0201 | FSWRTRASV | 3712 | 17.334 |
| 51 | HCV-1b | 18 | 53 | 9 | A0201 | LMPWTERWL | 3713 | 28.851 |
| 52 | HCV-1b | 18 | 29 | 9 | A0201 | SLGRHMLSM | 3714 | 11.426 |
| 53 | HCV-1b | 18 | 60 | 10 | A0201 | WLHRAEARFL | 3715 | 108.094 |
| 54 | HCV-1b | 18 | 29 | 10 | A0201 | SLGRHMLSMA | 3716 | 11.426 |
| 55 | HCV-1b | 13 | 4 | 10 | A0201 | FLPMVVALGA | 3717 | 22.853 |
| 56 | HCV-1b | 14 | 5 | 9 | A0201 | QLTRLQSWA | 3718 | 27.324 |
| 57 | HCV-1b | 14 | 53 | 9 | A0201 | LILERSPSM | 3719 | 17.616 |
| 58 | HCV-1b | 14 | 27 | 10 | A0201 | GLSCSPPLRL | 3720 | 21.362 |
| 59 | HCV-1b | 14 | 53 | 10 | A0201 | LILERSPSMA | 3721 | 17.616 |
| 60 | HCV-1b | 14 | 4 | 10 | A0201 | IQLTRLQSWA | 3722 | 17.426 |
| 61 | HCV-1b | 14 | 70 | 10 | A0201 | SGGEGISFSV | 3723 | 10.797 |
| 62 | HCV-1b | 14 | 93 | 10 | A0201 | QASESTLWRI | 3724 | 10.248 |
| 63 | HCV-1b | 19 | 3 | 10 | A0201 | QEWPARSWPL | 3725 | 25.857 |
| 64 | HCV-1b | 20 | 10 | 9 | A0201 | VLLRSSPAL | 3726 | 134.369 |
| 65 | HCV-1b | 23 | 22 | 10 | A0201 | ILGRCGGWPL | 3727 | 272.371 |
| 66 | HCV-1b | 29 | 34 | 9 | A0201 | SMMWSPPFL | 3728 | 313.968 |
| 67 | HCV-1b | 30 | 16 | 9 | A0201 | VLRSQFTNV | 3729 | 17.074 |
| 68 | HCV-1b | 31 | 30 | 9 | A0201 | KQLDTLQLT | 3730 | 92.267 |
| 69 | HCV-1b | 33 | 2 | 9 | A0201 | ALAHFHSIV | 3731 | 108.362 |
| 70 | HCV-1b | 33 | 11 | 10 | A0201 | TLQVRSIGWL | 3732 | 35.130 |
| 71 | HCV-1b | 36 | 47 | 9 | A0201 | FLYLPLSFA | 3733 | 925.081 |
| 72 | HCV-1b | 36 | 79 | 9 | A0201 | RLLQLKYCV | 3734 | 257.342 |
| 73 | HCV-1b | 36 | 44 | 9 | A0201 | RLLFLYLPL | 3735 | 118.561 |
| 74 | HCV-1b | 36 | 49 | 9 | A0201 | YLPLSFAVL | 3736 | 76.550 |
| 75 | HCV-1b | 36 | 47 | 10 | A0201 | FLYLPLSFAV | 3737 | 5938.072 |
| 76 | HCV-1b | 36 | 36 | 10 | A0201 | VLFDHPSFRL | 3738 | 3195.307 |
| 77 | HCV-1b | 40 | 6 | 10 | A0201 | ALAGFTTTSL | 3739 | 21.362 |
| 78 | HCV-1b | 43 | 11 | 10 | A0201 | SLCPNGLHEA | 3740 | 11.426 |
| 79 | HCV-1b | 45 | 30 | 9 | A0201 | LIPPGRTAV | 3741 | 16.258 |
| 80 | HCV-1b | 45 | 29 | 10 | A0201 | QLIPPGRTAV | 3742 | 69.552 |
| 81 | HCV-1b | 52 | 1 | 9 | A0201 | MLLEGLCSL | 3743 | 1267.104 |
| 82 | HCV-1b | 52 | 8 | 10 | A0201 | SLSSCEAPGL | 3744 | 21.362 |
| 83 | HCV-1b | 53 | 2 | 10 | A0201 | FLQCVGPRC | 3745 | 22.853 |
| 84 | HCV-1b | 18 | 48 | 10 | A1 | SGEPLRHSGR | 3746 | 22.500 |

TABLE 4c-continued 1b (1-3)

| No. Strain | ORF | Start | AA | HLA | Peptide sequence | SEQ ID NO: | Score |
|---|---|---|---|---|---|---|---|
| 85 HCV-1b | 48 | 3 | 9 | A1 | STDHRTCQK | 3747 | 25.000 |
| 86 HCV-1b | 48 | 3 | 10 | A1 | STDHRTCQKR | 3748 | 21.500 |
| 87 HCV-1b | 1 | 26 | 9 | B3501 | TPGVGRVIW | 3749 | 10.000 |
| 88 HCV-1b | 5 | 12 | 10 | B3501 | IPATYQVTAW | 3750 | 10.000 |
| 89 HCV-1b | 6 | 95 | 9 | B3501 | SPRIAGGRM | 3751 | 120.000 |
| 90 HCV-1b | 6 | 2 | 9 | B3501 | TPSKLGSLL | 3752 | 20.000 |
| 91 HCV-1b | 6 | 89 | 10 | B3501 | RPTVPESPRI | 3753 | 24.000 |
| 92 HCV-1b | 6 | 51 | 10 | B3501 | RTRGLIAGTM | 3754 | 12.000 |
| 93 HCV-1b | 6 | 94 | 10 | B3501 | ESPRIAGGRM | 3755 | 10.000 |
| 94 HCV-1b | 18 | 25 | 10 | B3501 | KAGWSLGRHM | 3756 | 12.000 |
| 95 HCV-1b | 18 | 28 | 10 | B3501 | WSLCRHMLSM | 3757 | 10.000 |
| 96 HCV-1b | 18 | 19 | 10 | B3501 | APPGTSKAGW | 3758 | 10.000 |
| 97 HCV-1b | 13 | 5 | 10 | B3501 | LPMVVALGAL | 3759 | 20.000 |
| 98 HCV-1b | 14 | 68 | 10 | B3501 | KPSGGEGISF | 3760 | 60.000 |
| 99 HCV-1b | 14 | 58 | 10 | B3501 | SPSMAKPSPL | 3761 | 20.000 |
| 100 HCV-1b | 14 | 46 | 10 | B3501 | TSRRWPCLIL | 3762 | 15.000 |
| 101 HCV-1b | 15 | 14 | 9 | B3501 | RPRLGCGPT | 3763 | 12.000 |
| 102 HCV-1b | 18 | 33 | 9 | B3501 | QPPNKRRLL | 3764 | 20.000 |
| 103 HCV-1b | 18 | 22 | 9 | B3501 | SSSRKRSGY | 3765 | 10.000 |
| 104 HCV-1b | 18 | 33 | 10 | B3501 | QPPNKRRLL | 3766 | 20.000 |
| 105 HCV-1b | 18 | 21 | 10 | B3501 | SSSSRKSGY | 3767 | 10.000 |
| 106 HCV-1b | 18 | 4 | 10 | B3501 | KSAPRTSLTL | 3768 | 10.000 |
| 107 HCV-1b | 20 | 13 | 9 | B3501 | RSSPALPSL | 3769 | 10.000 |
| 108 HCV-1b | 23 | 9 | 9 | B3501 | TPRAPAHPL | 3770 | 60.000 |
| 109 HCV-1b | 23 | 15 | 9 | B3501 | HPLQRQTIL | 3771 | 20.000 |
| 110 HCV-1b | 24 | 10 | 10 | B3501 | RPTSCGGRRW | 3772 | 20.000 |
| 111 HCV-1b | 24 | 23 | 10 | B3501 | SPAWSRRTRW | 3773 | 10.000 |
| 112 HCV-1b | 27 | 15 | 9 | B3501 | SPLTDCKSW | 3774 | 15.000 |
| 113 HCV-1b | 29 | 28 | 9 | B3501 | YARRWPSMM | 3775 | 18.000 |
| 114 HCV-1b | 29 | 20 | 9 | B3501 | YSQIWESVY | 3776 | 10.000 |
| 115 HCV-1b | 29 | 32 | 10 | B3501 | WSPMMWSPPF | 3777 | 20.000 |
| 116 HCV-1b | 29 | 15 | 10 | B3501 | QPALSYSQIW | 3778 | 10.000 |
| 117 HCV-1b | 30 | 9 | 9 | B3501 | RSPRTTSVL | 3779 | 10.000 |
| 118 HCV-1b | 31 | 19 | 9 | B3501 | IPPPPSHGL | 3780 | 20.000 |
| 119 HCV-1b | 33 | 46 | 9 | B3501 | CPRGGGPPL | 3781 | 60.000 |
| 120 HCV-1b | 33 | 37 | 9 | B3501 | GPGASALGY | 3782 | 40.000 |
| 121 HCV-1b | 33 | 46 | 10 | B3501 | CPRGGGPPLV | 3783 | 12.000 |
| 122 HCV-1b | 36 | 50 | 9 | B3501 | LPLSFAVLF | 3784 | 20.000 |
| 123 HCV-1b | 36 | 41 | 9 | B3501 | ESARLLFLY | 3785 | 10.000 |
| 124 HCV-1b | 36 | 28 | 10 | B3501 | RPGSGGRREL | 3786 | 40.000 |
| 125 HCV-1b | 36 | 74 | 10 | B3501 | IPCHERLLQL | 3787 | 20.000 |
| 126 HCV-1b | 39 | 10 | 10 | B3501 | SPGGRARLCL | 3788 | 20.000 |
| 127 HCV-1b | 39 | 8 | 10 | B3501 | LPSPGGRARL | 3789 | 20.000 |
| 128 HCV-1b | 43 | 30 | 9 | B3501 | QPSYPATGL | 3790 | 20.000 |
| 129 HCV-1b | 43 | 3 | 10 | B3501 | VSAEGRWGSL | 3791 | 10.000 |
| 130 HCV-1b | 45 | 46 | 9 | B3501 | RSHWQRQEY | 3792 | 20.000 |
| 131 HCV-1b | 45 | 12 | 9 | B3501 | CARRVHGNY | 3793 | 18.000 |
| 132 HCV-1b | 45 | 2 | 10 | B3501 | HPGGCEGGGL | 3794 | 30.000 |
| 133 HCV-1b | 45 | 12 | 10 | B3501 | CARRVHGNYY | 3795 | 18.000 |
| 134 HCV-1b | 53 | 8 | 10 | B3501 | RPRCIRQKGV | 3796 | 24.000 |
| 135 HCV-1b | 54 | 1 | 10 | B3501 | MPQETWGTTL | 3797 | 40.000 |
| 136 HCV-1b | 8 | 51 | 10 | B4403 | HELMPWTERW | 3798 | 36.000 |
| 137 HCV-1b | 19 | 1 | 10 | B4403 | MEQEWPARSW | 3799 | 18.000 |
| 138 HCV-1b | 29 | 24 | 9 | B4403 | WESVYARRW | 3800 | 18.000 |
| 139 HCV-1b | 36 | 77 | 9 | B4403 | HERLLQLKY | 3801 | 180.000 |
| 140 HCV-1b | 36 | 40 | 10 | B4403 | RESARLLFLY | 3802 | 270.000 |
| 141 HCV-1b | 43 | 18 | 10 | B4403 | HEAGRADRHV | 3803 | 18.000 |
| 142 HCV-1b | 47 | 5 | 9 | B4403 | VEVSHTAET | 3804 | 12.000 |
| 143 HCV-1b | 47 | 5 | 10 | B4403 | VEVSHTAETY | 3805 | 360.000 |
| 144 HCV-1b | 47 | 11 | 10 | B4403 | AETYAARANT | 3806 | 12.000 |
| 145 HCV-1b | 52 | 21 | 9 | B4403 | RERRRPCRY | 3807 | 120.000 |
| 146 HCV-1b | 52 | 12 | 9 | B4403 | CEAPGLHDA | 3808 | 24.000 |
| 147 HCV-1b | 1 | 45 | 10 | B7 | SPTSWGTFRL | 3809 | 80.000 |
| 148 HCV-1b | 1 | 23 | 10 | B7 | APQTPGVGRV | 3810 | 12.000 |
| 149 HCV-1b | 5 | 14 | 9 | B7 | ATYQVTAWL | 3811 | 12.000 |
| 150 HCV-1b | 6 | 95 | 9 | B7 | SPRIAGGRM | 3812 | 200.000 |
| 151 HCV-1b | 6 | 2 | 9 | B7 | TPSKLGSLL | 3813 | 80.000 |
| 152 HCV-1b | 6 | 36 | 9 | B7 | SLRGGVPSL | 3814 | 40.000 |
| 153 HCV-1b | 6 | 29 | 9 | B7 | AAAPSTSSL | 3815 | 36.000 |
| 154 HCV-1b | 6 | 40 | 9 | B7 | GVPSLTLCL | 3816 | 20.000 |
| 155 HCV-1b | 6 | 68 | 10 | B7 | YPRRCVAQC | 3817 | 20.000 |
| 156 HCV-1b | 6 | 58 | 10 | B7 | GMTHPNRAVL | 3818 | 18.000 |
| 157 HCV-1b | 6 | 75 | 10 | B7 | AQCIASPRVL | 3819 | 12.000 |
| 158 HCV-1b | 6 | 51 | 10 | B7 | RTRGLIAGTM | 3820 | 10.000 |
| 159 HCV-1b | 8 | 39 | 10 | B7 | YGRCSCSCWL | 3821 | 40.000 |

TABLE 4c-continued 1b (1-3)

| No. Strain | ORF | Start | AA | HLA | Peptide sequence | SEQ ID NO: | Score |
|---|---|---|---|---|---|---|---|
| 160 HCV-1b | 8 | 26 | 10 | B7 | AGWSLGRHML | 3822 | 18.000 |
| 161 HCV-1b | 8 | 52 | 10 | B7 | ELMPWTERWL | 3823 | 12.000 |
| 162 HCV-1b | 9 | 4 | 9 | B7 | EAAMPSSSL | 3824 | 18.000 |
| 163 HCV-1b | 13 | 5 | 10 | B7 | LPMVVALGAL | 3825 | 240.000 |
| 164 HCV-1b | 13 | 2 | 10 | B7 | ASFLPMVVAL | 3826 | 12.000 |
| 165 HCV-1b | 14 | 105 | 9 | B7 | GSMCPSYQL | 3827 | 18.000 |
| 166 HCV-1b | 14 | 58 | 10 | B7 | SPSMAKPSPL | 3828 | 80.000 |
| 167 HCV-1b | 14 | 46 | 10 | B7 | TSRRWPCLIL | 3829 | 60.000 |
| 168 HCV-1b | 14 | 15 | 10 | B7 | AQSWTKRRRL | 3830 | 18.000 |
| 169 HCV-1b | 15 | 14 | 9 | B7 | RPRLGCGPT | 3831 | 20.000 |
| 170 HCV-1b | 16 | 5 | 9 | B7 | CPRPSRQET | 3832 | 30.000 |
| 171 HCV-1b | 16 | 5 | 10 | B7 | CPRPSRQETT | 3833 | 20.000 |
| 172 HCV-1b | 18 | 33 | 9 | B7 | QPPNKRRLL | 3834 | 120.000 |
| 173 HCV-1b | 18 | 6 | 9 | B7 | APRTSLTLS | 3835 | 12.000 |
| 174 HCV-1b | 18 | 34 | 9 | B7 | PPNKRRLLL | 3836 | 12.000 |
| 175 HCV-1b | 18 | 5 | 9 | B7 | SAPRTSLTL | 3837 | 12.000 |
| 176 HCV-1b | 18 | 33 | 10 | B7 | QPPNKRRLLL | 3838 | 120.000 |
| 177 HCV-1b | 20 | 4 | 9 | B7 | RATPQRVLL | 3839 | 18.000 |
| 178 HCV-1b | 20 | 2 | 10 | B7 | CLRATPQRVL | 3840 | 60.000 |
| 179 HCV-1b | 20 | 9 | 10 | B7 | RVLLRSSPAL | 3841 | 20.000 |
| 180 HCV-1b | 23 | 9 | 9 | B7 | TPRAPAHPL | 3842 | 1200.000 |
| 181 HCV-1b | 23 | 15 | 9 | B7 | HLPQRQTIL | 3843 | 80.000 |
| 182 HCV-1b | 23 | 23 | 9 | B7 | LGRCGGWPL | 3844 | 40.000 |
| 183 HCV-1b | 25 | 24 | 9 | B7 | SGRARITTL | 3845 | 40.000 |
| 184 HCV-1b | 25 | 14 | 9 | B7 | NPRSSPQRC | 3846 | 20.000 |
| 185 HCV-1b | 25 | 9 | 9 | B7 | ACGRRRSPL | 3847 | 18.000 |
| 186 HCV-1b | 25 | 8 | 10 | B7 | QACGRRRSPL | 3848 | 18.000 |
| 187 HCV-1b | 28 | 20 | 9 | B7 | CGRTCWKTL | 3849 | 40.000 |
| 188 HCV-1b | 29 | 28 | 9 | B7 | YARRWPSMM | 3850 | 30.000 |
| 189 HCV-1b | 29 | 34 | 9 | B7 | SMMWSPPFL | 3851 | 12.000 |
| 190 HCV-1b | 31 | 19 | 9 | B7 | IPPPPSHGL | 3852 | 120.000 |
| 191 HCV-1b | 31 | 26 | 10 | B7 | GLGRKQLDTL | 3853 | 40.000 |
| 192 HCV-1b | 33 | 46 | 9 | B7 | CPRGGGPPL | 3854 | 800.000 |
| 193 HCV-1b | 33 | 46 | 10 | B7 | CPRGGGPPLV | 3855 | 40.000 |
| 194 HCV-1b | 33 | 3 | 10 | B7 | LAHFHSIVTL | 3856 | 12.000 |
| 195 HCV-1b | 36 | 42 | 9 | B7 | SARLLFLYL | 3857 | 120.000 |
| 196 HCV-1b | 36 | 38 | 9 | B7 | CNRESARLL | 3858 | 40.000 |
| 197 HCV-1b | 36 | 28 | 10 | B7 | RPGSGGRREL | 3859 | 120.000 |
| 198 HCV-1b | 36 | 74 | 10 | B7 | IPCHERLLQL | 3860 | 80.000 |
| 199 HCV-1b | 39 | 12 | 9 | B7 | GGRARLCLL | 3861 | 40.000 |
| 200 HCV-1b | 39 | 10 | 10 | B7 | SPGGRARLCL | 3862 | 120.000 |
| 201 HCV-1b | 39 | 8 | 10 | B7 | LPSPGGRARL | 3863 | 120.000 |
| 202 HCV-1b | 40 | 30 | 9 | B7 | FCRSGTLDL | 3864 | 40.000 |
| 203 HCV-1b | 40 | 7 | 9 | B7 | LAGFTTTSL | 3865 | 12.000 |
| 204 HCV-1b | 40 | 6 | 10 | B7 | ALAGFTTTSL | 3866 | 12.000 |
| 205 HCV-1b | 43 | 30 | 9 | B7 | QPSYPATGL | 3867 | 120.000 |
| 206 HCV-1b | 43 | 39 | 9 | B7 | GPRGPTRFC | 3868 | 30.000 |
| 207 HCV-1b | 43 | 20 | 10 | B7 | AGRADRHVHL | 3869 | 120.000 |
| 208 HCV-1b | 45 | 22 | 9 | B7 | AVSGLHGQL | 3870 | 60.000 |
| 209 HCV-1b | 45 | 2 | 10 | B7 | HPGGCEGGGL | 3871 | 80.000 |
| 210 HCV-1b | 45 | 21 | 10 | B7 | YAVSGLHGQL | 3872 | 12.000 |
| 211 HCV-1b | 46 | 5 | 10 | B7 | DSRLQGSHL | 3873 | 40.000 |
| 212 HCV-1b | 47 | 15 | 9 | B7 | AARANTLAV | 3874 | 18.000 |
| 213 HCV-1b | 49 | 9 | 9 | B7 | SAHFHAHRPL | 3875 | 12.000 |
| 214 HCV-1b | 51 | 16 | 9 | B7 | AAHQRVEQL | 3876 | 36.000 |
| 215 HCV-1b | 51 | 15 | 10 | B7 | QAAHQRVEQL | 3877 | 12.000 |
| 216 HCV-1b | 53 | 8 | 10 | B7 | RPRCIRQKGV | 3878 | 40.000 |
| 217 HCV-1b | 54 | 1 | 10 | B7 | MPQETWGTTL | 3879 | 80.000 |
| 218 HCV-1b | 56 | 3 | 9 | B7 | VVQPPGPPL | 3880 | 30.000 |
| 219 HCV-1b | 56 | 2 | 10 | B7 | SVVQPPGPPL | 3881 | 30.000 |
| 220 HCV-1b | 6 | 46 | 10 | B8 | LCLTSRTRGL | 3882 | 16.000 |
| 221 HCV-1b | 14 | 85 | 10 | B8 | SPSMAKPSPL | 3883 | 16.000 |
| 222 HCV-1b | 18 | 33 | 9 | B8 | QPPNKRRLL | 3884 | 16.000 |
| 223 HCV-1b | 18 | 33 | 10 | B8 | QPPNKRRLLL | 3885 | 16.000 |
| 224 HCV-1b | 23 | 15 | 9 | B8 | HPLQRQTIL | 3886 | 16.000 |
| 225 HCV-1b | 23 | 9 | 9 | B8 | TPRAPAHPL | 3887 | 16.000 |
| 226 HCV-1b | 25 | 24 | 9 | B8 | SGRARITTL | 3888 | 16.000 |
| 227 HCV-1b | 27 | 9 | 9 | B8 | ACGRRRSPL | 3889 | 16.000 |
| 228 HCV-1b | 27 | 8 | 10 | B8 | QACGRRRSPL | 3890 | 16.000 |
| 229 HCV-1b | 33 | 46 | 9 | B8 | CPRGGGPPL | 3891 | 16.000 |
| 230 HCV-1b | 36 | 42 | 9 | B8 | SARLLFLYL | 3892 | 16.000 |
| 231 HCV-1b | 36 | 74 | 10 | B8 | IPCHERLLQL | 3893 | 16.000 |
| 232 HCV-1b | 39 | 12 | 9 | B8 | GGRARLCLL | 3894 | 16.000 |
| 233 HCV-1b | 40 | 30 | 9 | B8 | FCRSGTLDL | 3895 | 16.000 |
| 234 HCV-1b | 43 | 20 | 10 | B8 | AGRADRHVHL | 3896 | 16.000 |

TABLE 4c-continued 1b (1-3)

| No. | Strain | ORF | Start | AA | HLA | Peptide sequence | SEQ ID NO: | Score |
|---|---|---|---|---|---|---|---|---|
| 235 | HCV-1b | 51 | 16 | 9 | B8 | AAHQRVEQL | 3897 | 16.000 |
| 236 | HCV-1b | 51 | 15 | 10 | B8 | QAAHQRVEQL | 3898 | 16.000 |
| 237 | HCV-1b | 52 | 19 | 9 | B8 | DARERRRPC | 3899 | 48.000 |
| 238 | HCV-1b | 53 | 8 | 10 | B8 | RPRCIRQKGV | 3900 | 24.000 |

TABLE 4d 1b (4-6)

| No. | Strain | ORF | Start | AA | HLA | Peptide sequence | SEQ ID NO: | Score |
|---|---|---|---|---|---|---|---|---|
| 1 | HCV 1b | 1 | 2 | 10 | B7 | ICREaSISTL | 3901 | 40.000 |
| 2 | HCV 1b | 1 | 2 | 10 | B8 | ICREaSISTL | 3902 | 24.000 |
| 3 | HCV 1b | 1 | 4 | 9 | B_4403 | REASISTLC | 3903 | 12.000 |
| 4 | HCV 1b | 1 | 4 | 10 | B_4403 | REASiSTLCS | 3904 | 12.000 |
| 5 | HCV 1b | 2 | 20 | 9 | A_0201 | CLPLQKVGV | 3905 | 69.552 |
| 6 | HCV 1b | 2 | 4 | 9 | B_3501 | WPGVFSSPF | 3906 | 20.000 |
| 7 | HCV 1b | 3 | 12 | 9 | A_0201 | MMLSAPSRI | 3907 | 47.394 |
| 8 | HCV 1b | 3 | 13 | 10 | A_0201 | MLSApSRILV | 3908 | 118.238 |
| 9 | HCV 1b | 3 | 11 | 10 | A_0201 | NMMLsAPSRI | 3909 | 27.879 |
| 10 | HCV 1b | 3 | 5 | 9 | B7 | RPTHWRNMM | 3910 | 30.000 |
| 11 | HCV 1b | 3 | 5 | 10 | B7 | RPTHwRNMML | 3911 | 80.000 |
| 12 | HCV 1b | 3 | 3 | 10 | B7 | RGRPtHWRNM | 3912 | 10.000 |
| 13 | HCV 1b | 3 | 5 | 9 | B_3501 | RPTHWRNMM | 3913 | 80.000 |
| 14 | HCV 1b | 3 | 5 | 10 | B_3501 | RPTHwRNMML | 3914 | 40.000 |
| 15 | HCV 1b | 3 | 3 | 10 | B_3501 | RGRPtHWRNM | 3915 | 12.000 |
| 16 | HCV 1b | 4 | 18 | 10 | A_0201 | RLAAqESTGI | 3916 | 10.433 |
| 17 | HCV 1b | 4 | 12 | 9 | A24 | RYSPGTRLA | 3917 | 12.000 |
| 18 | HCV 1b | 4 | 44 | 10 | A24 | RGPSsRIHGL | 3918 | 12.000 |
| 19 | HCV 1b | 4 | 12 | 10 | A24 | RYSPgTRLAA | 3919 | 12.000 |
| 20 | HCV 1b | 4 | 45 | 9 | B7 | GPSSRIHGL | 3920 | 80.000 |
| 21 | HCV 1b | 4 | 10 | 10 | B7 | ISRYsPGTRL | 3921 | 60.000 |
| 22 | HCV 1b | 4 | 47 | 10 | B7 | SSRIhGLPDL | 3922 | 40.000 |
| 23 | HCV 1b | 4 | 45 | 9 | B7 | GPSSRIHGL | 3923 | 16.000 |
| 24 | HCV 1b | 4 | 45 | 9 | B_3501 | GPSSRIHGL | 3924 | 20.000 |
| 25 | HCV 1b | 4 | 31 | 9 | B_3501 | SPSRPEEGW | 3925 | 10.000 |
| 26 | HCV 1b | 4 | 10 | 10 | B_3501 | ISRYsPGTRL | 3926 | 15.000 |
| 27 | HCV 1b | 4 | 47 | 10 | B_3501 | SSRIhGLPDL | 3927 | 15.000 |
| 28 | HCV 1b | 4 | 20 | 10 | B_3501 | AAQEsTGIRM | 3928 | 12.000 |
| 29 | HCV 1b | 5 | | | | no hits | | |
| 30 | HCV 1b | 6 | | | | no hits | | |
| 31 | HCV 1b | 7 | | | | no hits | | |
| 32 | HCV 1b | 8 | | | | no hits | | |
| 33 | HCV 1b | 9 | | | | no hits | | |
| 34 | HCV 1b | 10 | | | | no hits | | |
| 35 | HCV 1b | 11 | | | | no hits | | |
| 36 | HCV 1b | 12 | 12 | 10 | A_0201 | AEWIsLLSTV | 3929 | 25.817 |
| 37 | HCV 1b | 12 | 3 | 10 | A_0201 | SMMLLRGSQA | 3930 | 13.276 |
| 38 | HCV 1b | 12 | 12 | 10 | B_4403 | AEWIsLLSTV | 3931 | 18.000 |
| 39 | HCV 1b | 13 | 14 | 9 | A_0201 | QQPPLVWWL | 3932 | 205.491 |
| 40 | HCV 1b | 13 | 21 | 9 | A_0201 | WLFAVTRAL | 3933 | 72.718 |
| 41 | HCV 1b | 13 | 17 | 9 | A_0201 | PLVWWLFAV | 3934 | 20.412 |
| 42 | HCV 1b | 13 | 13 | 10 | A_0201 | EQQPpLVWWL | 3935 | 15.412 |
| 43 | HCV 1b | 13 | 4 | 9 | A3 | GLATWTPPR | 3936 | 36.000 |
| 44 | HCV 1b | 13 | 10 | 9 | B7 | PPREQQPPL | 3937 | 80.000 |
| 45 | HCV 1b | 13 | 9 | 10 | B7 | TPPReQQPPL | 3938 | 80.000 |
| 46 | HCV 1b | 13 | 15 | 9 | B_3501 | QPPLVWWLF | 3939 | 20.000 |
| 47 | HCV 1b | 13 | 10 | 9 | B_3501 | PPREQQPPL | 3940 | 12.000 |
| 48 | HCV 1b | 13 | 9 | 10 | B_3501 | TPPReQQPPL | 3941 | 20.000 |
| 49 | HCV 1b | 13 | 12 | 10 | B_4403 | REQQpPLVWW | 3942 | 18.000 |
| 50 | HCV 1b | 14 | 15 | 10 | A_0201 | GMLPgRGSCLL | 3943 | 57.085 |
| 51 | HCV 1b | 14 | 16 | 10 | A_0201 | MLPGrGSCLL | 3944 | 36.316 |
| 52 | HCV 1b | 14 | 23 | 9 | A_0201 | CLLPAWSGT | 3945 | 46.873 |
| 53 | HCV 1b | 14 | 16 | 9 | A_0201 | MLPGRGSCL | 3946 | 36.316 |
| 54 | HCV 1b | 14 | 17 | 9 | B7 | LPGRGSCLL | 3947 | 80.000 |
| 55 | HCV 1b | 14 | 7 | 10 | B7 | EPWRtPWLGM | 3948 | 30.000 |
| 56 | HCV 1b | 14 | 5 | 10 | B7 | GPEPwRTPWL | 3949 | 24.000 |
| 57 | HCV 1b | 14 | 7 | 10 | B_3501 | EPWRtPWLGM | 3950 | 40.000 |
| 58 | HCV 1b | 14 | 17 | 9 | B_3501 | LPGRGSCLL | 3951 | 20.000 |
| 59 | HCV 1b | 14 | 2 | 10 | B_4403 | MEVGpEPWRT | 3952 | 12.000 |
| 60 | HCV 1b | 14 | 19 | 9 | A_0201 | RLLPRQRRL | 3953 | 15.808 |
| 61 | HCV 1b | 14 | 12 | 9 | A24 | PYSPSSERL | 3954 | 24.000 |

TABLE 4d-continued 1b (4-6)

| No. | Strain | ORF | Start | AA | HLA | Peptide sequence | SEQ ID NO: | Score |
|---|---|---|---|---|---|---|---|---|
| 62 | HCV 1b | 14 | 19 | 9 | A24 | RLLPRQRRL | 3955 | 14.400 |
| 63 | HCV 1b | 14 | 12 | 10 | A24 | PYSPsSERLL | 3956 | 24.000 |
| 64 | HCV 1b | 14 | 11 | 10 | B7 | RPYSpSSERL | 3957 | 80.000 |
| 65 | HCV 1b | 14 | 5 | 9 | B_3501 | RSLSQSRPY | 3958 | 20.000 |
| 66 | HCV 1b | 14 | 11 | 10 | B_3501 | RPYSpSSERL | 3959 | 40.000 |
| 67 | HCV 1b | 15 | 19 | 9 | A_0201 | RLLPRQRRL | 3960 | 15.808 |
| 68 | HCV 1b | 15 | 12 | 9 | A24 | PYSPSSERL | 3961 | 24.000 |
| 69 | HCV 1b | 15 | 19 | 9 | A24 | RLLPRQRRL | 3962 | 14.400 |
| 70 | HCV 1b | 15 | 12 | 10 | A24 | PYSPsSERLL | 3963 | 24.000 |
| 71 | HCV 1b | 15 | 11 | 10 | B7 | RPYSpSSERL | 3964 | 80.000 |
| 72 | HCV 1b | 15 | 5 | 9 | B_3501 | RSLSQSRPY | 3965 | 20.000 |
| 73 | HCV 1b | 15 | 11 | 10 | B_3501 | RPYSpSSERL | 3966 | 40.000 |
| 74 | HCV 1b | 16 | 3 | 9 | B7 | AVRPGGMSC | 3967 | 15.000 |
| 75 | HCV 1b | 17 | | 7 | | no hits | | |
| 76 | HCV 1b | 18 | 21 | 10 | A_0201 | SLGPwHKLVV | 3968 | 28.516 |
| 77 | HCV 1b | 18 | 27 | 10 | A_0201 | KLVVvKPARA | 3969 | 17.388 |
| 78 | HCV 1b | 18 | 6 | 10 | A24 | RVPDlQKPRL | 3970 | 14.400 |
| 79 | HCV 1b | 18 | 27 | 9 | A3 | KLVVVKPAR | 3971 | 27.000 |
| 80 | HCV 1b | 18 | 47 | 9 | B7 | MPPQGPACL | 3972 | 80.000 |
| 81 | HCV 1b | 18 | 14 | 9 | B7 | RLRTMQPSL | 3973 | 40.000 |
| 82 | HCV 1b | 18 | 2 | 9 | B7 | VTRSRVPDL | 3974 | 40.000 |
| 83 | HCV 1b | 18 | 7 | 9 | B7 | VPDLQKPRL | 3975 | 24.000 |
| 84 | HCV 1b | 18 | 19 | 10 | B7 | QPSLgPWHKL | 3976 | 120.000 |
| 85 | HCV 1b | 18 | 1 | 10 | B7 | MVTRsRVPDL | 3977 | 20.000 |
| 86 | HCV 1b | 18 | 6 | 10 | B7 | RVPDlQKPRL | 3978 | 20.000 |
| 87 | HCV 1b | 18 | 2 | 9 | B8 | VTRSRVPDL | 3979 | 80.000 |
| 88 | HCV 1b | 18 | 19 | 10 | B_3501 | QPSLgPWHKL | 3980 | 20.000 |
| 89 | HCV 1b | 18 | 32 | 10 | B_3501 | KPARaGATAI | 3981 | 16.000 |
| 90 | HCV 1b | 18 | 12 | 10 | B_3501 | KPRLrTMQPS | 3982 | 12.000 |
| 91 | HCV 1b | 19 | | 7 | | no hits | | |
| 92 | HCV 1b | 20 | 7 | 10 | B7 | RTRGsGCWRL | 3983 | 40.000 |
| 93 | HCV 1b | 20 | 24 | 9 | B8 | CARQRQQRV | 3984 | 48.000 |
| 94 | HCV 1b | 21 | 8 | 9 | A1 | VLEAARHSY | 3985 | 45.000 |
| 95 | HCV 1b | 21 | 2 | 10 | A_0201 | ALPGgGVLEA | 3986 | 11.426 |
| 96 | HCV 1b | 21 | 1 | 9 | B7 | MALPGGGVL | 3987 | 12.000 |
| 97 | HCV 1b | 22 | 14 | 10 | B7 | NQRGrARDRL | 3988 | 60.000 |
| 98 | HCV 1b | 23 | 3 | 10 | A_0201 | MLPSqELTGV | 3989 | 271.948 |
| 99 | HCV 1b | 23 | 1 | 9 | A_0201 | MIMLPSQEL | 3990 | 18.476 |
| 100 | HCV 1b | 23 | 2 | 9 | A_0201 | IMLPSQELT | 3991 | 16.588 |
| 101 | HCV 1b | 23 | 1 | 9 | B7 | MIMLPSQEL | 3992 | 18.000 |
| 102 | HCV 1b | 23 | 7 | 10 | B_4403 | QELTgVCLAV | 3993 | 12.000 |
| 103 | HCV 1b | 23 | 7 | 9 | B_4403 | QELTGVCLA | 3994 | 24.000 |
| 104 | HCV 1b | 24 | | 7 | | no hits | | |
| 105 | HCV 1b | 25 | 6 | 10 | A1 | TVESkQRVSY | 3995 | 90.000 |
| 106 | HCV 1b | 25 | 19 | 9 | A_0201 | MGFFFDFQV | 3996 | 62.942 |
| 107 | HCV 1b | 25 | 18 | 10 | A_0201 | PMGFfFDFQV | 3997 | 24.356 |
| 108 | HCV 1b | 25 | 14 | 9 | A24 | SYEKPMGFF | 3998 | 150.000 |
| 109 | HCV 1b | 25 | 20 | 9 | A24 | GFFFDFQVF | 3999 | 14.400 |
| 110 | HCV 1b | 25 | 14 | 10 | A24 | SYEKpMGFFF | 4000 | 150.000 |
| 111 | HCV 1b | 25 | 38 | 10 | A24 | EYWNpYEEPI | 4001 | 50.000 |
| 112 | HCV 1b | 25 | 10 | 10 | B7 | KQRVsYEKPM | 4002 | 10.000 |
| 113 | HCV 1b | 25 | 10 | 10 | B_3501 | KQRVsYEKPM | 4003 | 12.000 |
| 114 | HCV 1b | 25 | 13 | 10 | B_3501 | VSYEkPMGFF | 4004 | 10.000 |
| 115 | HCV 1b | 25 | 25 | 9 | B_3501 | CPGEYWNPY | 4005 | 80.000 |
| 116 | HCV 1b | 25 | 17 | 9 | B_3501 | KPMGFFFDF | 4006 | 40.000 |
| 117 | HCV 1b | 25 | 13 | 9 | B_3501 | VSYEKPMGF | 4007 | 10.000 |
| 118 | HCV 1b | 25 | 31 | 9 | B_3501 | NSTRCPGEY | 4008 | 10.000 |
| 119 | HCV 1b | 25 | 15 | 9 | B_4403 | YEKPMGFFF | 4009 | 120.000 |
| 120 | HCV 1b | 25 | 7 | 9 | B_4403 | VESKQRVSY | 4010 | 120.000 |
| 121 | HCV 1b | 26 | 17 | 9 | A1 | HTEWMWLTA | 4011 | 11.250 |
| 122 | HCV 1b | 26 | 1 | 10 | A_0201 | MMVVsIGVTV | 4012 | 85.394 |
| 123 | HCV 1b | 26 | 26 | 10 | A_0201 | LLDRfRTSFA | 4013 | 18.580 |
| 124 | HCV 1b | 26 | 14 | 10 | A_0201 | KSFHtEWMWL | 4014 | 16.885 |
| 125 | HCV 1b | 26 | 2 | 9 | A_0201 | MVVSIGVTV | 4015 | 10.346 |
| 126 | HCV 1b | 26 | 15 | 9 | A24 | SFHTEWMWL | 4016 | 20.000 |
| 127 | HCV 1b | 26 | 20 | 10 | A3 | WMWLtALLDR | 4017 | 60.000 |
| 128 | HCV 1b | 26 | 12 | 10 | B_3501 | SSKSfHTEWM | 4018 | 30.000 |
| 129 | HCV 1b | 26 | 14 | 10 | B_3501 | KSFHtEWMWL | 4019 | 15.000 |
| 130 | HCV 1b | 27 | 16 | 10 | A_0201 | SLLSsAAHGV | 4020 | 257.342 |
| 131 | HCV 1b | 27 | 1 | 10 | A_0201 | MLWWrSKELL | 4021 | 147.697 |
| 132 | HCV 1b | 27 | 12 | 10 | A_0201 | ALMGsLLSSA | 4022 | 42.278 |
| 133 | HCV 1b | 27 | 9 | 10 | A_0201 | LLNAlMGSLL | 4023 | 36.316 |
| 134 | HCV 1b | 27 | 5 | 9 | A24 | RSKELLNAL | 4024 | 13.824 |
| 135 | HCV 1b | 27 | 5 | 9 | B_3501 | RSKELLNAL | 4025 | 60.000 |
| 136 | HCV 1b | 27 | 5 | 10 | B_3501 | RSKElLNALM | 4026 | 120.000 |

TABLE 4d-continued 1b (4-6)

| No. | Strain | ORF | Start | AA | HLA | Peptide sequence | SEQ ID NO: | Score |
|---|---|---|---|---|---|---|---|---|
| 137 | HCV 1b | 27 | 7 | 10 | B_4403 | KELLnALMGS | 4027 | 18.000 |
| 138 | HCV 1b | 28 | 29 | 9 | A1 | TADDSELPK | 4028 | 50.000 |
| 139 | HCV 1b | 28 | 7 | 9 | A1 | TSDPLSPSS | 4029 | 15.000 |
| 140 | HCV 1b | 28 | 3 | 9 | A24 | EYDSTSDPL | 4030 | 200.000 |
| 141 | HCV 1b | 28 | 61 | 9 | A24 | RGGGIGGAL | 4031 | 11.200 |
| 142 | HCV 1b | 28 | 52 | 9 | B7 | SVRTTVLFL | 4032 | 200.000 |
| 143 | HCV 1b | 28 | 19 | 9 | B7 | SGRAVAVPL | 4033 | 40.000 |
| 144 | HCV 1b | 28 | 9 | 10 | B_3501 | DPLSpSSEAW | 4034 | 10.000 |
| 145 | HCV 1b | 28 | 33 | 10 | B_4403 | SELPkVLVAS | 4035 | 72.000 |
| 146 | HCV 1b | 28 | 15 | 10 | B_4403 | SEAWsGRAVA | 4036 | 16.000 |
| 147 | HCV 1b | 28 | 33 | 9 | B_4403 | SELPKVLVA | 4037 | 144.000 |
| 148 | HCV 1b | 28 | 15 | 9 | B_4403 | SEAWSGRAV | 4038 | 16.000 |
| 149 | HCV 1b | 29 | 40 | 9 | A1 | FSDSTRVMF | 4039 | 15.000 |
| 150 | HCV 1b | 29 | 92 | 9 | A1 | GGDPLANLR | 4040 | 12.500 |
| 151 | HCV 1b | 29 | 128 | 9 | A1 | SCDPTRYWL | 4041 | 10.000 |
| 152 | HCV 1b | 29 | 62 | 10 | A_0201 | RSASgETWWV | 4042 | 18.728 |
| 153 | HCV 1b | 29 | 38 | 9 | A_0201 | TLFSDSTRV | 4043 | 257.342 |
| 154 | HCV 1b | 29 | 106 | 9 | A_0201 | VMWEGSVSM | 4044 | 207.569 |
| 155 | HCV 1b | 29 | 63 | 9 | A_0201 | SASGETWWV | 4045 | 39.848 |
| 156 | HCV 1b | 29 | 177 | 9 | A_0201 | FTLSVVMPV | 4046 | 37.815 |
| 157 | HCV 1b | 29 | 155 | 9 | A_0201 | YLCNRTPST | 4047 | 34.279 |
| 158 | HCV 1b | 29 | 135 | 9 | A_0201 | WLSPTWNVT | 4048 | 23.893 |
| 159 | HCV 1b | 29 | 171 | 9 | A_0201 | GTWHGHFTL | 4049 | 14.283 |
| 160 | HCV 1b | 29 | 98 | 9 | A_0201 | NLRLAVSAV | 4050 | 12.158 |
| 161 | HCV 1b | 29 | 148 | 9 | A24 | RGLHAGAYL | 4051 | 12.000 |
| 162 | HCV 1b | 29 | 133 | 9 | A24 | RYWLSPTWN | 4052 | 10.000 |
| 163 | HCV 1b | 29 | 75 | 10 | A24 | AFKEgADNWL | 4053 | 28.800 |
| 164 | HCV 1b | 29 | 39 | 10 | A24 | LFSDsTRVMF | 4054 | 12.000 |
| 165 | HCV 1b | 29 | 133 | 10 | A24 | RYWLsPTWNV | 4055 | 10.000 |
| 166 | HCV 1b | 29 | 46 | 9 | A3 | VMFPPISCR | 4056 | 67.500 |
| 167 | HCV 1b | 29 | 88 | 9 | B7 | LAKEGGDPL | 4057 | 12.000 |
| 168 | HCV 1b | 29 | 105 | 10 | B7 | AVMWeGSVSM | 4058 | 45.000 |
| 169 | HCV 1b | 29 | 141 | 10 | B7 | NVTSsRRRGL | 4059 | 30.000 |
| 170 | HCV 1b | 29 | 170 | 10 | B7 | AGTWhGHFTL | 4060 | 12.000 |
| 171 | HCV 1b | 29 | 52 | 10 | B7 | SCRHrRLASM | 4061 | 10.000 |
| 172 | HCV 1b | 29 | 98 | 10 | B7 | NLRLaVSAVM | 4062 | 10.000 |
| 173 | HCV 1b | 29 | 30 | 10 | B8 | GSKEsRTTTL | 4063 | 120.000 |
| 174 | HCV 1b | 29 | 52 | 10 | B8 | SCRHrRLASM | 4064 | 80.000 |
| 175 | HCV 1b | 29 | 88 | 9 | B8 | LAKEGGDPL | 4065 | 24.000 |
| 176 | HCV 1b | 29 | 88 | 9 | B_3501 | LAKEGGDPL | 4066 | 18.000 |
| 177 | HCV 1b | 29 | 30 | 10 | B_3501 | GSKEsRTTTL | 4067 | 30.000 |
| 178 | HCV 1b | 29 | 127 | 10 | B_3501 | GSCDpTRYWL | 4068 | 10.000 |
| 179 | HCV 1b | 29 | 164 | 10 | B_4403 | SEKNsGAGTW | 4069 | 36.000 |
| 180 | HCV 1b | 29 | 114 | 10 | B_4403 | MEVStATSGS | 4070 | 18.000 |
| 181 | HCV 1b | 29 | 66 | 10 | B_4403 | GETWwVVHVA | 4071 | 18.000 |
| 182 | HCV 1b | 29 | 32 | 9 | B_4403 | KESRTTTLF | 4072 | 90.000 |
| 183 | HCV 1b | 29 | 66 | 9 | B_4403 | GETWWVVHV | 4073 | 12.000 |
| 184 | HCV 1b | 30 | 64 | 9 | A1 | SLDWSQVLK | 4074 | 20.000 |
| 185 | HCV 1b | 30 | 84 | 10 | A_0201 | SLSHePEHGV | 4075 | 69.552 |
| 186 | HCV 1b | 30 | 8 | 10 | A_0201 | VLLQvLGPTI | 4076 | 65.622 |
| 187 | HCV 1b | 30 | 38 | 10 | A_0201 | MMPSpRQTPL | 4077 | 26.228 |
| 188 | HCV 1b | 30 | 68 | 10 | A_0201 | SQVLkSVNTV | 4078 | 16.219 |
| 189 | HCV 1b | 30 | 9 | 10 | A_0201 | LLQVlGPTIL | 4079 | 14.890 |
| 190 | HCV 1b | 30 | 3 | 10 | A_0201 | NVPChVLLQV | 4080 | 13.997 |
| 191 | HCV 1b | 30 | 17 | 9 | A_0201 | ILMEPFLTC | 4081 | 243.428 |
| 192 | HCV 1b | 30 | 22 | 9 | A_0201 | FLTCPVICA | 4082 | 52.561 |
| 193 | HCV 1b | 30 | 69 | 9 | A_0201 | QVLKSVNTV | 4083 | 51.790 |
| 194 | HCV 1b | 30 | 16 | 9 | A_0201 | TILMEPFLT | 4084 | 21.989 |
| 195 | HCV 1b | 30 | 9 | 9 | A_0201 | LLQVLGPTI | 4085 | 17.736 |
| 196 | HCV 1b | 30 | 8 | 9 | A_0201 | VLLQVLGPT | 4086 | 14.015 |
| 197 | HCV 1b | 30 | 63 | 9 | A24 | RSLDWSQVL | 4087 | 17.280 |
| 198 | HCV 1b | 30 | 46 | 10 | A3 | PLYPrWHEKK | 4088 | 45.000 |
| 199 | HCV 1b | 30 | 64 | 9 | A3 | SLDWSQVLK | 4089 | 20.000 |
| 200 | HCV 1b | 30 | 46 | 9 | A3 | PLYPRWHEK | 4090 | 15.000 |
| 201 | HCV 1b | 30 | 39 | 9 | B7 | MPSPRQTPL | 4091 | 80.000 |
| 202 | HCV 1b | 30 | 57 | 9 | B7 | TPGSCGRSL | 4092 | 80.000 |
| 203 | HCV 1b | 30 | 30 | 9 | B7 | APHGQVVCM | 4093 | 60.000 |
| 204 | HCV 1b | 30 | 4 | 10 | B7 | VPCHvLLQVL | 4094 | 80.000 |
| 205 | HCV 1b | 30 | 14 | 10 | B7 | GPTIIMEPFL | 4095 | 80.000 |
| 206 | HCV 1b | 30 | 30 | 10 | B7 | APHGqVVCMM | 4096 | 60.000 |
| 207 | HCV 1b | 30 | 76 | 10 | B7 | TVHIqSQTSL | 4097 | 20.000 |
| 208 | HCV 1b | 30 | 48 | 10 | B7 | YPRWhEKKGT | 4098 | 20.000 |
| 209 | HCV 1b | 30 | 39 | 9 | B8 | MPSPRQTPL | 4099 | 16.000 |
| 210 | HCV 1b | 30 | 30 | 9 | B_3501 | APHGQVVCM | 4100 | 40.000 |
| 211 | HCV 1b | 30 | 14 | 9 | B_3501 | GPTILMEPF | 4101 | 20.000 |

TABLE 4d-continued 1b (4-6)

| No. | Strain | ORF | Start | AA | HLA | Peptide sequence | SEQ ID NO: | Score |
|---|---|---|---|---|---|---|---|---|
| 212 | HCV 1b | 30 | 39 | 9 | B_3501 | MPSPRQTPL | 4102 | 20.000 |
| 213 | HCV 1b | 30 | 57 | 9 | B_3501 | TPGSCGRSL | 4103 | 20.000 |
| 214 | HCV 1b | 30 | 63 | 9 | B_3501 | RSLDWSQVL | 4104 | 20.000 |
| 215 | HCV 1b | 30 | 39 | 10 | B_3501 | MPSPrQTPLY | 4105 | 40.000 |
| 216 | HCV 1b | 30 | 30 | 10 | B_3501 | APHGqVVCMM | 4106 | 40.000 |
| 217 | HCV 1b | 30 | 14 | 10 | B_3501 | GPTIIMEPFL | 4107 | 20.000 |
| 218 | HCV 1b | 30 | 4 | 10 | B_3501 | VPCHvLLQVL | 4108 | 20.000 |
| 219 | HCV 1b | 30 | 87 | 10 | B_4403 | HEPEhGVEQS | 4109 | 12.000 |
| 220 | HCV 1b | 30 | 93 | 10 | B_4403 | VEQSsLIHWW | 4110 | 12.000 |
| 221 | HCV 1b | 30 | 93 | 9 | B_4403 | VEQSSLIHW | 4111 | 18.000 |
| 222 | HCV 1b | 31 | 5 | 10 | A_0201 | RLTRsSVEGI | 4112 | 11.758 |
| 223 | HCV 1b | 31 | 13 | 9 | A3 | GISPLMTLK | 4113 | 13.500 |
| 224 | HCV 1b | 31 | 9 | 10 | B_3501 | SSVEgISPLM | 4114 | 20.000 |
| 225 | HCV 1b | 31 | 8 | 10 | B_3501 | RSSVeGISPL | 4115 | 10.000 |
| 226 | HCV 1b | 32 | 35 | 10 | A1 | ATHPpKMLNR | 4116 | 12.500 |
| 227 | HCV 1b | 32 | 40 | 10 | A_0201 | KMLNrRVLWV | 4117 | 8.228.881 |
| 228 | HCV 1b | 32 | 41 | 10 | A_0201 | MLNRrVLWVV | 4118 | 836.241 |
| 229 | HCV 1b | 32 | 46 | 10 | A_0201 | VLWVvSGLVI | 4119 | 60.355 |
| 230 | HCV 1b | 32 | 52 | 10 | A_0201 | GLVIeAVNAI | 4120 | 23.995 |
| 231 | HCV 1b | 32 | 27 | 10 | A_0201 | ALGGaSWAAT | 4121 | 12.668 |
| 232 | HCV 1b | 32 | 49 | 10 | A_0201 | VVSGlVIEAV | 4122 | 11.660 |
| 233 | HCV 1b | 32 | 77 | 9 | A24 | KYCIPLMKF | 4123 | 220.000 |
| 234 | HCV 1b | 32 | 45 | 9 | A24 | RVLWVVSGL | 4124 | 16.800 |
| 235 | HCV 1b | 32 | 20 | 9 | B7 | APTKAEAAL | 4125 | 240.000 |
| 236 | HCV 1b | 32 | 74 | 9 | B7 | KPAKYCIPL | 4126 | 80.000 |
| 237 | HCV 1b | 32 | 34 | 9 | B7 | AATHPPKML | 4127 | 54.000 |
| 238 | HCV 1b | 32 | 45 | 9 | B7 | RVLWVVSGL | 4128 | 20.000 |
| 239 | HCV 1b | 32 | 6 | 9 | B7 | FPRPMLPTA | 4129 | 20.000 |
| 240 | HCV 1b | 32 | 74 | 10 | B7 | KPAKyCIPLM | 4130 | 20.000 |
| 241 | HCV 1b | 32 | 6 | 10 | B7 | FPRPmLPTAA | 4131 | 20.000 |
| 242 | HCV 1b | 32 | 33 | 10 | B7 | WAAThPPKML | 4132 | 18.000 |
| 243 | HCV 1b | 32 | 90 | 10 | B7 | AQNVsRARHL | 4133 | 12.000 |
| 244 | HCV 1b | 32 | 38 | 10 | B7 | PPKMlNRRVL | 4134 | 12.000 |
| 245 | HCV 1b | 32 | 74 | 10 | B_3501 | KPAKyCIPLM | 4135 | 80.000 |
| 246 | HCV 1b | 32 | 80 | 10 | B_3501 | IPLMkFHMCF | 4136 | 20.000 |
| 247 | HCV 1b | 32 | 125 | 10 | B_3501 | CSAScIPCSM | 4137 | 10.000 |
| 248 | HCV 1b | 32 | 1 | 10 | B_3501 | MSTStFPRPM | 4138 | 10.000 |
| 249 | HCV 1b | 32 | 74 | 9 | B_3501 | KPAKYCIPL | 4139 | 40.000 |
| 250 | HCV 1b | 32 | 20 | 9 | B_3501 | APTKAEAAL | 4140 | 20.000 |
| 251 | HCV 1b | 32 | 24 | 9 | B_4403 | AEAALGGAS | 4141 | 16.000 |
| 252 | HCV 1b | 32 | 24 | 10 | B_4403 | AEAAlGGASW | 4142 | 48.000 |
| 253 | HCV 1b | 32 | 55 | 10 | B_4403 | IEAVnAINDA | 4143 | 12.000 |
| 254 | HCV 1b | 33 | 31 | 9 | A1 | SADMHAMMY | 4144 | 125.000 |
| 255 | HCV 1b | 33 | 2 | 9 | A1 | TTLPVVRQY | 4145 | 12.500 |
| 256 | HCV 1b | 33 | 51 | 9 | A1 | WTAPSLYSK | 4146 | 10.000 |
| 257 | HCV 1b | 33 | 36 | 10 | A_0201 | AMMYIVMGWV | 4147 | 305.644 |
| 258 | HCV 1b | 33 | 39 | 9 | A_0201 | YLVMGWVRV | 4148 | 543.897 |
| 259 | HCV 1b | 33 | 37 | 9 | A_0201 | MMYLVMGWV | 4149 | 449.379 |
| 260 | HCV 1b | 33 | 3 | 9 | A_0201 | TLPVVRQYA | 4150 | 27.324 |
| 261 | HCV 1b | 33 | 16 | 10 | A24 | RTPPtSTQVL | 4151 | 17.280 |
| 262 | HCV 1b | 33 | 37 | 10 | A3 | MMYLvMGWVR | 4152 | 60.000 |
| 263 | HCV 1b | 33 | 17 | 9 | B7 | TPPTSTQVL | 4153 | 80.000 |
| 264 | HCV 1b | 33 | 14 | 9 | B7 | AARTPPTST | 4154 | 13.500 |
| 265 | HCV 1b | 33 | 53 | 9 | B7 | APSLYSKGV | 4155 | 12.000 |
| 266 | HCV 1b | 33 | 62 | 10 | B7 | GPCSvGFSRM | 4156 | 20.000 |
| 267 | HCV 1b | 33 | 28 | 10 | B7 | TSRSaDMHAM | 4157 | 10.000 |
| 268 | HCV 1b | 33 | 68 | 9 | B8 | FSRMRHFHI | 4158 | 20.000 |
| 269 | HCV 1b | 33 | 11 | 10 | B8 | AARAaRTPPT | 4159 | 16.000 |
| 270 | HCV 1b | 33 | 28 | 10 | B_3501 | TSRSaDMHAM | 4160 | 45.000 |
| 271 | HCV 1b | 33 | 30 | 10 | B_3501 | RSADmHAMMY | 4161 | 40.000 |
| 272 | HCV 1b | 33 | 62 | 10 | B_3501 | GPCSvGFSRM | 4162 | 40.000 |
| 273 | HCV 1b | 33 | 48 | 10 | B_3501 | TSFWtAPSLY | 4163 | 10.000 |
| 274 | HCV 1b | 33 | 30 | 9 | B_3501 | RSADMHAMM | 4164 | 40.000 |
| 275 | HCV 1b | 33 | 17 | 9 | B_3501 | TPPTSTQVL | 4165 | 20.000 |
| 276 | HCV 1b | 33 | 2 | 9 | B_4403 | TTLPVVRQY | 4166 | 54.000 |
| 277 | HCV 1b | 33 | 1 | 10 | B_4403 | MTTLpVVRQY | 4167 | 13.500 |
| 278 | HCV 1b | 34 | 15 | 10 | A_0201 | WSWQtGNPGV | 4168 | 17.334 |
| 279 | HCV 1b | 35 | 3 | 10 | B7 | EGRSpGVTNL | 4169 | 40.000 |
| 280 | HCV 1b | 36 | 3 | 9 | A3 | LLPLPVLPR | 4170 | 36.000 |
| 281 | HCV 1b | 36 | 9 | 10 | B7 | LPRRcERDTA | 4171 | 30.000 |
| 282 | HCV 1b | 36 | 1 | 9 | B7 | MPLLPLPVL | 4172 | 120.000 |
| 283 | HCV 1b | 36 | 9 | 9 | B7 | LPRRCERDT | 4173 | 20.000 |
| 284 | HCV 1b | 36 | 1 | 9 | B_3501 | MPLLPLPVL | 4174 | 20.000 |
| 285 | HCV 1b | 37 | 3 | 10 | A_0201 | KVGSkLKSTV | 4175 | 21.300 |
| 286 | HCV 1b | 37 | 20 | 9 | A_0201 | SITESKSPV | 4176 | 39.210 |

TABLE 4d-continued 1b (4-6)

| No. | Strain | ORF | Start | AA | HLA | Peptide sequence | SEQ ID NO: | Score |
|---|---|---|---|---|---|---|---|---|
| 287 | HCV 1b | 37 | 9 | 10 | A24 | KSTVwVTHVL | 4177 | 11.200 |
| 288 | HCV 1b | 37 | 17 | 9 | A3 | VLQSITESK | 4178 | 30.000 |
| 289 | HCV 1b | 37 | 9 | 10 | B_3501 | KSTVwVTHVL | 4179 | 10.000 |
| 290 | HCV 1b | 38 | | | | no hits | | |
| 291 | HCV 1b | 39 | 7 | 9 | A_0201 | LMASMGMAL | 4180 | 26.228 |
| 292 | HCV 1b | 39 | 3 | 9 | A_0201 | CLPPLMASM | 4181 | 11.426 |
| 293 | HCV 1b | 39 | 4 | 10 | B7 | LPPLmASMGM | 4182 | 20.000 |
| 294 | HCV 1b | 39 | 4 | 10 | B_3501 | LPPLmASMGM | 4183 | 40.000 |
| 295 | HCV 1b | 40 | 7 | 9 | A1 | VTDPGGVAV | 4184 | 25.000 |
| 296 | HCV 1b | 40 | 7 | 10 | A1 | VTDPgGVAVA | 4185 | 25.000 |
| 297 | HCV 1b | 40 | 6 | 10 | A_0201 | TVTDpGGVAV | 4186 | 24.952 |
| 298 | HCV 1b | 40 | 34 | 9 | B_3501 | MPKIVVESV | 4187 | 12.000 |
| 299 | HCV 1b | 40 | 25 | 10 | B_3501 | VSAWsRTVPM | 4188 | 10.000 |
| 300 | HCV 1b | 41 | 15 | 10 | A1 | ALDIyAPNPK | 4189 | 10.000 |
| 301 | HCV 1b | 41 | 7 | 10 | A_0201 | LMLGsIPCAL | 4190 | 97.045 |
| 302 | HCV 1b | 41 | 6 | 10 | A_0201 | VLMLgSIPCA | 4191 | 71.872 |
| 303 | HCV 1b | 41 | 35 | 10 | A_0201 | TLYPwAAYAA | 4192 | 15.898 |
| 304 | HCV 1b | 41 | 35 | 9 | A_0201 | TLYPWAAYA | 4193 | 87.437 |
| 305 | HCV 1b | 41 | 46 | 9 | A_0201 | TLVLLPLPV | 4194 | 69.552 |
| 306 | HCV 1b | 41 | 7 | 9 | A_0201 | LMLGSIPCA | 4195 | 51.908 |
| 307 | HCV 1b | 41 | 8 | 9 | A_0201 | MLGSIPCAL | 4196 | 36.316 |
| 308 | HCV 1b | 41 | 48 | 9 | A_0201 | VLLPLPVGA | 4197 | 31.249 |
| 309 | HCV 1b | 41 | 6 | 9 | A_0201 | VLMLGSIPC | 4198 | 31.249 |
| 310 | HCV 1b | 41 | 1 | 9 | A_0201 | MVLTPVLML | 4199 | 27.042 |
| 311 | HCV 1b | 41 | 41 | 9 | A24 | AYAAGTLVL | 4200 | 200.000 |
| 312 | HCV 1b | 41 | 41 | 10 | A24 | AYAAgTLVLL | 4201 | 200.000 |
| 313 | HCV 1b | 41 | 15 | 10 | A3 | ALDIyAPNPK | 4202 | 20.000 |
| 314 | HCV 1b | 41 | 1 | 9 | B7 | MVLTPVLML | 4203 | 30.000 |
| 315 | HCV 1b | 41 | 42 | 9 | B7 | YAAGTLVLL | 4204 | 12.000 |
| 316 | HCV 1b | 41 | 44 | 9 | B7 | AGTLVLLPL | 4205 | 12.000 |
| 317 | HCV 1b | 41 | 39 | 9 | B7 | WAAYAAGTL | 4206 | 12.000 |
| 318 | HCV 1b | 41 | 22 | 10 | B8 | NPKVaATDGL | 4207 | 16.000 |
| 319 | HCV 1b | 41 | 22 | 10 | B_3501 | NPKVaATDGL | 4208 | 60.000 |
| 320 | HCV 1b | 41 | 50 | 10 | B_3501 | LPLPvGACRW | 4209 | 10.000 |
| 321 | HCV 1b | 41 | 10 | 10 | B_3501 | GSIPcALDIY | 4210 | 10.000 |
| 322 | HCV 1b | 41 | 33 | 10 | B_3501 | TSTLyPWAAY | 4211 | 10.000 |
| 323 | HCV 1b | 41 | 10 | 10 | B_4403 | GSIPcALDIY | 4212 | 67.500 |
| 324 | HCV 1b | 41 | 28 | 10 | B_4403 | TDGLrTSTLY | 4213 | 22.500 |
| 325 | HCV 1b | 41 | 29 | 9 | B_4403 | DGLRTSTLY | 4214 | 27.000 |
| 326 | HCV 1b | 41 | 34 | 9 | B_4403 | STLYPWAAY | 4215 | 12.000 |
| 327 | HCV 1b | 42 | 2 | 10 | B_4403 | DSTGtKSTAF | 4216 | 10.125 |
| 328 | HCV 1b | 43 | | | | no hits | | |
| 329 | HCV 1b | 44 | 1 | 9 | A_0201 | MMQPSRPRV | 4217 | 85.394 |
| 330 | HCV 1b | 44 | 3 | 9 | B_3501 | QPSRPRVCW | 4218 | 10.000 |
| 331 | HCV 1b | 45 | 32 | 9 | A_0201 | KMMSPHAAV | 4219 | 650.504 |
| 332 | HCV 1b | 45 | 16 | 9 | B7 | GPRSISFPL | 4220 | 800.000 |
| 333 | HCV 1b | 45 | 71 | 9 | B7 | QSRSGVRWL | 4221 | 40.000 |
| 334 | HCV 1b | 45 | 7 | 9 | B7 | HPRPSRLSA | 4222 | 30.000 |
| 335 | HCV 1b | 45 | 16 | 9 | B8 | GPRSISFPL | 4223 | 16.000 |
| 336 | HCV 1b | 45 | 16 | 9 | B_3501 | GPRSISFPL | 4224 | 60.000 |
| 337 | HCV 1b | 45 | 71 | 9 | B_3501 | QSRSGVRWL | 4225 | 15.000 |
| 338 | HCV 1b | 45 | 30 | 9 | B_3501 | RPKMMSPHA | 4226 | 12.000 |
| 339 | HCV 1b | 45 | 26 | 9 | B_4403 | AETGRPKMM | 4227 | 18.000 |
| 340 | HCV 1b | 45 | 47 | 10 | A_0201 | ILVSmSEKTT | 4228 | 12.668 |
| 341 | HCV 1b | 45 | 45 | 10 | A3 | VMILvSMSEK | 4229 | 45.000 |
| 342 | HCV 1b | 45 | 39 | 10 | B7 | AVSApQVMIL | 4230 | 60.000 |
| 343 | HCV 1b | 45 | 42 | 10 | B7 | APQVmILVSM | 4231 | 60.000 |
| 344 | HCV 1b | 45 | 4 | 10 | B7 | RSRHpRPSRL | 4232 | 40.000 |
| 345 | HCV 1b | 45 | 70 | 10 | B7 | AQSRsGVRWL | 4233 | 12.000 |
| 346 | HCV 1b | 45 | 15 | 10 | B7 | AGPRsISFPL | 4234 | 12.000 |
| 347 | HCV 1b | 45 | 4 | 10 | B8 | RSRHpRPSRL | 4235 | 40.000 |
| 348 | HCV 1b | 45 | 61 | 10 | B8 | TARSrRPAWA | 4236 | 16.000 |
| 349 | HCV 1b | 45 | 42 | 10 | B_3501 | APQVmILVSM | 4237 | 40.000 |
| 350 | HCV 1b | 45 | 4 | 10 | B_3501 | RSRHpRPSRL | 4238 | 30.000 |
| 351 | HCV 1b | 45 | 30 | 10 | B_3501 | RPKMmSPHAA | 4239 | 12.000 |
| 352 | HCV 1b | 45 | 26 | 10 | B_4403 | AETGrPKMMS | 4240 | 12.000 |
| 353 | HCV 1b | 45 | 52 | 10 | B_4403 | SEKTtGSTAT | 4241 | 12.000 |
| 354 | HCV 1b | 46 | 1 | 9 | A24 | MYVPVSAPS | 4242 | 12.600 |
| 355 | HCV 1b | 46 | 3 | 9 | B7 | VPVSAPSFM | 4243 | 20.000 |
| 356 | HCV 1b | 46 | 3 | 9 | B_3501 | VPVSAPSFM | 4244 | 40.000 |
| 357 | HCV 1b | 46 | 7 | 9 | B_3501 | APSFMKAIW | 4245 | 10.000 |
| 358 | HCV 1b | 46 | 2 | 10 | A_0201 | YVPVsAPSFM | 4246 | 10.998 |
| 359 | HCV 1b | 46 | 1 | 10 | A24 | MYVPvSAPSF | 4247 | 180.000 |
| 360 | HCV 1b | 47 | 58 | 9 | A24 | KYCNHHMSL | 4248 | 400.000 |
| 361 | HCV 1b | 47 | 9 | 9 | B7 | GPSMASRSL | 4249 | 80.000 |

TABLE 4d-continued 1b (4-6)

| No. | Strain | ORF | Start | AA | HLA | Peptide sequence | SEQ ID NO: | Score |
|---|---|---|---|---|---|---|---|---|
| 362 | HCV 1b | 47 | 34 | 9 | B7 | MASRPPRTL | 4250 | 18.000 |
| 363 | HCV 1b | 47 | 9 | 9 | B_3501 | GPSMASRSL | 4251 | 20.000 |
| 364 | HCV 1b | 47 | 4 | 9 | B_3501 | WSTMSGPSM | 4252 | 10.000 |
| 365 | HCV 1b | 47 | 51 | 9 | B_4403 | CASALVIKY | 4253 | 13.500 |
| 366 | HCV 1b | 47 | 21 | 10 | A_0201 | KISSgWTAHV | 4254 | 33.472 |
| 367 | HCV 1b | 47 | 32 | 10 | A_0201 | RMMAsRPPRT | 4255 | 19.913 |
| 368 | HCV 1b | 47 | 58 | 10 | A24 | KYCNhHMSLA | 4256 | 10.000 |
| 369 | HCV 1b | 47 | 41 | 10 | A3 | TLRGgTHTCK | 4257 | 30.000 |
| 370 | HCV 1b | 47 | 13 | 10 | B7 | ASRSlVMSKI | 4258 | 12.000 |
| 371 | HCV 1b | 47 | 50 | 10 | B_4403 | KCASaLVIKY | 4259 | 27.000 |
| 372 | HCV 1b | 48 | 70 | 9 | A1 | TTDPTPYRY | 4260 | 1.250.000 |
| 373 | HCV 1b | 48 | 23 | 9 | A3 | ALRTTRFSK | 4261 | 60.000 |
| 374 | HCV 1b | 48 | 16 | 9 | B7 | CAPATDAAL | 4262 | 12.000 |
| 375 | HCV 1b | 48 | 56 | 9 | B_3501 | KSSRTYSHL | 4263 | 10.000 |
| 376 | HCV 1b | 48 | 21 | 9 | B_4403 | DAALRTTRF | 4264 | 13.500 |
| 377 | HCV 1b | 48 | 70 | 10 | A1 | TTDPtPYRYC | 4265 | 12.500 |
| 378 | HCV 1b | 48 | 19 | 10 | A1 | ATDAaLRTTR | 4266 | 12.500 |
| 379 | HCV 1b | 48 | 23 | 10 | A_0201 | ALRTtRFSKV | 4267 | 10.043 |
| 380 | HCV 1b | 48 | 75 | 10 | A24 | PYRYcTSTIF | 4268 | 10.000 |
| 381 | HCV 1b | 48 | 23 | 10 | B8 | ALRTtRFSKV | 4269 | 24.000 |
| 382 | HCV 1b | 48 | 51 | 10 | B8 | SARRrKSSRT | 4270 | 16.000 |
| 383 | HCV 1b | 48 | 67 | 10 | B_4403 | TETTtDPTPY | 4271 | 180.000 |
| 384 | HCV 1b | 48 | 20 | 10 | B_4403 | TDAAlRTTRF | 4272 | 22.500 |
| 385 | HCV 1b | 49 | | | | no hits | | |
| 386 | HCV 1b | 50 | 30 | 9 | A_0201 | VLLSSSTSV | 4273 | 437.482 |
| 387 | HCV 1b | 50 | 9 | 9 | A_0201 | VLVNPVLFI | 4274 | 224.357 |
| 388 | HCV 1b | 50 | 1 | 9 | A_0201 | MLHGGPPHV | 4275 | 118.238 |
| 389 | HCV 1b | 50 | 38 | 9 | A_0201 | VSFSPQLYV | 4276 | 15.707 |
| 390 | HCV 1b | 50 | 16 | 9 | A_0201 | FIHVQPNQL | 4277 | 13.512 |
| 391 | HCV 1b | 50 | 43 | 9 | A3 | QLYVGTPER | 4278 | 20.000 |
| 392 | HCV 1b | 50 | 24 | 9 | B7 | LPCGGRVLL | 4279 | 120.000 |
| 393 | HCV 1b | 50 | 52 | 9 | B7 | SVVPTTTGL | 4280 | 20.000 |
| 394 | HCV 1b | 50 | 24 | 9 | B_3501 | LPCGGRVLL | 4281 | 20.000 |
| 395 | HCV 1b | 50 | 57 | 9 | B_4403 | TTGLGVKQY | 4282 | 13.500 |
| 396 | HCV 1b | 50 | 37 | 10 | A_0201 | SVSFsPQLYV | 4283 | 33.472 |
| 397 | HCV 1b | 50 | 29 | 10 | A_0201 | RVLLsSSTSV | 4284 | 22.517 |
| 398 | HCV 1b | 50 | 23 | 10 | A_0201 | QLPCgGRVLL | 4285 | 21.362 |
| 399 | HCV 1b | 50 | 10 | 10 | A_0201 | LVNPvLFIHV | 4286 | 19.657 |
| 400 | HCV 1b | 50 | 1 | 10 | A_0201 | MLHGgPPHVL | 4287 | 14.890 |
| 401 | HCV 1b | 50 | 45 | 10 | A_0201 | YVGTpERSVV | 4288 | 11.478 |
| 402 | HCV 1b | 50 | 53 | 10 | A_0201 | VVPTtTGLGV | 4289 | 10.346 |
| 403 | HCV 1b | 50 | 15 | 10 | A24 | LFIHvQPNQL | 4290 | 36.000 |
| 404 | HCV 1b | 50 | 51 | 10 | A24 | RSVVpTTTGL | 4291 | 12.000 |
| 405 | HCV 1b | 50 | 67 | 10 | B_3501 | GPHTcDAGTI | 4292 | 12.000 |
| 406 | HCV 1b | 50 | 51 | 10 | B_3501 | RSVVpTTTGL | 4293 | 10.000 |
| 407 | HCV 1b | 50 | 36 | 10 | B_3501 | TSVSfSPQLY | 4294 | 10.000 |
| 408 | HCV 1b | 50 | 56 | 10 | B_4403 | TTTGLGVKQY | 4295 | 20.250 |
| 409 | HCV 1b | 51 | 6 | 10 | B7 | AMRSgHPDAL | 4296 | 120.000 |
| 410 | HCV 1b | 51 | 8 | 10 | B_3501 | RSGHpDALNL | 4297 | 15.000 |
| 411 | HCV 1b | 52 | 15 | 9 | A_0201 | LLMCQLPLV | 4298 | 1.006.209 |
| 412 | HCV 1b | 52 | 14 | 9 | A_0201 | VLLMCQLPL | 4299 | 134.369 |
| 413 | HCV 1b | 52 | 8 | 9 | A_0201 | SLQFRAVLL | 4300 | 21.362 |
| 414 | HCV 1b | 52 | 12 | 9 | A24 | RAVLLMCQL | 4301 | 14.400 |
| 415 | HCV 1b | 52 | 12 | 9 | B7 | RAVLLMCQL | 4302 | 12.000 |
| 416 | HCV 1b | 52 | 14 | 10 | A_0201 | VLLMcQLPLV | 4303 | 1.006.209 |
| 417 | HCV 1b | 52 | 19 | 10 | A_0201 | QLPLvFTSWI | 4304 | 218.046 |
| 418 | HCV 1b | 52 | 16 | 10 | A_0201 | LMCQlPLVFT | 4305 | 115.740 |
| 419 | HCV 1b | 52 | 8 | 10 | A_0201 | SLQFrAVLLM | 4306 | 11.426 |
| 420 | HCV 1b | 52 | 13 | 10 | B7 | AVLLmCQLPL | 4307 | 60.000 |
| 421 | HCV 1b | 52 | 2 | 10 | B_3501 | NPVWrESLQF | 4308 | 30.000 |
| 422 | HCV 1b | 52 | 20 | 10 | B_3501 | LPLVfTSWIF | 4309 | 20.000 |
| 423 | HCV 1b | 53 | | | | no hits | | |
| 424 | HCV 1b | 54 | 1 | 9 | A_0201 | MLLFLAASV | 4310 | 437.482 |
| 425 | HCV 1b | 54 | 19 | 9 | A_0201 | KLLSRTQGT | 4311 | 96.503 |
| 426 | HCV 1b | 54 | 42 | 9 | A_0201 | ILELEQSFV | 4312 | 41.620 |
| 427 | HCV 1b | 54 | 33 | 9 | A_0201 | MIMSAASYT | 4313 | 35.448 |
| 428 | HCV 1b | 54 | 34 | 9 | A_0201 | IMSAASYTI | 4314 | 12.809 |
| 429 | HCV 1b | 54 | 37 | 9 | B7 | AASYTILEL | 4315 | 36.000 |
| 430 | HCV 1b | 54 | 12 | 9 | B7 | SATQQREKL | 4316 | 18.000 |
| 431 | HCV 1b | 54 | 13 | 9 | B7 | ATQQREKLL | 4317 | 12.000 |
| 432 | HCV 1b | 54 | 45 | 9 | B_4403 | LEQSFVTWY | 4318 | 540.000 |
| 433 | HCV 1b | 54 | 43 | 9 | B_4403 | LELEQSFVT | 4319 | 12.000 |
| 434 | HCV 1b | 54 | 44 | 10 | A1 | ELEQsFVTWY | 4320 | 45.000 |
| 435 | HCV 1b | 54 | 41 | 10 | A_0201 | TILElEQSFV | 4321 | 797.922 |
| 436 | HCV 1b | 54 | 2 | 10 | A_0201 | LLFLaASVGV | 4322 | 437.482 |

TABLE 4d-continued 1b (4-6)

| No. | Strain | ORF | Start | AA | HLA | Peptide sequence | SEQ ID NO: | Score |
|---|---|---|---|---|---|---|---|---|
| 437 | HCV 1b | 54 | 32 | 10 | A_0201 | CMIMsAASYT | 4323 | 29.601 |
| 438 | HCV 1b | 54 | 4 | 10 | A_0201 | FLAAsVGVSA | 4324 | 22.853 |
| 439 | HCV 1b | 54 | 34 | 10 | A_0201 | IMSAaSYTIL | 4325 | 16.130 |
| 440 | HCV 1b | 54 | 45 | 10 | A_0201 | LEQSfVTWYI | 4326 | 14.226 |
| 441 | HCV 1b | 54 | 44 | 10 | A3 | ELEQsFVTWY | 4327 | 10.800 |
| 442 | HCV 1b | 54 | 49 | 10 | B7 | FVTWyIPDTL | 4328 | 20.000 |
| 443 | HCV 1b | 54 | 12 | 10 | B7 | SATQqREKLL | 4329 | 12.000 |
| 444 | HCV 1b | 54 | 36 | 10 | B7 | SAASyTILEL | 4330 | 12.000 |
| 445 | HCV 1b | 54 | 12 | 10 | B8 | SATQqREKLL | 4331 | 16.000 |
| 446 | HCV 1b | 54 | 43 | 10 | B_4403 | LELEqSFVTW | 4332 | 24.000 |
| 447 | HCV 1b | 54 | 31 | 10 | B_4403 | VCMImSAASY | 4333 | 13.500 |
| 448 | HCV 1b | 55 | 14 | 9 | A_0201 | KEQPGRFPV | 4334 | 27.454 |
| 449 | HCV 1b | 55 | 12 | 9 | B_4403 | IEKEQPGRF | 4335 | 40.000 |
| 450 | HCV 1b | 55 | 14 | 9 | B_4403 | KEQPGRFPV | 4336 | 12.000 |
| 451 | HCV 1b | 56 | 42 | 9 | B7 | HPAHPIPSL | 4337 | 120.000 |
| 452 | HCV 1b | 56 | 12 | 9 | B7 | RVSMTLPKL | 4338 | 20.000 |
| 453 | HCV 1b | 56 | 42 | 9 | B_3501 | HPAHPIPSL | 4339 | 20.000 |
| 454 | HCV 1b | 56 | 8 | 10 | A24 | KPHVrVSMTL | 4340 | 11.200 |
| 455 | HCV 1b | 56 | 8 | 10 | B7 | KPHVrVSMTL | 4341 | 80.000 |
| 456 | HCV 1b | 56 | 35 | 10 | B7 | EPRGdRSHPA | 4342 | 20.000 |
| 457 | HCV 1b | 56 | 2 | 10 | B7 | YPMRsAKPHV | 4343 | 12.000 |
| 458 | HCV 1b | 56 | 35 | 10 | B8 | EPRGdRSHPA | 4344 | 32.000 |
| 459 | HCV 1b | 56 | 19 | 10 | B8 | KLRDlRRGSV | 4345 | 18.000 |
| 460 | HCV 1b | 56 | 8 | 10 | B_3501 | KPHVrVSMTL | 4346 | 40.000 |
| 461 | HCV 1b | 56 | 6 | 10 | B_3501 | SAKPhRVSM | 4347 | 18.000 |
| 462 | HCV 1b | 57 | 15 | 9 | A24 | PYQAVPQGL | 4348 | 50.400 |
| 463 | HCV 1b | 57 | 22 | 9 | A3 | GLSRPNTTR | 4349 | 18.000 |
| 464 | HCV 1b | 57 | 23 | 9 | B7 | LSRPNTTRL | 4350 | 40.000 |
| 465 | HCV 1b | 57 | 8 | 9 | B_3501 | LPGHSQAPY | 4351 | 40.000 |
| 466 | HCV 1b | 57 | 23 | 9 | B_3501 | LSRPNTTRL | 4352 | 15.000 |
| 467 | HCV 1b | 57 | 22 | 10 | A_0201 | GLSRpNTTRL | 4353 | 21.362 |
| 468 | HCV 1b | 57 | 14 | 10 | B7 | APYQaVPQGL | 4354 | 240.000 |
| 469 | HCV 1b | 57 | 14 | 10 | B_3501 | APYQaVPQGL | 4355 | 20.000 |
| 470 | HCV 1b | 58 | 63 | 9 | A1 | QVDAYPYRK | 4356 | 20.000 |
| 471 | HCV 1b | 58 | 2 | 9 | A_0201 | RLTDLSQLA | 4357 | 20.369 |
| 472 | HCV 1b | 58 | 46 | 9 | A24 | KWPIGLECL | 4358 | 12.000 |
| 473 | HCV 1b | 58 | 63 | 9 | A3 | QVDAYPYRK | 4359 | 18.000 |
| 474 | HCV 1b | 58 | 43 | 9 | B7 | KNRKWPIGL | 4360 | 40.000 |
| 475 | HCV 1b | 58 | 61 | 9 | B_4403 | GEQVDAYPY | 4361 | 180.000 |
| 476 | HCV 1b | 58 | 60 | 10 | A1 | VGEQvDAYPY | 4362 | 22.500 |
| 477 | HCV 1b | 58 | 2 | 10 | A_0201 | RLTDLSQLAV | 4363 | 285.163 |
| 478 | HCV 1b | 58 | 55 | 10 | B7 | APRSsVGEQV | 4364 | 120.000 |
| 479 | HCV 1b | 58 | 11 | 10 | B7 | VTRAkMEPPL | 4365 | 40.000 |
| 480 | HCV 1b | 58 | 55 | 10 | B_3501 | APRSsVGEQV | 4366 | 12.000 |
| 481 | HCV 1b | 58 | 58 | 10 | B_3501 | SSVGeQVDAY | 4367 | 10.000 |
| 482 | HCV 1b | 58 | 58 | 10 | B_4403 | SSVGeQVDAY | 4368 | 54.000 |
| 483 | HCV 1b | 59 | 1 | 9 | B_3501 | MSPDSQGWY | 4369 | 20.000 |
| 484 | HCV 1b | 60 | | | | no hits | | |
| 485 | HCV 1b | 61 | 2 | 9 | B7 | WGRQLAGFL | 4370 | 40.000 |
| 486 | HCV 1b | 62 | 7 | 9 | B7 | VAQRVDGQL | 4371 | 12.000 |
| 487 | HCV 1b | 62 | 10 | 10 | A1 | RVDGqLAFLR | 4372 | 25.000 |
| 488 | HCV 1b | 62 | 6 | 10 | A24 | RVAQrVDGQL | 4373 | 11.200 |
| 489 | HCV 1b | 62 | 6 | 10 | B7 | RVAQrVDGQL | 4374 | 20.000 |
| 490 | HCV 1b | 63 | 7 | 9 | A24 | RLQGRRRQL | 4375 | 12.000 |
| 491 | HCV 1b | 64 | 16 | 9 | B7 | TVFDMSGDL | 4376 | 20.000 |
| 492 | HCV 1b | 64 | 12 | 9 | B7 | DPHGTVFDM | 4377 | 20.000 |
| 493 | HCV 1b | 64 | 34 | 9 | B7 | DAVSPPDSL | 4378 | 18.000 |
| 494 | HCV 1b | 64 | 12 | 9 | B_3501 | DPHGTVFDM | 4379 | 40.000 |
| 495 | HCV 1b | 64 | 37 | 10 | B7 | SPPDsLVPAL | 4380 | 80.000 |
| 496 | HCV 1b | 64 | 37 | 10 | B_3501 | SPPDsLVPAL | 4381 | 40.000 |
| 497 | HCV 1b | 64 | 9 | 10 | B_3501 | RPDDpHGTVF | 4382 | 24.000 |
| 498 | HCV 1b | 65 | 53 | 9 | B7 | KPRSSRLRL | 4383 | 1.200.000 |
| 499 | HCV 1b | 65 | 53 | 9 | B_3501 | KPRSSRLRL | 4384 | 120.000 |
| 500 | HCV 1b | 65 | 28 | 10 | A_0201 | RQGHLLDVWV | 4385 | 38.785 |
| 501 | HCV 1b | 65 | 53 | 10 | B7 | KPRSsRLRLV | 4386 | 40.000 |
| 502 | HCV 1b | 65 | 53 | 10 | B8 | KPRSsRLRLV | 4387 | 24.000 |
| 503 | HCV 1b | 65 | 23 | 10 | B8 | DLSSiRQGHL | 4388 | 16.000 |
| 504 | HCV 1b | 65 | 53 | 10 | B_3501 | KPRSsRLRLV | 4389 | 24.000 |
| 505 | HCV 1b | 65 | 4 | 10 | B_4403 | NEMPsPPDGF | 4390 | 160.000 |
| 506 | HCV 1b | 66 | 42 | 9 | B7 | DVGVNTVCL | 4391 | 20.000 |
| 507 | HCV 1b | 66 | 14 | 9 | B7 | RATTIGKKL | 4392 | 12.000 |
| 508 | HCV 1b | 67 | | | | no hits | | |
| 509 | HCV 1b | 68 | 25 | 9 | A_0201 | NLSLDLVLV | 4393 | 159.970 |
| 510 | HCV 1b | 68 | 16 | 9 | A_0201 | GLCCGGNHL | 4394 | 21.362 |
| 511 | HCV 1b | 68 | 1 | 9 | A_0201 | MVNGPTHAV | 4395 | 10.346 |

TABLE 4d-continued 1b (4-6)

| No. | Strain | ORF | Start | AA | HLA | Peptide sequence | SEQ ID NO: | Score |
|---|---|---|---|---|---|---|---|---|
| 512 | HCV 1b | 68 | 29 | 9 | A3 | DLVLVPACK | 4396 | 13.500 |
| 513 | HCV 1b | 68 | 8 | 10 | B7 | AVDAgRQEGL | 4397 | 18.000 |
| 514 | HCV 1b | 69 | 12 | 9 | A_0201 | QLHEGHLDI | 4398 | 42.774 |
| 515 | HCV 1b | 69 | 10 | 9 | A24 | RAQLHEGHL | 4399 | 12.000 |
| 516 | HCV 1b | 69 | 10 | 9 | B7 | RAQLHEGHL | 4400 | 12.000 |
| 517 | HCV 1b | 69 | 4 | 10 | B7 | NVRAcQRAQL | 4401 | 300.000 |
| 518 | HCV 1b | 70 | 18 | 9 | B_4403 | LEHHERTEY | 4402 | 180.000 |
| 519 | HCV 1b | 70 | 17 | 10 | A1 | SLEHhERTEY | 4403 | 45.000 |
| 520 | HCV 1b | 70 | 9 | 10 | B7 | EVRHsGYASL | 4404 | 200.000 |
| 521 | HCV 1b | 70 | 6 | 10 | B_3501 | SAHEvRHSGY | 4405 | 12.000 |
| 522 | HCV 1b | 71 | 19 | 9 | A1 | RGDPHLQVR | 4406 | 12.500 |
| 523 | HCV 1b | 71 | 19 | 10 | A24 | RGDPhLQVRL | 4407 | 11.520 |
| 524 | HCV 1b | 71 | 25 | 10 | B7 | QVRLgPGDKI | 4408 | 30.000 |
| 525 | HCV 1b | 72 | | | | no hits | | |
| 526 | HCV 1b | 73 | | | | no hits | | |
| 527 | HCV 1b | 74 | 2 | 9 | A24 | VYPGHVAHL | 4409 | 300.000 |
| 528 | HCV 1b | 74 | 1 | 10 | A_0201 | MVYPgHVAHL | 4410 | 23.388 |
| 529 | HCV 1b | 74 | 2 | 10 | A24 | VYPGhVAHLV | 4411 | 10.500 |
| 530 | HCV 1b | 74 | 2 | 9 | A24 | VYPGhVAHLV | 4411 | 10.500 |
| 530 | HCV 1b | 74 | 1 | 10 | B7 | MVYPgHVAHL | 4412 | 20.000 |
| 531 | HCV 1b | 75 | | | | no hits | | |

TABLE 4e 2a (1-3)

| No. | Strain | ORF | Start | AA | HLA | Peptide sequence | SEQ ID NO | Score |
|---|---|---|---|---|---|---|---|---|
| 1 | 2a | 1 | 2 | 9 | B3501 | TPGIGRVTW | 44413 | 10 |
| 2 | 2a | 2 | 40 | 9 | A0201 | QMWLCSSAA | 4414 | 29.78 |
| 3 | 2a | 2 | 35 | 9 | A24 | GYRSHQMWL | 4415 | 200 |
| 4 | 2a | 2 | 3 | 10 | B3501 | VPMTASPGSF | 4416 | 20 |
| 5 | 2a | 2 | 19 | 10 | B3501 | SPGASRAREW | 4417 | 10 |
| 6 | 2a | 2 | 34 | 10 | B7 | AGYRSHQMWL | 4418 | 12 |
| 7 | 2a | 2 | 22 | 9 | B7 | ASRAREWEI | 4419 | 12 |
| 8 | 2a | 2 | 22 | 9 | B8 | ASRAREWEI | 4420 | 20 |
| 9 | 2a | 4 | 16 | 10 | A0201 | ILTPLTSNVV | 4421 | 48.478 |
| 10 | 2a | 4 | 15 | 10 | A0201 | SILTPLTSNV | 4422 | 35.385 |
| 11 | 2a | 4 | 11 | 10 | A0201 | TVLGSILTPL | 4423 | 15.907 |
| 12 | 2a | 4 | 12 | 10 | A0201 | VLGSILTPLT | 4424 | 12.668 |
| 13 | 2a | 4 | 16 | 9 | A0201 | ILTPLTSNV | 4425 | 118.238 |
| 14 | 2a | 4 | 12 | 9 | A0201 | VLGSILTPL | 4426 | 83.527 |
| 15 | 2a | 4 | 5 | 9 | A24 | TFCAPRTVL | 4427 | 20 |
| 16 | 2a | 4 | 8 | 10 | B3501 | APRTVLGSIL | 4428 | 60 |
| 17 | 2a | 4 | 8 | 9 | B3501 | APRTVLGSI | 4429 | 24 |
| 18 | 2a | 4 | 18 | 9 | B3501 | TPLTSNVVL | 4430 | 20 |
| 19 | 2a | 4 | 27 | 9 | B3501 | GPGSRRGAW | 4431 | 10 |
| 20 | 2a | 4 | 8 | 10 | B7 | APRTVLGSIL | 4432 | 2400 |
| 21 | 2a | 4 | 11 | 10 | B7 | TVLGSILTPL | 4433 | 20 |
| 22 | 2a | 4 | 8 | 9 | B7 | APRTVLGSI | 4434 | 240 |
| 23 | 2a | 4 | 18 | 9 | B7 | TPLTSNVVL | 4435 | 80 |
| 24 | 2a | 4 | 8 | 10 | B8 | APRTVLGSIL | 4436 | 16 |
| 25 | 2a | 4 | 6 | 8 | B8 | FCAPRTVL | 4437 | 16 |
| 26 | 2a | 5 | 5 | 8 | B3501 | LPLQNMSF | 4438 | 20 |
| 27 | 2a | 6 | 4 | 10 | A0201 | YILSSFSWLL | 4439 | 1424.811 |
| 28 | 2a | 6 | 9 | 10 | A0201 | FSWLLGTSKV | 4440 | 17.334 |
| 29 | 2a | 6 | 5 | 9 | A0201 | ILSSFSWLL | 4441 | 1035.008 |
| 30 | 2a | 6 | 4 | 9 | A0201 | YILSSFSWL | 4442 | 522.431 |
| 31 | 2a | 6 | 44 | 9 | A0201 | RLMPMMHLC | 4443 | 42.278 |
| 32 | 2a | 6 | 44 | 10 | A1 | RLMPMMHLCK | 4444 | 10 |
| 33 | 2a | 6 | 3 | 10 | A24 | SYILSSFSWL | 4445 | 360 |
| 34 | 2a | 6 | 45 | 9 | A3 | LWPMMHLCK | 4446 | 40 |
| 35 | 2a | 6 | 37 | 10 | B3501 | CSSHCPNRLM | 4447 | 10 |
| 36 | 2a | 6 | 41 | 8 | B3501 | CPNRLMPM | 4448 | 40 |
| 37 | 2a | 6 | 23 | 9 | B3501 | WPPIPSPAY | 4449 | 40 |
| 38 | 2a | 6 | 28 | 9 | B3501 | SPAYGPFAY | 4450 | 40 |
| 39 | 2a | 6 | 41 | 9 | B3501 | CPNRLMPMM | 4451 | 40 |
| 40 | 2a | 6 | 26 | 9 | B3501 | IPSPAYGPF | 4452 | 20 |
| 41 | 2a | 6 | 38 | 9 | B3501 | SSHCPNRLM | 4453 | 10 |
| 42 | 2a | 6 | 41 | 9 | B7 | CPNRLMPMM | 4454 | 20 |
| 43 | 2a | 7 | 2 | 10 | A0201 | ALYGLPPYSA | 4455 | 15.898 |
| 44 | 2a | 7 | 5 | 9 | A0201 | GLPPYSARV | 4456 | 69.552 |
| 45 | 2a | 7 | 8 | 9 | A24 | PYSARVWCL | 4457 | 20 |

TABLE 4e-continued 2a (1-3)

| No. Strain | ORF | Start | AA | HLA | Peptide sequence | SEQ ID NO | Score |
|---|---|---|---|---|---|---|---|
| 46 2a | 8 | 10 | 10 | A3 | GLPTACGTWR | 4458 | 12 |
| 47 2a | 8 | 4 | 8 | B3501 | SPLCRIGL | 4459 | 20 |
| 48 2a | 8 | 11 | 8 | B3501 | LPTACGTW | 4460 | 10 |
| 49 2a | 8 | 13 | 9 | B7 | TACGTWRSL | 4461 | 12 |
| 50 2a | 8 | 4 | 8 | B8 | SPLCRIGL | 4462 | 16 |
| 51 2a | 9 | 21 | 8 | B3501 | TPPRGGSF | 4463 | 20 |
| 52 2a | 9 | 5 | 9 | B3501 | CPPDSVGRF | 4464 | 40 |
| 53 2a | 9 | 35 | 9 | B3501 | TPSRHEVSW | 4465 | 10 |
| 54 2a | 9 | 9 | 10 | B7 | SVGRFSLAQL | 4466 | 20 |
| 55 2a | 9 | 10 | 9 | B7 | VGRFSLAQL | 4467 | 40 |
| 56 2a | 10 | 8 | 10 | A24 | KAPKSLSRTL | 4468 | 14.4 |
| 57 2a | 10 | 9 | 9 | B3501 | APKSLSRTL | 4469 | 60 |
| 58 2a | 10 | 8 | 10 | B7 | KAPKSLSRTL | 4470 | 12 |
| 59 2a | 10 | 9 | 9 | B7 | APKSLSRTL | 4471 | 240 |
| 60 2a | 10 | 5 | 9 | B7 | AVEKAPKSL | 4472 | 18 |
| 61 2a | 10 | 9 | 9 | B8 | APKSLSRTL | 4473 | 16 |
| 62 2a | 11 | 4 | 10 | B3501 | IPTLGLESEL | 4474 | 20 |
| 63 2a | 11 | 4 | 10 | B7 | IPTLGLESEL | 4475 | 80 |
| 64 2a | 11 | 1 | 9 | B7 | MASIPTLGL | 4476 | 18 |
| 65 2a | 12 | 19 | 10 | A0201 | YATNATPWTL | 4477 | 10.236 |
| 66 2a | 12 | 33 | 10 | A1 | ASEQFLTKQR | 4478 | 13.5 |
| 67 2a | 12 | 28 | 10 | B3501 | LPPSSASEQF | 4479 | 20 |
| 68 2a | 12 | 11 | 9 | B3501 | RAAPMTSSY | 4480 | 12 |
| 69 2a | 12 | 11 | 9 | B4403 | RAAPMTSSY | 4481 | 18 |
| 70 2a | 12 | 19 | 10 | B7 | YATNATPWTL | 4482 | 12 |
| 71 2a | 12 | 13 | 9 | B7 | APMTSSYAT | 4483 | 18 |
| 72 2a | 12 | 20 | 9 | B7 | ATNATPWTL | 4484 | 12 |
| 73 2a | 14 | 12 | 10 | A0201 | MLWHTTEGWT | 4485 | 75.181 |
| 74 2a | 14 | 8 | 9 | A0201 | GAWAMLWHT | 4486 | 14.819 |
| 75 2a | 14 | 5 | 10 | B3501 | RPFGAWAMLW | 4487 | 20 |
| 76 2a | 14 | 5 | 8 | B3501 | RPFGAWAM | 4488 | 80 |
| 77 2a | 14 | 5 | 9 | B3501 | RPFGAWAML | 4489 | 40 |
| 78 2a | 14 | 4 | 10 | B3901 | RRPFGAWAML | 4490 | 15 |
| 79 2a | 14 | 5 | 9 | B7 | RPFGAWAML | 4491 | 80 |
| 80 2a | 15 | 5 | 10 | A1 | VSEPQGCLIA | 4492 | 67.5 |
| 81 2a | 15 | 5 | 9 | A1 | VSEPQGCLI | 4493 | 13.5 |
| 82 2a | 15 | 26 | 10 | A24 | RGMSLRQRRL | 4494 | 12 |
| 83 2a | 15 | 6 | 10 | B4403 | SEPQGCLIAW | 4495 | 36 |
| 84 2a | 15 | 26 | 10 | B7 | RGMSLRQRRL | 4496 | 12 |
| 85 2a | 15 | 4 | 9 | B7 | LVSEPQGCL | 4497 | 30 |
| 86 2a | 15 | 17 | 9 | B7 | SVSATTQGL | 4498 | 20 |
| 87 2a | 16 | 5 | 10 | B3501 | FPKQSNRGRI | 4499 | 24 |
| 88 2a | 16 | 5 | 10 | B7 | FPKQSNRGRI | 4500 | 12 |
| 89 2a | 17 | 3 | 10 | A0201 | LLMKWRNVPL | 4501 | 134.369 |
| 90 2a | 17 | 2 | 9 | A0201 | RLLMKWRNV | 4502 | 87.496 |
| 91 2a | 17 | 8 | 10 | A24 | RNVPLKRLSL | 4503 | 14.4 |
| 92 2a | 17 | 4 | 10 | A3 | LMKWRNVPLK | 4504 | 60 |
| 93 2a | 17 | 16 | 10 | A3 | SLKRGSGWPR | 4505 | 12 |
| 94 2a | 17 | 10 | 8 | B3501 | VPLKRLSL | 4506 | 20 |
| 95 2a | 17 | 3 | 10 | B7 | LLMKWRNVPL | 4507 | 12 |
| 96 2a | 17 | 9 | 9 | B7 | NVPLKRLSL | 4508 | 30 |
| 97 2a | 17 | 10 | 8 | B8 | VPLKRLSL | 4509 | 16 |
| 98 2a | 17 | 4 | 9 | B8 | LMKWRNVPL | 4510 | 80 |
| 99 2a | 18 | 15 | 10 | A0201 | TLARSPPWRT | 4511 | 55.89 |
| 100 2a | 18 | 26 | 9 | A0201 | SICCLGFCL | 4512 | 17.037 |
| 101 2a | 18 | 9 | 10 | A3302 | SSHSRSTLAR | 4513 | 15 |
| 102 2a | 18 | 7 | 10 | B3501 | GPSSHSRSTL | 4514 | 20 |
| 103 2a | 18 | 7 | 10 | B7 | GPSSHSRSTL | 4515 | 120 |
| 104 2a | 20 | 4 | 9 | A0201 | RLPLGSIHL | 4516 | 21.362 |
| 105 2a | 20 | 4 | 9 | A24 | RLPLGSIHL | 4517 | 12 |
| 106 2a | 20 | 5 | 8 | B3501 | LPLGSIHL | 4518 | 20 |
| 107 2a | 20 | 2 | 9 | B3501 | RSRLPLGSI | 4519 | 12 |
| 108 2a | 21 | 1 | 10 | A0201 | MMWTWWMPTC | 4520 | 116.441 |
| 109 2a | 21 | 1 | 9 | A0201 | MMWTWWMPT | 4521 | 129.098 |
| 110 2a | 21 | 6 | 9 | A0201 | WMPTCSWGA | 4522 | 123.786 |
| 111 2a | 21 | 7 | 9 | B3501 | MPTCSWGAM | 4523 | 40 |
| 112 2a | 21 | 7 | 9 | B7 | MPTCSWGAM | 4524 | 20 |
| 113 2a | 22 | 37 | 10 | A0201 | LMSWPFRRQV | 4525 | 64.9 |
| 114 2a | 22 | 57 | 10 | A0201 | SLGIQTWSPT | 4526 | 12.668 |
| 115 2a | 22 | 6 | 10 | B3501 | WPSKPSASPL | 4527 | 20 |
| 116 2a | 22 | 35 | 8 | B3501 | RPLMSWPF | 4528 | 40 |
| 117 2a | 22 | 30 | 8 | B3501 | TPAVGRPL | 4529 | 20 |
| 118 2a | 22 | 40 | 8 | B3501 | WPFRRQVL | 4530 | 20 |
| 119 2a | 22 | 51 | 8 | B3501 | CPPSRGSL | 4531 | 20 |
| 120 2a | 22 | 30 | 9 | B3501 | TPAVGRPLM | 4532 | 40 |

TABLE 4e-continued 2a (1-3)

| No. | Strain | ORF | Start | AA | HLA | Peptide sequence | SEQ ID NO | Score |
|---|---|---|---|---|---|---|---|---|
| 121 | 2a | 22 | 6 | 10 | B7 | WPSKPSASPL | 4533 | 80 |
| 122 | 2a | 22 | 49 | 10 | B7 | PPCPPSRGSL | 4534 | 12 |
| 123 | 2a | 22 | 30 | 9 | B7 | TPAVGRPLM | 4535 | 30 |
| 124 | 2a | 22 | 40 | 8 | B8 | WPFRRQVL | 4536 | 16 |
| 125 | 2a | 22 | 51 | 8 | B8 | CPPSRGSL | 4537 | 16 |
| 126 | 2a | 24 | 55 | 10 | A0201 | KQLALSFTLT | 4538 | 18.59 |
| 127 | 2a | 24 | 57 | 10 | A0201 | LALSFTLTSV | 4539 | 13.975 |
| 128 | 2a | 24 | 75 | 9 | A0201 | FMMSHKSFL | 4540 | 1444.253 |
| 129 | 2a | 24 | 55 | 9 | A0201 | KQLALSFTL | 4541 | 162.682 |
| 130 | 2a | 24 | 58 | 9 | A0201 | ALSFTLTSV | 4542 | 159.97 |
| 131 | 2a | 24 | 56 | 9 | A0201 | QLALSFTLT | 4543 | 14.159 |
| 132 | 2a | 24 | 47 | 9 | A1 | WTPPRGVRK | 4544 | 10 |
| 133 | 2a | 24 | 7 | 10 | A24 | RFAACPGGPL | 4545 | 40 |
| 134 | 2a | 24 | 55 | 9 | A24 | KQLALSFTL | 4546 | 14.4 |
| 135 | 2a | 24 | 51 | 9 | A24 | RGVRKQLAL | 4547 | 12 |
| 136 | 2a | 24 | 75 | 10 | A3 | FMMSHKSFLR | 4548 | 18 |
| 137 | 2a | 24 | 32 | 10 | A3 | HQFLRPSWPK | 4549 | 13.5 |
| 138 | 2a | 24 | 76 | 9 | A3 | MMSHKSFLR | 4550 | 12 |
| 139 | 2a | 24 | 48 | 10 | B3501 | TPPRGVRKQL | 4551 | 20 |
| 140 | 2a | 24 | 73 | 10 | B3501 | WPFMMSHKSF | 4552 | 20 |
| 141 | 2a | 24 | 68 | 10 | B3501 | GSARRWPFMM | 4553 | 10 |
| 142 | 2a | 24 | 69 | 8 | B3501 | SARRWPFM | 4554 | 18 |
| 143 | 2a | 24 | 20 | 8 | B3501 | SPCGRTSW | 4555 | 10 |
| 144 | 2a | 24 | 39 | 9 | B3501 | WPKMRCSAW | 4556 | 30 |
| 145 | 2a | 24 | 69 | 9 | B3501 | SARRWPFMM | 4557 | 18 |
| 146 | 2a | 24 | 68 | 9 | B3501 | GSARRWPFM | 4558 | 10 |
| 147 | 2a | 24 | 48 | 10 | B7 | TPPRGVRKQL | 4559 | 120 |
| 148 | 2a | 24 | 58 | 10 | B7 | ALSFTLTSVL | 4560 | 12 |
| 149 | 2a | 24 | 49 | 9 | B7 | PPRGVRKQL | 4561 | 120 |
| 150 | 2a | 24 | 69 | 9 | B7 | SARRWPFMM | 4562 | 30 |
| 151 | 2a | 24 | 8 | 9 | B7 | FAACPGGPL | 4563 | 18 |
| 152 | 2a | 24 | 75 | 9 | B7 | FMMSHKSFL | 4564 | 12 |
| 153 | 2a | 24 | 34 | 9 | B7 | FLRPSWPKM | 4565 | 10 |
| 154 | 2a | 24 | 39 | 8 | B8 | WPKMRCSA | 4566 | 16 |
| 155 | 2a | 26 | 23 | 10 | A0201 | RLAPCLRRPV | 4567 | 13.91 |
| 156 | 2a | 26 | 7 | 9 | A0201 | TLPSLRETL | 4568 | 10.468 |
| 157 | 2a | 26 | 14 | 10 | A1 | TLELRRPYTR | 4569 | 18 |
| 158 | 2a | 26 | 20 | 9 | A24 | PYTRLAPCL | 4570 | 24 |
| 159 | 2a | 26 | 14 | 10 | A3101 | TLELRRPYTR | 4571 | 10 |
| 160 | 2a | 26 | 10 | 10 | A3 | SLRETLELRR | 4572 | 12 |
| 161 | 2a | 26 | 14 | 10 | A3 | TLELRRPYTR | 4573 | 12 |
| 162 | 2a | 26 | 27 | 9 | A3 | CLRRPVLPY | 4574 | 36 |
| 163 | 2a | 26 | 19 | 10 | B3501 | RPYTRLAPCL | 4575 | 40 |
| 164 | 2a | 26 | 8 | 10 | B3501 | LPSLRETLEL | 4576 | 30 |
| 165 | 2a | 26 | 8 | 8 | B3501 | LPSLRETL | 4577 | 20 |
| 166 | 2a | 26 | 25 | 9 | B3501 | APCLRRPVL | 4578 | 20 |
| 167 | 2a | 26 | 8 | 10 | B7 | LPSLRETLEL | 4579 | 80 |
| 168 | 2a | 26 | 19 | 10 | B7 | RPYTRLAPCL | 4580 | 80 |
| 169 | 2a | 26 | 2 | 10 | B7 | TPDALTLPSL | 4581 | 24 |
| 170 | 2a | 26 | 24 | 10 | B7 | LAPCLRRPVL | 4582 | 18 |
| 171 | 2a | 26 | 25 | 9 | B7 | APCLRRPVL | 4583 | 360 |
| 172 | 2a | 26 | 16 | 9 | B7 | ELRRPYTRL | 4584 | 60 |
| 173 | 2a | 26 | 24 | 10 | B8 | LAPCLRRPVL | 4585 | 16 |
| 174 | 2a | 26 | 8 | 8 | B8 | LPSLRETL | 4586 | 16 |
| 175 | 2a | 26 | 10 | 8 | B8 | SLRETLEL | 4587 | 12 |
| 176 | 2a | 26 | 16 | 9 | B8 | ELRRPYTRL | 4588 | 16 |
| 177 | 2a | 26 | 25 | 9 | B8 | APCLRRPVL | 4589 | 16 |
| 178 | 2a | 27 | 3 | 10 | A0201 | WLSSQKARGL | 4590 | 19.653 |
| 179 | 2a | 28 | 2 | 10 | A0201 | CLWHSAYRAA | 4591 | 12.37 |
| 180 | 2a | 28 | 2 | 9 | A0201 | CLWHSAYRA | 4592 | 41.234 |
| 181 | 2a | 31 | 2 | 10 | B7 | APVPPRFSSL | 4593 | 240 |
| 182 | 2a | 31 | 4 | 9 | B7 | VPPRFSSLL | 4594 | 80 |
| 183 | 2a | 31 | 2 | 10 | B8 | APVPPRFSSL | 4595 | 16 |
| 184 | 2a | 32 | 14 | 10 | A24 | SYGVGHDDEL | 4596 | 220 |
| 185 | 2a | 32 | 19 | 9 | B4403 | HDDELVTHY | 4597 | 67.5 |
| 186 | 2a | 34 | 14 | 9 | A3 | VLFHPQPSR | 4598 | 30 |
| 187 | 2a | 34 | 4 | 10 | B3501 | SPREVRVRPS | 4599 | 12 |
| 188 | 2a | 34 | 7 | 9 | B7 | EVRVRPSVL | 4600 | 200 |
| 189 | 2a | 34 | 4 | 10 | B8 | SPREVRVRPS | 4601 | 12 |
| 190 | 2a | 34 | 7 | 8 | B8 | EVRVRPSV | 4602 | 24 |
| 191 | 2a | 34 | 7 | 9 | B8 | EVRVRPSVL | 4603 | 160 |
| 192 | 2a | 35 | 1 | 9 | B7 | MVRLHVDEL | 4604 | 200 |
| 193 | 2a | 36 | 14 | 9 | A0201 | RLPLQALAL | 4605 | 21.362 |
| 194 | 2a | 36 | 2 | 10 | A24 | WFWALAHAEF | 4606 | 11 |
| 195 | 2a | 36 | 14 | 9 | A24 | RLPLQALAL | 4607 | 12 |

TABLE 4e-continued 2a (1-3)

| No. | Strain | ORF | Start | AA | HLA | Peptide sequence | SEQ ID NO | Score |
|---|---|---|---|---|---|---|---|---|
| 196 | 2a | 36 | 5 | 10 | A3 | ALAHAEFPGR | 4608 | 12 |
| 197 | 2a | 36 | 11 | 10 | B3501 | FPGRLPLQAL | 4609 | 20 |
| 198 | 2a | 36 | 15 | 10 | B3501 | LPLQALALPL | 4610 | 20 |
| 199 | 2a | 36 | 15 | 8 | B3501 | LPLQALAL | 4611 | 20 |
| 200 | 2a | 36 | 11 | 10 | B7 | FPGRLPLQAL | 4612 | 120 |
| 201 | 2a | 36 | 15 | 10 | B7 | LPLQALALPL | 4613 | 80 |
| 202 | 2a | 36 | 6 | 10 | B7 | LAHAEFPGRL | 4614 | 12 |
| 203 | 2a | 37 | 6 | 10 | A0201 | LLFLRLARFV | 4615 | 481.23 |
| 204 | 2a | 37 | 10 | 10 | A0201 | RLARFVDWST | 4616 | 55.89 |
| 205 | 2a | 37 | 3 | 9 | A0205 | HLALLFLRL | 4617 | 14 |
| 206 | 2a | 37 | 17 | 9 | A1 | WSTPPPPKY | 4618 | 15 |
| 207 | 2a | 37 | 35 | 9 | A1 | VTCPYKICR | 4619 | 12.5 |
| 208 | 2a | 37 | 24 | 10 | A24 | KYRGRTIHVW | 4620 | 10 |
| 209 | 2a | 37 | 43 | 9 | A24 | RSMGVGSAL | 4621 | 16.8 |
| 210 | 2a | 37 | 24 | 9 | A24 | KYRGRTIHV | 4622 | 10 |
| 211 | 2a | 37 | 31 | 10 | A3 | HVWPVTCPYK | 4623 | 15 |
| 212 | 2a | 37 | 60 | 9 | A3 | GLRLRVDAY | 4624 | 36 |
| 213 | 2a | 37 | 6 | 9 | A3 | LLFLRLARF | 4625 | 15 |
| 214 | 2a | 37 | 5 | 9 | A3 | ALLFLRLAR | 4626 | 12 |
| 215 | 2a | 37 | 52 | 10 | B3501 | IPSPSGRQGL | 4627 | 20 |
| 216 | 2a | 37 | 54 | 10 | B3501 | SPSGRQGLRL | 4628 | 20 |
| 217 | 2a | 37 | 54 | 8 | B3501 | SPSGRQGL | 4629 | 20 |
| 218 | 2a | 37 | 37 | 9 | B3501 | CPYKICRSM | 4630 | 40 |
| 219 | 2a | 37 | 17 | 9 | B3501 | WSTPPPPKY | 4631 | 10 |
| 220 | 2a | 37 | 43 | 9 | B3501 | RSMGVGSAL | 4632 | 10 |
| 221 | 2a | 37 | 59 | 10 | B4403 | QGLRLRVDAY | 4633 | 18 |
| 222 | 2a | 37 | 78 | 9 | B4403 | REAGRLARC | 4634 | 18 |
| 223 | 2a | 37 | 52 | 10 | B7 | IPSPSGRQGL | 4635 | 120 |
| 224 | 2a | 37 | 54 | 10 | B7 | SPSGRQGLRL | 4636 | 80 |
| 225 | 2a | 37 | 60 | 10 | B7 | GLRLRVDAYL | 4637 | 40 |
| 226 | 2a | 37 | 37 | 9 | B7 | CPYKICRSM | 4638 | 20 |
| 227 | 2a | 37 | 43 | 9 | B7 | RSMGVGSAL | 4639 | 12 |
| 228 | 2a | 37 | 54 | 8 | B8 | SPSGRQGL | 4640 | 16 |
| 229 | 2a | 38 | 2 | 9 | A0201 | ALLPTAPRT | 4641 | 27.572 |
| 230 | 2a | 38 | 7 | 9 | B3501 | APRTAPTGL | 4642 | 60 |
| 231 | 2a | 38 | 7 | 10 | B7 | APRTAPTGLC | 4643 | 90 |
| 232 | 2a | 38 | 6 | 10 | B7 | TAPRTAPTGL | 4644 | 12 |
| 233 | 2a | 38 | 7 | 9 | B7 | APRTAPTGL | 4645 | 2400 |
| 234 | 2a | 38 | 7 | 9 | B8 | APRTAPTGL | 4646 | 16 |
| 235 | 2a | 40 | 12 | 10 | B3501 | RPTRSGDSPW | 4647 | 20 |
| 236 | 2a | 42 | 9 | 10 | A24 | RYHHPRHRNS | 4648 | 10 |
| 237 | 2a | 42 | 9 | 9 | A24 | RYHHPRHRN | 4649 | 10 |
| 238 | 2a | 43 | 6 | 10 | A0201 | AILGQTHVEL | 4650 | 10.868 |
| 239 | 2a | 43 | 7 | 9 | A0201 | ILGQTHVEL | 4651 | 36.316 |
| 240 | 2a | 43 | 6 | 10 | B7 | AILGQTHVEL | 4652 | 12 |
| 241 | 2a | 44 | 29 | 10 | A1 | ACDPTAWLPY | 4653 | 1250 |
| 242 | 2a | 44 | 13 | 8 | B3501 | KPRRPYPL | 4654 | 120 |
| 243 | 2a | 44 | 31 | 8 | B3501 | DPTAWLPY | 4655 | 40 |
| 244 | 2a | 44 | 31 | 9 | B3501 | DPTAWLPYY | 4656 | 40 |
| 245 | 2a | 44 | 30 | 10 | B4403 | CDPTAWLPYY | 4657 | 22.5 |
| 246 | 2a | 44 | 29 | 10 | B4403 | ACDPTAWLPY | 4658 | 18 |
| 247 | 2a | 44 | 2 | 9 | B4403 | DEQAHSLCF | 4659 | 120 |
| 248 | 2a | 44 | 30 | 9 | B4403 | CDPTAWLPY | 4660 | 22.5 |
| 249 | 2a | 44 | 31 | 9 | B4403 | DPTAWLPYY | 4661 | 13.5 |
| 250 | 2a | 44 | 27 | 10 | B7 | VAACDPTAWL | 4662 | 18 |
| 251 | 2a | 44 | 28 | 9 | B7 | AACDPTAWL | 4663 | 54 |
| 252 | 2a | 45 | 1 | 9 | A0201 | MLCEGPSGL | 4664 | 148.896 |
| 253 | 2a | 46 | 12 | 10 | A0201 | YMGPHGPDDT | 4665 | 12.131 |
| 254 | 2a | 46 | 14 | 10 | B3501 | GPHGPDDTFF | 4666 | 30 |
| 255 | 2a | 46 | 6 | 8 | B3501 | HPVCSNYM | 4667 | 40 |
| 256 | 2a | 46 | 17 | 8 | B3501 | GPDDTFFL | 4668 | 12 |
| 257 | 2a | 46 | 14 | 9 | B3501 | GPHGPDDTF | 4669 | 20 |
| 258 | 2a | 47 | 2 | 10 | B7 | SVVQPPGPPL | 4670 | 30 |
| 259 | 2a | 47 | 3 | 9 | B7 | VVQPPGPPL | 4671 | 30 |

TABLE 4f 2a (4-6)

| No. | Strain | ORF | Start | AA | HLA | Peptide sequence | SEQ ID NO | Score |
|---|---|---|---|---|---|---|---|---|
| 1 | HCV 2a | 1 | 10 | 9 | A_0201 | YSWSILDDV | 4672 | 19.536 |
| 2 | HCV 2a | 2 | 8 | 10 | A_0201 | RLLQgEELCA | 4673 | 18.382 |
| 3 | HCV 2a | 2 | 10 | 10 | A_0201 | LQGEeLCADL | 4674 | 15.096 |
| 4 | HCV 2a | 2 | 6 | 10 | B7 | LARLLQGEEL | 4675 | 120.000 |
| 5 | HCV 2a | 2 | 6 | 10 | B8 | LARLLQGEEL | 4676 | 16.000 |
| 6 | HCV 2a | 3 | | | | no hits | | |
| 7 | HCV 2a | 4 | 12 | 9 | A_0201 | KGYEPVHPL | 4677 | 14.728 |
| 8 | HCV 2a | 4 | 56 | 9 | A3 | VLHGGLLAR | 4678 | 18.000 |
| 9 | HCV 2a | 4 | 48 | 9 | B7 | NPRQQIDDV | 4679 | 40.000 |
| 10 | HCV 2a | 4 | 48 | 9 | B_3501 | NPRQQIDDV | 4680 | 12.000 |
| 11 | HCV 2a | 4 | 70 | 9 | B_4403 | DEGPRNARA | 4681 | 24.000 |
| 12 | HCV 2a | 4 | 13 | 10 | A1 | GYEPvHPLDR | 4682 | 22.500 |
| 13 | HCV 2a | 4 | 60 | 10 | A_0201 | GLLArHDLEC | 4683 | 18.382 |
| 14 | HCV 2a | 4 | 79 | 10 | B7 | IPRQdIHQHL | 4684 | 800.000 |
| 15 | HCV 2a | 4 | 48 | 10 | B7 | NPRQqIDDVL | 4685 | 800.000 |
| 16 | HCV 2a | 4 | 75 | 10 | B7 | NARAiPRQDI | 4686 | 27.000 |
| 17 | HCV 2a | 4 | 79 | 10 | B8 | IPRQdIHQHL | 4687 | 16.000 |
| 18 | HCV 2a | 4 | 48 | 10 | B8 | NPRQqIDDVL | 4688 | 16.000 |
| 19 | HCV 2a | 4 | 79 | 10 | B_3501 | IPRQdIHQHL | 4689 | 60.000 |
| 20 | HCV 2a | 4 | 48 | 10 | B_3501 | NPRQqIDDVL | 4690 | 60.000 |
| 21 | HCV 2a | 4 | 15 | 10 | B_3501 | EPVHpLDRAF | 4691 | 20.000 |
| 22 | HCV 2a | 4 | 70 | 10 | B_4403 | DEGPrNARAI | 4692 | 36.000 |
| 23 | HCV 2a | 5 | 6 | 9 | A_0201 | LVGNRAQTV | 4693 | 10.346 |
| 24 | HCV 2a | 6 | 10 | 9 | A1 | RVEIRSKPY | 4694 | 45.000 |
| 25 | HCV 2a | 6 | 36 | 9 | A1 | LTEHHAIKH | 4695 | 11.250 |
| 26 | HCV 2a | 6 | 25 | 9 | A_0201 | KLIPRSPCV | 4696 | 243.432 |
| 27 | HCV 2a | 6 | 35 | 9 | A3 | ALTEHHAIK | 4697 | 30.000 |
| 28 | HCV 2a | 6 | 27 | 9 | B7 | IPRSPCVVA | 4698 | 30.000 |
| 29 | HCV 2a | 6 | 25 | 10 | A_0201 | KLIPrSPCVV | 4699 | 99.807 |
| 30 | HCV 2a | 6 | 2 | 10 | A_0201 | VLAHgQARRV | 4700 | 23.648 |
| 31 | HCV 2a | 6 | 17 | 10 | A24 | PYGSlRWRKL | 4701 | 22.000 |
| 32 | HCV 2a | 6 | 16 | 10 | A3 | KPYGsLRWRK | 4702 | 13.500 |
| 33 | HCV 2a | 6 | 20 | 10 | A3 | SLRWrKLIPR | 4703 | 12.000 |
| 34 | HCV 2a | 6 | 27 | 10 | B7 | IPRSpCVVAL | 4704 | 800.000 |
| 35 | HCV 2a | 6 | 12 | 10 | B7 | EIRSkPYGSL | 4705 | 60.000 |
| 36 | HCV 2a | 6 | 27 | 10 | B8 | IPRSpCVVAL | 4706 | 16.000 |
| 37 | HCV 2a | 6 | 27 | 10 | B_3501 | IPRSpCVVAL | 4707 | 60.000 |
| 38 | HCV 2a | 6 | 14 | 10 | B_3501 | RSKPyGSLRW | 4708 | 15.000 |
| 39 | HCV 2a | 6 | 11 | 10 | B_4403 | VEIRsKPYGS | 4709 | 30.000 |
| 40 | HCV 2a | 7 | 25 | 9 | A_0201 | TLLPEGHLL | 4710 | 79.041 |
| 41 | HCV 2a | 7 | 26 | 9 | A3 | LLPEGHLLY | 4711 | 12.000 |
| 42 | HCV 2a | 7 | 18 | 9 | B7 | SPIEGDLTL | 4712 | 80.000 |
| 43 | HCV 2a | 7 | 18 | 9 | B_3501 | SPIEGDLTL | 4713 | 40.000 |
| 44 | HCV 2a | 7 | 2 | 9 | B_4403 | AEDQVSPSL | 4714 | 12.000 |
| 45 | HCV 2a | 7 | 25 | 10 | A1 | TLLPeGHLLY | 4715 | 25.000 |
| 46 | HCV 2a | 7 | 26 | 10 | A_0201 | LLPEgHLLYI | 4716 | 919.865 |
| 47 | HCV 2a | 7 | 17 | 10 | A24 | RSPIeGDLTL | 4717 | 12.000 |
| 48 | HCV 2a | 7 | 1 | 10 | A24 | MAEDqVSPSL | 4718 | 10.080 |
| 49 | HCV 2a | 7 | 25 | 10 | A3 | TLLPeGHLLY | 4719 | 18.000 |
| 50 | HCV 2a | 7 | 18 | 10 | B7 | SPIEgDLTLL | 4720 | 80.000 |
| 51 | HCV 2a | 7 | 11 | 10 | B7 | DVRQgKRSPI | 4721 | 30.000 |
| 52 | HCV 2a | 7 | 11 | 10 | B8 | DVRQgKRSPI | 4722 | 40.000 |
| 53 | HCV 2a | 7 | 42 | 10 | B_3501 | RPRGsGRGQY | 4723 | 240.000 |
| 54 | HCV 2a | 7 | 18 | 10 | B_3501 | SPIEgDLTLL | 4724 | 60.000 |
| 55 | HCV 2a | 7 | 17 | 10 | B_3501 | RSPIeGDLTL | 4725 | 10.000 |
| 56 | HCV 2a | 8 | 9 | 10 | B_3501 | KPQGgSHRGI | 4726 | 16.000 |
| 57 | HCV 2a | 9 | 8 | 9 | A_0201 | GLGHSWWCA | 4727 | 63.342 |
| 58 | HCV 2a | 9 | 23 | 9 | B_3501 | RPRDDVECF | 4728 | 360.000 |
| 59 | HCV 2a | 9 | 34 | 9 | B_4403 | DEVYGLSHA | 4729 | 36.000 |
| 60 | HCV 2a | 9 | 8 | 10 | A_0201 | GLGHsWWCAV | 4730 | 118.238 |
| 61 | HCV 2a | 9 | 6 | 10 | A_0201 | LVGLgHSWWC | 4731 | 30.483 |
| 62 | HCV 2a | 9 | 30 | 10 | A24 | CFNGdEVYGL | 4732 | 30.000 |
| 63 | HCV 2a | 9 | 23 | 10 | B_3501 | RPRDdVECFN | 4733 | 24.000 |
| 64 | HCV 2a | 9 | 28 | 10 | B_4403 | VECFnGDEVY | 4734 | 120.000 |
| 65 | HCV 2a | 10 | 22 | 9 | B7 | AARWRATSL | 4735 | 360.000 |
| 66 | HCV 2a | 10 | 22 | 9 | B8 | AARWRATSL | 4736 | 320.000 |
| 67 | HCV 2a | 10 | 15 | 10 | A1 | GIEVgSNAAR | 4737 | 18.000 |
| 68 | HCV 2a | 10 | 21 | 10 | B7 | NAARwRATSL | 4738 | 12.000 |
| 69 | HCV 2a | 10 | 21 | 10 | B8 | NAARwRATSL | 4739 | 16.000 |
| 70 | HCV 2a | 10 | 16 | 10 | B_4403 | IEVGsNAARW | 4740 | 54.000 |
| 71 | HCV 2a | 11 | 45 | 9 | A24 | STNDVYDDL | 4741 | 10.080 |
| 72 | HCV 2a | 11 | 26 | 9 | B7 | GPRSLHREV | 4742 | 40.000 |
| 73 | HCV 2a | 11 | 41 | 9 | B7 | APMSSTNDV | 4743 | 36.000 |
| 74 | HCV 2a | 11 | 26 | 9 | B_3501 | GPRSLHREV | 4744 | 12.000 |
| 75 | HCV 2a | 11 | 37 | 9 | B_4403 | AEHNAPMSS | 4745 | 12.000 |

TABLE 4f-continued

2a (4-6)

| No. Strain | ORF | Start | AA | HLA | Peptide sequence | SEQ ID NO | Score |
|---|---|---|---|---|---|---|---|
| 76 HCV 2a | 11 | 41 | 10 | B_3501 | APMSsTNDVY | 4746 | 40.000 |
| 77 HCV 2a | 11 | 32 | 10 | B_4403 | REVGqAEHNA | 4747 | 18.000 |
| 78 HCV 2a | 11 | 41 | 10 | B_4403 | APMSsTNDVY | 4748 | 12.000 |
| 79 HCV 2a | 12 | 13 | 9 | A24 | AFLHKPVVL | 4749 | 30.000 |
| 80 HCV 2a | 12 | 14 | 9 | A3 | FLHKPVVLR | 4750 | 18.000 |
| 81 HCV 2a | 12 | 60 | 9 | B7 | ALREGAALL | 4751 | 120.000 |
| 82 HCV 2a | 12 | 20 | 9 | B7 | VLRRDNEHL | 4752 | 40.000 |
| 83 HCV 2a | 12 | 59 | 9 | B7 | QALREGAAL | 4753 | 12.000 |
| 84 HCV 2a | 12 | 60 | 9 | B8 | ALREGAALL | 4754 | 12.000 |
| 85 HCV 2a | 12 | 25 | 9 | B_4403 | NEHLGCQHY | 4755 | 120.000 |
| 86 HCV 2a | 12 | 24 | 10 | A1 | DNEHlGCQHY | 4756 | 11.250 |
| 87 HCV 2a | 12 | 53 | 10 | A1 | HVDVrPQALR | 4757 | 10.000 |
| 88 HCV 2a | 12 | 6 | 10 | A_0201 | TQVDgAIAFL | 4758 | 112.335 |
| 89 HCV 2a | 12 | 14 | 10 | A3 | FLHKpVVLRR | 4759 | 36.000 |
| 90 HCV 2a | 12 | 19 | 10 | B7 | VVLRrDNEHL | 4760 | 20.000 |
| 91 HCV 2a | 12 | 12 | 10 | B7 | IAFLhKPVVL | 4761 | 12.000 |
| 92 HCV 2a | 12 | 59 | 10 | B7 | QALReGAALL | 4762 | 12.000 |
| 93 HCV 2a | 12 | 12 | 10 | B8 | IAFLhKPVVL | 4763 | 16.000 |
| 94 HCV 2a | 12 | 36 | 10 | B_4403 | AEVPhVESRA | 4764 | 48.000 |
| 95 HCV 2a | 13 | | | | no hits | | |
| 96 HCV 2a | 14 | 18 | 9 | B7 | EPSCPAESL | 4765 | 120.000 |
| 97 HCV 2a | 14 | 18 | 9 | B_3501 | EPSCPAESL | 4766 | 20.000 |
| 98 HCV 2a | 15 | 7 | 9 | A_0201 | RQARVTFQL | 4767 | 12.562 |
| 99 HCV 2a | 15 | 7 | 9 | A24 | RQARVtFQL | 4768 | 11.200 |
| 100 HCV 2a | 15 | 8 | 10 | B7 | QARVtFQLWL | 4769 | 120.000 |
| 101 HCV 2a | 15 | 8 | 10 | B8 | QARVtFQLWL | 4770 | 16.000 |
| 102 HCV 2a | 15 | 22 | 10 | B_3501 | DSRStPIRTF | 4771 | 15.000 |
| 103 HCV 2a | 15 | 3 | 10 | B_4403 | AEGRrQARVT | 4772 | 12.000 |
| 104 HCV 2a | 16 | 1 | 10 | A_0201 | MLSApGHIPV | 4773 | 118.238 |
| 105 HCV 2a | 17 | 19 | 10 | B_3501 | MPPSlPEEAF | 4774 | 20.000 |
| 106 HCV 2a | 17 | 4 | 10 | B_4403 | RETPpAGRGS | 4775 | 12.000 |
| 107 HCV 2a | 18 | | | | no hits | | |
| 108 HCV 2a | 19 | 16 | 9 | B_4403 | RESPERPLW | 4776 | 24.000 |
| 109 HCV 2a | 19 | 2 | 10 | A_0201 | VLRArGRSFL | 4777 | 15.180 |
| 110 HCV 2a | 19 | 14 | 10 | B7 | SGREsPERPL | 4778 | 60.000 |
| 111 HCV 2a | 19 | 2 | 10 | B7 | VLRArGRSFL | 4779 | 60.000 |
| 112 HCV 2a | 20 | 6 | 9 | B_3501 | GSPRSLPQM | 4780 | 10.000 |
| 113 HCV 2a | 20 | 10 | 10 | A_0201 | SLPQmGVTPA | 4781 | 11.426 |
| 114 HCV 2a | 20 | 2 | 10 | B7 | APIAgSPRSL | 4782 | 240.000 |
| 115 HCV 2a | 20 | 11 | 10 | B7 | LPQMgVTPAL | 4783 | 80.000 |
| 116 HCV 2a | 20 | 7 | 10 | B7 | SPRSlPQMGV | 4784 | 60.000 |
| 117 HCV 2a | 20 | 15 | 10 | B7 | GVTPaLSAAL | 4785 | 20.000 |
| 118 HCV 2a | 20 | 2 | 10 | B_3501 | APIAgSPRSL | 4786 | 20.000 |
| 119 HCV 2a | 20 | 11 | 10 | B_3501 | LPQMgVTPAL | 4787 | 20.000 |
| 120 HCV 2a | 20 | 7 | 10 | B_3501 | SPRSlPQMGV | 4788 | 12.000 |
| 121 HCV 2a | 21 | | | | no hits | | |
| 122 HCV 2a | 22 | 19 | 9 | B7 | APCPGLCCL | 4789 | 240.000 |
| 123 HCV 2a | 22 | 16 | 9 | B7 | YPPAPCPGL | 4790 | 120.000 |
| 124 HCV 2a | 22 | 8 | 9 | B_3501 | CPRHTPPGY | 4791 | 120.000 |
| 125 HCV 2a | 22 | 16 | 9 | B_3501 | YPPAPCPGL | 4792 | 20.000 |
| 126 HCV 2a | 22 | 19 | 9 | B_3501 | APCPGLCCL | 4793 | 20.000 |
| 127 HCV 2a | 22 | 23 | 10 | A_0201 | GLCCLQQPPL | 4794 | 21.362 |
| 128 HCV 2a | 22 | 15 | 10 | A24 | GYPPaPCPGL | 4795 | 360.000 |
| 129 HCV 2a | 23 | 5 | 9 | B_3501 | KPQQDSLVV | 4796 | 12.000 |
| 130 HCV 2a | 23 | 5 | 10 | A24 | KPQQdSLVVL | 4797 | 12.000 |
| 131 HCV 2a | 23 | 5 | 10 | B7 | KPQQdSLVVL | 4798 | 80.000 |
| 132 HCV 2a | 23 | 5 | 10 | B_3501 | KPQQdSLVVL | 4799 | 40.000 |
| 133 HCV 2a | 24 | | | | no hits | | |
| 134 HCV 2a | 25 | 5 | 10 | B7 | LPRPpQLGPT | 4800 | 20.000 |
| 135 HCV 2a | 25 | 7 | 10 | B_3501 | RPPQLGPTCW | 4801 | 20.000 |
| 136 HCV 2a | 26 | | | | no hits | | |
| 137 HCV 2a | 27 | 9 | 9 | A24 | LFGKGSGHL | 4802 | 20.000 |
| 138 HCV 2a | 27 | 3 | 10 | A1 | NSPPIALFGK | 4803 | 15.000 |
| 139 HCV 2a | 27 | 8 | 10 | A_0201 | ALFGkGSGHL | 4804 | 10.275 |
| 140 HCV 2a | 27 | 8 | 10 | B7 | ALFGkGSGHL | 4805 | 12.000 |
| 141 HCV 2a | 28 | 20 | 9 | A_0201 | SLNGRRSSV | 4806 | 69.552 |
| 142 HCV 2a | 28 | 22 | 9 | B7 | NGRRSSVSL | 4807 | 40.000 |
| 143 HCV 2a | 28 | 11 | 9 | B_3501 | GPPRAHHTF | 4808 | 20.000 |
| 144 HCV 2a | 28 | 12 | 10 | B7 | PPRAhHTFSL | 4809 | 80.000 |
| 145 HCV 2a | 29 | 4 | 10 | A3 | TLWPpRSSQF | 4810 | 15.000 |
| 146 HCV 2a | 30 | | | | no hits | | |
| 147 HCV 2a | 31 | 10 | 10 | B7 | AVRGaVGKRA | 4811 | 15.000 |
| 148 HCV 2a | 32 | 28 | 9 | A24 | VYRSCPPRL | 4812 | 200.000 |
| 149 HCV 2a | 32 | 18 | 9 | B7 | SPPTCKWAL | 4813 | 80.000 |
| 150 HCV 2a | 32 | 18 | 9 | B_3501 | SPPTCKWAL | 4814 | 20.000 |

TABLE 4f-continued 2a (4-6)

| No. Strain | ORF | Start | AA | HLA | Peptide sequence | SEQ ID NO | Score |
|---|---|---|---|---|---|---|---|
| 151 HCV 2a | 32 | 14 | 10 | A3 | HLSHsPPTCK | 4815 | 30.000 |
| 152 HCV 2a | 32 | 27 | 10 | B7 | QVYRsCPPRL | 4816 | 20.000 |
| 153 HCV 2a | 33 | | | | no hits | | |
| 154 HCV 2a | 34 | | | | no hits | | |
| 155 HCV 2a | 35 | 8 | 9 | A1 | GLEAVRHSY | 4817 | 45.000 |
| 156 HCV 2a | 35 | 8 | 9 | A3 | GLEAVRHSY | 4818 | 18.000 |
| 157 HCV 2a | 35 | 1 | 9 | B7 | MALPGGGGL | 4819 | 12.000 |
| 158 HCV 2a | 36 | 83 | 9 | A1 | RSEVFLVVR | 4820 | 27.000 |
| 159 HCV 2a | 36 | 121 | 9 | A_0201 | RLVFLLVFL | 4821 | 270.234 |
| 160 HCV 2a | 36 | 87 | 9 | A_0201 | FLVVRTPNL | 4822 | 98.267 |
| 161 HCV 2a | 36 | 56 | 9 | A24 | GYPGFPQDL | 4823 | 360.000 |
| 162 HCV 2a | 36 | 121 | 9 | A24 | RLVFLLVFL | 4824 | 14.400 |
| 163 HCV 2a | 36 | 69 | 9 | A24 | RSLGMGWRL | 4825 | 12.000 |
| 164 HCV 2a | 36 | 118 | 9 | B7 | CGRRLVFLL | 4826 | 40.000 |
| 165 HCV 2a | 36 | 12 | 9 | B7 | RVSMTLPTL | 4827 | 20.000 |
| 166 HCV 2a | 36 | 117 | 9 | B8 | SCGRRLVFL | 4828 | 16.000 |
| 167 HCV 2a | 36 | 42 | 9 | B_3501 | HPAQPSPSF | 4829 | 20.000 |
| 168 HCV 2a | 36 | 69 | 9 | B_3501 | RSLGMGWRL | 4830 | 10.000 |
| 169 HCV 2a | 36 | 84 | 9 | B_4403 | SEVFLVVRT | 4831 | 48.000 |
| 170 HCV 2a | 36 | 79 | 10 | A_0201 | RGWDrSEVFL | 4832 | 26.100 |
| 171 HCV 2a | 36 | 114 | 10 | A_0201 | NLTScGRRLV | 4833 | 13.910 |
| 172 HCV 2a | 36 | 86 | 10 | A24 | VFLVvRTPNL | 4834 | 30.000 |
| 173 HCV 2a | 36 | 8 | 10 | A24 | KPHVrVSMTL | 4835 | 11.200 |
| 174 HCV 2a | 36 | 51 | 10 | A24 | PYRGqGYPGF | 4836 | 10.000 |
| 175 HCV 2a | 36 | 70 | 10 | A3 | SLGMgWRLPR | 4837 | 24.000 |
| 176 HCV 2a | 36 | 89 | 10 | B7 | VVRTpNLGPL | 4838 | 200.000 |
| 177 HCV 2a | 36 | 8 | 10 | B7 | KPHVrVSMTL | 4839 | 80.000 |
| 178 HCV 2a | 36 | 77 | 10 | B7 | LPRGwDRSEV | 4840 | 60.000 |
| 179 HCV 2a | 36 | 19 | 10 | B7 | TLRDlCRGSL | 4841 | 60.000 |
| 180 HCV 2a | 36 | 64 | 10 | B7 | LPVErRSLGM | 4842 | 20.000 |
| 181 HCV 2a | 36 | 35 | 10 | B7 | EPRGdRSHPA | 4843 | 20.000 |
| 182 HCV 2a | 36 | 35 | 10 | B8 | EPRGdRSHPA | 4844 | 32.000 |
| 183 HCV 2a | 36 | 19 | 10 | B8 | TLRDlCRGSL | 4845 | 12.000 |
| 184 HCV 2a | 36 | 64 | 10 | B_3501 | LPVErRSLGM | 4846 | 80.000 |
| 185 HCV 2a | 36 | 8 | 10 | B_3501 | KPHVrVSMTL | 4847 | 40.000 |
| 186 HCV 2a | 36 | 6 | 10 | B_3501 | SAKPhVRVSM | 4848 | 18.000 |
| 187 HCV 2a | 36 | 77 | 10 | B_3501 | LPRGwDRSEV | 4849 | 18.000 |
| 188 HCV 2a | 36 | 66 | 10 | B_4403 | VERRsLGMGW | 4850 | 12.000 |
| 189 HCV 2a | 37 | 109 | 9 | A1 | YTDPYISKL | 4851 | 12.500 |
| 190 HCV 2a | 37 | 147 | 9 | A_0201 | WMMFPNHEL | 4852 | 262.591 |
| 191 HCV 2a | 37 | 77 | 9 | A_0201 | RVSSWGVYV | 4853 | 33.472 |
| 192 HCV 2a | 37 | 70 | 9 | A_0201 | FLRAEATRV | 4854 | 24.315 |
| 193 HCV 2a | 37 | 148 | 9 | A_0201 | MMFPNHELT | 4855 | 16.588 |
| 194 HCV 2a | 37 | 36 | 9 | A24 | RYRPQTAAL | 4856 | 480.000 |
| 195 HCV 2a | 37 | 167 | 9 | A24 | RAIGVVGSL | 4857 | 16.800 |
| 196 HCV 2a | 37 | 105 | 9 | A3 | GLTEYTDPY | 4858 | 54.000 |
| 197 HCV 2a | 37 | 27 | 9 | A3 | SLVFTAQLK | 4859 | 30.000 |
| 198 HCV 2a | 37 | 45 | 9 | B7 | PPREMRDAL | 4860 | 120.000 |
| 199 HCV 2a | 37 | 147 | 9 | B7 | WMMFPNHEL | 4861 | 18.000 |
| 200 HCV 2a | 37 | 51 | 9 | B7 | DALTARARL | 4862 | 18.000 |
| 201 HCV 2a | 37 | 167 | 9 | B7 | RAIGVVGSL | 4863 | 12.000 |
| 202 HCV 2a | 37 | 18 | 9 | B7 | RASGNGVSL | 4864 | 12.000 |
| 203 HCV 2a | 37 | 54 | 9 | B8 | TARARLFHA | 4865 | 16.000 |
| 204 HCV 2a | 37 | 45 | 9 | B_3501 | PPREMRDAL | 4866 | 12.000 |
| 205 HCV 2a | 37 | 91 | 9 | B_3501 | SSPCNLSIM | 4867 | 10.000 |
| 206 HCV 2a | 37 | 73 | 9 | B_4403 | AEATRVSSW | 4868 | 144.000 |
| 207 HCV 2a | 37 | 129 | 9 | B_4403 | MEKKCVIRT | 4869 | 12.000 |
| 208 HCV 2a | 37 | 47 | 9 | B_4403 | REMRDALTA | 4870 | 12.000 |
| 209 HCV 2a | 37 | 157 | 9 | B_4403 | GECLTVSQA | 4871 | 12.000 |
| 210 HCV 2a | 37 | 109 | 10 | A1 | YTDPyISKLR | 4872 | 125.000 |
| 211 HCV 2a | 37 | 105 | 10 | A_0201 | GLTEyTDPYI | 4873 | 235.260 |
| 212 HCV 2a | 37 | 25 | 10 | A_0201 | SLSLvFTAQL | 4874 | 81.177 |
| 213 HCV 2a | 37 | 147 | 10 | A_0201 | WMMFpNHELT | 4875 | 44.885 |
| 214 HCV 2a | 37 | 108 | 10 | A24 | EYTDpYISKL | 4876 | 264.000 |
| 215 HCV 2a | 37 | 27 | 10 | A3 | SLVFtAQLKR | 4877 | 12.000 |
| 216 HCV 2a | 37 | 62 | 10 | B7 | ALRGgAPSFL | 4878 | 120.000 |
| 217 HCV 2a | 37 | 44 | 10 | B7 | LPPReMRDAL | 4879 | 120.000 |
| 218 HCV 2a | 37 | 54 | 10 | B7 | TARArLFHAL | 4880 | 120.000 |
| 219 HCV 2a | 37 | 126 | 10 | B7 | AIRMeKKCVI | 4881 | 12.000 |
| 220 HCV 2a | 37 | 19 | 10 | B7 | ASGNgVSLSL | 4882 | 12.000 |
| 221 HCV 2a | 37 | 97 | 10 | B7 | SIMAgRSRGL | 4883 | 12.000 |
| 222 HCV 2a | 37 | 120 | 10 | B7 | WSRVsWAIRM | 4884 | 10.000 |
| 223 HCV 2a | 37 | 126 | 10 | B8 | AIRMeKKCVI | 4885 | 20.000 |
| 224 HCV 2a | 37 | 54 | 10 | B8 | TARArLFHAL | 4886 | 16.000 |
| 225 HCV 2a | 37 | 134 | 10 | B8 | VIRTmRTHIV | 4887 | 12.000 |

TABLE 4f-continued 2a (4-6)

| No. | Strain | ORF | Start | AA | HLA | Peptide sequence | SEQ ID NO | Score |
|---|---|---|---|---|---|---|---|---|
| 226 | HCV 2a | 37 | 120 | 10 | B_3501 | WSRVsWAIRM | 4888 | 30.000 |
| 227 | HCV 2a | 37 | 44 | 10 | B_3501 | LPPReMRDAL | 4889 | 20.000 |
| 228 | HCV 2a | 37 | 90 | 10 | B_3501 | ASSPcNLSIM | 4890 | 10.000 |
| 229 | HCV 2a | 37 | 111 | 10 | B_3501 | DPYIsKLRSW | 4891 | 10.000 |
| 230 | HCV 2a | 37 | 100 | 10 | B_4403 | AGRSrGLTEY | 4892 | 13.500 |
| 231 | HCV 2a | 38 | 19 | 9 | A_0201 | ALQAARAFT | 4893 | 40.986 |
| 232 | HCV 2a | 38 | 11 | 10 | B7 | IVGAtIPAAL | 4894 | 20.000 |
| 233 | HCV 2a | 39 | 16 | 9 | A_0201 | RLYPQVWPL | 4895 | 1.179.204 |
| 234 | HCV 2a | 39 | 24 | 9 | A_0201 | LLLNIGPPT | 4896 | 46.873 |
| 235 | HCV 2a | 39 | 20 | 9 | A_0201 | QVWPLLLNI | 4897 | 17.427 |
| 236 | HCV 2a | 39 | 17 | 9 | A24 | LYPQVWPLL | 4898 | 420.000 |
| 237 | HCV 2a | 39 | 16 | 9 | A3 | RLYPQVWPL | 4899 | 40.500 |
| 238 | HCV 2a | 39 | 18 | 9 | B7 | YPQVWPLLL | 4900 | 80.000 |
| 239 | HCV 2a | 39 | 10 | 9 | B_3501 | TPLARQRLY | 4901 | 40.000 |
| 240 | HCV 2a | 39 | 18 | 9 | B_3501 | YPQVWPLLL | 4902 | 20.000 |
| 241 | HCV 2a | 39 | 16 | 10 | A_0201 | RLYPqVWPLL | 4903 | 116.211 |
| 242 | HCV 2a | 39 | 17 | 10 | A24 | LYPQvWPLLL | 4904 | 300.000 |
| 243 | HCV 2a | 39 | 16 | 10 | A24 | RLYPqVWPLL | 4905 | 13.440 |
| 244 | HCV 2a | 39 | 5 | 10 | A3 | MLVVsTPLAR | 4906 | 12.000 |
| 245 | HCV 2a | 39 | 3 | 10 | B7 | FPMLvVSTPL | 4907 | 240.000 |
| 246 | HCV 2a | 39 | 3 | 10 | B_3501 | FPMLvVSTPL | 4908 | 20.000 |
| 247 | HCV 2a | 40 | 19 | 9 | A_0201 | VLMSLSVTV | 4909 | 437.482 |
| 248 | HCV 2a | 40 | 34 | 9 | A24 | SYEKPIGSF | 4910 | 150.000 |
| 249 | HCV 2a | 40 | 13 | 9 | A24 | WYMASSVLM | 4911 | 37.500 |
| 250 | HCV 2a | 40 | 22 | 9 | A3 | SLSVTVESK | 4912 | 60.000 |
| 251 | HCV 2a | 40 | 42 | 9 | A3 | FLSAHAFKR | 4913 | 12.000 |
| 252 | HCV 2a | 40 | 15 | 9 | B7 | MASSVLMSL | 4914 | 12.000 |
| 253 | HCV 2a | 40 | 6 | 9 | B_3501 | SSGKEQAWY | 4915 | 15.000 |
| 254 | HCV 2a | 40 | 7 | 9 | B_3501 | SGKEQAWYM | 4916 | 12.000 |
| 255 | HCV 2a | 40 | 51 | 9 | B_3501 | NSTRWAGEY | 4917 | 10.000 |
| 256 | HCV 2a | 40 | 22 | 9 | B_4403 | VESKHRVSY | 4918 | 120.000 |
| 257 | HCV 2a | 40 | 26 | 10 | A1 | TVESkHRVSY | 4919 | 90.000 |
| 258 | HCV 2a | 40 | 14 | 10 | A_0201 | YMASsVLMSL | 4920 | 163.232 |
| 259 | HCV 2a | 40 | 18 | 10 | A_0201 | SVLMsLSVTV | 4921 | 22.517 |
| 260 | HCV 2a | 40 | 34 | 10 | A24 | SYEKpIGSFL | 4922 | 420.000 |
| 261 | HCV 2a | 40 | 11 | 10 | B7 | QAWYmASSVL | 4923 | 12.000 |
| 262 | HCV 2a | 40 | 5 | 10 | B_3501 | ASSGkEQAWY | 4924 | 15.000 |
| 263 | HCV 2a | 40 | 6 | 10 | B_3501 | SSGKeQAWYM | 4925 | 10.000 |
| 264 | HCV 2a | 40 | 33 | 10 | B_3501 | VSYEkPIGSF | 4926 | 10.000 |
| 265 | HCV 2a | 40 | 35 | 10 | B_4403 | YEKPIGSFLS | 4927 | 12.000 |
| 266 | HCV 2a | 41 | 22 | 9 | A_0201 | WLTALPDKL | 4928 | 48.151 |
| 267 | HCV 2a | 41 | 60 | 9 | A_0201 | ALTLEAASL | 4929 | 21.362 |
| 268 | HCV 2a | 41 | 15 | 9 | A24 | SFHTDLMWL | 4930 | 20.000 |
| 269 | HCV 2a | 41 | 29 | 9 | A3 | KLRTSLAPY | 4931 | 18.000 |
| 270 | HCV 2a | 41 | 55 | 9 | B7 | KVRSFALTL | 4932 | 200.000 |
| 271 | HCV 2a | 41 | 26 | 9 | B7 | LPDKLRTSL | 4933 | 36.000 |
| 272 | HCV 2a | 41 | 34 | 9 | B7 | LAPYPYLDL | 4934 | 18.000 |
| 273 | HCV 2a | 41 | 60 | 9 | B7 | ALTLEAASL | 4935 | 12.000 |
| 274 | HCV 2a | 41 | 53 | 9 | B8 | SSKVRSFAL | 4936 | 80.000 |
| 275 | HCV 2a | 41 | 53 | 9 | B_3501 | SSKVRSFAL | 4937 | 15.000 |
| 276 | HCV 2a | 41 | 37 | 9 | B_3501 | YPYLDLAEW | 4938 | 15.000 |
| 277 | HCV 2a | 41 | 29 | 9 | B_3501 | KLRTSLAPY | 4939 | 12.000 |
| 278 | HCV 2a | 41 | 63 | 9 | B_4403 | LEAASLMSF | 4940 | 120.000 |
| 279 | HCV 2a | 41 | 62 | 10 | A1 | TLEAaSLMSF | 4941 | 45.000 |
| 280 | HCV 2a | 41 | 25 | 10 | A_0201 | ALPDkLRTSL | 4942 | 87.586 |
| 281 | HCV 2a | 41 | 33 | 10 | A_0201 | SLAPyPYLDL | 4943 | 32.044 |
| 282 | HCV 2a | 41 | 39 | 10 | A_0201 | YLDLaEWGGV | 4944 | 28.283 |
| 283 | HCV 2a | 41 | 20 | 10 | A3 | LMWLtALPDK | 4945 | 150.000 |
| 284 | HCV 2a | 41 | 11 | 10 | B7 | SSRRsFHTDL | 4946 | 40.000 |
| 285 | HCV 2a | 41 | 25 | 10 | B7 | ALPDkLRTSL | 4947 | 18.000 |
| 286 | HCV 2a | 41 | 59 | 10 | B7 | FALTlEAASL | 4948 | 12.000 |
| 287 | HCV 2a | 41 | 52 | 10 | B7 | ASSKvRSFAL | 4949 | 12.000 |
| 288 | HCV 2a | 41 | 14 | 10 | B_3501 | RSFHtDLMWL | 4950 | 15.000 |
| 289 | HCV 2a | 41 | 11 | 10 | B_3501 | SSRRsFHTDL | 4951 | 15.000 |
| 290 | HCV 2a | 41 | 43 | 10 | B_4403 | AEWGgVNWHA | 4952 | 18.000 |
| 291 | HCV 2a | 42 | 115 | 9 | A_0201 | RLLGGGVGV | 4953 | 257.342 |
| 292 | HCV 2a | 42 | 94 | 9 | A_0201 | VLMASCWRA | 4954 | 234.365 |
| 293 | HCV 2a | 42 | 105 | 9 | A_0201 | MVLSLRPTV | 4955 | 38.280 |
| 294 | HCV 2a | 42 | 108 | 9 | B7 | SLRPTVRRL | 4956 | 40.000 |
| 295 | HCV 2a | 42 | 21 | 9 | B_3501 | EPGAASPPW | 4957 | 10.000 |
| 296 | HCV 2a | 42 | 97 | 9 | B_3501 | ASCWRASPM | 4958 | 10.000 |
| 297 | HCV 2a | 42 | 29 | 9 | B_4403 | WEGGRSSTW | 4959 | 18.000 |
| 298 | HCV 2a | 42 | 116 | 10 | A_0201 | LLGGgVGVFL | 4960 | 199.738 |
| 299 | HCV 2a | 42 | 93 | 10 | A_0201 | KVLMaSCWRA | 4961 | 42.220 |
| 300 | HCV 2a | 42 | 124 | 10 | A_0201 | FLGGgRAQPA | 4962 | 22.853 |

TABLE 4f-continued

2a (4-6)

| No. | Strain | ORF | Start | AA | HLA | Peptide sequence | SEQ ID NO | Score |
|---|---|---|---|---|---|---|---|---|
| 301 | HCV 2a | 42 | 78 | 10 | B7 | APVErPESPL | 4963 | 360.000 |
| 302 | HCV 2a | 42 | 108 | 10 | B7 | SLRPtVRRLL | 4964 | 60.000 |
| 303 | HCV 2a | 42 | 44 | 10 | B7 | SPGSpSRGGM | 4965 | 30.000 |
| 304 | HCV 2a | 42 | 112 | 10 | B7 | TVRRlLGGGV | 4966 | 10.000 |
| 305 | HCV 2a | 42 | 44 | 10 | B_3501 | SPGSpSRGGM | 4967 | 40.000 |
| 306 | HCV 2a | 42 | 78 | 10 | B_3501 | APVErPESPL | 4968 | 40.000 |
| 307 | HCV 2a | 42 | 91 | 10 | B_3501 | WPKVlMASCW | 4969 | 30.000 |
| 308 | HCV 2a | 42 | 20 | 10 | B_4403 | SEPGaASPPW | 4970 | 54.000 |
| 309 | HCV 2a | 42 | 54 | 10 | B_4403 | EEVEpVSERA | 4971 | 12.000 |
| 310 | HCV 2a | 43 | | | | no hits | | |
| 311 | HCV 2a | 44 | | | | no hits | | |
| 312 | HCV 2a | 45 | | | | no hits | | |
| 313 | HCV 2a | 46 | 1 | 9 | A_0201 | MLAPQGHRV | 4972 | 118.238 |
| 314 | HCV 2a | 46 | 10 | 9 | A_0201 | VMMPVPAHT | 4973 | 33.853 |
| 315 | HCV 2a | 46 | 3 | 9 | B7 | APQGHRVVM | 4974 | 90.000 |
| 316 | HCV 2a | 46 | 12 | 9 | B7 | MPVPAHTPL | 4975 | 80.000 |
| 317 | HCV 2a | 46 | 3 | 9 | B_3501 | APQGHRVVM | 4976 | 40.000 |
| 318 | HCV 2a | 46 | 12 | 9 | B_3501 | MPVPAHTPL | 4977 | 20.000 |
| 319 | HCV 2a | 46 | 11 | 10 | A_0201 | MMPVpAHTPL | 4978 | 26.228 |
| 320 | HCV 2a | 46 | 3 | 10 | B7 | APQGhRVVMM | 4979 | 60.000 |
| 321 | HCV 2a | 46 | 3 | 10 | B_3501 | APQGhRVVMM | 4980 | 40.000 |
| 322 | HCV 2a | 47 | 25 | 9 | A_0201 | QLWSLLSRL | 4981 | 407.808 |
| 323 | HCV 2a | 47 | 28 | 9 | A_0201 | SLLSRLVIV | 4982 | 242.674 |
| 324 | HCV 2a | 47 | 35 | 9 | A_0201 | IVREPSSWV | 4983 | 17.731 |
| 325 | HCV 2a | 47 | 29 | 9 | A3 | LLSRLVIVR | 4984 | 24.000 |
| 326 | HCV 2a | 47 | 22 | 9 | B7 | SVIQLWSLL | 4985 | 20.000 |
| 327 | HCV 2a | 47 | 35 | 9 | B7 | IVREPSSWV | 4986 | 15.000 |
| 328 | HCV 2a | 47 | 10 | 9 | B_3501 | RSHEPAHGM | 4987 | 40.000 |
| 329 | HCV 2a | 47 | 25 | 10 | A_0201 | QLWSlLSRLV | 4988 | 115.456 |
| 330 | HCV 2a | 47 | 34 | 10 | A_0201 | VIVRePSSWV | 4989 | 89.418 |
| 331 | HCV 2a | 47 | 17 | 10 | A_0201 | GMGQsSVIQL | 4990 | 35.485 |
| 332 | HCV 2a | 47 | 24 | 10 | A_0201 | IQLWsLLSRL | 4991 | 31.334 |
| 333 | HCV 2a | 47 | 28 | 10 | A3 | SLLSrLVIVR | 4992 | 36.000 |
| 334 | HCV 2a | 47 | 17 | 10 | A3 | GMGQsSVIQL | 4993 | 10.800 |
| 335 | HCV 2a | 47 | 37 | 10 | B_4403 | REPSsWVTRC | 4994 | 18.000 |
| 336 | HCV 2a | 48 | 109 | 9 | A_0201 | RMLRRIVVL | 4995 | 53.831 |
| 337 | HCV 2a | 48 | 110 | 9 | A_0201 | MLRRIVVLV | 4996 | 20.668 |
| 338 | HCV 2a | 48 | 74 | 9 | A_0201 | TLPRPMLPT | 4997 | 17.140 |
| 339 | HCV 2a | 48 | 19 | 9 | A_0201 | RMPAQMTPT | 4998 | 12.379 |
| 340 | HCV 2a | 48 | 109 | 9 | A24 | RMLRRIVVL | 4999 | 12.000 |
| 341 | HCV 2a | 48 | 114 | 9 | A24 | IVVLVDNGL | 5000 | 10.080 |
| 342 | HCV 2a | 48 | 116 | 9 | A3 | VLVDNGLVR | 5001 | 12.000 |
| 343 | HCV 2a | 48 | 114 | 9 | B7 | IVVLVDNGL | 5002 | 20.000 |
| 344 | HCV 2a | 48 | 75 | 9 | B7 | LPRPMLPTA | 5003 | 20.000 |
| 345 | HCV 2a | 48 | 122 | 9 | B7 | LVRAALNAI | 5004 | 20.000 |
| 346 | HCV 2a | 48 | 103 | 9 | B7 | DASQPPRML | 5005 | 18.000 |
| 347 | HCV 2a | 48 | 67 | 9 | B7 | PARISTSTL | 5006 | 12.000 |
| 348 | HCV 2a | 48 | 37 | 9 | B7 | GSRLMTSSM | 5007 | 10.000 |
| 349 | HCV 2a | 48 | 37 | 9 | B_3501 | GSRLMTSSM | 5008 | 30.000 |
| 350 | HCV 2a | 48 | 58 | 9 | B_3501 | RAPEMPAPY | 5009 | 24.000 |
| 351 | HCV 2a | 48 | 139 | 9 | B_3501 | GSVDSPARY | 5010 | 20.000 |
| 352 | HCV 2a | 48 | 109 | 10 | A_0201 | RMLRrIVVLV | 5011 | 427.474 |
| 353 | HCV 2a | 48 | 116 | 10 | A_0201 | VLVDnGLVRA | 5012 | 79.642 |
| 354 | HCV 2a | 48 | 121 | 10 | A_0201 | GLVRaALNAI | 5013 | 23.995 |
| 355 | HCV 2a | 48 | 74 | 10 | A_0201 | TLPRpMLPTA | 5014 | 11.426 |
| 356 | HCV 2a | 48 | 113 | 10 | A24 | RIVVLVDNGL | 5015 | 20.160 |
| 357 | HCV 2a | 48 | 80 | 10 | B7 | LPTAaPTRPL | 5016 | 120.000 |
| 358 | HCV 2a | 48 | 66 | 10 | B7 | YPARiSTSTL | 5017 | 80.000 |
| 359 | HCV 2a | 48 | 122 | 10 | B7 | LVRAaLNAIM | 5018 | 50.000 |
| 360 | HCV 2a | 48 | 11 | 10 | B7 | SPGPtWRRRM | 5019 | 30.000 |
| 361 | HCV 2a | 48 | 75 | 10 | B7 | LPRPmLPTAA | 5020 | 20.000 |
| 362 | HCV 2a | 48 | 11 | 10 | B_3501 | SPGPtWRRRM | 5021 | 40.000 |
| 363 | HCV 2a | 48 | 66 | 10 | B_3501 | YPARiSTSTL | 5022 | 20.000 |
| 364 | HCV 2a | 48 | 80 | 10 | B_3501 | LPTAaPTRPL | 5023 | 20.000 |
| 365 | HCV 2a | 48 | 43 | 10 | B_3501 | SSMEgFSPDM | 5024 | 20.000 |
| 366 | HCV 2a | 48 | 92 | 10 | B_3501 | KPVApAGGAI | 5025 | 16.000 |
| 367 | HCV 2a | 48 | 70 | 10 | B_3501 | ISTStLPRPM | 5026 | 10.000 |
| 368 | HCV 2a | 48 | 128 | 10 | B_4403 | NAIMeATAGF | 5027 | 11.250 |
| 369 | HCV 2a | 49 | 40 | 9 | A_0201 | WILDFSISA | 5028 | 181.139 |
| 370 | HCV 2a | 49 | 9 | 9 | A_0201 | CLAQNCSTL | 5029 | 21.362 |
| 371 | HCV 2a | 49 | 41 | 9 | A_0201 | ILDFSISAI | 5030 | 16.317 |
| 372 | HCV 2a | 49 | 38 | 9 | A_0201 | KPWILDFSI | 5031 | 11.475 |
| 373 | HCV 2a | 49 | 51 | 9 | B7 | CPSSMRAAL | 5032 | 120.000 |
| 374 | HCV 2a | 49 | 34 | 9 | B7 | ACCNKPWIL | 5033 | 12.000 |
| 375 | HCV 2a | 49 | 24 | 9 | B7 | AGCMSWACL | 5034 | 12.000 |

TABLE 4f-continued

2a (4-6)

| No. | Strain | ORF | Start | AA | HLA | Peptide sequence | SEQ ID NO | Score |
|---|---|---|---|---|---|---|---|---|
| 376 | HCV 2a | 49 | 34 | 9 | B8 | ACCNKPWIL | 5035 | 16.000 |
| 377 | HCV 2a | 49 | 51 | 9 | B_3501 | CPSSMRAAL | 5036 | 20.000 |
| 378 | HCV 2a | 49 | 38 | 9 | B_3501 | KPWILDFSI | 5037 | 16.000 |
| 379 | HCV 2a | 49 | 32 | 9 | B_4403 | LEACCNKPW | 5038 | 36.000 |
| 380 | HCV 2a | 49 | 19 | 9 | B_4403 | HEASTAGCM | 5039 | 12.000 |
| 381 | HCV 2a | 49 | 41 | 10 | A1 | ILDFsISAIR | 5040 | 10.000 |
| 382 | HCV 2a | 49 | 40 | 10 | A_0201 | WILDfSISAI | 5041 | 230.237 |
| 383 | HCV 2a | 49 | 50 | 10 | A24 | RCPSsMRAAL | 5042 | 12.000 |
| 384 | HCV 2a | 49 | 1 | 10 | B7 | MPLMkFHMCL | 5043 | 80.000 |
| 385 | HCV 2a | 49 | 23 | 10 | B7 | TAGCmSWACL | 5044 | 12.000 |
| 386 | HCV 2a | 49 | 33 | 10 | B7 | EACCnKPWIL | 5045 | 12.000 |
| 387 | HCV 2a | 49 | 33 | 10 | B8 | EACCnKPWIL | 5046 | 32.000 |
| 388 | HCV 2a | 49 | 1 | 10 | B_3501 | MPLMkFHMCL | 5047 | 20.000 |
| 389 | HCV 2a | 49 | 46 | 10 | B_3501 | ISAIrCPSSM | 5048 | 10.000 |
| 390 | HCV 2a | 49 | 19 | 10 | B_4403 | HEAStAGCMS | 5049 | 12.000 |
| 391 | HCV 2a | 50 | 57 | 9 | A1 | VTEPKRYRR | 5050 | 450.000 |
| 392 | HCV 2a | 50 | 6 | 9 | A1 | MMETHPVAK | 5051 | 18.000 |
| 393 | HCV 2a | 50 | 8 | 9 | A1 | ETHPVAKQY | 5052 | 12.500 |
| 394 | HCV 2a | 50 | 39 | 9 | A_0201 | CMHVAMYFV | 5053 | 635.435 |
| 395 | HCV 2a | 50 | 43 | 9 | A_0201 | AMYFVTGCV | 5054 | 20.897 |
| 396 | HCV 2a | 50 | 62 | 9 | A24 | RYRRGVGPT | 5055 | 10.000 |
| 397 | HCV 2a | 50 | 6 | 9 | A3 | MMETHPVAK | 5056 | 20.000 |
| 398 | HCV 2a | 50 | 23 | 9 | B7 | TPPARTHVL | 5057 | 80.000 |
| 399 | HCV 2a | 50 | 66 | 9 | B7 | GVGPTRVGL | 5058 | 30.000 |
| 400 | HCV 2a | 50 | 4 | 9 | B7 | RPMMETHPV | 5059 | 12.000 |
| 401 | HCV 2a | 50 | 74 | 9 | B7 | LSRVRHFHM | 5060 | 10.000 |
| 402 | HCV 2a | 50 | 74 | 9 | B8 | LSRVRHFHM | 5061 | 20.000 |
| 403 | HCV 2a | 50 | 23 | 9 | B8 | TPPARTHVL | 5062 | 16.000 |
| 404 | HCV 2a | 50 | 74 | 9 | B_3501 | LSRVRHFHM | 5063 | 30.000 |
| 405 | HCV 2a | 50 | 36 | 9 | B_3501 | RSACMHVAM | 5064 | 20.000 |
| 406 | HCV 2a | 50 | 23 | 9 | B_3501 | TPPARTHVL | 5065 | 20.000 |
| 407 | HCV 2a | 50 | 59 | 9 | B_3501 | EPKRYRRGV | 5066 | 12.000 |
| 408 | HCV 2a | 50 | 4 | 9 | B_3501 | RPMMETHPV | 5067 | 12.000 |
| 409 | HCV 2a | 50 | 83 | 9 | B_3501 | TSQDGGGAL | 5068 | 10.000 |
| 410 | HCV 2a | 50 | 8 | 9 | B_4403 | ETHPVAKQY | 5069 | 20.250 |
| 411 | HCV 2a | 50 | 37 | 9 | B_4403 | SACMHVAMY | 5070 | 18.000 |
| 412 | HCV 2a | 50 | 57 | 10 | A1 | VTEPkRYRRG | 5071 | 22.500 |
| 413 | HCV 2a | 50 | 73 | 10 | A_0201 | GLSRvRHFHM | 5072 | 28.814 |
| 414 | HCV 2a | 50 | 38 | 10 | A_0201 | ACMHvAMYFV | 5073 | 21.250 |
| 415 | HCV 2a | 50 | 39 | 10 | A_0201 | CMHVaMYFVT | 5074 | 19.198 |
| 416 | HCV 2a | 50 | 22 | 10 | A24 | KTPPaRTHVL | 5075 | 14.400 |
| 417 | HCV 2a | 50 | 65 | 10 | A24 | RGVGpTRVGL | 5076 | 12.000 |
| 418 | HCV 2a | 50 | 43 | 10 | A3 | AMYFvTGCVK | 5077 | 100.000 |
| 419 | HCV 2a | 50 | 31 | 10 | B7 | LVMTsRSACM | 5078 | 15.000 |
| 420 | HCV 2a | 50 | 36 | 10 | B_3501 | RSACmHVAMY | 5079 | 20.000 |
| 421 | HCV 2a | 50 | 54 | 10 | B_3501 | TSLVtEPKRY | 5080 | 15.000 |
| 422 | HCV 2a | 50 | 7 | 10 | B_4403 | METHpVAKQY | 5081 | 405.000 |
| 423 | HCV 2a | 50 | 31 | 10 | B_4403 | RSACmHVAMY | 5082 | 18.000 |
| 424 | HCV 2a | 51 | 30 | 9 | A_0201 | SLTVVSAGV | 5083 | 69.552 |
| 425 | HCV 2a | 51 | 28 | 9 | A_0201 | ALSLTVVSA | 5084 | 11.426 |
| 426 | HCV 2a | 51 | 26 | 9 | A24 | KYALSLTVV | 5085 | 10.000 |
| 427 | HCV 2a | 51 | 21 | 9 | B7 | KPGVLKYAL | 5086 | 80.000 |
| 428 | HCV 2a | 51 | 23 | 9 | B7 | GVLKYALSL | 5087 | 20.000 |
| 429 | HCV 2a | 51 | 21 | 9 | B_3501 | KPGVLKYAL | 5088 | 40.000 |
| 430 | HCV 2a | 51 | 19 | 9 | B_4403 | TGKPGVLKY | 5089 | 27.000 |
| 431 | HCV 2a | 51 | 15 | 10 | A_0201 | WSWHtGKPGV | 5090 | 17.334 |
| 432 | HCV 2a | 51 | 26 | 10 | A24 | KYALsLTVVS | 5091 | 12.000 |
| 433 | HCV 2a | 51 | 18 | 10 | B_4403 | HTGKpGVLKY | 5092 | 13.500 |
| 434 | HCV 2a | 52 | | | | no hits | | |
| 435 | HCV 2a | 53 | 14 | 9 | A_0201 | FEWQKIKCL | 5093 | 36.476 |
| 436 | HCV 2a | 53 | 18 | 9 | B_3501 | KIKCLPPLM | 5094 | 12.000 |
| 437 | HCV 2a | 53 | 13 | 10 | A24 | FFEWqKIKCL | 5095 | 30.000 |
| 438 | HCV 2a | 54 | 1 | 9 | B7 | MPRMVVAST | 5096 | 20.000 |
| 439 | HCV 2a | 54 | 1 | 10 | B7 | MPRMvVASTA | 5097 | 20.000 |
| 440 | HCV 2a | 54 | 7 | 10 | B_3501 | ASTAwHSSHM | 5098 | 10.000 |
| 441 | HCV 2a | 55 | 16 | 9 | A1 | GLMPCALDK | 5099 | 10.000 |
| 442 | HCV 2a | 55 | 52 | 9 | A_0201 | TLVLFPLPV | 5100 | 264.298 |
| 443 | HCV 2a | 55 | 41 | 9 | A_0201 | TLYPWAAYA | 5101 | 87.437 |
| 444 | HCV 2a | 55 | 12 | 9 | A_0201 | VLMLGLMPC | 5102 | 71.872 |
| 445 | HCV 2a | 55 | 13 | 9 | A_0201 | LMLGLMPCA | 5103 | 51.908 |
| 446 | HCV 2a | 55 | 14 | 9 | A_0201 | MLGLMPCAL | 5104 | 36.316 |
| 447 | HCV 2a | 55 | 54 | 9 | A_0201 | VLFPLPVGA | 5105 | 31.249 |
| 448 | HCV 2a | 55 | 7 | 9 | A_0201 | TVLTPVLML | 5106 | 15.907 |
| 449 | HCV 2a | 55 | 47 | 9 | A24 | AYATGTLVL | 5107 | 200.000 |
| 450 | HCV 2a | 55 | 24 | 9 | A24 | KYAPNPRVA | 5108 | 12.000 |

TABLE 4f-continued 2a (4-6)

| No. | Strain | ORF | Start | AA | HLA | Peptide sequence | SEQ ID NO | Score |
|---|---|---|---|---|---|---|---|---|
| 451 | HCV 2a | 55 | 16 | 9 | A3 | GLMPCALDK | 5109 | 270.000 |
| 452 | HCV 2a | 55 | 7 | 9 | B7 | TVLTPVLML | 5110 | 30.000 |
| 453 | HCV 2a | 55 | 5 | 9 | B7 | VVTVLTPVL | 5111 | 20.000 |
| 454 | HCV 2a | 55 | 10 | 9 | B7 | TPVLMLGLM | 5112 | 20.000 |
| 455 | HCV 2a | 55 | 45 | 9 | B7 | WAAYATGTL | 5113 | 12.000 |
| 456 | HCV 2a | 55 | 1 | 9 | B7 | MAAPVVTVL | 5114 | 12.000 |
| 457 | HCV 2a | 55 | 10 | 9 | B_3501 | TPVLMLGLM | 5115 | 40.000 |
| 458 | HCV 2a | 55 | 40 | 9 | B_4403 | STLYPWAAY | 5116 | 12.000 |
| 459 | HCV 2a | 55 | 13 | 10 | A_0201 | LMLGLMPCAL | 5117 | 97.045 |
| 460 | HCV 2a | 55 | 8 | 10 | A_0201 | VLTPvLMLGL | 5118 | 83.527 |
| 461 | HCV 2a | 55 | 12 | 10 | A_0201 | VLMLgLMPCA | 5119 | 71.872 |
| 462 | HCV 2a | 55 | 17 | 10 | A_0201 | LMPCaLDKYA | 5120 | 33.548 |
| 463 | HCV 2a | 55 | 41 | 10 | A_0201 | TLYPwAAYAT | 5121 | 23.846 |
| 464 | HCV 2a | 55 | 51 | 10 | A_0201 | GTLVLFPLPV | 5122 | 13.582 |
| 465 | HCV 2a | 55 | 47 | 10 | A24 | AYATgTLVLF | 5123 | 100.000 |
| 466 | HCV 2a | 55 | 24 | 10 | A24 | KYAPnPRVAA | 5124 | 12.000 |
| 467 | HCV 2a | 55 | 16 | 10 | A3 | GLMPcALDKY | 5125 | 40.500 |
| 468 | HCV 2a | 55 | 28 | 10 | B7 | NPRVaATEGL | 5126 | 800.000 |
| 469 | HCV 2a | 55 | 46 | 10 | B7 | AAYAtGTLVL | 5127 | 36.000 |
| 470 | HCV 2a | 55 | 3 | 10 | B7 | APVVtVLTPV | 5128 | 12.000 |
| 471 | HCV 2a | 55 | 49 | 10 | B7 | ATGTlVLFPL | 5129 | 12.000 |
| 472 | HCV 2a | 55 | 28 | 10 | B8 | NPRVaATEGL | 5130 | 16.000 |
| 473 | HCV 2a | 55 | 28 | 10 | B_3501 | NPRVaATEGL | 5131 | 60.000 |
| 474 | HCV 2a | 55 | 56 | 10 | B_3501 | FPLPvGACKY | 5132 | 40.000 |
| 475 | HCV 2a | 55 | 39 | 10 | B_3501 | TSTLyPWAAY | 5133 | 10.000 |
| 476 | HCV 2a | 55 | 34 | 10 | B_4403 | TEGLsTSTLY | 5134 | 180.000 |
| 477 | HCV 2a | 55 | 56 | 10 | B_4403 | FPLPvGACKY | 5135 | 27.000 |
| 478 | HCV 2a | 56 | 36 | 9 | A_0201 | GPPEDPFKV | 5136 | 10.797 |
| 479 | HCV 2a | 56 | 47 | 9 | A3 | GLGESNAPR | 5137 | 18.000 |
| 480 | HCV 2a | 56 | 108 | 9 | B7 | GPREPARVL | 5138 | 1.200.000 |
| 481 | HCV 2a | 56 | 93 | 9 | B7 | HPTKSPSAL | 5139 | 80.000 |
| 482 | HCV 2a | 56 | 40 | 9 | B7 | DPFKVERGL | 5140 | 80.000 |
| 483 | HCV 2a | 56 | 57 | 9 | B7 | SPRLRAGMT | 5141 | 20.000 |
| 484 | HCV 2a | 56 | 52 | 9 | B7 | NAPRLSPRL | 5142 | 12.000 |
| 485 | HCV 2a | 56 | 108 | 9 | B8 | GPREPARVL | 5143 | 24.000 |
| 486 | HCV 2a | 56 | 57 | 9 | B8 | SPRLRAGMT | 5144 | 16.000 |
| 487 | HCV 2a | 56 | 108 | 9 | B_3501 | GPREPARVL | 5145 | 120.000 |
| 488 | HCV 2a | 56 | 40 | 9 | B_3501 | DPFKVERGL | 5146 | 20.000 |
| 489 | HCV 2a | 56 | 93 | 9 | B_3501 | HPTKSPSAL | 5147 | 20.000 |
| 490 | HCV 2a | 56 | 36 | 9 | B_3501 | GPPEDPFKV | 5148 | 12.000 |
| 491 | HCV 2a | 56 | 65 | 9 | B_3501 | TSAFRVTRY | 5149 | 10.000 |
| 492 | HCV 2a | 56 | 56 | 9 | B_3501 | LSPRLRAGM | 5150 | 10.000 |
| 493 | HCV 2a | 56 | 65 | 9 | B_4403 | TSAFRVTRY | 5151 | 27.000 |
| 494 | HCV 2a | 56 | 17 | 9 | B_4403 | REHTAARKI | 5152 | 13.500 |
| 495 | HCV 2a | 56 | 34 | 10 | A1 | STGPpEDPFK | 5153 | 10.000 |
| 496 | HCV 2a | 56 | 47 | 10 | A_0201 | GLGEsNAPRL | 5154 | 87.586 |
| 497 | HCV 2a | 56 | 63 | 10 | A3 | GMTSaFRVTR | 5155 | 36.000 |
| 498 | HCV 2a | 56 | 108 | 10 | B7 | GREpARVLL | 5156 | 1.200.000 |
| 499 | HCV 2a | 56 | 77 | 10 | B7 | APHEhGSKDL | 5157 | 240.000 |
| 500 | HCV 2a | 56 | 53 | 10 | B7 | APRLsPRLRA | 5158 | 135.000 |
| 501 | HCV 2a | 56 | 4 | 10 | B7 | ASTGmKSMDL | 5159 | 12.000 |
| 502 | HCV 2a | 56 | 108 | 10 | B8 | GPREpARVLL | 5160 | 24.000 |
| 503 | HCV 2a | 56 | 108 | 10 | B_3501 | GPREpARVLL | 5161 | 120.000 |
| 504 | HCV 2a | 56 | 77 | 10 | B_3501 | APHEhGSKDL | 5162 | 40.000 |
| 505 | HCV 2a | 56 | 82 | 10 | B_3501 | GSKDlVPGGL | 5163 | 30.000 |
| 506 | HCV 2a | 56 | 2 | 10 | B_3501 | SSAStGMKSM | 5164 | 10.000 |
| 507 | HCV 2a | 56 | 64 | 10 | B_4403 | MTSAfRVTRY | 5165 | 13.500 |
| 508 | HCV 2a | 57 | 31 | 9 | A_0201 | TMAPKRPRV | 5166 | 50.232 |
| 509 | HCV 2a | 57 | 22 | 9 | A_0201 | VLSRPVMLT | 5167 | 29.137 |
| 510 | HCV 2a | 57 | 8 | 9 | A_0201 | WVTVDRTWI | 5168 | 23.096 |
| 511 | HCV 2a | 57 | 27 | 9 | A3 | VMLTTMAPK | 5169 | 45.000 |
| 512 | HCV 2a | 57 | 3 | 9 | B7 | VPRKDWVTV | 5170 | 40.000 |
| 513 | HCV 2a | 57 | 21 | 9 | B7 | SVLSRPVML | 5171 | 20.000 |
| 514 | HCV 2a | 57 | 33 | 9 | B_3501 | APKRPRVCW | 5172 | 30.000 |
| 515 | HCV 2a | 57 | 3 | 9 | B_3501 | VPRKDWVTV | 5173 | 18.000 |
| 516 | HCV 2a | 57 | 20 | 9 | B_3501 | CSVLSRPVM | 5174 | 10.000 |
| 517 | HCV 2a | 57 | 22 | 10 | A_0201 | VLSRpVMLTT | 5175 | 29.137 |
| 518 | HCV 2a | 57 | 23 | 10 | B7 | LSRPvMLTTM | 5176 | 10.000 |
| 519 | HCV 2a | 57 | 33 | 10 | B8 | APKRpRVCWA | 5177 | 16.000 |
| 520 | HCV 2a | 57 | 23 | 10 | B_3501 | LSRPvMLTTM | 5178 | 30.000 |
| 521 | HCV 2a | 58 | | | | no hits | | |
| 522 | HCV 2a | 59 | 12 | 9 | A_0201 | TMTFFSIGL | 5179 | 58.628 |
| 523 | HCV 2a | 59 | 21 | 9 | A_0201 | KMIGSTATA | 5180 | 12.558 |
| 524 | HCV 2a | 59 | 27 | 9 | B7 | ATAKSRRPL | 5181 | 18.000 |
| 525 | HCV 2a | 59 | 28 | 9 | B8 | TAKSRRPLA | 5182 | 16.000 |

TABLE 4f-continued

2a (4-6)

| No. Strain | ORF | Start | AA | HLA | Peptide sequence | SEQ ID NO | Score |
|---|---|---|---|---|---|---|---|
| 526 HCV 2a | 59 | 33 | 9 | B_3501 | RPLAAQSDI | 5183 | 16.000 |
| 527 HCV 2a | 59 | 21 | 10 | A3 | KMIGsTATAK | 5184 | 135.000 |
| 528 HCV 2a | 59 | 9 | 10 | B7 | APQTmTFFSI | 5185 | 24.000 |
| 529 HCV 2a | 59 | 26 | 10 | B7 | TATAkSRRPL | 5186 | 18.000 |
| 530 HCV 2a | 59 | 11 | 10 | B7 | QTMTfFSIGL | 5187 | 12.000 |
| 531 HCV 2a | 59 | 28 | 10 | B8 | TAKSrRPLAA | 5188 | 16.000 |
| 532 HCV 2a | 60 | 16 | 10 | B7 | MPSRpPRACM | 5189 | 45.000 |
| 533 HCV 2a | 60 | 16 | 10 | B_3501 | MPSRpPRACM | 5190 | 40.000 |
| 534 HCV 2a | 60 | 1 | 10 | B_3501 | MSNTtPGQNM | 5191 | 10.000 |
| 535 HCV 2a | 61 |  |  |  | no hits |  |  |
| 536 HCV 2a | 62 | 8 | 9 | A_0201 | KMTKYRKPL | 5192 | 53.999 |
| 537 HCV 2a | 62 | 133 | 9 | A_0201 | KLHAAVSLC | 5193 | 39.992 |
| 538 HCV 2a | 62 | 104 | 9 | A_0201 | KMAHSVVEC | 5194 | 28.883 |
| 539 HCV 2a | 62 | 1 | 9 | A24 | MYQAATKKM | 5195 | 41.250 |
| 540 HCV 2a | 62 | 11 | 9 | A24 | KYRKPLQLA | 5196 | 12.000 |
| 541 HCV 2a | 62 | 17 | 9 | A3 | QLAALAACK | 5197 | 20.000 |
| 542 HCV 2a | 62 | 82 | 9 | A3 | TIFWWRWSR | 5198 | 18.000 |
| 543 HCV 2a | 62 | 76 | 9 | A3 | YMYCTSTIF | 5199 | 10.000 |
| 544 HCV 2a | 62 | 126 | 9 | B7 | SQRSPRVKL | 5200 | 90.000 |
| 545 HCV 2a | 62 | 143 | 9 | B7 | IPPTYILIL | 5201 | 80.000 |
| 546 HCV 2a | 62 | 112 | 9 | B7 | CNRGDSWLL | 5202 | 40.000 |
| 547 HCV 2a | 62 | 129 | 9 | B7 | SPRVKLHAA | 5203 | 20.000 |
| 548 HCV 2a | 62 | 129 | 9 | B8 | SPRVKLHAA | 5204 | 16.000 |
| 549 HCV 2a | 62 | 51 | 9 | B8 | SARRRNKST | 5205 | 16.000 |
| 550 HCV 2a | 62 | 70 | 9 | B_3501 | RAGDRPYMY | 5206 | 24.000 |
| 551 HCV 2a | 62 | 143 | 9 | B_3501 | IPPTYILIL | 5207 | 20.000 |
| 552 HCV 2a | 62 | 4 | 9 | B_4403 | AATKKMTKY | 5208 | 20.250 |
| 553 HCV 2a | 62 | 98 | 9 | B_4403 | SEKEQGKMA | 5209 | 12.000 |
| 554 HCV 2a | 62 | 110 | 9 | B_4403 | VECNRGDSW | 5210 | 12.000 |
| 555 HCV 2a | 62 | 139 | 10 | A_0201 | SLCSiPPTYI | 5211 | 57.380 |
| 556 HCV 2a | 62 | 75 | 10 | A24 | PYMYcTSTIF | 5212 | 15.000 |
| 557 HCV 2a | 62 | 125 | 10 | A24 | KSQRsPRVKL | 5213 | 13.200 |
| 558 HCV 2a | 62 | 11 | 10 | A24 | KYRKpLQLAA | 5214 | 12.000 |
| 559 HCV 2a | 62 | 68 | 10 | B7 | FVRAgDRPYM | 5215 | 75.000 |
| 560 HCV 2a | 62 | 129 | 10 | B7 | SPRVkLHAAV | 5216 | 40.000 |
| 561 HCV 2a | 62 | 131 | 10 | B7 | RVKLhAAVSL | 5217 | 20.000 |
| 562 HCV 2a | 62 | 9 | 10 | B8 | MTKYrKPLQL | 5218 | 80.000 |
| 563 HCV 2a | 62 | 123 | 10 | B8 | SSKSqRSPRV | 5219 | 12.000 |
| 564 HCV 2a | 62 | 74 | 10 | B_3501 | RPYMyCTSTI | 5220 | 16.000 |
| 565 HCV 2a | 62 | 129 | 10 | B_3501 | SPRVkLHAAV | 5221 | 12.000 |
| 566 HCV 2a | 62 | 138 | 10 | B_3501 | VSLCsIPPTY | 5222 | 10.000 |
| 567 HCV 2a | 62 | 125 | 10 | B_3501 | KSQRsPRVKL | 5223 | 10.000 |
| 568 HCV 2a | 62 | 3 | 10 | B_4403 | QAATkKMTKY | 5224 | 20.250 |
| 569 HCV 2a | 63 | 30 | 9 | A_0201 | VLFNRKTSV | 5225 | 437.482 |
| 570 HCV 2a | 63 | 9 | 9 | A_0201 | VLVKPVEFI | 5226 | 109.935 |
| 571 HCV 2a | 63 | 6 | 9 | B7 | APQVLVKPV | 5227 | 12.000 |
| 572 HCV 2a | 63 | 24 | 9 | B_3501 | DPRGGRVLF | 5228 | 60.000 |
| 573 HCV 2a | 63 | 29 | 10 | A_0201 | RVLFnRKTSV | 5229 | 22.517 |
| 574 HCV 2a | 63 | 8 | 10 | A_0201 | QVLVkPVEFI | 5230 | 20.936 |
| 575 HCV 2a | 63 | 35 | 10 | A_0201 | KTSVsFSPHV | 5231 | 12.848 |
| 576 HCV 2a | 63 | 31 | 10 | A24 | LFNRkTSVSF | 5232 | 15.000 |
| 577 HCV 2a | 63 | 24 | 10 | B8 | DPRGgRVLFN | 5233 | 16.000 |
| 578 HCV 2a | 64 | 7 | 9 | A_0201 | VLISWMFCL | 5234 | 484.457 |
| 579 HCV 2a | 64 | 6 | 9 | A_0201 | LVLISWMFC | 5235 | 25.565 |
| 580 HCV 2a | 64 | 7 | 9 | A3 | VLISWMFCL | 5236 | 12.150 |
| 581 HCV 2a | 64 | 4 | 9 | B7 | LPLVLISWM | 5237 | 20.000 |
| 582 HCV 2a | 64 | 4 | 9 | B_3501 | LPLVLISWM | 5238 | 40.000 |
| 583 HCV 2a | 64 | 6 | 10 | A_0201 | LVLIsWMFCL | 5239 | 156.843 |
| 584 HCV 2a | 64 | 3 | 10 | A_0201 | QLPLvLISWM | 5240 | 62.845 |
| 585 HCV 2a | 64 | 16 | 10 | B7 | EPGErRPAKL | 5241 | 80.000 |
| 586 HCV 2a | 64 | 6 | 10 | B7 | LVLIsWMFCL | 5242 | 20.000 |
| 587 HCV 2a | 64 | 16 | 10 | B8 | EPGErRPAKL | 5243 | 48.000 |
| 588 HCV 2a | 64 | 19 | 10 | B8 | ERRPaKLSVL | 5244 | 16.000 |
| 589 HCV 2a | 64 | 16 | 10 | B_3501 | EPGErRPAKL | 5245 | 40.000 |
| 590 HCV 2a | 64 | 4 | 10 | B_3501 | LPLVLISWMF | 5246 | 20.000 |
| 591 HCV 2a | 65 | 4 | 10 | A3 | TLAHaPCIEK | 5247 | 60.000 |
| 592 HCV 2a | 66 | 3 | 9 | A_0201 | SMMTSGTRI | 5248 | 27.879 |
| 593 HCV 2a | 67 | 19 | 9 | A_0201 | VMVPRMEQL | 5249 | 29.559 |
| 594 HCV 2a | 67 | 39 | 9 | A_0201 | IMNIWAASI | 5250 | 12.809 |
| 595 HCV 2a | 67 | 37 | 9 | B_4403 | GEIMNIWAA | 5251 | 20.000 |
| 596 HCV 2a | 67 | 10 | 10 | A_0201 | IMSHaIRCPV | 5252 | 85.394 |
| 597 HCV 2a | 67 | 26 | 10 | A_0201 | QLHScTNQWC | 5253 | 27.324 |
| 598 HCV 2a | 67 | 21 | 10 | B7 | VPRMeQLHSC | 5254 | 20.000 |
| 599 HCV 2a | 67 | 11 | 10 | B_3501 | MSHAiRCPVM | 5255 | 10.000 |
| 600 HCV 2a | 67 | 37 | 10 | B_4403 | GEIMnIWAAS | 5256 | 20.000 |

TABLE 4f-continued

2a (4-6)

| No. | Strain | ORF | Start | AA | HLA | Peptide sequence | SEQ ID NO | Score |
|---|---|---|---|---|---|---|---|---|
| 601 | HCV 2a | 68 | 2 | 9 | A_0201 | SMCVRKPCV | 5257 | 50.232 |
| 602 | HCV 2a | 68 | 25 | 9 | A_0201 | IQHRDVFPT | 5258 | 17.134 |
| 603 | HCV 2a | 68 | 12 | 9 | B7 | APRCCTATF | 5259 | 12.000 |
| 604 | HCV 2a | 68 | 9 | 9 | B7 | CVRAPRCCT | 5260 | 11.250 |
| 605 | HCV 2a | 68 | 12 | 9 | B_3501 | APRCCTATF | 5261 | 60.000 |
| 606 | HCV 2a | 68 | 24 | 10 | A_0201 | GIQHrDVFPT | 5262 | 13.669 |
| 607 | HCV 2a | 69 | 1 | 9 | A_0201 | MLSLEQSLV | 5263 | 118.238 |
| 608 | HCV 2a | 69 | 2 | 10 | B_3501 | LSLEqSLVTM | 5264 | 20.000 |
| 609 | HCV 2a | 70 | 14 | 9 | A_0201 | KEQPGRFPV | 5265 | 27.454 |
| 610 | HCV 2a | 70 | 12 | 9 | B_4403 | IEKEQPGRF | 5266 | 40.000 |
| 611 | HCV 2a | 70 | 14 | 9 | B_4403 | KEQPGRFPV | 5267 | 12.000 |
| 612 | HCV 2a | 71 | 83 | 9 | A1 | RSEVFLVVR | 5268 | 27.000 |
| 613 | HCV 2a | 71 | 121 | 9 | A_0201 | RLVFLLVFL | 5269 | 270.234 |
| 614 | HCV 2a | 71 | 87 | 9 | A_0201 | FLVVRTPNL | 5270 | 98.267 |
| 615 | HCV 2a | 71 | 56 | 9 | A24 | GYPGFPQDL | 5271 | 360.000 |
| 616 | HCV 2a | 71 | 121 | 9 | A24 | RLVFLLVFL | 5272 | 14.400 |
| 617 | HCV 2a | 71 | 69 | 9 | A24 | RSLGMGWRL | 5273 | 12.000 |
| 618 | HCV 2a | 71 | 118 | 9 | B7 | CGRRLVFLL | 5274 | 40.000 |
| 619 | HCV 2a | 71 | 12 | 9 | B7 | RVSMTLPTL | 5275 | 20.000 |
| 620 | HCV 2a | 71 | 117 | 9 | B8 | SCGRRLVFL | 5276 | 16.000 |
| 621 | HCV 2a | 71 | 42 | 9 | B_3501 | HPAQPSPSF | 5277 | 20.000 |
| 622 | HCV 2a | 71 | 69 | 9 | B_3501 | RSLGMGWRL | 5278 | 10.000 |
| 623 | HCV 2a | 71 | 84 | 9 | B_4403 | SEVFLVVRT | 5279 | 48.000 |
| 624 | HCV 2a | 71 | 79 | 10 | A_0201 | RGWDrSEVFL | 5280 | 26.100 |
| 625 | HCV 2a | 71 | 114 | 10 | A_0201 | NLTScGRRLV | 5281 | 13.910 |
| 626 | HCV 2a | 71 | 86 | 10 | A24 | VFLVvRTPNL | 5282 | 30.000 |
| 627 | HCV 2a | 71 | 8 | 10 | A24 | KPHVrVSMTL | 5283 | 11.200 |
| 628 | HCV 2a | 71 | 51 | 10 | A24 | PYRGqGYPGF | 5284 | 10.000 |
| 629 | HCV 2a | 71 | 70 | 10 | A3 | SLGMgWRLPR | 5285 | 24.000 |
| 630 | HCV 2a | 71 | 89 | 10 | B7 | VVRTpNLGPL | 5286 | 200.000 |
| 631 | HCV 2a | 71 | 8 | 10 | B7 | KPHVrVSMTL | 5287 | 80.000 |
| 632 | HCV 2a | 71 | 77 | 10 | B7 | LPRGwDRSEV | 5288 | 60.000 |
| 633 | HCV 2a | 71 | 19 | 10 | B7 | TLRDlCRGSL | 5289 | 60.000 |
| 634 | HCV 2a | 71 | 64 | 10 | B7 | LPVErRSLGM | 5290 | 20.000 |
| 635 | HCV 2a | 71 | 35 | 10 | B7 | EPRGdRSHPA | 5291 | 20.000 |
| 636 | HCV 2a | 71 | 2 | 10 | B7 | YPMRsAKPHV | 5292 | 12.000 |
| 637 | HCV 2a | 71 | 35 | 10 | B8 | EPRGdRSHPA | 5293 | 32.000 |
| 638 | HCV 2a | 71 | 19 | 10 | B8 | TLRDlCRGSL | 5294 | 12.000 |
| 639 | HCV 2a | 71 | 64 | 10 | B_3501 | LPVErRSLGM | 5295 | 80.000 |
| 640 | HCV 2a | 71 | 8 | 10 | B_3501 | KPHVrVSMTL | 5296 | 40.000 |
| 641 | HCV 2a | 71 | 6 | 10 | B_3501 | SAKPhVRVSM | 5297 | 18.000 |
| 642 | HCV 2a | 71 | 77 | 10 | B_3501 | LPRGwDRSEV | 5298 | 18.000 |
| 643 | HCV 2a | 71 | 66 | 10 | B_4403 | VERRsLGMGW | 5299 | 12.000 |

TABLE 4g

2b (1-3)

| No. | Strain | ORF | Start | AA | HLA | Peptide sequence | SEQ ID NO: | Score |
|---|---|---|---|---|---|---|---|---|
| 1 | HCV 2b | 1 | 15 | 9 | A_0201 | LLSSRRKRL | 5257 | 36.32 |
| 2 | HCV 2b | 1 | 17 | 9 | B7 | SSRRKRLAM | 5258 | 15 |
| 3 | HCV 2b | 1 | 2 | 9 | B7 | GATLRHESL | 5259 | 12 |
| 4 | HCV 2b | 1 | 17 | 9 | B8 | SSRRKRLAM | 5260 | 20 |
| 5 | HCV 2b | 1 | 2 | 9 | B8 | GATLRHESL | 5261 | 16 |
| 6 | HCV 2b | 1 | 14 | 10 | B8 | ELLSSRRKRL | 5262 | 16 |
| 7 | HCV 2b | 1 | 17 | 9 | B_3501 | SSRRKRLAM | 5263 | 30 |
| 8 | HCV 2b | 1 | 16 | 10 | B_3501 | LSSRRKRLAM | 5264 | 10 |
| 9 | HCV 2b | 2 | 43 | 9 | A_0201 | VVLPISWGT | 5265 | 30.76 |
| 10 | HCV 2b | 2 | 44 | 10 | A_0201 | VLPISWGTSL | 5266 | 36.32 |
| 11 | HCV 2b | 2 | 20 | 10 | A_0201 | LLGAPATPGI | 5267 | 17.74 |
| 12 | HCV 2b | 2 | 52 | 10 | A_0201 | SLSLaPLSEA | 5268 | 11.43 |
| 13 | HCV 2b | 2 | 45 | 9 | B7 | LPISWGTSL | 5269 | 80 |
| 14 | HCV 2b | 2 | 13 | 9 | B7 | CPLAGLVLL | 5270 | 80 |
| 15 | HCV 2b | 2 | 62 | 9 | B7 | SPELWHTVL | 5271 | 24 |
| 16 | HCV 2b | 2 | 56 | 10 | B7 | APLSEASPEL | 5272 | 240 |
| 17 | HCV 2b | 2 | 6 | 10 | B7 | AVGQVGSCPL | 5273 | 60 |
| 18 | HCV 2b | 2 | 9 | 10 | B7 | QVGSCPLAGL | 5274 | 30 |
| 19 | HCV 2b | 2 | 61 | 10 | B7 | ASPElWHTVL | 5275 | 12 |
| 20 | HCV 2b | 2 | 45 | 9 | B_3501 | LPISWGTSL | 5276 | 20 |
| 21 | HCV 2b | 2 | 13 | 9 | B_3501 | CPLAGLVLL | 5277 | 20 |
| 22 | HCV 2b | 2 | 56 | 10 | B_3501 | APLSEASPEL | 5278 | 20 |

TABLE 4g-continued

2b (1-3)

| No. | Strain | ORF | Start | AA | HLA | Peptide sequence | SEQ ID NO: | Score |
|---|---|---|---|---|---|---|---|---|
| 23 | HCV 2b | 2 | 61 | 10 | B_3501 | ASPELWHTVL | 5279 | 10 |
| 24 | HCV 2b | 2 | 59 | 10 | B_4403 | SEASPELWHT | 5280 | 24 |
| 25 | HCV 2b | 2 | 1 | 10 | B_4403 | METRVAVGQV | 5281 | 18 |
| 26 | HCV 2b | 3 | 37 | 9 | A1 | ATTPLMIAR | 5282 | 12.5 |
| 27 | HCV 2b | 3 | 53 | 9 | A_0201 | SLTQFSIFL | 5283 | 446.47 |
| 28 | HCV 2b | 3 | 11 | 9 | A_0201 | FLSSYLLFC | 5284 | 289.09 |
| 29 | HCV 2b | 3 | 9 | 9 | A_0201 | ALFLSSYLL | 5285 | 79.04 |
| 30 | HCV 2b | 3 | 4 | 9 | A_0201 | GIYPVALFL | 5286 | 51.7 |
| 31 | HCV 2b | 3 | 55 | 9 | A_0201 | TQFSIFLDV | 5287 | 49.57 |
| 32 | HCV 2b | 3 | 16 | 9 | A_0201 | LLFCRALQC | 5288 | 31.25 |
| 33 | HCV 2b | 3 | 35 | 9 | A_0201 | ALATTPLMI | 5289 | 10.43 |
| 34 | HCV 2b | 3 | 8 | 9 | A_0201 | VALFLSSYL | 5290 | 10.26 |
| 35 | HCV 2b | 3 | 15 | 10 | A_0201 | YLLFCRALQC | 5291 | 84.56 |
| 36 | HCV 2b | 3 | 27 | 10 | A_0201 | LQWKSGTSAL | 5292 | 30.56 |
| 37 | HCV 2b | 3 | 52 | 10 | A_0201 | SSLTQFSIFL | 5293 | 10.78 |
| 38 | HCV 2b | 3 | 14 | 9 | A24 | SYLLFCRAL | 5294 | 300 |
| 39 | HCV 2b | 3 | 10 | 9 | A24 | LFLSSYLLF | 5295 | 15 |
| 40 | HCV 2b | 3 | 3 | 10 | A24 | RGIYPVALFL | 5296 | 16.8 |
| 41 | HCV 2b | 3 | 5 | 10 | A24 | IYPVALFLSS | 5297 | 10.8 |
| 42 | HCV 2b | 3 | 21 | 10 | A3 | ALQCQCLQWK | 5298 | 30 |
| 43 | HCV 2b | 3 | 9 | 10 | A3 | ALFLSSYLLF | 5299 | 20 |
| 44 | HCV 2b | 3 | 11 | 10 | A3 | FLSSYLLFCR | 5300 | 18 |
| 45 | HCV 2b | 3 | 69 | 10 | A3 | TMVPCAAGYK | 5301 | 13.5 |
| 46 | HCV 2b | 3 | 9 | 9 | B7 | ALFLSSYLL | 5302 | 12 |
| 47 | HCV 2b | 3 | 8 | 9 | B7 | VALFLSSYL | 5303 | 12 |
| 48 | HCV 2b | 3 | 1 | 10 | B7 | MQRGiYPVAL | 5304 | 40 |
| 49 | HCV 2b | 3 | 18 | 10 | B7 | FCRAlQCQCL | 5305 | 40 |
| 50 | HCV 2b | 3 | 8 | 10 | B7 | VALFlSSYLL | 5306 | 12 |
| 51 | HCV 2b | 3 | 18 | 10 | B8 | FCRAlQCQCL | 5307 | 16 |
| 52 | HCV 2b | 3 | 49 | 9 | B_3501 | SPGSSLTQF | 5308 | 20 |
| 53 | HCV 2b | 3 | 6 | 10 | B_3501 | YPVALFLSSY | 5309 | 40 |
| 54 | HCV 2b | 3 | 33 | 10 | B_3501 | TSALATTPLM | 5310 | 10 |
| 55 | HCV 2b | 3 | 3 | 9 | B_4403 | RGIYPVALF | 5311 | 15 |
| 56 | HCV 2b | 4 | 17 | 9 | A_0201 | ALLASLSLV | 5312 | 591.89 |
| 57 | HCV 2b | 4 | 7 | 9 | B7 | PARQWAGPL | 5313 | 12 |
| 58 | HCV 2b | 4 | 16 | 9 | B7 | GALLASLSL | 5314 | 12 |
| 59 | HCV 2b | 4 | 11 | 9 | B7 | WAGPLGALL | 5315 | 12 |
| 60 | HCV 2b | 4 | 13 | 10 | B7 | GPLGALLASL | 5316 | 80 |
| 61 | HCV 2b | 4 | 2 | 10 | B_3501 | RPPIPPARQW | 5317 | 20 |
| 62 | HCV 2b | 4 | 13 | 10 | B_3501 | GPLGALLASL | 5318 | 20 |
| 63 | HCV 2b | 5 | 27 | 9 | A_0201 | CLPAVGWMI | 5319 | 78.25 |
| 64 | HCV 2b | 5 | 13 | 9 | A_0201 | FMPTNSTAL | 5320 | 70.97 |
| 65 | HCV 2b | 5 | 20 | 9 | A_0201 | ALAAPSVCL | 5321 | 21.36 |
| 66 | HCV 2b | 5 | 36 | 10 | A_0201 | FVSGGEPWNT | 5322 | 22.5 |
| 67 | HCV 2b | 5 | 13 | 10 | A_0201 | FMPTNSTALA | 5323 | 16.51 |
| 68 | HCV 2b | 5 | 12 | 10 | A24 | CFMPTNSTAL | 5324 | 36 |
| 69 | HCV 2b | 5 | 44 | 9 | B7 | NTRPTSPML | 5325 | 40 |
| 70 | HCV 2b | 5 | 20 | 9 | B7 | ALAAPSVCL | 5326 | 18 |
| 71 | HCV 2b | 5 | 23 | 9 | B7 | APSVCLPAV | 5327 | 12 |
| 72 | HCV 2b | 5 | 19 | 10 | B7 | TALAAPSVCL | 5328 | 18 |
| 73 | HCV 2b | 5 | 28 | 9 | B_3501 | LPAVGWMIF | 5329 | 20 |
| 74 | HCV 2b | 6 | | | | no hits | | |
| 75 | HCV 2b | 7 | | | | no hits | | |
| 76 | HCV 2b | 8 | 1 | 10 | B7 | MGRCGSSSFL | 5330 | 40 |
| 77 | HCV 2b | 9 | 43 | 10 | A1 | HVETSCMASR | 5331 | 18 |
| 78 | HCV 2b | 9 | 2 | 10 | A1 | TTSPPCQLGR | 5332 | 12.5 |
| 79 | HCV 2b | 9 | 16 | 9 | A1 | GTWRLPWSL | 5333 | 18.47 |
| 80 | HCV 2b | 9 | 8 | 10 | A1 | QLGRPRVCGT | 5334 | 17.14 |
| 81 | HCV 2b | 9 | 23 | 10 | A1 | SLSCSAQWRR | 5335 | 12 |
| 82 | HCV 2b | 9 | 11 | 10 | B7 | RPRVCGTWRL | 5336 | 800 |
| 83 | HCV 2b | 9 | 11 | 10 | B_3501 | RPRVCGTWRL | 5337 | 120 |
| 84 | HCV 2b | 9 | 44 | 10 | B_4403 | VETSCMASRF | 5338 | 60 |
| 85 | HCV 2b | 10 | | | | no hits | | |
| 86 | HCV 2b | 11 | 32 | 9 | A_0201 | GLVTRPWLA | 5339 | 37.26 |
| 87 | HCV 2b | 11 | 24 | 10 | A24 | GFSGrYITGL | 5340 | 20 |
| 88 | HCV 2b | 11 | 20 | 9 | A3 | HLFRGFSGR | 5341 | 60 |
| 89 | HCV 2b | 11 | 20 | 10 | A3 | HLFRGFSGRY | 5342 | 18 |
| 90 | HCV 2b | 11 | 51 | 10 | B7 | AQRGTSWDGL | 5343 | 120 |
| 91 | HCV 2b | 11 | 1 | 9 | B_3501 | MSRPGRSRF | 5344 | 15 |
| 92 | HCV 2b | 11 | 49 | 9 | B_3501 | TPAQRGTSW | 5345 | 10 |
| 93 | HCV 2b | 11 | 10 | 9 | B_3501 | CPPSHNPSW | 5346 | 10 |
| 94 | HCV 2b | 12 | 26 | 9 | A_0201 | ALGDTPWAC | 5347 | 152.77 |
| 95 | HCV 2b | 12 | 65 | 9 | A_0201 | FLTTARHQL | 5348 | 98.27 |
| 96 | HCV 2b | 12 | 58 | 9 | A_0201 | SLDGRPVFL | 5349 | 47 |
| 97 | HCV 2b | 12 | 47 | 9 | A_0201 | LLTSSRLNL | 5350 | 36.32 |

TABLE 4g-continued

2b (1-3)

| No. | Strain | ORF | Start | AA | HLA | Peptide sequence | SEQ ID NO: | Score |
|---|---|---|---|---|---|---|---|---|
| 98 | HCV 2b | 12 | 76 | 9 | A_0201 | KLTRWATCT | 5351 | 26.08 |
| 99 | HCV 2b | 12 | 46 | 10 | A_0201 | NLLTSSRLNL | 5352 | 79.04 |
| 100 | HCV 2b | 12 | 58 | 10 | A_0201 | SLDGRPVELT | 5353 | 39.76 |
| 101 | HCV 2b | 12 | 65 | 10 | A_0201 | FLTTARHQLC | 5354 | 22.85 |
| 102 | HCV 2b | 12 | 57 | 10 | A_0201 | TSLDGRPVFL | 5355 | 11.64 |
| 103 | HCV 2b | 12 | 64 | 10 | A24 | VFLTTARHQL | 5356 | 30 |
| 104 | HCV 2b | 12 | 40 | 9 | B7 | APGVWPNLL | 5357 | 240 |
| 105 | HCV 2b | 12 | 19 | 9 | B7 | HPEDPCSAL | 5358 | 36 |
| 106 | HCV 2b | 12 | 4 | 9 | B7 | GVHCCRQGL | 5359 | 30 |
| 107 | HCV 2b | 12 | 96 | 9 | B7 | LPHIPVRGI | 5360 | 12 |
| 108 | HCV 2b | 12 | 39 | 9 | B7 | CAPGVWPNL | 5361 | 12 |
| 109 | HCV 2b | 12 | 88 | 9 | B7 | VAGRAPRSL | 5362 | 12 |
| 110 | HCV 2b | 12 | 92 | 10 | B7 | APRSLPHIPV | 5363 | 180 |
| 111 | HCV 2b | 12 | 68 | 10 | B7 | TARHQLCPKL | 5364 | 120 |
| 112 | HCV 2b | 12 | 44 | 10 | B7 | WPNLLTSSRL | 5365 | 80 |
| 113 | HCV 2b | 12 | 50 | 10 | B7 | SSRLNLSTSL | 5366 | 40 |
| 114 | HCV 2b | 12 | 87 | 10 | B7 | QVAGRAPRSL | 5367 | 20 |
| 115 | HCV 2b | 12 | 39 | 10 | B7 | CAPGVWPNLL | 5368 | 12 |
| 116 | HCV 2b | 12 | 68 | 10 | B7 | TARHQLCPKL | 5369 | 16 |
| 117 | HCV 2b | 12 | 74 | 10 | B7 | CPKLTRWATC | 5370 | 16 |
| 118 | HCV 2b | 12 | 40 | 9 | B_3501 | APGVWPNLL | 5371 | 20 |
| 119 | HCV 2b | 12 | 19 | 9 | B_3501 | HPEDPCSAL | 5372 | 12 |
| 120 | HCV 2b | 12 | 57 | 9 | B_3501 | TSLDGRPVF | 5373 | 10 |
| 121 | HCV 2b | 12 | 44 | 10 | B_3501 | WPNLLTSSRL | 5374 | 20 |
| 122 | HCV 2b | 12 | 50 | 10 | B_3501 | SSRLNLSTSL | 5375 | 15 |
| 123 | HCV 2b | 12 | 92 | 10 | B_3501 | APRSLPHIPV | 5376 | 12 |
| 124 | HCV 2b | 12 | 57 | 10 | B_3501 | TSLDGRPVFL | 5377 | 10 |
| 125 | HCV 2b | 12 | 35 | 9 | B_4403 | SERPCAPGV | 5378 | 24 |
| 126 | HCV 2b | 12 | 35 | 10 | B_4403 | SERPCAPGVW | 5379 | 72 |
| 127 | HCV 2b | 13 | 33 | 10 | A1 | ASEQSLTRLR | 5380 | 13.5 |
| 128 | HCV 2b | 13 | 37 | 9 | A_0201 | SLTRLRPQV | 5381 | 69.55 |
| 129 | HCV 2b | 13 | 24 | 9 | A_0201 | IQWTLPPSL | 5382 | 30.56 |
| 130 | HCV 2b | 13 | 38 | 9 | B7 | LTRLRPQVL | 5383 | 40 |
| 131 | HCV 2b | 13 | 13 | 9 | B7 | APMISSSAT | 5384 | 18 |
| 132 | HCV 2b | 13 | 20 | 9 | B7 | ATSAIQWTL | 5385 | 12 |
| 133 | HCV 2b | 13 | 19 | 11 | B7 | SATSAaIQWTL | 5386 | 12 |
| 134 | HCV 2b | 13 | 23 | 10 | B7 | AIQWTLPPSL | 5387 | 12 |
| 135 | HCV 2b | 13 | 32 | 10 | B7 | LASEQSLTRL | 5388 | 12 |
| 136 | HCV 2b | 13 | 38 | 9 | B8 | LTRLRPQVL | 5389 | 80 |
| 137 | HCV 2b | 13 | 42 | 9 | B_3501 | RPQVLGWWF | 5390 | 40 |
| 138 | HCV 2b | 13 | 7 | 10 | B_4403 | MEAAQPAPMI | 5391 | 12 |
| 139 | HCV 2b | 14 | 5 | 9 | A_0201 | SLFMARLSL | 5392 | 79.04 |
| 140 | HCV 2b | 14 | 4 | 10 | A24 | RSLFmARLSL | 5393 | 12 |
| 141 | HCV 2b | 14 | 2 | 10 | B7 | RARSLFMARL | 5394 | 120 |
| 142 | HCV 2b | 14 | 2 | 10 | B_3501 | RARSLFMARL | 5395 | 18 |
| 143 | HCV 2b | 14 | 4 | 10 | B_3501 | RSLFMARLSL | 5396 | 10 |
| 144 | HCV 2b | 15 | 12 | 9 | A_0201 | SMPSPTTGV | 5397 | 50.23 |
| 145 | HCV 2b | 15 | 3 | 9 | A_0201 | SQQPFGAWA | 5398 | 10.53 |
| 146 | HCV 2b | 15 | 5 | 9 | B7 | QPFGAWASM | 5399 | 20 |
| 147 | HCV 2b | 15 | 19 | 9 | B7 | GVSTsPLYQL | 5400 | 30 |
| 148 | HCV 2b | 15 | 5 | 9 | B_3501 | QPFGAWASM | 5401 | 40 |
| 149 | HCV 2b | 16 | | | | no hits | | |
| 150 | HCV 2b | 17 | 1 | 10 | A_0201 | MMPGQLGTSL | 5402 | 26.23 |
| 151 | HCV 2b | 17 | 2 | 9 | B7 | MPGQLGTSL | 5403 | 80 |
| 152 | HCV 2b | 17 | 2 | 9 | B_3501 | MPGQLGTSL | 5404 | 20 |
| 153 | HCV 2b | 18 | 5 | 10 | B7 | SPRRSKEEIT | 5405 | 20 |
| 154 | HCV 2b | 18 | 5 | 10 | B7 | SPRRSKEEIT | 5406 | 16 |
| 155 | HCV 2b | 18 | 5 | 9 | B_3501 | SPRRSKEEI | 5407 | 24 |
| 156 | HCV 2b | 18 | 8 | 10 | B_3501 | RSKEEITLRI | 5408 | 24 |
| 157 | HCV 2b | 18 | 5 | 9 | B7 | SPRRSKEEI | 5409 | 80.000 |
| 158 | HCV 2b | 19 | 17 | 10 | A3 | LMRWkNAPPK | 5410 | 20 |
| 159 | HCV 2b | 19 | 4 | 10 | A3 | WLWPlTRKSY | 5411 | 15 |
| 160 | HCV 2b | 19 | 29 | 10 | A3 | SLRKGSGWRR | 5412 | 12 |
| 161 | HCV 2b | 19 | 6 | 9 | B7 | WPLTRKSYM | 5413 | 20 |
| 162 | HCV 2b | 19 | 22 | 9 | B7 | NAPPKPPSL | 5414 | 12 |
| 163 | HCV 2b | 19 | 8 | 10 | B7 | LTRKsYMRPL | 5415 | 40 |
| 164 | HCV 2b | 19 | 22 | 9 | B8 | NAPPKPPSL | 5416 | 16 |
| 165 | HCV 2b | 19 | 6 | 9 | B_3501 | WPLTRKSYM | 5417 | 40 |
| 166 | HCV 2b | 20 | 4 | 9 | A_0201 | LLTTWRSLT | 5418 | 12.67 |
| 167 | HCV 2b | 20 | 2 | 10 | B7 | LPLLTTWRSL | 5419 | 80 |
| 168 | HCV 2b | 20 | 2 | 10 | B_3501 | LPLLtTWRSL | 5420 | 20 |
| 169 | HCV 2b | 21 | 6 | 10 | A_0201 | WMPTfSWEAM | 5421 | 13.748 |
| 170 | HCV 2b | 21 | 6 | 9 | A_0201 | WMPTFSWEA | 5422 | 470.387 |
| 171 | HCV 2b | 21 | 7 | 9 | B7 | MPTFSWEAM | 5423 | 20.000 |
| 172 | HCV 2b | 21 | 7 | 9 | B_3501 | MPTFSWEAM | 5424 | 40.000 |

TABLE 4g-continued

2b (1-3)

| No. | Strain | ORF | Start | AA | HLA | Peptide sequence | SEQ ID NO: | Score |
|---|---|---|---|---|---|---|---|---|
| 173 | HCV 2b | 22 | | | | no hits | | |
| 174 | HCV 2b | 23 | 70 | 9 | A1 | QRDPLPLPR | 5425 | 12.500 |
| 175 | HCV 2b | 23 | 91 | 9 | A_0201 | GLQSPIKRI | 5426 | 23.995 |
| 176 | HCV 2b | 23 | 100 | 9 | A_0201 | LLSAAPCHT | 5427 | 12.668 |
| 177 | HCV 2b | 23 | 8 | 9 | A24 | RWQTKCSAL | 5428 | 12.000 |
| 178 | HCV 2b | 23 | 18 | 10 | A24 | KTPMtPVTPL | 5429 | 12.000 |
| 179 | HCV 2b | 23 | 19 | 9 | B7 | TPMTPVTPL | 5430 | 360.000 |
| 180 | HCV 2b | 23 | 80 | 9 | B7 | SVRSSTRTL | 5431 | 200.000 |
| 181 | HCV 2b | 23 | 84 | 9 | B7 | STRTLSRGL | 5432 | 40.000 |
| 182 | HCV 2b | 23 | 35 | 9 | B7 | ASSSPLARL | 5433 | 18.000 |
| 183 | HCV 2b | 23 | 22 | 9 | B7 | TPVTPLGRI | 5434 | 12.000 |
| 184 | HCV 2b | 23 | 55 | 10 | B7 | LPLRgSRGTL | 5435 | 120.000 |
| 185 | HCV 2b | 23 | 46 | 10 | B7 | QMRDhCPPCL | 5436 | 40.000 |
| 186 | HCV 2b | 23 | 59 | 10 | B7 | GSRGtLTWSL | 5437 | 40.000 |
| 187 | HCV 2b | 23 | 76 | 10 | B7 | LPRGsVRSST | 5438 | 30.000 |
| 188 | HCV 2b | 23 | 38 | 10 | B7 | SPLArLPLQM | 5439 | 20.000 |
| 189 | HCV 2b | 23 | 34 | 10 | B7 | TASSsPLARL | 5440 | 18.000 |
| 190 | HCV 2b | 23 | 19 | 9 | B8 | TPMTPVTPL | 5441 | 20.000 |
| 191 | HCV 2b | 23 | 13 | 9 | B8 | CSALSKTPM | 5442 | 10.000 |
| 192 | HCV 2b | 23 | 38 | 10 | B8 | SPLArLPLQM | 5443 | 40.000 |
| 193 | HCV 2b | 23 | 55 | 10 | B8 | LPLRgSRGTL | 5444 | 20.000 |
| 194 | HCV 2b | 23 | 59 | 10 | B8 | GSRGtLTWSL | 5445 | 15.000 |
| 195 | HCV 2b | 24 | 7 | 9 | A_0201 | TLSGLPLRL | 5446 | 21.362 |
| 196 | HCV 2b | 24 | 7 | 10 | A_0201 | TLSGlPLRLV | 5447 | 31.994 |
| 197 | HCV 2b | 24 | 6 | 10 | A24 | RTLSgLPLRL | 5448 | 14.400 |
| 198 | HCV 2b | 24 | 4 | 10 | B7 | SCRTlSGLPL | 5449 | 40.000 |
| 199 | HCV 2b | 24 | 4 | 10 | B8 | SCRTlSGLPL | 5450 | 16.000 |
| 200 | HCV 2b | 25 | 11 | 9 | B_4403 | AEKSQLASS | 5451 | 12.000 |
| 201 | HCV 2b | 25 | 11 | 10 | B_4403 | AEKSqLASSY | 5452 | 360.000 |
| 202 | HCV 2b | 26 | 11 | 10 | A_0201 | SIFSsKLGEV | 5453 | 10.580 |
| 203 | HCV 2b | 27 | 21 | 9 | A_0201 | RLSGNLERL | 5454 | 24.075 |
| 204 | HCV 2b | 27 | 4 | 9 | B7 | TPSHCTHTL | 5455 | 80.000 |
| 205 | HCV 2b | 27 | 4 | 9 | B_3501 | TPSHCTHTL | 5456 | 20.000 |
| 206 | HCV 2b | 27 | 31 | 9 | B_4403 | LERGRVGRV | 5457 | 18.000 |
| 207 | HCV 2b | 28 | 1 | 9 | A1 | MPDPAYYSF | 5458 | 25 |
| 208 | HCV 2b | 28 | 6 | 9 | A24 | YYSFAYSYL | 5459 | 200 |
| 209 | HCV 2b | 28 | 5 | 10 | A24 | AYYSfAYSYL | 5460 | 200 |
| 210 | HCV 2b | 28 | 3 | 9 | B_3501 | DPAYYSFAY | 5461 | 40 |
| 211 | HCV 2b | 28 | 3 | 9 | B_4403 | DPAYYSFAY | 5462 | 27 |
| 212 | HCV 2b | 29 | | | | no hits | | |
| 213 | HCV 2b | 30 | | | | no hits | | |
| 214 | HCV 2b | 31 | 4 | 9 | A1 | DAELVTNSY | 5463 | 45 |
| 215 | HCV 2b | 31 | 41 | 9 | A_0201 | GLFLHAGSV | 5464 | 33.46 |
| 216 | HCV 2b | 31 | 37 | 10 | A_0201 | GIWLGLFLHA | 5465 | 10.77 |
| 217 | HCV 2b | 31 | 32 | 9 | A24 | RPLGCGIWL | 5466 | 12 |
| 218 | HCV 2b | 31 | 32 | 9 | B7 | RPLGCGIWL | 5467 | 80 |
| 219 | HCV 2b | 31 | 25 | 10 | B7 | GPGNCLRRPL | 5468 | 120 |
| 220 | HCV 2b | 31 | 21 | 10 | B7 | CSRVgPGNCL | 5469 | 60.000 |
| 221 | HCV 2b | 31 | 14 | 9 | B8 | DPRLRCSCS | 5470 | 16 |
| 222 | HCV 2b | 31 | 32 | 9 | B_3501 | RPLGCGIWL | 5471 | 40 |
| 223 | HCV 2b | 31 | 25 | 10 | B_3501 | GPGNcLRRPL | 5472 | 20 |
| 224 | HCV 2b | 31 | 21 | 10 | B_3501 | CSRVgPGNCL | 5473 | 15 |
| 225 | HCV 2b | 31 | 4 | 9 | B_4403 | DAELVTNSY | 5474 | 20.25 |
| 226 | HCV 2b | 31 | 3 | 10 | B_4403 | HDAElVTNSY | 5475 | 67.5 |
| 227 | HCV 2b | 32 | 2 | 9 | A24 | RYRPSSVGL | 5476 | 480 |
| 228 | HCV 2b | 32 | 9 | 9 | A3 | GLRAGLLLY | 5477 | 36 |
| 229 | HCV 2b | 32 | 7 | 9 | B7 | SVGLRAGLL | 5478 | 20 |
| 230 | HCV 2b | 32 | 7 | 10 | B7 | SVGLRAGLLL | 5479 | 20 |
| 231 | HCV 2b | 33 | | | | no hits | | |
| 232 | HCV 2b | 34 | | | | no hits | | |
| 233 | HCV 2b | 35 | | | | no hits | | |
| 234 | HCV 2b | 36 | 41 | 9 | A_0201 | GMGGPPFPV | 5480 | 291.35 |
| 235 | HCV 2b | 36 | 1 | 9 | A_0201 | MLLLRPTGT | 5481 | 46.87 |
| 236 | HCV 2b | 36 | 40 | 10 | A_0201 | VGMGgPPFPV | 5482 | 16.56 |
| 237 | HCV 2b | 36 | 33 | 10 | A24 | CYEIHRKVGM | 5483 | 37.5 |
| 238 | HCV 2b | 36 | 50 | 9 | B7 | AGRRQDLCM | 5484 | 30 |
| 239 | HCV 2b | 36 | 47 | 10 | B7 | FPVAGRRQDL | 5485 | 120 |
| 240 | HCV 2b | 36 | 17 | 9 | B_3501 | SPKHRGRAV | 5486 | 12 |
| 241 | HCV 2b | 36 | 25 | 10 | B_3501 | VPLWtFSSCY | 5487 | 40 |
| 242 | HCV 2b | 36 | 34 | 9 | B_4403 | YEIHRKVGM | 5488 | 20 |
| 243 | HCV 2b | 37 | | | | no hits | | |
| 244 | HCV 2b | 38 | | | | no hits | | |
| 245 | HCV 2b | 39 | 14 | 9 | A_0201 | LLPGDRLHL | 5489 | 36.32 |
| 246 | HCV 2b | 39 | 13 | 10 | A_0201 | SLLPGDRLHL | 5490 | 79.04 |
| 247 | HCV 2b | 39 | 19 | 10 | A_0201 | RLHLHHWPHT | 5491 | 12.67 |

TABLE 4g-continued 2b (1-3)

| No. | Strain | ORF | Start | AA | HLA | Peptide sequence | SEQ ID NO: | Score |
|---|---|---|---|---|---|---|---|---|
| 248 | HCV 2b | 39 | 7 | 9 | B7 | GASRRGSLL | 5492 | 12 |
| 249 | HCV 2b | 39 | 7 | 9 | B8 | GASRRGSLL | 5493 | 16 |
| 250 | HCV 2b | 40 | | | | no hits | | |
| 251 | HCV 2b | 41 | 7 | 9 | A_0201 | ILGQTHVEL | 5494 | 36.32 |
| 252 | HCV 2b | 41 | 13 | 9 | A_0201 | VELHQWHTV | 5495 | 14.46 |
| 253 | HCV 2b | 41 | 6 | 10 | A_0201 | TILGqTHVEL | 5496 | 10.87 |
| 254 | HCV 2b | 41 | 20 | 9 | B7 | TVPGGTLHL | 5497 | 20 |
| 255 | HCV 2b | 41 | 31 | 10 | B_3501 | KSRSGINDGF | 5498 | 30 |
| 256 | HCV 2b | 42 | 33 | 9 | A_0201 | QLLHRRALC | 5499 | 18.38 |
| 257 | HCV 2b | 42 | 33 | 10 | A_0201 | QLLHRRALCA | 5500 | 18.38 |
| 258 | HCV 2b | 42 | 29 | 9 | A3 | NLPHQLLHR | 5501 | 12 |
| 259 | HCV 2b | 42 | 34 | 10 | A3 | LLHRrALCAK | 5502 | 30 |
| 260 | HCV 2b | 42 | 22 | 9 | B7 | LPKHVAGNL | 5503 | 80 |
| 261 | HCV 2b | 42 | 27 | 9 | B7 | AGNLPHQLL | 5504 | 18 |
| 262 | HCV 2b | 42 | 26 | 9 | B7 | VAGNLPHQL | 5505 | 12 |
| 263 | HCV 2b | 42 | 25 | 10 | B7 | HVAGnLPHQL | 5506 | 20 |
| 264 | HCV 2b | 42 | 26 | 10 | B7 | VAGNlPHQLL | 5507 | 18 |
| 265 | HCV 2b | 42 | 22 | 9 | B8 | LPKHVAGNL | 5508 | 16 |
| 266 | HCV 2b | 42 | 22 | 9 | B8 | LPKHVAGNL | 5509 | 60 |
| 267 | HCV 2b | 42 | 2 | 10 | B_3501 | RSKHlGPRPL | 5510 | 30 |
| 268 | HCV 2b | 43 | 33 | 9 | A_0201 | QLLHRRALC | 5511 | 18.38 |
| 269 | HCV 2b | 43 | 33 | 10 | A_0201 | QLLHrRALCA | 5512 | 18.38 |
| 270 | HCV 2b | 43 | 29 | 9 | A3 | NLPHQLLHR | 5513 | 12 |
| 271 | HCV 2b | 43 | 34 | 10 | A3 | LLHRRALCAK | 5514 | 30 |
| 272 | HCV 2b | 43 | 22 | 9 | B7 | LPKHVAGNL | 5515 | 80 |
| 273 | HCV 2b | 43 | 27 | 9 | B7 | AGNLPHQLL | 5516 | 18 |
| 274 | HCV 2b | 43 | 26 | 9 | B7 | VAGNLPHQL | 5517 | 12 |
| 275 | HCV 2b | 43 | 25 | 10 | B7 | HVAGnLPHQL | 5518 | 20 |
| 276 | HCV 2b | 43 | 26 | 10 | B7 | VAGNlPHQLL | 5519 | 18 |
| 277 | HCV 2b | 43 | 22 | 9 | B8 | LPKHVAGNL | 5520 | 16 |
| 278 | HCV 2b | 43 | 22 | 9 | B_3501 | LPKHVAGNL | 5521 | 60 |
| 279 | HCV 2b | 43 | 2 | 10 | B_3501 | RSKHlGPRPL | 5522 | 30 |
| 280 | HCV 2b | 44 | | | | no hits | | |
| 281 | HCV 2b | 45 | 2 | 10 | B7 | SVVQpPGPPL | 5523 | 30 |
| 282 | HCV 2b | 45 | 3 | 9 | B7 | VVQPPGPPL | 5524 | 30 |

TABLE 4h 2b (4-6)

| No. | Strain | ORF | Start | AA | HLA | Peptide sequence | SEQ ID NO: | Score |
|---|---|---|---|---|---|---|---|---|
| 1 | HCV 2b | 1 | 2 | 9 | A_0201 | RLTDLSQLA | 5525 | 20.369 |
| 2 | HCV 2b | 1 | 15 | 10 | A1 | KMEPpRKEEK | 5526 | 90.000 |
| 3 | HCV 2b | 1 | 2 | 10 | A_0201 | RLTDLSQLAV | 5527 | 285.163 |
| 4 | HCV 2b | 1 | 15 | 10 | A3 | KMEPpRKEEK | 5528 | 90.000 |
| 5 | HCV 2b | 2 | 13 | 9 | A_0201 | FQLWPAGLV | 5529 | 15.603 |
| 6 | HCV 2b | 2 | 7 | 9 | A_0201 | RQAHVAFQL | 5530 | 12.562 |
| 7 | HCV 2b | 2 | 12 | 9 | A24 | AFQLWPAGL | 5531 | 30.000 |
| 8 | HCV 2b | 2 | 7 | 9 | A24 | RQAHVAFQL | 5532 | 11.200 |
| 9 | HCV 2b | 2 | 3 | 9 | B8 | AMRRRQAHV | 5533 | 12.000 |
| 10 | HCV 2b | 3 | | | | no hits | | |
| 11 | HCV 2b | 4 | | | | no hits | | |
| 12 | HCV 2b | 5 | 21 | 9 | A24 | TFSSWSSTL | 5534 | 20.000 |
| 13 | HCV 2b | 5 | 55 | 9 | A24 | RTQFGSHRL | 5535 | 12.000 |
| 14 | HCV 2b | 5 | 22 | 9 | B_3501 | FSSWSSTLM | 5536 | 10.000 |
| 15 | HCV 2b | 5 | 50 | 9 | B_3501 | RSPWSRTQF | 5537 | 10.000 |
| 16 | HCV 2b | 5 | 17 | 9 | B_3501 | VPVGTFSSW | 5538 | 10.000 |
| 17 | HCV 2b | 5 | 14 | 9 | B_4403 | REVVPVGTF | 5539 | 240.000 |
| 18 | HCV 2b | 5 | 1 | 10 | B7 | MSRSqEGCSL | 5540 | 40.000 |
| 19 | HCV 2b | 5 | 12 | 10 | B7 | GPREvVPVGT | 5541 | 20.000 |
| 20 | HCV 2b | 5 | 30 | 10 | B7 | MVQKaHDHPL | 5542 | 20.000 |
| 21 | HCV 2b | 5 | 1 | 10 | B_3501 | MSRSqEGCSL | 5543 | 22.500 |
| 22 | HCV 2b | 5 | 12 | 10 | B_3501 | GPREvVPVGT | 5544 | 12.000 |
| 23 | HCV 2b | 5 | 14 | 10 | B_4403 | REVVpVGTFS | 5545 | 18.000 |
| 24 | HCV 2b | 6 | | | | no hits | | |
| 25 | HCV 2b | 7 | 1 | 10 | B_3501 | MPLRdFPVRW | 5546 | 10.000 |
| 26 | HCV 2b | 8 | 13 | 9 | A_0201 | VLWPVVGGL | 5547 | 90.126 |
| 27 | HCV 2b | 8 | 5 | 9 | A_0201 | WLAVCPGPV | 5548 | 41.592 |
| 28 | HCV 2b | 8 | 6 | 9 | B7 | LAVCPGPVL | 5549 | 18.000 |
| 29 | HCV 2b | 8 | 13 | 10 | A_0201 | VLWPvVGGLV | 5550 | 127.579 |

TABLE 4h-continued

2b (4-6)

| No. | Strain | ORF | Start | AA | HLA | Peptide sequence | SEQ ID NO: | Score |
|---|---|---|---|---|---|---|---|---|
| 30 | HCV 2b | 8 | 5 | 10 | A_0201 | WLAVcPGPVL | 5551 | 40.289 |
| 31 | HCV 2b | 8 | 8 | 10 | A_0201 | VCPGpVLWPV | 5552 | 13.314 |
| 32 | HCV 2b | 9 | 10 | 9 | B7 | APSQFSLYV | 5553 | 12.000 |
| 33 | HCV 2b | 9 | 9 | 10 | A_0201 | IAPSqFSLYV | 5554 | 34.322 |
| 34 | HCV 2b | 9 | 7 | 10 | B7 | CPIApSQFSL | 5555 | 80.000 |
| 35 | HCV 2b | 9 | 7 | 10 | B_3501 | CPIApSQFSL | 5556 | 20.000 |
| 36 | HCV 2b | 10 | 10 | 9 | A24 | RYLSVRAGS | 5557 | 21.000 |
| 37 | HCV 2b | 10 | 26 | 9 | A3 | QLVACCCQK | 5558 | 30.000 |
| 38 | HCV 2b | 10 | 4 | 9 | B7 | GPWCSSRYL | 5559 | 80.000 |
| 39 | HCV 2b | 10 | 4 | 9 | B_3501 | GPWCSSRYL | 5560 | 20.000 |
| 40 | HCV 2b | 10 | 18 | 10 | B7 | SPPGkFGAQL | 5561 | 80.000 |
| 41 | HCV 2b | 10 | 18 | 10 | B_3501 | SPPGkFGAQL | 5562 | 20.000 |
| 42 | HCV 2b | 11 | | | | no hits | | |
| 43 | HCV 2b | 12 | | | | no hits | | |
| 44 | HCV 2b | 13 | | | | no hits | | |
| 45 | HCV 2b | 14 | 2 | 9 | B7 | WPRGPLCPL | 5563 | 1.200.000 |
| 46 | HCV 2b | 14 | 2 | 9 | B8 | WPRGPLCPL | 5564 | 16.000 |
| 47 | HCV 2b | 14 | 2 | 9 | B_3501 | WPRGPLCPL | 5565 | 60.000 |
| 48 | HCV 2b | 15 | | | | no hits | | |
| 49 | HCV 2b | 16 | 20 | 9 | A24 | PYLPICSGL | 5566 | 50.400 |
| 50 | HCV 2b | 16 | 11 | 9 | B_3501 | AAVDSADPY | 5567 | 12.000 |
| 51 | HCV 2b | 16 | 14 | 9 | B_3501 | DSADPYPYL | 5568 | 10.000 |
| 52 | HCV 2b | 16 | 11 | 9 | B_4403 | AAVDSADPY | 5569 | 18.000 |
| 53 | HCV 2b | 16 | 13 | 9 | B_4403 | VDSADPYPY | 5570 | 15.000 |
| 54 | HCV 2b | 16 | 12 | 10 | A1 | AVDSaDPYPY | 5571 | 50.000 |
| 55 | HCV 2b | 16 | 15 | 10 | A1 | SADPyPYLPI | 5572 | 25.000 |
| 56 | HCV 2b | 16 | 21 | 10 | A_0201 | YLPicSGLRV | 5573 | 319.939 |
| 57 | HCV 2b | 16 | 19 | 10 | B7 | YPYLpICSGL | 5574 | 80.000 |
| 58 | HCV 2b | 16 | 19 | 10 | B_3501 | YPYLpICSGL | 5575 | 20.000 |
| 59 | HCV 2b | 16 | 10 | 10 | B_4403 | SAAVdSADPY | 5576 | 18.000 |
| 60 | HCV 2b | 17 | 2 | 10 | B7 | LQRIyAPPPL | 5577 | 40.000 |
| 61 | HCV 2b | 18 | 3 | 9 | B7 | NATVCKGSL | 5578 | 12.000 |
| 62 | HCV 2b | 18 | 10 | 10 | A3 | SLSGtWGSTR | 5579 | 18.000 |
| 63 | HCV 2b | 19 | 6 | 9 | B7 | NASSTASCL | 5580 | 12.000 |
| 64 | HCV 2b | 20 | | | | no hits | | |
| 65 | HCV 2b | 21 | 8 | 9 | A1 | GLEAVRHSY | 5581 | 45.000 |
| 66 | HCV 2b | 21 | 8 | 9 | A3 | GLEAVRHSY | 5582 | 18.000 |
| 67 | HCV 2b | 21 | 1 | 9 | B7 | MALPGGGGL | 5583 | 12.000 |
| 68 | HCV 2b | 22 | 2 | 10 | B7 | ICREtSYGTL | 5584 | 40.000 |
| 69 | HCV 2b | 22 | 2 | 10 | B8 | ICREtSYGTL | 5585 | 24.000 |
| 70 | HCV 2b | 23 | | | | no hits | | |
| 71 | HCV 2b | 24 | 24 | 9 | A_0201 | VSLSFVFTA | 5586 | 10.340 |
| 72 | HCV 2b | 24 | 18 | 9 | B7 | LASGNGVSL | 5587 | 12.000 |
| 73 | HCV 2b | 24 | 25 | 10 | A_0201 | SLSFvFTAQL | 5588 | 81.177 |
| 74 | HCV 2b | 24 | 23 | 10 | A_0201 | GVSLsFVFTA | 5589 | 22.036 |
| 75 | HCV 2b | 24 | 17 | 10 | A_0201 | RLASgNGVSL | 5590 | 21.362 |
| 76 | HCV 2b | 25 | 100 | 9 | A_0201 | WMMLPSQEL | 5591 | 262.591 |
| 77 | HCV 2b | 25 | 88 | 9 | A_0201 | IMTIRTQIV | 5592 | 35.012 |
| 78 | HCV 2b | 25 | 51 | 9 | A_0201 | IMAGRSSGL | 5593 | 26.228 |
| 79 | HCV 2b | 25 | 168 | 9 | A_0201 | YLVIASVKA | 5594 | 22.853 |
| 80 | HCV 2b | 25 | 101 | 9 | A_0201 | MMLPSQELT | 5595 | 16.588 |
| 81 | HCV 2b | 25 | 121 | 9 | A_0201 | VIGVVGSLV | 5596 | 16.258 |
| 82 | HCV 2b | 25 | 116 | 9 | A_0201 | SQAARVIGV | 5597 | 16.219 |
| 83 | HCV 2b | 25 | 68 | 9 | A_0201 | SKLRFWFRV | 5598 | 13.392 |
| 84 | HCV 2b | 25 | 120 | 9 | A24 | RVIGVVGSL | 5599 | 16.800 |
| 85 | HCV 2b | 25 | 161 | 9 | A24 | RSPGGAEYL | 5600 | 12.000 |
| 86 | HCV 2b | 25 | 131 | 9 | A24 | KYRRRPRES | 5601 | 11.000 |
| 87 | HCV 2b | 25 | 58 | 9 | A3 | GLTEYTAPY | 5602 | 54.000 |
| 88 | HCV 2b | 25 | 123 | 9 | A3 | GVVGSLVKK | 5603 | 20.250 |
| 89 | HCV 2b | 25 | 208 | 9 | B7 | AALHAARAL | 5604 | 36.000 |
| 90 | HCV 2b | 25 | 120 | 9 | B7 | RVIGVVGSL | 5605 | 20.000 |
| 91 | HCV 2b | 25 | 95 | 9 | B7 | IVGAYWMML | 5606 | 20.000 |
| 92 | HCV 2b | 25 | 169 | 9 | B7 | LVIASVKAL | 5607 | 20.000 |
| 93 | HCV 2b | 25 | 4 | 9 | B7 | EALTARARL | 5608 | 18.000 |
| 94 | HCV 2b | 25 | 100 | 9 | B7 | WMMLPSQEL | 5609 | 18.000 |
| 95 | HCV 2b | 25 | 7 | 9 | B8 | TARARLFHA | 5610 | 16.000 |
| 96 | HCV 2b | 25 | 64 | 9 | B_3501 | APYISKLRF | 5611 | 20.000 |
| 97 | HCV 2b | 25 | 180 | 9 | B_3501 | RSSSSLPWL | 5612 | 10.000 |
| 98 | HCV 2b | 25 | 161 | 9 | B_3501 | RSPGGAEYL | 5613 | 10.000 |
| 99 | HCV 2b | 25 | 183 | 9 | B_3501 | SSLPWLSEM | 5614 | 10.000 |
| 100 | HCV 2b | 25 | 44 | 9 | B_3501 | SSPCSLSIM | 5615 | 10.000 |
| 101 | HCV 2b | 25 | 137 | 9 | B_4403 | RESSATDTF | 5616 | 90.000 |
| 102 | HCV 2b | 25 | 148 | 9 | B_4403 | QDVISSKSY | 5617 | 67.500 |
| 103 | HCV 2b | 25 | 82 | 9 | B_4403 | MEKKWVIMT | 5618 | 12.000 |

TABLE 4h-continued

2b (4-6)

| No. | Strain | ORF | Start | AA | HLA | Peptide sequence | SEQ ID NO: | Score |
|---|---|---|---|---|---|---|---|---|
| 104 | HCV 2b | 25 | 166 | 9 | B_4403 | AEYLVIASV | 5619 | 12.000 |
| 105 | HCV 2b | 25 | 110 | 9 | B_4403 | GECLTVSQA | 5620 | 12.000 |
| 106 | HCV 2b | 25 | 145 | 9 | B_4403 | FEEQDVISS | 5621 | 12.000 |
| 107 | HCV 2b | 25 | 2 | 10 | A1 | MSEAlTARAR | 5622 | 13.500 |
| 108 | HCV 2b | 25 | 58 | 10 | A_0201 | GLTEyTAPYI | 5623 | 235.260 |
| 109 | HCV 2b | 25 | 168 | 10 | A_0201 | YLVIaSVKAL | 5624 | 226.014 |
| 110 | HCV 2b | 25 | 112 | 10 | A_0201 | CLTVsQAARV | 5625 | 69.552 |
| 111 | HCV 2b | 25 | 100 | 10 | A_0201 | WMMLpSQELT | 5626 | 44.885 |
| 112 | HCV 2b | 25 | 1 | 10 | A_0201 | MMSEaLTARA | 5627 | 25.008 |
| 113 | HCV 2b | 25 | 87 | 10 | A_0201 | VIMTiRTQIV | 5628 | 24.663 |
| 114 | HCV 2b | 25 | 78 | 10 | A_0201 | WASSmEKKWV | 5629 | 24.440 |
| 115 | HCV 2b | 25 | 50 | 10 | A_0201 | SIMAgRSSGL | 5630 | 10.868 |
| 116 | HCV 2b | 25 | 61 | 10 | A24 | EYTApYISKL | 5631 | 220.000 |
| 117 | HCV 2b | 25 | 65 | 10 | A24 | PYISkLRFWF | 5632 | 18.000 |
| 118 | HCV 2b | 25 | 131 | 10 | A24 | KYRRrPRESS | 5633 | 10.000 |
| 119 | HCV 2b | 25 | 176 | 10 | B7 | ALRFrSSSSL | 5634 | 120.000 |
| 120 | HCV 2b | 25 | 15 | 10 | B7 | ALRGgAPSFL | 5635 | 120.000 |
| 121 | HCV 2b | 25 | 7 | 10 | B7 | TARArLFHAL | 5636 | 120.000 |
| 122 | HCV 2b | 25 | 201 | 10 | B7 | IVGStIPAAL | 5637 | 20.000 |
| 123 | HCV 2b | 25 | 135 | 10 | B7 | RPREsSATDT | 5638 | 20.000 |
| 124 | HCV 2b | 25 | 208 | 10 | B7 | AALHaARALM | 5639 | 13.500 |
| 125 | HCV 2b | 25 | 50 | 10 | B7 | SIMAgRSSGL | 5640 | 12.000 |
| 126 | HCV 2b | 25 | 7 | 10 | B8 | TARArLFHAL | 5641 | 16.000 |
| 127 | HCV 2b | 25 | 135 | 10 | B_3501 | RPREsSATDT | 5642 | 24.000 |
| 128 | HCV 2b | 25 | 80 | 10 | B_3501 | SSMEkKWVIM | 5643 | 20.000 |
| 129 | HCV 2b | 25 | 28 | 10 | B_3501 | ATREsSWGEY | 5644 | 12.000 |
| 130 | HCV 2b | 25 | 162 | 10 | B_3501 | SPGGaEYLVI | 5645 | 12.000 |
| 131 | HCV 2b | 25 | 64 | 10 | B_3501 | APYIsKLRFW | 5646 | 10.000 |
| 132 | HCV 2b | 25 | 182 | 10 | B_3501 | SSSLpWLSEM | 5647 | 10.000 |
| 133 | HCV 2b | 25 | 43 | 10 | B_3501 | ASSPcSLSIM | 5648 | 10.000 |
| 134 | HCV 2b | 25 | 3 | 10 | B_4403 | SEALtARARL | 5649 | 24.000 |
| 135 | HCV 2b | 25 | 57 | 10 | B_4403 | SGLTeYTAPY | 5650 | 18.000 |
| 136 | HCV 2b | 25 | 53 | 10 | B_4403 | AGRSsGLTEY | 5651 | 13.500 |
| 137 | HCV 2b | 26 | 9 | 9 | A24 | KTPLARQRL | 5652 | 14.400 |
| 138 | HCV 2b | 26 | 1 | 9 | A3 | MVFPMLVVK | 5653 | 22.500 |
| 139 | HCV 2b | 26 | 5 | 10 | A3 | MLVVkTPLAR | 5654 | 12.000 |
| 140 | HCV 2b | 26 | 3 | 10 | B7 | FPMLvVKTPL | 5655 | 240.000 |
| 141 | HCV 2b | 26 | 3 | 10 | B_3501 | FPMLvVKTPL | 5656 | 20.000 |
| 142 | HCV 2b | 27 | 5 | 9 | A_0201 | VLMSLSVTV | 5657 | 437.482 |
| 143 | HCV 2b | 27 | 21 | 9 | A_0201 | YENPIGSFL | 5658 | 10.509 |
| 144 | HCV 2b | 27 | 20 | 9 | A24 | SYENPIGSF | 5659 | 150.000 |
| 145 | HCV 2b | 27 | 8 | 9 | A3 | SLSVTVESK | 5660 | 60.000 |
| 146 | HCV 2b | 27 | 28 | 9 | A3 | FLLPQALRR | 5661 | 18.000 |
| 147 | HCV 2b | 27 | 37 | 9 | B_3501 | KSTRSAGEY | 5662 | 20.000 |
| 148 | HCV 2b | 27 | 13 | 9 | B_4403 | VESKQRVSY | 5663 | 120.000 |
| 149 | HCV 2b | 27 | 12 | 10 | A1 | TVESkQRVSY | 5664 | 90.000 |
| 150 | HCV 2b | 27 | 4 | 10 | A_0201 | SVLMsLSVTV | 5665 | 22.517 |
| 151 | HCV 2b | 27 | 21 | 10 | A_0201 | YENPiGSFLL | 5666 | 11.082 |
| 152 | HCV 2b | 27 | 20 | 10 | A24 | SYENpIGSFL | 5667 | 420.000 |
| 153 | HCV 2b | 27 | 19 | 10 | B_3501 | VSYEnPIGSF | 5668 | 10.000 |
| 154 | HCV 2b | 27 | 21 | 10 | B_4403 | YENPiGSFLL | 5669 | 12.000 |
| 155 | HCV 2b | 28 | 43 | 9 | A_0201 | WLTAPLDKL | 5670 | 110.747 |
| 156 | HCV 2b | 28 | 19 | 9 | A_0201 | FLAMAVVSI | 5671 | 110.379 |
| 157 | HCV 2b | 28 | 21 | 9 | A_0201 | AMAVVSIGV | 5672 | 50.232 |
| 158 | HCV 2b | 28 | 81 | 9 | A_0201 | ALTLEAARL | 5673 | 21.362 |
| 159 | HCV 2b | 28 | 6 | 9 | A24 | FFPPLAGSI | 5674 | 10.800 |
| 160 | HCV 2b | 28 | 55 | 9 | B7 | FAPNPYRDL | 5675 | 18.000 |
| 161 | HCV 2b | 28 | 72 | 9 | B7 | QASSTERSL | 5676 | 12.000 |
| 162 | HCV 2b | 28 | 81 | 9 | B7 | ALTLEAARL | 5677 | 12.000 |
| 163 | HCV 2b | 28 | 58 | 9 | B_3501 | NPYRDLAEW | 5678 | 15.000 |
| 164 | HCV 2b | 28 | 74 | 9 | B_3501 | SSTERSLAL | 5679 | 10.000 |
| 165 | HCV 2b | 28 | 84 | 9 | B_4403 | LEAARLTSC | 5680 | 18.000 |
| 166 | HCV 2b | 28 | 54 | 10 | A24 | SFAPnPYRDL | 5681 | 24.000 |
| 167 | HCV 2b | 28 | 41 | 10 | A3 | RMWLtAPLDK | 5682 | 200.000 |
| 168 | HCV 2b | 28 | 71 | 10 | B7 | AQASsTERSL | 5683 | 12.000 |
| 169 | HCV 2b | 28 | 11 | 10 | B7 | AGSIqNTSFL | 5684 | 12.000 |
| 170 | HCV 2b | 28 | 80 | 10 | B7 | LALTlEAARL | 5685 | 12.000 |
| 171 | HCV 2b | 28 | 73 | 10 | B7 | ASSTeRSLAL | 5686 | 12.000 |
| 172 | HCV 2b | 28 | 46 | 10 | B_3501 | APLDkLRTSF | 5687 | 40.000 |
| 173 | HCV 2b | 28 | 35 | 10 | B_3501 | RSSHtDRMWL | 5688 | 15.000 |
| 174 | HCV 2b | 28 | 64 | 10 | B_4403 | AEWGgVNAQA | 5689 | 18.000 |
| 175 | HCV 2b | 29 | 2 | 9 | B_3501 | RAPVQEYDM | 5690 | 12.000 |
| 176 | HCV 2b | 30 | 5 | 9 | B7 | SPSEGGADL | 5691 | 80.000 |
| 177 | HCV 2b | 30 | 5 | 9 | B_3501 | SPSEGGADL | 5692 | 40.000 |

TABLE 4h-continued

2b (4-6)

| No. | Strain | ORF | Start | AA | HLA | Peptide sequence | SEQ ID NO: | Score |
|---|---|---|---|---|---|---|---|---|
| 178 | HCV 2b | 30 | 42 | 9 | B_3501 | VSPEGCWTL | 5693 | 10.000 |
| 179 | HCV 2b | 30 | 33 | 10 | A1 | DSDPaSEAAV | 5694 | 15.000 |
| 180 | HCV 2b | 30 | 49 | 10 | A_0201 | TLSPpVSAPV | 5695 | 69.552 |
| 181 | HCV 2b | 30 | 41 | 10 | A_0201 | AVSPeGCWTL | 5696 | 14.019 |
| 182 | HCV 2b | 30 | 41 | 10 | B7 | AVSPeGCWTL | 5697 | 60.000 |
| 183 | HCV 2b | 30 | 22 | 10 | B7 | SPGSpSRGGM | 5698 | 30.000 |
| 184 | HCV 2b | 30 | 22 | 10 | B_3501 | SPGSpSRGGM | 5699 | 40.000 |
| 185 | HCV 2b | 30 | 7 | 10 | B_4403 | SEGGaDLAGS | 5700 | 18.000 |
| 186 | HCV 2b | 30 | 38 | 10 | B_4403 | SEAAvSPEGC | 5701 | 16.000 |
| 187 | HCV 2b | 31 | 74 | 9 | A_0201 | VMWDGSVNM | 5702 | 207.569 |
| 188 | HCV 2b | 31 | 31 | 9 | A_0201 | SQSYAVLWV | 5703 | 89.205 |
| 189 | HCV 2b | 31 | 80 | 9 | A_0201 | VNMEANTSV | 5704 | 11.709 |
| 190 | HCV 2b | 31 | 32 | 9 | A_0201 | QSYAVLWVV | 5705 | 10.275 |
| 191 | HCV 2b | 31 | 34 | 9 | A_0201 | YAVLWVVQV | 5706 | 10.220 |
| 192 | HCV 2b | 31 | 36 | 9 | A3 | VLWVVQVAF | 5707 | 15.000 |
| 193 | HCV 2b | 31 | 56 | 9 | B7 | LACEGGDPL | 5708 | 12.000 |
| 194 | HCV 2b | 31 | 15 | 9 | B7 | SIRVTSPPM | 5709 | 10.000 |
| 195 | HCV 2b | 31 | 31 | 10 | A_0201 | SQSYaVLWVV | 5710 | 49.874 |
| 196 | HCV 2b | 31 | 9 | 10 | A_0201 | ITLEsDSIRV | 5711 | 24.912 |
| 197 | HCV 2b | 31 | 43 | 10 | A24 | AFKDgADSWL | 5712 | 24.000 |
| 198 | HCV 2b | 31 | 36 | 10 | A3 | VLWVvQVAFK | 5713 | 300.000 |
| 199 | HCV 2b | 31 | 73 | 10 | B7 | AVMWdGSVNM | 5714 | 45.000 |
| 200 | HCV 2b | 31 | 2 | 10 | B7 | ESREsRTITL | 5715 | 40.000 |
| 201 | HCV 2b | 31 | 17 | 10 | B7 | RVTSpPMKRL | 5716 | 30.000 |
| 202 | HCV 2b | 31 | 28 | 10 | B7 | STMSqSYAVL | 5717 | 12.000 |
| 203 | HCV 2b | 31 | 2 | 10 | B8 | ESREsRTITL | 5718 | 240.000 |
| 204 | HCV 2b | 31 | 2 | 10 | B_3501 | ESREsRTITL | 5719 | 30.000 |
| 205 | HCV 2b | 31 | 14 | 10 | B_3501 | DSIRvTSPPM | 5720 | 10.000 |
| 206 | HCV 2b | 32 | 103 | 9 | A_0201 | SLLSKLVIV | 5721 | 242.674 |
| 207 | HCV 2b | 32 | 110 | 9 | A_0201 | IVSELNTCV | 5722 | 42.418 |
| 208 | HCV 2b | 32 | 11 | 9 | A_0201 | QVFGPVIFM | 5723 | 20.346 |
| 209 | HCV 2b | 32 | 30 | 9 | B7 | APHEHRVVM | 5724 | 90.000 |
| 210 | HCV 2b | 32 | 39 | 9 | B7 | TPVPAHTPL | 5725 | 80.000 |
| 211 | HCV 2b | 32 | 20 | 9 | B7 | VPKRTWPEM | 5726 | 20.000 |
| 212 | HCV 2b | 32 | 97 | 9 | B7 | SVIQACSLL | 5727 | 20.000 |
| 213 | HCV 2b | 32 | 100 | 9 | B7 | QACSLLSKL | 5728 | 12.000 |
| 214 | HCV 2b | 32 | 53 | 9 | B8 | EMKGRPGIL | 5729 | 160.000 |
| 215 | HCV 2b | 32 | 20 | 9 | B_3501 | VPKRTWPEM | 5730 | 120.000 |
| 216 | HCV 2b | 32 | 30 | 9 | B_3501 | APHEHRVVM | 5731 | 80.000 |
| 217 | HCV 2b | 32 | 57 | 9 | B_3501 | RPGILGSNF | 5732 | 40.000 |
| 218 | HCV 2b | 32 | 39 | 9 | B_3501 | TPVPAHTPL | 5733 | 20.000 |
| 219 | HCV 2b | 32 | 111 | 10 | A1 | VSELnTCVTR | 5734 | 27.000 |
| 220 | HCV 2b | 32 | 11 | 10 | A_0201 | QVFGpVIFMV | 5735 | 300.383 |
| 221 | HCV 2b | 32 | 107 | 10 | A_0201 | KLVIvSELNT | 5736 | 26.082 |
| 222 | HCV 2b | 32 | 109 | 10 | A_0201 | VIVSeLNTCV | 5737 | 16.258 |
| 223 | HCV 2b | 32 | 65 | 10 | A_0201 | FADSqFLKSV | 5738 | 15.535 |
| 224 | HCV 2b | 32 | 27 | 10 | A_0201 | EMFApHEHRV | 5739 | 13.939 |
| 225 | HCV 2b | 32 | 46 | 10 | A3 | PLYPfWQEMK | 5740 | 45.000 |
| 226 | HCV 2b | 32 | 45 | 10 | B7 | TPLYpFWQEM | 5741 | 20.000 |
| 227 | HCV 2b | 32 | 20 | 10 | B_3501 | VPKRtWPEMF | 5742 | 60.000 |
| 228 | HCV 2b | 32 | 45 | 10 | B_3501 | TPLYpFWQEM | 5743 | 40.000 |
| 229 | HCV 2b | 32 | 39 | 10 | B_3501 | TPVPaHTPLY | 5744 | 40.000 |
| 230 | HCV 2b | 32 | 41 | 10 | B_3501 | VPAHtPLYPF | 5745 | 20.000 |
| 231 | HCV 2b | 32 | 4 | 10 | B_3501 | VPCHmFRQVF | 5746 | 20.000 |
| 232 | HCV 2b | 32 | 105 | 10 | B_3501 | LSKLvIVSEL | 5747 | 15.000 |
| 233 | HCV 2b | 32 | 67 | 10 | B_3501 | DSQFlKSVRM | 5748 | 10.000 |
| 234 | HCV 2b | 32 | 112 | 10 | B_4403 | SELNtCVTRS | 5749 | 72.000 |
| 235 | HCV 2b | 32 | 39 | 10 | B_4403 | TPVPaHTPLY | 5750 | 18.000 |
| 236 | HCV 2b | 33 | 86 | 9 | A_0201 | MMFKRMVVL | 5751 | 91.513 |
| 237 | HCV 2b | 33 | 147 | 9 | A_0201 | CMAGCMSWA | 5752 | 45.388 |
| 238 | HCV 2b | 33 | 51 | 9 | A_0201 | ILPRPILPT | 5753 | 29.137 |
| 239 | HCV 2b | 33 | 125 | 9 | A_0201 | CMPLMKFHM | 5754 | 20.810 |
| 240 | HCV 2b | 33 | 11 | 9 | A_0201 | KIAGRRFTT | 5755 | 20.800 |
| 241 | HCV 2b | 33 | 166 | 9 | A_0201 | ILDLSISAI | 5756 | 16.317 |
| 242 | HCV 2b | 33 | 165 | 9 | A_0201 | SILDLSISA | 5757 | 10.363 |
| 243 | HCV 2b | 33 | 123 | 9 | A24 | RYCMPLMKF | 5758 | 220.000 |
| 244 | HCV 2b | 33 | 176 | 9 | B7 | CPSSMRAAL | 5759 | 120.000 |
| 245 | HCV 2b | 33 | 120 | 9 | B7 | SPARYCMPL | 5760 | 80.000 |
| 246 | HCV 2b | 33 | 91 | 9 | B7 | MVVLVGSGL | 5761 | 20.000 |
| 247 | HCV 2b | 33 | 52 | 9 | B7 | LPRPILPTA | 5762 | 20.000 |
| 248 | HCV 2b | 33 | 83 | 9 | B7 | HPPMMFKRM | 5763 | 20.000 |
| 249 | HCV 2b | 33 | 44 | 9 | B7 | PARTSTNIL | 5764 | 12.000 |
| 250 | HCV 2b | 33 | 159 | 9 | B7 | ACCRRPSIL | 5765 | 12.000 |
| 251 | HCV 2b | 33 | 159 | 9 | B8 | ACCRRPSIL | 5766 | 16.000 |

TABLE 4h-continued

2b (4-6)

| No. | Strain | ORF | Start | AA | HLA | Peptide sequence | SEQ ID NO: | Score |
|---|---|---|---|---|---|---|---|---|
| 252 | HCV 2b | 33 | 83 | 9 | B_3501 | HPPMMFKRM | 5767 | 40.000 |
| 253 | HCV 2b | 33 | 35 | 9 | B_3501 | RAPEMPAPY | 5768 | 24.000 |
| 254 | HCV 2b | 33 | 120 | 9 | B_3501 | SPARYCMPL | 5769 | 20.000 |
| 255 | HCV 2b | 33 | 176 | 9 | B_3501 | CPSSMRAAL | 5770 | 20.000 |
| 256 | HCV 2b | 33 | 163 | 9 | B_3501 | RPSILDLSI | 5771 | 16.000 |
| 257 | HCV 2b | 33 | 20 | 9 | B_3501 | SSTEGFSPL | 5772 | 10.000 |
| 258 | HCV 2b | 33 | 188 | 9 | B_3501 | SSISSKASY | 5773 | 10.000 |
| 259 | HCV 2b | 33 | 188 | 9 | B_4403 | SSISSKASY | 5774 | 30.000 |
| 260 | HCV 2b | 33 | 118 | 9 | B_4403 | VESPARYCM | 5775 | 12.000 |
| 261 | HCV 2b | 33 | 9 | 9 | B_4403 | GDKIAGRRF | 5776 | 11.250 |
| 262 | HCV 2b | 33 | 21 | 10 | A1 | STEGfSPLMI | 5777 | 11.250 |
| 263 | HCV 2b | 33 | 166 | 10 | A1 | ILDLsISAIR | 5778 | 10.000 |
| 264 | HCV 2b | 33 | 86 | 10 | A_0201 | MMFKrMVVLV | 5779 | 726.706 |
| 265 | HCV 2b | 33 | 165 | 10 | A_0201 | SILDlSISAI | 5780 | 50.051 |
| 266 | HCV 2b | 33 | 147 | 10 | A_0201 | CMAGcMSWAC | 5781 | 26.910 |
| 267 | HCV 2b | 33 | 98 | 10 | A_0201 | GLVNaALKAI | 5782 | 23.995 |
| 268 | HCV 2b | 33 | 77 | 10 | A_0201 | AIWEaNHPPM | 5783 | 23.246 |
| 269 | HCV 2b | 33 | 51 | 10 | A_0201 | ILPRpILPTA | 5784 | 19.425 |
| 270 | HCV 2b | 33 | 93 | 10 | A_0201 | VLVGsGLVNA | 5785 | 19.425 |
| 271 | HCV 2b | 33 | 90 | 10 | A_0201 | RMVVlVGSGL | 5786 | 15.428 |
| 272 | HCV 2b | 33 | 16 | 10 | A24 | RFTTsSTEGF | 5787 | 20.000 |
| 273 | HCV 2b | 33 | 90 | 10 | A24 | RMVVlVGSGL | 5788 | 16.800 |
| 274 | HCV 2b | 33 | 175 | 10 | A24 | RCPSsMRAAL | 5789 | 12.000 |
| 275 | HCV 2b | 33 | 57 | 10 | B7 | LPTAaPTRPL | 5790 | 120.000 |
| 276 | HCV 2b | 33 | 126 | 10 | B7 | MPLMkFHMCL | 5791 | 80.000 |
| 277 | HCV 2b | 33 | 43 | 10 | B7 | YPARtSTNIL | 5792 | 80.000 |
| 278 | HCV 2b | 33 | 160 | 10 | B7 | CCRRpSILDL | 5793 | 40.000 |
| 279 | HCV 2b | 33 | 52 | 10 | B7 | LPRPiLPTAA | 5794 | 20.000 |
| 280 | HCV 2b | 33 | 120 | 10 | B7 | SPARyCMPLM | 5795 | 20.000 |
| 281 | HCV 2b | 33 | 158 | 10 | B7 | VACCrRPSIL | 5796 | 12.000 |
| 282 | HCV 2b | 33 | 30 | 10 | B8 | ILKAtRAPEM | 5797 | 40.000 |
| 283 | HCV 2b | 33 | 158 | 10 | B8 | VACCrRPSIL | 5798 | 16.000 |
| 284 | HCV 2b | 33 | 160 | 10 | B8 | CCRRpSILDL | 5799 | 16.000 |
| 285 | HCV 2b | 33 | 120 | 10 | B_3501 | SPARyCMPLM | 5800 | 40.000 |
| 286 | HCV 2b | 33 | 43 | 10 | B_3501 | YPARtSTNIL | 5801 | 20.000 |
| 287 | HCV 2b | 33 | 57 | 10 | B_3501 | LPTAaPTRPL | 5802 | 20.000 |
| 288 | HCV 2b | 33 | 126 | 10 | B_3501 | MPLMkFHMCL | 5803 | 20.000 |
| 289 | HCV 2b | 33 | 20 | 10 | B_3501 | SSTEgFSPLM | 5804 | 20.000 |
| 290 | HCV 2b | 33 | 69 | 10 | B_3501 | KPVApAGGAI | 5805 | 16.000 |
| 291 | HCV 2b | 33 | 191 | 10 | B_3501 | SSKAsYKISL | 5806 | 15.000 |
| 292 | HCV 2b | 33 | 139 | 10 | B_3501 | CSILgHDDCM | 5807 | 10.000 |
| 293 | HCV 2b | 33 | 171 | 10 | B_3501 | ISAIrCPSSM | 5808 | 10.000 |
| 294 | HCV 2b | 33 | 187 | 10 | B_3501 | HSSIsSKASY | 5809 | 10.000 |
| 295 | HCV 2b | 33 | 79 | 10 | B_4403 | WEANhPPMMF | 5810 | 80.000 |
| 296 | HCV 2b | 33 | 105 | 10 | B_4403 | KAIIdATAGF | 5811 | 16.875 |
| 297 | HCV 2b | 34 | 2 | 9 | B7 | RPMMEMQPV | 5812 | 12.000 |
| 298 | HCV 2b | 34 | 2 | 9 | B_3501 | RPMMEMQPV | 5813 | 12.000 |
| 299 | HCV 2b | 35 | 7 | 9 | A_0201 | CMHVAIYFV | 5814 | 635.435 |
| 300 | HCV 2b | 35 | 11 | 9 | A_0201 | AIYFVTGWV | 5815 | 21.881 |
| 301 | HCV 2b | 35 | 30 | 9 | A24 | RYRRGVGPV | 5816 | 10.000 |
| 302 | HCV 2b | 35 | 36 | 9 | B7 | GPVSVGFSL | 5817 | 80.000 |
| 303 | HCV 2b | 35 | 27 | 9 | B7 | APKRYRRGV | 5818 | 18.000 |
| 304 | HCV 2b | 35 | 36 | 9 | B_3501 | GPVSVGFSL | 5819 | 20.000 |
| 305 | HCV 2b | 35 | 27 | 9 | B_3501 | APKRYRRGV | 5820 | 12.000 |
| 306 | HCV 2b | 35 | 51 | 9 | B_3501 | TSHEGGGAF | 5821 | 10.000 |
| 307 | HCV 2b | 35 | 6 | 10 | A_0201 | ACMHvAIYFV | 5822 | 21.250 |
| 308 | HCV 2b | 35 | 7 | 10 | A_0201 | CMHVaIYFVT | 5823 | 19.198 |
| 309 | HCV 2b | 35 | 30 | 10 | A24 | RYRRgVGPVS | 5824 | 14.000 |
| 310 | HCV 2b | 35 | 4 | 10 | B_3501 | RSACmHVAIY | 5825 | 20.000 |
| 311 | HCV 2b | 35 | 22 | 10 | B_3501 | ISLVtAPKRY | 5826 | 10.000 |
| 312 | HCV 2b | 35 | 4 | 10 | B_4403 | RSACmHVAIY | 5827 | 18.000 |
| 313 | HCV 2b | 35 | 22 | 10 | B_4403 | ISLVtAPKRY | 5828 | 13.500 |
| 314 | HCV 2b | 36 | | | | no hits | | |
| 315 | HCV 2b | 37 | | | | no hits | | |
| 316 | HCV 2b | 38 | 1 | 9 | A1 | MTESKSPVY | 5829 | 225.000 |
| 317 | HCV 2b | 38 | 8 | 9 | A24 | VYPVIRASV | 5830 | 10.500 |
| 318 | HCV 2b | 38 | 2 | 10 | B_4403 | TESKsPVYPV | 5831 | 12.000 |
| 319 | HCV 2b | 39 | 18 | 9 | B7 | NIRCLPPLM | 5832 | 10.000 |
| 320 | HCV 2b | 39 | 16 | 10 | A_0201 | WQNIrCLPPL | 5833 | 22.915 |
| 321 | HCV 2b | 39 | 13 | 10 | A24 | FFEWqNIRCL | 5834 | 30.000 |
| 322 | HCV 2b | 39 | 22 | 10 | B_3501 | LPPLmEARGI | 5835 | 12.000 |
| 323 | HCV 2b | 40 | 1 | 9 | A_0201 | MLAWGVVTV | 5836 | 271.948 |
| 324 | HCV 2b | 40 | 34 | 9 | B7 | MPRMVVAST | 5837 | 20.000 |
| 325 | HCV 2b | 40 | 13 | 9 | B7 | VAVARTTSL | 5838 | 12.000 |

TABLE 4h-continued

2b (4-6)

| No. | Strain | ORF | Start | AA | HLA | Peptide sequence | SEQ ID NO: | Score |
|---|---|---|---|---|---|---|---|---|
| 326 | HCV 2b | 40 | 13 | 9 | B8 | VAVARTTSL | 5839 | 16.000 |
| 327 | HCV 2b | 40 | 6 | 10 | A_0201 | VVTVpGGVAV | 5840 | 10.346 |
| 328 | HCV 2b | 40 | 12 | 10 | B7 | GVAVaRTTSL | 5841 | 20.000 |
| 329 | HCV 2b | 40 | 28 | 10 | B7 | WSRTvPMPRM | 5842 | 15.000 |
| 330 | HCV 2b | 40 | 28 | 10 | B_3501 | WSRTvPMPRM | 5843 | 30.000 |
| 331 | HCV 2b | 40 | 40 | 10 | B_3501 | ASTEwHSSQM | 5844 | 20.000 |
| 332 | HCV 2b | 40 | 25 | 10 | B_3501 | VSAWsRTVPM | 5845 | 10.000 |
| 333 | HCV 2b | 41 | 1 | 9 | A_0201 | MLGLIPWAL | 5846 | 272.371 |
| 334 | HCV 2b | 42 | 9 | 9 | A24 | KSIDLATPL | 5847 | 17.280 |
| 335 | HCV 2b | 42 | 47 | 9 | A3 | GLGDSNAPR | 5848 | 12.000 |
| 336 | HCV 2b | 42 | 15 | 9 | B7 | TPLAHTAAL | 5849 | 80.000 |
| 337 | HCV 2b | 42 | 40 | 9 | B7 | DPLRVERGL | 5850 | 80.000 |
| 338 | HCV 2b | 42 | 52 | 9 | B7 | NAPRLSSFL | 5851 | 12.000 |
| 339 | HCV 2b | 42 | 9 | 9 | B_3501 | KSIDLATPL | 5852 | 20.000 |
| 340 | HCV 2b | 42 | 40 | 9 | B_3501 | DPLRVERGL | 5853 | 20.000 |
| 341 | HCV 2b | 42 | 15 | 9 | B_3501 | TPLAHTAAL | 5854 | 20.000 |
| 342 | HCV 2b | 42 | 36 | 9 | B_3501 | GPPDDPLRV | 5855 | 12.000 |
| 343 | HCV 2b | 42 | 56 | 9 | B_3501 | LSSFLRTGM | 5856 | 10.000 |
| 344 | HCV 2b | 42 | 51 | 9 | B_4403 | SNAPRLSSF | 5857 | 12.000 |
| 345 | HCV 2b | 42 | 47 | 10 | A_0201 | GLGDsNAPRL | 5858 | 87.586 |
| 346 | HCV 2b | 42 | 22 | 10 | A_0201 | ALNKpTACPL | 5859 | 21.362 |
| 347 | HCV 2b | 42 | 63 | 10 | A3 | GMTSaFRVTR | 5860 | 36.000 |
| 348 | HCV 2b | 42 | 53 | 10 | B7 | APRLsSFLRT | 5861 | 60.000 |
| 349 | HCV 2b | 42 | 22 | 10 | B7 | ALNKpTACPL | 5862 | 12.000 |
| 350 | HCV 2b | 42 | 14 | 10 | B7 | ATPLaHTAAL | 5863 | 12.000 |
| 351 | HCV 2b | 43 | 2 | 9 | B7 | APRRPRVC. | 5864 | 135.000 |
| 352 | HCV 2b | 44 | | | | no hits | | |
| 353 | HCV 2b | 45 | 12 | 9 | A_0201 | TMTFFSIGL | 5865 | 58.628 |
| 354 | HCV 2b | 45 | 28 | 9 | B8 | TARSRKPWA | 5866 | 16.000 |
| 355 | HCV 2b | 45 | 9 | 10 | B7 | APHTmTFFSI | 5867 | 24.000 |
| 356 | HCV 2b | 45 | 11 | 10 | B7 | HTMTfFSIGL | 5868 | 12.000 |
| 357 | HCV 2b | 45 | 28 | 10 | B8 | TARSrKPWAA | 5869 | 16.000 |
| 358 | HCV 2b | 46 | 2 | 9 | A_0201 | VINSIWIYL | 5870 | 46.689 |
| 359 | HCV 2b | 46 | 9 | 9 | A_0201 | YLAPARCLT | 5871 | 34.279 |
| 360 | HCV 2b | 46 | 5 | 9 | A_0201 | SIWIYLAPA | 5872 | 13.040 |
| 361 | HC2Vb | 46 | 7 | 9 | A_0201 | WIYLAPARC | 5873 | 10.055 |
| 362 | HCV 2b | 46 | 8 | 9 | A24 | IYLAPARCL | 5874 | 300.000 |
| 363 | HCV 2b | 46 | 11 | 9 | B7 | APARCLTRV | 5875 | 12.000 |
| 364 | HCV 2b | 46 | 1 | 10 | A_0201 | MVINsIWIYL | 5876 | 29.711 |
| 365 | HCV 2b | 46 | 9 | 10 | A3 | YLAPaRCLTR | 5877 | 12.000 |
| 366 | HCV 2b | 46 | 1 | 10 | B7 | MVINsIWIYL | 5878 | 20.000 |
| 367 | HCV 2b | 47 | | | | no hits | | |
| 368 | HCV 2b | 48 | | | | no hits | | |
| 369 | HCV 2b | 49 | 13 | 9 | A1 | LAECKMMSF | 5879 | 45.000 |
| 370 | HCV 2b | 49 | 17 | 9 | A_0201 | KMMSFSSAA | 5880 | 176.565 |
| 371 | HCV 2b | 49 | 40 | 9 | A3 | ILASASNRK | 5881 | 20.000 |
| 372 | HCV 2b | 49 | 9 | 9 | A3 | ALAALAECK | 5882 | 20.000 |
| 373 | HCV 2b | 49 | 31 | 10 | A_0201 | MMSIqRHAQI | 5883 | 12.809 |
| 374 | HCV 2b | 49 | 22 | 10 | B_3501 | SSAAsAWPSM | 5884 | 10.000 |
| 375 | HCV 2b | 49 | 14 | 10 | B_4403 | AECKmMSFSS | 5885 | 12.000 |
| 376 | HCV 2b | 50 | | | | no hits | | |
| 377 | HCV 2b | 51 | 30 | 9 | A_0201 | VLFSRKTSV | 5886 | 437.482 |
| 378 | HCV 2b | 51 | 9 | 9 | A_0201 | VLVNPVPFI | 5887 | 224.357 |
| 379 | HCV 2b | 51 | 32 | 9 | B7 | FSRKTSVSL | 5888 | 40.000 |
| 380 | HCV 2b | 51 | 23 | 9 | B7 | QAPRGGLVL | 5889 | 12.000 |
| 381 | HCV 2b | 51 | 6 | 9 | B7 | APHVLVNPV | 5890 | 12.000 |
| 382 | HCV 2b | 51 | 24 | 9 | B7 | APRGGLVLF | 5891 | 12.000 |
| 383 | HCV 2b | 51 | 24 | 9 | B_3501 | APRGGLVLF | 5892 | 60.000 |
| 384 | HCV 2b | 51 | 32 | 9 | B_3501 | FSRKTSVSL | 5893 | 15.000 |
| 385 | HCV 2b | 51 | 29 | 10 | A_0201 | LVLFsRKTSV | 5894 | 38.280 |
| 386 | HCV 2b | 51 | 10 | 10 | A_0201 | LVNPvPFIQV | 5895 | 19.657 |
| 387 | HCV 2b | 51 | 31 | 10 | A24 | LFSRkTSVSL | 5896 | 20.000 |
| 388 | HCV 2b | 51 | 20 | 10 | B7 | QPNQaPRGGL | 5897 | 180.000 |
| 389 | HCV 2b | 51 | 24 | 10 | B7 | APRGgLVLFS | 5898 | 12.000 |
| 390 | HCV 2b | 51 | 20 | 10 | B_3501 | QPNQaPRGGL | 5899 | 20.000 |
| 391 | HCV 2b | 52 | 32 | 9 | A_0201 | GQPELLNLL | 5900 | 20.425 |
| 392 | HCV 2b | 52 | 10 | 9 | A24 | SYSKVPHPI | 5901 | 70.000 |
| 393 | HCV 2b | 52 | 32 | 9 | A24 | GQPELLNLL | 5902 | 10.368 |
| 394 | HCV 2b | 52 | 3 | 9 | B_4403 | STLVTLVSY | 5903 | 18.000 |
| 395 | HCV 2b | 52 | 5 | 10 | A_0201 | LVTLvSYSKV | 5904 | 15.519 |
| 396 | HCV 2b | 52 | 31 | 10 | A24 | SGQPeLLNLL | 5905 | 10.368 |
| 397 | HCV 2b | 52 | 4 | 10 | A3 | TLVTlVSYSK | 5906 | 135.000 |
| 398 | HCV 2b | 52 | 30 | 10 | B_3501 | RSGQpELLNL | 5907 | 15.000 |
| 399 | HCV 2b | 52 | 2 | 10 | B_3501 | SSTLvTLVSY | 5908 | 10.000 |

TABLE 4h-continued

2b (4-6)

| No. | Strain | ORF | Start | AA | HLA | Peptide sequence | SEQ ID NO: | Score |
|---|---|---|---|---|---|---|---|---|
| 400 | HCV 2b | 53 | 40 | 9 | A_0201 | KLPTVRPTV | 5909 | 243.432 |
| 401 | HCV 2b | 53 | 6 | 9 | A_0201 | KLSLQLRAV | 5910 | 111.979 |
| 402 | HCV 2b | 53 | 16 | 9 | A_0201 | FMCQLPLVL | 5911 | 29.098 |
| 403 | HCV 2b | 53 | 22 | 9 | A_0201 | LVLINWTFC | 5912 | 25.565 |
| 404 | HCV 2b | 53 | 24 | 9 | A_0201 | LINWTFCWA | 5913 | 12.135 |
| 405 | HCV 2b | 53 | 12 | 9 | A24 | RAVRFMCQL | 5914 | 12.000 |
| 406 | HCV 2b | 53 | 12 | 9 | B7 | RAVRFMCQL | 5915 | 12.000 |
| 407 | HCV 2b | 53 | 43 | 9 | B7 | TVRPTVAPV | 5916 | 10.000 |
| 408 | HCV 2b | 53 | 19 | 10 | A_0201 | QLPLvLINWT | 5917 | 94.268 |
| 409 | HCV 2b | 53 | 23 | 10 | A_0201 | VLINwTFCWA | 5918 | 88.257 |
| 410 | HCV 2b | 53 | 16 | 10 | A_0201 | FMCQlPLVLI | 5919 | 79.718 |
| 411 | HCV 2b | 53 | 9 | 10 | A_0201 | LQLRaVRFMC | 5920 | 18.376 |
| 412 | HCV 2b | 53 | 8 | 10 | A_0201 | SLQLrAVRFM | 5921 | 12.569 |
| 413 | HCV 2b | 53 | 15 | 10 | A24 | RFMCqLPLVL | 5922 | 72.000 |
| 414 | HCV 2b | 53 | 2 | 10 | A24 | KPVCkLSLQL | 5923 | 14.400 |
| 415 | HCV 2b | 53 | 6 | 10 | A3 | KLSLqLRAVR | 5924 | 12.000 |
| 416 | HCV 2b | 53 | 13 | 10 | B7 | AVRFmCQLPL | 5925 | 600.000 |
| 417 | HCV 2b | 53 | 32 | 10 | B7 | APSLkRPAKL | 5926 | 240.000 |
| 418 | HCV 2b | 53 | 2 | 10 | B7 | KPVCkLSLQL | 5927 | 80.000 |
| 419 | HCV 2b | 53 | 32 | 10 | B8 | APSLkRPAKL | 5928 | 16.000 |
| 420 | HCV 2b | 53 | 2 | 10 | B_3501 | KPVCkLSLQL | 5929 | 40.000 |
| 421 | HCV 2b | 53 | 32 | 10 | B_3501 | APSLkRPAKL | 5930 | 20.000 |
| 422 | HCV 2b | 53 | 20 | 10 | B_3501 | LPLVlINWTF | 5931 | 20.000 |
| 423 | HCV 2b | 54 | 4 | 10 | A3 | TLAHaPCMEK | 5932 | 60.000 |
| 424 | HCV 2b | 55 | 10 | 10 | A_0201 | IMSHaMRWPV | 5933 | 640.458 |
| 425 | HCV 2b | 55 | 1 | 10 | B7 | MVRVgDQFSI | 5934 | 20.000 |
| 426 | HCV 2b | 56 | 9 | 9 | A_0201 | KLWRSGDTI | 5935 | 148.506 |
| 427 | HCV 2b | 56 | 35 | 9 | B_4403 | AEQTVAAIT | 5936 | 18.000 |
| 428 | HCV 2b | 56 | 24 | 10 | A1 | ITAPhTSPTY | 5937 | 25.000 |
| 429 | HCV 2b | 56 | 9 | 10 | A3 | KLWRsGDTIR | 5938 | 60.000 |
| 430 | HCV 2b | 56 | 3 | 10 | A3 | QLHSwVKLWR | 5939 | 12.000 |
| 431 | HCV 2b | 56 | 35 | 10 | B_4403 | AEQTvAAITI | 5940 | 18.000 |
| 432 | HCV 2b | 56 | 24 | 10 | B_4403 | ITAPhTSPTY | 5941 | 12.000 |
| 432 | HCV 2b | 56 | 24 | 10 | B_4403 | ITAPhTSPTY | 5942 | 12.000 |
| 433 | HCV 2b | 57 | 1 | 9 | A_0201 | MLLFEQSLV | 5943 | 437.482 |
| 434 | HCV 2b | 57 | 2 | 9 | A_0201 | LLFEQSLVA | 5944 | 52.529 |
| 435 | HCV 2b | 58 | 24 | 9 | A_0201 | KEQPGKFLV | 5945 | 27.454 |
| 436 | HCV 2b | 58 | 22 | 9 | B_4403 | IEKEQPGKF | 5946 | 60.000 |
| 437 | HCV 2b | 58 | 24 | 9 | B_4403 | KEQPGKFLV | 5947 | 12.000 |
| 438 | HCV 2b | 58 | 2 | 10 | A_0201 | FLIStEDTGT | 5948 | 34.279 |
| 439 | HCV 2b | 58 | 24 | 10 | B_4403 | KEQPgKFLVA | 5949 | 12.000 |
| 440 | HCV 2b | 59 | 83 | 9 | A1 | RSEVFLVAR | 5950 | 27.000 |
| 441 | HCV 2b | 59 | 87 | 9 | A_0201 | FLVARTPNL | 5951 | 98.267 |
| 442 | HCV 2b | 59 | 56 | 9 | A24 | GYPGFPQDL | 5952 | 360.000 |
| 443 | HCV 2b | 59 | 11 | 9 | A3 | VMVSMTLPK | 5953 | 60.000 |
| 444 | HCV 2b | 59 | 12 | 9 | B7 | MVSMTLPKL | 5954 | 20.000 |
| 445 | HCV 2b | 59 | 42 | 9 | B_3501 | QPAQPQPSF | 5955 | 20.000 |
| 446 | HCV 2b | 59 | 69 | 9 | B_3501 | RSFGMGWRL | 5956 | 10.000 |
| 447 | HCV 2b | 59 | 84 | 9 | B_4403 | SEVFLVART | 5957 | 48.000 |
| 448 | HCV 2b | 59 | 11 | 10 | A_0201 | VMVSmTLPKL | 5958 | 60.325 |
| 449 | HCV 2b | 59 | 79 | 10 | A_0201 | RGWDrSEVFL | 5959 | 26.100 |
| 450 | HCV 2b | 59 | 86 | 10 | A24 | VFLVaRTPNL | 5960 | 30.000 |
| 451 | HCV 2b | 59 | 8 | 10 | A24 | KPHVmVSMTL | 5961 | 11.200 |
| 452 | HCV 2b | 59 | 51 | 10 | A24 | PYRGqGYPGF | 5962 | 10.000 |
| 453 | HCV 2b | 59 | 89 | 10 | B7 | VARTpNLGPL | 5963 | 120.000 |
| 454 | HCV 2b | 59 | 8 | 10 | B7 | KPHVmVSMTL | 5964 | 80.000 |
| 455 | HCV 2b | 59 | 19 | 10 | B7 | KLRDlCRGSL | 5965 | 60.000 |
| 456 | HCV 2b | 59 | 77 | 10 | B7 | LPRGwDRSEV | 5966 | 60.000 |
| 457 | HCV 2b | 59 | 35 | 10 | B7 | DPRGdRSQPA | 5967 | 20.000 |
| 458 | HCV 2b | 59 | 64 | 10 | B7 | LPVErRSFGM | 5968 | 20.000 |
| 459 | HCV 2b | 59 | 2 | 10 | B7 | YPMRsAKPHV | 5969 | 12.000 |
| 460 | HCV 2b | 59 | 35 | 10 | B8 | DPRGdRSQPA | 5970 | 32.000 |
| 461 | HCV 2b | 59 | 89 | 10 | B8 | VARTpNLGPL | 5971 | 16.000 |
| 462 | HCV 2b | 59 | 64 | 10 | B_3501 | LPVErRSFGM | 5972 | 80.000 |
| 463 | HCV 2b | 59 | 8 | 10 | B_3501 | KPHVmVSMTL | 5973 | 40.000 |
| 464 | HCV 2b | 59 | 77 | 10 | B_3501 | LPRGwDRSEV | 5974 | 18.000 |
| 465 | HCV 2b | 59 | 6 | 10 | B_3501 | SAKPhVMVSM | 5975 | 18.000 |
| 466 | HCV 2b | 59 | 19 | 10 | B_3501 | KLRDlCRGSL | 5976 | 12.000 |
| 467 | HCV 2b | 59 | 62 | 10 | B_4403 | QDLPvERRSF | 5977 | 20.000 |
| 468 | HCV 2b | 59 | 66 | 10 | B_4403 | VERRsFGMGW | 5978 | 12.000 |
| 469 | HCV 2b | 60 | | | | no hits | | |
| 470 | HCV 2b | 61 | 7 | 9 | A_0201 | VLPHGPDVV | 5979 | 23.754 |
| 471 | HCV 2b | 62 | 15 | 9 | A_0201 | LLLLGPTWC | 5980 | 171.868 |
| 472 | HCV 2b | 62 | 16 | 9 | A3 | LLLGPTWCY | 5981 | 40.500 |

TABLE 4h-continued

2b (4-6)

| No. | Strain | ORF | Start | AA | HLA | Peptide sequence | SEQ ID NO: | Score |
|---|---|---|---|---|---|---|---|---|
| 473 | HCV 2b | 62 | 8 | 9 | B7 | TQRADWQLL | 5982 | 40.000 |
| 474 | HCV 2b | 62 | 14 | 10 | A_0201 | QLLLlGPTWC | 5983 | 101.099 |
| 475 | HCV 2b | 62 | 22 | 10 | A_0201 | WCYEgSCPGV | 5984 | 27.401 |
| 476 | HCV 2b | 62 | 6 | 10 | A_0201 | RVTQrADWQL | 5985 | 14.019 |
| 477 | HCV 2b | 62 | 15 | 10 | A3 | LLLLgPTWCY | 5986 | 27.000 |
| 478 | HCV 2b | 62 | 8 | 10 | B7 | TQRAdWQLLL | 5987 | 40.000 |
| 479 | HCV 2b | 62 | 6 | 10 | B7 | RVTQrADWQL | 5988 | 20.000 |
| 480 | HCV 2b | 63 | | | | no hits | | |
| 481 | HCV 2b | 64 | | | | no hits | | |
| 482 | HCV 2b | 65 | 13 | 9 | B7 | HPLDRPLSL | 5989 | 80.000 |
| 483 | HCV 2b | 65 | 11 | 9 | B7 | SVHPLDRPL | 5990 | 20.000 |
| 484 | HCV 2b | 65 | 13 | 9 | B8 | HPLDRPLSL | 5991 | 24.000 |
| 485 | HCV 2b | 65 | 13 | 9 | B_3501 | HPLDRPLSL | 5992 | 40.000 |
| 486 | HCV 2b | 65 | 20 | 10 | A_0201 | SLADvAAQDC | 5993 | 20.369 |
| 487 | HCV 2b | 65 | 3 | 10 | B7 | SPRGkGDQSV | 5994 | 40.000 |
| 488 | HCV 2b | 65 | 3 | 10 | B_3501 | SPRGkGDQSV | 5995 | 12.000 |
| 489 | HCV 2b | 65 | 27 | 10 | B_4403 | QDCCaNDSHY | 5996 | 15.000 |
| 490 | HCV 2b | 66 | 6 | 9 | A_0201 | LVGHGTQAV | 5997 | 10.346 |
| 491 | HCV 2b | 66 | 5 | 10 | A_0201 | NLVGhGTQAV | 5998 | 69.552 |
| 492 | HCV 2b | 67 | | | | no hits | | |
| 493 | HCV 2b | 68 | | | | no hits | | |
| 494 | HCV 2b | 69 | 9 | 9 | A_0201 | CLSPPHDDL | 5999 | 10.468 |
| 495 | HCV 2b | 69 | 11 | 9 | B7 | SPPHDDLLL | 6000 | 80.000 |
| 496 | HCV 2b | 69 | 29 | 9 | B7 | GNRQVPQTL | 6001 | 40.000 |
| 497 | HCV 2b | 69 | 11 | 9 | B_3501 | SPPHDDLLL | 6002 | 30.000 |
| 498 | HCV 2b | 69 | 18 | 10 | A_0201 | LLHWaEHDRL | 6003 | 17.795 |
| 499 | HCV 2b | 69 | 9 | 10 | A_0201 | CLSPpHDDLL | 6004 | 10.468 |
| 500 | HCV 2b | 69 | 28 | 10 | A24 | HGNRqVPQTL | 6005 | 10.080 |
| 501 | HCV 2b | 70 | | | | no hits | | |
| 502 | HCV 2b | 71 | 42 | 9 | A_0201 | TLNIGSIWV | 6006 | 382.536 |
| 503 | HCV 2b | 71 | 20 | 9 | A_0201 | WIMPQSVRV | 6007 | 162.769 |
| 504 | HCV 2b | 71 | 47 | 9 | A_0201 | SIWVLPKTV | 6008 | 79.376 |
| 505 | HCV 2b | 71 | 50 | 9 | A_0201 | VLPKTVCRA | 6009 | 19.425 |
| 506 | HCV 2b | 71 | 21 | 9 | A_0201 | IMPQSVRVV | 6010 | 16.105 |
| 507 | HCV 2b | 71 | 3 | 9 | B7 | HPPYIHPHL | 6011 | 80.000 |
| 508 | HCV 2b | 71 | 22 | 9 | B_3501 | MPQSVRVVY | 6012 | 40.000 |
| 509 | HCV 2b | 71 | 3 | 9 | B_3501 | HPPYIHPHL | 6013 | 20.000 |
| 510 | HCV 2b | 71 | 8 | 9 | B_3501 | HPHLEDGEI | 6014 | 12.000 |
| 511 | HCV 2b | 71 | 14 | 9 | B_4403 | GEIYGAWIM | 6015 | 30.000 |
| 512 | HCV 2b | 71 | 42 | 10 | A_0201 | TLNIgSIWVL | 6016 | 151.086 |
| 513 | HCV 2b | 71 | 20 | 10 | A_0201 | WIMPqSVRVV | 6017 | 30.698 |
| 514 | HCV 2b | 71 | 41 | 10 | A_0201 | STLNigSIWV | 6018 | 19.658 |
| 515 | HCV 2b | 71 | 49 | 10 | A_0201 | WVLPkTVCRA | 6019 | 17.017 |
| 516 | HCV 2b | 71 | 44 | 10 | A3 | NIGSiWVLPK | 6020 | 36.000 |
| 517 | HCV 2b | 71 | 8 | 10 | B_3501 | HPHLeDGEIY | 6021 | 60.000 |
| 518 | HCV 2b | 71 | 11 | 10 | B_4403 | LEDGeIYGAW | 6022 | 18.000 |
| 519 | HCV 2b | 72 | 49 | 9 | A_0201 | KQGGHETRV | 6023 | 24.681 |
| 520 | HCV 2b | 72 | 68 | 9 | A24 | VYVPAAVGI | 6024 | 90.000 |
| 521 | HCV 2b | 72 | 8 | 9 | A24 | VFNIGDVGL | 6025 | 30.000 |
| 522 | HCV 2b | 72 | 29 | 9 | B7 | QPTAGRQTL | 6026 | 120.000 |
| 523 | HCV 2b | 72 | 3 | 9 | B7 | AVRPHVFNI | 6027 | 60.000 |
| 524 | HCV 2b | 72 | 1 | 9 | B_3501 | MPAVRPHVF | 6028 | 20.000 |
| 525 | HCV 2b | 72 | 29 | 9 | B_3501 | QPTAGRQTL | 6029 | 20.000 |
| 526 | HCV 2b | 72 | 61 | 9 | B_3501 | IAVEGGPVY | 6030 | 12.000 |
| 527 | HCV 2b | 72 | 61 | 10 | A_0201 | IAVEgGPVYV | 6031 | 37.032 |
| 528 | HCV 2b | 72 | 39 | 10 | B7 | AARAvEFVGI | 6032 | 36.000 |
| 529 | HCV 2b | 72 | 7 | 10 | B7 | HVFNiGDVGL | 6033 | 20.000 |
| 530 | HCV 2b | 72 | 9 | 10 | B_4403 | FNIGdVGLVF | 6034 | 11.250 |
| 531 | HCV 2b | 73 | 2 | 10 | B7 | AAEDnFQDQL | 6035 | 10.800 |
| 532 | HCV 2b | 74 | 57 | 9 | A1 | VSECTAVFY | 6036 | 135.000 |
| 533 | HCV 2b | 74 | 71 | 9 | A_0201 | YLYPAAQGT | 6037 | 109.693 |
| 534 | HCV 2b | 74 | 2 | 9 | A_0201 | TLVDGTVAL | 6038 | 87.586 |
| 535 | HCV 2b | 74 | 64 | 9 | A24 | FYSHIRCYL | 6039 | 280.000 |
| 536 | HCV 2b | 74 | 72 | 9 | A24 | LYPAAQGTI | 6040 | 75.000 |
| 537 | HCV 2b | 74 | 16 | 9 | A24 | AFWRYYKSL | 6041 | 20.000 |
| 538 | HCV 2b | 74 | 90 | 9 | A24 | KMENCVSEL | 6042 | 13.200 |
| 539 | HCV 2b | 74 | 82 | 9 | A3 | ILAWDTSRK | 6043 | 20.000 |
| 540 | HCV 2b | 74 | 14 | 9 | A3 | VVAFWRYYK | 6044 | 18.000 |
| 541 | HCV 2b | 74 | 9 | 9 | A3 | ALLGKVVAF | 6045 | 13.500 |
| 542 | HCV 2b | 74 | 75 | 9 | B7 | AAQGTIVIL | 6046 | 36.000 |
| 543 | HCV 2b | 74 | 103 | 9 | B7 | VVRAIISGV | 6047 | 10.000 |
| 544 | HCV 2b | 74 | 83 | 9 | B_3501 | LAWDTSRKM | 6048 | 12.000 |
| 545 | HCV 2b | 74 | 65 | 9 | B_3501 | YSHIRCYLY | 6049 | 10.000 |
| 546 | HCV 2b | 74 | 58 | 9 | B_4403 | SECTAVFYS | 6050 | 54.000 |

TABLE 4h-continued

2b (4-6)

| No. | Strain | ORF | Start | AA | HLA | Peptide sequence | SEQ ID NO: | Score |
|---|---|---|---|---|---|---|---|---|
| 547 | HCV 2b | 74 | 96 | 9 | B_4403 | SELPGDAVV | 6051 | 32.000 |
| 548 | HCV 2b | 74 | 2 | 10 | A_0201 | TLVDgTVALL | 6052 | 201.447 |
| 549 | HCV 2b | 74 | 71 | 10 | A_0201 | YLYPaAQGTI | 6053 | 19.964 |
| 550 | HCV 2b | 74 | 102 | 10 | A_0201 | AVVRaIISGV | 6054 | 13.997 |
| 551 | HCV 2b | 74 | 94 | 10 | A_0201 | CVSElPGDAV | 6055 | 12.226 |
| 552 | HCV 2b | 74 | 63 | 10 | A24 | VFYShIRCYL | 6056 | 28.000 |
| 553 | HCV 2b | 74 | 13 | 10 | A3 | KVVAfWRYYK | 6057 | 81.000 |
| 554 | HCV 2b | 74 | 10 | 10 | A3 | LLGKvVAFWR | 6058 | 18.000 |
| 555 | HCV 2b | 74 | 15 | 10 | B7 | VAFWrYYKSL | 6059 | 12.000 |
| 556 | HCV 2b | 74 | 103 | 10 | B7 | VVRAiISGVV | 6060 | 10.000 |
| 557 | HCV 2b | 74 | 38 | 10 | B_3501 | QSRAdRSCHY | 6061 | 30.000 |
| 558 | HCV 2b | 74 | 98 | 10 | B_3501 | LPGDaVVRAI | 6062 | 16.000 |
| 559 | HCV 2b | 75 | 90 | 9 | A_0201 | RELDVLWAA | 6063 | 25.279 |
| 560 | HCV 2b | 75 | 18 | 9 | B7 | EPTCPTATL | 6064 | 120.000 |
| 561 | HCV 2b | 75 | 29 | 9 | B7 | IQRPRISWL | 6065 | 40.000 |
| 562 | HCV 2b | 75 | 139 | 9 | B7 | TQRYSASSL | 6066 | 40.000 |
| 563 | HCV 2b | 75 | 87 | 9 | B7 | AATRELDVL | 6067 | 36.000 |
| 564 | HCV 2b | 75 | 44 | 9 | B7 | GAPIFRDGL | 6068 | 18.000 |
| 565 | HCV 2b | 75 | 53 | 9 | B7 | ASPTRLGSL | 6069 | 12.000 |
| 566 | HCV 2b | 75 | 29 | 9 | B8 | IQRPRISWL | 6070 | 24.000 |
| 567 | HCV 2b | 75 | 18 | 9 | B_3501 | EPTCPTATL | 6071 | 20.000 |
| 568 | HCV 2b | 75 | 117 | 9 | B_3501 | RSTRPPGAL | 6072 | 10.000 |
| 569 | HCV 2b | 75 | 90 | 9 | B_4403 | RELDVLWAA | 6073 | 18.000 |
| 570 | HCV 2b | 75 | 98 | 10 | A_0201 | AVCVsFGFSL | 6074 | 41.197 |
| 571 | HCV 2b | 75 | 28 | 10 | A_0201 | SIQRpRISWL | 6075 | 37.157 |
| 572 | HCV 2b | 75 | 90 | 10 | A_0201 | RELDvLWAAV | 6076 | 34.877 |
| 573 | HCV 2b | 75 | 25 | 10 | A_0201 | TLVSiQRPRI | 6077 | 10.433 |
| 574 | HCV 2b | 75 | 77 | 10 | A24 | RQQVnSANDL | 6078 | 14.400 |
| 575 | HCV 2b | 75 | 120 | 10 | A24 | RPPGaLASTL | 6079 | 14.400 |
| 576 | HCV 2b | 75 | 141 | 10 | A24 | RYSAsSLAGA | 6080 | 10.000 |
| 577 | HCV 2b | 75 | 40 | 10 | A3 | GLAGgAPIFR | 6081 | 36.000 |
| 578 | HCV 2b | 75 | 94 | 10 | A3 | VLWAaVCVSF | 6082 | 15.000 |
| 579 | HCV 2b | 75 | 52 | 10 | B8 | LASPStRLGSL | 6083 | 16.000 |
| 580 | HCV 2b | 75 | 115 | 10 | B8 | GARStRPPGA | 6084 | 16.000 |
| 581 | HCV 2b | 75 | 120 | 10 | B_3501 | RPPGaLASTL | 6085 | 40.000 |
| 582 | HCV 2b | 75 | 133 | 10 | B_4403 | TTRPfATQRY | 6086 | 13.500 |

TABLE 4i

3a (1-3)

| No. | Strain | ORF | Start | AA | HLA | Peptide sequence | SEQ ID NO: | Score |
|---|---|---|---|---|---|---|---|---|
| 1 | HCV 3a | 1 | 2 | 9 | A_0201 | ALVRVSCSL | 6087 | 21.362 |
| 2 | HCV 3a | 1 | 2 | 9 | B7 | ALVRVSCSL | 6088 | 12.000 |
| 3 | HCV 3a | 1 | 1 | 10 | B7 | MALVRVSCSL | 6089 | 12.000 |
| 4 | HCV 3a | 2 | 32 | 10 | A_0201 | AIWVKSSIPL | 6090 | 24.380 |
| 5 | HCV 3a | 2 | 13 | 9 | B7 | CPRAAPVHL | 6091 | 800.000 |
| 6 | HCV 3a | 2 | 17 | 9 | B7 | APVHLGAQM | 6092 | 60.000 |
| 7 | HCV 3a | 2 | 32 | 10 | B7 | AIWVKSSIPL | 6093 | 12.000 |
| 8 | HCV 3a | 2 | 13 | 9 | B8 | CPRAAPVHL | 6094 | 16.000 |
| 9 | HCV 3a | 2 | 13 | 9 | B_3501 | CPRAAPVHL | 6095 | 60.000 |
| 10 | HCV 3a | 2 | 17 | 9 | B_3501 | APVHLGAQM | 6096 | 40.000 |
| 11 | HCV 3a | 2 | 26 | 9 | B_3501 | TPGGGPAIW | 6097 | 10.000 |
| 12 | HCV 3a | 3 | 8 | 10 | A1 | CTHPAAYLVF | 6098 | 12.500 |
| 13 | HCV 3a | 3 | 13 | 9 | A24 | AYLVFRTTI | 6099 | 75.000 |
| 14 | HCV 3a | 3 | 6 | 10 | A24 | SFCTHPAAYL | 6100 | 20.000 |
| 15 | HCV 3a | 3 | 5 | 10 | B_3501 | TSFCtHPAAY | 6101 | 10.000 |
| 16 | HCV 3a | 4 | 1 | 10 | A_0201 | MPPEgLLAFL | 6102 | 12.295 |
| 17 | HCV 3a | 4 | 13 | 9 | B7 | APNRNCSWL | 6103 | 240.000 |
| 18 | HCV 3a | 4 | 24 | 9 | B7 | MARGTSTAL | 6104 | 120.000 |
| 19 | HCV 3a | 4 | 1 | 10 | B7 | MPPEgLLAFL | 6105 | 80.000 |
| 20 | HCV 3a | 4 | 12 | 10 | B7 | WAPNrNCSWL | 6106 | 12.000 |
| 21 | HCV 3a | 4 | 24 | 9 | B8 | MARGTSTAL | 6107 | 16.000 |
| 22 | HCV 3a | 4 | 1 | 9 | B_3501 | MPPEGLLAF | 6108 | 40.000 |
| 23 | HCV 3a | 4 | 13 | 9 | B_3501 | APNRNCSWL | 6109 | 20.000 |
| 24 | HCV 3a | 4 | 1 | 10 | B_3501 | MPPEgLLAFL | 6110 | 40.000 |
| 25 | HCV 3a | 5 | 5 | 9 | A_0201 | GLLAFLVWA | 6111 | 883.604 |
| 26 | HCV 3a | 5 | 1 | 10 | A_0201 | MPPEgLLAFL | 6112 | 12.295 |
| 27 | HCV 3a | 5 | 32 | 9 | A3 | VLYTASHHR | 6113 | 20.000 |
| 28 | HCV 3a | 5 | 18 | 9 | A3 | HLDLVKLSR | 6114 | 12.000 |

TABLE 4i-continued

3a (1-3)

| No. | Strain | ORF | Start | AA | HLA | Peptide sequence | SEQ ID NO: | Score |
|---|---|---|---|---|---|---|---|---|
| 29 | HCV | 3a | 5 | 13 | 9 B7 | TAGTTHLDL | 6115 | 12.000 |
| 30 | HCV | 3a | 5 | 24 | 10 B7 | LSRHqVSAVL | 6116 | 40.000 |
| 31 | HCV | 3a | 5 | 10 | 10 B7 | TNRTaGTTHL | 6117 | 40.000 |
| 32 | HCV | 3a | 5 | 24 | 10 B_3501 | LSRHqVSAVL | 6118 | 15.000 |
| 33 | HCV | 3a | 6 | 23 | 9 A24 | CGLPVVGGL | 6119 | 10.080 |
| 34 | HCV | 3a | 6 | 8 | 9 B7 | TPGVRMIPM | 6120 | 20.000 |
| 35 | HCV | 3a | 6 | 8 | 9 B_3501 | TPGVRMIPM | 6121 | 40.000 |
| 36 | HCV | 3a | 7 | 22 | 10 A_0201 | NILRpHTAGV | 6122 | 35.385 |
| 37 | HCV | 3a | 7 | 15 | 9 B7 | APPTASGNI | 6123 | 24.000 |
| 38 | HCV | 3a | 7 | 15 | 10 B7 | APPTaSGNIL | 6124 | 240.000 |
| 39 | HCV | 3a | 7 | 15 | 10 B_3501 | APPTaSGNIL | 6125 | 20.000 |
| 40 | HCV | 3a | 8 | 7 | 10 A3 | ALDLaWWDGR | 6126 | 12.000 |
| 41 | HCV | 3a | 8 | 43 | 9 A1 | YVDASPPSK | 6127 | 20.000 |
| 42 | HCV | 3a | 9 | 57 | 9 A_0201 | YLHAGVGTV | 6128 | 95.662 |
| 43 | HCV | 3a | 9 | 36 | 9 A_0201 | YGGTSTPYV | 6129 | 11.487 |
| 44 | HCV | 3a | 9 | 21 | 10 A_0201 | SLPYhPGTSI | 6130 | 10.433 |
| 45 | HCV | 3a | 9 | 34 | 10 A3 | ALYGgTSTPY | 6131 | 30.000 |
| 46 | HCV | 3a | 9 | 2 | 9 B7 | RGRVKTALL | 6132 | 40.000 |
| 47 | HCV | 3a | 9 | 22 | 9 B7 | LPYHPGTSI | 6133 | 12.000 |
| 48 | HCV | 3a | 9 | 4 | 10 B7 | RVKTaLLSAL | 6134 | 20.000 |
| 49 | HCV | 3a | 9 | 16 | 9 B_3501 | WPSSASLPY | 6135 | 40.000 |
| 50 | HCV | 3a | 9 | 28 | 9 B_3501 | TSIGSAALY | 6136 | 10.000 |
| 51 | HCV | 3a | 9 | 28 | 9 B_4403 | TSIGSAALY | 6137 | 33.750 |
| 52 | HCV | 3a | 10 | 20 | 9 A_0201 | KLGAFLGLL | 6138 | 84.952 |
| 53 | HCV | 3a | 10 | 13 | 9 A24 | RSQHTPSKL | 6139 | 13.200 |
| 54 | HCV | 3a | 10 | 17 | 9 B7 | TPSKLGAFL | 6140 | 80.000 |
| 55 | HCV | 3a | 10 | 17 | 9 B_3501 | TPSKLGAFL | 6141 | 20.000 |
| 56 | HCV | 3a | 10 | 13 | 9 B_3501 | RSQHTPSKL | 6142 | 10.000 |
| 57 | HCV | 3a | 11 | 13 | 9 B7 | IPRSKCTQM | 6143 | 200.000 |
| 58 | HCV | 3a | 11 | 10 | 9 B7 | APNIPRSKC | 6144 | 13.500 |
| 59 | HCV | 3a | 11 | 13 | 9 B8 | IPRSKCTQM | 6145 | 80.000 |
| 60 | HCV | 3a | 11 | 13 | 9 B_3501 | IPRSKCTQM | 6146 | 120.000 |
| 61 | HCV | 3a | 12 | 19 | 9 A1 | VLDLSPVSK | 6147 | 20.000 |
| 62 | HCV | 3a | 12 | 38 | 10 A24 | RGMLqGSLGL | 6148 | 12.000 |
| 63 | HCV | 3a | 12 | 19 | 9 A3 | VLDLSPVSK | 6149 | 20.000 |
| 64 | HCV | 3a | 12 | 12 | 9 B7 | TPQRACSVL | 6150 | 80.000 |
| 65 | HCV | 3a | 12 | 36 | 10 B7 | ALRGmLQGSL | 6151 | 120.000 |
| 66 | HCV | 3a | 12 | 28 | 10 B7 | VPLEvLLCAL | 6152 | 80.000 |
| 67 | HCV | 3a | 12 | 38 | 10 B7 | RGMLqGSLGL | 6153 | 12.000 |
| 68 | HCV | 3a | 12 | 12 | 9 B_3501 | TPQRACSVL | 6154 | 20.000 |
| 69 | HCV | 3a | 12 | 25 | 9 B_3501 | VSKVPLEVL | 6155 | 15.000 |
| 70 | HCV | 3a | 12 | 28 | 10 B_3501 | VPLEvLLCAL | 6156 | 40.000 |
| 71 | HCV | 3a | 12 | 25 | 10 B_3501 | VSKVpLEVLL | 6157 | 15.000 |
| 72 | HCV | 3a | 13 | 13 | 10 A24 | RPLTwHKDIL | 6158 | 12.000 |
| 73 | HCV | 3a | 13 | 1 | 9 B7 | MPRPAAVKA | 6159 | 20.000 |
| 74 | HCV | 3a | 13 | 13 | 10 B7 | RPLTwHKDIL | 6160 | 80.000 |
| 75 | HCV | 3a | 13 | 6 | 10 B7 | AVKAqRSRPL | 6161 | 60.000 |
| 76 | HCV | 3a | 13 | 6 | 10 B8 | AVKAqRSRPL | 6162 | 80.000 |
| 77 | HCV | 3a | 13 | 13 | 9 B_3501 | RPLTWHKDI | 6163 | 16.000 |
| 78 | HCV | 3a | 13 | 13 | 10 B_3501 | RPLTwHKDIL | 6164 | 40.000 |
| 79 | HCV | 3a | 14 | 8 | 9 A_0201 | ALGTAPLQL | 6165 | 21.362 |
| 80 | HCV | 3a | 14 | 8 | 10 A_0201 | ALGTaPLQLV | 6166 | 159.970 |
| 81 | HCV | 3a | 14 | 8 | 9 B7 | ALGTAPLQL | 6167 | 12.000 |
| 82 | HCV | 3a | 14 | 7 | 9 B7 | SALGtAPLQL | 6168 | 12.000 |
| 83 | HCV | 3a | 15 | 2 | 10 A1 | NVMPkTLLAY | 6169 | 25.000 |
| 84 | HCV | 3a | 15 | 7 | 9 A_0201 | TLLAYWVSA | 6170 | 31.249 |
| 85 | HCV | 3a | 15 | 8 | 9 A3 | LLAYWVSAR | 6171 | 36.000 |
| 86 | HCV | 3a | 15 | 3 | 9 A3 | VMPKTLLAY | 6172 | 12.000 |
| 87 | HCV | 3a | 15 | 7 | 10 A3 | TLLAyWVSAR | 6173 | 54.000 |
| 88 | HCV | 3a | 15 | 4 | 9 B_3501 | MPKTLLAYW | 6174 | 30.000 |
| 89 | HCV | 3a | 15 | 4 | 10 B_3501 | MPKTlLAYWV | 6175 | 12.000 |
| 90 | HCV | 3a | 17 | 19 | 9 A1 | HTDMSPPVK | 6176 | 50.000 |
| 91 | HCV | 3a | 17 | 35 | 9 A_0201 | RLFSVSAMT | 6177 | 27.572 |
| 92 | HCV | 3a | 17 | 22 | 9 A24 | MSPPVKDRL | 6178 | 10.080 |
| 93 | HCV | 3a | 17 | 30 | 10 A_0201 | LECLtRLFSV | 6179 | 30.670 |
| 94 | HCV | 3a | 17 | 32 | 10 A_0201 | CLTRlFSVSA | 6180 | 18.878 |
| 95 | HCV | 3a | 17 | 35 | 10 A3 | RLFSvSAMTR | 6181 | 40.000 |
| 96 | HCV | 3a | 17 | 10 | 9 B7 | AVRAEVDSV | 6182 | 30.000 |
| 97 | HCV | 3a | 17 | 45 | 10 B7 | AARGtISSPL | 6183 | 360.000 |
| 98 | HCV | 3a | 17 | 33 | 10 B7 | LTRLfSVSAM | 6184 | 10.000 |
| 99 | HCV | 3a | 17 | 25 | 9 B8 | PVKDRLECL | 6185 | 12.000 |
| 100 | HCV | 3a | 17 | 45 | 10 B8 | AARGtISSPL | 6186 | 16.000 |
| 101 | HCV | 3a | 17 | 13 | 10 B_4403 | AEVDsVHTDM | 6187 | 36.000 |
| 102 | HCV | 3a | 19 | 4 | 9 A24 | RPFYIGWGL | 6188 | 11.200 |
| 103 | HCV | 3a | 19 | 6 | 10 A24 | FYIGwGLSKM | 6189 | 41.250 |

TABLE 4i-continued

3a (1-3)

| No. | Strain | ORF | Start | AA | HLA | Peptide sequence | SEQ ID NO: | Score |
|---|---|---|---|---|---|---|---|---|
| 104 | HCV | 3a | 19 | 4 | 9 B7 | RPFYIGWGL | 6190 | 80.000 |
| 105 | HCV | 3a | 19 | 4 | 9 B_3501 | RPFYIGWGL | 6191 | 40.000 |
| 106 | HCV | 3a | 20 | 8 | 9 A24 | KPPRTSSKL | 6192 | 13.200 |
| 107 | HCV | 3a | 20 | 8 | 9 B7 | KPPRTSSKL | 6193 | 80.000 |
| 108 | HCV | 3a | 20 | 8 | 9 B_3501 | KPPRTSSKL | 6194 | 40.000 |
| 109 | HCV | 3a | 21 | 3 | 9 A_0201 | LVSQAPWWL | 6195 | 131.078 |
| 110 | HCV | 3a | 21 | 33 | 9 A_0201 | YLRVLSSSV | 6196 | 24.315 |
| 111 | HCV | 3a | 21 | 2 | 10 A_0201 | ELVSqAPWWL | 6197 | 66.090 |
| 112 | HCV | 3a | 21 | 3 | 10 A_0201 | LVSQaPWWLL | 6198 | 40.515 |
| 113 | HCV | 3a | 21 | 32 | 9 A24 | YYLRVLSSS | 6199 | 10.500 |
| 114 | HCV | 3a | 21 | 29 | 9 B7 | CPPYYLRVL | 6200 | 80.000 |
| 115 | HCV | 3a | 21 | 3 | 9 B7 | LVSQAPWWL | 6201 | 20.000 |
| 116 | HCV | 3a | 21 | 3 | 10 B7 | LVSQaPWWLL | 6202 | 30.000 |
| 117 | HCV | 3a | 21 | 29 | 9 B_3501 | CPPYYLRVL | 6203 | 20.000 |
| 118 | HCV | 3a | 21 | 25 | 9 B_3501 | WSTCCPPYY | 6204 | 10.000 |
| 119 | HCV | 3a | 21 | 7 | 9 B_3501 | APWWLLRSW | 6205 | 10.000 |
| 120 | HCV | 3a | 21 | 13 | 10 B_3501 | RSWEeNSPPL | 6206 | 20.000 |
| 121 | HCV | 3a | 21 | 1 | 9 B_4403 | MELVSQAPW | 6207 | 24.000 |
| 122 | HCV | 3a | 21 | 1 | 10 B_4403 | MELVsQAPWW | 6208 | 36.000 |
| 123 | HCV | 3a | 21 | 16 | 10 B_4403 | EENSpPLRTW | 6209 | 18.000 |
| 124 | HCV | 3a | 23 | 24 | 9 B7 | CPTSSHGSL | 6210 | 80.000 |
| 125 | HCV | 3a | 23 | 24 | 10 B7 | CPTSsHGSLL | 6211 | 80.000 |
| 126 | HCV | 3a | 23 | 24 | 9 B_3501 | CPTSSHGSL | 6212 | 20.000 |
| 127 | HCV | 3a | 23 | 24 | 10 B_3501 | CPTSsHGSLL | 6213 | 20.000 |
| 128 | HCV | 3a | 24 | 38 | 9 A_0201 | TLARYGAWL | 6214 | 117.493 |
| 129 | HCV | 3a | 24 | 78 | 9 A_0201 | LLSSSLKWM | 6215 | 106.837 |
| 130 | HCV | 3a | 24 | 22 | 9 A_0201 | SMSTPPDPV | 6216 | 24.614 |
| 131 | HCV | 3a | 24 | 45 | 9 A_0201 | WLPTATLKC | 6217 | 22.853 |
| 132 | HCV | 3a | 24 | 5 | 9 A_0201 | GLQGRVHVL | 6218 | 20.145 |
| 133 | HCV | 3a | 24 | 77 | 10 A_0201 | RLLSsSLKWM | 6219 | 232.527 |
| 134 | HCV | 3a | 24 | 45 | 10 A_0201 | WLPTaTLKCA | 6220 | 52.561 |
| 135 | HCV | 3a | 24 | 75 | 9 A24 | KYRLLSSSL | 6221 | 480.000 |
| 136 | HCV | 3a | 24 | 41 | 9 A24 | RYGAWLPTA | 6222 | 10.000 |
| 137 | HCV | 3a | 24 | 67 | 10 A3 | KMSSsVRAKY | 6223 | 18.000 |
| 138 | HCV | 3a | 24 | 71 | 9 B7 | SVRAKYRLL | 6224 | 200.000 |
| 139 | HCV | 3a | 24 | 11 | 9 B7 | HVLTCGTVL | 6225 | 20.000 |
| 140 | HCV | 3a | 24 | 43 | 9 B7 | GAWLPTATL | 6226 | 18.000 |
| 141 | HCV | 3a | 24 | 71 | 9 B8 | SVRAKYRLL | 6227 | 80.000 |
| 142 | HCV | 3a | 24 | 68 | 9 B_3501 | MSSSVRAKY | 6228 | 10.000 |
| 143 | HCV | 3a | 24 | 54 | 9 B_4403 | AEWGTSIIL | 6229 | 12.000 |
| 144 | HCV | 3a | 25 | 72 | 10 A1 | WTVPmCPRRY | 6230 | 12.500 |
| 145 | HCV | 3a | 25 | 18 | 9 A_0201 | ILQPFLSGL | 6231 | 317.403 |
| 146 | HCV | 3a | 25 | 22 | 9 A_0201 | FLSGLGQTT | 6232 | 34.279 |
| 147 | HCV | 3a | 25 | 7 | 9 A_0201 | WLQSVSRNL | 6233 | 19.653 |
| 148 | HCV | 3a | 25 | 42 | 10 A_0201 | IMYHqLSMDV | 6234 | 273.262 |
| 149 | HCV | 3a | 25 | 14 | 10 A_0201 | NLPSiLQPFL | 6235 | 117.493 |
| 150 | HCV | 3a | 25 | 17 | 10 A_0201 | SILQpFLSGL | 6236 | 94.987 |
| 151 | HCV | 3a | 25 | 22 | 10 A_0201 | FLSGlGQTTI | 6237 | 47.991 |
| 152 | HCV | 3a | 25 | 25 | 10 A_0201 | GLGQtTILHC | 6238 | 11.426 |
| 153 | HCV | 3a | 25 | 6 | 10 A24 | RWLQsVSRNL | 6239 | 16.800 |
| 154 | HCV | 3a | 25 | 13 | 10 A24 | RNLPsILQPF | 6240 | 12.096 |
| 155 | HCV | 3a | 25 | 31 | 9 A3 | ILHCWTAGK | 6241 | 60.000 |
| 156 | HCV | 3a | 25 | 15 | 9 B7 | LPSILQPFL | 6242 | 80.000 |
| 157 | HCV | 3a | 25 | 11 | 9 B7 | VSRNLPSIL | 6243 | 40.000 |
| 158 | HCV | 3a | 25 | 39 | 9 B7 | KLRIMYHQL | 6244 | 40.000 |
| 159 | HCV | 3a | 25 | 74 | 9 B7 | VPMCPRRYV | 6245 | 27.000 |
| 160 | HCV | 3a | 25 | 50 | 9 B7 | DVPYHHGAL | 6246 | 20.000 |
| 161 | HCV | 3a | 25 | 56 | 9 B7 | GALRRSLLL | 6247 | 12.000 |
| 162 | HCV | 3a | 25 | 10 | 10 B7 | SVSRnLPSIL | 6248 | 20.000 |
| 163 | HCV | 3a | 25 | 56 | 9 B8 | GALRRSLLL | 6249 | 16.000 |
| 164 | HCV | 3a | 25 | 15 | 9 B_3501 | LPSILQPFL | 6250 | 20.000 |
| 165 | HCV | 3a | 25 | 11 | 9 B_3501 | VSRNLPSIL | 6251 | 15.000 |
| 166 | HCV | 3a | 25 | 72 | 10 B_4403 | WTVPmCPRRY | 6252 | 12.000 |
| 167 | HCV | 3a | 25 | 5 | 10 A_0201 | ALTQlSLNRT | 6253 | 17.140 |
| 168 | HCV | 3a | 25 | 20 | 9 A24 | RYTNAATLN | 6254 | 10.000 |
| 169 | HCV | 3a | 25 | 10 | 10 A3 | SLNRtSGWKR | 6255 | 12.000 |
| 170 | HCV | 3a | 25 | 2 | 10 B7 | TPAAlTQLSL | 6256 | 80.000 |
| 171 | HCV | 3a | 25 | 2 | 10 B_3501 | TPAAlTQLSL | 6257 | 20.000 |
| 172 | HCV | 3a | 26 | 5 | 10 A_0201 | ALTQlSLNRT | 6258 | 17.140 |
| 173 | HCV | 3a | 26 | 20 | 9 A24 | RYTNAATLN | 6259 | 10.000 |
| 174 | HCV | 3a | 26 | 10 | 10 A3 | SLNRtSGWKR | 6260 | 12.000 |
| 175 | HCV | 3a | 26 | 2 | 10 B7 | TPAAlTQLSL | 6261 | 80.000 |
| 176 | HCV | 3a | 26 | 2 | 10 B_3501 | TPAAlTQLSL | 6262 | 20.000 |
| 177 | HCV | 3a | 27 | 1 | 9 A_0201 | MIWSWWPRV | 6263 | 229.4 |
| 178 | HCV | 3a | 27 | 6 | 10 B7 | WPRVtASMRM | 6264 | 200 |

TABLE 4i-continued

3a (1-3)

| No. | Strain | ORF | Start | AA | HLA | Peptide sequence | SEQ ID NO: | Score |
|---|---|---|---|---|---|---|---|---|
| 179 | HCV 3a | 27 | 6 | 10 | B_3501 | WPRVtASMRM | 6265 | 120 |
| 180 | HCV 3a | 28 | 1 | 9 | A_0201 | MLHSPPTTL | 6266 | 36.32 |
| 181 | HCV 3a | 29 | 1 | 9 | B_4403 | MDHSPVRNF | 6267 | 15 |
| 182 | HCV 3a | 30 | 6 | 9 | A_0201 | QQLQAHHFL | 6268 | 44.08 |
| 183 | HCV 3a | 30 | 13 | 9 | A_0201 | FLQAGVGSL | 6269 | 29.38 |
| 184 | HCV 3a | 30 | 5 | 10 | A_0201 | AQQLqAHHFL | 6270 | 11.91 |
| 185 | HCV 3a | 30 | 12 | 10 | A24 | HFLQaGVGSL | 6271 | 30 |
| 186 | HCV 3a | 30 | 5 | 10 | B7 | AQQLqAHHFL | 6272 | 12 |
| 187 | HCV 3a | 31 | 16 | 10 | B7 | WVRApVYRRL | 6273 | 200 |
| 188 | HCV 3a | 31 | 18 | 10 | B7 | RAPVyRRLQL | 6274 | 18 |
| 189 | HCV 3a | 31 | 12 | 10 | B7 | DVRGwVRAPV | 6275 | 15 |
| 190 | HCV 3a | 31 | 19 | 9 | B7 | APVYRRLQL | 6276 | 360 |
| 191 | HCV 3a | 31 | 19 | 9 | B8 | APVYRRLQL | 6277 | 16 |
| 192 | HCV 3a | 31 | 24 | 10 | A24 | RLQLdQGGAL | 6278 | 12 |
| 193 | HCV 3a | 31 | 18 | 10 | A24 | RAPVyRRLQL | 6279 | 12 |
| 194 | HCV 3a | 31 | 26 | 10 | A1 | QLDQgGALRY | 6280 | 125 |
| 195 | HCV 3a | 31 | 26 | 9 | A1 | QLDQGGALR | 6281 | 10 |
| 196 | HCV 3a | 32 | 37 | 9 | A1 | LGEPCHAER | 6282 | 45 |
| 197 | HCV 3a | 32 | 37 | 10 | A1 | LGEPcHAERR | 6283 | 22.5 |
| 198 | HCV 3a | 32 | 56 | 10 | A_0201 | LVPGgLLCGV | 6284 | 23.8 |
| 199 | HCV 3a | 32 | 60 | 9 | A_0201 | GLLCGVVRA | 6285 | 42.28 |
| 200 | HCV 3a | 32 | 53 | 9 | A24 | RYRLVPGGL | 6286 | 560 |
| 201 | HCV 3a | 32 | 53 | 10 | A24 | RYRLvPGGLL | 6287 | 400 |
| 202 | HCV 3a | 32 | 68 | 10 | B7 | AGQTcPGGDL | 6288 | 18 |
| 203 | HCV 3a | 32 | 17 | 9 | B7 | GPTRVRCPL | 6289 | 120 |
| 204 | HCV 3a | 33 | | | | no hits | | |
| 205 | HCV 3a | 34 | 4 | 9 | B_3501 | RPPSVGPPL | 6290 | 40 |
| 206 | HCV 3a | 35 | 50 | 9 | A1 | IAEFSNCHK | 6291 | 18 |
| 207 | HCV 3a | 35 | 44 | 10 | A1 | CSEGhRIAEF | 6292 | 27 |
| 208 | HCV 3a | 35 | 30 | 9 | B7 | QPRFTNALC | 6293 | 20 |
| 209 | HCV 3a | 35 | 45 | 9 | B_4403 | SEGHRIAEF | 6294 | 80 |
| 210 | HCV 3a | 35 | 19 | 9 | B_4403 | DEQAHRIRI | 6295 | 12 |
| 211 | HCV 3a | 35 | 51 | 10 | B_4403 | AEFSnCHKPA | 6296 | 12 |
| 212 | HCV 3a | 35 | 45 | 10 | B_4403 | SEGHrIAEFS | 6297 | 12 |
| 213 | HCV 3a | 36 | | | | no hits | | |
| 214 | HCV 3a | 37 | 33 | 10 | B7 | CASGkIISVL | 6298 | 12 |
| 215 | HCV 3a | 37 | 34 | 9 | B7 | ASGKIISVL | 6299 | 12 |
| 216 | HCV 3a | 37 | 16 | 10 | B_4403 | EEKNnSAGRF | 6300 | 60 |
| 217 | HCV 3a | 38 | 15 | 10 | A1 | GLELrLLVHR | 6301 | 18 |
| 218 | HCV 3a | 38 | 15 | 10 | A3 | GLELrLLVHR | 6302 | 18 |
| 219 | HCV 3a | 38 | 11 | 10 | B7 | TGRSgLELRL | 6303 | 40 |
| 220 | HCV 3a | 38 | 8 | 9 | B7 | RGRTGRSGL | 6304 | 60 |
| 221 | HCV 3a | 38 | 13 | 9 | B_3501 | RSGLELRLL | 6305 | 15 |

TABLE 4j

3a (4-6)

| No. | Strain | ORF | Start | AA | HLA | Peptide sequence | SEQ ID NO: | Score |
|---|---|---|---|---|---|---|---|---|
| 1 | HCV 3a | 1 | | | | no hits | | |
| 2 | HCV 3a | 2 | 1 | 9 | A_0201 | MVVEHLQSV | 6349 | 97.561 |
| 3 | HCV 3a | 2 | 7 | 9 | B_3501 | QSVEGNLPL | 6350 | 10.000 |
| 4 | HCV 3a | 3 | 15 | 9 | A_0201 | FLLLSTTRC | 6351 | 84.555 |
| 5 | HCV 3a | 3 | 8 | 9 | A_0201 | AEWADGQFL | 6352 | 18.962 |
| 6 | HCV 3a | 3 | 54 | 9 | B7 | QVRIARFSL | 6353 | 300.000 |
| 7 | HCV 3a | 3 | 28 | 9 | B7 | GPRVRHRAA | 6354 | 20.000 |
| 8 | HCV 3a | 3 | 34 | 9 | B7 | RAADHALLL | 6355 | 12.000 |
| 9 | HCV 3a | 3 | 28 | 9 | B8 | GPRVRHRAA | 6356 | 16.000 |
| 10 | HCV 3a | 3 | 34 | 9 | B_3501 | RAADHALLL | 6357 | 12.000 |
| 11 | HCV 3a | 3 | 8 | 10 | A_0201 | AEWAdGQFLL | 6358 | 19.996 |
| 12 | HCV 3a | 3 | 53 | 10 | A_0201 | TQVRiARFSL | 6359 | 12.562 |
| 13 | HCV 3a | 3 | 48 | 10 | B7 | GPRVaTQVRI | 6360 | 80.000 |
| 14 | HCV 3a | 3 | 48 | 10 | B_3501 | GPRVaTQVRI | 6361 | 24.000 |
| 15 | HCV 3a | 3 | 8 | 10 | B_4403 | AEWAdGQFLL | 6362 | 12.000 |
| 16 | HCV 3a | 4 | 32 | 9 | A_0201 | ILGRFLETL | 6363 | 155.527 |
| 17 | HCV 3a | 4 | 6 | 9 | A_0201 | YIIRSFPAV | 6364 | 83.584 |
| 18 | HCV 3a | 4 | 20 | 9 | A3 | VVWPSPDRK | 6365 | 15.000 |
| 19 | HCV 3a | 4 | 22 | 9 | B_3501 | WPSPDRKGW | 6366 | 15.000 |
| 20 | HCV 3a | 4 | 39 | 10 | A_0201 | TLCShRELGV | 6367 | 69.552 |
| 21 | HCV 3a | 4 | 31 | 10 | A_0201 | RILGrFLETL | 6368 | 46.544 |
| 22 | HCV 3a | 4 | 31 | 10 | A24 | RILGrFLETL | 6369 | 12.000 |

TABLE 4j-continued 3a (4-6)

| No. | Strain | ORF | Start | AA | HLA | Peptide sequence | SEQ ID NO: | Score |
|---|---|---|---|---|---|---|---|---|
| 23 | HCV 3a | 4 | 24 | 10 | B7 | SPDRkGWRIL | 6370 | 24.000 |
| 24 | HCV 3a | 5 | 2 | 9 | A24 | RPMRLASGL | 6371 | 14.400 |
| 25 | HCV 3a | 5 | 2 | 9 | B7 | RPMRLASGL | 6372 | 240.000 |
| 26 | HCV 3a | 5 | 2 | 9 | B_3501 | RPMRLASGL | 6373 | 40.000 |
| 27 | HCV 3a | 6 | 30 | 9 | B7 | QPYRESDLL | 6374 | 80.000 |
| 28 | HCV 3a | 6 | 30 | 9 | B_3501 | QPYRESDLL | 6375 | 30.000 |
| 29 | HCV 3a | 6 | 9 | 10 | A_0201 | GQHRnIWFWL | 6376 | 117.457 |
| 30 | HCV 3a | 6 | 23 | 10 | B_3501 | RSYRvGIQPY | 6377 | 20.000 |
| 31 | HCV 3a | 7 | 1 | 9 | B_4403 | MEVPHSAHF | 6378 | 160.000 |
| 32 | HCV 3a | 8 | 33 | 9 | B7 | QPGERWHNL | 6379 | 80.000 |
| 33 | HCV 3a | 8 | 15 | 9 | B7 | HAVPPPHAL | 6380 | 18.000 |
| 34 | HCV 3a | 8 | 33 | 9 | B8 | QPGERWHNL | 6381 | 24.000 |
| 35 | HCV 3a | 8 | 33 | 9 | B_3501 | QPGERWHNL | 6382 | 40.000 |
| 36 | HCV 3a | 8 | 30 | 9 | B_4403 | NEGQPGERW | 6383 | 12.000 |
| 37 | HCV 3a | 8 | 17 | 10 | B7 | VPPPhALVSL | 6384 | 80.000 |
| 38 | HCV 3a | 8 | 17 | 10 | B_3501 | VPPPhALVSL | 6385 | 20.000 |
| 39 | HCV 3a | 9 | | | | no hits | | |
| 40 | HCV 3a | 10 | 28 | 9 | A_0201 | LQQSKDFFL | 6386 | 117.457 |
| 41 | HCV 3a | 10 | 44 | 9 | A_0201 | SLLDVRGGL | 6387 | 42.129 |
| 42 | HCV 3a | 10 | 1 | 9 | A_0201 | MLVPEGLKL | 6388 | 36.316 |
| 43 | HCV 3a | 10 | 2 | 9 | A_0201 | LVPEGLKLL | 6389 | 29.965 |
| 44 | HCV 3a | 10 | 14 | 9 | A24 | SYYGLNDSL | 6390 | 240.000 |
| 45 | HCV 3a | 10 | 15 | 9 | A24 | YYGLNDSLL | 6391 | 200.000 |
| 46 | HCV 3a | 10 | 44 | 9 | A24 | SLLDVRGGL | 6392 | 10.080 |
| 47 | HCV 3a | 10 | 8 | 9 | A3 | KLLPVGSYY | 6393 | 40.500 |
| 48 | HCV 3a | 10 | 10 | 9 | B7 | LPVGSYYGL | 6394 | 80.000 |
| 49 | HCV 3a | 10 | 38 | 9 | B7 | LVGYCLSLL | 6395 | 20.000 |
| 50 | HCV 3a | 10 | 2 | 9 | B7 | LVPEGLKLL | 6396 | 20.000 |
| 51 | HCV 3a | 10 | 30 | 9 | B_3501 | QSKDFFLEL | 6397 | 30.000 |
| 52 | HCV 3a | 10 | 10 | 9 | B_3501 | LPVGSYYGL | 6398 | 20.000 |
| 53 | HCV 3a | 10 | 27 | 10 | A_0201 | SLQQsKDFFL | 6399 | 681.461 |
| 54 | HCV 3a | 10 | 1 | 10 | A_0201 | MLVPeGLKLL | 6400 | 83.527 |
| 55 | HCV 3a | 10 | 9 | 10 | A_0201 | LLPVgSYYGL | 6401 | 54.474 |
| 56 | HCV 3a | 10 | 29 | 10 | A_0201 | QQSKdFFLEL | 6402 | 15.638 |
| 57 | HCV 3a | 10 | 15 | 10 | A24 | YYGLnDSLLL | 6403 | 200.000 |
| 58 | HCV 3a | 10 | 14 | 10 | A24 | SYYGLNDSLL | 6404 | 200.000 |
| 59 | HCV 3a | 10 | 34 | 10 | A24 | FFLELVGYCL | 6405 | 50.400 |
| 60 | HCV 3a | 10 | 23 | 10 | A3 | LLGGsLQQSK | 6406 | 30.000 |
| 61 | HCV 3a | 10 | 6 | 10 | A3 | GLKLlPVGSY | 6407 | 16.200 |
| 62 | HCV 3a | 10 | 32 | 10 | B_4403 | KDFFLELVGY | 6408 | 22.500 |
| 63 | HCV 3a | 10 | 15 | 10 | A24 | YYGLnDSLLL | 6409 | 200.000 |
| 64 | HCV 3a | 10 | 14 | 10 | A24 | SYYGLNDSLL | 6410 | 200.000 |
| 65 | HCV 3a | 10 | 34 | 10 | A24 | FFLElVGYCL | 6411 | 50.400 |
| 66 | HCV 3a | 10 | 23 | 10 | A3 | LLGGsLQQSK | 6412 | 30.000 |
| 67 | HCV 3a | 10 | 6 | 10 | A3 | GLKLLPVGSY | 6413 | 16.200 |
| 68 | HCV 3a | 10 | 32 | 10 | B_4403 | KDFFlELVGY | 6414 | 22.500 |
| 69 | HCV 3a | 11 | | | | no hits | | |
| 70 | HCV 3a | 12 | 27 | 9 | A_0201 | RAQGHFFDV | 6415 | 10.645 |
| 71 | HCV 3a | 12 | 25 | 9 | A24 | TFRAQGHFF | 6416 | 10.000 |
| 72 | HCV 3a | 12 | 6 | 9 | B_3501 | VPPPLEQGY | 6417 | 40.000 |
| 73 | HCV 3a | 12 | 15 | 10 | A24 | RYSLtVEGDL | 6418 | 560.000 |
| 74 | HCV 3a | 12 | 1 | 10 | B7 | MAKDkVPPPL | 6419 | 12.000 |
| 75 | HCV 3a | 12 | 1 | 10 | B8 | MAKDkVPPPL | 6420 | 24.000 |
| 76 | HCV 3a | 12 | 1 | 10 | B_3501 | MAKDkVPPPL | 6421 | 18.000 |
| 77 | HCV 3a | 13 | 14 | 9 | B7 | GATPVREKL | 6422 | 18.000 |
| 78 | HCV 3a | 13 | 19 | 9 | B_4403 | REKLTVGGI | 6423 | 12.000 |
| 79 | HCV 3a | 13 | 9 | 10 | A_0201 | IVCPpGATPV | 6424 | 10.346 |
| 80 | HCV 3a | 14 | 5 | 10 | A3 | YLIALWNSRR | 6425 | 18.000 |
| 81 | HCV 3a | 15 | 32 | 9 | B7 | APSRDDIGI | 6426 | 24.000 |
| 82 | HCV 3a | 15 | 1 | 9 | B7 | MPRRAHNRT | 6427 | 20.000 |
| 83 | HCV 3a | 15 | 32 | 9 | B_3501 | APSRDDIGI | 6428 | 12.000 |
| 84 | HCV 3a | 15 | 29 | 10 | B7 | VPPApSRDDI | 6429 | 12.000 |
| 85 | HCV 3a | 15 | 36 | 10 | B_4403 | DDIGiAGNQV | 6430 | 16.875 |
| 86 | HCV 3a | 16 | 16 | 9 | B7 | SPRNPPHCC | 6431 | 30.000 |
| 87 | HCV 3a | 16 | 3 | 9 | B8 | GARERSRTC | 6432 | 24.000 |
| 88 | HCV 3a | 16 | 16 | 10 | B7 | SPRNpPHCCT | 6433 | 30.000 |
| 89 | HCV 3a | 17 | 43 | 9 | B_4403 | CEIDCTWVM | 6434 | 30.000 |
| 90 | HCV 3a | 17 | 35 | 9 | B_4403 | HEHPHLEQC | 6435 | 12.000 |
| 91 | HCV 3a | 17 | 50 | 9 | A_0201 | VMPKPVWIV | 6436 | 603.952 |
| 92 | HCV 3a | 17 | 2 | 9 | A_0201 | QQWMLLAAV | 6437 | 134.619 |
| 93 | HCV 3a | 17 | 4 | 9 | A_0201 | WMLLAAVTI | 6438 | 128.242 |
| 94 | HCV 3a | 17 | 49 | 9 | A_0201 | WVMPKPVWI | 6439 | 85.454 |
| 95 | HCV 3a | 17 | 56 | 9 | A_0201 | WIVDHAAGC | 6440 | 12.883 |
| 96 | HCV 3a | 17 | 32 | 9 | B7 | EPTHEHPHL | 6441 | 80.000 |
| 97 | HCV 3a | 17 | 71 | 9 | B7 | TPAVCGLRM | 6442 | 20.000 |

TABLE 4j-continued 3a (4-6)

| No. | Strain | ORF | Start | AA | HLA | Peptide sequence | SEQ ID NO: | Score |
|---|---|---|---|---|---|---|---|---|
| 98 | HCV 3a | 17 | 67 | 9 | B7 | GPRTTPAVC | 6443 | 20.000 |
| 99 | HCV 3a | 17 | 23 | 9 | B7 | VASGGKPVL | 6444 | 12.000 |
| 100 | HCV 3a | 17 | 71 | 9 | B_3501 | TPAVCGLRM | 6445 | 40.000 |
| 101 | HCV 3a | 17 | 32 | 9 | B_3501 | EPTHEHPHL | 6446 | 30.000 |
| 102 | HCV 3a | 17 | 37 | 9 | B_3501 | HPHLEQCEI | 6447 | 12.000 |
| 103 | HCV 3a | 17 | 43 | 9 | B_4403 | CEIDCTWVM | 6448 | 30.000 |
| 104 | HCV 3a | 17 | 35 | 9 | B_4403 | HEHPHLEQC | 6449 | 12.000 |
| 105 | HCV 3a | 17 | 44 | 10 | A1 | EIDCtWVMPK | 6450 | 50.000 |
| 106 | HCV 3a | 17 | 49 | 10 | A_0201 | WVMPkPVWIV | 6451 | 732.572 |
| 107 | HCV 3a | 17 | 6 | 10 | A_0201 | LLAAvTIFDI | 6452 | 236.595 |
| 108 | HCV 3a | 17 | 1 | 10 | A_0201 | MQQWmLLAAV | 6453 | 27.573 |
| 109 | HCV 3a | 17 | 41 | 10 | A_0201 | EQCEiDCTWV | 6454 | 11.926 |
| 110 | HCV 3a | 17 | 44 | 10 | A3 | EIDCtWVMPK | 6455 | 10.800 |
| 111 | HCV 3a | 17 | 9 | 10 | B7 | AVTIFDIAAL | 6456 | 60.000 |
| 112 | HCV 3a | 17 | 71 | 10 | B_3501 | TPAVcGLRMF | 6457 | 20.000 |
| 113 | HCV 3a | 17 | 40 | 10 | B_4403 | LEQCeIDCTW | 6458 | 12.000 |
| 114 | HCV 3a | 18 | 4 | 9 | A_0201 | KQPSYEPGV | 6459 | 24.681 |
| 115 | HCV 3a | 18 | 32 | 9 | A_0201 | NQLQFLLGA | 6460 | 16.289 |
| 116 | HCV 3a | 18 | 15 | 9 | A_0201 | LITVQGSAV | 6461 | 16.258 |
| 117 | HCV 3a | 18 | 30 | 9 | A_0201 | GVNQLQFLL | 6462 | 10.841 |
| 118 | HCV 3a | 18 | 7 | 9 | A24 | SYEPGVYGL | 6463 | 360.000 |
| 119 | HCV 3a | 18 | 36 | 9 | A3 | FLLGAHTKK | 6464 | 45.000 |
| 120 | HCV 3a | 18 | 30 | 9 | B7 | GVNQLQFLL | 6465 | 20.000 |
| 121 | HCV 3a | 18 | 5 | 9 | B_3501 | QPSYEPGVY | 6466 | 60.000 |
| 122 | HCV 3a | 18 | 44 | 9 | B_3501 | KASKPSGGM | 6467 | 12.000 |
| 123 | HCV 3a | 18 | 36 | 10 | A_0201 | FLLGaHTKKA | 6468 | 84.555 |
| 124 | HCV 3a | 18 | 14 | 10 | A_0201 | GLITvQGSAV | 6469 | 69.552 |
| 125 | HCV 3a | 18 | 28 | 10 | A_0201 | AIGVnQLQFL | 6470 | 37.157 |
| 126 | HCV 3a | 18 | 7 | 10 | A24 | SYEPgVYGLI | 6471 | 126.000 |
| 127 | HCV 3a | 18 | 25 | 10 | B7 | VPRAiGVNQL | 6472 | 800.000 |
| 128 | HCV 3a | 18 | 28 | 10 | B7 | AIGVnQLQFL | 6473 | 12.000 |
| 129 | HCV 3a | 18 | 25 | 10 | B8 | VPRAiGVNQL | 6474 | 16.000 |
| 130 | HCV 3a | 18 | 25 | 10 | B_3501 | VPRAiGVNQL | 6475 | 60.000 |
| 131 | HCV 3a | 19 | 10 | 9 | A3 | GLGHPQDVR | 6476 | 18.000 |
| 132 | HCV 3a | 19 | 2 | 10 | B7 | GPGYyVEQGL | 6477 | 80.000 |
| 133 | HCV 3a | 19 | 2 | 10 | B_3501 | GPGYyVEQGL | 6478 | 20.000 |
| 134 | HCV 3a | 20 | 34 | 9 | A24 | RYAAGCVQN | 6479 | 10.000 |
| 135 | HCV 3a | 20 | 39 | 9 | B7 | CVQNDVIGL | 6480 | 20.000 |
| 136 | HCV 3a | 20 | 23 | 9 | B7 | PARGYIVVL | 6481 | 12.000 |
| 137 | HCV 3a | 20 | 22 | 10 | B7 | GPARgYIVVL | 6482 | 80.000 |
| 138 | HCV 3a | 20 | 22 | 10 | B_3501 | GPARgYIVVL | 6483 | 20.000 |
| 139 | HCV 3a | 21 | 65 | 9 | A_0201 | LITIEGPRV | 6484 | 16.258 |
| 140 | HCV 3a | 21 | 83 | 9 | A_0201 | ALTRLGDRL | 6485 | 10.468 |
| 141 | HCV 3a | 21 | 57 | 9 | B7 | EPPCPPAAL | 6486 | 120.000 |
| 142 | HCV 3a | 21 | 79 | 9 | B7 | GPASALTRL | 6487 | 80.000 |
| 143 | HCV 3a | 21 | 83 | 9 | B7 | ALTRLGDRL | 6488 | 12.000 |
| 144 | HCV 3a | 21 | 57 | 9 | B_3501 | EPPCPPAAL | 6489 | 20.000 |
| 145 | HCV 3a | 21 | 79 | 9 | B_3501 | GPASALTRL | 6490 | 20.000 |
| 146 | HCV 3a | 21 | 68 | 9 | B_4403 | IEGPRVPGL | 6491 | 24.000 |
| 147 | HCV 3a | 21 | 14 | 9 | B_4403 | DERDVPHEV | 6492 | 18.000 |
| 148 | HCV 3a | 21 | 64 | 10 | A_0201 | ALITiEGPRV | 6493 | 69.552 |
| 149 | HCV 3a | 21 | 75 | 10 | A_0201 | GLSPgPASAL | 6494 | 21.362 |
| 150 | HCV 3a | 21 | 86 | 10 | A_0201 | RLGDrLSSSA | 6495 | 20.369 |
| 151 | HCV 3a | 21 | 43 | 10 | A_0201 | VIWApRWTGA | 6496 | 16.386 |
| 152 | HCV 3a | 21 | 82 | 10 | B7 | SALTrLGDRL | 6497 | 12.000 |
| 153 | HCV 3a | 21 | 57 | 10 | B7 | EPPCpPAALI | 6498 | 12.000 |
| 154 | HCV 3a | 21 | 68 | 10 | B_4403 | IEGPrVPGLS | 6499 | 12.000 |
| 155 | HCV 3a | 22 | 14 | 9 | A_0201 | QGSDPWWSV | 6500 | 23.734 |
| 156 | HCV 3a | 22 | 5 | 9 | B_3501 | FPREDRSSS | 6501 | 18.000 |
| 157 | HCV 3a | 22 | 15 | 10 | A1 | GSDPwWSVAS | 6502 | 15.000 |
| 158 | HCV 3a | 22 | 13 | 10 | A_0201 | SQGSdPWWSV | 6503 | 89.910 |
| 159 | HCV 3a | 23 | 2 | 9 | A_0201 | SMTLSRTPL | 6504 | 15.428 |
| 160 | HCV 3a | 23 | 1 | 10 | B7 | MSMTLSRTPL | 6505 | 18.000 |
| 161 | HCV 3a | 23 | 8 | 10 | B_3501 | TPLPgRGAPW | 6506 | 10.000 |
| 162 | HCV 3a | 24 | 42 | 9 | A_0201 | QLVVHNPEL | 6507 | 21.362 |
| 163 | HCV 3a | 24 | 35 | 9 | B7 | VVRHIHGQL | 6508 | 200.000 |
| 164 | HCV 3a | 24 | 53 | 9 | B7 | GPTVEDCSL | 6509 | 80.000 |
| 165 | HCV 3a | 24 | 53 | 9 | B_3501 | GPTVEDCSL | 6510 | 30.000 |
| 166 | HCV 3a | 24 | 26 | 9 | B_4403 | EEGPAERPV | 6511 | 12.000 |
| 167 | HCV 3a | 24 | 23 | 10 | A1 | SSEEeGPAER | 6512 | 27.000 |
| 168 | HCV 3a | 24 | 34 | 10 | B7 | VVVRhIHGQL | 6513 | 20.000 |
| 169 | HCV 3a | 24 | 9 | 10 | B7 | TPRThWNRPA | 6514 | 20.000 |
| 170 | HCV 3a | 24 | 35 | 10 | B7 | VVRHiNGQLV | 6515 | 10.000 |
| 171 | HCV 3a | 24 | 30 | 10 | B_4403 | AERPvVVRHI | 6516 | 72.000 |
| 172 | HCV 3a | 25 | | | | no hits | | |

TABLE 4j-continued

| | | | | 3a (4-6) | | | |
|---|---|---|---|---|---|---|---|
| No. | Strain | ORF | Start | AA | HLA | Peptide sequence | SEQ ID NO: | Score |
| 173 | HCV 3a | 26 | | | | no hits | | |
| 174 | HCV 3a | 27 | | | | no hits | | |
| 175 | HCV 3a | 28 | 3 | 9 | A_0201 | KVYWVRWCT | 6517 | 54.772 |
| 176 | HCV 3a | 29 | 17 | 9 | A_0201 | LLLPRKDSV | 6518 | 214.366 |
| 177 | HCV 3a | 29 | 19 | 9 | B7 | LPRKDSVST | 6519 | 20.000 |
| 178 | HCV 3a | 29 | 30 | 9 | B7 | RPPATRPCI | 6520 | 12.000 |
| 179 | HCV 3a | 29 | 30 | 9 | B_3501 | RPPATRPCI | 6521 | 16.000 |
| 180 | HCV 3a | 29 | 16 | 10 | A_0201 | RLLLpRKDSV | 6522 | 126.098 |
| 181 | HCV 3a | 29 | 18 | 10 | A_0201 | LLPRkDSVST | 6523 | 12.668 |
| 182 | HCV 3a | 30 | 5 | 9 | A_0201 | YLGPYGHDV | 6524 | 319.939 |
| 183 | HCV 3a | 30 | 12 | 9 | B7 | DVGCGKPHL | 6525 | 20.000 |
| 184 | HCV 3a | 31 | 16 | 9 | B7 | WNRSVWHQL | 6526 | 40.000 |
| 185 | HCV 3a | 31 | 8 | 9 | B_3501 | RPRETYRRW | 6527 | 120.000 |
| 186 | HCV 3a | 31 | 15 | 10 | A24 | RWNRsVWHQL | 6528 | 16.800 |
| 187 | HCV 3a | 31 | 8 | 10 | B_3501 | RPREtYRRWN | 6529 | 24.000 |
| 188 | HCV 3a | 31 | 4 | 10 | B_3501 | RSNPrPRETY | 6530 | 20.000 |
| 189 | HCV 3a | 32 | 41 | 9 | B_4403 | EELNCQRKM | 6531 | 12.000 |
| 190 | HCV 3a | 32 | 23 | 10 | B7 | RCRSgHEGIL | 6532 | 40.000 |
| 191 | HCV 3a | 32 | 11 | 10 | B7 | VPRKrPGPLC | 6533 | 30.000 |
| 192 | HCV 3a | 32 | 10 | 10 | B7 | LVPRkRPGPL | 6534 | 20.000 |
| 193 | HCV 3a | 33 | | | | no hits | | |
| 194 | HCV 3a | 34 | 19 | 9 | B_3501 | RAPHHTGCM | 6535 | 12.000 |
| 195 | HCV 3a | 34 | 20 | 9 | B_3501 | APHHTGCMW | 6536 | 10.000 |
| 196 | HCV 3a | 34 | 7 | 10 | A_0201 | GMDSrPCSGV | 6537 | 20.093 |
| 197 | HCV 3a | 35 | | | | no hits | | |
| 198 | HCV 3a | 36 | | | | no hits | | |
| 199 | HCV 3a | 37 | 27 | 9 | A1 | RAEPRTGLR | 6538 | 90.000 |
| 200 | HCV 3a | 37 | 27 | 10 | A1 | RAEPrTGLRS | 6539 | 45.000 |
| 201 | HCV 3a | 37 | 10 | 10 | A1 | ATLPtRSPHY | 6540 | 25.000 |
| 202 | HCV 3a | 37 | 25 | 10 | B7 | GTRAePRTGL | 6541 | 90.000 |
| 203 | HCV 3a | 37 | 3 | 10 | B7 | GSRAgTGATL | 6542 | 40.000 |
| 204 | HCV 3a | 37 | 29 | 10 | B7 | EPRTgLRSDA | 6543 | 30.000 |
| 205 | HCV 3a | 37 | 3 | 10 | B_3501 | GSRAgTGATL | 6544 | 15.000 |
| 206 | HCV 3a | 37 | 10 | 10 | B_4403 | ATLPtRSPHY | 6545 | 24.000 |
| 207 | HCV 3a | 38 | 8 | 9 | A1 | GLEAARHSY | 6546 | 45.000 |
| 208 | HCV 3a | 38 | 8 | 9 | A3 | GLEAARHSY | 6547 | 12.000 |
| 209 | HCV 3a | 38 | 1 | 9 | B7 | MALPGGGGL | 6548 | 12.000 |
| 210 | HCV 3a | 39 | | | | no hits | | |
| 211 | HCV 3a | 40 | 26 | 9 | A_0201 | LVLVRTAQL | 6549 | 11.757 |
| 212 | HCV 3a | 40 | 11 | 9 | A_0201 | QMDKSNWPA | 6550 | 10.764 |
| 213 | HCV 3a | 40 | 20 | 9 | A24 | RGSGVSLVL | 6551 | 11.200 |
| 214 | HCV 3a | 40 | 27 | 9 | A3 | VLVRTAQLK | 6552 | 30.000 |
| 215 | HCV 3a | 40 | 26 | 9 | B7 | LVLVRTAQL | 6553 | 20.000 |
| 216 | HCV 3a | 40 | 18 | 9 | B7 | PARGSGVSL | 6554 | 12.000 |
| 217 | HCV 3a | 40 | 10 | 10 | A_0201 | NQMDkSNWPA | 6555 | 57.308 |
| 218 | HCV 3a | 40 | 25 | 10 | A_0201 | SLVLvRTAQL | 6556 | 21.362 |
| 219 | HCV 3a | 40 | 27 | 10 | A3 | VLVRtAQLKR | 6557 | 12.000 |
| 220 | HCV 3a | 40 | 17 | 10 | B7 | WPARgSGVSL | 6558 | 80.000 |
| 221 | HCV 3a | 40 | 3 | 10 | B7 | FPPTpTVNQM | 6559 | 20.000 |
| 222 | HCV 3a | 40 | 3 | 10 | B_3501 | FPPTpTVNQM | 6560 | 40.000 |
| 223 | HCV 3a | 40 | 17 | 10 | B_3501 | WPARgSGVSL | 6561 | 20.000 |
| 224 | HCV 3a | 41 | 1 | 9 | A_0201 | MIAGKSSGV | 6562 | 16.258 |
| 225 | HCV 3a | 42 | 19 | 9 | A_0201 | MMMLPNQEL | 6563 | 97.045 |
| 226 | HCV 3a | 42 | 20 | 9 | A_0201 | MMLPNQELT | 6564 | 16.588 |
| 227 | HCV 3a | 42 | 7 | 9 | A_0201 | IITMRTQMV | 6565 | 16.258 |
| 228 | HCV 3a | 42 | 14 | 9 | B7 | MVGAYMMML | 6566 | 20.000 |
| 229 | HCV 3a | 42 | 19 | 9 | B7 | MMMLPNQEL | 6567 | 18.000 |
| 230 | HCV 3a | 42 | 1 | 9 | B_4403 | MEKKCVIIT | 6568 | 12.000 |
| 231 | HCV 3a | 42 | 21 | 10 | A_0201 | MLPNqELTGV | 6569 | 271.948 |
| 232 | HCV 3a | 42 | 18 | 10 | A_0201 | YMMMlPNQEL | 6570 | 262.591 |
| 233 | HCV 3a | 42 | 13 | 10 | A_0201 | QMVGaYMMML | 6571 | 35.485 |
| 234 | HCV 3a | 42 | 19 | 10 | A_0201 | MMMLpNQELT | 6572 | 16.588 |
| 235 | HCV 3a | 42 | 6 | 10 | A_0201 | VIITmRTQMV | 6573 | 16.258 |
| 236 | HCV 3a | 42 | 13 | 10 | A3 | QMVGaYMMML | 6574 | 12.150 |
| 237 | HCV 3a | 42 | 18 | 10 | B7 | YMMMLPNQEL | 6575 | 18.000 |
| 238 | HCV 3a | 43 | 13 | 9 | A_0201 | VSYENPKGV | 6576 | 10.126 |
| 239 | HCV 3a | 43 | 14 | 9 | A24 | SYENPKGVF | 6577 | 150.000 |
| 240 | HCV 3a | 43 | 20 | 9 | B7 | GVFFEVHIL | 6578 | 20.000 |
| 241 | HCV 3a | 43 | 17 | 9 | B_3501 | NPKGVFFEV | 6579 | 12.000 |
| 242 | HCV 3a | 43 | 15 | 9 | B_4403 | YENPKGVFF | 6580 | 120.000 |
| 243 | HCV 3a | 43 | 7 | 9 | B_4403 | VESKQRVSY | 6581 | 120.000 |
| 244 | HCV 3a | 43 | 6 | 10 | A1 | TVESkQRVSY | 6582 | 90.000 |
| 245 | HCV 3a | 43 | 14 | 10 | A24 | SYENpKGVFF | 6583 | 150.000 |
| 246 | HCV 3a | 43 | 19 | 10 | A24 | KGVFfEVHIL | 6584 | 12.000 |
| 247 | HCV 3a | 43 | 13 | 10 | B_3501 | VSYEnPKGVF | 6585 | 10.000 |

TABLE 4j-continued 3a (4-6)

| No. | Strain | ORF | Start | AA | HLA | Peptide sequence | SEQ ID NO: | Score |
|---|---|---|---|---|---|---|---|---|
| 248 | HCV 3a | 44 | 16 | 9 | A_0201 | SQTERIWLM | 6586 | 35.624 |
| 249 | HCV 3a | 44 | 35 | 9 | A_0201 | ALYPNFDRA | 6587 | 14.801 |
| 250 | HCV 3a | 44 | 1 | 9 | A_0201 | MMVVGIGVV | 6588 | 10.468 |
| 251 | HCV 3a | 44 | 29 | 9 | B_4403 | KERTSFALY | 6589 | 120.000 |
| 252 | HCV 3a | 44 | 1 | 10 | A_0201 | MMVVgIGVVV | 6590 | 35.012 |
| 253 | HCV 3a | 44 | 26 | 10 | A_0201 | LLDKeRTSFA | 6591 | 18.580 |
| 254 | HCV 3a | 44 | 20 | 10 | A3 | RIWLmALLDK | 6592 | 30.000 |
| 255 | HCV 3a | 44 | 14 | 10 | B_3501 | KSSQtERIWL | 6593 | 15.000 |
| 256 | HCV 3a | 44 | 15 | 10 | B_3501 | SSQTeRIWLM | 6594 | 10.000 |
| 257 | HCV 3a | 45 | 7 | 9 | A_0201 | FTLDARSFT | 6595 | 39.723 |
| 258 | HCV 3a | 45 | 1 | 9 | A_0201 | MVSMRAFTL | 6596 | 18.430 |
| 259 | HCV 3a | 45 | 13 | 9 | A24 | SFTSFNTVL | 6597 | 20.000 |
| 260 | HCV 3a | 45 | 6 | 9 | A24 | AFTLDARSF | 6598 | 10.000 |
| 261 | HCV 3a | 45 | 1 | 9 | B7 | MVSMRAFTL | 6599 | 20.000 |
| 262 | HCV 3a | 45 | 9 | 9 | B_4403 | LDARSFTSF | 6600 | 15.000 |
| 263 | HCV 3a | 45 | 12 | 10 | B_3501 | RSFTsFNTVL | 6601 | 10.000 |
| 264 | HCV 3a | 46 | 35 | 9 | A1 | TVDQESQLK | 6602 | 10.000 |
| 265 | HCV 3a | 46 | 27 | 9 | A_0201 | TLCSSLSLT | 6603 | 17.140 |
| 266 | HCV 3a | 46 | 101 | 9 | B7 | SARNAADTL | 6604 | 120.000 |
| 267 | HCV 3a | 46 | 64 | 9 | B7 | SPPGEGGTL | 6605 | 80.000 |
| 268 | HCV 3a | 46 | 78 | 9 | B7 | CVSTPEEEL | 6606 | 30.000 |
| 269 | HCV 3a | 46 | 101 | 9 | B8 | SARNAADTL | 6607 | 16.000 |
| 270 | HCV 3a | 46 | 64 | 9 | B_3501 | SPPGEGGTL | 6608 | 30.000 |
| 271 | HCV 3a | 46 | 84 | 9 | B_4403 | EELFSSCGF | 6609 | 80.000 |
| 272 | HCV 3a | 46 | 56 | 9 | B_4403 | DEHDSESDS | 6610 | 12.000 |
| 273 | HCV 3a | 46 | 8 | 10 | A_0201 | ALHGvIRAPV | 6611 | 69.552 |
| 274 | HCV 3a | 46 | 27 | 10 | A_0201 | TLCSsLSLTV | 6612 | 69.552 |
| 275 | HCV 3a | 46 | 33 | 10 | A_0201 | SLTVdQESQL | 6613 | 21.362 |
| 276 | HCV 3a | 46 | 70 | 10 | A_0201 | GTLEvVLDCV | 6614 | 16.515 |
| 277 | HCV 3a | 46 | 19 | 10 | A24 | EYDIeQQTTL | 6615 | 200.000 |
| 278 | HCV 3a | 46 | 46 | 10 | B7 | SPGSpSRGGM | 6616 | 30.000 |
| 279 | HCV 3a | 46 | 100 | 10 | B7 | ASARnAADTL | 6617 | 12.000 |
| 280 | HCV 3a | 46 | 46 | 10 | B_3501 | SPGSpSRGGM | 6618 | 40.000 |
| 281 | HCV 3a | 46 | 83 | 10 | B_4403 | EEELfSSCGF | 6619 | 40.000 |
| 282 | HCV 3a | 47 | 2 | 10 | A3 | LLPIsCRHNK | 6620 | 20.000 |
| 283 | HCV 3a | 47 | 3 | 10 | B7 | LPIScRHNKL | 6621 | 80.000 |
| 284 | HCV 3a | 47 | 6 | 10 | B8 | SCRHnKLAFT | 6622 | 16.000 |
| 285 | HCV 3a | 47 | 3 | 10 | B8 | LPIScRHNKL | 6623 | 16.000 |
| 286 | HCV 3a | 47 | 3 | 10 | B_3501 | LPIScRHNKL | 6624 | 20.000 |
| 287 | HCV 3a | 48 | 11 | 9 | B7 | HVRGPASRM | 6625 | 75.000 |
| 288 | HCV 3a | 48 | 14 | 9 | B_3501 | GPASRMDPF | 6626 | 20.000 |
| 289 | HCV 3a | 48 | 3 | 10 | A_0201 | KVPChMLAHV | 6627 | 48.991 |
| 290 | HCV 3a | 48 | 14 | 10 | B_3501 | GPASrMDPFF | 6628 | 20.000 |
| 291 | HCV 3a | 49 | 10 | 9 | A_0201 | IILAESHDL | 6629 | 18.476 |
| 292 | HCV 3a | 49 | 29 | 9 | A_0201 | QMIRSQSSL | 6630 | 15.428 |
| 293 | HCV 3a | 49 | 32 | 9 | A24 | RSQSSLQGL | 6631 | 14.400 |
| 294 | HCV 3a | 49 | 11 | 9 | A3 | ILAESHDLK | 6632 | 30.000 |
| 295 | HCV 3a | 49 | 4 | 9 | B7 | SPGSAGIIL | 6633 | 80.000 |
| 296 | HCV 3a | 49 | 4 | 9 | B_3501 | SPGSAGIIL | 6634 | 20.000 |
| 297 | HCV 3a | 49 | 32 | 9 | B_3501 | RSQSSLQGL | 6635 | 10.000 |
| 298 | HCV 3a | 49 | 28 | 10 | B7 | SQMIrSQSSL | 6636 | 12.000 |
| 299 | HCV 3a | 50 | 123 | 9 | A1 | VTEAVNAIR | 6637 | 45.000 |
| 300 | HCV 3a | 50 | 104 | 9 | A1 | ATHPPSMLK | 6638 | 25.000 |
| 301 | HCV 3a | 50 | 47 | 9 | A1 | GSSPPMILK | 6639 | 15.000 |
| 302 | HCV 3a | 50 | 109 | 9 | A_0201 | SMLKNIVWL | 6640 | 722.126 |
| 303 | HCV 3a | 50 | 95 | 9 | A_0201 | ELWGPAKWV | 6641 | 238.129 |
| 304 | HCV 3a | 50 | 110 | 9 | A_0201 | MLKNIVWLV | 6642 | 71.386 |
| 305 | HCV 3a | 50 | 148 | 9 | A_0201 | WIPLTKFHI | 6643 | 38.273 |
| 306 | HCV 3a | 50 | 122 | 9 | A_0201 | LVTEAVNAI | 6644 | 14.634 |
| 307 | HCV 3a | 50 | 116 | 9 | A_0201 | WLVVRGLVT | 6645 | 14.054 |
| 308 | HCV 3a | 50 | 161 | 9 | A_0201 | KASSFCQLV | 6646 | 12.848 |
| 309 | HCV 3a | 50 | 19 | 9 | A_0201 | SMAAHITPT | 6647 | 12.379 |
| 310 | HCV 3a | 50 | 114 | 9 | A_0201 | IVWLVVRGL | 6648 | 12.132 |
| 311 | HCV 3a | 50 | 74 | 9 | A_0201 | TLPRPIPPM | 6649 | 11.426 |
| 312 | HCV 3a | 50 | 174 | 9 | A_0201 | SMTACCWVA | 6650 | 11.033 |
| 313 | HCV 3a | 50 | 188 | 9 | A_0201 | RTFSLNWWA | 6651 | 10.531 |
| 314 | HCV 3a | 50 | 146 | 9 | A24 | RYWIPLTKF | 6652 | 220.000 |
| 315 | HCV 3a | 50 | 129 | 9 | B7 | AIRDATAGL | 6653 | 120.000 |
| 316 | HCV 3a | 50 | 143 | 9 | B7 | RPARYWIPL | 6654 | 80.000 |
| 317 | HCV 3a | 50 | 62 | 9 | B7 | TPAPYPARM | 6655 | 20.000 |
| 318 | HCV 3a | 50 | 75 | 9 | B7 | LPRPIPPMA | 6656 | 20.000 |
| 319 | HCV 3a | 50 | 114 | 9 | B7 | IVWLVVRGL | 6657 | 20.000 |
| 320 | HCV 3a | 50 | 103 | 9 | B7 | VATHPPSML | 6658 | 18.000 |
| 321 | HCV 3a | 50 | 27 | 9 | B7 | TTRAPGDSM | 6659 | 15.000 |
| 322 | HCV 3a | 50 | 67 | 9 | B7 | PARMSSKTL | 6660 | 12.000 |

TABLE 4j-continued 3a (4-6)

| No. | Strain | ORF | Start | AA | HLA | Peptide sequence | SEQ ID NO: | Score |
|---|---|---|---|---|---|---|---|---|
| 323 | HCV 3a | 50 | 143 | 9 | B_3501 | RPARYWIPL | 6661 | 40.000 |
| 324 | HCV 3a | 50 | 62 | 9 | B_3501 | TPAPYPARM | 6662 | 40.000 |
| 325 | HCV 3a | 50 | 186 | 9 | B_3501 | NPRTFSLNW | 6663 | 30.000 |
| 326 | HCV 3a | 50 | 58 | 9 | B_3501 | KAPETPAPY | 6664 | 24.000 |
| 327 | HCV 3a | 50 | 94 | 9 | B_4403 | EELWGPAKW | 6665 | 36.000 |
| 328 | HCV 3a | 50 | 141 | 9 | B_4403 | VERPARYWI | 6666 | 12.000 |
| 329 | HCV 3a | 50 | 109 | 10 | A_0201 | SMLKnIVWLV | 6667 | 3.206.057 |
| 330 | HCV 3a | 50 | 157 | 10 | A_0201 | CLCQkASSFC | 6668 | 27.324 |
| 331 | HCV 3a | 50 | 121 | 10 | A_0201 | GLVTeAVNAI | 6669 | 23.995 |
| 332 | HCV 3a | 50 | 114 | 10 | A_0201 | IVWLvVRGLV | 6670 | 11.163 |
| 333 | HCV 3a | 50 | 87 | 10 | A24 | KPLTtNAEEL | 6671 | 13.200 |
| 334 | HCV 3a | 50 | 45 | 10 | B7 | AVGSsPPMIL | 6672 | 90.000 |
| 335 | HCV 3a | 50 | 66 | 10 | B7 | YPARmSSKTL | 6673 | 80.000 |
| 336 | HCV 3a | 50 | 87 | 10 | B7 | KPLTtNAEEL | 6674 | 80.000 |
| 337 | HCV 3a | 50 | 149 | 10 | B7 | IPLTkFHICL | 6675 | 80.000 |
| 338 | HCV 3a | 50 | 80 | 10 | B7 | PPMAaPAKPL | 6676 | 36.000 |
| 339 | HCV 3a | 50 | 75 | 10 | B7 | LPRPiPPMAA | 6677 | 30.000 |
| 340 | HCV 3a | 50 | 102 | 10 | B7 | WVAThPPSML | 6678 | 30.000 |
| 341 | HCV 3a | 50 | 11 | 10 | B7 | SPGPtCRRSM | 6679 | 30.000 |
| 342 | HCV 3a | 50 | 128 | 10 | B7 | NAIRdATAGL | 6680 | 12.000 |
| 343 | HCV 3a | 50 | 118 | 10 | B7 | VVRGlVTEAV | 6681 | 10.000 |
| 344 | HCV 3a | 50 | 11 | 10 | B_3501 | SPGPtCRRSM | 6682 | 40.000 |
| 345 | HCV 3a | 50 | 87 | 10 | B_3501 | KPLTtNAEEL | 6683 | 40.000 |
| 346 | HCV 3a | 50 | 186 | 10 | B_3501 | NPRTfSLNWW | 6684 | 30.000 |
| 347 | HCV 3a | 50 | 149 | 10 | B_3501 | IPLTkFHICL | 6685 | 20.000 |
| 348 | HCV 3a | 50 | 66 | 10 | B_3501 | YPARmSSKTL | 6686 | 20.000 |
| 349 | HCV 3a | 50 | 163 | 10 | B_3501 | SSFCqLVATM | 6687 | 10.000 |
| 350 | HCV 3a | 50 | 33 | 10 | B_3501 | DSMAgNRLTM | 6688 | 10.000 |
| 351 | HCV 3a | 50 | 43 | 10 | B_3501 | SSAVgSSPPM | 6689 | 10.000 |
| 352 | HCV 3a | 50 | 93 | 10 | B_4403 | AEELwGPAKW | 6690 | 36.000 |
| 353 | HCV 3a | 50 | 94 | 10 | B_4403 | EELWgPAKWV | 6691 | 18.000 |
| 354 | HCV 3a | 50 | 124 | 10 | B_4403 | TEAVnAIRDA | 6692 | 12.000 |
| 355 | HCV 3a | 51 | 6 | 9 | B_4403 | CEHSSISSY | 6693 | 120.000 |
| 356 | HCV 3a | 51 | 5 | 10 | A1 | ACEHsSISSY | 6694 | 45.000 |
| 357 | HCV 3a | 52 | 3 | 9 | A_0201 | AMTYFVMGC | 6695 | 31.359 |
| 358 | HCV 3a | 52 | 7 | 9 | A_0201 | FVMGCDKQI | 6696 | 15.537 |
| 359 | HCV 3a | 52 | 23 | 9 | A24 | RYKRGVGPC | 6697 | 10.000 |
| 360 | HCV 3a | 52 | 27 | 9 | B7 | GVGPCSVGL | 6698 | 20.000 |
| 361 | HCV 3a | 52 | 35 | 9 | B8 | LSRTRHFHV | 6699 | 12.000 |
| 362 | HCV 3a | 52 | 34 | 10 | A_0201 | GLSRtRHFHV | 6700 | 403.402 |
| 363 | HCV 3a | 52 | 23 | 10 | A24 | RYKRgVGPCS | 6701 | 14.000 |
| 364 | HCV 3a | 52 | 26 | 10 | A24 | RGVGpCSVGL | 6702 | 12.000 |
| 365 | HCV 3a | 52 | 15 | 10 | B_3501 | ISFWtGPNRY | 6703 | 10.000 |
| 366 | HCV 3a | 53 | 21 | 9 | A1 | MTESKSPVY | 6704 | 225.000 |
| 367 | HCV 3a | 53 | 20 | 9 | A_0201 | SMTESKSPV | 6705 | 205.951 |
| 368 | HCV 3a | 53 | 46 | 9 | A_0201 | GMTDTSRPL | 6706 | 12.651 |
| 369 | HCV 3a | 53 | 17 | 9 | A3 | TLQSMTESK | 6707 | 20.000 |
| 370 | HCV 3a | 53 | 13 | 9 | B_3501 | CSTATLQSM | 6708 | 10.000 |
| 371 | HCV 3a | 53 | 45 | 10 | B7 | VGMTdTSRPL | 6709 | 12.000 |
| 372 | HCV 3a | 53 | 23 | 10 | B_3501 | ESKSpVYPVM | 6710 | 30.000 |
| 373 | HCV 3a | 53 | 9 | 10 | B_3501 | KSTYcSTATL | 6711 | 10.000 |
| 374 | HCV 3a | 53 | 22 | 10 | B_4403 | TESKsPVYPV | 6712 | 12.000 |
| 375 | HCV 3a | 54 | 7 | 9 | A_0201 | VMLPGGVRV | 6713 | 315.959 |
| 376 | HCV 3a | 54 | 6 | 10 | A_0201 | TVMLpGGVRV | 6714 | 22.517 |
| 377 | HCV 3a | 54 | 8 | 10 | A3 | MLPGgVRVAK | 6715 | 45.000 |
| 378 | HCV 3a | 54 | 12 | 10 | B7 | GVRVaKTVSL | 6716 | 200.000 |
| 379 | HCV 3a | 54 | 12 | 10 | B8 | GVRVaKTVSL | 6717 | 80.000 |
| 380 | HCV 3a | 55 | 12 | 9 | B_4403 | DGFSTRTVY | 6718 | 13.500 |
| 381 | HCV 3a | 55 | 5 | 10 | B_3501 | KPSVaATDGF | 6719 | 40.000 |
| 382 | HCV 3a | 55 | 11 | 10 | B_4403 | TDGFsTRTVY | 6720 | 22.500 |
| 383 | HCV 3a | 55 | 2 | 10 | B_4403 | KEPKpSVAAT | 6721 | 12.000 |
| 384 | HCV 3a | 56 | 40 | 9 | A_0201 | GLGLSKLAV | 6722 | 69.552 |
| 385 | HCV 3a | 56 | 65 | 9 | A24 | KYKSAEPQA | 6723 | 10.000 |
| 386 | HCV 3a | 56 | 45 | 9 | A3 | KLAVESPLR | 6724 | 12.000 |
| 387 | HCV 3a | 56 | 33 | 9 | B7 | EPLRQARGL | 6725 | 80.000 |
| 388 | HCV 3a | 56 | 8 | 9 | B7 | TPLVHTAAL | 6726 | 80.000 |
| 389 | HCV 3a | 56 | 2 | 9 | B7 | NCRAFATPL | 6727 | 40.000 |
| 390 | HCV 3a | 56 | 2 | 9 | B8 | NCRAFATPL | 6728 | 16.000 |
| 391 | HCV 3a | 56 | 8 | 9 | B_3501 | TPLVHTAAL | 6729 | 20.000 |
| 392 | HCV 3a | 56 | 33 | 9 | B_3501 | EPLRQARGL | 6730 | 20.000 |
| 393 | HCV 3a | 56 | 58 | 9 | B_3501 | TSASRVTKY | 6731 | 10.000 |
| 394 | HCV 3a | 56 | 49 | 9 | B_3501 | ESPLRRAGM | 6732 | 10.000 |
| 395 | HCV 3a | 56 | 58 | 9 | B_4403 | TSASRVTKY | 6733 | 40.500 |
| 396 | HCV 3a | 56 | 68 | 10 | A1 | SAEPqAHGSR | 6734 | 90.000 |
| 397 | HCV 3a | 56 | 56 | 10 | A3 | GMTSaSRVTK | 6735 | 60.000 |

TABLE 4j-continued 3a (4-6)

| No. | Strain | ORF | Start | AA | HLA | Peptide sequence | SEQ ID NO: | Score |
|---|---|---|---|---|---|---|---|---|
| 398 | HCV 3a | 56 | 45 | 10 | A3 | KLAVeSPLRR | 6736 | 24.000 |
| 399 | HCV 3a | 56 | 37 | 10 | B7 | QARGlGLSKL | 6737 | 120.000 |
| 400 | HCV 3a | 56 | 70 | 10 | B7 | EPQAhGSRDL | 6738 | 80.000 |
| 401 | HCV 3a | 56 | 7 | 10 | B7 | ATPLvHTAAL | 6739 | 12.000 |
| 402 | HCV 3a | 56 | 18 | 10 | B7 | IPATcPEGHI | 6740 | 12.000 |
| 403 | HCV 3a | 56 | 37 | 10 | B8 | QARGLGLSKL | 6741 | 16.000 |
| 404 | HCV 3a | 56 | 34 | 10 | B8 | PLRQaRGLGL | 6742 | 16.000 |
| 405 | HCV 3a | 56 | 70 | 10 | B_3501 | EPQAhGSRDL | 6743 | 20.000 |
| 406 | HCV 3a | 56 | 43 | 10 | B_3501 | LSKLaVESPL | 6744 | 15.000 |
| 407 | HCV 3a | 56 | 57 | 10 | B_4403 | MTSAsRVTKY | 6745 | 20.250 |
| 408 | HCV 3a | 57 | 2 | 9 | A_0201 | TLISMGLNI | 6746 | 10.433 |
| 409 | HCV 3a | 57 | 21 | 9 | B_3501 | RPAAAQCCI | 6747 | 16.000 |
| 410 | HCV 3a | 57 | 27 | 9 | B_4403 | CCIGARWSY | 6748 | 33.750 |
| 411 | HCV 3a | 57 | 16 | 10 | B8 | TARSLRPAAA | 6749 | 16.000 |
| 412 | HCV 3a | 58 | 13 | 9 | A1 | ITERTSMQR | 6750 | 11.250 |
| 413 | HCV 3a | 58 | 5 | 9 | A_0201 | IIWKYFPPI | 6751 | 38.458 |
| 414 | HCV 3a | 58 | 1 | 9 | A3 | MLSMIIWKY | 6752 | 27.000 |
| 415 | HCV 3a | 58 | 5 | 10 | A_0201 | IIWKyFPPIT | 6753 | 22.525 |
| 416 | HCV 3a | 58 | 8 | 10 | A24 | KYFPpITERT | 6754 | 16.800 |
| 417 | HCV 3a | 58 | 10 | 10 | B7 | FPPItERTSM | 6755 | 30.000 |
| 418 | HCV 3a | 58 | 10 | 10 | B_3501 | FPPItERTSM | 6756 | 60.000 |
| 419 | HCV 3a | 59 | 52 | 9 | A24 | KTPAPRVAL | 6757 | 12.000 |
| 420 | HCV 3a | 59 | 38 | 9 | A3 | CLYQGDKVK | 6758 | 50.000 |
| 421 | HCV 3a | 59 | 31 | 9 | B7 | HIRRPIQCL | 6759 | 60.000 |
| 422 | HCV 3a | 59 | 6 | 9 | B7 | LPRASKGGT | 6760 | 20.000 |
| 423 | HCV 3a | 59 | 47 | 9 | B_3501 | KPKRAKTPA | 6761 | 12.000 |
| 424 | HCV 3a | 59 | 19 | 9 | B_4403 | ADSHLHMVY | 6762 | 30.000 |
| 425 | HCV 3a | 59 | 18 | 10 | A1 | RADShLHMVY | 6763 | 125.000 |
| 426 | HCV 3a | 59 | 59 | 10 | A_0201 | ALSSpDHAYA | 6764 | 27.324 |
| 427 | HCV 3a | 59 | 38 | 10 | A3 | CLYQgDKVKK | 6765 | 100.000 |
| 428 | HCV 3a | 59 | 24 | 10 | A3 | HMVYwFHHIR | 6766 | 18.000 |
| 429 | HCV 3a | 59 | 77 | 10 | B7 | KARGqRPVRL | 6767 | 120.000 |
| 430 | HCV 3a | 59 | 77 | 10 | B8 | KARGqRPVRL | 6768 | 160.000 |
| 431 | HCV 3a | 59 | 77 | 10 | B_3501 | KARGqRPVRL | 6769 | 18.000 |
| 432 | HCV 3a | 60 | 2 | 9 | A_0201 | RMTNSHFSA | 6770 | 20.810 |
| 433 | HCV 3a | 60 | 5 | 10 | B_3501 | NSHFsAHPTM | 6771 | 10.000 |
| 434 | HCV 3a | 61 | 68 | 9 | A_0201 | TLNNVKLTV | 6772 | 69.552 |
| 435 | HCV 3a | 61 | 66 | 9 | A_0201 | ILTLNNVKL | 6773 | 36.316 |
| 436 | HCV 3a | 61 | 51 | 9 | A_0201 | QLQAAVNRC | 6774 | 11.426 |
| 437 | HCV 3a | 61 | 61 | 9 | B7 | NPPTNILTL | 6775 | 80.000 |
| 438 | HCV 3a | 61 | 44 | 9 | B7 | SQRSPLVQL | 6776 | 60.000 |
| 439 | HCV 3a | 61 | 61 | 9 | B_3501 | NPPTNILTL | 6777 | 20.000 |
| 440 | HCV 3a | 61 | 66 | 10 | A_0201 | ILTLnNVKLT | 6778 | 29.137 |
| 441 | HCV 3a | 61 | 65 | 10 | A_0201 | NILTINNVKL | 6779 | 10.868 |
| 442 | HCV 3a | 61 | 6 | 10 | B7 | CIRPvDSAGM | 6780 | 10.000 |
| 443 | HCV 3a | 61 | 8 | 10 | B_3501 | RPVDsAGMGV | 6781 | 16.000 |
| 444 | HCV 3a | 61 | 40 | 10 | B_3501 | RSSIsQRSPL | 6782 | 10.000 |
| 445 | HCV 3a | 62 | 14 | 9 | A24 | LYVASGCFL | 6783 | 300.000 |
| 446 | HCV 3a | 62 | 21 | 9 | A3 | FLKQSVGQK | 6784 | 18.000 |
| 447 | HCV 3a | 62 | 13 | 10 | A_0201 | RLYVaSGCFL | 6785 | 375.978 |
| 448 | HCV 3a | 63 | 9 | 9 | A_0201 | VLTNPVEFI | 6786 | 109.935 |
| 449 | HCV 3a | 63 | 6 | 9 | B7 | APHVLTNPV | 6787 | 12.000 |
| 450 | HCV 3a | 63 | 32 | 9 | B_3501 | SSRNTSVSF | 6788 | 15.000 |
| 451 | HCV 3a | 63 | 4 | 9 | B_4403 | GEAPHVLTN | 6789 | 14.400 |
| 452 | HCV 3a | 64 | 15 | 9 | A_0201 | VMGLQLLSL | 6790 | 60.325 |
| 453 | HCV 3a | 64 | 4 | 9 | B7 | SVKGPHPCL | 6791 | 30.000 |
| 454 | HCV 3a | 64 | 14 | 10 | A_0201 | KVMGLQLLSL | 6792 | 55.674 |
| 455 | HCV 3a | 64 | 14 | 10 | A24 | KVMGLQLLSL | 6793 | 12.000 |
| 456 | HCV 3a | 64 | 9 | 10 | B7 | HPCLkKVMGL | 6794 | 80.000 |
| 457 | HCV 3a | 64 | 14 | 10 | B7 | KVMGlQLLSL | 6795 | 60.000 |
| 458 | HCV 3a | 64 | 7 | 10 | B7 | GPHPcLKKVM | 6796 | 20.000 |
| 459 | HCV 3a | 64 | 3 | 10 | B7 | ASVKgPHPCL | 6797 | 18.000 |
| 460 | HCV 3a | 64 | 9 | 10 | B8 | HPCLkKVMGL | 6798 | 16.000 |
| 461 | HCV 3a | 64 | 7 | 10 | B_3501 | GPHPcLKKVM | 6799 | 40.000 |
| 462 | HCV 3a | 64 | 9 | 10 | B_3501 | HPCLkKVMGL | 6800 | 20.000 |
| 463 | HCV 3a | 65 | 15 | 9 | A_0201 | LLMCHEPLV | 6801 | 437.482 |
| 464 | HCV 3a | 65 | 14 | 9 | A_0201 | VLLMCHEPL | 6802 | 65.841 |
| 465 | HCV 3a | 65 | 5 | 9 | A_0201 | FMDSLQFRA | 6803 | 38.291 |
| 466 | HCV 3a | 65 | 8 | 9 | A_0201 | SLQFRAVLL | 6804 | 21.362 |
| 467 | HCV 3a | 65 | 22 | 9 | A_0201 | LVLTSCSFC | 6805 | 15.038 |
| 468 | HCV 3a | 65 | 16 | 9 | A_0201 | LMCHEPLVL | 6806 | 10.754 |
| 469 | HCV 3a | 65 | 19 | 9 | B_4403 | HEPLVLTSC | 6807 | 13.500 |
| 470 | HCV 3a | 65 | 14 | 10 | A_0201 | VLLMcHEPLV | 6808 | 437.482 |
| 471 | HCV 3a | 65 | 23 | 10 | A_0201 | VLTScSFCWA | 6809 | 88.257 |
| 472 | HCV 3a | 65 | 15 | 10 | A_0201 | LLMChEPLVL | 6810 | 55.091 |

TABLE 4j-continued

| | | | | 3a (4-6) | | | |
|---|---|---|---|---|---|---|---|
| No. Strain | ORF | Start | AA | HLA | Peptide sequence | SEQ ID NO: | Score |
| 473 HCV 3a | 65 | 5 | 10 | A_0201 | FMDSlQFRAV | 6811 | 35.122 |
| 474 HCV 3a | 65 | 16 | 10 | A_0201 | LMCHePLVLT | 6812 | 21.044 |
| 475 HCV 3a | 65 | 29 | 10 | A_0201 | FCWApTLKRL | 6813 | 12.246 |
| 476 HCV 3a | 65 | 8 | 10 | A_0201 | SLQFrAVLLM | 6814 | 11.426 |
| 477 HCV 3a | 65 | 13 | 10 | B7 | AVLLmCHEPL | 6815 | 60.000 |
| 478 HCV 3a | 65 | 15 | 10 | B7 | LLMChEPLVL | 6816 | 12.000 |
| 479 HCV 3a | 65 | 2 | 10 | B_3501 | NPVFmDSLQF | 6817 | 30.000 |
| 480 HCV 3a | 65 | 20 | 10 | B_3501 | EPLVLTSCSF | 6818 | 20.000 |
| 481 HCV 3a | 66 | 1 | 9 | A_0201 | MMIATLAQL | 6819 | 60.325 |
| 482 HCV 3a | 67 | 8 | 9 | A_0201 | IMSNKVWGT | 6820 | 157.827 |
| 483 HCV 3a | 67 | 48 | 9 | A_0201 | SEQLQVWTV | 6821 | 23.329 |
| 484 HCV 3a | 67 | 30 | 9 | A24 | QFIIISQAI | 6822 | 12.600 |
| 485 HCV 3a | 67 | 43 | 9 | A24 | RWPGYSEQL | 6823 | 12.000 |
| 486 HCV 3a | 67 | 24 | 9 | B7 | IPRAGNQFI | 6824 | 80.000 |
| 487 HCV 3a | 67 | 1 | 9 | B7 | MPQWAPAIM | 6825 | 20.000 |
| 488 HCV 3a | 67 | 5 | 9 | B7 | APAIMSNKV | 6826 | 12.000 |
| 489 HCV 3a | 67 | 1 | 9 | B_3501 | MPQWAPAIM | 6827 | 40.000 |
| 490 HCV 3a | 67 | 24 | 9 | B_3501 | IPRAGNQFI | 6828 | 24.000 |
| 491 HCV 3a | 67 | 48 | 9 | B_4403 | SEQLQVWTV | 6829 | 24.000 |
| 492 HCV 3a | 67 | 7 | 10 | A_0201 | AIMSnKVWGT | 6830 | 65.398 |
| 493 HCV 3a | 67 | 55 | 10 | A_0201 | TVWWrRGLNV | 6831 | 50.512 |
| 494 HCV 3a | 67 | 12 | 10 | A_0201 | KVWGtRRTCA | 6832 | 12.628 |
| 495 HCV 3a | 67 | 50 | 10 | A3 | QLQVwTVWWR | 6833 | 36.000 |
| 496 HCV 3a | 67 | 61 | 10 | A3 | GLNVkACPTR | 6834 | 12.000 |
| 497 HCV 3a | 67 | 24 | 10 | B7 | IPRAgNQFII | 6835 | 80.000 |
| 498 HCV 3a | 67 | 24 | 10 | B_3501 | IPRAgNQFII | 6836 | 24.000 |
| 499 HCV 3a | 67 | 5 | 10 | B_3501 | APAImSNKVW | 6837 | 10.000 |
| 500 HCV 3a | 67 | 48 | 10 | B_4403 | SEQLqVWTVW | 6838 | 54.000 |
| 501 HCV 3a | 67 | 22 | 10 | B_4403 | TAIPrAGNQF | 6839 | 15.000 |
| 502 HCV 3a | 68 | 9 | 9 | A_0201 | ILLLEQSLV | 6840 | 437.482 |
| 503 HCV 3a | 68 | 8 | 9 | A_0201 | TILLLEQSL | 6841 | 10.868 |
| 504 HCV 3a | 68 | 10 | 9 | A3 | LLLEQSLVR | 6842 | 18.000 |
| 505 HCV 3a | 68 | 4 | 9 | B7 | SASYTILLL | 6843 | 12.000 |
| 506 HCV 3a | 68 | 10 | 10 | A_0201 | LLLEqSLVRT | 6844 | 442.013 |
| 507 HCV 3a | 68 | 8 | 10 | A_0201 | TILLLEQSLV | 6845 | 35.385 |
| 508 HCV 3a | 68 | 9 | 10 | A3 | ILLLeQSLVR | 6846 | 12.000 |
| 509 HCV 3a | 69 | 42 | 9 | B7 | HPAHPQPSL | 6847 | 120.000 |
| 510 HCV 3a | 69 | 12 | 9 | B7 | RVSMTLPKL | 6848 | 20.000 |
| 511 HCV 3a | 69 | 42 | 9 | B_3501 | HPAHPQPSL | 6849 | 20.000 |
| 512 HCV 3a | 69 | 8 | 10 | B7 | NPHVrVSMTL | 6850 | 80.000 |
| 513 HCV 3a | 69 | 35 | 10 | B7 | EPRGdRSHPA | 6851 | 20.000 |
| 514 HCV 3a | 69 | 2 | 10 | B7 | YPMRsANPHV | 6852 | 12.000 |
| 515 HCV 3a | 69 | 35 | 10 | B8 | EPRGdRSHPA | 6853 | 32.000 |
| 516 HCV 3a | 69 | 8 | 10 | B_3501 | NPHVrVSMTL | 6854 | 20.000 |
| 517 HCV 3a | 69 | 19 | 10 | B_3501 | KLRDLRRGSF | 6855 | 12.000 |
| 518 HCV 3a | 70 | 3 | 9 | A_0201 | FLLVFLCGL | 6856 | 3.177.760 |
| 519 HCV 3a | 70 | 15 | 9 | A_0201 | LMLHGLRDL | 6857 | 44.641 |
| 520 HCV 3a | 70 | 7 | 9 | A_0201 | FLCGLGSVL | 6858 | 40.289 |
| 521 HCV 3a | 70 | 1 | 9 | A_0201 | MVFLLVFLC | 6859 | 36.475 |
| 522 HCV 3a | 70 | 30 | 9 | A24 | PYQAVPQGL | 6860 | 50.400 |
| 523 HCV 3a | 70 | 37 | 9 | A3 | GLSRPNTTR | 6861 | 18.000 |
| 524 HCV 3a | 70 | 38 | 9 | B7 | LSRPNTTRL | 6862 | 40.000 |
| 525 HCV 3a | 70 | 40 | 9 | B7 | RPNTTRLVI | 6863 | 12.000 |
| 526 HCV 3a | 70 | 23 | 9 | B_3501 | LPGHSQAPY | 6864 | 40.000 |
| 527 HCV 3a | 70 | 40 | 9 | B_3501 | RPNTTRLVI | 6865 | 16.000 |
| 528 HCV 3a | 70 | 38 | 9 | B_3501 | LSRPNTTRL | 6866 | 15.000 |
| 529 HCV 3a | 70 | 14 | 10 | A_0201 | VLMLhGLRDL | 6867 | 61.810 |
| 530 HCV 3a | 70 | 7 | 10 | A_0201 | FLCGLGSVLM | 6868 | 22.853 |
| 531 HCV 3a | 70 | 37 | 10 | A_0201 | GLSRpNTTRL | 6869 | 21.362 |
| 532 HCV 3a | 70 | 5 | 10 | A_0201 | LVFLcGLGSV | 6870 | 11.446 |
| 533 HCV 3a | 70 | 6 | 10 | A24 | VFLCgLGSVL | 6871 | 36.000 |
| 534 HCV 3a | 70 | 2 | 10 | A24 | VFLLvFLCGL | 6872 | 30.000 |
| 535 HCV 3a | 70 | 29 | 10 | B7 | APYQaVPQGL | 6873 | 240.000 |
| 536 HCV 3a | 70 | 14 | 10 | B7 | VLMLhGLRDL | 6874 | 12.000 |
| 537 HCV 3a | 70 | 29 | 10 | B_3501 | APYQaVPQGL | 6875 | 20.000 |

TABLE 4k

3b (1-3)

| No. | Strain | ORF | Start | AA | HLA | Peptide sequence | SEQ ID NO: | Score |
|---|---|---|---|---|---|---|---|---|
| 1 | HCV 3b | 1 | 2 | 9 | A_0201 | ALVRVSCSL | 6876 | 21.36 |
| 2 | HCV 3b | 1 | 1 | 10 | B7 | MALVRVSCSL | 6877 | 12 |
| 3 | HCV 3b | 1 | 2 | 9 | B7 | ALVRVSCSL | 6878 | 12 |
| 4 | HCV 3b | 2 | 79 | 9 | A1 | GVDPATWVR | 6879 | 50 |
| 5 | HCV 3b | 2 | 79 | 10 | A1 | GVDPaTWVRS | 6880 | 10 |
| 6 | HCV 3b | 2 | 24 | 10 | A1 | LADGvSLPPR | 6881 | 10 |
| 7 | HCV 3b | 2 | 75 | 9 | A_0201 | KMTPGVDPA | 6882 | 14.15 |
| 8 | HCV 3b | 2 | 75 | 10 | A_0201 | KMTPgVDPAT | 6883 | 18.84 |
| 9 | HCV 3b | 2 | 68 | 10 | A_0201 | VLAPaGAKMT | 6884 | 12.67 |
| 10 | HCV 3b | 2 | 40 | 9 | B7 | GPGPSPGTL | 6885 | 80 |
| 11 | HCV 3b | 2 | 10 | 9 | B7 | WVCAKQVRL | 6886 | 20 |
| 12 | HCV 3b | 2 | 15 | 10 | B7 | QVRLpSDHNL | 6887 | 200 |
| 13 | HCV 3b | 2 | 40 | 9 | B_3501 | GPGPSPGTL | 6888 | 20 |
| 14 | HCV 3b | 2 | 77 | 9 | B_3501 | TPGVDPATW | 6889 | 15 |
| 15 | HCV 3b | 3 | 2 | 10 | A_0201 | RLAYiCLPTT | 6890 | 17.14 |
| 16 | HCV 3b | 3 | 8 | 10 | B7 | LPTTaPTGAL | 6891 | 120 |
| 17 | HCV 3b | 3 | 8 | 10 | B_3501 | LPTTaPTGAL | 6892 | 20 |
| 18 | HCV 3b | 4 | | | | no hits | | |
| 19 | HCV 3b | 5 | | | | no hits | | |
| 20 | HCV 3b | 6 | | | | no hits | | |
| 21 | HCV 3b | 7 | 8 | 10 | A_0201 | ALHPhRWWWA | 6893 | 348.38 |
| 22 | HCV 3b | 7 | 17 | 10 | B7 | APLIIKACQL | 6894 | 240 |
| 23 | HCV 3b | 7 | 10 | 10 | B7 | HPHRwWWAPL | 6895 | 80 |
| 24 | HCV 3b | 7 | 10 | 10 | B_3501 | HPHRwWWAPL | 6896 | 20 |
| 25 | HCV 3b | 7 | 17 | 10 | B_3501 | APLILKACQL | 6897 | 20 |
| 26 | HCV 3b | 8 | 5 | 10 | B7 | LPAAgPGPGL | 6898 | 120 |
| 27 | HCV 3b | 8 | 11 | 9 | B_3501 | GPGLRQGVW | 6899 | 10 |
| 28 | HCV 3b | 9 | 12 | 9 | A1 | RGESAVILK | 6900 | 22.5 |
| 29 | HCV 3b | 9 | 17 | 9 | A_0201 | VILKIVTAV | 6901 | 138.35 |
| 30 | HCV 3b | 9 | 16 | 10 | A_0201 | AVILKIVTAV | 6902 | 14 |
| 31 | HCV 3b | 9 | 10 | 10 | B7 | TGRGESAVIL | 6903 | 40 |
| 32 | HCV 3b | 10 | 50 | 9 | A_0201 | CLFEVVGTV | 6904 | 315.48 |
| 33 | HCV 3b | 10 | 45 | 10 | A_0201 | YGSPPCLFEV | 6905 | 27.86 |
| 34 | HCV 3b | 10 | 44 | 9 | A24 | KYGSPPCLF | 6906 | 200 |
| 35 | HCV 3b | 10 | 16 | 10 | A24 | PYHHGISTGL | 6907 | 28 |
| 36 | HCV 3b | 10 | 27 | 10 | A3 | VLSGGTSMPY | 6908 | 12 |
| 37 | HCV 3b | 10 | 26 | 9 | B7 | AVLSGGTSM | 6909 | 15 |
| 38 | HCV 3b | 10 | 28 | 10 | B_3501 | LSGGTSMPY | 6910 | 10 |
| 39 | HCV 3b | 10 | 8 | 10 | B_3501 | CSCSsGSLPY | 6911 | 10 |
| 40 | HCV 3b | 10 | 37 | 9 | B_4403 | AGVRPPCKY | 6912 | 18 |
| 41 | HCV 3b | 11 | 86 | 9 | A_0201 | KLGDYLELL | 6913 | 345.48 |
| 42 | HCV 3b | 11 | 26 | 9 | A_0201 | SLVLWRLRL | 6914 | 21.36 |
| 43 | HCV 3b | 11 | 55 | 10 | A_0201 | RGWAASCCWV | 6915 | 20.73 |
| 44 | HCV 3b | 11 | 79 | 9 | A24 | RSQHTPSKL | 6916 | 13.2 |
| 45 | HCV 3b | 11 | 19 | 9 | A24 | RWPRSPSSL | 6917 | 12 |
| 46 | HCV 3b | 11 | 89 | 9 | A24 | DYLELLSPA | 6918 | 10.8 |
| 47 | HCV 3b | 11 | 10 | 10 | A3 | GLPRVSKDWR | 6919 | 12 |
| 48 | HCV 3b | 11 | 83 | 9 | B7 | TPSKLGDYL | 6920 | 80 |
| 49 | HCV 3b | 11 | 20 | 9 | B7 | WPRSPSSLV | 6921 | 60 |
| 50 | HCV 3b | 11 | 58 | 9 | B7 | AASCCWVRL | 6922 | 36 |
| 51 | HCV 3b | 11 | 20 | 10 | B7 | WPRSPSSLVL | 6923 | 800 |
| 52 | HCV 3b | 11 | 23 | 10 | B7 | SPSSLVLWRL | 6924 | 80 |
| 53 | HCV 3b | 11 | 57 | 10 | B7 | WAASCCWVRL | 6925 | 12 |
| 54 | HCV 3b | 11 | 20 | 10 | B8 | WPRSPSSLVL | 6926 | 16 |
| 55 | HCV 3b | 11 | 83 | 9 | B_3501 | TPSKLGDYL | 6927 | 20 |
| 56 | HCV 3b | 11 | 20 | 9 | B_3501 | WPRSPSSLV | 6928 | 12 |
| 57 | HCV 3b | 11 | 79 | 9 | B_3501 | RSQHTPSKL | 6929 | 10 |
| 58 | HCV 3b | 11 | 20 | 10 | B_3501 | WPRSPSSLVL | 6930 | 60 |
| 59 | HCV 3b | 11 | 11 | 10 | B_3501 | LPRVSKDWRW | 6931 | 30 |
| 60 | HCV 3b | 11 | 23 | 10 | B_3501 | SPSSLVLWRL | 6932 | 20 |
| 61 | HCV 3b | 11 | 44 | 10 | B_4403 | AETSCAGCPF | 6933 | 120 |
| 62 | HCV 3b | 12 | 2 | 9 | A_0201 | VLGRGLLLV | 6934 | 271.95 |
| 63 | HCV 3b | 12 | 1 | 9 | A_0201 | MVLGRGLLL | 6935 | 11.76 |
| 64 | HCV 3b | 12 | 1 | 10 | A_0201 | MVLGRGLLLV | 6936 | 88.04 |
| 65 | HCV 3b | 12 | 2 | 10 | A_0201 | VLGRGLLLVT | 6937 | 11.95 |
| 66 | HCV 3b | 12 | 13 | 9 | B7 | GPRFKCTPM | 6938 | 200 |
| 67 | HCV 3b | 12 | 1 | 9 | B7 | MVLGRGLLL | 6939 | 20 |
| 68 | HCV 3b | 12 | 13 | 9 | B8 | GPRFKCTPM | 6940 | 80 |
| 69 | HCV 3b | 12 | 13 | 9 | B_3501 | GPRFKCTPM | 6941 | 120 |
| 70 | HCV 3b | 12 | 13 | 10 | B_3501 | GPRFKCTPMW | 6942 | 30 |
| 71 | HCV 3b | 13 | | | | no hits | | |
| 72 | HCV 3b | 14 | 22 | 10 | B7 | TPHTaSSSPM | 6943 | 20 |
| 73 | HCV 3b | 14 | 26 | 10 | B7 | ASSSpMGVVL | 6944 | 12 |
| 74 | HCV 3b | 14 | 22 | 10 | B_3501 | TPHTaSSSPM | 6945 | 40 |
| 75 | HCV 3b | 15 | | | | no hits | | |

TABLE 4k-continued 3b (1-3)

| No. | Strain | ORF | Start | AA | HLA | Peptide sequence | SEQ ID NO: | Score |
|---|---|---|---|---|---|---|---|---|
| 76 | HCV 3b | 16 | | | | no hits | | |
| 77 | HCV 3b | 17 | 5 | 9 | B7 | VPGMTYNLL | 6946 | 80 |
| 78 | HCV 3b | 17 | 4 | 9 | B7 | VVPGMTYNL | 6947 | 20 |
| 79 | HCV 3b | 17 | 4 | 10 | B7 | VVPGMTYNLL | 6948 | 20 |
| 80 | HCV 3b | 17 | 3 | 10 | B7 | QVVPGMTYNL | 6949 | 20 |
| 81 | HCV 3b | 17 | 5 | 9 | B_3501 | VPGMTYNLL | 6950 | 20 |
| 82 | HCV 3b | 18 | | | | no hits | | |
| 83 | HCV 3b | 19 | | | | no hits | | |
| 84 | HCV 3b | 20 | 11 | 9 | A_0201 | LLTSSKHRL | 6951 | 36.32 |
| 85 | HCV 3b | 20 | 10 | 10 | A_0201 | LLLTSSKHRL | 6952 | 134.37 |
| 86 | HCV 3b | 20 | 3 | 9 | A24 | RWKNVPSLL | 6953 | 11.2 |
| 87 | HCV 3b | 20 | 1 | 10 | B7 | MMRWKNVPSL | 6954 | 40 |
| 88 | HCV 3b | 20 | 31 | 10 | B8 | CCKGRANKKL | 6955 | 16 |
| 89 | HCV 3b | 21 | | | | no hits | | |
| 90 | HCV 3b | 22 | | | | no hits | | |
| 91 | HCV 3b | 23 | 26 | 9 | A_0201 | CQAYPFSHV | 6956 | 13.4 |
| 92 | HCV 3b | 23 | 9 | 10 | A24 | SYLVtLRPGF | 6957 | 180 |
| 93 | HCV 3b | 23 | 37 | 9 | B7 | GTREYGEGM | 6958 | 10 |
| 94 | HCV 3b | 23 | 19 | 10 | B7 | RPRScPRCQA | 6959 | 45 |
| 95 | HCV 3b | 23 | 23 | 9 | B_3501 | CPRCQAYPF | 6960 | 60 |
| 96 | HCV 3b | 23 | 21 | 9 | B_3501 | RSCPRCQAY | 6961 | 20 |
| 97 | HCV 3b | 23 | 37 | 9 | B_3501 | GTREYGEGM | 6962 | 12 |
| 98 | HCV 3b | 23 | 2 | 9 | B_3501 | TSGTGSVSY | 6963 | 10 |
| 99 | HCV 3b | 24 | 6 | 9 | A_0201 | SMNTPLGRV | 6964 | 15.02 |
| 100 | HCV 3b | 24 | 2 | 10 | B7 | APSPSMNTPL | 6965 | 240 |
| 101 | HCV 3b | 24 | 17 | 10 | B7 | SPRTITRVPC | 6966 | 30 |
| 102 | HCV 3b | 24 | 2 | 10 | B_3501 | APSPSMNTPL | 6967 | 20 |
| 103 | HCV 3b | 25 | 9 | 10 | A_0201 | ILITWWGPRT | 6968 | 12.67 |
| 104 | HCV 3b | 25 | 1 | 10 | B7 | MSRCVGWGIL | 6969 | 40 |
| 105 | HCV 3b | 25 | 1 | 10 | B_3501 | MSRCvGWGIL | 6970 | 15 |
| 106 | HCV 3b | 26 | | | | no hits | | |
| 107 | HCV 3b | 27 | 1 | 9 | A_0201 | MQMGPSFHA | 6971 | 18.38 |
| 108 | HCV 3b | 28 | 1 | 10 | B7 | MGRMcPRHSL | 6972 | 90 |
| 109 | HCV 3b | 29 | 1 | 9 | A_0201 | MLTLGPPSV | 6973 | 118.24 |
| 110 | HCV 3b | 29 | 18 | 9 | B7 | AVLCHTPGL | 6974 | 60 |
| 111 | HCV 3b | 29 | 12 | 9 | B7 | KSRAWFAVL | 6975 | 40 |
| 112 | HCV 3b | 29 | 17 | 10 | B7 | FAVLCHTPGL | 6976 | 12 |
| 113 | HCV 3b | 29 | 10 | 9 | B8 | TPKSRAWFA | 6977 | 16 |
| 114 | HCV 3b | 29 | 12 | 9 | B_3501 | KSRAWFAVL | 6978 | 30 |
| 115 | HCV 3b | 29 | 10 | 10 | B_3501 | TPKSRAWFAV | 6979 | 12 |
| 116 | HCV 3b | 30 | | | | no hits | | |
| 117 | HCV 3b | 31 | | | | no hits | | |
| 118 | HCV 3b | 32 | 50 | 10 | A_0201 | ALAAsCLPAL | 6980 | 49.13 |
| 119 | HCV 3b | 32 | 48 | 9 | B7 | AAALAASCL | 6981 | 36 |
| 120 | HCV 3b | 32 | 11 | 9 | B7 | NVVTLNQRL | 6982 | 20 |
| 121 | HCV 3b | 32 | 51 | 9 | B7 | LAASCLPAL | 6983 | 12 |
| 122 | HCV 3b | 32 | 43 | 9 | B7 | NAVIAAAAL | 6984 | 12 |
| 123 | HCV 3b | 32 | 16 | 10 | B7 | NQRLgRQSAL | 6985 | 40 |
| 124 | HCV 3b | 32 | 47 | 10 | B7 | AAAALAASCL | 6986 | 36 |
| 125 | HCV 3b | 32 | 50 | 10 | B7 | ALAASCLPAL | 6987 | 12 |
| 126 | HCV 3b | 32 | 16 | 10 | B8 | NQRLGRQSAL | 6988 | 24 |
| 127 | HCV 3b | 33 | | | | no hits | | |
| 128 | HCV 3b | 34 | 8 | 9 | B7 | TTRSMPGNL | 6989 | 40 |
| 129 | HCV 3b | 34 | 3 | 10 | B_3501 | GSFLGTTRSM | 6990 | 10 |
| 130 | HCV 3b | 35 | 4 | 9 | B7 | APPRFSPQL | 6991 | 240 |
| 131 | HCV 3b | 35 | 3 | 10 | B7 | LAPPRFSPQL | 6992 | 12 |
| 132 | HCV 3b | 35 | 4 | 9 | B_3501 | APPRFSPQL | 6993 | 20 |
| 133 | HCV 3b | 36 | 32 | 9 | A1 | RVDPKSCEY | 6994 | 250 |
| 134 | HCV 3b | 36 | 40 | 9 | A_0201 | YVGGPANAV | 6995 | 28 |
| 135 | HCV 3b | 36 | 60 | 10 | A24 | RVPCgTSVHL | 6996 | 12 |
| 136 | HCV 3b | 36 | 61 | 9 | B7 | VPCGTSVHL | 6997 | 80 |
| 137 | HCV 3b | 36 | 6 | 10 | B7 | RNRQQQHIVL | 6998 | 40 |
| 138 | HCV 3b | 36 | 40 | 10 | B7 | YVGGPANAVL | 6999 | 20 |
| 139 | HCV 3b | 36 | 60 | 10 | B7 | RVPCGTSVHL | 7000 | 20 |
| 140 | HCV 3b | 36 | 61 | 9 | B_3501 | VPCGTSVHL | 7001 | 20 |
| 141 | HCV 3b | 37 | 2 | 10 | A1 | CVDEqYRVCK | 7002 | 20 |
| 142 | HCV 3b | 37 | 12 | 10 | A_0201 | DLWGsPLQHL | 7003 | 30.59 |
| 143 | HCV 3b | 37 | 9 | 10 | B8 | VCKDlWGSPL | 7004 | 24 |
| 144 | HCV 3b | 37 | 4 | 10 | B_4403 | DEQYrVCKDL | 7005 | 27 |
| 145 | HCV 3b | 38 | | | | no hits | | |
| 146 | HCV 3b | 39 | 108 | 9 | A1 | SADNLWFDR | 7006 | 25 |
| 147 | HCV 3b | 39 | 2 | 9 | A_0201 | LIYTYAPPV | 7007 | 52.03 |
| 148 | HCV 3b | 39 | 151 | 9 | A_0201 | RVLYLITMV | 7008 | 51.79 |
| 149 | HCV 3b | 39 | 111 | 9 | A_0201 | NLWFDRPVA | 7009 | 16.91 |
| 150 | HCV 3b | 39 | 1 | 10 | A_0201 | MLIYtYAPPV | 7010 | 118.24 |

TABLE 4k-continued

3b (1-3)

| No. | Strain | ORF | Start | AA | HLA | Peptide sequence | SEQ ID NO: | Score |
|---|---|---|---|---|---|---|---|---|
| 151 | HCV 3b | 39 | 124 | 9 | A24 | RPPAPSACL | 7011 | 12 |
| 152 | HCV 3b | 39 | 80 | 10 | A24 | RPQRsGTTGL | 7012 | 12 |
| 153 | HCV 3b | 39 | 90 | 9 | A3 | RLVPGCILR | 7013 | 18 |
| 154 | HCV 3b | 39 | 35 | 9 | A3 | GLGSQVGVR | 7014 | 10.8 |
| 155 | HCV 3b | 39 | 90 | 10 | A3 | RLVPgCILRR | 7015 | 27 |
| 156 | HCV 3b | 39 | 35 | 10 | A3 | GLGSqVGVRR | 7016 | 18 |
| 157 | HCV 3b | 39 | 147 | 9 | B7 | APAPRVLYL | 7017 | 240 |
| 158 | HCV 3b | 39 | 124 | 9 | B7 | RPPAPSACL | 7018 | 120 |
| 159 | HCV 3b | 39 | 149 | 9 | B7 | APRVLYLIT | 7019 | 60 |
| 160 | HCV 3b | 39 | 39 | 9 | B7 | QVGVRRPRL | 7020 | 30 |
| 161 | HCV 3b | 39 | 92 | 9 | B7 | VPGCILRRM | 7021 | 20 |
| 162 | HCV 3b | 39 | 149 | 10 | B7 | APRVlYLITM | 7022 | 600 |
| 163 | HCV 3b | 39 | 80 | 10 | B7 | RPQRsGTTGL | 7023 | 80 |
| 164 | HCV 3b | 39 | 88 | 10 | B7 | GLRLvPGCIL | 7024 | 60 |
| 165 | HCV 3b | 39 | 51 | 10 | B7 | GGRTrVCGPL | 7025 | 40 |
| 166 | HCV 3b | 39 | 147 | 10 | B7 | APAPrVLYLI | 7026 | 24 |
| 167 | HCV 3b | 39 | 146 | 10 | B7 | GAPApRVLYL | 7027 | 12 |
| 168 | HCV 3b | 39 | 147 | 9 | B8 | APAPRVLYL | 7028 | 16 |
| 169 | HCV 3b | 39 | 19 | 9 | B8 | EHRGRAIPL | 7029 | 16 |
| 170 | HCV 3b | 39 | 146 | 10 | B8 | GAPApRVLYL | 7030 | 16 |
| 171 | HCV 3b | 39 | 58 | 9 | B_3501 | GPLDDVTDF | 7031 | 60 |
| 172 | HCV 3b | 39 | 92 | 9 | B_3501 | VPGCILRRM | 7032 | 40 |
| 173 | HCV 3b | 39 | 124 | 9 | B_3501 | RPPAPSACL | 7033 | 40 |
| 174 | HCV 3b | 39 | 147 | 9 | B_3501 | APAPRVLYL | 7034 | 20 |
| 175 | HCV 3b | 39 | 83 | 9 | B_3501 | RSGTTGLRL | 7035 | 10 |
| 176 | HCV 3b | 39 | 149 | 10 | B_3501 | APRVLYLITM | 7036 | 120 |
| 177 | HCV 3b | 39 | 80 | 10 | B_3501 | RPQRsGTTGL | 7037 | 40 |
| 178 | HCV 3b | 39 | 105 | 10 | B_3501 | EARSaDNLWF | 7038 | 13.5 |
| 179 | HCV 3b | 39 | 78 | 9 | B_4403 | AERPQRSGT | 7039 | 16 |
| 180 | HCV 3b | 39 | 104 | 9 | B_4403 | GEARSADNL | 7040 | 12 |
| 181 | HCV 3b | 39 | 23 | 9 | B_4403 | RAIPLWCWF | 7041 | 10 |
| 182 | HCV 3b | 39 | 104 | 10 | B_4403 | GEARsADNLW | 7042 | 36 |
| 183 | HCV 3b | 39 | 78 | 10 | B_4403 | AERPqRSGTT | 7043 | 16 |
| 184 | HCV 3b | 39 | 145 | 10 | B_4403 | RGAPaPRVLY | 7044 | 12 |
| 185 | HCV 3b | 40 | | | | no hits | | |
| 186 | HCV 3b | 41 | 2 | 9 | B7 | APTVPDLSI | 7045 | 36 |
| 187 | HCV 3b | 41 | 11 | 9 | B_3501 | RPANSGTIW | 7046 | 20 |
| 188 | HCV 3b | 42 | 3 | 10 | B_3501 | RARRYLHTGY | 7047 | 36 |
| 189 | HCV 3b | 43 | 4 | 10 | A1 | TPEAdSARPY | 7048 | 11.25 |
| 190 | HCV 3b | 43 | 4 | 10 | B_3501 | TPEAdSARPY | 7049 | 12 |
| 191 | HCV 3b | 43 | 5 | 9 | B_4403 | PEADSARPY | 7050 | 36 |
| 192 | HCV 3b | 44 | 17 | 9 | B7 | AIQGQSPRL | 7051 | 12 |
| 193 | HCV 3b | 44 | 16 | 10 | B7 | SAIQgQSPRL | 7052 | 12 |
| 194 | HCV 3b | 44 | 5 | 10 | B_3501 | CSLHrASTGY | 7053 | 10 |
| 195 | HCV 3b | 44 | 5 | 10 | B_4403 | CSLHrASTGY | 7054 | 13.5 |
| 196 | HCV 3b | 45 | 2 | 9 | B_4403 | AESGGVLAT | 7055 | 36 |
| 197 | HCV 3b | 45 | 7 | 9 | A_0201 | VLATAHVEL | 7056 | 36.32 |
| 198 | HCV 3b | 45 | 35 | 9 | A24 | GFPYGLHRL | 7057 | 30 |
| 199 | HCV 3b | 45 | 31 | 10 | B7 | QPCRgFPYGL | 7058 | 80 |
| 200 | HCV 3b | 45 | 6 | 10 | B7 | GVLAtAHVEL | 7059 | 20 |
| 201 | HCV 3b | 45 | 47 | 10 | B7 | PPHNqPDYVL | 7060 | 12 |
| 202 | HCV 3b | 45 | 46 | 9 | B_3501 | QPPHNQPDY | 7061 | 40 |
| 203 | HCV 3b | 45 | 31 | 10 | B_3501 | QPCRgFPYGL | 7062 | 20 |
| 204 | HCV 3b | 45 | 2 | 9 | B_4403 | AESGGVLAT | 7063 | 36 |
| 205 | HCV 3b | 45 | 2 | 10 | B_4403 | AESGgVLATA | 7064 | 27 |
| 206 | HCV 3b | 46 | 28 | 10 | A24 | SGEPcITNTL | 7065 | 12.096 |
| 207 | HCV 3b | 46 | 24 | 10 | B7 | SVRIsGEPCI | 7066 | 20.000 |
| 208 | HCV 3b | 46 | 38 | 10 | B8 | CPRErRGSKS | 7067 | 12.000 |
| 209 | HCV 3b | 46 | 44 | 10 | B_3501 | GSKSnSIAEL | 7068 | 15.000 |
| 210 | HCV 3b | 46 | 38 | 10 | B_3501 | CPRErRGSKS | 7069 | 12.000 |
| 211 | HCV 3b | 46 | 51 | 9 | B_4403 | AELSNRHPI | 7070 | 16.000 |
| 212 | HCV 3b | 46 | 19 | 9 | B_4403 | DEQTHSVRI | 7071 | 12.000 |
| 213 | HCV 3b | 46 | 19 | 10 | B_4403 | DEQThSVRIS | 7072 | 36.000 |
| 214 | HCV 3b | 46 | 51 | 10 | B_4403 | AELSnRHPIA | 7073 | 16.000 |
| 215 | HCV 3b | 47 | 24 | 10 | A_0201 | RLYRtRKEWV | 7074 | 599.816 |
| 216 | HCV 3b | 47 | 17 | 9 | B7 | NALPLWGRL | 7075 | 12.000 |
| 217 | HCV 3b | 47 | 1 | 9 | B_3501 | MSKGVQGSM | 7076 | 30.000 |
| 218 | HCV 3b | 47 | 17 | 10 | B_4403 | NALPlWGRLY | 7077 | 12.000 |
| 219 | HCV 3b | 48 | 1 | 9 | B7 | MPGASARVL | 7078 | 80.000 |
| 220 | HCV 3b | 48 | 16 | 9 | B7 | EAPPLCSSL | 7079 | 12.000 |
| 221 | HCV 3b | 48 | 11 | 10 | B7 | RVRRsEAPPL | 7080 | 200.000 |
| 222 | HCV 3b | 48 | 1 | 9 | B_3501 | MPGASARVL | 7081 | 20.000 |
| 223 | HCV 3b | 48 | 15 | 9 | B_4403 | SEAPPLCSS | 7082 | 48.000 |
| 224 | HCV 3b | 48 | 15 | 10 | B_4403 | SEApPLCSSL | 7083 | 32.000 |
| 225 | HCV 3b | 49 | 28 | 9 | B7 | APCARFTSI | 7084 | 24.000 |

TABLE 4k-continued 3b (1-3)

| No. | Strain | ORF | Start | AA | HLA | Peptide sequence | SEQ ID NO: | Score |
|---|---|---|---|---|---|---|---|---|
| 226 | HCV 3b | 49 | 4 | 9 | B7 | RAGRRSVNL | 7085 | 12.000 |
| 227 | HCV 3b | 50 | 63 | 9 | A_0201 | ILLRSRYRI | 7086 | 65.622 |
| 228 | HCV 3b | 50 | 64 | 10 | A3 | LLRSrYRIHR | 7087 | 24.000 |
| 229 | HCV 3b | 50 | 8 | 9 | B7 | AARSSRVCL | 7088 | 540.000 |
| 230 | HCV 3b | 50 | 57 | 9 | B7 | TGRDRHILL | 7089 | 40.000 |
| 231 | HCV 3b | 50 | 7 | 10 | B7 | RAARsSRVCL | 7090 | 18.000 |
| 232 | HCV 3b | 50 | 57 | 9 | B8 | TGRDRHILL | 7091 | 24.000 |
| 233 | HCV 3b | 50 | 8 | 9 | B8 | AARSSRVCL | 7092 | 16.000 |
| 234 | HCV 3b | 50 | 5 | 10 | B8 | NLRAaRSSRV | 7093 | 24.000 |
| 235 | HCV 3b | 50 | 8 | 10 | B8 | AARSsRVCLA | 7094 | 16.000 |
| 236 | HCV 3b | 50 | 44 | 9 | B_3501 | TPCPGREIF | 7095 | 20.000 |
| 237 | HCV 3b | 50 | 49 | 9 | B_4403 | REIFPVDET | 7096 | 60.000 |
| 238 | HCV 3b | 50 | 55 | 9 | B_4403 | DETGRDRHI | 7097 | 18.000 |
| 239 | HCV 3b | 50 | 1 | 9 | B_4403 | MEGPNLRAA | 7098 | 12.000 |
| 240 | HCV 3b | 51 | 16 | 10 | A_0201 | LVAEtPQSCL | 7099 | 13.028 |
| 241 | HCV 3b | 51 | 25 | 9 | A3 | LLYVISKRR | 7100 | 15.000 |
| 242 | HCV 3b | 51 | 24 | 9 | A3 | CLLYVISKR | 7101 | 13.500 |
| 243 | HCV 3b | 51 | 16 | 10 | B7 | LVAEtPQSCL | 7102 | 30.000 |
| 244 | HCV 3b | 51 | 36 | 9 | B_4403 | SEEGYLRQT | 7103 | 18.000 |
| 245 | HCV 3b | 51 | 18 | 9 | B_4403 | AETPQSCLL | 7104 | 16.000 |
| 246 | HCV 3b | 51 | 18 | 10 | B_4403 | AETPqSCLLY | 7105 | 480.000 |
| 247 | HCV 3b | 51 | 36 | 10 | B_4403 | SEEGyLRQTA | 7106 | 12.000 |
| 248 | HCV 3b | 52 | | | | no hits | | |
| 249 | HCV 3b | 53 | | | | no hits | | |

TABLE 4l 3b (4-6)

| No. | Strain | ORF | Start | AA | HLA | Peptide sequence | SEQ ID NO: | Score |
|---|---|---|---|---|---|---|---|---|
| 1 | HCV 3b | 1 | | | | no hits | | |
| 2 | HCV 3b | 2 | | | | no hits | | |
| 3 | HCV 3b | 3 | 4 | 9 | B8 | DSRVKATSV | 7107 | 24.000 |
| 4 | HCV 3b | 4 | 1 | 9 | A_0201 | MLHSLFGRV | 7108 | 29.205 |
| 5 | HCV 3b | 4 | 9 | 10 | A1 | VLEPvGRPHR | 7109 | 180.000 |
| 6 | HCV 3b | 4 | 4 | 10 | A_0201 | SLFGrVLEPV | 7110 | 290.025 |
| 7 | HCV 3b | 4 | 1 | 10 | A_0201 | MLHSLFGRVL | 7111 | 11.316 |
| 8 | HCV 3b | 5 | 1 | 9 | A_0201 | MVIEHLQSV | 7112 | 97.561 |
| 9 | HCV 3b | 5 | 7 | 9 | B_3501 | QSVEGNLLL | 7113 | 10.000 |
| 10 | HCV 3b | 6 | 2 | 9 | B_3501 | RPVRLTSGF | 7114 | 40.000 |
| 11 | HCV 3b | 7 | 14 | 9 | A_0201 | GLTRRSIAV | 7115 | 69.552 |
| 12 | HCV 3b | 7 | 4 | 10 | A1 | YTEGdLVPQK | 7116 | 90.000 |
| 13 | HCV 3b | 8 | 17 | 9 | B7 | APQGTRVIV | 7117 | 18.000 |
| 14 | HCV 3b | 9 | 23 | 9 | A_0201 | YMPAQHCST | 7118 | 24.757 |
| 15 | HCV 3b | 9 | 24 | 9 | B_3501 | MPAQHCSTY | 7119 | 40.000 |
| 16 | HCV 3b | 9 | 8 | 10 | A24 | RYESvHPLHC | 7120 | 15.000 |
| 17 | HCV 3b | 9 | 6 | 10 | B_4403 | CERYeSVHPL | 7121 | 12.000 |
| 18 | HCV 3b | 10 | 1 | 9 | B_3501 | MPHDDDTTY | 7122 | 120.000 |
| 19 | HCV 3b | 11 | | | | no hits | | |
| 20 | HCV 3b | 12 | 60 | 9 | A_0201 | CLIQHRAYT | 7123 | 40.986 |
| 21 | HCV 3b | 12 | 18 | 9 | A_0201 | FAIKGDFSV | 7124 | 25.773 |
| 22 | HCV 3b | 12 | 90 | 9 | A24 | RTTPIGEEL | 7125 | 14.784 |
| 23 | HCV 3b | 12 | 13 | 9 | A3 | CQWEGFAIK | 7126 | 13.500 |
| 24 | HCV 3b | 12 | 53 | 9 | B7 | QPHPGCLCL | 7127 | 80.000 |
| 25 | HCV 3b | 12 | 25 | 9 | B7 | SVTGEAHLL | 7128 | 20.000 |
| 26 | HCV 3b | 12 | 53 | 9 | B_3501 | QPHPGCLCL | 7129 | 20.000 |
| 27 | HCV 3b | 12 | 95 | 9 | B_4403 | GEELAVCGV | 7130 | 18.000 |
| 28 | HCV 3b | 12 | 2 | 9 | B_4403 | AEYKVSSSL | 7131 | 12.000 |
| 29 | HCV 3b | 12 | 68 | 10 | A_0201 | TQYGgSVLRV | 7132 | 51.901 |
| 30 | HCV 3b | 12 | 79 | 10 | A_0201 | FIADdHVIGA | 7133 | 29.632 |
| 31 | HCV 3b | 12 | 50 | 10 | A24 | QYRQpHPGCL | 7134 | 200.000 |
| 32 | HCV 3b | 12 | 66 | 10 | A24 | AYTQyGGSVL | 7135 | 200.000 |
| 33 | HCV 3b | 12 | 23 | 10 | A24 | DFSVtGEAHL | 7136 | 20.000 |
| 34 | HCV 3b | 12 | 52 | 10 | A24 | RQPHpGCLCL | 7137 | 12.000 |
| 35 | HCV 3b | 12 | 15 | 10 | B_4403 | WEGFaIKGDF | 7138 | 40.000 |
| 36 | HCV 3b | 12 | 117 | 10 | B_4403 | TDVGvNPIGF | 7139 | 15.000 |
| 37 | HCV 3b | 13 | 16 | 9 | A_0201 | GLGGRGQHL | 7140 | 21.362 |
| 38 | HCV 3b | 13 | 9 | 9 | A24 | PYCRTQEGL | 7141 | 20.000 |
| 39 | HCV 3b | 13 | 18 | 9 | B7 | GGRGQHLHL | 7142 | 40.000 |
| 40 | HCV 3b | 14 | 4 | 9 | A_0201 | WLLLTAVTI | 7143 | 177.566 |
| 41 | HCV 3b | 14 | 2 | 9 | A_0201 | EQWLLLTAV | 7144 | 10.096 |

TABLE 4l-continued

3b (4-6)

| No. | Strain | ORF | Start | AA | HLA | Peptide sequence | SEQ ID NO: | Score |
|---|---|---|---|---|---|---|---|---|
| 42 | HCV 3b | 14 | 6 | 9 | A3 | LLTAVTIFK | 7145 | 60.000 |
| 43 | HCV 3b | 14 | 6 | 10 | A_0201 | LLTAvTIFKI | 7146 | 236.595 |
| 44 | HCV 3b | 14 | 5 | 10 | A3 | LLLTaVTIFK | 7147 | 90.000 |
| 45 | HCV 3b | 14 | 9 | 10 | B7 | AVTIfKITAL | 7148 | 60.000 |
| 46 | HCV 3b | 15 | 5 | 9 | A1 | SYEHSDLEY | 7149 | 11.250 |
| 47 | HCV 3b | 15 | 60 | 9 | A_0201 | KVGLICFNV | 7150 | 123.542 |
| 48 | HCV 3b | 15 | 20 | 9 | A_0201 | RIMPQSVRV | 7151 | 35.385 |
| 49 | HCV 3b | 15 | 67 | 9 | A_0201 | NVLHPPIDV | 7152 | 22.517 |
| 50 | HCV 3b | 15 | 21 | 9 | A_0201 | IMPQSVRVV | 7153 | 16.105 |
| 51 | HCV 3b | 15 | 50 | 9 | A_0201 | VLPETIGRA | 7154 | 10.353 |
| 52 | HCV 3b | 15 | 58 | 9 | A24 | AFKVGLICF | 7155 | 10.000 |
| 53 | HCV 3b | 15 | 28 | 9 | A3 | VVYQTPWRK | 7156 | 30.000 |
| 54 | HCV 3b | 15 | 75 | 9 | B7 | VARGSPTSL | 7157 | 120.000 |
| 55 | HCV 3b | 15 | 55 | 9 | B7 | IGRAFKVGL | 7158 | 40.000 |
| 56 | HCV 3b | 15 | 43 | 9 | B7 | AGKRGIMVL | 7159 | 12.000 |
| 57 | HCV 3b | 15 | 75 | 9 | B8 | VARGSPTSL | 7160 | 16.000 |
| 58 | HCV 3b | 15 | 22 | 9 | B_3501 | MPQSVRVVY | 7161 | 40.000 |
| 59 | HCV 3b | 15 | 14 | 9 | B_4403 | REVHSARIM | 7162 | 12.000 |
| 60 | HCV 3b | 15 | 11 | 9 | B_4403 | LEYREVHSA | 7163 | 12.000 |
| 61 | HCV 3b | 15 | 2 | 10 | A_0201 | FMSSyEHSDL | 7164 | 70.971 |
| 62 | HCV 3b | 15 | 54 | 10 | A_0201 | TIGRaFKVGL | 7165 | 11.162 |
| 63 | HCV 3b | 15 | 12 | 10 | A24 | EYREvHSARI | 7166 | 60.000 |
| 64 | HCV 3b | 15 | 60 | 10 | A24 | KVGLiCFNVL | 7167 | 11.520 |
| 65 | HCV 3b | 15 | 48 | 10 | A3 | IMVLpETIGR | 7168 | 12.000 |
| 66 | HCV 3b | 15 | 90 | 10 | B7 | HPHTsKPPAL | 7169 | 80.000 |
| 67 | HCV 3b | 15 | 42 | 10 | B7 | AAGKrGIMVL | 7170 | 36.000 |
| 68 | HCV 3b | 15 | 40 | 10 | B7 | GPAAgKRGIM | 7171 | 30.000 |
| 69 | HCV 3b | 15 | 74 | 10 | B7 | DVARgSPTSL | 7172 | 20.000 |
| 70 | HCV 3b | 15 | 60 | 10 | B7 | KVGLiCFNVL | 7173 | 20.000 |
| 71 | HCV 3b | 15 | 90 | 10 | B8 | HPHTsKPPAL | 7174 | 16.000 |
| 72 | HCV 3b | 15 | 40 | 10 | B_3501 | GPAAgKRGIM | 7175 | 40.000 |
| 73 | HCV 3b | 15 | 90 | 10 | B_3501 | HPHTsKPPAL | 7176 | 20.000 |
| 74 | HCV 3b | 15 | 4 | 10 | B_3501 | SSYEhSDLEY | 7177 | 20.000 |
| 75 | HCV 3b | 15 | 75 | 10 | B_3501 | VARGsPTSLY | 7178 | 18.000 |
| 76 | HCV 3b | 16 | | | | no hits | | |
| 77 | HCV 3b | 17 | 2 | 9 | B_4403 | SEGSCDAPY | 7179 | 240.000 |
| 78 | HCV 3b | 17 | 14 | 9 | B_4403 | DERNVPHEV | 7180 | 18.000 |
| 79 | HCV 3b | 17 | 1 | 10 | A1 | MSEGsCDAPY | 7181 | 135.000 |
| 80 | HCV 3b | 18 | 9 | 9 | A3 | KMKSAPSRR | 7182 | 12.000 |
| 81 | HCV 3b | 18 | 11 | 10 | A_0201 | KSAPsRRWAV | 7183 | 11.918 |
| 82 | HCV 3b | 18 | 1 | 10 | B7 | MPRRrLRSKM | 7184 | 300.000 |
| 83 | HCV 3b | 18 | 1 | 10 | B_3501 | MPRRrLRSKM | 7185 | 120.000 |
| 84 | HCV 3b | 19 | | | | no hits | | |
| 85 | HCV 3b | 20 | 6 | 9 | B_3501 | RAGDPSPQM | 7186 | 24.000 |
| 86 | HCV 3b | 20 | 6 | 10 | A24 | RAGDpSPQML | 7187 | 11.520 |
| 87 | HCV 3b | 20 | 6 | 10 | B7 | RAGDpSPQML | 7188 | 12.000 |
| 88 | HCV 3b | 20 | 6 | 10 | B_3501 | RAGDpSPQML | 7189 | 12.000 |
| 89 | HCV 3b | 21 | 3 | 9 | A_0201 | LLWRQSRSM | 7190 | 14.020 |
| 90 | HCV 3b | 21 | 3 | 10 | A_0201 | LLWRqSRSMT | 7191 | 105.148 |
| 91 | HCV 3b | 22 | 22 | 9 | A_0201 | YLLLRRMCL | 7192 | 363.588 |
| 92 | HCV 3b | 22 | 39 | 9 | A_0201 | KISLPGQGV | 7193 | 33.472 |
| 93 | HCV 3b | 22 | 29 | 9 | A_0201 | CLSLPVSST | 7194 | 17.140 |
| 94 | HCV 3b | 22 | 20 | 9 | A_0201 | ILYLLLRRM | 7195 | 12.432 |
| 95 | HCV 3b | 22 | 15 | 9 | A24 | RTQRWILYL | 7196 | 12.000 |
| 96 | HCV 3b | 22 | 31 | 9 | A3 | SLPVSSTGK | 7197 | 20.000 |
| 97 | HCV 3b | 22 | 16 | 9 | B7 | TQRWILYLL | 7198 | 40.000 |
| 98 | HCV 3b | 22 | 24 | 9 | B7 | LLRRMCLSL | 7199 | 40.000 |
| 99 | HCV 3b | 22 | 2 | 9 | B_3501 | TPRPILRQF | 7200 | 60.000 |
| 100 | HCV 3b | 22 | 23 | 10 | A_0201 | LLLRrMCLSL | 7201 | 134.369 |
| 101 | HCV 3b | 22 | 41 | 10 | A_0201 | SLPGqGVPRT | 7202 | 17.140 |
| 102 | HCV 3b | 22 | 21 | 10 | A24 | LYLLLRRMCL | 7203 | 300.000 |
| 103 | HCV 3b | 22 | 15 | 10 | A24 | RTQRwILYLL | 7204 | 16.800 |
| 104 | HCV 3b | 22 | 16 | 10 | B7 | TQRWiLYLLL | 7205 | 40.000 |
| 105 | HCV 3b | 22 | 47 | 10 | B7 | VPRThSTHRA | 7206 | 20.000 |
| 106 | HCV 3b | 22 | 12 | 10 | B7 | ASHRtQRWIL | 7207 | 18.000 |
| 107 | HCV 3b | 23 | | | | no hits | | |
| 108 | HCV 3b | 24 | 1 | 9 | B_4403 | MEVNRAQGA | 7208 | 12.000 |
| 109 | HCV 3b | 24 | 3 | 10 | B7 | VNRAqGAGPL | 7209 | 40.000 |
| 110 | HCV 3b | 25 | | | | no hits | | |
| 111 | HCV 3b | 26 | 42 | 9 | A_0201 | RVYSAQWCI | 7210 | 21.909 |
| 112 | HCV 3b | 26 | 21 | 9 | B7 | APRHNCRRS | 7211 | 12.000 |
| 113 | HCV 3b | 26 | 38 | 9 | B8 | CARGRVYSA | 7212 | 16.000 |
| 114 | HCV 3b | 26 | 7 | 10 | B_3501 | RSWPpPRNEY | 7213 | 20.000 |
| 115 | HCV 3b | 26 | 11 | 10 | B_3501 | PPRNeYPPPY | 7214 | 12.000 |
| 116 | HCV 3b | 26 | 35 | 10 | B_3501 | ASNCaRGRVY | 7215 | 10.000 |

TABLE 4l-continued

3b (4-6)

| No. | Strain | ORF | Start | AA | HLA | Peptide sequence | SEQ ID NO: | Score |
|---|---|---|---|---|---|---|---|---|
| 117 | HCV 3b | 27 | 2 | 9 | B_4403 | RERVCLAPW | 7216 | 18.000 |
| 118 | HCV 3b | 28 | 6 | 10 | B7 | LPRRsRGHSV | 7217 | 40.000 |
| 119 | HCV 3b | 28 | 6 | 10 | B8 | LPRRsRGHSV | 7218 | 48.000 |
| 120 | HCV 3b | 28 | 6 | 10 | B_3501 | LPRRsRGHSV | 7219 | 12.000 |
| 121 | HCV 3b | 28 | 9 | 10 | B_3501 | RSRGhSVLVI | 7220 | 12.000 |
| 122 | HCV 3b | 29 | 2 | 9 | A_0201 | LQVPLGVWL | 7221 | 20.251 |
| 123 | HCV 3b | 29 | 1 | 10 | A_0201 | MLQVpLGVWL | 7222 | 199.738 |
| 124 | HCV 3b | 29 | 4 | 10 | B7 | VPLGvWLPNL | 7223 | 80.000 |
| 125 | HCV 3b | 29 | 4 | 10 | B_3501 | VPLGvWLPNL | 7224 | 20.000 |
| 126 | HCV 3b | 30 | 21 | 9 | A_0201 | SLGPAVLPV | 7225 | 159.970 |
| 127 | HCV 3b | 30 | 18 | 9 | A_0201 | SMQSLGPAV | 7226 | 50.232 |
| 128 | HCV 3b | 30 | 5 | 9 | A_0201 | PLHERRQWL | 7227 | 10.598 |
| 129 | HCV 3b | 30 | 27 | 9 | B7 | LPVTRSGHL | 7228 | 80.000 |
| 130 | HCV 3b | 30 | 27 | 9 | B8 | LPVTRSGHL | 7229 | 16.000 |
| 131 | HCV 3b | 30 | 27 | 9 | B_3501 | LPVTRSGHL | 7230 | 20.000 |
| 132 | HCV 3b | 30 | 4 | 9 | B_3501 | SPLHERRQW | 7231 | 15.000 |
| 133 | HCV 3b | 30 | 4 | 10 | B7 | SPLHeRRQWL | 7232 | 120.000 |
| 134 | HCV 3b | 30 | 4 | 10 | B8 | SPLHeRRQWL | 7233 | 16.000 |
| 135 | HCV 3b | 30 | 27 | 10 | B_3501 | LPVTrSGHLY | 7234 | 40.000 |
| 136 | HCV 3b | 30 | 4 | 10 | B_3501 | SPLHeRRQWL | 7235 | 20.000 |
| 137 | HCV 3b | 31 | 11 | 9 | B7 | VVGHTRNNL | 7236 | 30.000 |
| 138 | HCV 3b | 31 | 10 | 10 | B7 | QVVGhTRNNL | 7237 | 30.000 |
| 139 | HCV 3b | 32 | 23 | 9 | A24 | RFQWGREGI | 7238 | 15.000 |
| 140 | HCV 3b | 32 | 24 | 10 | A_0201 | FQWGrEGILL | 7239 | 82.694 |
| 141 | HCV 3b | 32 | 23 | 10 | A24 | RFQWgREGIL | 7240 | 60.000 |
| 142 | HCV 3b | 32 | 9 | 10 | B7 | IPVQhKRRGL | 7241 | 120.000 |
| 143 | HCV 3b | 32 | 9 | 10 | B8 | IPVQhKRRGL | 7242 | 16.000 |
| 144 | HCV 3b | 32 | 9 | 10 | B_3501 | IPVQhKRRGL | 7243 | 20.000 |
| 145 | HCV 3b | 33 | 36 | 9 | A24 | RCLRRLLCL | 7244 | 12.000 |
| 146 | HCV 3b | 33 | 34 | 9 | B7 | RTRCLRRLL | 7245 | 60.000 |
| 147 | HCV 3b | 33 | 32 | 10 | B7 | ATRTrCLRRL | 7246 | 120.000 |
| 148 | HCV 3b | 34 | 5 | 10 | A_0201 | MQPGtRRNPV | 7247 | 11.988 |
| 149 | HCV 3b | 34 | 8 | 10 | B7 | GTRRnPVVPL | 7248 | 60.000 |
| 150 | HCV 3b | 35 | 39 | 9 | A1 | RIDVHVLLR | 7249 | 25.000 |
| 151 | HCV 3b | 35 | 30 | 9 | B7 | LPSSSCRRL | 7250 | 80.000 |
| 152 | HCV 3b | 35 | 37 | 9 | B7 | RLRIDVHVL | 7251 | 40.000 |
| 153 | HCV 3b | 35 | 16 | 9 | B7 | VVAHCGHDL | 7252 | 20.000 |
| 154 | HCV 3b | 35 | 3 | 9 | B7 | MAILASQSL | 7253 | 12.000 |
| 155 | HCV 3b | 35 | 30 | 9 | B_3501 | LPSSSCRRL | 7254 | 20.000 |
| 156 | HCV 3b | 35 | 5 | 10 | A_0201 | ILASqSLNGA | 7255 | 19.425 |
| 157 | HCV 3b | 35 | 2 | 10 | A_0201 | SMAILASQSL | 7256 | 15.428 |
| 158 | HCV 3b | 35 | 37 | 10 | A24 | RLRIdVHVLL | 7257 | 11.200 |
| 159 | HCV 3b | 35 | 37 | 10 | B7 | RLRIdVHVLL | 7258 | 40.000 |
| 160 | HCV 3b | 35 | 15 | 10 | B7 | VVVAhCGHDL | 7259 | 20.000 |
| 161 | HCV 3b | 35 | 29 | 10 | B7 | ALPSsSCRRL | 7260 | 12.000 |
| 162 | HCV 3b | 35 | 40 | 10 | B_4403 | IDVHvLLRTF | 7261 | 15.000 |
| 163 | HCV 3b | 36 | 1 | 9 | B7 | MVCPHWDHL | 7262 | 20.000 |
| 164 | HCV 3b | 37 | 22 | 9 | B_3501 | RPHTQCSCW | 7263 | 20.000 |
| 165 | HCV 3b | 37 | 4 | 10 | B8 | CCRFrRRARI | 7264 | 80.000 |
| 166 | HCV 3b | 37 | 16 | 10 | B8 | SARSrRRPHT | 7265 | 16.000 |
| 167 | HCV 3b | 38 | 8 | 9 | A1 | GLEAARHSY | 7266 | 45.000 |
| 168 | HCV 3b | 38 | 8 | 9 | A3 | GLEAARHSY | 7267 | 12.000 |
| 169 | HCV 3b | 38 | 1 | 9 | B7 | MALPEGGGL | 7268 | 12.000 |
| 170 | HCV 3b | 38 | 2 | 10 | A_0201 | ALPEgGGLEA | 7269 | 20.369 |
| 171 | HCV 3b | 39 | | | | no hits | | |
| 172 | HCV 3b | 40 | 41 | 9 | A_0201 | ILAFPPWAM | 7270 | 63.342 |
| 173 | HCV 3b | 40 | 19 | 9 | A_0201 | AVGNGVSLV | 7271 | 13.997 |
| 174 | HCV 3b | 40 | 26 | 9 | A_0201 | LVLVRTAQL | 7272 | 11.757 |
| 175 | HCV 3b | 40 | 36 | 9 | A24 | RYRPHILAF | 7273 | 240.000 |
| 176 | HCV 3b | 40 | 43 | 9 | A24 | AFPPWAMSL | 7274 | 36.000 |
| 177 | HCV 3b | 40 | 69 | 9 | A24 | SFLRAPATL | 7275 | 30.000 |
| 178 | HCV 3b | 40 | 27 | 9 | A3 | VLVRTAQLK | 7276 | 30.000 |
| 179 | HCV 3b | 40 | 70 | 9 | B7 | FLRAPATLL | 7277 | 60.000 |
| 180 | HCV 3b | 40 | 26 | 9 | B7 | LVLVRTAQL | 7278 | 20.000 |
| 181 | HCV 3b | 40 | 73 | 9 | B7 | APATLLSSV | 7279 | 12.000 |
| 182 | HCV 3b | 40 | 54 | 9 | B8 | TARARCLHA | 7280 | 16.000 |
| 183 | HCV 3b | 40 | 10 | 10 | A_0201 | NQLErSSWPA | 7281 | 57.308 |
| 184 | HCV 3b | 40 | 25 | 10 | A_0201 | SLVLvRTAQL | 7282 | 21.362 |
| 185 | HCV 3b | 40 | 69 | 10 | A24 | SFLRaPATLL | 7283 | 30.000 |
| 186 | HCV 3b | 40 | 27 | 10 | A3 | VLVRtAQLKR | 7284 | 12.000 |
| 187 | HCV 3b | 40 | 51 | 10 | B7 | LARTaRARCL | 7285 | 120.000 |
| 188 | HCV 3b | 40 | 3 | 10 | B7 | FPPTpTVNQL | 7286 | 80.000 |
| 189 | HCV 3b | 40 | 17 | 10 | B7 | WPAVgNGVSL | 7287 | 80.000 |
| 190 | HCV 3b | 40 | 19 | 10 | B7 | AVGNgVSLVL | 7288 | 60.000 |
| 191 | HCV 3b | 40 | 62 | 10 | B7 | ARRGgIPSFL | 7289 | 12.000 |

TABLE 4l-continued 3b (4-6)

| No. Strain | ORF | Start | AA | HLA | Peptide sequence | SEQ ID NO: | Score |
|---|---|---|---|---|---|---|---|
| 192 HCV 3b | 40 | 42 | 10 | B7 | LAFPpWAMSL | 7290 | 12.000 |
| 193 HCV 3b | 40 | 51 | 10 | B8 | LARTaRARCL | 7291 | 320.000 |
| 194 HCV 3b | 40 | 33 | 10 | B8 | QLKRyRPHIL | 7292 | 160.000 |
| 195 HCV 3b | 40 | 3 | 10 | B_3501 | FPPTpTVNQL | 7293 | 20.000 |
| 196 HCV 3b | 40 | 38 | 10 | B_3501 | RPHILAFPPW | 7294 | 20.000 |
| 197 HCV 3b | 40 | 17 | 10 | B_3501 | WPAVgNGVSL | 7295 | 20.000 |
| 198 HCV 3b | 41 | 1 | 9 | A_0201 | MIAGKSSGV | 7296 | 16.258 |
| 199 HCV 3b | 42 | 19 | 9 | A_0201 | MMIFPNQEL | 7297 | 26.228 |
| 200 HCV 3b | 42 | 25 | 9 | B_4403 | QELTGVWRA | 7298 | 24.000 |
| 201 HCV 3b | 42 | 1 | 9 | B_4403 | MEKKWVINT | 7299 | 12.000 |
| 202 HCV 3b | 42 | 18 | 10 | A_0201 | NMMIfPNQEL | 7300 | 57.085 |
| 203 HCV 3b | 42 | 6 | 10 | A_0201 | VINTmRTQMV | 7301 | 16.258 |
| 204 HCV 3b | 42 | 13 | 10 | A3 | QMVGaNMMIF | 7302 | 13.500 |
| 205 HCV 3b | 42 | 18 | 10 | B7 | NMMIfPNQEL | 7303 | 18.000 |
| 206 HCV 3b | 42 | 22 | 10 | B_3501 | FPNQeLTGVW | 7304 | 10.000 |
| 207 HCV 3b | 42 | 25 | 10 | B_4403 | QELTgVWRAV | 7305 | 12.000 |
| 208 HCV 3b | 43 | 39 | 9 | A_0201 | ALLAAVALM | 7306 | 42.278 |
| 209 HCV 3b | 43 | 10 | 9 | A_0201 | VLSSSTPQL | 7307 | 36.316 |
| 210 HCV 3b | 43 | 33 | 9 | A24 | GFLRPAALL | 7308 | 30.000 |
| 211 HCV 3b | 43 | 38 | 9 | B7 | AALLAAVAL | 7309 | 36.000 |
| 212 HCV 3b | 43 | 3 | 9 | B7 | SVKARRAVL | 7310 | 30.000 |
| 213 HCV 3b | 43 | 3 | 9 | B8 | SVKARRAVL | 7311 | 80.000 |
| 214 HCV 3b | 43 | 26 | 9 | B_3501 | SPQTRKDGF | 7312 | 20.000 |
| 215 HCV 3b | 43 | 26 | 10 | B7 | SPQTrKDGFL | 7313 | 80.000 |
| 216 HCV 3b | 43 | 9 | 10 | B7 | AVLSsSTPQL | 7314 | 60.000 |
| 217 HCV 3b | 43 | 2 | 10 | B7 | ASVKaRRAVL | 7315 | 18.000 |
| 218 HCV 3b | 43 | 26 | 10 | B8 | SPQTrKDGFL | 7316 | 16.000 |
| 219 HCV 3b | 43 | 26 | 10 | B_3501 | SPQTrKDGFL | 7317 | 20.000 |
| 220 HCV 3b | 44 | 32 | 9 | A_0201 | VLMSCSVTV | 7318 | 437.482 |
| 221 HCV 3b | 44 | 46 | 9 | A_0201 | VSYENPKGV | 7319 | 10.126 |
| 222 HCV 3b | 44 | 5 | 9 | A24 | MYSRSVRAL | 7320 | 200.000 |
| 223 HCV 3b | 44 | 47 | 9 | A24 | SYENPKGVF | 7321 | 150.000 |
| 224 HCV 3b | 44 | 26 | 9 | A24 | WYIPSSVLM | 7322 | 45.000 |
| 225 HCV 3b | 44 | 53 | 9 | B7 | GVFFDVHIL | 7323 | 20.000 |
| 226 HCV 3b | 44 | 50 | 9 | B_3501 | NPKGVFFDV | 7324 | 12.000 |
| 227 HCV 3b | 44 | 64 | 9 | B_3501 | CSTRCLGEY | 7325 | 10.000 |
| 228 HCV 3b | 44 | 8 | 9 | B_3501 | RSVRALIAF | 7326 | 10.000 |
| 229 HCV 3b | 44 | 48 | 9 | B_4403 | YENPKGVFF | 7327 | 120.000 |
| 230 HCV 3b | 44 | 40 | 9 | B_4403 | VESKQRVSY | 7328 | 120.000 |
| 231 HCV 3b | 44 | 39 | 10 | A1 | TVESkQRVSY | 7329 | 90.000 |
| 232 HCV 3b | 44 | 31 | 10 | A_0201 | SVLMsCSVTV | 7330 | 22.517 |
| 233 HCV 3b | 44 | 47 | 10 | A24 | SYENpKGVFF | 7331 | 150.000 |
| 234 HCV 3b | 44 | 5 | 10 | A24 | MYSRsVRALI | 7332 | 70.000 |
| 235 HCV 3b | 44 | 52 | 10 | A24 | KGVFfDVHIL | 7333 | 12.000 |
| 236 HCV 3b | 44 | 53 | 10 | A3 | GVFFdVHILR | 7334 | 18.000 |
| 237 HCV 3b | 44 | 60 | 10 | B7 | ILRRcSTRCL | 7335 | 40.000 |
| 238 HCV 3b | 44 | 18 | 10 | B_3501 | ASGSrSQHWY | 7336 | 10.000 |
| 239 HCV 3b | 44 | 46 | 10 | B_3501 | VSYEnPKGVF | 7337 | 10.000 |
| 240 HCV 3b | 45 | 37 | 9 | A_0201 | SQTERIWFM | 7338 | 195.933 |
| 241 HCV 3b | 45 | 14 | 9 | A_0201 | TLNTSFFAI | 7339 | 114.969 |
| 242 HCV 3b | 45 | 13 | 9 | A_0201 | FTLNTSFFA | 7340 | 37.463 |
| 243 HCV 3b | 45 | 21 | 9 | A_0201 | AIMVVGIGV | 7341 | 35.385 |
| 244 HCV 3b | 45 | 82 | 9 | A_0201 | FTPDARSFT | 7342 | 10.736 |
| 245 HCV 3b | 45 | 88 | 9 | A24 | SFTSLSTFL | 7343 | 24.000 |
| 246 HCV 3b | 45 | 7 | 9 | A24 | RPPFAGFTL | 7344 | 12.000 |
| 247 HCV 3b | 45 | 12 | 9 | A24 | GFTLNTSFF | 7345 | 10.000 |
| 248 HCV 3b | 45 | 5 | 9 | A3 | GLRPPFAGF | 7346 | 40.500 |
| 249 HCV 3b | 45 | 7 | 9 | B7 | RPPFAGFTL | 7347 | 80.000 |
| 250 HCV 3b | 45 | 23 | 9 | B7 | MVVGIGVLL | 7348 | 20.000 |
| 251 HCV 3b | 45 | 7 | 9 | B_3501 | RPPFAGFTL | 7349 | 40.000 |
| 252 HCV 3b | 45 | 74 | 9 | B_3501 | SSKESRRPF | 7350 | 30.000 |
| 253 HCV 3b | 45 | 58 | 9 | B_3501 | YPYFDRPEW | 7351 | 15.000 |
| 254 HCV 3b | 45 | 87 | 9 | B_3501 | RSFTSLSTF | 7352 | 10.000 |
| 255 HCV 3b | 45 | 50 | 9 | B_4403 | KERTSFALY | 7353 | 120.000 |
| 256 HCV 3b | 45 | 13 | 10 | A_0201 | FTLNtSFFAI | 7354 | 27.178 |
| 257 HCV 3b | 45 | 22 | 10 | A_0201 | IMVVgIGVLL | 7355 | 26.228 |
| 258 HCV 3b | 45 | 37 | 10 | A_0201 | SQTErIWFMA | 7356 | 20.363 |
| 259 HCV 3b | 45 | 47 | 10 | A_0201 | LLDKeRTSFA | 7357 | 18.580 |
| 260 HCV 3b | 45 | 14 | 10 | A_0201 | TLNTsFFAIM | 7358 | 14.706 |
| 261 HCV 3b | 45 | 30 | 10 | A_0201 | LLSSnKSSQT | 7359 | 12.668 |
| 262 HCV 3b | 45 | 44 | 10 | A_0201 | FMALlDKERT | 7360 | 12.131 |
| 263 HCV 3b | 45 | 41 | 10 | A3 | RIWFmALLDK | 7361 | 30.000 |
| 264 HCV 3b | 45 | 21 | 10 | B7 | AIMVvGIGVL | 7362 | 36.000 |
| 265 HCV 3b | 45 | 83 | 10 | B7 | TPDArSFTSL | 7363 | 24.000 |
| 266 HCV 3b | 45 | 80 | 10 | B_3501 | RPFTpDARSF | 7364 | 60.000 |

TABLE 4l-continued

3b (4-6)

| No. | Strain | ORF | Start | AA | HLA | Peptide sequence | SEQ ID NO: | Score |
|---|---|---|---|---|---|---|---|---|
| 267 | HCV 3b | 45 | 35 | 10 | B_3501 | KSSQtERIWF | 7365 | 15.000 |
| 268 | HCV 3b | 45 | 36 | 10 | B_3501 | SSQTeRIWFM | 7366 | 10.000 |
| 269 | HCV 3b | 45 | 87 | 10 | B_3501 | RSFTsLSTFL | 7367 | 10.000 |
| 270 | HCV 3b | 45 | 22 | 9 | A1 | TVDQESASR | 7368 | 10.000 |
| 271 | HCV 3b | 46 | 97 | 9 | B_3501 | DPSSLIVLF | 7369 | 20.000 |
| 272 | HCV 3b | 46 | 88 | 9 | B_3501 | RARSAADTF | 7370 | 18.000 |
| 273 | HCV 3b | 46 | 71 | 9 | B_4403 | EDVPVPSGF | 7371 | 30.000 |
| 274 | HCV 3b | 46 | 43 | 9 | B_4403 | DEYDSTSDS | 7372 | 18.000 |
| 275 | HCV 3b | 46 | 14 | 10 | A_0201 | TLCSsESLTV | 7373 | 69.552 |
| 276 | HCV 3b | 46 | 6 | 10 | A24 | EYDIeQQTTL | 7374 | 200.000 |
| 277 | HCV 3b | 46 | 95 | 10 | A24 | TFDPsSLIVL | 7375 | 24.000 |
| 278 | HCV 3b | 46 | 97 | 10 | B7 | DPSSLIVLFL | 7376 | 80.000 |
| 279 | HCV 3b | 46 | 33 | 10 | B7 | SPGSpSRGGM | 7377 | 30.000 |
| 280 | HCV 3b | 46 | 92 | 10 | B7 | AADTfDPSSL | 7378 | 10.800 |
| 281 | HCV 3b | 46 | 33 | 10 | B_3501 | SPGSpSRGGM | 7379 | 40.000 |
| 282 | HCV 3b | 46 | 36 | 10 | B_3501 | SPSRgGMDEY | 7380 | 40.000 |
| 283 | HCV 3b | 46 | 97 | 10 | B_3501 | DPSSLIVLFL | 7381 | 20.000 |
| 284 | HCV 3b | 46 | 70 | 10 | B_4403 | EEDVpVPSGF | 7382 | 60.000 |
| 285 | HCV 3b | 46 | 18 | 10 | B_4403 | SESLtVDQES | 7383 | 12.000 |
| 286 | HCV 3b | 46 | 43 | 10 | B_4403 | DEYDsTSDSS | 7384 | 12.000 |
| 287 | HCV 3b | 46 | 56 | 10 | B_4403 | GESPdSAVDS | 7385 | 12.000 |
| 288 | HCV 3b | 47 | 17 | 9 | A_0201 | ILMDPFLTC | 7386 | 243.428 |
| 289 | HCV 3b | 47 | 16 | 9 | A_0201 | AILMDPFLT | 7387 | 21.989 |
| 290 | HCV 3b | 47 | 10 | 9 | B7 | AQRPDPAIL | 7388 | 120.000 |
| 291 | HCV 3b | 47 | 39 | 9 | B7 | TPSPRHTPL | 7389 | 80.000 |
| 292 | HCV 3b | 47 | 30 | 9 | B7 | SPQGQRVVI | 7390 | 12.000 |
| 293 | HCV 3b | 47 | 39 | 9 | B8 | TPSPRHTPL | 7391 | 16.000 |
| 294 | HCV 3b | 47 | 14 | 9 | B_3501 | DPAILMDPF | 7392 | 20.000 |
| 295 | HCV 3b | 47 | 39 | 9 | B_3501 | TPSPRHTPL | 7393 | 20.000 |
| 296 | HCV 3b | 47 | 18 | 10 | A_0201 | LMDPfLTCPV | 7394 | 34.158 |
| 297 | HCV 3b | 47 | 8 | 10 | A_0201 | MLAQrPDPAI | 7395 | 17.736 |
| 298 | HCV 3b | 47 | 14 | 10 | B7 | DPAIlMDPFL | 7396 | 80.000 |
| 299 | HCV 3b | 47 | 10 | 10 | B7 | AQRPdPAILM | 7397 | 45.000 |
| 300 | HCV 3b | 47 | 9 | 10 | B7 | LAQRpDPAIL | 7398 | 12.000 |
| 301 | HCV 3b | 47 | 41 | 10 | B_3501 | SPRHtPLYPF | 7399 | 60.000 |
| 302 | HCV 3b | 47 | 39 | 10 | B_3501 | TPSPrHTPLY | 7400 | 40.000 |
| 303 | HCV 3b | 47 | 14 | 10 | B_3501 | DPAILMDPFL | 7401 | 20.000 |
| 304 | HCV 3b | 48 | 6 | 9 | A_0201 | GMILAESQV | 7402 | 50.232 |
| 305 | HCV 3b | 48 | 26 | 9 | A_0201 | QMSCNQSPL | 7403 | 15.428 |
| 306 | HCV 3b | 48 | 8 | 9 | A3 | ILAESQVLK | 7404 | 30.000 |
| 307 | HCV 3b | 48 | 1 | 9 | B7 | MPGTLGMIL | 7405 | 80.000 |
| 308 | HCV 3b | 48 | 1 | 9 | B_3501 | MPGTLGMIL | 7406 | 20.000 |
| 309 | HCV 3b | 48 | 10 | 9 | B_4403 | AESQVLKSL | 7407 | 27.000 |
| 310 | HCV 3b | 48 | 25 | 10 | B7 | SQMScNQSPL | 7408 | 12.000 |
| 311 | HCV 3b | 48 | 18 | 10 | B_3501 | LSTIqTQSQM | 7409 | 10.000 |
| 312 | HCV 3b | 49 | 123 | 9 | A1 | VTEAVKAIR | 7410 | 45.000 |
| 313 | HCV 3b | 49 | 104 | 9 | A1 | ATQPPRMLK | 7411 | 25.000 |
| 314 | HCV 3b | 49 | 47 | 9 | A1 | GSSPPMILK | 7412 | 15.000 |
| 315 | HCV 3b | 49 | 109 | 9 | A_0201 | RMLKNIVWL | 7413 | 722.126 |
| 316 | HCV 3b | 49 | 110 | 9 | A_0201 | MLKNIVWLV | 7414 | 71.386 |
| 317 | HCV 3b | 49 | 148 | 9 | A_0201 | WIPLTKFHM | 7415 | 18.225 |
| 318 | HCV 3b | 49 | 74 | 9 | A_0201 | TLPMPMPPT | 7416 | 17.140 |
| 319 | HCV 3b | 49 | 122 | 9 | A_0201 | LVTEAVKAI | 7417 | 14.634 |
| 320 | HCV 3b | 49 | 116 | 9 | A_0201 | WLVVRGLVT | 7418 | 14.054 |
| 321 | HCV 3b | 49 | 34 | 9 | A_0201 | KMAGRRLTM | 7419 | 12.558 |
| 322 | HCV 3b | 49 | 114 | 9 | A_0201 | IVWLVVRGL | 7420 | 12.132 |
| 323 | HCV 3b | 49 | 146 | 9 | A24 | RYWIPLTKF | 7421 | 220.000 |
| 324 | HCV 3b | 49 | 109 | 9 | A24 | RMLKNIVWL | 7422 | 12.000 |
| 325 | HCV 3b | 49 | 129 | 9 | B7 | AIREATAGL | 7423 | 120.000 |
| 326 | HCV 3b | 49 | 143 | 9 | B7 | RPARYWIPL | 7424 | 80.000 |
| 327 | HCV 3b | 49 | 186 | 9 | B7 | KPRTLSLNC | 7425 | 20.000 |
| 328 | HCV 3b | 49 | 114 | 9 | B7 | IVWLVVRGL | 7426 | 20.000 |
| 329 | HCV 3b | 49 | 103 | 9 | B7 | VATQPPRML | 7427 | 18.000 |
| 330 | HCV 3b | 49 | 182 | 9 | B7 | ALCSKPRTL | 7428 | 12.000 |
| 331 | HCV 3b | 49 | 184 | 9 | B8 | CSKPRTLSL | 7429 | 80.000 |
| 332 | HCV 3b | 49 | 143 | 9 | B_3501 | RPARYWIPL | 7430 | 40.000 |
| 333 | HCV 3b | 49 | 58 | 9 | B_3501 | RAPETPAPY | 7431 | 24.000 |
| 334 | HCV 3b | 49 | 139 | 9 | B_3501 | GSVERPARY | 7432 | 20.000 |
| 335 | HCV 3b | 49 | 184 | 9 | B_3501 | CSKPRTLSL | 7433 | 15.000 |
| 336 | HCV 3b | 49 | 186 | 9 | B_3501 | KPRTLSLNC | 7434 | 12.000 |
| 337 | HCV 3b | 49 | 71 | 9 | B_3501 | SSNTLPMPM | 7435 | 10.000 |
| 338 | HCV 3b | 49 | 141 | 9 | B_4403 | VERPARYWI | 7436 | 12.000 |
| 339 | HCV 3b | 49 | 92 | 10 | A1 | NAEDaAGPAR | 7437 | 18.000 |
| 340 | HCV 3b | 49 | 109 | 10 | A_0201 | RMLKnIVWLV | 7438 | 3.206.057 |
| 341 | HCV 3b | 49 | 180 | 10 | A_0201 | WLALcSKPRT | 7439 | 34.279 |

TABLE 4l-continued

3b (4-6)

| No. Strain | ORF | Start | AA | HLA | Peptide sequence | SEQ ID NO: | Score |
|---|---|---|---|---|---|---|---|
| 342 HCV 3b | 49 | 121 | 10 | A_0201 | GLVTeAVKAI | 7440 | 23.995 |
| 343 HCV 3b | 49 | 114 | 10 | A_0201 | IVWLvVRGLV | 7441 | 11.163 |
| 344 HCV 3b | 49 | 128 | 10 | A24 | KAIReATAGL | 7442 | 12.000 |
| 345 HCV 3b | 49 | 66 | 10 | B7 | YPAStSSNTL | 7443 | 80.000 |
| 346 HCV 3b | 49 | 172 | 10 | B7 | MGRIsASCWL | 7444 | 40.000 |
| 347 HCV 3b | 49 | 45 | 10 | B7 | VVGSsPPMIL | 7445 | 30.000 |
| 348 HCV 3b | 49 | 102 | 10 | B7 | CVATqPPRML | 7446 | 30.000 |
| 349 HCV 3b | 49 | 181 | 10 | B7 | LALCsKPRTL | 7447 | 12.000 |
| 350 HCV 3b | 49 | 128 | 10 | B7 | KAIReATAGL | 7448 | 12.000 |
| 351 HCV 3b | 49 | 80 | 10 | B7 | PPTAaPAKPL | 7449 | 12.000 |
| 352 HCV 3b | 49 | 118 | 10 | B7 | VVRGlVTEAV | 7450 | 10.000 |
| 353 HCV 3b | 49 | 181 | 10 | B8 | LALCsKPRTL | 7451 | 16.000 |
| 354 HCV 3b | 49 | 183 | 10 | B8 | LCSKpRTLSL | 7452 | 16.000 |
| 355 HCV 3b | 49 | 66 | 10 | B_3501 | YPAStSSNTL | 7453 | 20.000 |
| 356 HCV 3b | 49 | 43 | 10 | B_3501 | SSVVgSSPPM | 7454 | 10.000 |
| 357 HCV 3b | 49 | 68 | 10 | B_3501 | ASTSsNTLPM | 7455 | 10.000 |
| 358 HCV 3b | 49 | 70 | 10 | B_3501 | TSSNtLPMPM | 7456 | 10.000 |
| 359 HCV 3b | 49 | 131 | 10 | B_4403 | REATaGLPGS | 7457 | 12.000 |
| 360 HCV 3b | 49 | 124 | 10 | B_4403 | TEAVkAIREA | 7458 | 12.000 |
| 361 HCV 3b | 50 | | | | no hits | | |
| 362 HCV 3b | 51 | 4 | 9 | A_0201 | MMYLVIGCV | 7459 | 81.705 |
| 363 HCV 3b | 51 | 3 | 9 | A_0201 | AMMYLVIGC | 7460 | 30.534 |
| 364 HCV 3b | 51 | 5 | 9 | A24 | MYLVIGCVM | 7461 | 52.500 |
| 365 HCV 3b | 51 | 3 | 10 | A_0201 | AMMYLVIGCV | 7462 | 55.572 |
| 366 HCV 3b | 51 | 6 | 10 | A_0201 | YLVIgCVMQM | 7463 | 52.561 |
| 367 HCV 3b | 52 | 12 | 10 | A_0201 | GLAFaRAQTV | 7464 | 69.552 |
| 368 HCV 3b | 53 | 5 | 9 | B_3501 | RSPGVTNRY | 7465 | 20.000 |
| 369 HCV 3b | 53 | 5 | 9 | B_4403 | RSPGVTNRY | 7466 | 10.125 |
| 370 HCV 3b | 53 | 12 | 10 | A24 | RYIPgLPRPV | 7467 | 21.600 |
| 371 HCV 3b | 53 | 16 | 10 | A3 | GLPRpVRPLR | 7468 | 18.000 |
| 372 HCV 3b | 53 | 8 | 10 | B7 | GVTNrYIPGL | 7469 | 20.000 |
| 373 HCV 3b | 54 | 17 | 9 | A3 | TLQSITVSK | 7470 | 30.000 |
| 374 HCV 3b | 54 | 22 | 10 | A_0201 | TVSKsPVYPV | 7471 | 13.997 |
| 375 HCV 3b | 54 | 23 | 10 | B_3501 | VSKSpVYPVM | 7472 | 30.000 |
| 376 HCV 3b | 54 | 9 | 10 | B_3501 | KSTYcSTATL | 7473 | 10.000 |
| 377 HCV 3b | 55 | 6 | 9 | B7 | VAVASTVSL | 7474 | 12.000 |
| 378 HCV 3b | 55 | 5 | 10 | B7 | GVAVaSTVSL | 7475 | 20.000 |
| 379 HCV 3b | 56 | 1 | 9 | B7 | MVRVPVRML | 7476 | 300.000 |
| 380 HCV 3b | 57 | 3 | 9 | B8 | VPKPRVAAT | 7477 | 16.000 |
| 381 HCV 3b | 57 | 12 | 9 | B_4403 | DGFSTRTEY | 7478 | 13.500 |
| 382 HCV 3b | 57 | 5 | 10 | B_3501 | KPRVaATDGF | 7479 | 120.000 |
| 383 HCV 3b | 57 | 11 | 10 | B_4403 | TDGFsTRTEY | 7480 | 22.500 |
| 384 HCV 3b | 58 | 40 | 9 | A_0201 | GLVLSKLAV | 7481 | 69.552 |
| 385 HCV 3b | 58 | 65 | 9 | A24 | RYRSEEPHV | 7482 | 10.000 |
| 386 HCV 3b | 58 | 45 | 9 | A3 | KLAVESPLR | 7483 | 12.000 |
| 387 HCV 3b | 58 | 33 | 9 | B7 | EPLRQDSGL | 7484 | 80.000 |
| 388 HCV 3b | 58 | 8 | 9 | B7 | TPLVHTAAL | 7485 | 80.000 |
| 389 HCV 3b | 58 | 86 | 9 | B7 | QPTRSWSTL | 7486 | 80.000 |
| 390 HCV 3b | 58 | 2 | 9 | B7 | NCRAFATPL | 7487 | 40.000 |
| 391 HCV 3b | 58 | 2 | 9 | B8 | NCRAFATPL | 7488 | 16.000 |
| 392 HCV 3b | 58 | 8 | 9 | B_3501 | TPLVHTAAL | 7489 | 20.000 |
| 393 HCV 3b | 58 | 33 | 9 | B_3501 | EPLRQDSGL | 7490 | 20.000 |
| 394 HCV 3b | 58 | 86 | 9 | B_3501 | QPTRSWSTL | 7491 | 20.000 |
| 395 HCV 3b | 58 | 58 | 9 | B_3501 | TSASRVTRY | 7492 | 10.000 |
| 396 HCV 3b | 58 | 68 | 9 | B_4403 | SEEPHVQGS | 7493 | 48.000 |
| 397 HCV 3b | 58 | 58 | 9 | B_4403 | TSASRVTRY | 7494 | 27.000 |
| 398 HCV 3b | 58 | 45 | 10 | A3 | KLAVeSPLRR | 7495 | 24.000 |
| 399 HCV 3b | 58 | 70 | 10 | B7 | EPHVqGSRDL | 7496 | 80.000 |
| 400 HCV 3b | 58 | 18 | 10 | B7 | IPTTcPEGHM | 7497 | 30.000 |
| 401 HCV 3b | 58 | 7 | 10 | B7 | ATPLvHTAAL | 7498 | 12.000 |
| 402 HCV 3b | 58 | 18 | 10 | B_3501 | IPTTcPEGHM | 7499 | 40.000 |
| 403 HCV 3b | 58 | 70 | 10 | B_3501 | EPHVqGSRDL | 7500 | 20.000 |
| 404 HCV 3b | 58 | 43 | 10 | B_3501 | LSKLaVESPL | 7501 | 15.000 |
| 405 HCV 3b | 58 | 57 | 10 | B_4403 | RTSAsRVTRY | 7502 | 13.500 |
| 406 HCV 3b | 59 | 1 | 9 | A1 | MTPPTVVPK | 7503 | 10.000 |
| 407 HCV 3b | 59 | 26 | 9 | A_0201 | FLSLPVRLV | 7504 | 147.172 |
| 408 HCV 3b | 59 | 5 | 9 | A_0201 | TVVPKKVWV | 7505 | 33.472 |
| 409 HCV 3b | 59 | 28 | 9 | A_0201 | SLPVRLVTI | 7506 | 23.995 |
| 410 HCV 3b | 59 | 10 | 9 | A_0201 | KVWVAVDST | 7507 | 21.348 |
| 411 HCV 3b | 59 | 25 | 9 | A24 | TFLSLPVRL | 7508 | 36.000 |
| 412 HCV 3b | 59 | 21 | 9 | B7 | SPVTTFLSL | 7509 | 80.000 |
| 413 HCV 3b | 59 | 52 | 9 | B7 | DSRRHPIFL | 7510 | 40.000 |
| 414 HCV 3b | 59 | 40 | 9 | B7 | SPRVCWAYA | 7511 | 20.000 |
| 415 HCV 3b | 59 | 21 | 9 | B_3501 | SPVTTFLSL | 7512 | 20.000 |
| 416 HCV 3b | 59 | 52 | 9 | B_3501 | DSRRHPIFL | 7513 | 15.000 |

TABLE 4l-continued

3b (4-6)

| No. | Strain | ORF | Start | AA | HLA | Peptide sequence | SEQ ID NO: | Score |
|---|---|---|---|---|---|---|---|---|
| 417 | HCV 3b | 59 | 7 | 9 | B_3501 | VPKKVWVAV | 7514 | 12.000 |
| 418 | HCV 3b | 59 | 39 | 9 | B_3501 | NSPRVCWAY | 7515 | 10.000 |
| 419 | HCV 3b | 59 | 37 | 9 | B_3501 | VPNSPRVCW | 7516 | 10.000 |
| 420 | HCV 3b | 59 | 1 | 10 | A1 | MTPPtVVPKK | 7517 | 10.000 |
| 421 | HCV 3b | 59 | 28 | 10 | A_0201 | SLPVrLVTIV | 7518 | 65.588 |
| 422 | HCV 3b | 59 | 6 | 10 | A_0201 | VVPKkVWVAV | 7519 | 17.588 |
| 423 | HCV 3b | 59 | 26 | 10 | A_0201 | FLSLpVRLVT | 7520 | 14.054 |
| 424 | HCV 3b | 59 | 10 | 10 | A_0201 | KVWVaVDSTC | 7521 | 12.628 |
| 425 | HCV 3b | 60 | 21 | 9 | A_0201 | KMTGSVATA | 7522 | 28.883 |
| 426 | HCV 3b | 60 | 33 | 9 | B7 | RPSAAQSCM | 7523 | 20.000 |
| 427 | HCV 3b | 60 | 33 | 9 | B_3501 | RPSAAQSCM | 7524 | 80.000 |
| 428 | HCV 3b | 60 | 39 | 9 | B_4403 | SCMGDRWSY | 7525 | 18.000 |
| 429 | HCV 3b | 60 | 14 | 10 | A_0201 | TLISiGLKMT | 7526 | 17.140 |
| 430 | HCV 3b | 60 | 6 | 10 | B7 | AVSApQVITL | 7527 | 60.000 |
| 431 | HCV 3b | 60 | 9 | 10 | B7 | APQViTLISI | 7528 | 24.000 |
| 432 | HCV 3b | 60 | 11 | 10 | B7 | QVITLISIGL | 7529 | 20.000 |
| 433 | HCV 3b | 60 | 38 | 10 | B_3501 | QSCMgDRWSY | 7530 | 15.000 |
| 434 | HCV 3b | 61 | | | | no hits | | |
| 435 | HCV 3b | 62 | 33 | 9 | A1 | AASPLHMAY | 7531 | 25.000 |
| 436 | HCV 3b | 62 | 7 | 9 | A24 | GYSRLASKI | 7532 | 66.000 |
| 437 | HCV 3b | 62 | 52 | 9 | A3 | CLYHGDKVK | 7533 | 50.000 |
| 438 | HCV 3b | 62 | 45 | 9 | B7 | QIRRPIQCL | 7534 | 60.000 |
| 439 | HCV 3b | 62 | 3 | 9 | B7 | KIREGYSRL | 7535 | 40.000 |
| 440 | HCV 3b | 62 | 20 | 9 | B7 | LPRTSRGGT | 7536 | 30.000 |
| 441 | HCV 3b | 62 | 61 | 9 | B7 | NPRSRSTPA | 7537 | 20.000 |
| 442 | HCV 3b | 62 | 12 | 9 | B7 | ASKITLSRL | 7538 | 12.000 |
| 443 | HCV 3b | 62 | 63 | 9 | B7 | RSRSTPAPM | 7539 | 10.000 |
| 444 | HCV 3b | 62 | 61 | 9 | B8 | NPRSRSTPA | 7540 | 16.000 |
| 445 | HCV 3b | 62 | 63 | 9 | B_3501 | RSRSTPAPM | 7541 | 60.000 |
| 446 | HCV 3b | 62 | 35 | 9 | B_3501 | SPLHMAYWF | 7542 | 20.000 |
| 447 | HCV 3b | 62 | 12 | 9 | B_3501 | ASKITLSRL | 7543 | 15.000 |
| 448 | HCV 3b | 62 | 3 | 9 | B_3501 | KIREGYSRL | 7544 | 12.000 |
| 449 | HCV 3b | 62 | 33 | 9 | B_4403 | AASPLHMAY | 7545 | 12.000 |
| 450 | HCV 3b | 62 | 10 | 10 | A3 | RLASkITLSR | 7546 | 12.000 |
| 451 | HCV 3b | 62 | 38 | 10 | A3 | HMAYwFHQIR | 7547 | 12.000 |
| 452 | HCV 3b | 62 | 8 | 10 | B7 | YSRLaSKITL | 7548 | 40.000 |
| 453 | HCV 3b | 62 | 69 | 10 | B7 | APMVaSSSPV | 7549 | 36.000 |
| 454 | HCV 3b | 62 | 11 | 10 | B7 | LASKiTLSRL | 7550 | 12.000 |
| 455 | HCV 3b | 62 | 8 | 10 | B_3501 | YSRLaSKITL | 7551 | 15.000 |
| 456 | HCV 3b | 62 | 32 | 10 | B_3501 | KAASpLHMAY | 7552 | 12.000 |
| 457 | HCV 3b | 63 | 3 | 9 | B_4403 | HAAQNATRY | 7553 | 13.500 |
| 458 | HCV 3b | 64 | 68 | 9 | A_0201 | TLNIEKFTV | 7554 | 403.402 |
| 459 | HCV 3b | 64 | 61 | 9 | B7 | CPPTNILTL | 7555 | 80.000 |
| 460 | HCV 3b | 64 | 44 | 9 | B7 | SQRSPLVQL | 7556 | 60.000 |
| 461 | HCV 3b | 64 | 41 | 9 | B7 | SSRSQRSPL | 7557 | 60.000 |
| 462 | HCV 3b | 64 | 61 | 9 | B_3501 | CPPTNILTL | 7558 | 20.000 |
| 463 | HCV 3b | 64 | 41 | 9 | B_3501 | SSRSQRSPL | 7559 | 15.000 |
| 464 | HCV 3b | 64 | 24 | 9 | B_4403 | SESVVEWSS | 7560 | 12.000 |
| 465 | HCV 3b | 64 | 66 | 10 | A_0201 | ILTLnIEKFT | 7561 | 69.676 |
| 466 | HCV 3b | 64 | 67 | 10 | A_0201 | LTLNiEKFTV | 7562 | 35.242 |
| 467 | HCV 3b | 64 | 43 | 10 | A24 | RSQRsPLVQL | 7563 | 12.000 |
| 468 | HCV 3b | 64 | 41 | 10 | B8 | SSRSqRSPLV | 7564 | 12.000 |
| 469 | HCV 3b | 64 | 40 | 10 | B_3501 | RSSRsQRSPL | 7565 | 10.000 |
| 470 | HCV 3b | 64 | 43 | 10 | B_3501 | RSQRsPLVQL | 7566 | 10.000 |
| 471 | HCV 3b | 65 | 1 | 9 | A_0201 | MLQGGAPQV | 7567 | 118.238 |
| 472 | HCV 3b | 65 | 6 | 9 | B7 | APQVFTNPV | 7568 | 12.000 |
| 473 | HCV 3b | 65 | 8 | 10 | A_0201 | QVFTnPVLFI | 7569 | 42.727 |
| 474 | HCV 3b | 65 | 6 | 10 | B7 | APQVfTNPVL | 7570 | 240.000 |
| 475 | HCV 3b | 65 | 20 | 10 | B7 | HPNHrPWGGL | 7571 | 120.000 |
| 476 | HCV 3b | 65 | 20 | 10 | B_3501 | HPNHrPWGGL | 7572 | 20.000 |
| 477 | HCV 3b | 65 | 6 | 10 | B_3501 | APQVfTNPVL | 7573 | 20.000 |
| 478 | HCV 3b | 65 | 30 | 10 | B_4403 | KEVNkKTSDS | 7574 | 18.000 |
| 479 | HCV 3b | 66 | | | | no hits | | |
| 480 | HCV 3b | 67 | 6 | 10 | B7 | DIRSgHPEEL | 7575 | 40.000 |
| 481 | HCV 3b | 67 | 8 | 10 | B_3501 | RSGHpEELNL | 7576 | 15.000 |
| 482 | HCV 3b | 68 | 4 | 10 | B_3501 | DPFELTNCKF | 7577 | 40.000 |
| 483 | HCV 3b | 69 | 3 | 9 | B7 | STMTTLAQL | 7578 | 12.000 |
| 484 | HCV 3b | 69 | 7 | 10 | A3 | TLAQLPCMEK | 7579 | 60.000 |
| 485 | HCV 3b | 70 | 3 | 9 | A1 | LLEQSLVSK | 7580 | 36.000 |
| 486 | HCV 3b | 70 | 1 | 9 | A_0201 | MLLLEQSLV | 7581 | 437.482 |
| 487 | HCV 3b | 70 | 39 | 9 | A_0201 | KEQPGRFPV | 7582 | 27.454 |
| 488 | HCV 3b | 70 | 11 | 9 | A24 | KYRPDAFLY | 7583 | 12.000 |
| 489 | HCV 3b | 70 | 3 | 9 | A3 | LLEQSLVSK | 7584 | 30.000 |
| 490 | HCV 3b | 70 | 9 | 9 | B_3501 | VSKYRPDAF | 7585 | 15.000 |
| 491 | HCV 3b | 70 | 4 | 9 | B_4403 | LEQSLVSKY | 7586 | 540.000 |

TABLE 4l-continued 3b (4-6)

| No. | Strain | ORF | Start | AA | HLA | Peptide sequence | SEQ ID NO: | Score |
|---|---|---|---|---|---|---|---|---|
| 492 | HCV 3b | 70 | 37 | 9 | B_4403 | IEKEQPGRF | 7587 | 40.000 |
| 493 | HCV 3b | 70 | 39 | 9 | B_4403 | KEQPGRFPV | 7588 | 12.000 |
| 494 | HCV 3b | 70 | 3 | 10 | A1 | LLEQsLVSKY | 7589 | 45.000 |
| 495 | HCV 3b | 70 | 11 | 10 | A24 | KYRPdAFLYS | 7590 | 14.400 |
| 496 | HCV 3b | 70 | 2 | 10 | A3 | LLLEqSLVSK | 7591 | 67.500 |
| 497 | HCV 3b | 70 | 3 | 10 | A3 | LLEQsLVSKY | 7592 | 12.000 |
| 498 | HCV 3b | 70 | 13 | 10 | B7 | RPDAfLYSRL | 7593 | 24.000 |
| 499 | HCV 3b | 70 | 9 | 10 | B_3501 | VSKYrPDAFL | 7594 | 15.000 |
| 500 | HCV 3b | 70 | 13 | 10 | B_3501 | RPDAfLYSRL | 7595 | 12.000 |
| 501 | HCV 3b | 71 | 15 | 9 | B7 | RVSMTLPKL | 7596 | 20.000 |
| 502 | HCV 3b | 71 | 45 | 9 | B_3501 | HPAQPQPSF | 7597 | 20.000 |
| 503 | HCV 3b | 71 | 11 | 10 | B7 | NPHVrVSMTL | 7598 | 80.000 |
| 504 | HCV 3b | 71 | 38 | 10 | B7 | EPRGgKSHPA | 7599 | 20.000 |
| 505 | HCV 3b | 71 | 5 | 10 | B7 | YPMRsANPHV | 7600 | 12.000 |
| 506 | HCV 3b | 71 | 38 | 10 | B8 | EPRGgKSHPA | 7601 | 32.000 |
| 507 | HCV 3b | 71 | 11 | 10 | B_3501 | NPHVrVSMTL | 7602 | 20.000 |
| 508 | HCV 3b | 71 | 22 | 10 | B_3501 | KLRDLRRGSF | 7603 | 12.000 |
| 509 | HCV 3b | 72 | 15 | 9 | A24 | PYQAVPQGL | 7604 | 50.400 |
| 510 | HCV 3b | 72 | 22 | 9 | A3 | GLSRPNTTR | 7605 | 18.000 |
| 511 | HCV 3b | 72 | 23 | 9 | B7 | LSRPNTTRL | 7606 | 40.000 |
| 512 | HCV 3b | 72 | 25 | 9 | B7 | RPNTTRLVI | 7607 | 12.000 |
| 513 | HCV 3b | 72 | 8 | 9 | B_3501 | LPGHSQAPY | 7608 | 40.000 |
| 514 | HCV 3b | 72 | 25 | 9 | B_3501 | RPNTTRLVI | 7609 | 16.000 |
| 515 | HCV 3b | 72 | 23 | 9 | B_3501 | LSRPNTTRL | 7610 | 15.000 |
| 516 | HCV 3b | 72 | 22 | 10 | A_0201 | GLSRpNTTRL | 7611 | 21.362 |
| 517 | HCV 3b | 72 | 14 | 10 | B7 | APYQaVPQGL | 7612 | 240.000 |
| 518 | HCV 3b | 72 | 14 | 10 | B_3501 | APYQaVPQGL | 7613 | 20.000 |

TABLE 4m

H77 (1-3)

| No. | Strain | ORF | Start | AA | HLA | Peptide sequence | SEQ ID NO: | Score |
|---|---|---|---|---|---|---|---|---|
| 1 | HCV H77 | 1 | 17 | 9 | B7 | SSRRKRLAM | 7614 | 15.000 |
| 2 | HCV H77 | 1 | 2 | 9 | B7 | GATLHHESL | 7615 | 12.000 |
| 3 | HCV H77 | 1 | 17 | 9 | B8 | SSRRKRLAM | 7616 | 20.000 |
| 4 | HCV H77 | 1 | 14 | 10 | B8 | ELLSSRRKRL | 7617 | 16.000 |
| 5 | HCV H77 | 1 | 17 | 9 | B3501 | SSRRKRLAM | 7618 | 30.000 |
| 6 | HCV H77 | 1 | 16 | 10 | B3501 | LSSRKRLAM | 7619 | 10.000 |
| 7 | HCV H77 | 1 | 15 | 9 | A0201 | LLSSRKRL | 7620 | 36.316 |
| 8 | HCV H77 | 2 | 43 | 10 | B4403 | AASPTSWGTY | 7621 | 12.000 |
| 9 | HCV H77 | 2 | 53 | 10 | B3501 | RSSAPLLEAL | 7622 | 10.000 |
| 10 | HCV H77 | 2 | 64 | 10 | B3501 | GPWRMASGFW | 7623 | 10.000 |
| 11 | HCV H77 | 2 | 64 | 9 | B3501 | GPWRMASGF | 7624 | 20.000 |
| 12 | HCV H77 | 2 | 44 | 9 | B3501 | ASPTSWGTY | 7625 | 10.000 |
| 13 | HCV H77 | 2 | 26 | 9 | B3501 | TPGVGRAIW | 7626 | 10.000 |
| 14 | HCV H77 | 2 | 5 | 10 | B7 | VAGGRDGSCL | 7627 | 12.000 |
| 15 | HCV H77 | 2 | 32 | 10 | B7 | AIWVRSSIPL | 7628 | 12.000 |
| 16 | HCV H77 | 2 | 6 | 9 | B7 | AGGRDGSCL | 7629 | 12.000 |
| 17 | HCV H77 | 2 | 51 | 9 | A24 | TYRSSAPLL | 7630 | 200.000 |
| 18 | HCV H77 | 2 | 12 | 9 | A24 | SCLPVALGL | 7631 | 10.080 |
| 19 | HCV H77 | 2 | 32 | 10 | A0201 | AIWVRSSIPL | 7632 | 24.380 |
| 20 | HCV H77 | 2 | 67 | 10 | A0201 | RMASGFWKTA | 7633 | 23.178 |
| 21 | HCV H77 | 2 | 67 | 9 | A0201 | RMASGFWKT | 7634 | 76.695 |
| 22 | HCV H77 | 2 | 58 | 10 | A1 | LLEALPGPWR | 7635 | 18.000 |
| 23 | HCV H77 | 3 | 2 | 9 | A0201 | QQGTFLVAL | 7636 | 18.930 |
| 24 | HCV H77 | 4 | 2 | 10 | B3501 | SPMIALTRVL | 7637 | 20.000 |
| 25 | HCV H77 | 4 | 19 | 9 | B8 | SCTLRGVSL | 7638 | 16.000 |
| 26 | HCV H77 | 4 | 2 | 10 | B7 | SPMIALTRVL | 7639 | 240.000 |
| 27 | HCV H77 | 4 | 2 | 9 | B7 | SPMIALTRV | 7640 | 12.000 |
| 28 | HCV H77 | 4 | 26 | 10 | A3 | SLAFARVTPR | 7641 | 12.000 |
| 29 | HCV H77 | 4 | 24 | 9 | A0201 | GVSLAFARV | 7642 | 11.563 |
| 30 | HCV H77 | 5 | 4 | 10 | B3501 | APRLGLLVSL | 7643 | 60.000 |
| 31 | HCV H77 | 5 | 1 | 10 | B3501 | MPAAPRLGLL | 7644 | 20.000 |
| 32 | HCV H77 | 5 | 1 | 10 | B8 | MPAAPRLGLL | 7645 | 16.000 |
| 33 | HCV H77 | 5 | 4 | 10 | B8 | APRLGLLVSL | 7646 | 16.000 |
| 34 | HCV H77 | 5 | 4 | 10 | B7 | APRLGLLVSL | 7647 | 240.000 |
| 35 | HCV H77 | 5 | 1 | 10 | B7 | MPAAPRLGLL | 7648 | 80.000 |
| 36 | HCV H77 | 5 | 8 | 9 | A0201 | GLLVSLHQA | 7649 | 42.278 |
| 37 | HCV H77 | 7 | 24 | 10 | B3501 | CPQRACVARY | 7650 | 40.000 |
| 38 | HCV H77 | 7 | 28 | 10 | B7 | ACVARYIASL | 7651 | 12.000 |

TABLE 4m-continued

H77 (1-3)

| No. | Strain | ORF | Start | AA | HLA | Peptide sequence | SEQ ID NO: | Score |
|---|---|---|---|---|---|---|---|---|
| 39 | HCV H77 | 7 | 57 | 10 | B7 | VQMIRMSSSL | 7652 | 12.000 |
| 40 | HCV H77 | 7 | 29 | 9 | B7 | CVARYIASL | 7653 | 20.000 |
| 41 | HCV H77 | 7 | 12 | 9 | B7 | TAGTTLQDL | 7654 | 12.000 |
| 42 | HCV H77 | 7 | 9 | 9 | B7 | NAPTAGTTL | 7655 | 12.000 |
| 43 | HCV H77 | 7 | 36 | 10 | A3 | SLPAPWWWER | 7656 | 36.000 |
| 44 | HCV H77 | 7 | 32 | 10 | A24 | RYIALPAPW | 7657 | 18.000 |
| 45 | HCV H77 | 7 | 51 | 10 | A0201 | RLPTAGVQMI | 7658 | 23.995 |
| 46 | HCV H77 | 7 | 57 | 10 | A0201 | VQMIRMSSSL | 7659 | 13.624 |
| 47 | HCV H77 | 7 | 22 | 9 | A0201 | ALCPQRACV | 7660 | 69.552 |
| 48 | HCV H77 | 7 | 16 | 9 | A0201 | TLQDLVALC | 7661 | 46.848 |
| 49 | HCV H77 | 7 | 58 | 9 | A0201 | QMIRMSSSL | 7662 | 15.428 |
| 50 | HCV H77 | 8 | 3 | 9 | B3501 | HPWPGRTVL | 7663 | 20.000 |
| 51 | HCV H77 | 8 | 12 | 9 | B3501 | CPSSCSSAL | 7664 | 20.000 |
| 52 | HCV H77 | 10 | 61 | 10 | A24 | RYCLGQFTEW | 7665 | 11.000 |
| 53 | HCV H77 | 10 | 13 | 10 | A24 | RTTACEIWPL | 7666 | 8.000 |
| 54 | HCV H77 | 10 | 2 | 10 | A0201 | CITISPLFET | 7667 | 13.669 |
| 55 | HCV H77 | 10 | 9 | 9 | B4403 | FETGRTTAC | 7668 | 13.500 |
| 56 | HCV H77 | 10 | 17 | 10 | B4403 | CEIWPLWNQS | 7669 | 20.000 |
| 57 | HCV H77 | 10 | 55 | 10 | B3501 | LPVGARRYCL | 7670 | 20.000 |
| 58 | HCV H77 | 10 | 32 | 10 | B3501 | RPSSSRGGQI | 7671 | 16.000 |
| 59 | HCV H77 | 10 | 55 | 10 | B8 | LPVGARRYCL | 7672 | 16.000 |
| 60 | HCV H77 | 10 | 55 | 10 | B7 | LPVGARRYCL | 7673 | 120.000 |
| 61 | HCV H77 | 11 | 33 | 10 | A0201 | TLWAGPLLKV | 7674 | 1.327.748 |
| 62 | HCV H77 | 11 | 32 | 10 | A24 | KTLWAGPLL | 7675 | 12.000 |
| 63 | HCV H77 | 11 | 25 | 10 | A24 | RCIPMWTKTL | 7676 | 14.400 |
| 64 | HCV H77 | 11 | 13 | 10 | A24 | RGPSHHPRVL | 7677 | 12.000 |
| 65 | HCV H77 | 11 | 33 | 9 | A3 | TLWAGPLLK | 7678 | 200.000 |
| 66 | HCV H77 | 11 | 5 | 9 | A3 | GLSTTGPER | 7679 | 12.000 |
| 67 | HCV H77 | 11 | 14 | 9 | B7 | GPSHHPRVL | 7680 | 80.000 |
| 68 | HCV H77 | 11 | 18 | 9 | B7 | HPRVLSSRC | 7681 | 20.000 |
| 69 | HCV H77 | 11 | 18 | 10 | B7 | HPRVLSSRCI | 7682 | 80.000 |
| 70 | HCV H77 | 11 | 14 | 9 | B3501 | GPSHHPRVL | 7683 | 20.000 |
| 71 | HCV H77 | 11 | 27 | 9 | B3501 | IPMWTKTLW | 7684 | 10.000 |
| 72 | HCV H77 | 11 | 18 | 10 | B3501 | HPRVLSSRCI | 7685 | 24.000 |
| 73 | HCV H77 | 12 | 7 | 9 | B4403 | GEVIAGVAC | 7686 | 18.000 |
| 74 | HCV H77 | 12 | 7 | 10 | B4403 | GEVIAGVACF | 7687 | 360.000 |
| 75 | HCV H77 | 13 | 40 | 10 | B3501 | CPRPMGLILI | 7688 | 24.000 |
| 76 | HCV H77 | 13 | 27 | 10 | B3501 | TPLLLQRWAL | 7689 | 20.000 |
| 77 | HCV H77 | 13 | 40 | 9 | B3501 | CPRPMGLIL | 7690 | 60.000 |
| 78 | HCV H77 | 13 | 40 | 9 | B8 | CPRPMGLIL | 7691 | 16.000 |
| 79 | HCV H77 | 13 | 27 | 10 | B7 | TPLLLQRWAL | 7692 | 120.000 |
| 80 | HCV H77 | 13 | 20 | 10 | B7 | ATRCWCSTPL | 7693 | 120.000 |
| 81 | HCV H77 | 13 | 5 | 10 | B7 | AAVRAPRSRL | 7694 | 81.000 |
| 82 | HCV H77 | 13 | 40 | 10 | B7 | CPRPMGLILI | 7695 | 80.000 |
| 83 | HCV H77 | 13 | 6 | 9 | B7 | AVRAPRSRL | 7696 | 1.350.000 |
| 84 | HCV H77 | 13 | 40 | 9 | B7 | CPRPMGLIL | 7697 | 800.000 |
| 85 | HCV H77 | 13 | 17 | 9 | B7 | QPRATRCWC | 7698 | 30.000 |
| 86 | HCV H77 | 13 | 29 | 10 | A0201 | LLLQRWALVL | 7699 | 55.091 |
| 87 | HCV H77 | 13 | 37 | 10 | A0201 | VLTCPRPMGL | 7700 | 36.316 |
| 88 | HCV H77 | 13 | 30 | 10 | A0201 | LLQRWALVLT | 7701 | 29.137 |
| 89 | HCV H77 | 13 | 29 | 9 | A0201 | LLLQRWALV | 7702 | 743.720 |
| 90 | HCV H77 | 13 | 30 | 9 | A0201 | LLQRWALVL | 7703 | 14.890 |
| 91 | HCV H77 | 13 | 28 | 9 | A0201 | PLLLQRWAL | 7704 | 13.042 |
| 92 | HCV H77 | 14 | 22 | 9 | A0201 | WLCSPLLPL | 7705 | 226.014 |
| 93 | HCV H77 | 14 | 27 | 9 | A0201 | LLPLRAPSL | 7706 | 36.316 |
| 94 | HCV H77 | 14 | 9 | 9 | A0201 | ALSLTKQRL | 7707 | 21.362 |
| 95 | HCV H77 | 14 | 31 | 9 | A24 | RAPSLCPIL | 7708 | 14.400 |
| 96 | HCV H77 | 14 | 1 | 10 | B3501 | MPHPSWASAL | 7709 | 20.000 |
| 97 | HCV H77 | 14 | 3 | 10 | B3501 | HPSWASALSL | 7710 | 20.000 |
| 98 | HCV H77 | 14 | 36 | 10 | B3501 | CPILTSRRLL | 7711 | 20.000 |
| 99 | HCV H77 | 14 | 18 | 10 | B3501 | RGRDWLCSPL | 7712 | 12.000 |
| 100 | HCV H77 | 14 | 46 | 9 | B3501 | CPPPERSPF | 7713 | 30.000 |
| 101 | HCV H77 | 14 | 36 | 9 | B3501 | CPILTSRRL | 7714 | 20.000 |
| 102 | HCV H77 | 14 | 36 | 10 | B7 | CPILTSRRLL | 7715 | 120.000 |
| 103 | HCV H77 | 14 | 1 | 10 | B7 | MPHPSWASAL | 7716 | 80.000 |
| 104 | HCV H77 | 14 | 3 | 10 | B7 | HPSWASALSL | 7717 | 80.000 |
| 105 | HCV H77 | 14 | 14 | 10 | B7 | KQRLRGRDWL | 7718 | 60.000 |
| 106 | HCV H77 | 14 | 18 | 10 | B7 | RGRDWLCSPL | 7719 | 40.000 |
| 107 | HCV H77 | 14 | 8 | 10 | B7 | SALSLTKQRL | 7720 | 12.000 |
| 108 | HCV H77 | 14 | 36 | 9 | B7 | CPILTSRRL | 7721 | 80.000 |
| 109 | HCV H77 | 14 | 31 | 9 | B7 | RAPSLCPIL | 7722 | 12.000 |
| 110 | HCV H77 | 14 | 9 | 9 | B7 | ALSLTKQRL | 7723 | 12.000 |
| 111 | HCV H77 | 14 | 34 | 9 | A3 | SLCPILTSR | 7724 | 13.500 |
| 112 | HCV H77 | 14 | 18 | 10 | A24 | RGRDWLCSPL | 7725 | 11.520 |
| 113 | HCV H77 | 15 | 3 | 10 | B7 | WPTTAVLTCL | 7726 | 80.000 |

TABLE 4m-continued

H77 (1-3)

| No. Strain | ORF | Start | AA | HLA | Peptide sequence | SEQ ID NO: | Score |
|---|---|---|---|---|---|---|---|
| 114 HCV H77 | 15 | 17 | 10 | B7 | AAMLSSCRPM | 7727 | 27.000 |
| 115 HCV H77 | 15 | 18 | 10 | B7 | AMLSSCRPML | 7728 | 18.000 |
| 116 HCV H77 | 15 | 1 | 9 | B3501 | MPWPTTAVL | 7729 | 20.000 |
| 117 HCV H77 | 15 | 3 | 10 | B3501 | WPTTAVLTCL | 7730 | 20.000 |
| 118 HCV H77 | 15 | 1 | 9 | B7 | MPWPTTAVL | 7731 | 80.000 |
| 119 HCV H77 | 15 | 18 | 10 | A0201 | AMLSSCRPML | 7732 | 57.085 |
| 120 HCV H77 | 15 | 11 | 10 | A0201 | CLSSRPAAML | 7733 | 21.362 |
| 121 HCV H77 | 15 | 19 | 9 | A0201 | MLSSCRPML | 7734 | 36.316 |
| 122 HCV H77 | 16 | 3 | 10 | B3501 | SPGLNAGAGL | 7735 | 20.000 |
| 123 HCV H77 | 16 | 52 | 9 | B3501 | RPPRLQLGY | 7736 | 80.000 |
| 124 HCV H77 | 16 | 3 | 10 | B7 | SPGLNAGAGL | 7737 | 80.000 |
| 125 HCV H77 | 16 | 38 | 10 | B7 | SVSAMTRAVL | 7738 | 30.000 |
| 126 HCV H77 | 16 | 47 | 10 | B7 | LGMSSRPPRL | 7739 | 12.000 |
| 127 HCV H77 | 16 | 13 | 10 | B7 | AGGSQASIDL | 7740 | 12.000 |
| 128 HCV H77 | 16 | 33 | 10 | B7 | STRPSSVSAM | 7741 | 10.000 |
| 129 HCV H77 | 16 | 50 | 9 | B7 | SSRPPRLQL | 7742 | 90.000 |
| 130 HCV H77 | 16 | 11 | 10 | A0201 | GLAGGSQASI | 7743 | 10.433 |
| 131 HCV H77 | 16 | 48 | 9 | A0201 | GMSSRPPRL | 7744 | 15.428 |
| 132 HCV H77 | 17 | 8 | 9 | B3501 | QSRVGRTFL | 7745 | 15.000 |
| 133 HCV H77 | 17 | 5 | 10 | B7 | YPRQSRVGRT | 7746 | 20.000 |
| 134 HCV H77 | 17 | 8 | 9 | B7 | QSRVGRTFL | 7747 | 60.000 |
| 135 HCV H77 | 17 | 7 | 10 | A0201 | RQSRVGRTFL | 7748 | 11.913 |
| 136 HCV H77 | 18 | 4 | 10 | B3501 | HPCYTDWALF | 7749 | 30.000 |
| 137 HCV H77 | 18 | 4 | 9 | B3501 | HPCYTDWAL | 7750 | 20.000 |
| 138 HCV H77 | 18 | 4 | 9 | B7 | HPCYTDWAL | 7751 | 80.000 |
| 139 HCV H77 | 18 | 6 | 10 | A24 | CYTDWALFRM | 7752 | 30.000 |
| 140 HCV H77 | 18 | 7 | 10 | A1 | YTDWALFRMK | 7753 | 25.000 |
| 141 HCV H77 | 19 | 6 | 10 | A3 | ALSTYRTSSK | 7754 | 20.000 |
| 142 HCV H77 | 20 | 39 | 9 | A24 | RCLVTPPLL | 7755 | 12.000 |
| 143 HCV H77 | 20 | 37 | 10 | B7 | CQRCLVTPPL | 7756 | 40.000 |
| 144 HCV H77 | 20 | 10 | 10 | B3501 | RPTGRNSRSF | 7757 | 40.000 |
| 145 HCV H77 | 21 | 2 | 9 | B7 | MARAWRELL | 7758 | 180.000 |
| 146 HCV H77 | 21 | 2 | 9 | B8 | MARAWRELL | 7759 | 16.000 |
| 147 HCV H77 | 22 | 11 | 10 | A1 | AMQPPASLPY | 7760 | 12.500 |
| 148 HCV H77 | 22 | 17 | 9 | A1 | SLPYSAASL | 7761 | 21.362 |
| 149 HCV H77 | 22 | 10 | 9 | A24 | RAMQPPASL | 7762 | 12.000 |
| 150 HCV H77 | 22 | 11 | 10 | A3 | AMQPPASLPY | 7763 | 12.000 |
| 151 HCV H77 | 22 | 10 | 9 | B7 | RAMQPPASL | 7764 | 54.000 |
| 152 HCV H77 | 22 | 3 | 10 | B7 | PPRTTCRRAM | 7765 | 30.000 |
| 153 HCV H77 | 22 | 16 | 10 | B7 | ASLPYSAASL | 7766 | 12.000 |
| 154 HCV H77 | 22 | 3 | 10 | B3501 | PPRTTCRRAM | 7767 | 12.000 |
| 155 HCV H77 | 24 | 6 | 10 | A24 | PYLQKFCGSL | 7768 | 30.000 |
| 156 HCV H77 | 24 | 7 | 9 | A0201 | YLQKFCGSL | 7769 | 48.544 |
| 157 HCV H77 | 25 | 96 | 10 | B3501 | RSVVGPTPKM | 7770 | 20.000 |
| 158 HCV H77 | 25 | 27 | 10 | B3501 | QPYLLPWPSL | 7771 | 20.000 |
| 159 HCV H77 | 25 | 75 | 10 | B3501 | LPCPPWRGSL | 7772 | 20.000 |
| 160 HCV H77 | 25 | 24 | 10 | B3501 | SPNQPYLLPW | 7773 | 10.000 |
| 161 HCV H77 | 25 | 33 | 9 | B3501 | WPSLPPKVL | 7774 | 20.000 |
| 162 HCV H77 | 25 | 72 | 9 | B3501 | SPILPCPPW | 7775 | 10.000 |
| 163 HCV H77 | 25 | 2 | 10 | B8 | AARYHLHGPL | 7776 | 16.000 |
| 164 HCV H77 | 25 | 2 | 10 | B7 | AARYHLHGPL | 7777 | 360.000 |
| 165 HCV H77 | 25 | 75 | 10 | B7 | LPCPPWRGSL | 7778 | 120.000 |
| 166 HCV H77 | 25 | 27 | 10 | B7 | QPYLLPWPSL | 7779 | 120.000 |
| 167 HCV H77 | 25 | 65 | 10 | B7 | APPTPTLSPI | 7780 | 24.000 |
| 168 HCV H77 | 25 | 33 | 9 | B7 | WPSLPPKVL | 7781 | 120.000 |
| 169 HCV H77 | 25 | 63 | 9 | B7 | LAAPPTPTL | 7782 | 18.000 |
| 170 HCV H77 | 25 | 116 | 9 | B7 | QAHSSPRAL | 7783 | 12.000 |
| 171 HCV H77 | 25 | 41 | 9 | B7 | LAAPQLPAL | 7784 | 12.000 |
| 172 HCV H77 | 25 | 50 | 9 | B7 | RATIRQHPL | 7785 | 12.000 |
| 173 HCV H77 | 25 | 30 | 10 | A3 | LLPWPSLPPK | 7786 | 30.000 |
| 174 HCV H77 | 25 | 4 | 10 | A24 | RYHLHGPLLC | 7787 | 10.000 |
| 175 HCV H77 | 25 | 4 | 9 | A24 | RYHLHGPLL | 7788 | 400.000 |
| 176 HCV H77 | 25 | 28 | 9 | A24 | PYLLPWPSL | 7789 | 30.000 |
| 177 HCV H77 | 25 | 54 | 9 | A24 | RQHPLSPPL | 7790 | 11.520 |
| 178 HCV H77 | 25 | 11 | 10 | A0201 | LLCLRLGKSV | 7791 | 118.238 |
| 179 HCV H77 | 25 | 40 | 10 | A0201 | VLAAPQLPAL | 7792 | 83.527 |
| 180 HCV H77 | 25 | 62 | 10 | A0201 | LLAAPPTPTL | 7793 | 36.316 |
| 181 HCV H77 | 25 | 104 | 10 | A0201 | KMSCAAQCLI | 7794 | 26.372 |
| 182 HCV H77 | 25 | 104 | 9 | A0201 | KMSCAAQCL | 7795 | 53.999 |
| 183 HCV H77 | 25 | 83 | 9 | A0201 | SLGIRISAT | 7796 | 17.140 |
| 184 HCV H77 | 25 | 62 | 9 | A0201 | LLAAPPTPT | 7797 | 12.668 |
| 185 HCV H77 | 25 | 35 | 9 | A0201 | SLPPKVLAA | 7798 | 11.426 |
| 186 HCV H77 | 25 | 45 | 9 | A0201 | QLPALRATI | 7799 | 10.433 |
| 187 HCV H77 | 25 | 118 | 9 | A1 | HSSPRALRK | 7800 | 15.000 |
| 188 HCV H77 | 27 | 57 | 10 | B4403 | ATAGAARAAY | 7801 | 27.000 |

TABLE 4m-continued

H77 (1-3)

| No. Strain | ORF | Start | AA | HLA | Peptide sequence | SEQ ID NO: | Score |
|---|---|---|---|---|---|---|---|
| 189 HCV H77 | 27 | 30 | 10 | B3501 | KPAWPSSLSL | 7802 | 40.000 |
| 190 HCV H77 | 27 | 33 | 10 | B3501 | WPSSPSLRGF | 7803 | 20.000 |
| 191 HCV H77 | 27 | 36 | 9 | B3501 | SPSLRGFML | 7804 | 20.000 |
| 192 HCV H77 | 27 | 35 | 9 | B3501 | SSPSLRGFM | 7805 | 10.000 |
| 193 HCV H77 | 27 | 36 | 9 | B8 | SPSLRGFML | 7806 | 16.000 |
| 194 HCV H77 | 27 | 2 | 10 | B7 | IPAVLTPQSL | 7807 | 80.000 |
| 195 HCV H77 | 27 | 30 | 10 | B7 | KPAWPSSLSL | 7808 | 80.000 |
| 196 HCV H77 | 27 | 38 | 10 | B7 | SLRGFMLGAL | 7809 | 40.000 |
| 197 HCV H77 | 27 | 15 | 10 | B7 | SVRRRQFTNV | 7810 | 10.000 |
| 198 HCV H77 | 27 | 36 | 9 | B7 | SPSLRGFML | 7811 | 80.000 |
| 199 HCV H77 | 27 | 46 | 9 | A3 | ALLPIQGGK | 7812 | 20.000 |
| 200 HCV H77 | 27 | 19 | 10 | A0201 | RQFTNVVTWT | 7813 | 35.364 |
| 201 HCV H77 | 27 | 42 | 9 | A0201 | FMLGALLPI | 7814 | 294.957 |
| 202 HCV H77 | 28 | 48 | 9 | B4403 | EEAGLPYVA | 7815 | 12.000 |
| 203 HCV H77 | 28 | 31 | 10 | B4403 | CELGDTGPGA | 7816 | 12.000 |
| 204 HCV H77 | 28 | 48 | 10 | B4403 | EEAGLPYVAS | 7817 | 12.000 |
| 205 HCV H77 | 28 | 46 | 9 | B3501 | CPEEAGLPY | 7818 | 24.000 |
| 206 HCV H77 | 28 | 37 | 9 | B3501 | GPGASALGF | 7819 | 20.000 |
| 207 HCV H77 | 28 | 3 | 10 | B7 | SAHFHSTVTL | 7820 | 12.000 |
| 208 HCV H77 | 28 | 44 | 9 | A24 | GFCPEEAGL | 7821 | 24.000 |
| 209 HCV H77 | 28 | 25 | 9 | A0201 | NLGSRPCEL | 7822 | 21.362 |
| 210 HCV H77 | 28 | 46 | 9 | A1 | CPEEAGLPY | 7823 | 56.250 |
| 211 HCV H77 | 29 | 3 | 9 | B4403 | GPAGSGFAY | 7824 | 13.500 |
| 212 HCV H77 | 29 | 3 | 9 | B3501 | GPAGSGFAY | 7825 | 40.000 |
| 213 HCV H77 | 29 | 1 | 9 | B3501 | MPGPAGSGF | 7826 | 20.000 |
| 214 HCV H77 | 33 | 47 | 10 | B4403 | GELGEGPGSA | 7827 | 12.000 |
| 215 HCV H77 | 33 | 50 | 10 | B4403 | GEGPGSAAAI | 7828 | 12.000 |
| 216 HCV H77 | 33 | 5 | 9 | B4403 | DELVPYGSV | 7829 | 24.000 |
| 217 HCV H77 | 33 | 47 | 9 | B4403 | GELGEGPGS | 7830 | 12.000 |
| 218 HCV H77 | 33 | 92 | 10 | B3501 | HPTDQHRQL | 7831 | 40.000 |
| 219 HCV H77 | 33 | 74 | 9 | B3501 | RPHHGWACW | 7832 | 20.000 |
| 220 HCV H77 | 33 | 36 | 9 | B3501 | SPGGHSVFL | 7833 | 20.000 |
| 221 HCV H77 | 33 | 92 | 10 | B7 | HPTDQHRQL | 7834 | 80.000 |
| 222 HCV H77 | 33 | 36 | 9 | B7 | SPGGHSVFL | 7835 | 80.000 |
| 223 HCV H77 | 33 | 41 | 9 | B7 | SVFLHGGEL | 7836 | 20.000 |
| 224 HCV H77 | 33 | 33 | 10 | A0201 | SLGSPGGHSV | 7837 | 69.552 |
| 225 HCV H77 | 34 | 37 | 10 | B3501 | SSRFPLIDTL | 7838 | 15.000 |
| 226 HCV H77 | 34 | 40 | 9 | B3501 | FPLIDTLYL | 7839 | 30.000 |
| 227 HCV H77 | 34 | 34 | 10 | B8 | LARSSRFPLI | 7840 | 80.000 |
| 228 HCV H77 | 34 | 26 | 9 | B8 | QCGPRPCGL | 7841 | 16.000 |
| 229 HCV H77 | 34 | 34 | 9 | B8 | LARSSRFPL | 7842 | 16.000 |
| 230 HCV H77 | 34 | 37 | 10 | B7 | SSRFPLIDTL | 7843 | 40.000 |
| 231 HCV H77 | 34 | 34 | 10 | B7 | LARSSRFPLI | 7844 | 12.000 |
| 232 HCV H77 | 34 | 34 | 9 | B7 | LARSSRFPL | 7845 | 180.000 |
| 233 HCV H77 | 34 | 40 | 9 | B7 | FPLIDTLYL | 7846 | 80.000 |
| 234 HCV H77 | 34 | 39 | 10 | A24 | RFPLIDTLYL | 7847 | 60.000 |
| 235 HCV H77 | 34 | 46 | 9 | A24 | LYLRLLGPL | 7848 | 360.000 |
| 236 HCV H77 | 34 | 33 | 10 | A0201 | GLARSSRFPL | 7849 | 193.902 |
| 237 HCV H77 | 34 | 45 | 10 | A0201 | TLYLRLLGPL | 7850 | 20.440 |
| 238 HCV H77 | 34 | 40 | 9 | A0201 | FPLIDTLYL | 7851 | 13.054 |
| 239 HCV H77 | 35 | 14 | 9 | B8 | GARWRRPGC | 7852 | 16.000 |
| 240 HCV H77 | 35 | 23 | 10 | B7 | SGRVLPVNRL | 7853 | 60.000 |
| 241 HCV H77 | 35 | 5 | 9 | B7 | RPGGRHEHL | 7854 | 80.000 |
| 242 HCV H77 | 35 | 19 | 9 | B7 | RPGCSGRVL | 7855 | 80.000 |
| 243 HCV H77 | 35 | 40 | 10 | A0201 | RLVREAGNYT | 7856 | 40.986 |
| 244 HCV H77 | 36 | 47 | 9 | B4403 | ASVDKLGVY | 7857 | 27.000 |
| 245 HCV H77 | 36 | 2 | 9 | B4403 | DEPANSLRL | 7858 | 12.000 |
| 246 HCV H77 | 36 | 62 | 10 | B3501 | LAKGHLGLDM | 7859 | 18.000 |
| 247 HCV H77 | 36 | 47 | 9 | B3501 | ASVDKLGVY | 7860 | 20.000 |
| 248 HCV H77 | 36 | 58 | 10 | B7 | MLRFLAKGHL | 7861 | 40.000 |
| 249 HCV H77 | 36 | 53 | 10 | B7 | GVYHSMLRFL | 7862 | 20.000 |
| 250 HCV H77 | 36 | 44 | 9 | B7 | EATASVDKL | 7863 | 12.000 |
| 251 HCV H77 | 36 | 51 | 10 | A3 | KLGVYHSMLR | 7864 | 24.000 |
| 252 HCV H77 | 36 | 68 | 9 | A3 | GLDMRGAER | 7865 | 12.000 |
| 253 HCV H77 | 36 | 60 | 10 | A24 | RFLAKGHLGL | 7866 | 60.000 |
| 254 HCV H77 | 36 | 54 | 9 | A24 | VYHSMLRFL | 7867 | 200.000 |
| 255 HCV H77 | 36 | 53 | 10 | A0201 | GVYHSMLRFL | 7868 | 15.133 |
| 256 HCV H77 | 36 | 61 | 9 | A0201 | FLAKGHLGL | 7869 | 98.267 |
| 257 HCV H77 | 36 | 51 | 9 | A0201 | KLGVYHSML | 7870 | 74.768 |
| 258 HCV H77 | 36 | 68 | 9 | A1 | GLDMRGAER | 7871 | 10.000 |
| 259 HCV H77 | 36 | 5 | 9 | B3501 | RPGGRHEHL | 7872 | 40.000 |
| 260 HCV H77 | 36 | 19 | 9 | B3501 | RPGCSGRVL | 7873 | 40.000 |
| 261 HCV H77 | 37 | 40 | 10 | B3501 | TPRVPGGVAI | 7874 | 24.000 |
| 262 HCV H77 | 37 | 18 | 9 | B3501 | APTQVCAPL | 7875 | 20.000 |
| 263 HCV H77 | 37 | 43 | 9 | B3501 | VPGGVAITL | 7876 | 20.000 |

TABLE 4m-continued

H77 (1-3)

| No. | Strain | ORF | Start | AA | HLA | Peptide sequence | SEQ ID NO: | Score |
|---|---|---|---|---|---|---|---|---|
| 264 | HCV H77 | 37 | 40 | 10 | B7 | TPRVPGGVAI | 7877 | 80.000 |
| 265 | HCV H77 | 37 | 42 | 10 | B7 | RVPGGVAITL | 7878 | 20.000 |
| 266 | HCV H77 | 37 | 1 | 10 | B7 | MPVPDPIARI | 7879 | 12.000 |
| 267 | HCV H77 | 37 | 17 | 10 | B7 | GAPTQVCAPL | 7880 | 12.000 |
| 268 | HCV H77 | 37 | 18 | 9 | B7 | APTQVCAPL | 7881 | 240.000 |
| 269 | HCV H77 | 37 | 43 | 9 | B7 | VPGGVAITL | 7882 | 80.000 |
| 270 | HCV H77 | 37 | 21 | 9 | B7 | QVCAPLQAL | 7883 | 30.000 |
| 271 | HCV H77 | 37 | 40 | 9 | B7 | TPRVPGGVA | 7884 | 30.000 |
| 272 | HCV H77 | 37 | 42 | 10 | A24 | RVPGGVAITL | 7885 | 16.800 |
| 273 | HCV H77 | 37 | 35 | 9 | A0201 | IIQSRTPRV | 7886 | 16.258 |
| 274 | HCV H77 | 37 | 3 | 9 | A1 | VPDPIARIF | 7887 | 12.500 |
| 275 | HCV H77 | 38 | 8 | 10 | B7 | RPRRRWKEGL | 7888 | 800.000 |
| 276 | HCV H77 | 38 | 8 | 10 | B3501 | RPRRRWKEGL | 7889 | 120.000 |
| 277 | HCV H77 | 39 | 1 | 10 | B3501 | MPQKTWGPAL | 7890 | 20.000 |
| 278 | HCV H77 | 39 | 12 | 9 | A1 | SLETPGPER | 7891 | 18.000 |
| 279 | HCV H77 | 39 | 4 | 10 | A0201 | KTWGPALASL | 7892 | 19.824 |
| 280 | HCV H77 | 39 | 1 | 10 | B7 | MPQKTWGPAL | 7893 | 80.000 |
| 281 | HCV H77 | 40 | 47 | 9 | B3501 | CPAPLVLVL | 7894 | 20.000 |
| 282 | HCV H77 | 40 | 57 | 10 | B3501 | TPARCRGRHL | 7895 | 20.000 |
| 283 | HCV H77 | 40 | 57 | 10 | B8 | TPARCRGRHL | 7896 | 16.000 |
| 284 | HCV H77 | 40 | 58 | 9 | B8 | PARCRGRHL | 7897 | 32.000 |
| 285 | HCV H77 | 40 | 57 | 10 | B7 | TPARCRGRHL | 7898 | 80.000 |
| 286 | HCV H77 | 40 | 42 | 10 | B7 | SQRVSCPAPL | 7899 | 40.000 |
| 287 | HCV H77 | 40 | 44 | 10 | B7 | RVSCPAPLVL | 7900 | 20.000 |
| 288 | HCV H77 | 40 | 27 | 9 | B7 | LVRLVHGWL | 7901 | 200.000 |
| 289 | HCV H77 | 40 | 47 | 9 | B7 | CPAPLVLVL | 7902 | 80.000 |
| 290 | HCV H77 | 40 | 58 | 9 | B7 | PARCRGRHL | 7903 | 12.000 |
| 291 | HCV H77 | 40 | 65 | 9 | A3 | HLPPPQPMK | 7904 | 45.000 |
| 292 | HCV H77 | 40 | 29 | 9 | A3 | RLVHGWLQR | 7905 | 12.000 |
| 293 | HCV H77 | 40 | 22 | 9 | A24 | RWPAGLVRL | 7906 | 12.000 |
| 294 | HCV H77 | 40 | 26 | 10 | A0201 | GLVRLVHGWL | 7907 | 15.274 |

TABLE 4n

H77 (4-6)

| No | Strain | ORF | HLA | Start | Sequence | SEQ ID NO: | Score |
|---|---|---|---|---|---|---|---|
| 1 | HCV H77 | 1 | B4403 | 4 | REASISTLC | 7908 | 12 |
| 2 | HCV H77 | 1 | B4403 | 4 | REASISTLCS | 7909 | 12 |
| 3 | HCV H77 | 1 | B7 | 2 | ICREASISTL | 7910 | 40 |
| 4 | HCV H77 | 1 | B8 | 2 | ICREASISTL | 7911 | 24 |
| 5 | HCV H77 | 2 | B7 | 16 | CVGAPRPIL | 7912 | 45 |
| 6 | HCV H77 | 2 | B8 | 6 | AARACKGAQT | 7913 | 16 |
| 7 | HCV H77 | 3 | B7 | 11 | DAVASGAGL | 7914 | 12 |
| 8 | HCV H77 | 4 | A68.1 | 22 | PVQRCRWRR | 7915 | 20 |
| 9 | HCV H77 | 4 | A68.1 | 21 | SPVQRCRWR | 7916 | 10 |
| 10 | HCV H77 | 4 | A68.1 | 30 | RQLGQHPQR | 7917 | 10 |
| 11 | HCV H77 | 4 | A68.1 | 21 | SPVQRCRWRR | 7918 | 10 |
| 12 | HCV H77 | 4 | B3501 | 5 | LPPRPRHTL | 7919 | 20 |
| 13 | HCV H77 | 4 | B3501 | 8 | RPRHTLQEC | 7920 | 12 |
| 14 | HCV H77 | 4 | B3501 | 19 | GPSPVQRCRW | 7921 | 10 |
| 15 | HCV H77 | 4 | B4403 | 3 | QELPPRPRHT | 7922 | 16 |
| 16 | HCV H77 | 4 | B7 | 5 | LPPRPRHTL | 7923 | 180 |
| 17 | HCV H77 | 4 | B7 | 8 | RPRHTLQEC | 7924 | 20 |
| 18 | HCV H77 | 4 | B7 | 23 | VQRCRWRRQL | 7925 | 60 |
| 19 | HCV H77 | 5 | A0201 | 10 | ALTGPPSIV | 7926 | 28.52 |
| 20 | HCV H77 | 5 | A0201 | 2 | KQWRGYQAA | 7927 | 21.95 |
| 21 | HCV H77 | 5 | A0201 | 2 | KQWR-GYQAAL | 7928 | 62.92 |
| 22 | HCV H77 | 6 | A68.1 | 10 | RTSSLSGRR | 7929 | 50 |
| 23 | HCV H77 | 6 | A68.1 | 2 | RPASRRARR | 7930 | 10 |
| 24 | HCV H77 | 7 | A0201 | 11 | KLLCHKHLL | 7931 | 276.64 |
| 25 | HCV H77 | 7 | A0201 | 12 | LLCHKHLLST | 7932 | 29.14 |
| 26 | HCV H77 | 7 | A0201 | 18 | LLSTRRRQGT | 7933 | 12.67 |
| 27 | HCV H77 | 7 | A24 | 11 | KLLCHKHLL | 7934 | 12 |
| 28 | HCV H77 | 7 | A68.1 | 20 | STRRRQGTCR | 7935 | 50 |
| 29 | HCV H77 | 7 | A68.1 | 7 | GTRHKLLCHK | 7936 | 45 |
| 30 | HCV H77 | 7 | B3501 | 3 | HPWSGTRHKL | 7937 | 20 |
| 31 | HCV H77 | 7 | B7 | 3 | HPWSGTRHKL | 7938 | 120 |
| 32 | HCV H77 | 8 | B3501 | 10 | SPQGLGPHW | 7939 | 10 |
| 33 | HCV H77 | 8 | B3501 | 10 | SPQGLGPHWY | 7940 | 40 |

TABLE 4n-continued

H77 (4-6)

| No | Strain | ORF | HLA | Start | Sequence | SEQ ID NO: | Score |
|---|---|---|---|---|---|---|---|
| 34 | HCV H77 | 9 | A68.1 | 3 | WSSFRPRGR | 7941 | 15 |
| 35 | HCV H77 | 9 | B3501 | 7 | RPRGRQSSI | 7942 | 48 |
| 36 | HCV H77 | 9 | B7 | 7 | RPRGRQSSI | 7943 | 80 |
| 37 | HCV H77 | 9 | B8 | 7 | RPRGRQSSI | 7944 | 40 |
| 38 | HCV H77 | 10 | A1 | 2 | ATESAPLTR | 7945 | 112.5 |
| 39 | HCV H77 | 10 | A68.1 | 57 | DTTQSRRTR | 7946 | 150 |
| 40 | HCV H77 | 10 | A68.1 | 2 | ATESAPLTR | 7947 | 50 |
| 41 | HCV H77 | 10 | A68.1 | 63 | RTRGRTQDR | 7948 | 50 |
| 42 | HCV H77 | 10 | A68.1 | 39 | EATSRRGRR | 7949 | 15 |
| 43 | HCV H77 | 10 | A68.1 | 6 | APLTRQEQR | 7950 | 10 |
| 44 | HCV H77 | 10 | A68.1 | 35 | GAGGEATSR | 7951 | 10 |
| 45 | HCV H77 | 10 | A68.1 | 17 | TTRPPPCPVR | 7952 | 75 |
| 46 | HCV H77 | 10 | A68.1 | 58 | TTQSRRTRGR | 7953 | 50 |
| 47 | HCV H77 | 10 | A68.1 | 6 | APLTRQEQRR | 7954 | 15 |
| 48 | HCV H77 | 10 | A68.1 | 41 | TSRRGRRPLR | 7955 | 15 |
| 49 | HCV H77 | 10 | A68.1 | 35 | GAGGEATSRR | 7956 | 10 |
| 50 | HCV H77 | 10 | B3501 | 19 | RPPPCPVRM | 7957 | 80 |
| 51 | HCV H77 | 10 | B3501 | 41 | TSRRGRRPL | 7958 | 15 |
| 52 | HCV H77 | 10 | B7 | 41 | TSRRGRRPL | 7959 | 60 |
| 53 | HCV H77 | 10 | B7 | 19 | RPPPCPVRM | 7960 | 20 |
| 54 | HCV H77 | 10 | B7 | 40 | ATSRRGRRPL | 7961 | 18 |
| 55 | HCV H77 | 11 | A68.1 | 8 | GSNQWGRAR | 7962 | 15 |
| 56 | HCV H77 | 11 | A68.1 | 6 | VCGSNQWGR | 7963 | 10 |
| 57 | HCV H77 | 11 | A68.1 | 50 | DVCGSN-QWGR | 7964 | 600 |
| 58 | HCV H77 | 11 | B3501 | 14 | RARCCCPPL | 7965 | 18 |
| 59 | HCV H77 | 11 | B7 | 14 | RARCCCPPL | 7966 | 120 |
| 60 | HCV H77 | 13 | A0201 | 2 | ALPGGGVLEA | 7967 | 11.43 |
| 61 | HCV H77 | 13 | A1 | 8 | VLEAARHSY | 7968 | 45 |
| 62 | HCV H77 | 13 | B7 | 1 | MALPGGGVL | 7969 | 12 |
| 63 | HCV H77 | 14 | A68.1 | 8 | RSRQNQNQR | 7970 | 15 |
| 64 | HCV H77 | 15 | A24 | 29 | SFLRHAATL | 7971 | 30 |
| 65 | HCV H77 | 15 | A24 | 29 | SFLRHAATLL | 7972 | 30 |
| 66 | HCV H77 | 15 | A68.1 | 1 | MAALPPLDR | 7973 | 10 |
| 67 | HCV H77 | 15 | A68.1 | 10 | SLARTLRAR | 7974 | 10 |
| 68 | HCV H77 | 15 | A68.1 | 9 | RSLARTLRAR | 7975 | 30 |
| 69 | HCV H77 | 15 | B7 | 30 | FLRHAATLL | 7976 | 40 |
| 70 | HCV H77 | 15 | B7 | 3 | ALPPLDRSL | 7977 | 12 |
| 71 | HCV H77 | 15 | B7 | 11 | LARTLRARCL | 7978 | 120 |
| 72 | HCV H77 | 15 | B7 | 2 | AALPPLDRSL | 7979 | 36 |
| 73 | HCV H77 | 15 | B8 | 11 | LARTLRARCL | 7980 | 320 |
| 74 | HCV H77 | 17 | A0201 | 33 | CLAVSHAAL | 7981 | 21.36 |
| 75 | HCV H77 | 17 | A0201 | 21 | MIMLPSQEL | 7982 | 18.48 |
| 76 | HCV H77 | 17 | A0201 | 22 | IMLPSQELT | 7983 | 16.59 |
| 77 | HCV H77 | 17 | A0201 | 23 | MLPSQELTGV | 7984 | 271.95 |
| 78 | HCV H77 | 17 | A0201 | 8 | VISIILAHSV | 7985 | 16.26 |
| 79 | HCV H77 | 17 | A0201 | 20 | NMIMLPSQEL | 7986 | 15.43 |
| 80 | HCV H77 | 17 | A3 | 3 | TLKKWVISI | 7987 | 10.8 |
| 81 | HCV H77 | 17 | A68.1 | 35 | AVSHAALAR | 7988 | 200 |
| 82 | HCV H77 | 17 | A68.1 | 34 | LAVSHAALAR | 7989 | 10 |
| 83 | HCV H77 | 17 | A68.1 | 40 | ALARGVVGSR | 7990 | 10 |
| 84 | HCV H77 | 17 | B3501 | 15 | HSVGANMIM | 7991 | 10 |
| 85 | HCV H77 | 17 | B4403 | 27 | QELTGVCLA | 7992 | 24 |
| 86 | HCV H77 | 17 | B4403 | 27 | QELTGVCLAV | 7993 | 12 |
| 87 | HCV H77 | 17 | B7 | 16 | SVGANMIML | 7994 | 20 |
| 88 | HCV H77 | 17 | B7 | 21 | MIMLPSQEL | 7995 | 18 |
| 89 | HCV H77 | 18 | A68.1 | 6 | SPAARQAAR | 7996 | 10 |
| 90 | HCV H77 | 18 | A68.1 | 1 | MVQSWSPAAR | 7997 | 200 |
| 91 | HCV H77 | 18 | A68.1 | 5 | WSPAARQAAR | 7998 | 15 |
| 92 | HCV H77 | 18 | B3501 | 8 | AAR-QAARALM | 7999 | 18 |
| 93 | HCV H77 | 18 | B7 | 8 | AARQAARAL | 8000 | 360 |
| 94 | HCV H77 | 18 | B7 | 8 | AAR-QAARALM | 8001 | 135 |
| 95 | HCV H77 | 18 | B8 | 8 | AARQAARAL | 8002 | 16 |
| 96 | HCV H77 | 20 | A0201 | 15 | YENPIGVFL | 8003 | 10.51 |
| 97 | HCV H77 | 20 | A0201 | 13 | VSYENPIGV | 8004 | 10.13 |
| 98 | HCV H77 | 20 | A1 | 6 | TVESKQRVSY | 8005 | 90 |
| 99 | HCV H77 | 20 | A24 | 14 | SYENPIGVF | 8006 | 150 |
| 100 | HCV H77 | 20 | A24 | 14 | SYENPIGVFL | 8007 | 420 |
| 101 | HCV H77 | 20 | A3 | 2 | SLSVTVESK | 8008 | 60 |
| 102 | HCV H77 | 20 | A68.1 | 4 | SVTVESKQR | 8009 | 200 |
| 103 | HCV H77 | 20 | A68.1 | 3 | LSVTVESKQR | 8010 | 30 |
| 104 | HCV H77 | 20 | A68.1 | 1 | MSLSVTVESK | 8011 | 18 |
| 105 | HCV H77 | 20 | B3501 | 17 | NPIGVFLDF | 8012 | 20 |

TABLE 4n-continued

H77 (4-6)

| No | Strain | ORF | HLA | Start | Sequence | SEQ ID NO: | Score |
|---|---|---|---|---|---|---|---|
| 106 | HCV H77 | 20 | B3501 | 31 | NSTRCPGEY | 8013 | 10 |
| 107 | HCV H77 | 20 | B3501 | 13 | VSYENPIGVF | 8014 | 10 |
| 108 | HCV H77 | 20 | B4403 | 7 | VESKQRVSY | 8015 | 120 |
| 109 | HCV H77 | 20 | B4403 | 17 | NPIGVFLDF | 8016 | 11.25 |
| 110 | HCV H77 | 22 | A0201 | 20 | LMWATAFLA | 8017 | 293.63 |
| 111 | HCV H77 | 22 | A0201 | 19 | ELMWATAFL | 8018 | 32.6 |
| 112 | HCV H77 | 22 | A0201 | 26 | FLAWQRTSFA | 8019 | 125.69 |
| 113 | HCV H77 | 22 | A0201 | 9 | TLSSRRSFHT | 8020 | 43.22 |
| 114 | HCV H77 | 22 | A0201 | 1 | MMVVSIGVTL | 8021 | 26.23 |
| 115 | HCV H77 | 22 | A1 | 17 | HTELMWATAF | 8022 | 22.5 |
| 116 | HCV H77 | 22 | A24 | 25 | AFLAWQRTSF | 8023 | 15 |
| 117 | HCV H77 | 22 | A68.1 | 23 | ATAFLAWQR | 8024 | 100 |
| 118 | HCV H77 | 22 | A68.1 | 5 | SIGVTLSSR | 8025 | 10 |
| 119 | HCV H77 | 22 | A68.1 | 4 | VSIGVTLSSR | 8026 | 30 |
| 120 | HCV H77 | 22 | A68.1 | 5 | SIGVTLSSRR | 8027 | 10 |
| 121 | HCV H77 | 22 | B3501 | 11 | SSRRSFHTEL | 8028 | 15 |
| 122 | HCV H77 | 22 | B4403 | 18 | TELMWATAF | 8029 | 180 |
| 123 | HCV H77 | 22 | B4403 | 18 | TELMWATAFL | 8030 | 18 |
| 124 | HCV H77 | 22 | B7 | 2 | MVVSIGVTL | 8031 | 20 |
| 125 | HCV H77 | 22 | B7 | 19 | ELMWATAFL | 8032 | 12 |
| 126 | HCV H77 | 22 | B7 | 11 | SSRRSFHTEL | 8033 | 40 |
| 127 | HCV H77 | 24 | A0201 | 17 | KAVDRVDSV | 8034 | 15.62 |
| 128 | HCV H77 | 24 | A0201 | 11 | LVASSAKAV | 8035 | 10.35 |
| 129 | HCV H77 | 24 | A0201 | 10 | LLVASSAKAV | 8036 | 118.24 |
| 130 | HCV H77 | 24 | A0201 | 9 | KLLVASSAKA | 8037 | 64.34 |
| 131 | HCV H77 | 24 | A1 | 1 | MPEVEELPK | 8038 | 22.5 |
| 132 | HCV H77 | 24 | A3 | 9 | KLLVASSAK | 8039 | 90 |
| 133 | HCV H77 | 24 | A68.1 | 18 | AVDRVDSVR | 8040 | 300 |
| 134 | HCV H77 | 24 | A68.1 | 13 | ASSAKAVDR | 8041 | 15 |
| 135 | HCV H77 | 24 | A68.1 | 3 | EVEELPKLL | 8042 | 12 |
| 136 | HCV H77 | 24 | A68.1 | 21 | RVDSVRTTVR | 8043 | 200 |
| 137 | HCV H77 | 24 | A68.1 | 24 | SVRTTVRFFR | 8044 | 200 |
| 138 | HCV H77 | 24 | A68.1 | 17 | KAVDRVDSVR | 8045 | 15 |
| 139 | HCV H77 | 24 | A68.1 | 3 | EVEELPKLLV | 8046 | 12 |
| 140 | HCV H77 | 24 | B4403 | 5 | EELPKLLVA | 8047 | 36 |
| 141 | HCV H77 | 24 | B4403 | 5 | EELPKLLVAS | 8048 | 24 |
| 142 | HCV H77 | 24 | B4403 | 23 | DSVRTTVRFF | 8049 | 18 |
| 143 | HCV H77 | 24 | B7 | 1 | MPEVEELPKL | 8050 | 24 |
| 144 | HCV H77 | 25 | A0201 | 52 | NLLPAASAV | 8051 | 257.34 |
| 145 | HCV H77 | 25 | A0201 | 60 | VIWEGSVSM | 8052 | 39.52 |
| 146 | HCV H77 | 25 | A0201 | 125 | GIWHGHLRL | 8053 | 24.38 |
| 147 | HCV H77 | 25 | A0201 | 132 | RLSVVIPDT | 8054 | 17.14 |
| 148 | HCV H77 | 25 | A0201 | 7 | CLHRRLASM | 8055 | 11.43 |
| 149 | HCV H77 | 25 | A0201 | 29 | ALRDGADSWL | 8056 | 36.61 |
| 150 | HCV H77 | 25 | A0201 | 52 | NLLPAASAVI | 8057 | 15.83 |
| 151 | HCV H77 | 25 | A1 | 82 | NCDPTGYSW | 8058 | 10 |
| 152 | HCV H77 | 25 | A24 | 102 | KGLQGGANL | 8059 | 12 |
| 153 | HCV H77 | 25 | A3 | 23 | WLAVQVALR | 8060 | 12 |
| 154 | HCV H77 | 25 | A3 | 103 | GLQGGANLCR | 8061 | 36 |
| 155 | HCV H77 | 25 | A3 | 1 | MLPPISCLHR | 8062 | 12 |
| 156 | HCV H77 | 25 | A68.1 | 23 | WLAVQVALR | 8063 | 10 |
| 157 | HCV H77 | 25 | A68.1 | 92 | PTLNDTSSR | 8064 | 10 |
| 158 | HCV H77 | 25 | A68.1 | 104 | LQGGANLCR | 8065 | 10 |
| 159 | HCV H77 | 25 | A68.1 | 1 | MLPPISCLHR | 8066 | 11.25 |
| 160 | HCV H77 | 25 | A68.1 | 104 | LQGGANLCRR | 8067 | 10 |
| 161 | HCV H77 | 25 | B3501 | 54 | LPAASAVIW | 8068 | 10 |
| 162 | HCV H77 | 25 | B4403 | 20 | GESWLAVQVA | 8069 | 18 |
| 163 | HCV H77 | 25 | B7 | 42 | LAIEGGDPL | 8070 | 12 |
| 164 | HCV H77 | 25 | B7 | 29 | ALRDGADSWL | 8071 | 120 |
| 165 | HCV H77 | 25 | B7 | 59 | AVIWEGSVSM | 8072 | 15 |
| 166 | HCV H77 | 25 | B8 | 29 | ALRDGADSWL | 8073 | 12 |
| 167 | HCV H77 | 26 | A0201 | 12 | VLGPTILIV | 8074 | 111.5 |
| 168 | HCV H77 | 26 | A0201 | 62 | GMSLAFSQV | 8075 | 95.44 |
| 169 | HCV H77 | 26 | A0201 | 22 | FLTCPVISA | 8076 | 52.56 |
| 170 | HCV H77 | 26 | A0201 | 9 | FLQVLGPTI | 8077 | 47.99 |
| 171 | HCV H77 | 26 | A0201 | 16 | TILIVPFLT | 8078 | 21.99 |
| 172 | HCV H77 | 26 | A0201 | 17 | ILIVPFLTC | 8079 | 16.05 |
| 173 | HCV H77 | 26 | A0201 | 19 | IVPFLTCPV | 8080 | 10.35 |
| 174 | HCV H77 | 26 | A0201 | 84 | SLSQEPEHGV | 8081 | 69.55 |
| 175 | HCV H77 | 26 | A0201 | 9 | FLQVLGPTIL | 8082 | 40.29 |
| 176 | HCV H77 | 26 | A0201 | 27 | VISAPQWRV | 8083 | 27.64 |
| 177 | HCV H77 | 26 | A0201 | 38 | IMPSPRQTPL | 8084 | 26.23 |
| 178 | HCV H77 | 26 | A0201 | 62 | GMSLAFSQVL | 8085 | 24.04 |
| 179 | HCV H77 | 26 | A0201 | 11 | QVLGPTILIV | 8086 | 21.23 |
| 180 | HCV H77 | 26 | A0201 | 18 | LIVPFLTCPV | 8087 | 16.26 |

TABLE 4n-continued

H77 (4-6)

| No | Strain | ORF | HLA | Start | Sequence | SEQ ID NO: | Score |
|---|---|---|---|---|---|---|---|
| 181 | HCV H77 | 26 | A0201 | 3 | NVPLHMFLQV | 8088 | 11.56 |
| 182 | HCV H77 | 26 | A24 | 66 | AFSQVLKSL | 8089 | 28 |
| 183 | HCV H77 | 26 | A3 | 64 | SLAFSQVLK | 8090 | 20 |
| 184 | HCV H77 | 26 | A3 | 46 | PLYPRWQDTK | 8091 | 45 |
| 185 | HCV H77 | 26 | A68.1 | 35 | RVCIMPSPR | 8092 | 200 |
| 186 | HCV H77 | 26 | A68.1 | 92 | GVVHSELIH | 8093 | 12 |
| 187 | HCV H77 | 26 | A68.1 | 26 | PVISAPQWQR | 8094 | 40 |
| 188 | HCV H77 | 26 | A68.1 | 63 | MSLAFSQVLK | 8095 | 18 |
| 189 | HCV H77 | 26 | B3501 | 14 | GPTILIVPF | 8096 | 20 |
| 190 | HCV H77 | 26 | B3501 | 39 | MPSPRQTPL | 8097 | 20 |
| 191 | HCV H77 | 26 | B3501 | 57 | IPGSCGMSL | 8098 | 20 |
| 192 | HCV H77 | 26 | B3501 | 25 | CPVISAPQW | 8099 | 10 |
| 193 | HCV H77 | 26 | B3501 | 30 | APQWQRVCIM | 8100 | 40 |
| 194 | HCV H77 | 26 | B3501 | 39 | MPSPRQTPLY | 8101 | 40 |
| 195 | HCV H77 | 26 | B3501 | 48 | YPRWQDTKGI | 8102 | 36 |
| 196 | HCV H77 | 26 | B3501 | 4 | VPLHMFLQVL | 8103 | 20 |
| 197 | HCV H77 | 26 | B3501 | 14 | GPTILIVPFL | 8104 | 20 |
| 198 | HCV H77 | 26 | B3501 | 74 | LSTSHIQSQM | 8105 | 10 |
| 199 | HCV H77 | 26 | B4403 | 87 | QEPEHGVVHS | 8106 | 12 |
| 200 | HCV H77 | 26 | B7 | 39 | MPSPRQTPL | 8107 | 80 |
| 201 | HCV H77 | 26 | B7 | 57 | IPGSCGMSL | 8108 | 80 |
| 202 | HCV H77 | 26 | B7 | 30 | APQWQRVCI | 8109 | 36 |
| 203 | HCV H77 | 26 | B7 | 4 | VPLHMFLQVL | 8110 | 80 |
| 204 | HCV H77 | 26 | B7 | 14 | GPTILIVPFL | 8111 | 80 |
| 205 | HCV H77 | 26 | B7 | 48 | YPRWQDTKGI | 8112 | 80 |
| 206 | HCV H77 | 26 | B7 | 30 | APQWQRVCIM | 8113 | 60 |
| 207 | HCV H77 | 26 | B7 | 65 | LAFSQVLKSL | 8114 | 12 |
| 208 | HCV H77 | 26 | B8 | 39 | MPSPRQTPL | 8115 | 16 |
| 209 | HCV H77 | 27 | B7 | 2 | AVTRAAASL | 8116 | 60 |
| 210 | HCV H77 | 27 | B7 | 1 | MAVTRAAASL | 8117 | 12 |
| 211 | HCV H77 | 28 | A0201 | 76 | MLKRRVWPV | 8118 | 71.39 |
| 212 | HCV H77 | 28 | A0201 | 80 | RVWPVVSGL | 8119 | 35.68 |
| 213 | HCV H77 | 28 | A0201 | 95 | AINEAMAGL | 8120 | 27.7 |
| 214 | HCV H77 | 28 | A0201 | 132 | CQLVWTAGV | 8121 | 26.09 |
| 215 | HCV H77 | 28 | A0201 | 127 | KTSSFCQLV | 8122 | 12.85 |
| 216 | HCV H77 | 28 | A0201 | 75 | NMLKRRVWPV | 8123 | 3206.06 |
| 217 | HCV H77 | 28 | A0201 | 87 | GLVTAAVKAI | 8124 | 24 |
| 218 | HCV H77 | 28 | A0201 | 19 | ILNATRAPAT | 8125 | 12.67 |
| 219 | HCV H77 | 28 | A0201 | 84 | VVSGLVTAAV | 8126 | 10.35 |
| 220 | HCV H77 | 28 | A1 | 70 | ATHPPNMLK | 8127 | 25 |
| 221 | HCV H77 | 28 | A1 | 70 | ATHPPNMLKR | 8128 | 12.5 |
| 222 | HCV H77 | 28 | A24 | 112 | KYCIPLMKF | 8129 | 220 |
| 223 | HCV H77 | 28 | A24 | 80 | RVWPVVSGL | 8130 | 13.44 |
| 224 | HCV H77 | 28 | A24 | 123 | CFAQKTSSF | 8131 | 10 |
| 225 | HCV H77 | 28 | A24 | 94 | KAINEAMAGL | 8132 | 12 |
| 226 | HCV H77 | 28 | A3 | 163 | SIIPCSMYGK | 8133 | 20.25 |
| 227 | HCV H77 | 28 | A68.1 | 27 | ATPAPYPAR | 8134 | 50 |
| 228 | HCV H77 | 28 | A68.1 | 70 | ATHPPNMLK | 8135 | 45 |
| 229 | HCV H77 | 28 | A68.1 | 70 | ATHPPNMLKR | 8136 | 75 |
| 230 | HCV H77 | 28 | A68.1 | 142 | TSAWRDAVCR | 8137 | 30 |
| 231 | HCV H77 | 28 | A68.1 | 85 | VSGLVTAAVK | 8138 | 18 |
| 232 | HCV H77 | 28 | A68.1 | 44 | PTLPMAAPAR | 8139 | 15 |
| 233 | HCV H77 | 28 | A68.1 | 15 | SPLMILNATR | 8140 | 10 |
| 234 | HCV H77 | 28 | A68.1 | 100 | MAGLPGSVDR | 8141 | 10 |
| 235 | HCV H77 | 28 | A68.1 | 137 | TAGVITSAWR | 8142 | 10 |
| 236 | HCV H77 | 28 | B3501 | 28 | TPAPYPARM | 8143 | 40 |
| 237 | HCV H77 | 28 | B3501 | 109 | RPAKYCIPL | 8144 | 40 |
| 238 | HCV H77 | 28 | B3501 | 105 | GSVDRPAKY | 8145 | 20 |
| 239 | HCV H77 | 28 | B3501 | 24 | RAPATPAPY | 8146 | 12 |
| 240 | HCV H77 | 28 | B3501 | 152 | RPRAFCLNC | 8147 | 12 |
| 241 | HCV H77 | 28 | B3501 | 9 | SSVEGTSPL | 8148 | 10 |
| 242 | HCV H77 | 28 | B3501 | 162 | ASIIPCSMY | 8149 | 10 |
| 243 | HCV H77 | 28 | B3501 | 109 | RPAKYCIPLM | 8150 | 80 |
| 244 | HCV H77 | 28 | B3501 | 115 | IPLMKFHMCF | 8151 | 20 |
| 245 | HCV H77 | 28 | B3501 | 9 | SSVEGTSPLM | 8152 | 20 |
| 246 | HCV H77 | 28 | B3501 | 32 | YPARMSTRTF | 8153 | 20 |
| 247 | HCV H77 | 28 | B3501 | 152 | RPRAFCLNCS | 8154 | 12 |
| 248 | HCV H77 | 28 | B3501 | 8 | RSSVEGTSPL | 8155 | 10 |
| 249 | HCV H77 | 28 | B3501 | 160 | CSASIIPCSM | 8156 | 10 |
| 250 | HCV H77 | 28 | B3501 | 162 | ASIIPCSMY | 8157 | 45 |
| 251 | HCV H77 | 28 | B4403 | 97 | NEAMAGLPGS | 8158 | 12 |
| 252 | HCV H77 | 28 | B7 | 109 | RPAKYCIPL | 8159 | 80 |
| 253 | HCV H77 | 28 | B7 | 69 | AATHPPNML | 8160 | 54 |
| 254 | HCV H77 | 28 | B7 | 28 | TPAPYPARM | 8161 | 20 |
| 255 | HCV H77 | 28 | B7 | 80 | RVWPVVSGL | 8162 | 20 |

TABLE 4n-continued

H77 (4-6)

| No | Strain | ORF | HLA | Start | Sequence | SEQ ID NO: | Score |
|---|---|---|---|---|---|---|---|
| 256 | HCV H77 | 28 | B7 | 152 | RPRAFCLNC | 8163 | 20 |
| 257 | HCV H77 | 28 | B7 | 92 | AVKAINEAM | 8164 | 15 |
| 258 | HCV H77 | 28 | B7 | 95 | AINEAMAGL | 8165 | 12 |
| 259 | HCV H77 | 28 | B7 | 37 | STRTFPSPTL | 8166 | 60 |
| 260 | HCV H77 | 28 | B7 | 149 | VCRRPRAFCL | 8167 | 40 |
| 261 | HCV H77 | 28 | B7 | 109 | RPAKYCIPLM | 8168 | 20 |
| 262 | HCV H77 | 28 | B7 | 68 | WAATHPPNML | 8169 | 18 |
| 263 | HCV H77 | 28 | B7 | 94 | KAINEAMAGL | 8170 | 12 |
| 264 | HCV H77 | 28 | B7 | 125 | AQKTSSFCQL | 8171 | 12 |
| 265 | HCV H77 | 28 | B8 | 76 | MLKRRVWPV | 8172 | 24 |
| 266 | HCV H77 | 28 | B8 | 149 | VCRRPRAFCL | 8173 | 320 |
| 267 | HCV H77 | 29 | A0201 | 39 | YLVIGCVRV | 8174 | 319.94 |
| 268 | HCV H77 | 29 | A0201 | 37 | MMYLVIGCV | 8175 | 81.71 |
| 269 | HCV H77 | 29 | A0201 | 36 | VMMYLVIGC | 8176 | 51.91 |
| 270 | HCV H77 | 29 | A0201 | 36 | VMMYLVIGCV | 8177 | 94.47 |
| 271 | HCV H77 | 29 | A1 | 31 | SADMHVMMY | 8178 | 125 |
| 272 | HCV H77 | 29 | A1 | 2 | TTQPVDRQY | 8179 | 12.5 |
| 273 | HCV H77 | 29 | A24 | 16 | RTPPTSTQVL | 8180 | 17.28 |
| 274 | HCV H77 | 29 | A3 | 37 | MMYLVIGCVR | 8181 | 30 |
| 275 | HCV H77 | 29 | A68.1 | 5 | PVDRQYAAR | 8182 | 20 |
| 276 | HCV H77 | 29 | A68.1 | 22 | TQVLVTTSR | 8183 | 10 |
| 277 | HCV H77 | 29 | A68.1 | 21 | STQVLVTTSR | 8184 | 50 |
| 278 | HCV H77 | 29 | A68.1 | 4 | QPVDRQYAAR | 8185 | 10 |
| 279 | HCV H77 | 29 | B3501 | 30 | RSADMHVMM | 8186 | 40 |
| 280 | HCV H77 | 29 | B3501 | 17 | TPPTSTQVL | 8187 | 20 |
| 281 | HCV H77 | 29 | B3501 | 28 | TSRSADM-HVM | 8188 | 45 |
| 282 | HCV H77 | 29 | B3501 | 30 | RSADMH-VMMY | 8189 | 40 |
| 283 | HCV H77 | 29 | B4403 | 31 | SADMHVMMY | 8190 | 18 |
| 284 | HCV H77 | 29 | B4403 | 30 | RSADMH-VMMY | 8191 | 18 |
| 285 | HCV H77 | 29 | B7 | 17 | TPPTSTQVL | 8192 | 80 |
| 286 | HCV H77 | 29 | B7 | 14 | AARTPPTST | 8193 | 13.5 |
| 287 | HCV H77 | 29 | B7 | 28 | TSRSADM-HVM | 8194 | 10 |
| 288 | HCV H77 | 29 | B8 | 11 | AARAARTPPT | 8195 | 16 |
| 289 | HCV H77 | 30 | A0201 | 5 | SLTVVSAGV | 8196 | 69.55 |
| 290 | HCV H77 | 31 | B7 | 3 | EGRSPGATNL | 8197 | 40 |
| 291 | HCV H77 | 32 | A68.1 | 4 | FPLPVLPRR | 8198 | 15 |
| 292 | HCV H77 | 32 | B3501 | 1 | MPGFPLPVL | 8199 | 20 |
| 293 | HCV H77 | 32 | B7 | 1 | MPGFPLPVL | 8200 | 120 |
| 294 | HCV H77 | 33 | A0201 | 3 | KVGSRLKSTV | 8201 | 21.3 |
| 295 | HCV H77 | 33 | A68.1 | 1 | MVKVGSRLK | 8202 | 120 |
| 296 | HCV H77 | 34 | A68.1 | 13 | LVGMTDTSR | 8203 | 600 |
| 297 | HCV H77 | 35 | A24 | 6 | SFAASSSHF | 8204 | 10 |
| 298 | HCV H77 | 35 | A24 | 15 | FFEWQKMRCL | 8205 | 30 |
| 299 | HCV H77 | 35 | A24 | 6 | SFAASSSHFF | 8206 | 10 |
| 300 | HCV H77 | 35 | A68.1 | 22 | RCLPPLITSR | 8207 | 15 |
| 301 | HCV H77 | 35 | A68.1 | 11 | SSHFFFEWQK | 8208 | 13.5 |
| 302 | HCV H77 | 36 | A0201 | 6 | TVTEPGGVAV | 8209 | 24.95 |
| 303 | HCV H77 | 36 | A1 | 7 | VTEPGGVAV | 8210 | 45 |
| 304 | HCV H77 | 36 | A1 | 7 | VTEPGGVAVA | 8211 | 45 |
| 305 | HCV H77 | 36 | A68.1 | 22 | APAVSAWSR | 8212 | 10 |
| 306 | HCV H77 | 36 | B3501 | 34 | MPKMDVASV | 8213 | 18 |
| 307 | HCV H77 | 36 | B3501 | 28 | WSRTVP-MPKM | 8214 | 30 |
| 308 | HCV H77 | 36 | B3501 | 25 | VSAWSRTVPM | 8215 | 10 |
| 309 | HCV H77 | 36 | B4403 | 8 | TEPGGVAVA | 8216 | 18 |
| 310 | HCV H77 | 36 | B4403 | 8 | TEPGGVAVAS | 8217 | 13.5 |
| 311 | HCV H77 | 36 | B7 | 13 | VAVASTTSL | 8218 | 12 |
| 312 | HCV H77 | 36 | B7 | 12 | GVAVASTTSL | 8219 | 20 |
| 313 | HCV H77 | 36 | B7 | 28 | WSRTVP-MPKM | 8220 | 15 |
| 314 | HCV H77 | 37 | A0201 | 14 | ILGSTPWAL | 8221 | 272.37 |
| 315 | HCV H77 | 37 | A0201 | 13 | LILGSTPWA | 8222 | 23.63 |
| 316 | HCV H77 | 37 | A0201 | 2 | GLPVVIVLT | 8223 | 17.14 |
| 317 | HCV H77 | 37 | A0201 | 7 | IVLTPVLIL | 8224 | 11.09 |
| 318 | HCV H77 | 37 | A0201 | 13 | LILGSTPWAL | 8225 | 138.57 |
| 319 | HCV H77 | 37 | A0201 | 12 | VLILGSTPWA | 8226 | 46.45 |
| 320 | HCV H77 | 37 | A24 | 1 | MGLPVVIVL | 8227 | 10.08 |
| 321 | HCV H77 | 37 | B3501 | 16 | GSTPWALDM | 8228 | 10 |
| 322 | HCV H77 | 37 | B7 | 7 | IVLTPVLIL | 8229 | 30 |
| 323 | HCV H77 | 37 | B7 | 5 | VVIVLTPVL | 8230 | 20 |
| 324 | HCV H77 | 38 | A0201 | 14 | ALATPRVHTA | 8231 | 11.43 |

TABLE 4n-continued

H77 (4-6)

| No | Strain | ORF | HLA | Start | Sequence | SEQ ID NO: | Score |
|---|---|---|---|---|---|---|---|
| 325 | HCV H77 | 38 | A68.1 | 19 | RVHTAALNR | 8232 | 200 |
| 326 | HCV H77 | 38 | A68.1 | 11 | KSTALATPR | 8233 | 15 |
| 327 | HCV H77 | 28 | A68.1 | 2 | VVPRFSTGIK | 8234 | 120 |
| 328 | HCV H77 | 38 | A68.1 | 36 | NSGPPEEPFK | 8235 | 40.5 |
| 329 | HCV H77 | 38 | A68.1 | 1 | MVVPRFSTGI | 8236 | 12 |
| 330 | HCV H77 | 38 | B3501 | 17 | TPRVHTAAL | 8237 | 60 |
| 331 | HCV H77 | 38 | B7 | 17 | TPRVHTAAL | 8238 | 800 |
| 332 | HCV H77 | 38 | B7 | 16 | ATPRVHTAAL | 8239 | 12 |
| 333 | HCV H77 | 38 | B8 | 17 | TPRVHTAAL | 8240 | 16 |
| 334 | HCV H77 | 39 | A24 | 3 | RGESRLPLL | 8241 | 12 |
| 335 | HCV H77 | 39 | A3 | 18 | GMTSACLVTR | 8242 | 18 |
| 336 | HCV H77 | 39 | A68.1 | 19 | MTSACLVTR | 8243 | 50 |
| 337 | HCV H77 | 39 | A68.1 | 8 | LPLLSPRRR | 8244 | 10 |
| 338 | HCV H77 | 39 | A68.1 | 5 | ESRLPLLSPR | 8245 | 45 |
| 339 | HCV H77 | 39 | B3501 | 11 | LSPRRRTGM | 8246 | 10 |
| 340 | HCV H77 | 39 | B7 | 12 | SPRRRTGMT | 8247 | 20 |
| 341 | HCV H77 | 39 | B7 | 1 | MGRGESRLPL | 8248 | 60 |
| 342 | HCV H77 | 39 | B8 | 12 | SPRRRTGMT | 8249 | 16 |
| 343 | HCV H77 | 40 | A0201 | 4 | PLGDAMVLV | 8250 | 14.43 |
| 344 | HCV H77 | 40 | B3501 | 3 | GPLGDAMVL | 8251 | 30 |
| 345 | HCV H77 | 40 | B7 | 3 | GPLGDAMVL | 8252 | 80 |
| 346 | HCV H77 | 41 | A0201 | 77 | LMMSPHAAV | 8253 | 315.96 |
| 347 | HCV H77 | 41 | A0201 | 22 | FLSRPVRLV | 8254 | 147.17 |
| 348 | HCV H77 | 41 | A0201 | 15 | WTSPSTWFL | 8255 | 56.3 |
| 349 | HCV H77 | 41 | A0201 | 6 | KVWVAVDTI | 8256 | 29.89 |
| 350 | HCV H77 | 41 | A0201 | 8 | WVAVDTIWT | 8257 | 16.5 |
| 351 | HCV H77 | 41 | A0201 | 31 | IIHPRRPLV | 8258 | 16.26 |
| 352 | HCV H77 | 41 | A0201 | 45 | VMGASNLHPL | 8259 | 60.33 |
| 353 | HCV H77 | 41 | A0201 | 22 | FLSRPVRLVI | 8260 | 19.68 |
| 354 | HCV H77 | 41 | A0201 | 30 | VIIHPRRPLV | 8261 | 16.26 |
| 355 | HCV H77 | 41 | A24 | 21 | WFLSRPVRL | 8262 | 30 |
| 356 | HCV H77 | 41 | A24 | 42 | AYAVMGASNL | 8263 | 200 |
| 357 | HCV H77 | 41 | A68.1 | 89 | HVMSLVSIR | 8264 | 400 |
| 358 | HCV H77 | 41 | A68.1 | 103 | STATARSRR | 8265 | 100 |
| 359 | HCV H77 | 41 | A68.1 | 100 | TTGSTATAR | 8266 | 100 |
| 360 | HCV H77 | 41 | A68.1 | 91 | MSLVSIREK | 8267 | 18 |
| 361 | HCV H77 | 41 | A68.1 | 102 | GSTATARSR | 8268 | 15 |
| 362 | HCV H77 | 41 | A68.1 | 28 | RLVIIHPRR | 8269 | 10 |
| 363 | HCV H77 | 41 | A68.1 | 111 | RPLCAQSRR | 8270 | 10 |
| 364 | HCV H77 | 41 | A68.1 | 19 | STWFLSRPVR | 8271 | 50 |
| 365 | HCV H77 | 41 | A68.1 | 99 | KTTGSTATAR | 8272 | 50 |
| 366 | HCV H77 | 41 | A68.1 | 26 | PVRLVIIHPR | 8273 | 20 |
| 367 | HCV H77 | 41 | A68.1 | 16 | TSPSTWFLSR | 8274 | 15 |
| 368 | HCV H77 | 41 | A68.1 | 102 | GSTATARSRR | 8275 | 15 |
| 369 | HCV H77 | 41 | A68.1 | 113 | LCAQSRRGVR | 8276 | 10 |
| 370 | HCV H77 | 41 | B3501 | 33 | HPRRPLVCW | 8277 | 30 |
| 371 | HCV H77 | 41 | B3501 | 61 | GPSSISWPL | 8278 | 20 |
| 372 | HCV H77 | 41 | B3501 | 116 | QSRRGVRWL | 8279 | 15 |
| 373 | HCV H77 | 41 | B3501 | 116 | QSRRGVRWLY | 8280 | 30 |
| 374 | HCV H77 | 41 | B4403 | 71 | AETGKPLMM | 8281 | 18 |
| 375 | HCV H77 | 41 | B4403 | 71 | AETGKPLMMS | 8282 | 18 |
| 376 | HCV H77 | 41 | B7 | 61 | GPSSISWPL | 8283 | 80 |
| 377 | HCV H77 | 41 | B7 | 116 | QSRRGVRWL | 8284 | 40 |
| 378 | HCV H77 | 41 | B7 | 105 | ATARSRRPL | 8285 | 18 |
| 379 | HCV H77 | 41 | B7 | 43 | YAVMGASNL | 8286 | 12 |
| 380 | HCV H77 | 41 | B7 | 84 | AVSAPHVMSL | 8287 | 60 |
| 381 | HCV H77 | 41 | B7 | 29 | LVIIHPRRPL | 8288 | 45 |
| 382 | HCV H77 | 41 | B7 | 87 | APHVMSLVSI | 8289 | 24 |
| 383 | HCV H77 | 41 | B7 | 33 | HPRRPLVCWA | 8290 | 20 |
| 384 | HCV H77 | 41 | B7 | 104 | TATARSRRPL | 8291 | 18 |
| 385 | HCV H77 | 41 | B7 | 60 | AGPSSISWPL | 8292 | 12 |
| 386 | HCV H77 | 41 | B7 | 115 | AQSRRGVRWL | 8293 | 12 |
| 387 | HCV H77 | 41 | B8 | 106 | TARSRRPLC | 8294 | 16 |
| 388 | HCV H77 | 41 | B8 | 23 | LSRPVRLVII | 8295 | 20 |
| 389 | HCV H77 | 41 | B8 | 106 | TARSRRPLCA | 8296 | 16 |
| 390 | HCV H77 | 42 | A0201 | 5 | SLVMSNTRV | 8297 | 69.55 |
| 391 | HCV H77 | 42 | A0201 | 21 | KMTASRPPRT | 8298 | 18.84 |
| 392 | HCV H77 | 42 | A3 | 21 | KMTASRPPR | 8299 | 12 |
| 393 | HCV H77 | 42 | A68.1 | 4 | SSLVMSNTR | 8300 | 30 |
| 394 | HCV H77 | 42 | A68.1 | 24 | ASRPPRTLR | 8301 | 22.5 |
| 395 | HCV H77 | 42 | A68.1 | 38 | CSCASTLVR | 8302 | 15 |
| 396 | HCV H77 | 42 | A68.1 | 12 | RVGCTTHMSK | 8303 | 240 |
| 397 | HCV H77 | 42 | A68.1 | 3 | RSSLVMSNTR | 8304 | 15 |
| 398 | HCV H77 | 42 | B4403 | 40 | CASTLVRKY | 8305 | 13.5 |
| 399 | HCV H77 | 42 | B4403 | 39 | SCASTLVRKY | 8306 | 54 |

TABLE 4n-continued

H77 (4-6)

| No | Strain | ORF | HLA | Start | Sequence | SEQ ID NO: | Score |
|---|---|---|---|---|---|---|---|
| 400 | HCV H77 | 42 | B7 | 23 | TASRPPRTL | 8307 | 18 |
| 401 | HCV H77 | 42 | B7 | 10 | NTRVGCTTHM | 8308 | 10 |
| 402 | HCV H77 | 43 | A0201 | 95 | VQLQAASSL | 8309 | 13.62 |
| 403 | HCV H77 | 43 | A0201 | 102 | SLCSTPPTYI | 8310 | 57.38 |
| 404 | HCV H77 | 43 | A0201 | 33 | MLDPTPYKYC | 8311 | 27.87 |
| 405 | HCV H77 | 43 | A1 | 33 | MLDPTPYKY | 8312 | 500 |
| 406 | HCV H77 | 43 | A24 | 40 | KYCTSTMFW | 8313 | 10 |
| 407 | HCV H77 | 43 | A24 | 88 | RSQRSPRVQL | 8314 | 12 |
| 408 | HCV H77 | 43 | A24 | 94 | RVQLQAASSL | 8315 | 12 |
| 409 | HCV H77 | 43 | A24 | 38 | PYKYCTSTMF | 8316 | 10 |
| 410 | HCV H77 | 43 | A24 | 40 | KYCTSTM-FWW | 8317 | 10 |
| 411 | HCV H77 | 43 | A3 | 45 | TMFWWR-WMR | 8318 | 180 |
| 412 | HCV H77 | 43 | A3 | 32 | AMLDPTPYK | 8319 | 45 |
| 413 | HCV H77 | 43 | A3 | 33 | MLDPTPYKY | 8320 | 18 |
| 414 | HCV H77 | 43 | A3 | 32 | AMLDPTPYKY | 8321 | 18 |
| 415 | HCV H77 | 43 | A68.1 | 42 | CTSTMFWWR | 8322 | 50 |
| 416 | HCV H77 | 43 | A68.1 | 10 | QTRASASRR | 8323 | 50 |
| 417 | HCV H77 | 43 | A68.1 | 83 | LSLSSRSQR | 8324 | 30 |
| 418 | HCV H77 | 43 | A68.1 | 13 | ASASRRNRR | 8325 | 30 |
| 419 | HCV H77 | 43 | A68.1 | 9 | EQTRASASR | 8326 | 15 |
| 420 | HCV H77 | 43 | A68.1 | 80 | SSDLSLSSR | 8327 | 15 |
| 421 | HCV H77 | 43 | A68.1 | 86 | SSRSQRSPR | 8328 | 15 |
| 422 | HCV H77 | 43 | A68.1 | 45 | TMFWWR-WMR | 8329 | 10 |
| 423 | HCV H77 | 43 | A68.1 | 44 | STMFWWR-WMR | 8330 | 100 |
| 424 | HCV H77 | 43 | A68.1 | 31 | DAMLDPTPYK | 8331 | 18 |
| 425 | HCV H77 | 43 | A68.1 | 3 | NIIHKQEQTR | 8332 | 15 |
| 426 | HCV H77 | 43 | A68.1 | 9 | EQTRASASRR | 8333 | 15 |
| 427 | HCV H77 | 43 | A68.1 | 79 | LSSDLSLSSR | 8334 | 15 |
| 428 | HCV H77 | 43 | A68.1 | 82 | DLSLSSRSQR | 8335 | 15 |
| 429 | HCV H77 | 43 | A68.1 | 85 | LSSRSQRSPR | 8336 | 15 |
| 430 | HCV H77 | 43 | A68.1 | 54 | PVDKAGRVVK | 8337 | 12 |
| 431 | HCV H77 | 43 | B3501 | 106 | TPPTYILTL | 8338 | 20 |
| 432 | HCV H77 | 43 | B3501 | 53 | RPVDKAGRV | 8339 | 16 |
| 433 | HCV H77 | 43 | B3501 | 37 | TPYKYCTSTM | 8340 | 40 |
| 434 | HCV H77 | 43 | B3501 | 15 | ASRRNRRTTY | 8341 | 30 |
| 435 | HCV H77 | 43 | B3501 | 53 | RPVDKAGRVV | 8342 | 16 |
| 436 | HCV H77 | 43 | B3501 | 24 | YSHLMAQDAM | 8343 | 10 |
| 437 | HCV H77 | 43 | B3501 | 43 | TSTMFW-WRWM | 8344 | 10 |
| 438 | HCV H77 | 43 | B3501 | 88 | RSQRSPRVQL | 8345 | 10 |
| 439 | HCV H77 | 43 | B3501 | 101 | SSLCSTPPTY | 8346 | 10 |
| 440 | HCV H77 | 43 | B4403 | 31 | DAMLDPTPY | 8347 | 27 |
| 441 | HCV H77 | 43 | B4403 | 30 | QDAMLDPTPY | 8348 | 45 |
| 442 | HCV H77 | 43 | B4403 | 101 | SSLCSTPPTY | 8349 | 12 |
| 443 | HCV H77 | 43 | B7 | 89 | SQRSPRVQL | 8350 | 90 |
| 444 | HCV H77 | 43 | B7 | 106 | TPPTYILTL | 8351 | 80 |
| 445 | HCV H77 | 43 | B7 | 71 | CVVDSSNGL | 8352 | 20 |
| 446 | HCV H77 | 43 | B7 | 92 | SPRVQLQAA | 8353 | 20 |
| 447 | HCV H77 | 43 | B7 | 26 | HLMAQDAML | 8354 | 12 |
| 448 | HCV H77 | 43 | B7 | 18 | RNRRTTYSHL | 8355 | 40 |
| 449 | HCV H77 | 43 | B7 | 37 | TPYKYCTSTM | 8356 | 20 |
| 450 | HCV H77 | 43 | B7 | 94 | RVQLQAASSL | 8357 | 20 |
| 451 | HCV H77 | 43 | B8 | 86 | SSRSQRSPRV | 8358 | 12 |
| 452 | HCV H77 | 44 | A0201 | 67 | VLLRTKTSV | 8359 | 437.48 |
| 453 | HCV H77 | 44 | A0201 | 46 | TLVNPVEFI | 8360 | 64.67 |
| 454 | HCV H77 | 44 | A0201 | 31 | VLLPTPPMT | 8361 | 46.87 |
| 455 | HCV H77 | 44 | A0201 | 23 | KQSVGQSKV | 8362 | 24.68 |
| 456 | HCV H77 | 44 | A0201 | 53 | FIQVQPNQL | 8363 | 13.51 |
| 457 | HCV H77 | 44 | A0201 | 60 | QLPSGGLVLL | 8364 | 49.13 |
| 458 | HCV H77 | 44 | A0201 | 66 | LVLLRTKTSV | 8365 | 38.28 |
| 459 | HCV H77 | 44 | A0201 | 47 | LVNPVEFIQV | 8366 | 19.66 |
| 460 | HCV H77 | 44 | A24 | 52 | EFIQVQPNQL | 8367 | 36 |
| 461 | HCV H77 | 44 | A68.1 | 15 | YVASGCLRK | 8368 | 240 |
| 462 | HCV H77 | 44 | A68.1 | 5 | VIQGPEPHR | 8369 | 11.25 |
| 463 | HCV H77 | 44 | A68.1 | 4 | GVIQGPEPHR | 8370 | 900 |
| 464 | HCV H77 | 44 | B3501 | 61 | LPSGGLVLL | 8371 | 20 |
| 465 | HCV H77 | 44 | B4403 | 57 | QPNQLPSGGL | 8372 | 20 |
| 466 | HCV H77 | 44 | B7 | 61 | LPSGGLVLL | 8373 | 80 |
| 467 | HCV H77 | 44 | B7 | 25 | SVGQSKVLL | 8374 | 20 |
| 468 | HCV H77 | 44 | B7 | 43 | APHTLVNPV | 8375 | 12 |

TABLE 4n-continued

H77 (4-6)

| No | Strain | ORF | HLA | Start | Sequence | SEQ ID NO: | Score |
|---|---|---|---|---|---|---|---|
| 469 | HCV H77 | 44 | B7 | 57 | QPNQLPSGGL | 8376 | 120 |
| 470 | HCV H77 | 45 | A0201 | 11 | WMFCLAPGV | 8377 | 854.95 |
| 471 | HCV H77 | 45 | A0201 | 7 | VLISWMFCL | 8378 | 484.46 |
| 472 | HCV H77 | 45 | A0201 | 6 | LVLISWMFC | 8379 | 25.57 |
| 473 | HCV H77 | 45 | A0201 | 6 | LVLISWMFCL | 8380 | 156.84 |
| 474 | HCV H77 | 45 | A0201 | 3 | QLPLVLISWM | 8381 | 62.85 |
| 475 | HCV H77 | 45 | A0201 | 7 | VLISWMFCLA | 8382 | 16.05 |
| 476 | HCV H77 | 45 | A0201 | 26 | AVVRPAFPPV | 8383 | 11.56 |
| 477 | HCV H77 | 45 | A0201 | 54 | AQFPTMEKYA | 8384 | 10.25 |
| 478 | HCV H77 | 45 | A3 | 7 | VLISWMFCL | 8385 | 12.15 |
| 479 | HCV H77 | 45 | A68.1 | 13 | FCLAPGVRR | 8386 | 10 |
| 480 | HCV H77 | 45 | B3501 | 56 | FPTMEKYAM | 8387 | 60 |
| 481 | HCV H77 | 45 | B3501 | 4 | LPLVLISWM | 8388 | 40 |
| 482 | HCV H77 | 45 | B3501 | 24 | SPAVVRPAF | 8389 | 20 |
| 483 | HCV H77 | 45 | B3501 | 29 | RPAFPPVTW | 8390 | 20 |
| 484 | HCV H77 | 45 | B3501 | 4 | LPLVLISWMF | 8391 | 20 |
| 485 | HCV H77 | 45 | B7 | 4 | LPLVLISWM | 8392 | 20 |
| 486 | HCV H77 | 45 | B7 | 56 | FPTMEKYAM | 8393 | 20 |
| 487 | HCV H77 | 45 | B7 | 27 | VVRPAFPPV | 8394 | 10 |
| 488 | HCV H77 | 45 | B7 | 6 | LVLISWMFCL | 8395 | 20 |
| 489 | HCV H77 | 45 | B7 | 18 | GVRRPTSPAV | 8396 | 10 |
| 490 | HCV H77 | 46 | A68.1 | 1 | MSMMACGIR | 8397 | 30 |
| 491 | HCV H77 | 47 | A0201 | 8 | TILELGQSL | 8398 | 44.56 |
| 492 | HCV H77 | 47 | A0201 | 8 | TILELGQSLV | 8399 | 145.08 |
| 493 | HCV H77 | 47 | A24 | 8 | TILELGQSL | 8400 | 10.37 |
| 494 | HCV H77 | 47 | B4403 | 10 | LELGQSLVT | 8401 | 12 |
| 495 | HCV H77 | 47 | B4403 | 10 | LELGQSLVTW | 8402 | 54 |
| 496 | HCV H77 | 47 | B7 | 4 | AASYTILEL | 8403 | 36 |
| 497 | HCV H77 | 47 | B7 | 2 | ASAASYTIL | 8404 | 12 |
| 498 | HCV H77 | 47 | B7 | 1 | MASAASYTIL | 8405 | 12 |
| 499 | HCV H77 | 47 | B7 | 3 | SAASYTILEL | 8406 | 12 |
| 500 | HCV H77 | 48 | A24 | 8 | KPHVRVSMTL | 8407 | 11.2 |
| 501 | HCV H77 | 48 | A68.1 | 13 | VSMTLPKLR | 8408 | 30 |
| 502 | HCV H77 | 48 | A68.1 | 26 | GSVGPQLGR | 8409 | 30 |
| 503 | HCV H77 | 48 | A68.1 | 12 | RVSMTLPKLR | 8410 | 200 |
| 504 | HCV H77 | 48 | A68.1 | 15 | MTLPKLRDLR | 8411 | 150 |
| 505 | HCV H77 | 48 | A68.1 | 10 | HVRVSMTLPK | 8412 | 120 |
| 506 | HCV H77 | 48 | A68.1 | 31 | QLGREPRGDR | 8413 | 10 |
| 507 | HCV H77 | 48 | B3501 | 42 | HPAHPQPSL | 8414 | 20 |
| 508 | HCV H77 | 48 | B3501 | 8 | KPHVRVSMTL | 8415 | 40 |
| 509 | HCV H77 | 48 | B3501 | 6 | SAKPHVRVSM | 8416 | 18 |
| 510 | HCV H77 | 48 | B7 | 42 | HPAHPQPSL | 8417 | 120 |
| 511 | HCV H77 | 48 | B7 | 12 | RVSMTLPKL | 8418 | 20 |
| 512 | HCV H77 | 48 | B7 | 8 | KPHVRVSMTL | 8419 | 80 |
| 513 | HCV H77 | 48 | B7 | 35 | EPRGDRSHPA | 8420 | 20 |
| 514 | HCV H77 | 48 | B7 | 2 | YPMRSAKPHV | 8421 | 12 |
| 515 | HCV H77 | 48 | B8 | 35 | EPRGDRSHPA | 8422 | 32 |
| 516 | HCV H77 | 48 | B8 | 19 | KLRDLRRGSV | 8423 | 18 |
| 517 | HCV H77 | 49 | A0201 | 22 | GLSRPNTTRL | 8424 | 21.36 |
| 518 | HCV H77 | 49 | A24 | 15 | PYQAVPQGL | 8425 | 50.4 |
| 519 | HCV H77 | 49 | A24 | 25 | RPNTTRLAVL | 8426 | 12 |
| 520 | HCV H77 | 49 | A3 | 22 | GLSRPNTTR | 8427 | 18 |
| 521 | HCV H77 | 49 | A3 | 33 | VLRGHAQISR | 8428 | 12 |
| 522 | HCV H77 | 49 | A68.1 | 27 | NTTRLAVLR | 8429 | 50 |
| 523 | HCV H77 | 49 | A68.1 | 17 | QAVPQGLSR | 8430 | 15 |
| 524 | HCV H77 | 49 | A68.1 | 16 | YQAVPQGLSR | 8431 | 10 |
| 525 | HCV H77 | 49 | B3501 | 8 | LPGHSQAPY | 8432 | 40 |
| 526 | HCV H77 | 49 | B3501 | 23 | LSRPNTTRL | 8433 | 15 |
| 527 | HCV H77 | 49 | B3501 | 25 | RPNTTRLAVL | 8434 | 40 |
| 528 | HCV H77 | 49 | B3501 | 14 | APYQAVPQGL | 8435 | 20 |
| 529 | HCV H77 | 49 | B7 | 23 | LSRPNTTRL | 8436 | 40 |
| 530 | HCV H77 | 49 | B7 | 14 | APYQAVPQGL | 8437 | 240 |
| 531 | HCV H77 | 49 | B7 | 25 | RPNTTRLAVL | 8438 | 80 |
| 532 | HCV H77 | 50 | A0201 | 2 | RLTDLSQLA | 8439 | 20.37 |
| 533 | HCV H77 | 50 | A0201 | 2 | RLTDLSQLAV | 8440 | 285.16 |
| 534 | HCV H77 | 50 | A1 | 15 | KMEPPLKKGK | 8441 | 90 |
| 535 | HCV H77 | 50 | A24 | 49 | KWLKRPECL | 8442 | 12 |
| 536 | HCV H77 | 50 | A3 | 15 | KMEPPLKKGK | 8443 | 45 |
| 537 | HCV H77 | 50 | A68.1 | 5 | DLSQLAVTR | 8444 | 15 |
| 538 | HCV H77 | 50 | A68.1 | 17 | EPPLKKGKR | 8445 | 15 |
| 539 | HCV H77 | 50 | B3501 | 61 | SSVGEEVDAY | 8446 | 15 |
| 540 | HCV H77 | 50 | B4403 | 65 | EEVDAYPCS | 8447 | 12 |
| 541 | HCV H77 | 50 | B4403 | 61 | SSVGEEVDAY | 8448 | 54 |
| 542 | HCV H77 | 50 | B7 | 11 | VTRAKMEPPL | 8449 | 40 |
| 543 | HCV H77 | 51 | A0201 | 32 | FELCSYCPV | 8450 | 34.53 |

TABLE 4n-continued

H77 (4-6)

| No | Strain | ORF | HLA | Start | Sequence | SEQ ID NO: | Score |
|---|---|---|---|---|---|---|---|
| 544 | HCV H77 | 51 | A1 | 29 | WSEFELCSY | 8451 | 67.5 |
| 545 | HCV H77 | 51 | A24 | 36 | SYCPVEEVL | 8452 | 336 |
| 546 | HCV H77 | 51 | A24 | 27 | RYWSEFELC | 8453 | 12 |
| 547 | HCV H77 | 51 | A24 | 75 | KFSEACGHPI | 8454 | 12 |
| 548 | HCV H77 | 51 | A24 | 27 | RYWSEFELCS | 8455 | 10 |
| 549 | HCV H77 | 51 | A68.1 | 7 | NVSPAVASR | 8456 | 300 |
| 550 | HCV H77 | 51 | A68.1 | 64 | PVSPSSQGR | 8457 | 30 |
| 551 | HCV H77 | 51 | A68.1 | 19 | GQVQPASGR | 8458 | 10 |
| 552 | HCV H77 | 51 | A68.1 | 42 | EVLATYGSPA | 8459 | 24 |
| 553 | HCV H77 | 51 | A68.1 | 63 | GPVSPSSQGR | 8460 | 10 |
| 554 | HCV H77 | 51 | B3501 | 38 | CPVEEVLATY | 8461 | 80 |
| 555 | HCV H77 | 51 | B4403 | 41 | EEVLATYGS | 8462 | 18 |
| 556 | HCV H77 | 51 | B4403 | 77 | SEACGHPIDF | 8463 | 160 |
| 557 | HCV H77 | 51 | B4403 | 38 | CPVEEVLATY | 8464 | 13.5 |
| 558 | HCV H77 | 51 | B4403 | 15 | REPTGQVQPA | 8465 | 12 |
| 559 | HCV H77 | 51 | B4403 | 59 | ADAPGPVSPS | 8466 | 12 |
| 560 | HCV H77 | 51 | B7 | 25 | SGRYWSEFEL | 8467 | 40 |
| 561 | HCV H77 | 53 | B3501 | 8 | RPQCGGKHDY | 8468 | 80 |
| 562 | HCV H77 | 54 | A1 | 2 | ATDVFCPIAK | 8469 | 125 |
| 563 | HCV H77 | 54 | A24 | 5 | VFCPIAKLGF | 8470 | 12 |
| 564 | HCV H77 | 54 | A68.1 | 4 | DVFCPIAKL | 8471 | 24 |
| 565 | HCV H77 | 54 | A68.1 | 2 | ATDVFCPIAK | 8472 | 30 |
| 566 | HCV H77 | 54 | B7 | 4 | DVFCPIAKL | 8473 | 30 |
| 567 | HCV H77 | 55 | B7 | 2 | WGRQAASFL | 8474 | 40 |
| 568 | HCV H77 | 56 | A0201 | 13 | FLLPLASTA | 8475 | 84.56 |
| 569 | HCV H77 | 56 | A0201 | 5 | NLQSVKCDFL | 8476 | 57.57 |
| 570 | HCV H77 | 56 | A0201 | 6 | LQSVKCDFLL | 8477 | 21.36 |
| 571 | HCV H77 | 56 | A68.1 | 2 | AVQNLQSVK | 8478 | 120 |
| 572 | HCV H77 | 56 | B7 | 8 | SVKCDFLLPL | 8479 | 20 |
| 573 | HCV H77 | 57 | A0201 | 6 | FVVRLFPRL | 8480 | 16.34 |
| 574 | HCV H77 | 57 | A24 | 5 | WFVVRLFPRL | 8481 | 43.2 |
| 575 | HCV H77 | 57 | B7 | 6 | FVVRLFPRL | 8482 | 20 |
| 576 | HCV H77 | 58 | A68.1 | 16 | ASRGAGHRR | 8483 | 15 |
| 577 | HCV H77 | 58 | A68.1 | 1 | MVGGASCLER | 8484 | 400 |
| 578 | HCV H77 | 58 | A68.1 | 14 | QLASRGAGHR | 8485 | 15 |
| 579 | HCV H77 | 59 | A0201 | 9 | RQHGYVRFGL | 8486 | 12.56 |
| 580 | HCV H77 | 59 | A1 | 4 | ISEHGRQHGY | 8487 | 67.5 |
| 581 | HCV H77 | 59 | A24 | 9 | RQHGYVRFGL | 8488 | 11.2 |
| 582 | HCV H77 | 59 | B4403 | 5 | SEHGRQHGY | 8489 | 360 |
| 583 | HCV H77 | 59 | B4403 | 5 | SEHGRQHGYV | 8490 | 12 |
| 584 | HCV H77 | 60 | A0201 | 48 | KVAQHLAYPV | 8491 | 21.3 |
| 585 | HCV H77 | 60 | A3 | 46 | GLKVAQHLAY | 8492 | 24 |
| 586 | HCV H77 | 60 | A68.1 | 40 | ELGFQPGLK | 8493 | 18 |
| 587 | HCV H77 | 60 | A68.1 | 27 | LAGHKGNPR | 8494 | 10 |
| 588 | HCV H77 | 60 | A68.1 | 26 | ALAGHKGNPR | 8495 | 10 |
| 589 | HCV H77 | 60 | B3501 | 33 | NPRQLWHEL | 8496 | 60 |
| 590 | HCV H77 | 60 | B3501 | 44 | QPGLKVAQHL | 8497 | 20 |
| 591 | HCV H77 | 60 | B3501 | 18 | SSPDPPIPAL | 8498 | 10 |
| 592 | HCV H77 | 60 | B4403 | 39 | HELGFQPGL | 8499 | 12 |
| 593 | HCV H77 | 60 | B7 | 33 | NPRQLWHEL | 8500 | 800 |
| 594 | HCV H77 | 60 | B7 | 19 | SPDPPIPAL | 8501 | 36 |
| 595 | HCV H77 | 60 | B7 | 44 | QPGLKVAQHL | 8502 | 80 |
| 596 | HCV H77 | 60 | B7 | 28 | AGHKGNPRQL | 8503 | 12 |
| 597 | HCV H77 | 60 | B8 | 33 | NPRQLWHEL | 8504 | 16 |
| 598 | HCV H77 | 61 | A24 | 14 | EYGSDAGGCI | 8505 | 50 |
| 599 | HCV H77 | 61 | A68.1 | 18 | DAGGCIALR | 8506 | 30 |
| 600 | HCV H77 | 61 | A68.1 | 22 | CIALRHVVR | 8507 | 10 |
| 601 | HCV H77 | 61 | A68.1 | 21 | GCIALRHVVR | 8508 | 10 |
| 602 | HCV H77 | 61 | B4403 | 5 | QELGYSEAA | 8509 | 12 |
| 603 | HCV H77 | 61 | B4403 | 13 | AEYGSDAGGC | 8510 | 18 |
| 604 | HCV H77 | 61 | B4403 | 10 | SEAAEYGSDA | 8511 | 16 |
| 605 | HCV H77 | 62 | A0201 | 16 | LLSEHHPLL | 8512 | 148.9 |
| 606 | HCV H77 | 62 | A0201 | 5 | GLQEAEGLL | 8513 | 11.39 |
| 607 | HCV H77 | 62 | A0201 | 5 | GLQEAEGLLL | 8514 | 87.59 |
| 608 | HCV H77 | 62 | A24 | 4 | RGLQEAEGL | 8515 | 12 |
| 609 | HCV H77 | 62 | A24 | 4 | RGLQEAEGLL | 8516 | 12 |
| 610 | HCV H77 | 62 | B4403 | 9 | AEGLLLELL | 8517 | 12 |
| 611 | HCV H77 | 62 | B4403 | 18 | SEHHPLLDV | 8518 | 12 |
| 612 | HCV H77 | 62 | B4403 | 7 | QEAEGLLLEL | 8519 | 12 |
| 613 | HCV H77 | 63 | A0201 | 37 | KVLPTLLCL | 8520 | 55.67 |
| 614 | HCV H77 | 63 | A0201 | 29 | GLVRYQVRKV | 8521 | 31.99 |
| 615 | HCV H77 | 63 | A0201 | 33 | YQVRKVLPTL | 8522 | 22.92 |
| 616 | HCV H77 | 63 | A24 | 37 | KVLPTLLCL | 8523 | 14.4 |
| 617 | HCV H77 | 63 | A24 | 32 | RYQVRKVLPT | 8524 | 15 |
| 618 | HCV H77 | 63 | A3 | 29 | GLVRYQVRK | 8525 | 270 |

TABLE 4n-continued

H77 (4-6)

| No | Strain | ORF | HLA | Start | Sequence | SEQ ID NO: | Score |
|---|---|---|---|---|---|---|---|
| 619 | HCV H77 | 63 | A68.1 | 9 | QTLPHLVPR | 8526 | 150 |
| 620 | HCV H77 | 63 | A68.1 | 37 | KVLPTLLCL | 8527 | 12 |
| 621 | HCV H77 | 63 | A68.1 | 8 | DQTLPHLVPR | 8528 | 15 |
| 622 | HCV H77 | 63 | B4403 | 25 | SAHGGLVRY | 8529 | 13.5 |
| 623 | HCV H77 | 63 | B4403 | 1 | MEGGFKADQT | 8530 | 13.5 |
| 624 | HCV H77 | 63 | B7 | 34 | QVRKVLPTL | 8531 | 200 |
| 625 | HCV H77 | 63 | B7 | 14 | LVPRWGRGL | 8532 | 20 |
| 626 | HCV H77 | 63 | B7 | 37 | KVLPTLLCL | 8533 | 20 |
| 627 | HCV H77 | 63 | B7 | 30 | LVRYQVRKV | 8534 | 10 |
| 628 | HCV H77 | 63 | B7 | 30 | LVRYQVRKVL | 8535 | 300 |
| 629 | HCV H77 | 63 | B7 | 34 | QVRKVLPTLL | 8536 | 200 |
| 630 | HCV H77 | 64 | A0201 | 8 | ALPKFKMVL | 8537 | 33.28 |
| 631 | HCV H77 | 64 | A0201 | 15 | VLAHGKPRGV | 8538 | 23.65 |
| 632 | HCV H77 | 64 | A0201 | 8 | ALPKFKMVLA | 8539 | 11.43 |
| 633 | HCV H77 | 64 | A68.1 | 14 | MVLAHGKPR | 8540 | 400 |
| 634 | HCV H77 | 64 | A68.1 | 13 | KMVLAHGKPR | 8541 | 10 |
| 635 | HCV H77 | 64 | B3501 | 20 | KPRGVHVRS | 8542 | 12 |
| 636 | HCV H77 | 64 | B7 | 8 | ALPKFKMVL | 8543 | 12 |
| 637 | HCV H77 | 64 | B7 | 7 | DALPKFKMVL | 8544 | 12 |
| 638 | HCV H77 | 64 | B8 | 9 | LPKFKMVLA | 8545 | 16 |
| 639 | HCV H77 | 65 | A0201 | 72 | VALVTNYYV | 8546 | 33.42 |
| 640 | HCV H77 | 65 | A0201 | 71 | GVALVTNYYV | 8547 | 33.47 |
| 641 | HCV H77 | 65 | A1 | 7 | HLEGDSLAVK | 8548 | 36 |
| 642 | HCV H77 | 65 | A3 | 7 | HLEGDSLAVK | 8549 | 45 |
| 643 | HCV H77 | 65 | A68.1 | 42 | SSGEHNQSR | 8550 | 30 |
| 644 | HCV H77 | 65 | A68.1 | 31 | RMGHSDGAR | 8551 | 15 |
| 645 | HCV H77 | 65 | A68.1 | 62 | DAQDGCGIR | 8552 | 15 |
| 646 | HCV H77 | 65 | A68.1 | 41 | GSSGEHNQSR | 8553 | 15 |
| 647 | HCV H77 | 65 | A68.1 | 29 | DVRMGHSDGA | 8554 | 12 |
| 648 | HCV H77 | 65 | A68.1 | 31 | RMGHSDGARR | 8555 | 10 |
| 649 | HCV H77 | 65 | B3501 | 48 | QSRPRSLCL | 8556 | 15 |
| 650 | HCV H77 | 65 | B3501 | 24 | QSNLLDVRM | 8557 | 10 |
| 651 | HCV H77 | 65 | B4403 | 70 | RGVALVTNY | 8558 | 27 |
| 652 | HCV H77 | 65 | B4403 | 70 | RGVALVTNYY | 8559 | 13.5 |
| 653 | HCV H77 | 65 | B7 | 48 | QSRPRSLCL | 8560 | 40 |
| 654 | HCV H77 | 65 | B8 | 48 | QSRPRSLCL | 8561 | 80 |
| 655 | HCV H77 | 65 | B8 | 66 | GCGIRGVAL | 8562 | 16 |
| 656 | HCV H77 | 66 | A0201 | 51 | ALGHCWWRGV | 8563 | 23.65 |
| 657 | HCV H77 | 66 | A0201 | 43 | SMQVGHLEAL | 8564 | 17.39 |
| 658 | HCV H77 | 66 | A68.1 | 50 | EALGHCWWR | 8565 | 30 |
| 659 | HCV H77 | 66 | A68.1 | 22 | HLVALGCVR | 8566 | 10 |
| 660 | HCV H77 | 66 | A68.1 | 24 | VALGCVRSR | 8567 | 10 |
| 661 | HCV H77 | 66 | A68.1 | 23 | LVALGCVRSR | 8568 | 400 |
| 662 | HCV H77 | 66 | A68.1 | 7 | STKAQRCSNR | 8569 | 50 |
| 663 | HCV H77 | 66 | B4403 | 49 | LEALGHCWW | 8570 | 24 |
| 664 | HCV H77 | 66 | B7 | 28 | CVRSRDLGAL | 8571 | 200 |
| 665 | HCV H77 | 66 | B7 | 14 | SNRGVEHQL | 8572 | 40 |
| 666 | HCV H77 | 66 | B7 | 25 | ALGCVRSRDL | 8573 | 12 |
| 667 | HCV H77 | 66 | B7 | 40 | AGGSMQVGHL | 8574 | 12 |
| 668 | HCV H77 | 67 | A68.1 | 1 | MVIHIGASK | 8575 | 240 |
| 669 | HCV H77 | 67 | A68.1 | 1 | MVIHIGASKR | 8576 | 400 |
| 670 | HCV H77 | 69 | A68.1 | 14 | VAHPSDDTR | 8577 | 11.25 |
| 671 | HCV H77 | 69 | A68.1 | 13 | VVAHPSDDTR | 8578 | 600 |
| 672 | HCV H77 | 69 | B4403 | 9 | AEQGVVAHPS | 8579 | 27 |
| 673 | HCV H77 | 69 | B4403 | 19 | DDTRGRSAHF | 8580 | 15 |
| 674 | HCV H77 | 70 | A0201 | 59 | KLRCGEFAV | 8581 | 107.3 |
| 675 | HCV H77 | 70 | A0201 | 52 | KQIDMTSKL | 8582 | 31.08 |
| 676 | HCV H77 | 70 | A1 | 44 | RAEGGAPDK | 8583 | 36 |
| 677 | HCV H77 | 70 | A24 | 52 | KQIDMTSKL | 8584 | 15.84 |
| 678 | HCV H77 | 70 | A24 | 3 | RYMAGIDRT | 8585 | 15 |
| 679 | HCV H77 | 70 | A24 | 3 | RYMAGIDRTI | 8586 | 210 |
| 680 | HCV H77 | 70 | A24 | 93 | RSVQDGIGRL | 8587 | 12 |
| 681 | HCV H77 | 70 | A68.1 | 18 | PVAPGREGK | 8588 | 36 |
| 682 | HCV H77 | 70 | A68.1 | 93 | RSVQDGIGR | 8589 | 30 |
| 683 | HCV H77 | 70 | A68.1 | 36 | AQVPHVEGR | 8590 | 15 |
| 684 | HCV H77 | 70 | A68.1 | 26 | KQLTNKKDR | 8591 | 10 |
| 685 | HCV H77 | 70 | A68.1 | 101 | RLVHNTRVR | 8592 | 10 |
| 686 | HCV H77 | 70 | A68.1 | 111 | IIGDMVKPR | 8593 | 10 |
| 687 | HCV H77 | 70 | A68.1 | 1 | MTRYMAGIDR | 8594 | 50 |
| 688 | HCV H77 | 70 | A68.1 | 67 | VPGGHRGGHR | 8595 | 15 |

TABLE 4n-continued

H77 (4-6)

| No | Strain | ORF | HLA | Start | Sequence | SEQ ID NO: | Score |
|---|---|---|---|---|---|---|---|
| 689 | HCV H77 | 70 | A68.1 | 84 | TLANARDTPR | 8596 | 15 |
| 690 | HCV H77 | 70 | A68.1 | 52 | KQIDMTSKLR | 8597 | 10 |
| 691 | HCV H77 | 70 | A68.1 | 98 | GIGRLVHNTR | 8598 | 10 |
| 692 | HCV H77 | 70 | A68.1 | 110 | AIIGDMVKPR | 8599 | 10 |
| 693 | HCV H77 | 70 | B3501 | 20 | APGREGKQL | 8600 | 30 |
| 694 | HCV H77 | 70 | B3501 | 117 | KPRGIAHLV | 8601 | 24 |
| 695 | HCV H77 | 70 | B3501 | 91 | TPRSVQDGI | 8602 | 24 |
| 696 | HCV H77 | 70 | B3501 | 77 | HPTPRGVTL | 8603 | 20 |
| 697 | HCV H77 | 70 | B3501 | 57 | TSKLRCGEF | 8604 | 15 |
| 698 | HCV H77 | 70 | B3501 | 107 | RVRAIIGDM | 8605 | 12 |
| 699 | HCV H77 | 70 | B3501 | 48 | GAPDKQIDM | 8606 | 12 |
| 700 | HCV H77 | 70 | B3501 | 93 | RSVQDGIGRL | 8607 | 10 |
| 701 | HCV H77 | 70 | B4403 | 45 | AEGGAPDKQI | 8608 | 18 |
| 702 | HCV H77 | 70 | B7 | 20 | APGREGKQL | 8609 | 240 |
| 703 | HCV H77 | 70 | B7 | 77 | HPTPRGVTL | 8610 | 80 |
| 704 | HCV H77 | 70 | B7 | 91 | TPRSVQDGI | 8611 | 80 |
| 705 | HCV H77 | 70 | B7 | 107 | RVRAIIGDM | 8612 | 50 |
| 706 | HCV H77 | 70 | B7 | 117 | KPRGIAHLV | 8613 | 40 |
| 707 | HCV H77 | 70 | B7 | 94 | SVQDGIGRL | 8614 | 20 |
| 708 | HCV H77 | 70 | B7 | 79 | TPRGVTLANA | 8615 | 20 |
| 709 | HCV H77 | 70 | B7 | 115 | MVKPRGIAHL | 8616 | 20 |
| 710 | HCV H77 | 70 | B7 | 6 | AGIDRTIAVL | 8617 | 12 |
| 711 | HCV H77 | 70 | B7 | 19 | VAPGREGKQL | 8618 | 12 |
| 712 | HCV H77 | 70 | B7 | 107 | RVRAIIGDMV | 8619 | 10 |
| 713 | HCV H77 | 70 | B8 | 77 | HPTPRGVTL | 8620 | 16 |
| 714 | HCV H77 | 70 | B8 | 29 | TNKKDRPAQV | 8621 | 12 |

Example 1.2

Immunogenicity of ncHCV Peptides According to the Present Invention

To determine if the peptides provided with the present invention are potentially immunogenic, three peptides from HCV 1b for the HLA-A*0201 allele were chosen and HLA-A*0201 transgenic mice (HHD) vaccinated therewith.

Example 1.2.1

Vaccination of Mice with ncORFs According to the Present Invention (Ipep 1371, Ipep 1372, Ipep 1373)

HLA-A*0201-transgenic mice (5 per group) were vaccinated subcutaneously as follows:

1) 1371 (HCV-H77 ncORF(1-3)11 TLWAGPLLKV-SEQ ID NO: 823) + CpG 1668

2) 1372 (HCV-H77 ncORF(1-3)13 LLLQRWALV-SEQ ID NO: 824) + CpG 1668

3) 1373 (HCV-H77 ncORF(1-3)27 FMLGALLPI-SEQ ID NO: 825) + CpG 1668

7 days after the vaccination draining lymph nodes were removed and the cells were activated ex vivo with peptides to determine the number of IFN-g-producing peptide-specific T cells (Elispot assay). As can be seen in FIG. 1, all peptides induce high numbers of peptide-specific T cells ("Background" means "Medium Control", i.e. cells cultured without peptide).

Example 1.2.2

Vaccination of Mice with ncORFs According to the Present Invention (Ipep 1445, Ipep 1447)

HLA-A*0201-transgenic mice (5 per group) were vaccinated subcutaneously as follows:

1) 1445 (HCV-1b ncORF(1-3)36 RLLQLKYCV (SEQ ID NO: 826) + CpG 1668

2) 1447 (HCV-1b ncORF(1-3)36 FLYLPLSFAV (SEQ ID NO: 827) + CpG 1668

Figure 2:
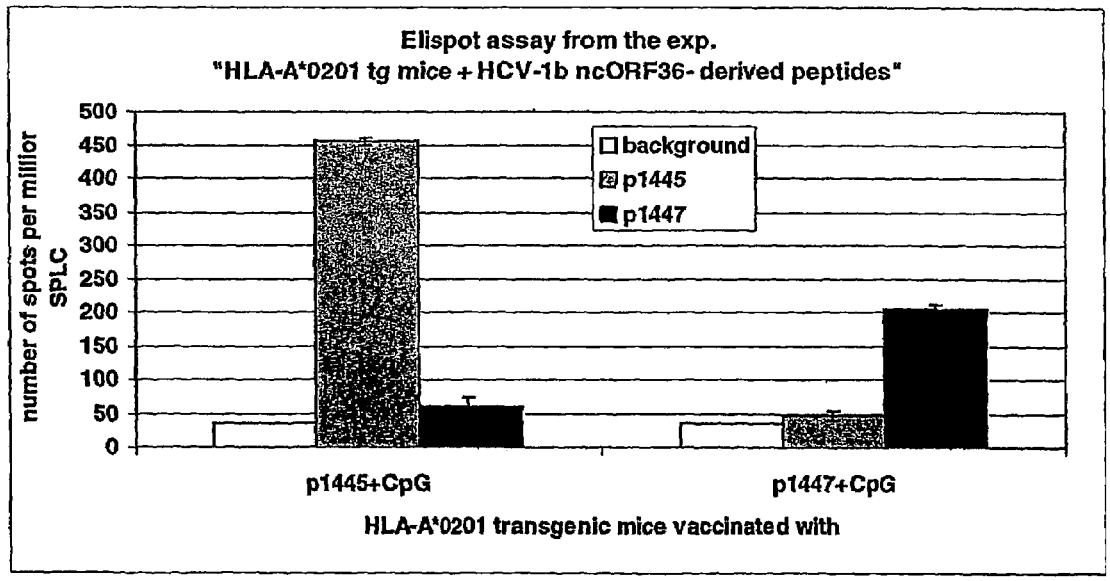
FIG. 2 shows the Elispot assay from the experiment with HLA-A*0201 tg mice+HCV-1b ncORF 36-derived peptides.

7 days after the vaccination spleens were removed and the cells were activated ex vivo with peptides to determine the number of IFN-g-producing peptide-specific T cells (Elispot assay). As can be seen in FIG. 2, both peptides induce high numbers of peptide-specific T cells ("Background" means "Medium Control", i.e. cells cultured without peptide).

Example 1.3

HCV Patient In Vivo Relevance of the ncHCV Peptides According to the Present Invention Since those ncORF peptides are immunogenic in tg-mice, the present peptides were ananlysed in an ELIspot assay on PBL's from HCV+ patients.

Example 1.3.1

Elispot with HCV patient-derived cells and with ncORFs according to the present invention (Ipep 1371, Ipep 1372, Ipep 1373)

The patient had a chronic HCV infection in 1992 that was cured under IFN-alpha mono-therapy from 1993 to 1994. Patient-derived peripheral blood mononuclear cells (PBMC) frozen in 1996 were thawed to perform an IFN-g Elispot assay with the following peptides:

```
1) 1371 (HCV-H77 ncORF(1-3)11   TLWAGPLLKV-SEQ ID NO: 823)

2) 1372 (HCV-H77 ncORF(1-3)13   LLLQRWALV-SEQ ID NO: 824)

3) 1373 (HCV-H77 ncORF(1-3)27   FMLGALLPI-SEQ ID NO: 825)

4) 1006 (HCV-derived)           MWNFISGIQYLAGLSTLPGN
                                (SEQ ID NO: 828)

5) 84 (HCV-derived)             GYKVLVLNPSVAAT
                                (SEQ ID NO: 829)

6) CMV pp65                     NLVPMVATV

7) Influenza A Matrix           GILGFVFTL
   (aa58-67)
```

Figure 3:
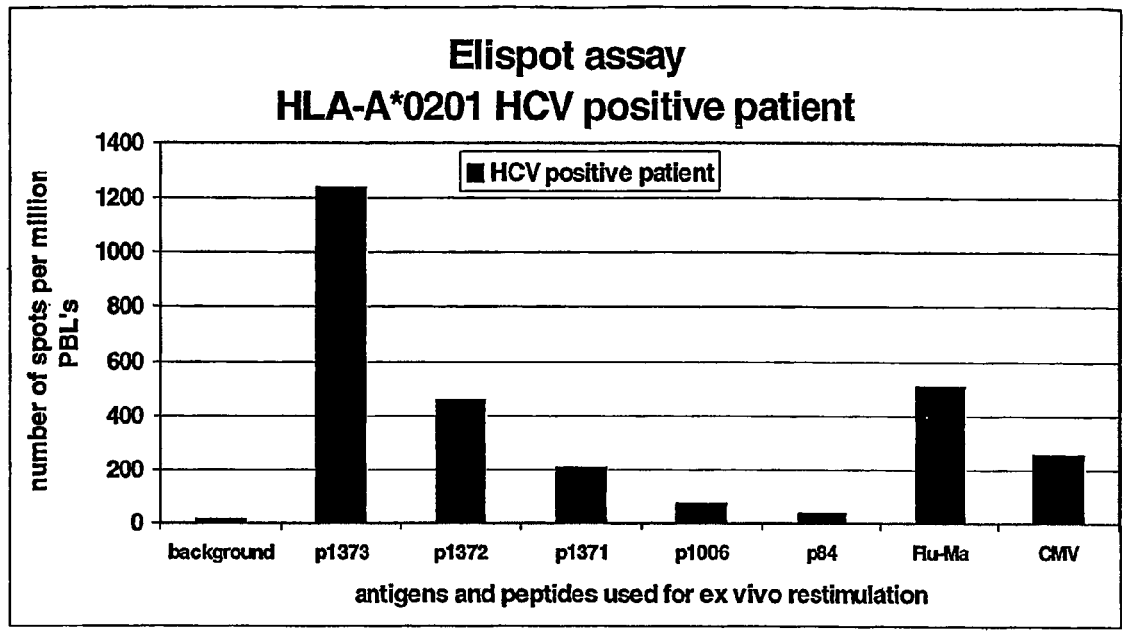
FIG. 3 shows an Elispot assay for an HLA-A*0201 HCV positive patient

As can be seen in Table 5 and FIG. 3, the peptides 1371, 1372, and 1373 as well as the positive control peptides (CMV-derived, Influenza-derived) induce high numbers of peptide-specific T cells.

TABLE 5

ELIspot results
ELISPOT-resuls Patient MRG Plate 11_01_03

| Peptide | Counts-mean size >10 | Counts-mean size >25 | Counts-mean size >75 |
|---|---|---|---|
| 1373 | 159 | 86 | 3 |
| 1372 | 43 | 36 | 13 |
| 1371 | 24 | 15 | 2 |
| Medium-control | 2 | 1 | 0 |
| PHA | Confluent | Confluent | Confluent |
| Flu-Ma | 48 | 36 | 17 |
| CMV | 28 | 17 | 6 |

Example 1.4

Peptides from Reading Frames 4 to 6 are Immunogenic in Transgenic Mice (Ipep 1490, Ipep 1491; Ipep 1492; Ipep 1493; Ipep 1494, Ipep 82) HLA-A*0201-transgenic mice (5 per group) were vaccinated subcutaneously as follows:

```
1) 1490 (HCV-1b ncORF(4-6) KMLNRRVLWV-SEQ ID
   NO: 830) + CpG 1668

2) 1491 (HCV-1b ncORF(4-6) VLLMCQLPLV-SEQ ID
   NO: 831) + CpG 1668

3) 1492 (HCV-1b ncORF(4-6) MLNRRVLWVV-SEQ ID
   NO: 832) + CpG 1668

4) 1493 (HCV-1b ncORF(4-6) TILELEQSFV-SEQ ID
   NO: 833) + CpG 1668

5) 1494 (HCV-1b ncORF(4-6) KMMSPHAAV-SEQ ID
   NO: 834) + CpG 1668

6) 82 (EBV, control GLCTLVAML-SEQ ID NO:
   1038) + CpG 1668
```

Figure 4:
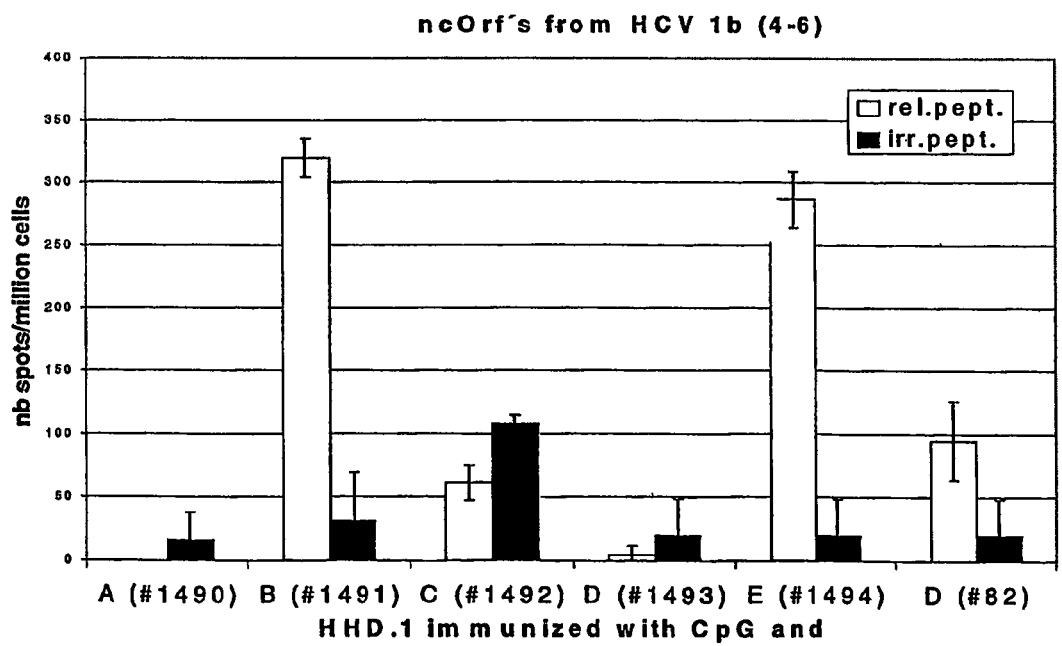
FIG. 4 shows the immunogenicity of peptides from HCV 1b reading frames 4 to 6 in transgenic mice

7 days after the vaccination spleens were removed and the cells were activated ex vivo with peptides to determine the number of IFN-g-producing peptide-specific T cells (Elispot assay). As can be seen in FIG. 4, two of the four peptides (#1491, #1494) induce high numbers of peptide-specific T cells.

With the present HCV model according to example 1, it could be clearly demonstrated that within different ORFs of a viral genome possible encoded CTL epitopes may be identified, peptides of those ORF's are immunogenic in tg-mice, especially also in reading frames 4 to 6 and give positive ELIspot results in HCV+ patients, i.e. are relevant pathological parameters in HCV infections.

Example 2

HIV

In the present example, the genome of HIV was analysed according to the present invention with respect to its non coding ORFs. The results are depicted in table 6. From there the HIV-ncORFs with a minimum length of 7 amino acid residues or those being longer than 7 amino acid residues are deriveable which may preferably be used as antigens for the preparation of a HIV vaccine.

More preferred, ORFs having a minimum length of 9 amino acid residues are selected from table 6, especially if they are T-cell antigens, B-cell antigens or both.

The HIV-ORFs are therefore preferably selected from ORF-Nos. 13, 23, 27, 69 and 80 in Table 6.

TABLE 6

| No. Seq of Id. | ORF | Start | Stop | Sequence | Length |
|---|---|---|---|---|---|
|  | 1 | 336 | 1874 | GAG-sequence |  |
| 835 | 2 | 380 | 424 | MGKNSVKARGKEKI | 14 |
| 836 | 3 | 440 | 474 | MGKQGARTIRS | 11 |
| 837 | 4 | 793 | 804 | MHG | 3 |
| 838 | 6 | 952 | 1020 | MRKLQNGIECIQCMQGLLHQAR | 22 |
| 839 | 7 | 968 | 976 | MG | 2 |
| 840 | 8 | 1079 | 1093 | MDDK | 4 |
| 841 | 9 | 1127 | 1150 | MDNPGIK | 7 |
|  | 10 | 1222 | 1227 | M | 1 |
| 842 | 11 | 1309 | 1338 | MRTQIVRLF | 9 |
| 843 | 12 | 1382 | 1411 | MSGSGRTRP | 9 |
| 844 | 13 | 1580 | 1618 | MWKGRTPNERLY | 12 |
|  | 14 | 1631 | 4674 | POL-sequence (no Initiation Meth.) |  |
| 845 | 15 | 1920 | 1934 | MIQY | 4 |
|  | 16 | 1940 | 4674 | POL-sequence |  |
| 846 | 17 | 1957 | 2013 | METKNDRGNWRFYQSKTV | 18 |
| 847 | 18 | 2010 | 2027 | MIRYS | 5 |

TABLE 6-continued

| No. Seq of Id. | ORF | Start | Stop | Sequence | Length |
|---|---|---|---|---|---|
| 848 | 19 | 2181 | 2209 | MAQKLNNGN | 9 |
| 849 | 20 | 2200 | 2289 | MAIDRRKNKSISRNLYRNGKGRENFKNWA | 29 |
| 850 | 21 | 2341 | 2373 | MEKISRFQRT | 10 |
| 851 | 22 | 2460 | 2492 | MWVNHIFQFP | 10 |
| 852 | 23 | 2493 | 2537 | MKTSGSILHLPYLV | 14 |
| 853 | 24 | 2541 | 2624 | MRHQGLDISTMCFHRDGKDHQQYSKVA | 27 |
| 854 | 25 | 2685 | 2699 | MICM | 4 |
| 855 | 26 | 2826 | 2864 | MNSILINGQYSL | 12 |
| 856 | 27 | 2845 | 2898 | MDSTAYSAARKRQLDCQ | 17 |
| 857 | 28 | 2895 | 2912 | MTYRS | 5 |
|  | 29 | 2968 | 2973 | M | 1 |
| 858 | 30 | 3075 | 3106 | MECIMTHQKT | 10 |
| 859 | 31 | 3139 | 3171 | MDISNLSRAI | 10 |
| 860 | 32 | 3192 | 3227 | MQERGVPTLMM | 11 |
| 861 | 33 | 3277 | 3294 | MGKDS | 5 |
| 862 | 34 | 3322 | 333369 | MGNMVDRVLASHLDS | 15 |
| 863 | 35 | 3406 | 3471 | MVPVRERTHSRSRNVLCRWGS | 21 |
|  | 36 | 3453 | 3458 | M | 1 |
| 864 | 37 | 3459 | 3488 | MGQLAGRLN | 9 |
| 865 | 38 | 3501 | 3539 | MLLIEEDKKLSP | 12 |
| 866 | 39 | 3633 | 3640 | MH | 2 |
| 867 | 40 | 3733 | 3768 | MGTSTQRNWRK | 11 |
| 868 | 41 | 3765 | 3776 | MNK | 3 |
| 869 | 42 | 3819 | 3827 | ME | 2 |
| 870 | 43 | 3840 | 3905 | MNMRNITVIGEQWLVILTCHL | 21 |
| 871 | 44 | 3937 | 3981 | MSAKRRSHAWTSRL | 14 |
| 872 | 45 | 3963 | 3974 | MDK | 3 |
| 873 | 46 | 3991 | 4191 | MATRLYTFRRKSYPGSSSCSQWIYRSRSYSSRNRAGNSILSFKISRKMASKNNTYRQWQQFHQYYG | 66 |
|  | 47 | 4044 | 4049 | M | 1 |
|  | 49 | 4623 | 5190 | VIF-SEQUENCE |  |
| 874 | 50 | 4682 | 4729 | MEKFSKTPYVCFRES | 15 |
| 875 | 51 | 4711 | 4776 | MFQGKLGDGFIDITMKALIQE | 21 |
| 876 | 52 | 4733 | 4744 | MVL | 3 |
| 877 | 53 | 4804 | 4818 | MLDW | 4 |
| 878 | 54 | 4886 | 4906 | MEEKEI | 6 |
|  | 55 | 5141 | 5427 | VPR-SEQUENCE |  |
| 879 | 56 | 5191 | 5220 | MDTRAFRGA | 9 |
| 880 | 57 | 5223 | 5267 | MKLLDIFLGFGSMA | 14 |
| 881 | 58 | 5280 | 5321 | MKLMGILGQEWKP | 13 |
|  | 59 | 5412 | 5626 | TAT-1-SEQUENCE |  |
|  | 60 | 5551 | 5626 | REV-1-SEQUENCE |  |
|  | 61 | 5638 | 5643 | M | 1 |
|  | 62 | 5643 | 5884 | VPU-SEQUENCE |  |
|  | 63 | 5803 | 8384 | ENV-SEQUENCE |  |
|  | 65 | 6065 | 6070 | M | 1 |
| 882 | 66 | 6095 | 6107 | MTW | 3 |
| 883 | 67 |  |  | MGSKPKAMCKINPT | 14 |
| 884 | 68 |  |  | MRI | 3 |
| 885 | 69 | 6209 | 6259 | MLLIPIVVIPIVVAGK | 16 |
| 886 | 70 | 6335 | 6361 | MHFINLI | 8 |
| 887 | 71 | 6374 | 6397 | MILPAIR | 7 |
|  | 72 | 6498 | 6503 | M | 1 |
| 888 | 73 | 6518 | 6580 | MEQDHVQMSAQYNVHMELGQ | 20 |
| 889 | 74 | 6531 | 6572 | MYKCQHSTMYTWN | 13 |
| 890 | 75 | 6602 | 6613 | MAV | 3 |
| 891 | 76 | 6656 | 6670 | MLKP | 4 |
| 892 | 77 | 6828 | 6857 | MECHFKTDS | 9 |
| 893 | 78 | 6833 | 6844 | MPL | 3 |
| 894 | 79 | 7068 | 7148 | MQNKTIYKHVAGSRKSNVCPSHQRTN | 26 |
| 895 | 80 | 7121 | 7180 | MPLPSADKLDVHQILQGCY | 19 |
| 896 | 81 | 7148 | 7196 | MFIKYYRAAINKRWW | 15 |
| 897 | 82 | 7187 | 7243 | MVVITTMGPRSSDLEEEI | 18 |
| 898 | 83 | 7649 | 7696 | MLVGVINLWNRFGIT | 15 |
| 899 | 84 | 7784 | 7807 | MNKNYWN | 7 |
| 900 | 85 | 7812 | 7838 | MGKEVELV | 8 |
| 901 | 86 | 8264 | 8278 | MPQP | 4 |
|  | 87 | 8390 | 9006 | NEF-SEQUENCE |  |
| 902 | 88 | 8425 | 8460 | MAYCKGKNETS | 11 |
| 903 | 89 | 8472 | 8564 | MGWEQHLETWKNMEQSQVAIQQLPMLLVPG | 30 |
| 904 | 90 | 8809 | 8835 | MVLQASTS | 8 |
| 905 | 91 | 8901 | 8933 | MEWMTLREKC | 10 |
| 906 | 92 | 9097 | 9147 | MLHISS | 6 |

Non-coding HIV-ORFs=all ORFs, except GAG, POL, VIF, VPR, TAT, REV, VPU, ENV and NEF (ORF-Nos. 1, 14, 16, 49, 55, 59, 60, 62, 63 and 87 in Table 6)

HIV selected ORFs: ORF-Nos. 2, 3, 6, 9, 11, 12, 13, 17, 19, 20, 21, 22, 23, 24, 26, 27, 30, 31, 32, 34, 35, 37, 38, 40, 43, 44, 46, 48, 50, 56, 57, 58, 64, 67, 69, 70, 71, 73, 74, 77, 79, 80, 81, 82, 83, 84, 85, 88, 89, 90 and 91 in Table 6.

3. Human Papilloma Virus (HPV)

In this example, possible ncORF epitopes with superior immunisation properties of HPV are identified as in Example 1 for HCV epitopes. The results are depicted in the following table 7:

TABLE 7

| No | Species | Strain type | Frame | ORF | HLA | Seq | Seq ID No. | Score | Length |
|---|---|---|---|---|---|---|---|---|---|
| 1 | HPV | 16 | 1 | 2 | A68.1 | IVCPICSQK | 1045 | 180.00 | 9 |
| 2 | HPV | 16 | 1 | 3 | B*2705 | LQKGDYLK | 1046 | 200.00 | 8 |
| 3 | HPV | 16 | 1 | 3 | B*5102 | MAILKWKL | 1047 | 181.50 | 8 |
| 4 | HPV | 16 | 1 | 3 | B*5103 | KAKTAGMAI | 1048 | 133.10 | 9 |
| 5 | HPV | 16 | 1 | 3 | B*5102 | KAKTAGMAI | 1048 | 110.00 | 9 |
| 6 | HPV | 16 | 1 | 3 | A*0201 | GMAILKWKL | 1049 | 115.71 | 9 |
| 7 | HPV | 16 | 1 | 3 | Cw*0401 | DYLKAKTAGM | 1050 | 120.00 | 10 |
| 8 | HPV | 16 | 1 | 3 | B*5801 | KTAGMAILKW | 1051 | 348.48 | 10 |
| 9 | HPV | 16 | 1 | 3 | B62 | ILKWKLSRCY | 1052 | 312.00 | 10 |
| 10 | HPV | 16 | 1 | 4 | B*2705 | TLYAKHHL | 1053 | 150.00 | 8 |
| 11 | HPV | 16 | 1 | 4 | B*5102 | YAKHHLQI | 1054 | 242.00 | 8 |
| 12 | HPV | 16 | 1 | 4 | B*5102 | VGVVAVSTV | 1055 | 132.00 | 9 |
| 13 | HPV | 16 | 1 | 4 | B*5103 | VAVSTVVEV | 1056 | 121.00 | 9 |
| 14 | HPV | 16 | 1 | 4 | B*5102 | VAVSTVVEV | 1056 | 330.00 | 9 |
| 15 | HPV | 16 | 1 | 4 | A68.1 | STVVEVGER | 1057 | 100.00 | 9 |
| 16 | HPV | 16 | 1 | 4 | A68.1 | EVGERVLVK | 1058 | 720.00 | 9 |
| 17 | HPV | 16 | 1 | 4 | B14 | ERVLVKDTL | 1059 | 180.00 | 9 |
| 18 | HPV | 16 | 1 | 4 | B*2705 | ERVLVKDTL | 1059 | 200.00 | 9 |
| 19 | HPV | 16 | 1 | 4 | A68.1 | LVKDTLYAK | 1060 | 120.00 | 9 |
| 20 | HPV | 16 | 1 | 4 | B*5102 | VGVVAVSTVV | 1061 | 132.00 | 10 |
| 21 | HPV | 16 | 1 | 4 | B*5201 | VGVVAVSTVV | 1061 | 198.00 | 10 |
| 22 | HPV | 16 | 1 | 4 | B60 | GERVLVKDTL | 1062 | 176.00 | 10 |
| 23 | HPV | 16 | 1 | 4 | B*2705 | ERVLVKDTLY | 1063 | 100.00 | 10 |
| 24 | HPV | 16 | 1 | 4 | A3 | VLVKDTLYAK | 1064 | 135.00 | 10 |
| 25 | HPV | 16 | 1 | 4 | Cw*0401 | LYAKHHLQIF | 1065 | 220.00 | 10 |
| 26 | HPV | 16 | 1 | 4 | A24 | LYAKHHLQIF | 1065 | 120.00 | 10 |
| 27 | HPV | 16 | 1 | 5 | B*3901 | LHLDLHPV | 1066 | 120.00 | 8 |
| 28 | HPV | 16 | 1 | 6 | B*2705 | IRTGNPFS | 1067 | 200.00 | 8 |
| 29 | HPV | 16 | 1 | 6 | B*2705 | VQILGGLIY | 1068 | 100.00 | 9 |
| 30 | HPV | 16 | 1 | 6 | B62 | VQILGGLIY | 1068 | 192.00 | 9 |
| 31 | HPV | 16 | 1 | 6 | A*0201 | LIYIIDWWC | 1069 | 153.29 | 9 |
| 32 | HPV | 16 | 1 | 6 | A24 | IYIIDWWCL | 1070 | 300.00 | 9 |
| 33 | HPV | 16 | 1 | 6 | Cw*0401 | IYIIDWWCL | 1070 | 200.00 | 9 |
| 34 | HPV | 16 | 1 | 6 | B*3701 | IDWWCLHFL | 1071 | 200.00 | 9 |
| 35 | HPV | 16 | 1 | 6 | B*3901 | LHFLMSFHL | 1072 | 180.00 | 9 |
| 36 | HPV | 16 | 1 | 6 | A3 | FLMSFHLTK | 1073 | 180.00 | 9 |
| 37 | HPV | 16 | 1 | 6 | B*2705 | IQCMSLMIR | 1074 | 100.00 | 9 |
| 38 | HPV | 16 | 1 | 6 | A*0201 | GLIYIIDWWC | 1075 | 204.93 | 10 |
| 39 | HPV | 16 | 1 | 6 | A*0201 | LIYIIDWWCL | 1076 | 203.73 | 10 |
| 40 | HPV | 16 | 1 | 6 | A*0201 | CLHFLMSFHL | 1077 | 123.90 | 10 |
| 41 | HPV | 16 | 1 | 6 | A*0201 | FLMSFHLTKT | 1078 | 291.72 | 10 |
| 42 | HPV | 16 | 1 | 6 | A68.1 | RTGNPFSQGR | 1079 | 100.00 | 10 |
| 43 | HPV | 16 | 1 | 7 | B*5102 | KALQAIEL | 1080 | 199.65 | 8 |
| 44 | HPV | 16 | 1 | 7 | B*2705 | LQAIELQL | 1081 | 200.00 | 8 |
| 45 | HPV | 16 | 1 | 7 | B*2705 | VQFDGDIC | 1082 | 100.00 | 8 |
| 46 | HPV | 16 | 1 | 7 | B*2705 | GQVDYYGL | 1083 | 200.00 | 8 |
| 47 | HPV | 16 | 1 | 7 | B*5102 | EGIRTYFV | 1084 | 145.20 | 8 |
| 48 | HPV | 16 | 1 | 7 | B*2705 | IRTYFVQF | 1085 | 1000.00 | 8 |
| 49 | HPV | 16 | 1 | 7 | B*2705 | RTYFVQFK | 1086 | 150.00 | 8 |
| 50 | HPV | 16 | 1 | 7 | B*2705 | IRQHLANH | 1087 | 200.00 | 8 |
| 51 | HPV | 16 | 1 | 7 | B*5102 | AATHTKAV | 1088 | 121.00 | 8 |
| 52 | HPV | 16 | 1 | 7 | B*3901 | THTKAVAL | 1089 | 135.00 | 8 |
| 53 | HPV | 16 | 1 | 7 | B*5102 | NPCHTTKL | 1090 | 146.41 | 8 |
| 54 | HPV | 16 | 1 | 7 | B*2705 | HRDSVDSA | 1091 | 200.00 | 8 |
| 55 | HPV | 16 | 1 | 7 | B*2705 | GRINCNSN | 1092 | 200.00 | 8 |
| 56 | HPV | 16 | 1 | 7 | B*2705 | LRYRFKKH | 1093 | 300.00 | 8 |
| 57 | HPV | 16 | 1 | 7 | B*2705 | YRFKKHCT | 1094 | 1000.00 | 8 |
| 58 | HPV | 16 | 1 | 7 | B*2705 | DQFLSQVK | 1095 | 100.00 | 8 |
| 59 | HPV | 16 | 1 | 7 | B*5102 | LAVSKNKAL | 1096 | 181.50 | 9 |
| 60 | HPV | 16 | 1 | 7 | B*5102 | QAIELQLTL | 1097 | 199.65 | 9 |
| 61 | HPV | 16 | 1 | 7 | B*2705 | LQLTLETIY | 1098 | 100.00 | 9 |
| 62 | HPV | 16 | 1 | 7 | A24 | QYSNEKWTL | 1099 | 200.00 | 9 |
| 63 | HPV | 16 | 1 | 7 | Cw*0401 | QYSNEKWTL | 1099 | 200.00 | 9 |
| 64 | HPV | 16 | 1 | 7 | A*0201 | TLQDVSLEV | 1100 | 285.16 | 9 |
| 65 | HPV | 16 | 1 | 7 | B*2705 | LQDVSLEVY | 1101 | 100.00 | 9 |
| 66 | HPV | 16 | 1 | 7 | B*2705 | VQFDGDICN | 1102 | 100.00 | 9 |
| 67 | HPV | 16 | 1 | 7 | B*2705 | GQVDYYGLY | 1103 | 100.00 | 9 |
| 68 | HPV | 16 | 1 | 7 | A1 | QVDYYGLYY | 1104 | 125.00 | 9 |
| 69 | HPV | 16 | 1 | 7 | B*3801 | VHEGIRTYF | 1105 | 280.80 | 9 |
| 70 | HPV | 16 | 1 | 7 | B*2705 | IRTYFVQFK | 1106 | 2000.00 | 9 |
| 71 | HPV | 16 | 1 | 7 | B*2705 | VQFKDDAEK | 1107 | 1000.00 | 9 |
| 72 | HPV | 16 | 1 | 7 | A68.1 | EVSSPEIIR | 1108 | 900.00 | 9 |
| 73 | HPV | 16 | 1 | 7 | B*2705 | QRPRSEPDT | 1109 | 200.00 | 9 |
| 74 | HPV | 16 | 1 | 7 | B*5102 | NPCHTTKLL | 1110 | 146.41 | 9 |

TABLE 7-continued

| No | Species | Strain type | Frame | ORF | HLA | Seq | Seq ID No. | Score | Length |
|---|---|---|---|---|---|---|---|---|---|
| 75 | HPV | 16 | 1 | 7 | B*2705 | GRINCNSNT | 1111 | 200.00 | 9 |
| 76 | HPV | 16 | 1 | 7 | A68.1 | NTLKCLRYR | 1112 | 100.00 | 9 |
| 77 | HPV | 16 | 1 | 7 | B62 | TLKCLRYRF | 1113 | 120.00 | 9 |
| 78 | HPV | 16 | 1 | 7 | B*2705 | LRYRFKKHC | 1114 | 300.00 | 9 |
| 79 | HPV | 16 | 1 | 7 | B14 | YRFKKHCTL | 1115 | 100.00 | 9 |
| 80 | HPV | 16 | 1 | 7 | B*2702 | YRFKKHCTL | 1115 | 300.00 | 9 |
| 81 | HPV | 16 | 1 | 7 | B*2705 | YRFKKHCTL | 1115 | 10000.00 | 9 |
| 82 | HPV | 16 | 1 | 7 | B*2705 | SEWQRDQFL | 1116 | 150.00 | 9 |
| 83 | HPV | 16 | 1 | 7 | B60 | SEWQRDQFL | 1116 | 160.00 | 9 |
| 84 | HPV | 16 | 1 | 7 | B*2705 | QRDQFLSQV | 1117 | 600.00 | 9 |
| 85 | HPV | 16 | 1 | 7 | B*5801 | KTITVSTGF | 1118 | 180.00 | 9 |
| 86 | HPV | 16 | 1 | 7 | B*5102 | KALQAIELQL | 1119 | 165.00 | 10 |
| 87 | HPV | 16 | 1 | 7 | B*2702 | LQAIELQLTL | 1120 | 200.00 | 10 |
| 88 | HPV | 16 | 1 | 7 | B*2705 | SQYSNEKWTL | 1121 | 1000.00 | 10 |
| 89 | HPV | 16 | 1 | 7 | B*2705 | LQDVSLEVYL | 1122 | 200.00 | 10 |
| 90 | HPV | 16 | 1 | 7 | B*2705 | VQFDGDICNT | 1123 | 100.00 | 10 |
| 91 | HPV | 16 | 1 | 7 | Cw*0401 | QFDGDICNTM | 1124 | 150.00 | 10 |
| 92 | HPV | 16 | 1 | 7 | A*0201 | YICEEASVTV | 1125 | 180.37 | 10 |
| 93 | HPV | 16 | 1 | 7 | B60 | VEGQVDYYGL | 1126 | 320.00 | 10 |
| 94 | HPV | 16 | 1 | 7 | B*2705 | GQVDYYGLYY | 1127 | 100.00 | 10 |
| 95 | HPV | 16 | 1 | 7 | B62 | GQVDYYGLYY | 1127 | 116.16 | 10 |
| 96 | HPV | 16 | 1 | 7 | B*5102 | YGLYYVHEGI | 1128 | 580.80 | 10 |
| 97 | HPV | 16 | 1 | 7 | A68.1 | FVQFKDDAEK | 1129 | 180.00 | 10 |
| 98 | HPV | 16 | 1 | 7 | B*2702 | VQFKDDAEKY | 1130 | 100.00 | 10 |
| 99 | HPV | 16 | 1 | 7 | B*2705 | VQFKDDAEKY | 1130 | 500.00 | 10 |
| 100 | HPV | 16 | 1 | 7 | B*5102 | DAEKYSKNKV | 1131 | 110.00 | 10 |
| 101 | HPV | 16 | 1 | 7 | B*5103 | DAEKYSKNKV | 1131 | 121.00 | 10 |
| 102 | HPV | 16 | 1 | 7 | B*2705 | IRQHLANHPA | 1132 | 200.00 | 10 |
| 103 | HPV | 16 | 1 | 7 | B*5102 | HPAATHTKAV | 1133 | 242.00 | 10 |
| 104 | HPV | 16 | 1 | 7 | B*5102 | LGTEETQTTI | 1134 | 117.13 | 10 |
| 105 | HPV | 16 | 1 | 7 | A68.1 | ETQTTIQRPR | 1135 | 150.00 | 10 |
| 106 | HPV | 16 | 1 | 7 | A68.1 | DTGNPCHTTK | 1136 | 180.00 | 10 |
| 107 | HPV | 16 | 1 | 7 | B*2705 | HRDSVDSAPI | 1137 | 600.00 | 10 |
| 108 | HPV | 16 | 1 | 7 | B*2705 | GRINCNSNTT | 1138 | 200.00 | 10 |
| 109 | HPV | 16 | 1 | 7 | B*3901 | VHLKGDANTL | 1139 | 180.00 | 10 |
| 110 | HPV | 16 | 1 | 7 | B*5801 | NTLKCLRYRF | 1140 | 145.20 | 10 |
| 111 | HPV | 16 | 1 | 7 | B*2702 | LRYRFKKHCT | 1141 | 100.00 | 10 |
| 112 | HPV | 16 | 1 | 7 | B*2705 | LRYRFKKHCT | 1141 | 1000.00 | 10 |
| 113 | HPV | 16 | 1 | 7 | Cw*0401 | RYRFKKHCTL | 1142 | 200.00 | 10 |
| 114 | HPV | 16 | 1 | 7 | A24 | RYRFKKHCTL | 1142 | 400.00 | 10 |
| 115 | HPV | 16 | 1 | 7 | B*2702 | YRFKKHCTLY | 1143 | 1000.00 | 10 |
| 116 | HPV | 16 | 1 | 7 | B*2705 | YRFKHHCTLY | 1143 | 5000.00 | 10 |
| 117 | HPV | 16 | 1 | 7 | B*2705 | QRDQFLSQVK | 1144 | 2000.00 | 10 |
| 118 | HPV | 16 | 1 | 8 | B*2705 | WRAFCFAL | 1145 | 2000.00 | 8 |
| 119 | HPV | 16 | 1 | 8 | B*5102 | CAFVCLPI | 1146 | 1000.00 | 8 |
| 120 | HPV | 16 | 1 | 8 | B*5102 | AAFVCVYI | 1147 | 1000.00 | 8 |
| 121 | HPV | 16 | 1 | 8 | B*2705 | WRAFCFALC | 1148 | 200.00 | 9 |
| 122 | HPV | 16 | 1 | 8 | Cw*0401 | AFCFALCAF | 1149 | 220.00 | 9 |
| 123 | HPV | 16 | 1 | 8 | Cw*0301 | FALCAFVCL | 1150 | 200.00 | 9 |
| 124 | HPV | 16 | 1 | 8 | B*5102 | FALCAFVCL | 1150 | 300.00 | 9 |
| 125 | HPV | 16 | 1 | 8 | B*5103 | SAAFVCVYI | 1151 | 121.00 | 9 |
| 126 | HPV | 16 | 1 | 8 | B*5102 | SAAFVCVYI | 1151 | 242.00 | 9 |
| 127 | HPV | 16 | 1 | 8 | A24 | VYIHIINNI | 1152 | 126.00 | 9 |
| 128 | HPV | 16 | 1 | 8 | Cw*0401 | HYWRAFCFAL | 1153 | 200.00 | 10 |
| 129 | HPV | 16 | 1 | 8 | A24 | HYWRAFCFAL | 1153 | 200.00 | 10 |
| 130 | HPV | 16 | 1 | 8 | B*2705 | WRAFCFALCA | 1154 | 200.00 | 10 |
| 131 | HPV | 16 | 1 | 8 | Cw*0401 | CFALCAFVCL | 1155 | 220.00 | 10 |
| 132 | HPV | 16 | 1 | 8 | B*5102 | LPINTSAAFV | 1156 | 660.00 | 10 |
| 133 | HPV | 16 | 1 | 8 | B*5102 | AAFVCVYIHI | 1157 | 1100.00 | 10 |
| 134 | HPV | 16 | 1 | 8 | B*5103 | AAFVCVYIHI | 1157 | 145.20 | 10 |
| 135 | HPV | 16 | 1 | 9 | B*2705 | TQTFCKTHK | 1158 | 200.00 | 9 |
| 136 | HPV | 16 | 1 | 10 | A*0201 | CLLSQYLRL | 1159 | 118.56 | 9 |
| 137 | HPV | 16 | 1 | 10 | Cw*0301 | CLLSQYLRL | 1159 | 100.00 | 9 |
| 138 | HPV | 16 | 1 | 10 | Cw*0301 | TCLLSQYLRL | 1160 | 100.00 | 10 |
| 139 | HPV | 16 | 1 | 11 | B*5102 | TPISLVFL | 1161 | 300.00 | 8 |
| 140 | HPV | 16 | 1 | 11 | B*5102 | TPHFIIQI | 1162 | 484.00 | 8 |
| 141 | HPV | 16 | 1 | 11 | B*2705 | IQIHSGWF | 1163 | 100.00 | 8 |
| 142 | HPV | 16 | 1 | 11 | A*0201 | FLTPHFIIQI | 1164 | 419.44 | 10 |
| 143 | HPV | 16 | 1 | 12 | B*5102 | LALVLWTL | 1165 | 150.00 | 8 |
| 144 | HPV | 16 | 1 | 12 | B*2705 | YRLTKVKF | 1166 | 300.00 | 8 |
| 145 | HPV | 16 | 1 | 12 | B*3901 | FHWIFVHL | 1167 | 270.00 | 8 |
| 146 | HPV | 16 | 1 | 12 | B*5102 | FANIQIIL | 1168 | 121.00 | 8 |
| 147 | HPV | 16 | 1 | 12 | B*5102 | MATAYFFI | 1169 | 200.00 | 8 |
| 148 | HPV | 16 | 1 | 12 | B*2705 | YQTIYTLK | 1170 | 200.00 | 8 |

TABLE 7-continued

| No | Species | Strain type | Frame | ORF | HLA | Seq | Seq ID No. | Score | Length |
|---|---|---|---|---|---|---|---|---|---|
| 149 | HPV | 16 | 1 | 12 | B*5102 | KALGLLQI | 1171 | 726.00 | 8 |
| 150 | HPV | 16 | 1 | 12 | B*5102 | LALVLWTLL | 1172 | 150.00 | 9 |
| 151 | HPV | 16 | 1 | 12 | A3 | TLLHYRLTK | 1173 | 180.00 | 9 |
| 152 | HPV | 16 | 1 | 12 | A*0201 | LLHYRLTKV | 1174 | 271.95 | 9 |
| 153 | HPV | 16 | 1 | 12 | A24 | HYRLTKVKF | 1175 | 110.00 | 9 |
| 154 | HPV | 16 | 1 | 12 | Cw*0401 | HYRLTKVKF | 1175 | 132.00 | 9 |
| 155 | HPV | 16 | 1 | 12 | Cw*0401 | KFHWIFVHL | 1176 | 330.00 | 9 |
| 156 | HPV | 16 | 1 | 12 | Cw*0401 | LFANIQIIL | 1177 | 200.00 | 9 |
| 157 | HPV | 16 | 1 | 12 | B*2705 | CQNHMATAY | 1178 | 100.00 | 9 |
| 158 | HPV | 16 | 1 | 12 | A*0201 | FIYEGNKCL | 1179 | 177.27 | 9 |
| 159 | HPV | 16 | 1 | 12 | A*0205 | FIYEGNKCL | 1179 | 189.00 | 9 |
| 160 | HPV | 16 | 1 | 12 | A24 | IYEGNKCLL | 1180 | 300.00 | 9 |
| 161 | HPV | 16 | 1 | 12 | Cw*0401 | IYEGNKCLL | 1180 | 200.00 | 9 |
| 162 | HPV | 16 | 1 | 12 | A24 | IYLIGLVLL | 1181 | 300.00 | 9 |
| 163 | HPV | 16 | 1 | 12 | Cw*0401 | IYLIGLVLL | 1181 | 400.00 | 9 |
| 164 | HPV | 16 | 1 | 12 | A*0201 | YLIGLVLLV | 1182 | 735.86 | 9 |
| 165 | HPV | 16 | 1 | 12 | A*0201 | VLLVKMYQT | 1183 | 107.81 | 9 |
| 166 | HPV | 16 | 1 | 12 | A*0201 | KMYQTIYTL | 1184 | 397.44 | 9 |
| 167 | HPV | 16 | 1 | 12 | A*0205 | KMYQTIYTL | 1184 | 126.00 | 9 |
| 168 | HPV | 16 | 1 | 12 | B*2705 | KMYQTIYTL | 1184 | 750.00 | 9 |
| 169 | HPV | 16 | 1 | 12 | A24 | IYTLKALGL | 1185 | 200.00 | 9 |
| 170 | HPV | 16 | 1 | 12 | Cw*0401 | IYTLKALGL | 1185 | 200.00 | 9 |
| 171 | HPV | 16 | 1 | 12 | A68.1 | LVLWTLLHYR | 1186 | 400.00 | 10 |
| 172 | HPV | 16 | 1 | 12 | A*0201 | VLWTLLHYRL | 1187 | 301.42 | 10 |
| 173 | HPV | 16 | 1 | 12 | B*2705 | VLWTLLHYRL | 1187 | 150.00 | 10 |
| 174 | HPV | 16 | 1 | 12 | A*0201 | TLLHYRLTKV | 1188 | 591.89 | 10 |
| 175 | HPV | 16 | 1 | 12 | B*2702 | YRLTKVKFHW | 1189 | 100.00 | 10 |
| 176 | HPV | 16 | 1 | 12 | B*2705 | YRLTKVKFHW | 1189 | 200.00 | 10 |
| 177 | HPV | 16 | 1 | 12 | A*0201 | RLTKVKFHWI | 1190 | 109.02 | 10 |
| 178 | HPV | 16 | 1 | 12 | Cw*0401 | KFHWIFVHLF | 1191 | 300.00 | 10 |
| 179 | HPV | 16 | 1 | 12 | B*2705 | HLFANIQIIL | 1192 | 150.00 | 10 |
| 180 | HPV | 16 | 1 | 12 | B*2705 | CQNHMATAYF | 1193 | 100.00 | 10 |
| 181 | HPV | 16 | 1 | 12 | A3 | HMATAYFFIY | 1194 | 108.00 | 10 |
| 182 | HPV | 16 | 1 | 12 | Cw*0401 | FFIYEGNKCL | 1195 | 200.00 | 10 |
| 183 | HPV | 16 | 1 | 12 | A*0201 | FIYEGNKCLL | 1196 | 177.27 | 10 |
| 184 | HPV | 16 | 1 | 12 | A*0205 | FIYEGNKCLL | 1196 | 189.00 | 10 |
| 185 | HPV | 16 | 1 | 12 | A*0201 | CLLDIYLIGL | 1197 | 745.36 | 10 |
| 186 | HPV | 16 | 1 | 12 | A*0205 | CLLDIYLIGL | 1197 | 151.20 | 10 |
| 187 | HPV | 16 | 1 | 12 | A3 | YLIGLVLLVK | 1198 | 202.50 | 10 |
| 188 | HPV | 16 | 1 | 12 | A3 | KMYQTIYTLK | 1199 | 450.00 | 10 |
| 189 | HPV | 16 | 1 | 12 | B*2705 | KMYQTIYTLK | 1199 | 750.00 | 10 |
| 190 | HPV | 16 | 1 | 12 | Cw*0401 | IYTLKALGLL | 1200 | 440.00 | 10 |
| 191 | HPV | 16 | 1 | 12 | A24 | IYTLKALGLL | 1200 | 200.00 | 10 |
| 192 | HPV | 16 | 1 | 13 | B*2705 | HRATIMAF | 1201 | 1000.00 | 8 |
| 193 | HPV | 16 | 1 | 13 | B*5102 | RATIMAFV | 1202 | 100.00 | 8 |
| 194 | HPV | 16 | 1 | 13 | B*2705 | TNYLLLLL | 1203 | 100.00 | 8 |
| 195 | HPV | 16 | 1 | 13 | B*2705 | VQICHYVL | 1204 | 200.00 | 8 |
| 196 | HPV | 16 | 1 | 13 | B*3901 | CHYVLPYL | 1205 | 180.00 | 8 |
| 197 | HPV | 16 | 1 | 13 | B*5102 | LPYLLQKL | 1206 | 665.50 | 8 |
| 198 | HPV | 16 | 1 | 13 | B*3901 | LHIKILTL | 1207 | 270.00 | 8 |
| 199 | HPV | 16 | 1 | 13 | B*2705 | GRNMIYSL | 1208 | 2000.00 | 8 |
| 200 | HPV | 16 | 1 | 13 | B*2705 | SLFFNCAK | 1209 | 150.00 | 8 |
| 201 | HPV | 16 | 1 | 13 | B*5102 | MPKYSINLI | 1210 | 220.00 | 9 |
| 202 | HPV | 16 | 1 | 13 | B*2705 | HRATIMAFV | 1211 | 600.00 | 9 |
| 203 | HPV | 16 | 1 | 13 | Cw*0401 | AFVGVTNYL | 1212 | 200.00 | 9 |
| 204 | HPV | 16 | 1 | 13 | Cw*0301 | VGVTNYLLL | 1213 | 120.00 | 9 |
| 205 | HPV | 16 | 1 | 13 | A24 | NYLLLLLIL | 1214 | 360.00 | 9 |
| 206 | HPV | 16 | 1 | 13 | Cw*0401 | NYLLLLLIL | 1214 | 400.00 | 9 |
| 207 | HPV | 16 | 1 | 13 | A*0201 | LLLLILHAV | 1215 | 1006.21 | 9 |
| 208 | HPV | 16 | 1 | 13 | B*5103 | HAVQICHYV | 1216 | 110.00 | 9 |
| 209 | HPV | 16 | 1 | 13 | B*5102 | HAVQICHYV | 1216 | 363.00 | 9 |
| 210 | HPV | 16 | 1 | 13 | B*3901 | CHYVLPYLL | 1217 | 180.00 | 9 |
| 211 | HPV | 16 | 1 | 13 | A68.1 | YVLPYLLQK | 1218 | 360.00 | 9 |
| 212 | HPV | 16 | 1 | 13 | A*0201 | KLHIKILTL | 1219 | 171.97 | 9 |
| 213 | HPV | 16 | 1 | 13 | B*2705 | LRSTYDMGR | 1220 | 1000.00 | 9 |
| 214 | HPV | 16 | 1 | 13 | B*2702 | GRNMIYSLF | 1221 | 200.00 | 9 |
| 215 | HPV | 16 | 1 | 13 | B*2705 | GRNMIYSLF | 1221 | 1000.00 | 9 |
| 216 | HPV | 16 | 1 | 13 | B*5102 | IGYNEHRATI | 1222 | 484.00 | 10 |
| 217 | HPV | 16 | 1 | 13 | B*5103 | IGYNEHRATI | 1222 | 132.00 | 10 |
| 218 | HPV | 16 | 1 | 13 | Cw*0401 | GYNEHRATIM | 1223 | 132.00 | 10 |
| 219 | HPV | 16 | 1 | 13 | B*5102 | RATIMAFVGV | 1224 | 100.00 | 10 |
| 220 | HPV | 16 | 1 | 13 | B*5103 | RATIMAFVGV | 1224 | 121.00 | 10 |
| 221 | HPV | 16 | 1 | 13 | B*5102 | MAFVGVTNYL | 1225 | 332.75 | 10 |
| 222 | HPV | 16 | 1 | 13 | Cw*0401 | AFVGVTNYLL | 1226 | 240.00 | 10 |

TABLE 7-continued

| No | Species | Strain type | Frame | ORF | HLA | Seq | Seq ID No. | Score | Length |
|---|---|---|---|---|---|---|---|---|---|
| 223 | HPV | 16 | 1 | 13 | B*2705 | TNYLLLLLIL | 1227 | 100.00 | 10 |
| 224 | HPV | 16 | 1 | 13 | A*0201 | YLLLLLILHA | 1228 | 194.48 | 10 |
| 225 | HPV | 16 | 1 | 13 | A*0201 | LLLLLILHAV | 1229 | 1006.21 | 10 |
| 226 | HPV | 16 | 1 | 13 | B*5102 | HAVQICHYVL | 1230 | 165.00 | 10 |
| 227 | HPV | 16 | 1 | 13 | B*2705 | VQICHYVLPY | 1231 | 100.00 | 10 |
| 228 | HPV | 16 | 1 | 13 | A*0205 | YVLPYLLQKL | 1232 | 252.00 | 10 |
| 229 | HPV | 16 | 1 | 13 | Cw*0301 | YVLPYLLQKL | 1232 | 120.00 | 10 |
| 230 | HPV | 16 | 1 | 13 | B*5102 | LPYLLQKLHI | 1233 | 2420.00 | 10 |
| 231 | HPV | 16 | 1 | 13 | B*5103 | LPYLLQKLHI | 1233 | 159.72 | 10 |
| 232 | HPV | 16 | 1 | 13 | A*0201 | YLLQKLHIKI | 1234 | 177.57 | 10 |
| 233 | HPV | 16 | 1 | 13 | B*2705 | LRSTYDMGRN | 1235 | 200.00 | 10 |
| 234 | HPV | 16 | 1 | 13 | B*2702 | GRNMIYSLFF | 1236 | 200.00 | 10 |
| 235 | HPV | 16 | 1 | 13 | B*2705 | GRNMIYSLFF | 1236 | 1000.00 | 10 |
| 236 | HPV | 16 | 1 | 14 | B*2705 | CMYVELVL | 1237 | 250.00 | 8 |
| 237 | HPV | 16 | 1 | 14 | Cw*0301 | CKYCMYVEL | 1238 | 100.00 | 9 |
| 238 | HPV | 16 | 1 | 14 | B*2705 | CMYVELVLF | 1239 | 125.00 | 9 |
| 239 | HPV | 16 | 1 | 14 | A*0201 | VLFVVYMFV | 1240 | 3609.23 | 9 |
| 240 | HPV | 16 | 1 | 14 | Cw*0401 | VYMFVCACM | 1241 | 120.00 | 9 |
| 241 | HPV | 16 | 1 | 14 | Cw*0401 | MFVCACMCL | 1242 | 220.00 | 9 |
| 242 | HPV | 16 | 1 | 14 | Cw*0401 | KYCMYVELVL | 1243 | 200.00 | 10 |
| 243 | HPV | 16 | 1 | 14 | A24 | KYCMYVELVL | 1243 | 560.00 | 10 |
| 244 | HPV | 16 | 1 | 14 | A*0201 | CMYVELVLFV | 1244 | 2033.39 | 10 |
| 245 | HPV | 16 | 1 | 14 | A*0201 | LVLFVVYMFV | 1245 | 315.81 | 10 |
| 246 | HPV | 16 | 1 | 14 | A*0201 | VLFVVYMFVC | 1246 | 170.91 | 10 |
| 247 | HPV | 16 | 1 | 14 | A*0201 | YMFVCACMCL | 1247 | 262.59 | 10 |
| 248 | HPV | 16 | 1 | 14 | B*2705 | YMFVCACMCL | 1247 | 250.00 | 10 |
| 249 | HPV | 16 | 1 | 15 | A*0201 | FLFYIYYIL | 1248 | 223.61 | 9 |
| 250 | HPV | 16 | 1 | 15 | A*0205 | FLFYIYYIL | 1248 | 126.00 | 9 |
| 251 | HPV | 16 | 1 | 15 | B*2705 | FLFYIYYIL | 1248 | 150.00 | 9 |
| 252 | HPV | 16 | 1 | 15 | Cw*0301 | LFLFYIYYIL | 1249 | 100.00 | 10 |
| 253 | HPV | 16 | 1 | 15 | Cw*0401 | LFLFYIYYIL | 1249 | 200.00 | 10 |
| 254 | HPV | 16 | 1 | 16 | B*2705 | CQPFHCFL | 1250 | 200.00 | 8 |
| 255 | HPV | 16 | 1 | 17 | A*0201 | LLGTYFWLV | 1251 | 1684.90 | 9 |
| 256 | HPV | 16 | 1 | 17 | Cw*0401 | YFWLVLTNL | 1252 | 400.00 | 9 |
| 257 | HPV | 16 | 1 | 17 | A*0201 | VLTNLIAYL | 1253 | 459.40 | 9 |
| 258 | HPV | 16 | 1 | 17 | Cw*0401 | TYFWLVLTNL | 1254 | 400.00 | 10 |
| 259 | HPV | 16 | 1 | 17 | A24 | TYFWLVLTNL | 1254 | 280.00 | 10 |
| 260 | HPV | 16 | 1 | 17 | A*0201 | LVLTNLIAYL | 1255 | 148.73 | 10 |
| 261 | HPV | 16 | 1 | 17 | A*0205 | LVLTNLIAYL | 1255 | 142.80 | 10 |
| 262 | HPV | 16 | 1 | 1 | B*2705 | HRAANNYT | 1256 | 200.00 | 8 |
| 263 | HPV | 16 | 1 | 3 | A*0201 | VLLQIIKNT | 1257 | 107.81 | 9 |
| 264 | HPV | 16 | 1 | 4 | B*3901 | MHGDTPTL | 1258 | 180.00 | 8 |
| 265 | HPV | 16 | 1 | 4 | B*3901 | LHEYMLDL | 1259 | 405.00 | 8 |
| 266 | HPV | 16 | 1 | 4 | B*2705 | LQPETTDL | 1260 | 200.00 | 8 |
| 267 | HPV | 16 | 1 | 4 | B*2705 | LRLCVQST | 1261 | 200.00 | 8 |
| 268 | HPV | 16 | 1 | 4 | B*3901 | THVDIRTL | 1262 | 180.00 | 8 |
| 269 | HPV | 16 | 1 | 4 | B*2705 | IRTLEDLL | 1263 | 2000.00 | 8 |
| 270 | HPV | 16 | 1 | 4 | B*5102 | TPTLHEYML | 1264 | 110.00 | 9 |
| 271 | HPV | 16 | 1 | 4 | A*0201 | TLHEYMLDL | 1265 | 201.45 | 9 |
| 272 | HPV | 16 | 1 | 4 | A*0201 | YMLDLQPET | 1266 | 375.57 | 9 |
| 273 | HPV | 16 | 1 | 4 | B*2705 | LQPETTDLY | 1267 | 100.00 | 9 |
| 274 | HPV | 16 | 1 | 4 | Cw*0301 | TDLYCYEQL | 1268 | 100.00 | 9 |
| 275 | HPV | 16 | 1 | 4 | A1 | QAEPDRAHY | 1269 | 900.00 | 9 |
| 276 | HPV | 16 | 1 | 4 | B*5102 | EPDRAHYNI | 1270 | 220.00 | 9 |
| 277 | HPV | 16 | 1 | 4 | B*2705 | LRLCVQSTH | 1271 | 200.00 | 9 |
| 278 | HPV | 16 | 1 | 4 | B*2705 | VQSTHVDIR | 1272 | 100.00 | 9 |
| 279 | HPV | 16 | 1 | 4 | B*2705 | IRTLEDLLM | 1273 | 600.00 | 9 |
| 280 | HPV | 16 | 1 | 4 | B60 | LEDLLMGTL | 1274 | 176.00 | 9 |
| 281 | HPV | 16 | 1 | 4 | A68.1 | IVCPICSQK | 1045 | 180.00 | 9 |
| 282 | HPV | 16 | 1 | 4 | A*0201 | YMLDLQPETT | 1275 | 184.03 | 10 |
| 283 | HPV | 16 | 1 | 4 | B40 | DEIDGPAGQA | 1276 | 120.00 | 10 |
| 284 | HPV | 16 | 1 | 4 | B*2705 | GQAEPDRAHY | 1277 | 100.00 | 10 |
| 285 | HPV | 16 | 1 | 4 | B*5102 | EPDRAHYNIV | 1278 | 110.00 | 10 |
| 286 | HPV | 16 | 1 | 4 | B*5201 | EPDRAHYNIV | 1278 | 100.00 | 10 |
| 287 | HPV | 16 | 1 | 4 | B*2705 | DRAHYNIVTF | 1279 | 100.00 | 10 |
| 288 | HPV | 16 | 1 | 4 | Cw*0401 | TFCCKCDSTL | 1280 | 200.00 | 10 |
| 289 | HPV | 16 | 1 | 4 | B*2705 | LRLCVQSTHV | 1281 | 600.00 | 10 |
| 290 | HPV | 16 | 1 | 4 | A68.1 | CVQSTHVDIR | 1282 | 200.00 | 10 |
| 291 | HPV | 16 | 1 | 4 | B*3701 | VDIRTLEDLL | 1283 | 200.00 | 10 |
| 292 | HPV | 16 | 1 | 5 | B*2705 | AQEAKQHR | 1284 | 100.00 | 8 |
| 293 | HPV | 16 | 1 | 5 | B*2705 | HRDAVQVL | 1285 | 2000.00 | 8 |
| 294 | HPV | 16 | 1 | 5 | B*2705 | KRKYLVVH | 1286 | 600.00 | 8 |
| 295 | HPV | 16 | 1 | 5 | B*5102 | NGWFYVEAV | 1287 | 220.00 | 9 |
| 296 | HPV | 16 | 1 | 5 | B*5201 | GWFYVEAVV | 1288 | 100.00 | 9 |

TABLE 7-continued

| No | Species | Strain type | Frame | ORF | HLA | Seq | Seq ID No. | Score | Length |
|---|---|---|---|---|---|---|---|---|---|
| 297 | HPV | 16 | 1 | 5 | A68.1 | YVEAVVEKK | 1289 | 120.00 | 9 |
| 298 | HPV | 16 | 1 | 5 | B60 | AETETAHAL | 1290 | 160.00 | 9 |
| 299 | HPV | 16 | 1 | 5 | A3 | ALFTAQEAK | 1291 | 100.00 | 9 |
| 300 | HPV | 16 | 1 | 5 | B*2705 | ALFTAQEAK | 1291 | 150.00 | 9 |
| 301 | HPV | 16 | 1 | 5 | B*5103 | EAKQHRDAV | 1292 | 110.00 | 9 |
| 302 | HPV | 16 | 1 | 5 | B*2705 | KQHRDAVQV | 1293 | 180.00 | 9 |
| 303 | HPV | 16 | 1 | 5 | B*2705 | HRDAVQVLK | 1294 | 2000.00 | 9 |
| 304 | HPV | 16 | 1 | 5 | B*2702 | KRKYLVVHL | 1295 | 180.00 | 9 |
| 305 | HPV | 16 | 1 | 5 | B*2705 | KRKYLVVHL | 1295 | 6000.00 | 9 |
| 306 | HPV | 16 | 1 | 5 | A24 | KYLVVHLVI | 1296 | 210.00 | 9 |
| 307 | HPV | 16 | 1 | 5 | B*5102 | NGWFYVEAVV | 1297 | 220.00 | 10 |
| 308 | HPV | 16 | 1 | 5 | B*5201 | NGWFYVEAVV | 1297 | 500.00 | 10 |
| 309 | HPV | 16 | 1 | 5 | B*5201 | TGEDLVDFIV | 1298 | 100.00 | 10 |
| 310 | HPV | 16 | 1 | 5 | Cw*0401 | DFIVNDNDYL | 1299 | 200.00 | 10 |
| 311 | HPV | 16 | 1 | 5 | A68.1 | FTAQEAKQHR | 1300 | 150.00 | 10 |
| 312 | HPV | 16 | 1 | 5 | B*2705 | KQHRDAVQVL | 1301 | 600.00 | 10 |
| 313 | HPV | 16 | 1 | 5 | B*2705 | HRDAVQVLKR | 1302 | 1000.00 | 10 |
| 314 | HPV | 16 | 1 | 5 | B*2705 | KRKYLVVHLV | 1303 | 1800.00 | 10 |
| 315 | HPV | 16 | 1 | 5 | Cw*0401 | KYLVVHLVIL | 1304 | 440.00 | 10 |
| 316 | HPV | 16 | 1 | 5 | A24 | KYLVVHLVIL | 1304 | 600.00 | 10 |
| 317 | HPV | 16 | 1 | 5 | A*0201 | YLVVHLVILV | 1305 | 735.86 | 10 |
| 318 | HPV | 16 | 1 | 6 | B*5102 | MAILKWKL | 1047 | 181.50 | 8 |
| 319 | HPV | 16 | 1 | 6 | B62 | ILKWKLSRCY | 1052 | 312.00 | 10 |
| 320 | HPV | 16 | 1 | 7 | B*2705 | MRLKHHVV | 1306 | 600.00 | 8 |
| 321 | HPV | 16 | 1 | 7 | B*2705 | TLYAKHHL | 1053 | 150.00 | 8 |
| 322 | HPV | 16 | 1 | 7 | B*5102 | YAKHHLQI | 1054 | 242.00 | 8 |
| 323 | HPV | 16 | 1 | 7 | B*2705 | MRLKHHVVS | 1307 | 200.00 | 9 |
| 324 | HPV | 16 | 1 | 7 | B*5102 | VGVVAVSTV | 1055 | 132.00 | 9 |
| 325 | HPV | 16 | 1 | 7 | B*5103 | VAVSTVVEV | 1056 | 121.00 | 9 |
| 326 | HPV | 16 | 1 | 7 | B*5102 | VAVSTVVEV | 1056 | 330.00 | 9 |
| 327 | HPV | 16 | 1 | 7 | A68.1 | STVVEVGER | 1057 | 100.00 | 9 |
| 328 | HPV | 16 | 1 | 7 | A68.1 | EVGERVLVK | 1058 | 720.00 | 9 |
| 329 | HPV | 16 | 1 | 7 | B14 | ERVLVKDTL | 1059 | 180.00 | 9 |
| 330 | HPV | 16 | 1 | 7 | B*2705 | ERVLVKDTL | 1059 | 200.00 | 9 |
| 331 | HPV | 16 | 1 | 7 | A68.1 | LVKDTLYAK | 1060 | 120.00 | 9 |
| 332 | HPV | 16 | 1 | 7 | B14 | MRLKHHVVSI | 1308 | 120.00 | 10 |
| 333 | HPV | 16 | 1 | 7 | B*2705 | MRLKHHVVSI | 1308 | 600.00 | 10 |
| 334 | HPV | 16 | 1 | 7 | B*5102 | VGVVAVSTVV | 1061 | 132.00 | 10 |
| 335 | HPV | 16 | 1 | 7 | B*5201 | VGVVAVSTVV | 1061 | 198.00 | 10 |
| 336 | HPV | 16 | 1 | 7 | B60 | GERVLVKDTL | 1062 | 176.00 | 10 |
| 337 | HPV | 16 | 1 | 7 | B*2705 | ERVLVKDTLY | 1063 | 100.00 | 10 |
| 338 | HPV | 16 | 1 | 7 | A3 | VLVKDTLYAK | 1064 | 135.00 | 10 |
| 339 | HPV | 16 | 1 | 7 | Cw*0401 | LYAKHHLQIF | 1065 | 220.00 | 10 |
| 340 | HPV | 16 | 1 | 7 | A24 | LYAKHHLQIF | 1065 | 120.00 | 10 |
| 341 | HPV | 16 | 1 | 8 | B*2705 | RQNGYKDK | 1309 | 600.00 | 8 |
| 342 | HPV | 16 | 1 | 8 | B*2705 | KQYYNIVL | 1310 | 3000.00 | 8 |
| 343 | HPV | 16 | 1 | 8 | B*2705 | HRWYNGPT | 1311 | 1000.00 | 8 |
| 344 | HPV | 16 | 1 | 8 | B*2705 | TRQNGYKDK | 1312 | 600.00 | 9 |
| 345 | HPV | 16 | 1 | 8 | B*2705 | KQYYNIVLM | 1313 | 900.00 | 9 |
| 346 | HPV | 16 | 1 | 8 | B*2702 | HRWYNGPTI | 1314 | 300.00 | 9 |
| 347 | HPV | 16 | 1 | 8 | B*2705 | HRWYNGPTI | 1314 | 3000.00 | 9 |
| 348 | HPV | 16 | 1 | 8 | B*2705 | KQYYNIVLMI | 1315 | 900.00 | 10 |
| 349 | HPV | 16 | 1 | 8 | B*5201 | KQYYNIVLMI | 1315 | 300.00 | 10 |
| 350 | HPV | 16 | 1 | 8 | B*5201 | QYYNIVLMIV | 1316 | 110.00 | 10 |
| 351 | HPV | 16 | 1 | 8 | B*2702 | HRWYNGPTIM | 1317 | 100.00 | 10 |
| 352 | HPV | 16 | 1 | 8 | B*2705 | HRWYNGPTIM | 1317 | 3000.00 | 10 |
| 353 | HPV | 16 | 1 | 10 | B60 | MEVIGSKLL | 1318 | 320.00 | 9 |
| 354 | HPV | 16 | 1 | 11 | B*2705 | VQLTQVNHY | 1319 | 100.00 | 9 |
| 355 | HPV | 16 | 1 | 11 | A*0201 | QLTQVNHYL | 1320 | 117.49 | 9 |
| 356 | HPV | 16 | 1 | 11 | B*2705 | VQLTQVNHYL | 1321 | 200.00 | 10 |
| 357 | HPV | 16 | 1 | 13 | B*2705 | IRTGNPFS | 1067 | 200.00 | 8 |
| 358 | HPV | 16 | 1 | 13 | B*2705 | VQILGGLIY | 1068 | 100.00 | 9 |
| 359 | HPV | 16 | 1 | 13 | B62 | VQILGGLIY | 1068 | 192.00 | 9 |
| 360 | HPV | 16 | 1 | 13 | A*0201 | LIYIIDWWC | 1069 | 153.29 | 9 |
| 361 | HPV | 16 | 1 | 13 | A24 | IYIIDWWCL | 1070 | 300.00 | 9 |
| 362 | HPV | 16 | 1 | 13 | Cw*0401 | IYIIDWWCL | 1070 | 200.00 | 9 |
| 363 | HPV | 16 | 1 | 13 | B*3701 | IDWWCLHFL | 1071 | 200.00 | 9 |
| 364 | HPV | 16 | 1 | 13 | B*3901 | LHFLMSFHL | 1072 | 180.00 | 9 |
| 365 | HPV | 16 | 1 | 13 | A3 | FLMSFHLTK | 1073 | 180.00 | 9 |
| 366 | HPV | 16 | 1 | 13 | B*2705 | IQCMSLMIR | 1074 | 100.00 | 9 |
| 367 | HPV | 16 | 1 | 13 | A*0201 | GLIYIIDWWC | 1075 | 204.93 | 10 |
| 368 | HPV | 16 | 1 | 13 | A*0201 | LIYIIDWWCL | 1076 | 203.73 | 10 |
| 369 | HPV | 16 | 1 | 13 | A*0201 | CLHFLMSFHL | 1077 | 123.90 | 10 |
| 370 | HPV | 16 | 1 | 13 | A*0201 | FLMSFHLTKT | 1078 | 291.72 | 10 |

TABLE 7-continued

| No | Species | Strain type | Frame | ORF | HLA | Seq | Seq ID No. | Score | Length |
|---|---|---|---|---|---|---|---|---|---|
| 371 | HPV | 16 | 1 | 13 | A68.1 | RTGNPFSQGR | 1079 | 100.00 | 10 |
| 372 | HPV | 16 | 1 | 14 | B*2705 | LRDHIDYW | 1322 | 200.00 | 8 |
| 373 | HPV | 16 | 1 | 14 | B*2705 | MRLECAIY | 1323 | 1000.00 | 8 |
| 374 | HPV | 16 | 1 | 14 | B*5102 | KALQAIEL | 1080 | 199.65 | 8 |
| 375 | HPV | 16 | 1 | 14 | B*2705 | LQAIELQL | 1081 | 200.00 | 8 |
| 376 | HPV | 16 | 1 | 14 | B*2705 | VQFDGDIC | 1082 | 100.00 | 8 |
| 377 | HPV | 16 | 1 | 14 | B*2705 | GQVDYYGL | 1083 | 200.00 | 8 |
| 378 | HPV | 16 | 1 | 14 | B*5102 | EGIRTYFV | 1084 | 145.20 | 8 |
| 379 | HPV | 16 | 1 | 14 | B*2705 | IRTYFVQF | 1085 | 1000.00 | 8 |
| 380 | HPV | 16 | 1 | 14 | B*2705 | RTYFVQFK | 1086 | 150.00 | 8 |
| 381 | HPV | 16 | 1 | 14 | B*2705 | IRQHLANH | 1087 | 200.00 | 8 |
| 382 | HPV | 16 | 1 | 14 | B*5102 | AATHTKAV | 1088 | 121.00 | 8 |
| 383 | HPV | 16 | 1 | 14 | B*3901 | THTKAVAL | 1089 | 135.00 | 8 |
| 384 | HPV | 16 | 1 | 14 | B*5102 | NPCHTTKL | 1090 | 146.41 | 8 |
| 385 | HPV | 16 | 1 | 14 | B*2705 | HRDSVDSA | 1091 | 200.00 | 8 |
| 386 | HPV | 16 | 1 | 14 | B*2705 | GRINCNSN | 1092 | 200.00 | 8 |
| 387 | HPV | 16 | 1 | 14 | B*2705 | LRYRFKKH | 1093 | 300.00 | 8 |
| 388 | HPV | 16 | 1 | 14 | B*2705 | YRFKKHCT | 1094 | 1000.00 | 8 |
| 389 | HPV | 16 | 1 | 14 | B*2705 | DQFLSQVK | 1095 | 100.00 | 8 |
| 390 | HPV | 16 | 1 | 14 | B*2705 | QRLNVCQDK | 1324 | 2000.00 | 9 |
| 391 | HPV | 16 | 1 | 14 | B*2705 | CQDKILTHY | 1325 | 100.00 | 9 |
| 392 | HPV | 16 | 1 | 14 | A24 | HYENDSTDL | 1326 | 300.00 | 9 |
| 393 | HPV | 16 | 1 | 14 | Cw*0401 | HYENDSTDL | 1326 | 200.00 | 9 |
| 394 | HPV | 16 | 1 | 14 | B*2705 | LRDHIDYWK | 1327 | 2000.00 | 9 |
| 395 | HPV | 16 | 1 | 14 | B*3901 | DHIDYWKHM | 1328 | 120.00 | 9 |
| 396 | HPV | 16 | 1 | 14 | B*2702 | MRLECAIYY | 1329 | 200.00 | 9 |
| 397 | HPV | 16 | 1 | 14 | B*2705 | MRLECAIYY | 1329 | 1000.00 | 9 |
| 398 | HPV | 16 | 1 | 14 | A24 | YYKAREMGF | 1330 | 100.00 | 9 |
| 399 | HPV | 16 | 1 | 14 | Cw*0401 | YYKAREMGF | 1330 | 110.00 | 9 |
| 400 | HPV | 16 | 1 | 14 | B*2705 | AREMGFKHI | 1331 | 180.00 | 9 |
| 401 | HPV | 16 | 1 | 14 | A68.1 | VVPTLAVSK | 1332 | 120.00 | 9 |
| 402 | HPV | 16 | 1 | 14 | B*5102 | LAVSKNKAL | 1096 | 181.50 | 9 |
| 403 | HPV | 16 | 1 | 14 | B*5102 | QAIELQLTL | 1097 | 199.65 | 9 |
| 404 | HPV | 16 | 1 | 14 | B*2705 | LQLTLETIY | 1098 | 100.00 | 9 |
| 405 | HPV | 16 | 1 | 14 | A24 | QYSNEKWTL | 1099 | 200.00 | 9 |
| 406 | HPV | 16 | 1 | 14 | Cw*0401 | QYSNEKWTL | 1099 | 200.00 | 9 |
| 407 | HPV | 16 | 1 | 14 | A*0201 | TLQDVSLEV | 1100 | 285.16 | 9 |
| 408 | HPV | 16 | 1 | 14 | B*2705 | LQDVSLEVY | 1101 | 100.00 | 9 |
| 409 | HPV | 16 | 1 | 14 | B*2705 | VQFDGDICN | 1102 | 100.00 | 9 |
| 410 | HPV | 16 | 1 | 14 | B*2705 | GQVDYYGLY | 1103 | 100.00 | 9 |
| 411 | HPV | 16 | 1 | 14 | A1 | QVDYYGLYY | 1104 | 125.00 | 9 |
| 412 | HPV | 16 | 1 | 14 | B*3801 | VHEGIRTYF | 1105 | 280.80 | 9 |
| 413 | HPV | 16 | 1 | 14 | B*2705 | IRTYFVQFK | 1106 | 2000.00 | 9 |
| 414 | HPV | 16 | 1 | 14 | B*2705 | VQFKDDAEK | 1107 | 1000.00 | 9 |
| 415 | HPV | 16 | 1 | 14 | A68.1 | EVSSPEIIR | 1108 | 900.00 | 9 |
| 416 | HPV | 16 | 1 | 14 | B*2705 | QRPRSEPDT | 1109 | 200.00 | 9 |
| 417 | HPV | 16 | 1 | 14 | B*5102 | NPCHTTKLL | 1110 | 146.41 | 9 |
| 418 | HPV | 16 | 1 | 14 | B*2705 | GRINCNSNT | 1111 | 200.00 | 9 |
| 419 | HPV | 16 | 1 | 14 | A68.1 | NTLKCLRYR | 1112 | 100.00 | 9 |
| 420 | HPV | 16 | 1 | 14 | B62 | TLKCLRYRF | 1113 | 120.00 | 9 |
| 421 | HPV | 16 | 1 | 14 | B*2705 | LRYRFKKHC | 1114 | 300.00 | 9 |
| 422 | HPV | 16 | 1 | 14 | B14 | YRFKKHCTL | 1115 | 100.00 | 9 |
| 423 | HPV | 16 | 1 | 14 | B*2702 | YRFKKHCTL | 1115 | 300.00 | 9 |
| 424 | HPV | 16 | 1 | 14 | B*2705 | YRFKKHCTL | 1115 | 10000.00 | 9 |
| 425 | HPV | 16 | 1 | 14 | B*2705 | SEWQRDQFL | 1116 | 150.00 | 9 |
| 426 | HPV | 16 | 1 | 14 | B60 | SEWQRDQFL | 1116 | 160.00 | 9 |
| 427 | HPV | 16 | 1 | 14 | B*2705 | QRDQFLSQV | 1117 | 600.00 | 9 |
| 428 | HPV | 16 | 1 | 14 | B*5801 | KTITVSTGF | 1118 | 180.00 | 9 |
| 429 | HPV | 16 | 1 | 14 | B*2705 | CQRLNVCQDK | 1333 | 200.00 | 10 |
| 430 | HPV | 16 | 1 | 14 | B*2705 | QRLNVCQDKI | 1334 | 600.00 | 10 |
| 431 | HPV | 16 | 1 | 14 | B*3901 | THYENDSTDL | 1335 | 360.00 | 10 |
| 432 | HPV | 16 | 1 | 14 | A1 | STDLRDHIDY | 1336 | 312.50 | 10 |
| 433 | HPV | 16 | 1 | 14 | B*2705 | LRDHIDYWKH | 1337 | 200.00 | 10 |
| 434 | HPV | 16 | 1 | 14 | B*2705 | MRLECAIYYK | 1338 | 2000.00 | 10 |
| 435 | HPV | 16 | 1 | 14 | Cw*0401 | IYYKAREMGF | 1339 | 110.00 | 10 |
| 436 | HPV | 16 | 1 | 14 | A24 | IYYKAREMGF | 1339 | 100.00 | 10 |
| 437 | HPV | 16 | 1 | 14 | B*5102 | KAREMGFKHI | 1340 | 133.10 | 10 |
| 438 | HPV | 16 | 1 | 14 | B*5103 | KAREMGFKHI | 1340 | 121.00 | 10 |
| 439 | HPV | 16 | 1 | 14 | B*2705 | AREMGFKHIN | 1341 | 200.00 | 10 |
| 440 | HPV | 16 | 1 | 14 | B*5102 | MGFKHINHQV | 1342 | 242.00 | 10 |
| 441 | HPV | 16 | 1 | 14 | A68.1 | QVVPTLAVSK | 1343 | 360.00 | 10 |
| 442 | HPV | 16 | 1 | 14 | B*5102 | KALQAIELQL | 1119 | 165.00 | 10 |
| 443 | HPV | 16 | 1 | 14 | B*2705 | LQAIELQLTL | 1120 | 200.00 | 10 |
| 444 | HPV | 16 | 1 | 14 | B*2705 | SQYSNEKWTL | 1121 | 1000.00 | 10 |
| 445 | HPV | 16 | 1 | 14 | B*2705 | LQDVSLEVYL | 1122 | 200.00 | 10 |
| 446 | HPV | 16 | 1 | 14 | B*2705 | VQFDGDICNT | 1123 | 100.00 | 10 |

TABLE 7-continued

| No | Species | Strain type | Frame | ORF | HLA | Seq | Seq ID No. | Score | Length |
|---|---|---|---|---|---|---|---|---|---|
| 447 | HPV | 16 | 1 | 14 | Cw*0401 | QFDGDICNTM | 1124 | 150.00 | 10 |
| 448 | HPV | 16 | 1 | 14 | A*0201 | YICEEASVTV | 1125 | 180.37 | 10 |
| 449 | HPV | 16 | 1 | 14 | B60 | VEGQVDYYGL | 1126 | 320.00 | 10 |
| 450 | HPV | 16 | 1 | 14 | B*2705 | GQVDYYGLYY | 1127 | 100.00 | 10 |
| 451 | HPV | 16 | 1 | 14 | B62 | GQVDYYGLYY | 1127 | 116.16 | 10 |
| 452 | HPV | 16 | 1 | 14 | B*5102 | YGLYYVHEGI | 1128 | 580.80 | 10 |
| 453 | HPV | 16 | 1 | 14 | A68.1 | FVQFKDDAEK | 1129 | 180.00 | 10 |
| 454 | HPV | 16 | 1 | 14 | B*2702 | VQFKDDAEKY | 1130 | 100.00 | 10 |
| 455 | HPV | 16 | 1 | 14 | B*2705 | VQFKDDAEKY | 1130 | 500.00 | 10 |
| 456 | HPV | 16 | 1 | 14 | B*5102 | DAEKYSKNKV | 1131 | 110.00 | 10 |
| 457 | HPV | 16 | 1 | 14 | B*5103 | DAEKYSKNKV | 1131 | 121.00 | 10 |
| 458 | HPV | 16 | 1 | 14 | B*2705 | IRQHLANHPA | 1132 | 200.00 | 10 |
| 459 | HPV | 16 | 1 | 14 | B*5102 | HPAATHTKAV | 1133 | 242.00 | 10 |
| 460 | HPV | 16 | 1 | 14 | B*5102 | LGTEETQTTI | 1134 | 117.13 | 10 |
| 461 | HPV | 16 | 1 | 14 | A68.1 | ETQTTIQRPR | 1135 | 150.00 | 10 |
| 462 | HPV | 16 | 1 | 14 | A68.1 | DTGNPCHTTK | 1136 | 180.00 | 10 |
| 463 | HPV | 16 | 1 | 14 | B*2705 | HRDSVDSAPI | 1137 | 600.00 | 10 |
| 464 | HPV | 16 | 1 | 14 | B*2705 | GRINCNSNTT | 1138 | 200.00 | 10 |
| 465 | HPV | 16 | 1 | 14 | B*3901 | VHLKGDANTL | 1139 | 180.00 | 10 |
| 466 | HPV | 16 | 1 | 14 | B*5801 | NTLKCLRYRF | 1140 | 145.20 | 10 |
| 467 | HPV | 16 | 1 | 14 | B*2702 | LRYRFKKHCT | 1141 | 100.00 | 10 |
| 468 | HPV | 16 | 1 | 14 | B*2705 | LRYRFKKHCT | 1141 | 1000.00 | 10 |
| 469 | HPV | 16 | 1 | 14 | Cw*0401 | RYRFKKHCTL | 1142 | 200.00 | 10 |
| 470 | HPV | 16 | 1 | 14 | A24 | RYRFKKHCTL | 1142 | 400.00 | 10 |
| 471 | HPV | 16 | 1 | 14 | B*2702 | YRFKKHCTLY | 1143 | 1000.00 | 10 |
| 472 | HPV | 16 | 1 | 14 | B*2705 | YRFKKHCTLY | 1143 | 5000.00 | 10 |
| 473 | HPV | 16 | 1 | 14 | B*2705 | QRDQFLSQVK | 1144 | 2000.00 | 10 |
| 474 | HPV | 16 | 1 | 16 | B*2705 | MQEHPDYL | 1344 | 200.00 | 8 |
| 475 | HPV | 16 | 1 | 16 | B*3901 | EHPDYLQL | 1345 | 270.00 | 8 |
| 476 | HPV | 16 | 1 | 16 | B*2705 | LQLDIPIF | 1346 | 100.00 | 8 |
| 477 | HPV | 16 | 1 | 16 | A*0201 | NMLHAQTYI | 1347 | 153.33 | 9 |
| 478 | HPV | 16 | 1 | 16 | A*0201 | IMQEHPDYL | 1348 | 289.81 | 9 |
| 479 | HPV | 16 | 1 | 16 | B60 | QEHPDYLQL | 1349 | 352.00 | 9 |
| 480 | HPV | 16 | 1 | 16 | B*5102 | HPDYLQLDI | 1350 | 220.00 | 9 |
| 481 | HPV | 16 | 1 | 16 | A*0201 | LQLDIPIFL | 1351 | 307.21 | 9 |
| 482 | HPV | 16 | 1 | 16 | B*2705 | LQLDIPIFL | 1351 | 200.00 | 9 |
| 483 | HPV | 16 | 1 | 16 | A*0201 | QLDIPIFLL | 1352 | 113.99 | 9 |
| 484 | HPV | 16 | 1 | 16 | Cw*0401 | IPIFLLKNL | 1353 | 160.00 | 9 |
| 485 | HPV | 16 | 1 | 16 | B*5102 | IPIFLLKNL | 1353 | 330.00 | 9 |
| 486 | HPV | 16 | 1 | 16 | A*0201 | FLLKNLTIT | 1354 | 119.60 | 9 |
| 487 | HPV | 16 | 1 | 16 | B*2705 | MQEHPDYLQL | 1355 | 200.00 | 10 |
| 488 | HPV | 16 | 1 | 16 | Cw*0401 | DYLQLDIPIF | 1356 | 200.00 | 10 |
| 489 | HPV | 16 | 1 | 16 | A24 | DYLQLDIPIF | 1356 | 150.00 | 10 |
| 490 | HPV | 16 | 1 | 16 | A*0201 | YLQLDIPIFL | 1357 | 540.47 | 10 |
| 491 | HPV | 16 | 1 | 16 | A*0201 | LQLDIPIFLL | 1358 | 745.13 | 10 |
| 492 | HPV | 16 | 1 | 16 | A*0205 | LQLDIPIFLL | 1358 | 205.63 | 10 |
| 493 | HPV | 16 | 1 | 16 | B*2705 | LQLDIPIFLL | 1358 | 200.00 | 10 |
| 494 | HPV | 16 | 1 | 16 | A3 | QLDIPIFLLK | 1359 | 180.00 | 10 |
| 495 | HPV | 16 | 1 | 16 | B62 | LLKNLTITKY | 1360 | 144.00 | 10 |
| 496 | HPV | 16 | 1 | 17 | A*0201 | KMLVLMQQM | 1361 | 106.87 | 9 |
| 497 | HPV | 16 | 1 | 17 | B*5201 | MQQMQVWII | 1362 | 150.00 | 9 |
| 498 | HPV | 16 | 1 | 17 | A68.1 | NVYLWITNK | 1363 | 120.00 | 9 |
| 499 | HPV | 16 | 1 | 17 | A*0201 | MLVLMQQMQV | 1364 | 118.24 | 10 |
| 500 | HPV | 16 | 1 | 17 | A*0201 | VLMQQMQVWI | 1365 | 360.92 | 10 |
| 501 | HPV | 16 | 1 | 17 | B*2705 | MQVWIIENVY | 1366 | 100.00 | 10 |
| 502 | HPV | 16 | 1 | 17 | A*0201 | WIIENVYLWI | 1367 | 223.20 | 10 |
| 503 | HPV | 16 | 1 | 17 | A*0201 | YLWITNKHNC | 1368 | 189.68 | 10 |
| 504 | HPV | 16 | 1 | 18 | B*5102 | LALVLWTL | 1165 | 150.00 | 8 |
| 505 | HPV | 16 | 1 | 18 | B*2705 | YRLTKVKF | 1166 | 300.00 | 8 |
| 506 | HPV | 16 | 1 | 18 | B*3901 | FHWIFVHL | 1167 | 270.00 | 8 |
| 507 | HPV | 16 | 1 | 18 | B*5102 | FANIQIIL | 1168 | 121.00 | 8 |
| 508 | HPV | 16 | 1 | 18 | B*5102 | MATAYFFI | 1169 | 200.00 | 8 |
| 509 | HPV | 16 | 1 | 18 | B*2705 | YQTIYTLK | 1170 | 200.00 | 8 |
| 510 | HPV | 16 | 1 | 18 | B*5102 | KALGLLQI | 1171 | 726.00 | 8 |
| 511 | HPV | 16 | 1 | 18 | A*0201 | VIWFILALV | 1369 | 310.36 | 9 |
| 512 | HPV | 16 | 1 | 18 | A*0201 | FILALVLWT | 1370 | 220.61 | 9 |
| 513 | HPV | 16 | 1 | 18 | A*0201 | ILALVLWTL | 1371 | 626.45 | 9 |
| 514 | HPV | 16 | 1 | 18 | B*5102 | LALVLWTLL | 1172 | 150.00 | 9 |
| 515 | HPV | 16 | 1 | 18 | A3 | TLLHYRLTK | 1173 | 180.00 | 9 |
| 516 | HPV | 16 | 1 | 18 | A*0201 | LLHYRLTKV | 1174 | 271.95 | 9 |
| 517 | HPV | 16 | 1 | 18 | A24 | HYRLTKVKF | 1175 | 110.00 | 9 |
| 518 | HPV | 16 | 1 | 18 | Cw*0401 | HYRLTKVKF | 1175 | 132.00 | 9 |
| 519 | HPV | 16 | 1 | 18 | Cw*0401 | KFHWIFVHL | 1176 | 330.00 | 9 |
| 520 | HPV | 16 | 1 | 18 | Cw*0401 | LFANIQIIL | 1177 | 200.00 | 9 |
| 521 | HPV | 16 | 1 | 18 | B*2705 | CQNHMATAY | 1178 | 100.00 | 9 |
| 522 | HPV | 16 | 1 | 18 | A*0201 | FIYEGNKCL | 1179 | 177.27 | 9 |

TABLE 7-continued

| No | Species | Strain type | Frame | ORF | HLA | Seq | Seq ID No. | Score | Length |
|---|---|---|---|---|---|---|---|---|---|
| 523 | HPV | 16 | 1 | 18 | A*0205 | FIYEGNKCL | 1179 | 189.00 | 9 |
| 524 | HPV | 16 | 1 | 18 | A24 | IYEGNKCLL | 1180 | 300.00 | 9 |
| 525 | HPV | 16 | 1 | 18 | Cw*0401 | IYEGNKCLL | 1180 | 200.00 | 9 |
| 526 | HPV | 16 | 1 | 18 | A24 | IYLIGLVLL | 1181 | 300.00 | 9 |
| 527 | HPV | 16 | 1 | 18 | Cw*0401 | IYLIGLVLL | 1181 | 400.00 | 9 |
| 528 | HPV | 16 | 1 | 18 | A*0201 | YLIGLVLLV | 1182 | 735.86 | 9 |
| 529 | HPV | 16 | 1 | 18 | A*0201 | VLLVKMYQT | 1183 | 107.81 | 9 |
| 530 | HPV | 16 | 1 | 18 | A*0201 | KMYQTIYTL | 1184 | 397.44 | 9 |
| 531 | HPV | 16 | 1 | 18 | A*0205 | KMYQTIYTL | 1184 | 126.00 | 9 |
| 532 | HPV | 16 | 1 | 18 | B*2705 | KMYQTIYTL | 1184 | 750.00 | 9 |
| 533 | HPV | 16 | 1 | 18 | A24 | IYTLKALGL | 1185 | 200.00 | 9 |
| 534 | HPV | 16 | 1 | 18 | Cw*0401 | IYTLKALGL | 1185 | 200.00 | 9 |
| 535 | HPV | 16 | 1 | 18 | A*0201 | FILALVLWTL | 1372 | 862.39 | 10 |
| 536 | HPV | 16 | 1 | 18 | A*0205 | FILALVLWTL | 1372 | 151.20 | 10 |
| 537 | HPV | 16 | 1 | 18 | A68.1 | LVLWTLLHYR | 1186 | 400.00 | 10 |
| 538 | HPV | 16 | 1 | 18 | A*0201 | VLWTLLHYRL | 1187 | 301.42 | 10 |
| 539 | HPV | 16 | 1 | 18 | B*2705 | VLWTLLHYRL | 1187 | 150.00 | 10 |
| 540 | HPV | 16 | 1 | 18 | A*0201 | TLLHYRLTKV | 1188 | 591.89 | 10 |
| 541 | HPV | 16 | 1 | 18 | B*2702 | YRLTKVKFHW | 1189 | 100.00 | 10 |
| 542 | HPV | 16 | 1 | 18 | B*2705 | YRLTKVKFHW | 1189 | 200.00 | 10 |
| 543 | HPV | 16 | 1 | 18 | A*0201 | RLTKVKFHWI | 1190 | 109.02 | 10 |
| 544 | HPV | 16 | 1 | 18 | Cw*0401 | KFHWIFVHLF | 1191 | 300.00 | 10 |
| 545 | HPV | 16 | 1 | 18 | B*2705 | HLFANIQIIL | 1192 | 150.00 | 10 |
| 546 | HPV | 16 | 1 | 18 | B*2705 | CQNHMATAYF | 1193 | 100.00 | 10 |
| 547 | HPV | 16 | 1 | 18 | A3 | HMATAYFFIY | 1194 | 108.00 | 10 |
| 548 | HPV | 16 | 1 | 18 | Cw*0401 | FFIYEGNKCL | 1195 | 200.00 | 10 |
| 549 | HPV | 16 | 1 | 18 | A*0201 | FIYEGNKCLL | 1196 | 177.27 | 10 |
| 550 | HPV | 16 | 1 | 18 | A*0205 | FIYEGNKCLL | 1196 | 189.00 | 10 |
| 551 | HPV | 16 | 1 | 18 | A*0201 | CLLDIYLIGL | 1197 | 745.36 | 10 |
| 552 | HPV | 16 | 1 | 18 | A*0205 | CLLDIYLIGL | 1197 | 151.20 | 10 |
| 553 | HPV | 16 | 1 | 18 | A3 | YLIGLVLLVK | 1198 | 202.50 | 10 |
| 554 | HPV | 16 | 1 | 18 | A3 | KMYQTIYTLK | 1199 | 450.00 | 10 |
| 555 | HPV | 16 | 1 | 18 | B*2705 | KMYQTIYTLK | 1199 | 750.00 | 10 |
| 556 | HPV | 16 | 1 | 18 | Cw*0401 | IYTLKALGLL | 1200 | 440.00 | 10 |
| 557 | HPV | 16 | 1 | 18 | A24 | IYTLKALGLL | 1200 | 200.00 | 10 |
| 558 | HPV | 16 | 1 | 19 | B*2705 | HRATIMAF | 1201 | 1000.00 | 8 |
| 559 | HPV | 16 | 1 | 19 | B*5102 | RATIMAFV | 1202 | 100.00 | 8 |
| 560 | HPV | 16 | 1 | 19 | B*2705 | TNYLLLLL | 1203 | 100.00 | 8 |
| 561 | HPV | 16 | 1 | 19 | B*2705 | VQICHYVL | 1204 | 200.00 | 8 |
| 562 | HPV | 16 | 1 | 19 | B*3901 | CHYVLPYL | 1205 | 180.00 | 8 |
| 563 | HPV | 16 | 1 | 19 | B*5102 | LPYLLQKL | 1206 | 665.50 | 8 |
| 564 | HPV | 16 | 1 | 19 | B*3901 | LHIKILTL | 1207 | 270.00 | 8 |
| 565 | HPV | 16 | 1 | 19 | B*2705 | GRNMIYSL | 1208 | 2000.00 | 8 |
| 566 | HPV | 16 | 1 | 19 | B*2705 | SLFFNCAK | 1209 | 150.00 | 8 |
| 567 | HPV | 16 | 1 | 19 | B*5102 | MPKYSINLI | 1210 | 220.00 | 9 |
| 568 | HPV | 16 | 1 | 19 | B*2705 | HRATIMAFV | 1211 | 600.00 | 9 |
| 569 | HPV | 16 | 1 | 19 | Cw*0401 | AFVGVTNYL | 1212 | 200.00 | 9 |
| 570 | HPV | 16 | 1 | 19 | Cw*0301 | VGVTNYLLL | 1213 | 120.00 | 9 |
| 571 | HPV | 16 | 1 | 19 | A24 | NYLLLLLIL | 1214 | 360.00 | 9 |
| 572 | HPV | 16 | 1 | 19 | Cw*0401 | NYLLLLLIL | 1214 | 400.00 | 9 |
| 573 | HPV | 16 | 1 | 19 | A*0201 | LLLLILHAV | 1215 | 1006.21 | 9 |
| 574 | HPV | 16 | 1 | 19 | B*5103 | HAVQICHYV | 1216 | 110.00 | 9 |
| 575 | HPV | 16 | 1 | 19 | B*5102 | HAVQICHYV | 1216 | 363.00 | 9 |
| 576 | HPV | 16 | 1 | 19 | B*3901 | CHYVLPYLL | 1217 | 180.00 | 9 |
| 577 | HPV | 16 | 1 | 19 | A68.1 | YVLPYLLQK | 1218 | 360.00 | 9 |
| 578 | HPV | 16 | 1 | 19 | A*0201 | KLHIKILTL | 1219 | 171.97 | 9 |
| 579 | HPV | 16 | 1 | 19 | B*2705 | LRSTYDMGR | 1220 | 1000.00 | 9 |
| 580 | HPV | 16 | 1 | 19 | B*2702 | GRNMIYSLF | 1221 | 200.00 | 9 |
| 581 | HPV | 16 | 1 | 19 | B*2705 | GRNMIYSLF | 1221 | 1000.00 | 9 |
| 582 | HPV | 16 | 1 | 19 | B*5102 | IGYNEHRATI | 1222 | 484.00 | 10 |
| 583 | HPV | 16 | 1 | 19 | B*5103 | IGYNEHRATI | 1222 | 132.00 | 10 |
| 584 | HPV | 16 | 1 | 19 | Cw*0401 | GYNEHRATIM | 1223 | 132.00 | 10 |
| 585 | HPV | 16 | 1 | 19 | B*5102 | RATIMAFVGV | 1224 | 100.00 | 10 |
| 586 | HPV | 16 | 1 | 19 | B*5103 | RATIMAFVGV | 1224 | 121.00 | 10 |
| 587 | HPV | 16 | 1 | 19 | B*5102 | MAFVGVTNYL | 1225 | 332.75 | 10 |
| 588 | HPV | 16 | 1 | 19 | Cw*0401 | AFVGVTNYLL | 1226 | 240.00 | 10 |
| 589 | HPV | 16 | 1 | 19 | B*2705 | TNYLLLLLIL | 1227 | 100.00 | 10 |
| 590 | HPV | 16 | 1 | 19 | A*0201 | YLLLLLILHA | 1228 | 194.48 | 10 |
| 591 | HPV | 16 | 1 | 19 | A*0201 | LLLLLILHAV | 1229 | 1006.21 | 10 |
| 592 | HPV | 16 | 1 | 19 | B*5102 | HAVQICHYVL | 1230 | 165.00 | 10 |
| 593 | HPV | 16 | 1 | 19 | B*2705 | VQICHYVLPY | 1231 | 100.00 | 10 |
| 594 | HPV | 16 | 1 | 19 | A*0205 | YVLPYLLQKL | 1232 | 252.00 | 10 |
| 595 | HPV | 16 | 1 | 19 | Cw*0301 | YVLPYLLQKL | 1232 | 120.00 | 10 |
| 596 | HPV | 16 | 1 | 19 | B*5102 | LPYLLQKLHI | 1233 | 2420.00 | 10 |
| 597 | HPV | 16 | 1 | 19 | B*5103 | LPYLLQKLHI | 1233 | 159.72 | 10 |
| 598 | HPV | 16 | 1 | 19 | A*0201 | YLLQKLHIKI | 1234 | 177.57 | 10 |

TABLE 7-continued

| No | Species | Strain type | Frame | ORF | HLA | Seq | Seq ID No. | Score | Length |
|---|---|---|---|---|---|---|---|---|---|
| 599 | HPV | 16 | 1 | 19 | B*2705 | LRSTYDMGRN | 1235 | 200.00 | 10 |
| 600 | HPV | 16 | 1 | 19 | B*2702 | GRNMIYSLFF | 1236 | 200.00 | 10 |
| 601 | HPV | 16 | 1 | 19 | B*2705 | GRNMIYSLFF | 1236 | 1000.00 | 10 |
| 602 | HPV | 16 | 1 | 21 | A*0201 | VLFVVYMFV | 1240 | 3609.23 | 9 |
| 603 | HPV | 16 | 1 | 21 | Cw*0401 | VYMFVCACM | 1241 | 120.00 | 9 |
| 604 | HPV | 16 | 1 | 21 | Cw*0401 | MFVCACMCL | 1242 | 220.00 | 9 |
| 605 | HPV | 16 | 1 | 21 | A*0201 | LVLFVVYMFV | 1245 | 315.81 | 10 |
| 606 | HPV | 16 | 1 | 21 | A*0201 | VLFVVYMFVC | 1246 | 170.91 | 10 |
| 607 | HPV | 16 | 1 | 21 | A*0201 | YMFVCACMCL | 1247 | 262.59 | 10 |
| 608 | HPV | 16 | 1 | 21 | B*2705 | YMFVCACMCL | 1247 | 250.00 | 10 |
| 609 | HPV | 16 | 1 | 22 | B*5102 | YGIINTCV | 1373 | 290.40 | 8 |
| 610 | HPV | 16 | 1 | 22 | Cw*0301 | TCVCVFKCL | 1374 | 120.00 | 9 |
| 611 | HPV | 16 | 1 | 22 | B*2705 | CNYCVMQHK | 1375 | 100.00 | 9 |
| 612 | HPV | 16 | 1 | 22 | A*0201 | CMYGIINTCV | 1376 | 160.74 | 10 |
| 613 | HPV | 16 | 1 | 22 | B*5102 | YGIINTCVCV | 1377 | 264.00 | 10 |
| 614 | HPV | 16 | 1 | 23 | Cw*0401 | LFGTKCVFL | 1378 | 200.00 | 9 |
| 615 | HPV | 16 | 1 | 23 | A*0201 | MLFGTKCVFL | 1379 | 739.03 | 10 |
| 616 | HPV | 16 | 1 | 23 | B*2705 | MLFGTKCVFL | 1379 | 150.00 | 10 |
| 617 | HPV | 16 | 1 | 24 | B*5102 | APTPYIPL | 1380 | 110.00 | 8 |
| 618 | HPV | 16 | 1 | 24 | B*5102 | YAPTPYIPL | 1381 | 110.00 | 9 |
| 619 | HPV | 16 | 1 | 24 | B7 | APTPYIPLL | 1382 | 240.00 | 9 |
| 620 | HPV | 16 | 1 | 24 | Cw*0401 | APTPYIPLL | 1382 | 192.00 | 9 |
| 621 | HPV | 16 | 1 | 24 | B*5102 | APTPYIPLL | 1382 | 110.00 | 9 |
| 622 | HPV | 16 | 1 | 24 | A*0201 | LLGTYFWLV | 1251 | 1684.90 | 9 |
| 623 | HPV | 16 | 1 | 24 | Cw*0401 | YFWLVLTNL | 1252 | 400.00 | 9 |
| 624 | HPV | 16 | 1 | 24 | A*0201 | VLTNLIAYL | 1253 | 459.40 | 9 |
| 625 | HPV | 16 | 1 | 24 | Cw*0401 | HYAPTPYIPL | 1383 | 240.00 | 10 |
| 626 | HPV | 16 | 1 | 24 | A24 | HYAPTPYIPL | 1383 | 240.00 | 10 |
| 627 | HPV | 16 | 1 | 24 | B*5102 | YAPTPYIPLL | 1384 | 121.00 | 10 |
| 628 | HPV | 16 | 1 | 24 | B*5102 | IPLLGTYFWL | 1385 | 363.00 | 10 |
| 629 | HPV | 16 | 1 | 24 | Cw*0301 | IPLLGTYFWL | 1385 | 100.00 | 10 |
| 630 | HPV | 16 | 1 | 24 | Cw*0401 | TYFWLVLTNL | 1254 | 400.00 | 10 |
| 631 | HPV | 16 | 1 | 24 | A24 | TYFWLVLTNL | 1254 | 280.00 | 10 |
| 632 | HPV | 16 | 1 | 24 | A*0201 | LVLTNLIAYL | 1255 | 148.73 | 10 |
| 633 | HPV | 16 | 1 | 24 | A*0205 | LVLTNLIAYL | 1255 | 142.80 | 10 |
| 634 | HPV | 16 | 2 | 1 | B*2705 | LRREVYDF | 1386 | 1000.00 | 8 |
| 635 | HPV | 16 | 2 | 1 | B*2705 | RREVYDFA | 1387 | 600.00 | 8 |
| 636 | HPV | 16 | 2 | 1 | B*5102 | FAFRDLCI | 1388 | 2200.00 | 8 |
| 637 | HPV | 16 | 2 | 1 | B*2705 | FRDLCIVY | 1389 | 1000.00 | 8 |
| 638 | HPV | 16 | 2 | 1 | B*2705 | YRDGNPYA | 1390 | 200.00 | 8 |
| 639 | HPV | 16 | 2 | 1 | B*5102 | YAVCDKCL | 1391 | 300.00 | 8 |
| 640 | HPV | 16 | 2 | 1 | B*2705 | YRHYCYSL | 1392 | 2000.00 | 8 |
| 641 | HPV | 16 | 2 | 1 | B*2705 | QQYNKPLC | 1393 | 100.00 | 8 |
| 642 | HPV | 16 | 2 | 1 | B*5102 | KPLCDLLI | 1394 | 1200.00 | 8 |
| 643 | HPV | 16 | 2 | 1 | B*2705 | IRCINCQK | 1395 | 2000.00 | 8 |
| 644 | HPV | 16 | 2 | 1 | B*2705 | KQRHLDKK | 1396 | 180.00 | 8 |
| 645 | HPV | 16 | 2 | 1 | B*2705 | KQRFHNIR | 1397 | 300.00 | 8 |
| 646 | HPV | 16 | 2 | 1 | B*2705 | IRGRWTGR | 1398 | 1000.00 | 8 |
| 647 | HPV | 16 | 2 | 1 | B*2705 | GRWTGRCM | 1399 | 3000.00 | 8 |
| 648 | HPV | 16 | 2 | 1 | B*2705 | GRCMSCCR | 1400 | 1000.00 | 8 |
| 649 | HPV | 16 | 2 | 1 | B*2705 | CRSSRTRR | 1401 | 300.00 | 8 |
| 650 | HPV | 16 | 2 | 1 | B*5201 | LQTTIHDII | 1402 | 300.00 | 9 |
| 651 | HPV | 16 | 2 | 1 | B*3901 | IHDIILECV | 1403 | 135.00 | 9 |
| 652 | HPV | 16 | 2 | 1 | B*2705 | QQLLRREVY | 1404 | 100.00 | 9 |
| 653 | HPV | 16 | 2 | 1 | B62 | LLRREVYDF | 1405 | 120.00 | 9 |
| 654 | HPV | 16 | 2 | 1 | B*2705 | LRREVYDFA | 1406 | 200.00 | 9 |
| 655 | HPV | 16 | 2 | 1 | B*2702 | RREVYDFAF | 1407 | 600.00 | 9 |
| 656 | HPV | 16 | 2 | 1 | B*2705 | RREVYDFAF | 1407 | 3000.00 | 9 |
| 657 | HPV | 16 | 2 | 1 | A24 | VYDFAFRDL | 1408 | 240.00 | 9 |
| 658 | HPV | 16 | 2 | 1 | Cw*0401 | VYDFAFRDL | 1408 | 330.00 | 9 |
| 659 | HPV | 16 | 2 | 1 | B*5103 | FAFRDLCIV | 1409 | 132.00 | 9 |
| 660 | HPV | 16 | 2 | 1 | B*5102 | FAFRDLCIV | 1409 | 1100.00 | 9 |
| 661 | HPV | 16 | 2 | 1 | B*2705 | FRDLCIVYR | 1410 | 1000.00 | 9 |
| 662 | HPV | 16 | 2 | 1 | B*2705 | YRDGNPYAV | 1411 | 600.00 | 9 |
| 663 | HPV | 16 | 2 | 1 | B*5102 | NPYAVCDKC | 1412 | 110.00 | 9 |
| 664 | HPV | 16 | 2 | 1 | A1 | ISEYRHYCY | 1413 | 135.00 | 9 |
| 665 | HPV | 16 | 2 | 1 | A24 | EYRHYCYSL | 1414 | 200.00 | 9 |
| 666 | HPV | 16 | 2 | 1 | Cw*0401 | EYRHYCYSL | 1414 | 220.00 | 9 |
| 667 | HPV | 16 | 2 | 1 | B*2702 | YRHYCYSLY | 1415 | 200.00 | 9 |
| 668 | HPV | 16 | 2 | 1 | B*2705 | YRHYCYSLY | 1415 | 1000.00 | 9 |
| 669 | HPV | 16 | 2 | 1 | A24 | CYSLYGTTL | 1416 | 200.00 | 9 |
| 670 | HPV | 16 | 2 | 1 | Cw*0401 | CYSLYGTTL | 1416 | 200.00 | 9 |
| 671 | HPV | 16 | 2 | 1 | B60 | LEQQYNKPL | 1417 | 160.00 | 9 |
| 672 | HPV | 16 | 2 | 1 | A24 | QYNKPLCDL | 1418 | 300.00 | 9 |
| 673 | HPV | 16 | 2 | 1 | Cw*0401 | QYNKPLCDL | 1418 | 400.00 | 9 |
| 674 | HPV | 16 | 2 | 1 | Cw*0401 | CPEEKQRHL | 1419 | 105.60 | 9 |

TABLE 7-continued

| No | Species | Strain type | Frame | ORF | HLA | Seq | Seq ID No. | Score | Length |
|---|---|---|---|---|---|---|---|---|---|
| 675 | HPV | 16 | 2 | 1 | B*2705 | QRHLDKKQR | 1420 | 300.00 | 9 |
| 676 | HPV | 16 | 2 | 1 | B*2705 | QRFHNIRGR | 1421 | 1500.00 | 9 |
| 677 | HPV | 16 | 2 | 1 | B*2705 | IRGRWTGRC | 1422 | 200.00 | 9 |
| 678 | HPV | 16 | 2 | 1 | B*2705 | GRWTGRCMS | 1423 | 1000.00 | 9 |
| 679 | HPV | 16 | 2 | 1 | B*2705 | GRCMSCCRS | 1424 | 200.00 | 9 |
| 680 | HPV | 16 | 2 | 1 | B14 | SRTRRETQL | 1425 | 300.00 | 9 |
| 681 | HPV | 16 | 2 | 1 | B*2705 | SRTRRETQL | 1425 | 2000.00 | 9 |
| 682 | HPV | 16 | 2 | 1 | B*2705 | LQTTIHDIIL | 1426 | 200.00 | 10 |
| 683 | HPV | 16 | 2 | 1 | B60 | LECVYCKQQL | 1427 | 176.00 | 10 |
| 684 | HPV | 16 | 2 | 1 | A68.1 | CVYCKQQLLR | 1428 | 200.00 | 10 |
| 685 | HPV | 16 | 2 | 1 | B*2705 | KQQLLRREVY | 1429 | 300.00 | 10 |
| 686 | HPV | 16 | 2 | 1 | B*2702 | LRREVYDFAF | 1430 | 200.00 | 10 |
| 687 | HPV | 16 | 2 | 1 | B*2705 | LRREVYDFAF | 1430 | 1000.00 | 10 |
| 688 | HPV | 16 | 2 | 1 | B*2705 | RREVYDFAFR | 1431 | 3000.00 | 10 |
| 689 | HPV | 16 | 2 | 1 | Cw*0301 | EVYDFAFRDL | 1432 | 100.00 | 10 |
| 690 | HPV | 16 | 2 | 1 | B*2705 | YRDGNPYAVC | 1433 | 200.00 | 10 |
| 691 | HPV | 16 | 2 | 1 | B*5102 | NPYAVCDKCL | 1434 | 550.00 | 10 |
| 692 | HPV | 16 | 2 | 1 | B*2705 | SEYRHYCYSL | 1435 | 150.00 | 10 |
| 693 | HPV | 16 | 2 | 1 | B60 | SEYRHYCYSL | 1435 | 320.00 | 10 |
| 694 | HPV | 16 | 2 | 1 | B*2705 | QQYNKPLCDL | 1436 | 1000.00 | 10 |
| 695 | HPV | 16 | 2 | 1 | Cw*0401 | QYNKPLCDLL | 1437 | 200.00 | 10 |
| 696 | HPV | 16 | 2 | 1 | A24 | QYNKPLCDLL | 1437 | 360.00 | 10 |
| 697 | HPV | 16 | 2 | 1 | B*2705 | IRCINCQKPL | 1438 | 600.00 | 10 |
| 698 | HPV | 16 | 2 | 1 | B*2705 | CQKPLCPEEK | 1439 | 200.00 | 10 |
| 699 | HPV | 16 | 2 | 1 | B*2702 | QRHLDKKQRF | 1440 | 200.00 | 10 |
| 700 | HPV | 16 | 2 | 1 | B*2705 | QRHLDKKQRF | 1440 | 1000.00 | 10 |
| 701 | HPV | 16 | 2 | 1 | B*2702 | QRFHNIRGRW | 1441 | 500.00 | 10 |
| 702 | HPV | 16 | 2 | 1 | B*2705 | QRFHNIRGRW | 1441 | 1000.00 | 10 |
| 703 | HPV | 16 | 2 | 1 | B*2705 | IRGRWTGRCM | 1442 | 180.00 | 10 |
| 704 | HPV | 16 | 2 | 1 | B*2702 | GRWTGRCMSC | 1443 | 100.00 | 10 |
| 705 | HPV | 16 | 2 | 1 | B*2705 | GRWTGRCMSC | 1443 | 1000.00 | 10 |
| 706 | HPV | 16 | 2 | 1 | A68.1 | WTGRCMSCCR | 1444 | 100.00 | 10 |
| 707 | HPV | 16 | 2 | 3 | B*2705 | KQNRTEPI | 1445 | 180.00 | 8 |
| 708 | HPV | 16 | 2 | 3 | B*2705 | NRTEPITI | 1446 | 600.00 | 8 |
| 709 | HPV | 16 | 2 | 3 | B*2705 | NRTEPITIL | 1447 | 2000.00 | 9 |
| 710 | HPV | 16 | 2 | 3 | B*2705 | KQNRTEPITI | 1448 | 180.00 | 10 |
| 711 | HPV | 16 | 2 | 4 | B*2705 | VRDVMDGF | 1449 | 1000.00 | 8 |
| 712 | HPV | 16 | 2 | 4 | A68.1 | QVPMGKRVR | 1450 | 200.00 | 9 |
| 713 | HPV | 16 | 2 | 4 | B*2705 | VRDVMDGFM | 1451 | 600.00 | 9 |
| 714 | HPV | 16 | 2 | 4 | A*0201 | ILQVPMGKRV | 1452 | 118.24 | 10 |
| 715 | HPV | 16 | 2 | 4 | B*5102 | VPMGKRVRDV | 1453 | 242.00 | 10 |
| 716 | HPV | 16 | 2 | 4 | B*2702 | KRVRDVMDGF | 1454 | 600.00 | 10 |
| 717 | HPV | 16 | 2 | 4 | B*2705 | KRVRDVMDGF | 1454 | 3000.00 | 10 |
| 718 | HPV | 16 | 2 | 5 | B*2705 | HRKQNNIEM | 1455 | 600.00 | 9 |
| 719 | HPV | 16 | 2 | 5 | B*2705 | KQNNIEMQY | 1456 | 300.00 | 9 |
| 720 | HPV | 16 | 2 | 5 | B*2705 | KQNNIEMQYR | 1457 | 300.00 | 10 |
| 721 | HPV | 16 | 2 | 6 | B*2705 | ARGRGQGK | 1458 | 2000.00 | 8 |
| 722 | HPV | 16 | 2 | 6 | B*2705 | KRWRLFAN | 1459 | 3000.00 | 8 |
| 723 | HPV | 16 | 2 | 6 | A68.1 | DVVQIKFAR | 1460 | 1200.00 | 9 |
| 724 | HPV | 16 | 2 | 6 | B*2705 | ARGRGQGKR | 1461 | 1000.00 | 9 |
| 725 | HPV | 16 | 2 | 6 | B*2705 | GRGQGKRWR | 1462 | 300.00 | 9 |
| 726 | HPV | 16 | 2 | 6 | B62 | GQGKRWRLF | 1463 | 160.00 | 9 |
| 727 | HPV | 16 | 2 | 6 | B*2702 | KRWRLFANV | 1464 | 300.00 | 9 |
| 728 | HPV | 16 | 2 | 6 | B*2705 | KRWRLFANV | 1464 | 9000.00 | 9 |
| 729 | HPV | 16 | 2 | 6 | A*0201 | ILFLKDVVQI | 1465 | 150.93 | 10 |
| 730 | HPV | 16 | 2 | 6 | B62 | FLKDVVQIKF | 1466 | 316.80 | 10 |
| 731 | HPV | 16 | 2 | 6 | A68.1 | VVQIKFARGR | 1467 | 200.00 | 10 |
| 732 | HPV | 16 | 2 | 6 | B14 | GRGQGKRWRL | 1468 | 100.00 | 10 |
| 733 | HPV | 16 | 2 | 6 | B*2705 | GRGQGKRWRL | 1468 | 2000.00 | 10 |
| 734 | HPV | 16 | 2 | 7 | B*2705 | YQRIKHYK | 1469 | 200.00 | 8 |
| 735 | HPV | 16 | 2 | 7 | B14 | QRIKHYKQL | 1470 | 180.00 | 9 |
| 736 | HPV | 16 | 2 | 7 | B*2705 | QRIKHYKQL | 1470 | 600.00 | 9 |
| 737 | HPV | 16 | 2 | 7 | Cw*0301 | QRIKHYKQL | 1470 | 240.00 | 9 |
| 738 | HPV | 16 | 2 | 7 | B*2705 | QRIKHYKQLN | 1471 | 200.00 | 10 |
| 739 | HPV | 16 | 2 | 8 | B*2705 | TQWTVLQS | 1472 | 100.00 | 8 |
| 740 | HPV | 16 | 2 | 8 | Cw*0301 | TKYPLLKLL | 1473 | 120.00 | 9 |
| 741 | HPV | 16 | 2 | 8 | A*0201 | KLLGSTWPT | 1474 | 723.78 | 9 |
| 742 | HPV | 16 | 2 | 8 | B*5102 | WPTTPPRPI | 1475 | 484.00 | 9 |
| 743 | HPV | 16 | 2 | 8 | B*5102 | WAPKKHRRL | 1476 | 121.00 | 9 |
| 744 | HPV | 16 | 2 | 8 | B*2705 | TQWTVLQSS | 1477 | 100.00 | 9 |
| 745 | HPV | 16 | 2 | 8 | B*5102 | AATKYPLLKL | 1478 | 110.00 | 10 |
| 746 | HPV | 16 | 2 | 8 | A*0201 | KLLGSTWPTT | 1479 | 164.06 | 10 |
| 747 | HPV | 16 | 2 | 8 | B*2705 | RRLSSDQDQS | 1480 | 600.00 | 10 |
| 748 | HPV | 16 | 2 | 8 | B*2705 | TQWTVLQSSL | 1481 | 1000.00 | 10 |
| 749 | HPV | 16 | 2 | 8 | B*5102 | TAHTKDGLTV | 1482 | 121.00 | 10 |
| 750 | HPV | 16 | 2 | 8 | B*5103 | TAHTKDGLTV | 1482 | 121.00 | 10 |

TABLE 7-continued

| No | Species | Strain type | Frame | ORF | HLA | Seq | Seq ID No. | Score | Length |
|---|---|---|---|---|---|---|---|---|---|
| 751 | HPV | 16 | 2 | 9 | B*2705 | CRLHGIGQDI | 1483 | 600.00 | 10 |
| 752 | HPV | 16 | 2 | 11 | B*5102 | SAFRCFIV | 1484 | 550.00 | 8 |
| 753 | HPV | 16 | 2 | 11 | B*2705 | FRCFIVYI | 1485 | 600.00 | 8 |
| 754 | HPV | 16 | 2 | 11 | A*0201 | LLLSVSTYT | 1486 | 257.80 | 9 |
| 755 | HPV | 16 | 2 | 11 | Cw*0301 | LSVSTYTSL | 1487 | 100.00 | 9 |
| 756 | HPV | 16 | 2 | 11 | A*0201 | IILVLLLWI | 1488 | 114.14 | 9 |
| 757 | HPV | 16 | 2 | 11 | B*5103 | AASAFRCFI | 1489 | 100.00 | 9 |
| 758 | HPV | 16 | 2 | 11 | B*5102 | AASAFRCFI | 1489 | 200.00 | 9 |
| 759 | HPV | 16 | 2 | 11 | B*2705 | FRCFIVYII | 1490 | 600.00 | 9 |
| 760 | HPV | 16 | 2 | 11 | Cw*0301 | YIIFVYIPL | 1491 | 100.00 | 9 |
| 761 | HPV | 16 | 2 | 11 | Cw*0401 | IFVYIPLFL | 1492 | 200.00 | 9 |
| 762 | HPV | 16 | 2 | 11 | A*0201 | FVYIPLFLI | 1493 | 179.26 | 9 |
| 763 | HPV | 16 | 2 | 11 | Cw*0401 | TYTSLIILVL | 1494 | 400.00 | 10 |
| 764 | HPV | 16 | 2 | 11 | A24 | TYTSLIILVL | 1494 | 280.00 | 10 |
| 765 | HPV | 16 | 2 | 11 | B*5102 | TAASAFRCFI | 1495 | 200.00 | 10 |
| 766 | HPV | 16 | 2 | 11 | B*5103 | TAASAFRCFI | 1495 | 110.00 | 10 |
| 767 | HPV | 16 | 2 | 11 | B*5102 | AASAFRCFIV | 1496 | 100.00 | 10 |
| 768 | HPV | 16 | 2 | 11 | B*5103 | AASAFRCFIV | 1496 | 110.00 | 10 |
| 769 | HPV | 16 | 2 | 11 | B*5102 | SAFRCFIVYI | 1497 | 1331.00 | 10 |
| 770 | HPV | 16 | 2 | 11 | B*5103 | SAFRCFIVYI | 1497 | 159.72 | 10 |
| 771 | HPV | 16 | 2 | 11 | B*2702 | FRCFIVYIIF | 1498 | 200.00 | 10 |
| 772 | HPV | 16 | 2 | 11 | B*2705 | FRCFIVYIIF | 1498 | 1000.00 | 10 |
| 773 | HPV | 16 | 2 | 11 | Cw*0301 | VYIIFVYIPL | 1499 | 100.00 | 10 |
| 774 | HPV | 16 | 2 | 11 | Cw*0401 | VYIIFVYIPL | 1499 | 200.00 | 10 |
| 775 | HPV | 16 | 2 | 11 | A24 | VYIIFVYIPL | 1499 | 420.00 | 10 |
| 776 | HPV | 16 | 2 | 11 | A*0201 | IIFVYIPLFL | 1500 | 101.62 | 10 |
| 777 | HPV | 16 | 2 | 11 | Cw*0401 | LFLIHTHARF | 1501 | 144.00 | 10 |
| 778 | HPV | 16 | 2 | 11 | A*0201 | FLIHTHARFL | 1502 | 108.09 | 10 |
| 779 | HPV | 16 | 2 | 12 | B*2705 | QRIPMYQC | 1503 | 200.00 | 8 |
| 780 | HPV | 16 | 2 | 12 | B*2705 | YQCCSKSR | 1504 | 100.00 | 8 |
| 781 | HPV | 16 | 2 | 12 | B*2705 | QRIPMYQCC | 1505 | 200.00 | 9 |
| 782 | HPV | 16 | 2 | 12 | B*2705 | QRIPMYQCCS | 1506 | 200.00 | 10 |
| 783 | HPV | 16 | 2 | 13 | B*2705 | RRHTRRYL | 1507 | 6000.00 | 8 |
| 784 | HPV | 16 | 2 | 13 | B*3501 | SPRRHTRRY | 1508 | 120.00 | 9 |
| 785 | HPV | 16 | 2 | 13 | B7 | SPRRHTRRYL | 1509 | 1200.00 | 10 |
| 786 | HPV | 16 | 2 | 14 | B*2705 | MRAKSLFS | 1510 | 200.00 | 8 |
| 787 | HPV | 16 | 2 | 15 | Cw*0301 | HSIVFYTAL | 1511 | 100.00 | 9 |
| 788 | HPV | 16 | 2 | 15 | B*5102 | TALCATTESL | 1512 | 199.65 | 10 |
| 789 | HPV | 16 | 2 | 2 | B*2705 | HQKRTAMF | 1513 | 100.00 | 8 |
| 790 | HPV | 16 | 2 | 2 | B*3501 | RPRKLPQL | 1514 | 120.00 | 8 |
| 791 | HPV | 16 | 2 | 2 | B*5102 | LPQLCTEL | 1515 | 133.10 | 8 |
| 792 | HPV | 16 | 2 | 2 | B*2705 | LRREVYDF | 1386 | 1000.00 | 8 |
| 793 | HPV | 16 | 2 | 2 | B*2705 | RREVYDFA | 1387 | 600.00 | 8 |
| 794 | HPV | 16 | 2 | 2 | B*5102 | FAFRDLCI | 1388 | 2200.00 | 8 |
| 795 | HPV | 16 | 2 | 2 | B*2705 | FRDLCIVY | 1389 | 1000.00 | 8 |
| 796 | HPV | 16 | 2 | 2 | B*2705 | YRDGNPYA | 1390 | 200.00 | 8 |
| 797 | HPV | 16 | 2 | 2 | B*5102 | YAVCDKCL | 1391 | 300.00 | 8 |
| 798 | HPV | 16 | 2 | 2 | B*2705 | YRHYCYSL | 1392 | 2000.00 | 8 |
| 799 | HPV | 16 | 2 | 2 | B*2705 | QQYNKPLC | 1393 | 100.00 | 8 |
| 800 | HPV | 16 | 2 | 2 | B*5102 | KPLCDLLI | 1394 | 1200.00 | 8 |
| 801 | HPV | 16 | 2 | 2 | B*2705 | IRCINCQK | 1395 | 2000.00 | 8 |
| 802 | HPV | 16 | 2 | 2 | B*2705 | KQRHLDKK | 1396 | 180.00 | 8 |
| 803 | HPV | 16 | 2 | 2 | B*2705 | KQRFHNIR | 1397 | 300.00 | 8 |
| 804 | HPV | 16 | 2 | 2 | B*2705 | IRGRWTGR | 1398 | 1000.00 | 8 |
| 805 | HPV | 16 | 2 | 2 | B*2705 | GRWTGRCM | 1399 | 3000.00 | 8 |
| 806 | HPV | 16 | 2 | 2 | B*2705 | GRCMSCCR | 1400 | 1000.00 | 8 |
| 807 | HPV | 16 | 2 | 2 | B*2705 | CRSSRTRR | 1401 | 300.00 | 8 |
| 808 | HPV | 16 | 2 | 2 | B*2705 | AMFQDPQER | 1516 | 125.00 | 9 |
| 809 | HPV | 16 | 2 | 2 | Cw*0401 | DPQERPRKL | 1517 | 116.16 | 9 |
| 810 | HPV | 16 | 2 | 2 | B*5102 | DPQERPRKL | 1517 | 242.00 | 9 |
| 811 | HPV | 16 | 2 | 2 | B14 | ERPRKLPQL | 1518 | 360.00 | 9 |
| 812 | HPV | 16 | 2 | 2 | B*2705 | ERPRKLPQL | 1518 | 200.00 | 9 |
| 813 | HPV | 16 | 2 | 2 | B*5201 | LQTTIHDII | 1402 | 300.00 | 9 |
| 814 | HPV | 16 | 2 | 2 | B*3901 | IHDIILECV | 1403 | 135.00 | 9 |
| 815 | HPV | 16 | 2 | 2 | B*2705 | QQLLRREVY | 1404 | 100.00 | 9 |
| 816 | HPV | 16 | 2 | 2 | B62 | LLRREVYDF | 1405 | 120.00 | 9 |
| 817 | HPV | 16 | 2 | 2 | B*2705 | LRREVYDFA | 1406 | 200.00 | 9 |
| 818 | HPV | 16 | 2 | 2 | B*2702 | RREVYDFAF | 1407 | 600.00 | 9 |
| 819 | HPV | 16 | 2 | 2 | B*2705 | RREVYDFAF | 1407 | 3000.00 | 9 |
| 820 | HPV | 16 | 2 | 2 | A24 | VYDFAFRDL | 1408 | 240.00 | 9 |
| 821 | HPV | 16 | 2 | 2 | Cw*0401 | VYDFAFRDL | 1408 | 330.00 | 9 |
| 822 | HPV | 16 | 2 | 2 | B*5103 | FAFRDLCIV | 1409 | 132.00 | 9 |
| 823 | HPV | 16 | 2 | 2 | B*5102 | FAFRDLCIV | 1409 | 1100.00 | 9 |
| 824 | HPV | 16 | 2 | 2 | B*2705 | FRDLCIVYR | 1410 | 1000.00 | 9 |
| 825 | HPV | 16 | 2 | 2 | B*2705 | YRDGNPYAV | 1411 | 600.00 | 9 |
| 826 | HPV | 16 | 2 | 2 | B*5102 | NPYAVCDKC | 1412 | 110.00 | 9 |

TABLE 7-continued

| No | Species | Strain type | Frame | ORF | HLA | Seq | Seq ID No. | Score | Length |
|---|---|---|---|---|---|---|---|---|---|
| 827 | HPV | 16 | 2 | 2 | A1 | ISEYRHYCY | 1413 | 135.00 | 9 |
| 828 | HPV | 16 | 2 | 2 | A24 | EYRHYCYSL | 1414 | 200.00 | 9 |
| 829 | HPV | 16 | 2 | 2 | Cw*0401 | EYRHYCYSL | 1414 | 220.00 | 9 |
| 830 | HPV | 16 | 2 | 2 | B*2702 | YRHYCYSLY | 1415 | 200.00 | 9 |
| 831 | HPV | 16 | 2 | 2 | B*2705 | YRHYCYSLY | 1415 | 1000.00 | 9 |
| 832 | HPV | 16 | 2 | 2 | A24 | CYSLYGTTL | 1416 | 200.00 | 9 |
| 833 | HPV | 16 | 2 | 2 | Cw*0401 | CYSLYGTTL | 1416 | 200.00 | 9 |
| 834 | HPV | 16 | 2 | 2 | B60 | LEQQYNKPL | 1417 | 160.00 | 9 |
| 835 | HPV | 16 | 2 | 2 | A24 | QYNKPLCDL | 1418 | 300.00 | 9 |
| 836 | HPV | 16 | 2 | 2 | Cw*0401 | QYNKPLCDL | 1418 | 400.00 | 9 |
| 837 | HPV | 16 | 2 | 2 | Cw*0401 | CPEEKQRHL | 1419 | 105.60 | 9 |
| 838 | HPV | 16 | 2 | 2 | B*2705 | QRHLDKKQR | 1420 | 300.00 | 9 |
| 839 | HPV | 16 | 2 | 2 | B*2705 | QRFHNIRGR | 1421 | 1500.00 | 9 |
| 840 | HPV | 16 | 2 | 2 | B*2705 | IRGRWTGRC | 1422 | 200.00 | 9 |
| 841 | HPV | 16 | 2 | 2 | B*2705 | GRWTGRCMS | 1423 | 1000.00 | 9 |
| 842 | HPV | 16 | 2 | 2 | B*2705 | GRCMSCCRS | 1424 | 200.00 | 9 |
| 843 | HPV | 16 | 2 | 2 | B14 | SRTRRETQL | 1425 | 300.00 | 9 |
| 844 | HPV | 16 | 2 | 2 | B*2705 | SRTRRETQL | 1425 | 2000.00 | 9 |
| 845 | HPV | 16 | 2 | 2 | B*2705 | FQDPQERPRK | 1519 | 200.00 | 10 |
| 846 | HPV | 16 | 2 | 2 | B60 | QERPRKLPQL | 1520 | 176.00 | 10 |
| 847 | HPV | 16 | 2 | 2 | Cw*0301 | RKLPQLCTEL | 1521 | 100.00 | 10 |
| 848 | HPV | 16 | 2 | 2 | B*2705 | LQTTIHDIIL | 1426 | 200.00 | 10 |
| 849 | HPV | 16 | 2 | 2 | B60 | LECVYCKQQL | 1427 | 176.00 | 10 |
| 850 | HPV | 16 | 2 | 2 | A68.1 | CVYCKQQLLR | 1428 | 200.00 | 10 |
| 851 | HPV | 16 | 2 | 2 | B*2705 | KQQLLRREVY | 1429 | 300.00 | 10 |
| 852 | HPV | 16 | 2 | 2 | B*2702 | LRREVYDFAF | 1430 | 200.00 | 10 |
| 853 | HPV | 16 | 2 | 2 | B*2705 | LRREVYDFAF | 1430 | 1000.00 | 10 |
| 854 | HPV | 16 | 2 | 2 | B*2705 | RREVYDFAFR | 1431 | 3000.00 | 10 |
| 855 | HPV | 16 | 2 | 2 | Cw*0301 | EVYDFAFRDL | 1432 | 100.00 | 10 |
| 856 | HPV | 16 | 2 | 2 | B*2705 | YRDGNPYAVC | 1433 | 200.00 | 10 |
| 857 | HPV | 16 | 2 | 2 | B*5102 | NPYAVCDKCL | 1434 | 550.00 | 10 |
| 858 | HPV | 16 | 2 | 2 | B*2705 | SEYRHYCYSL | 1435 | 150.00 | 10 |
| 859 | HPV | 16 | 2 | 2 | B60 | SEYRHYCYSL | 1435 | 320.00 | 10 |
| 860 | HPV | 16 | 2 | 2 | B*2705 | QQYNKPLCDL | 1436 | 1000.00 | 10 |
| 861 | HPV | 16 | 2 | 2 | Cw*0401 | QYNKPLCDLL | 1437 | 200.00 | 10 |
| 862 | HPV | 16 | 2 | 2 | A24 | QYNKPLCDLL | 1437 | 360.00 | 10 |
| 863 | HPV | 16 | 2 | 2 | B*2705 | IRCINCQKPL | 1438 | 600.00 | 10 |
| 864 | HPV | 16 | 2 | 2 | B*2705 | CQKPLCPEEK | 1439 | 200.00 | 10 |
| 865 | HPV | 16 | 2 | 2 | B*2702 | QRHLDKKQRF | 1440 | 200.00 | 10 |
| 866 | HPV | 16 | 2 | 2 | B*2705 | QRHLDKKQRF | 1440 | 1000.00 | 10 |
| 867 | HPV | 16 | 2 | 2 | B*2702 | QRFHNIRGRW | 1441 | 500.00 | 10 |
| 868 | HPV | 16 | 2 | 2 | B*2705 | QRFHNIRGRW | 1441 | 1000.00 | 10 |
| 869 | HPV | 16 | 2 | 2 | B*2705 | IRGRWTGRCM | 1442 | 180.00 | 10 |
| 870 | HPV | 16 | 2 | 2 | B*2702 | GRWTGRCMSC | 1443 | 100.00 | 10 |
| 871 | HPV | 16 | 2 | 2 | B*2705 | GRWTGRCMSC | 1443 | 1000.00 | 10 |
| 872 | HPV | 16 | 2 | 2 | A68.1 | WTGRCMSCCR | 1444 | 100.00 | 10 |
| 873 | HPV | 16 | 2 | 5 | B*2705 | VQLDKQNR | 1522 | 100.00 | 8 |
| 874 | HPV | 16 | 2 | 5 | B*2705 | KQNRTEPI | 1445 | 180.00 | 8 |
| 875 | HPV | 16 | 2 | 5 | B*2705 | NRTEPITI | 1446 | 600.00 | 8 |
| 876 | HPV | 16 | 2 | 5 | A68.1 | MVQLDKQNR | 1523 | 200.00 | 9 |
| 877 | HPV | 16 | 2 | 5 | B*2705 | NRTEPITIL | 1447 | 2000.00 | 9 |
| 878 | HPV | 16 | 2 | 5 | B*2705 | KQNRTEPITI | 1448 | 180.00 | 10 |
| 879 | HPV | 16 | 2 | 6 | B*2705 | VRDVMDGF | 1449 | 1000.00 | 8 |
| 880 | HPV | 16 | 2 | 6 | B*2705 | VRDVMDGFM | 1451 | 600.00 | 9 |
| 881 | HPV | 16 | 2 | 6 | B*2702 | KRVRDVMDGF | 1454 | 600.00 | 10 |
| 882 | HPV | 16 | 2 | 6 | B*2705 | KRVRDVMDGF | 1454 | 3000.00 | 10 |
| 883 | HPV | 16 | 2 | 7 | B*2705 | TRTKMTVI | 1524 | 600.00 | 8 |
| 884 | HPV | 16 | 2 | 7 | B*2705 | KMTVIQVK | 1525 | 150.00 | 8 |
| 885 | HPV | 16 | 2 | 7 | Cw*0401 | LYQMTRTKM | 1526 | 132.00 | 9 |
| 886 | HPV | 16 | 2 | 7 | A*0201 | YQMTRTKMTV | 1527 | 120.02 | 10 |
| 887 | HPV | 16 | 2 | 7 | B*2705 | TRTKMTVIQV | 1528 | 600.00 | 10 |
| 888 | HPV | 16 | 2 | 8 | B*2705 | MRCLLHRK | 1529 | 600.00 | 8 |
| 889 | HPV | 16 | 2 | 8 | B*2705 | HRKQNNIEM | 1455 | 600.00 | 9 |
| 890 | HPV | 16 | 2 | 8 | B*2705 | KQNNIEMQY | 1456 | 300.00 | 9 |
| 891 | HPV | 16 | 2 | 8 | B*2705 | KQNNIEMQYR | 1457 | 300.00 | 10 |
| 892 | HPV | 16 | 2 | 10 | B*5102 | NGCVTISKI | 1530 | 193.60 | 9 |
| 893 | HPV | 16 | 2 | 11 | A68.1 | CVSNVYDDR | 1531 | 200.00 | 9 |
| 894 | HPV | 16 | 2 | 11 | A68.1 | NVYDDRASK | 1532 | 120.00 | 9 |
| 895 | HPV | 16 | 2 | 13 | B*5102 | MPSIINYI | 1533 | 440.00 | 8 |
| 896 | HPV | 16 | 2 | 15 | B*3901 | GHYKTLAL | 1534 | 270.00 | 8 |
| 897 | HPV | 16 | 2 | 16 | B*2705 | IQWKCSLM | 1535 | 300.00 | 8 |
| 898 | HPV | 16 | 2 | 16 | B*5201 | ETYAIQCII | 1536 | 120.00 | 9 |
| 899 | HPV | 16 | 2 | 16 | B*2705 | IQTGHIYIF | 1537 | 100.00 | 9 |
| 900 | HPV | 16 | 2 | 16 | B62 | IQTGHIYIF | 1537 | 124.80 | 9 |
| 901 | HPV | 16 | 2 | 16 | B*2705 | IQWKCSLMET | 1538 | 100.00 | 10 |
| 902 | HPV | 16 | 2 | 17 | A24 | EYEHILCSL | 1539 | 420.00 | 9 |

TABLE 7-continued

| No | Species | Strain type | Frame | ORF | HLA | Seq | Seq ID No. | Score | Length |
|---|---|---|---|---|---|---|---|---|---|
| 903 | HPV | 16 | 2 | 17 | Cw*0401 | EYEHILCSL | 1539 | 440.00 | 9 |
| 904 | HPV | 16 | 2 | 17 | A3 | KMMQKNIVK | 1540 | 180.00 | 9 |
| 905 | HPV | 16 | 2 | 17 | B*2705 | KMMQKNIVK | 1540 | 150.00 | 9 |
| 906 | HPV | 16 | 2 | 17 | Cw*0401 | MFMKEYEHIL | 1541 | 200.00 | 10 |
| 907 | HPV | 16 | 2 | 17 | B*2705 | KEYEHILCSL | 1542 | 450.00 | 10 |
| 908 | HPV | 16 | 2 | 17 | B60 | KEYEHILCSL | 1542 | 176.00 | 10 |
| 909 | HPV | 16 | 2 | 17 | A*0201 | KMMQKNIVKI | 1543 | 224.42 | 10 |
| 910 | HPV | 16 | 2 | 17 | B*2705 | MQKNIVKIKY | 1544 | 100.00 | 10 |
| 911 | HPV | 16 | 2 | 17 | B62 | MQKNIVKIKY | 1544 | 288.00 | 10 |
| 912 | HPV | 16 | 2 | 18 | B*2705 | TNFCLKLK | 1545 | 100.00 | 8 |
| 913 | HPV | 16 | 2 | 18 | B*2705 | YQKLLQCL | 1546 | 200.00 | 8 |
| 914 | HPV | 16 | 2 | 18 | B8 | CLKLKYQKL | 1547 | 160.00 | 9 |
| 915 | HPV | 16 | 2 | 18 | A24 | KYQKLLQCL | 1548 | 864.00 | 9 |
| 916 | HPV | 16 | 2 | 18 | Cw*0401 | KYQKLLQCL | 1548 | 400.00 | 9 |
| 917 | HPV | 16 | 2 | 18 | B*2705 | YQKLLQCLL | 1549 | 200.00 | 9 |
| 918 | HPV | 16 | 2 | 18 | A*0201 | KLLQCLLDL | 1550 | 636.28 | 9 |
| 919 | HPV | 16 | 2 | 18 | A*0205 | KLLQCLLDL | 1550 | 126.00 | 9 |
| 920 | HPV | 16 | 2 | 18 | B*2705 | LQCLLDLCL | 1551 | 200.00 | 9 |
| 921 | HPV | 16 | 2 | 18 | A68.1 | NVTNFCLKLK | 1552 | 120.00 | 10 |
| 922 | HPV | 16 | 2 | 18 | Cw*0301 | FCLKLKYQKL | 1553 | 120.00 | 10 |
| 923 | HPV | 16 | 2 | 18 | Cw*0401 | KYQKLLQCLL | 1554 | 200.00 | 10 |
| 924 | HPV | 16 | 2 | 18 | A24 | KYQKLLQCLL | 1554 | 720.00 | 10 |
| 925 | HPV | 16 | 2 | 18 | B*2705 | LQCLLDLCLY | 1555 | 100.00 | 10 |
| 926 | HPV | 16 | 2 | 18 | A3 | CLLDLCLYDK | 1556 | 135.00 | 10 |
| 927 | HPV | 16 | 2 | 19 | B*2705 | MRHKRSAK | 1557 | 2000.00 | 8 |
| 928 | HPV | 16 | 2 | 19 | B*2705 | KRSAKRTK | 1558 | 6000.00 | 8 |
| 929 | HPV | 16 | 2 | 19 | B*2705 | KRTKRASA | 1559 | 600.00 | 8 |
| 930 | HPV | 16 | 2 | 19 | B*2705 | KRASATQL | 1560 | 6000.00 | 8 |
| 931 | HPV | 16 | 2 | 19 | B*2705 | TQLYKTCK | 1561 | 200.00 | 8 |
| 932 | HPV | 16 | 2 | 19 | B*2705 | LQYGSMGV | 1562 | 300.00 | 8 |
| 933 | HPV | 16 | 2 | 19 | B*2705 | GRTGYIPL | 1563 | 2000.00 | 8 |
| 934 | HPV | 16 | 2 | 19 | B*5102 | GPSDPSIV | 1564 | 200.00 | 8 |
| 935 | HPV | 16 | 2 | 19 | B*5102 | DPSIVSLV | 1565 | 220.00 | 8 |
| 936 | HPV | 16 | 2 | 19 | B*5102 | DAGAPTSV | 1566 | 110.00 | 8 |
| 937 | HPV | 16 | 2 | 19 | B*5102 | APTSVPSI | 1567 | 440.00 | 8 |
| 938 | HPV | 16 | 2 | 19 | B*5102 | VPSIPPDV | 1568 | 200.00 | 8 |
| 939 | HPV | 16 | 2 | 19 | B*5102 | IPMDTFIV | 1569 | 220.00 | 8 |
| 940 | HPV | 16 | 2 | 19 | B*5102 | RPVARLGL | 1570 | 300.00 | 8 |
| 941 | HPV | 16 | 2 | 19 | B*2705 | ARLGLYSR | 1571 | 1000.00 | 8 |
| 942 | HPV | 16 | 2 | 19 | B*2705 | SRTTQQVK | 1572 | 2000.00 | 8 |
| 943 | HPV | 16 | 2 | 19 | B*5102 | DPDFLDIV | 1573 | 100.00 | 8 |
| 944 | HPV | 16 | 2 | 19 | B*5102 | VALHRPAL | 1574 | 165.00 | 8 |
| 945 | HPV | 16 | 2 | 19 | B*2705 | HRPALTSR | 1575 | 1000.00 | 8 |
| 946 | HPV | 16 | 2 | 19 | B*2705 | SRRTGIRY | 1576 | 300.00 | 8 |
| 947 | HPV | 16 | 2 | 19 | B*2705 | RRTGIRYS | 1577 | 600.00 | 8 |
| 948 | HPV | 16 | 2 | 19 | B*5102 | TGIRYSRI | 1578 | 290.40 | 8 |
| 949 | HPV | 16 | 2 | 19 | B*2705 | IRYSRIGN | 1579 | 1000.00 | 8 |
| 950 | HPV | 16 | 2 | 19 | B*2705 | SRIGNKQT | 1580 | 200.00 | 8 |
| 951 | HPV | 16 | 2 | 19 | B*5102 | DPAEEIEL | 1581 | 133.10 | 8 |
| 952 | HPV | 16 | 2 | 19 | B*5102 | HAASPTSI | 1582 | 220.00 | 8 |
| 953 | HPV | 16 | 2 | 19 | B*5102 | GAYNIPLV | 1583 | 550.00 | 8 |
| 954 | HPV | 16 | 2 | 19 | B*5102 | GPDIPINI | 1584 | 220.00 | 8 |
| 955 | HPV | 16 | 2 | 19 | B*5102 | QAPSLIPI | 1585 | 220.00 | 8 |
| 956 | HPV | 16 | 2 | 19 | B*5102 | APSLIPIV | 1586 | 220.00 | 8 |
| 957 | HPV | 16 | 2 | 19 | B*2705 | LRKRRKRL | 1587 | 600.00 | 8 |
| 958 | HPV | 16 | 2 | 19 | B*2705 | KRRKRLPY | 1588 | 3000.00 | 8 |
| 959 | HPV | 16 | 2 | 19 | B*2705 | RRKRLPYF | 1589 | 3000.00 | 8 |
| 960 | HPV | 16 | 2 | 19 | B*2705 | KRLPYFFS | 1590 | 600.00 | 8 |
| 961 | HPV | 16 | 2 | 19 | B*5102 | LPYFFSDV | 1591 | 1000.00 | 8 |
| 962 | HPV | 16 | 2 | 19 | B*2705 | MRHKRSAKR | 1592 | 1000.00 | 9 |
| 963 | HPV | 16 | 2 | 19 | B*2705 | KRSAKRTKR | 1593 | 3000.00 | 9 |
| 964 | HPV | 16 | 2 | 19 | B*2705 | KRTKRASAT | 1594 | 600.00 | 9 |
| 965 | HPV | 16 | 2 | 19 | B*2702 | KRASATQLY | 1595 | 600.00 | 9 |
| 966 | HPV | 16 | 2 | 19 | B*2705 | KRASATQLY | 1595 | 3000.00 | 9 |
| 967 | HPV | 16 | 2 | 19 | B*5103 | QAGTCPPDI | 1596 | 110.00 | 9 |
| 968 | HPV | 16 | 2 | 19 | B*5102 | QAGTCPPDI | 1596 | 220.00 | 9 |
| 969 | HPV | 16 | 2 | 19 | B*5102 | CPPDIIPKV | 1597 | 440.00 | 9 |
| 970 | HPV | 16 | 2 | 19 | B*5102 | IPKVEGKTI | 1598 | 242.00 | 9 |
| 971 | HPV | 16 | 2 | 19 | A*0201 | ILQYGSMGV | 1599 | 118.24 | 9 |
| 972 | HPV | 16 | 2 | 19 | B*2702 | LQYGSMGVF | 1600 | 100.00 | 9 |
| 973 | HPV | 16 | 2 | 19 | B*2705 | LQYGSMGVF | 1600 | 500.00 | 9 |
| 974 | HPV | 16 | 2 | 19 | B*5201 | LQYGSMGVF | 1600 | 375.00 | 9 |
| 975 | HPV | 16 | 2 | 19 | B62 | LQYGSMGVF | 1600 | 105.60 | 9 |
| 976 | HPV | 16 | 2 | 19 | A24 | QYGSMGVFF | 1601 | 100.00 | 9 |
| 977 | HPV | 16 | 2 | 19 | Cw*0401 | QYGSMGVFF | 1601 | 110.00 | 9 |
| 978 | HPV | 16 | 2 | 19 | A68.1 | GTGSGTGGR | 1602 | 100.00 | 9 |

TABLE 7-continued

| No | Species | Strain type | Frame | ORF | HLA | Seq | Seq ID No. | Score | Length |
|---|---|---|---|---|---|---|---|---|---|
| 979 | HPV | 16 | 2 | 19 | B*2705 | TRPPTATDT | 1603 | 200.00 | 9 |
| 980 | HPV | 16 | 2 | 19 | B*5102 | RPPTATDTL | 1604 | 133.10 | 9 |
| 981 | HPV | 16 | 2 | 19 | B*5103 | TATDTLAPV | 1605 | 110.00 | 9 |
| 982 | HPV | 16 | 2 | 19 | B*5102 | TATDTLAPV | 1605 | 110.00 | 9 |
| 983 | HPV | 16 | 2 | 19 | B*5102 | APVRPPLTV | 1606 | 726.00 | 9 |
| 984 | HPV | 16 | 2 | 19 | B*5102 | RPPLTVDPV | 1607 | 242.00 | 9 |
| 985 | HPV | 16 | 2 | 19 | B*5201 | VGPSDPSIV | 1608 | 150.00 | 9 |
| 986 | HPV | 16 | 2 | 19 | A*0201 | SLVEETSFI | 1609 | 235.26 | 9 |
| 987 | HPV | 16 | 2 | 19 | B*5103 | GAPTSVPSI | 1610 | 110.00 | 9 |
| 988 | HPV | 16 | 2 | 19 | B*5102 | GAPTSVPSI | 1610 | 220.00 | 9 |
| 989 | HPV | 16 | 2 | 19 | A*0201 | AILDINNTV | 1611 | 145.08 | 9 |
| 990 | HPV | 16 | 2 | 19 | B*5102 | NPTFTDPSV | 1612 | 220.00 | 9 |
| 991 | HPV | 16 | 2 | 19 | B60 | AETGGHFTL | 1613 | 160.00 | 9 |
| 992 | HPV | 16 | 2 | 19 | B*5102 | TPIPGSRPV | 1614 | 726.00 | 9 |
| 993 | HPV | 16 | 2 | 19 | B14 | SRPVARLGL | 1615 | 200.00 | 9 |
| 994 | HPV | 16 | 2 | 19 | B*2705 | SRPVARLGL | 1615 | 2000.00 | 9 |
| 995 | HPV | 16 | 2 | 19 | B*2705 | ARLGLYSRT | 1616 | 200.00 | 9 |
| 996 | HPV | 16 | 2 | 19 | B*2705 | SRTTQQVKV | 1617 | 600.00 | 9 |
| 997 | HPV | 16 | 2 | 19 | Cw*0401 | AFVTTPTKL | 1618 | 264.00 | 9 |
| 998 | HPV | 16 | 2 | 19 | B*5102 | NPAYEGIDV | 1619 | 200.00 | 9 |
| 999 | HPV | 16 | 2 | 19 | B*5102 | APDPDFLDI | 1620 | 200.00 | 9 |
| 1000 | HPV | 16 | 2 | 19 | B*2705 | HRPALTSRR | 1621 | 1000.00 | 9 |
| 1001 | HPV | 16 | 2 | 19 | B*2705 | RRTGIRYSR | 1622 | 3000.00 | 9 |
| 1002 | HPV | 16 | 2 | 19 | B*2705 | IRYSRIGNK | 1623 | 10000.00 | 9 |
| 1003 | HPV | 16 | 2 | 19 | B*2705 | SRIGNKQTL | 1624 | 2000.00 | 9 |
| 1004 | HPV | 16 | 2 | 19 | B*2705 | LRTRSGKSI | 1625 | 180.00 | 9 |
| 1005 | HPV | 16 | 2 | 19 | B*2705 | TRSGKSIGA | 1626 | 200.00 | 9 |
| 1006 | HPV | 16 | 2 | 19 | Cw*0301 | AKVHYYYDL | 1627 | 100.00 | 9 |
| 1007 | HPV | 16 | 2 | 19 | B*2705 | LQTITPSTY | 1628 | 100.00 | 9 |
| 1008 | HPV | 16 | 2 | 19 | B*5102 | SPTSINNGL | 1629 | 110.00 | 9 |
| 1009 | HPV | 16 | 2 | 19 | A24 | LYDIYADDF | 1630 | 100.00 | 9 |
| 1010 | HPV | 16 | 2 | 19 | Cw*0401 | LYDIYADDF | 1630 | 150.00 | 9 |
| 1011 | HPV | 16 | 2 | 19 | B*3701 | YDIYADDFI | 1631 | 200.00 | 9 |
| 1012 | HPV | 16 | 2 | 19 | B7 | VPSVPSTSL | 1632 | 120.00 | 9 |
| 1013 | HPV | 16 | 2 | 19 | B*5102 | VPSVPSTSL | 1632 | 100.00 | 9 |
| 1014 | HPV | 16 | 2 | 19 | B*5102 | IPFGGAYNI | 1633 | 2420.00 | 9 |
| 1015 | HPV | 16 | 2 | 19 | B*5102 | IPLVSGPDI | 1634 | 1200.00 | 9 |
| 1016 | HPV | 16 | 2 | 19 | B*5103 | QAPSLIPIV | 1635 | 110.00 | 9 |
| 1017 | HPV | 16 | 2 | 19 | B*5102 | QAPSLIPIV | 1635 | 110.00 | 9 |
| 1018 | HPV | 16 | 2 | 19 | B*5102 | VPGSPQYTI | 1636 | 484.00 | 9 |
| 1019 | HPV | 16 | 2 | 19 | Cw*0401 | FYLHPSYYM | 1637 | 100.00 | 9 |
| 1020 | HPV | 16 | 2 | 19 | A*0201 | YLHPSYYML | 1638 | 147.40 | 9 |
| 1021 | HPV | 16 | 2 | 19 | B8 | MLRKRRKRL | 1639 | 160.00 | 9 |
| 1022 | HPV | 16 | 2 | 19 | B*2702 | KRRKRLPYF | 1640 | 600.00 | 9 |
| 1023 | HPV | 16 | 2 | 19 | B*2705 | KRRKRLPYF | 1640 | 3000.00 | 9 |
| 1024 | HPV | 16 | 2 | 19 | B*2702 | RRKRLPYFF | 1641 | 600.00 | 9 |
| 1025 | HPV | 16 | 2 | 19 | B*2705 | RRKRLPYFF | 1641 | 3000.00 | 9 |
| 1026 | HPV | 16 | 2 | 19 | A*0201 | RLPYFFSDV | 1642 | 502.17 | 9 |
| 1027 | HPV | 16 | 2 | 19 | B*2705 | KRSAKRTKRA | 1643 | 180.00 | 10 |
| 1028 | HPV | 16 | 2 | 19 | B*2705 | KRASATQLYK | 1644 | 6000.00 | 10 |
| 1029 | HPV | 16 | 2 | 19 | B*2705 | KQAGTCPPDI | 1645 | 180.00 | 10 |
| 1030 | HPV | 16 | 2 | 19 | B*5102 | QAGTCPPDII | 1646 | 220.00 | 10 |
| 1031 | HPV | 16 | 2 | 19 | B*5103 | QAGTCPPDII | 1646 | 110.00 | 10 |
| 1032 | HPV | 16 | 2 | 19 | B*2702 | LQYGSMGVFF | 1647 | 100.00 | 10 |
| 1033 | HPV | 16 | 2 | 19 | B*2705 | LQYGSMGVFF | 1647 | 500.00 | 10 |
| 1034 | HPV | 16 | 2 | 19 | B*5201 | LQYGSMGVFF | 1647 | 168.75 | 10 |
| 1035 | HPV | 16 | 2 | 19 | B62 | LQYGSMGVFF | 1647 | 115.20 | 10 |
| 1036 | HPV | 16 | 2 | 19 | Cw*0301 | GSMGVFFGGL | 1648 | 100.00 | 10 |
| 1037 | HPV | 16 | 2 | 19 | B*5102 | MGVFFGGLGI | 1649 | 264.00 | 10 |
| 1038 | HPV | 16 | 2 | 19 | B*5102 | SGTGGRTGYI | 1650 | 106.48 | 10 |
| 1039 | HPV | 16 | 2 | 19 | B*2705 | GRTGYIPLGT | 1651 | 200.00 | 10 |
| 1040 | HPV | 16 | 2 | 19 | A68.1 | RTGYIPLGTR | 1652 | 100.00 | 10 |
| 1041 | HPV | 16 | 2 | 19 | B*2705 | TRPPTATDTL | 1653 | 2000.00 | 10 |
| 1042 | HPV | 16 | 2 | 19 | B*5102 | LAPVRPPLTV | 1654 | 110.00 | 10 |
| 1043 | HPV | 16 | 2 | 19 | B*5103 | LAPVRPPLTV | 1654 | 110.00 | 10 |
| 1044 | HPV | 16 | 2 | 19 | B*2705 | VRPPLTVDPV | 1655 | 600.00 | 10 |
| 1045 | HPV | 16 | 2 | 19 | B*5102 | DPVGPSDPSI | 1656 | 1320.00 | 10 |
| 1046 | HPV | 16 | 2 | 19 | B*5102 | GPSDPSIVSL | 1657 | 110.00 | 10 |
| 1047 | HPV | 16 | 2 | 19 | Cw*0401 | GPSDPSIVSL | 1657 | 211.20 | 10 |
| 1048 | HPV | 16 | 2 | 19 | B*5102 | IPPDVSGFSI | 1658 | 400.00 | 10 |
| 1049 | HPV | 16 | 2 | 19 | B*5102 | NPTFTDPSVL | 1659 | 100.00 | 10 |
| 1050 | HPV | 16 | 2 | 19 | Cw*0401 | NYEEIPMDTF | 1660 | 144.00 | 10 |
| 1051 | HPV | 16 | 2 | 19 | A24 | NYEEIPMDTF | 1660 | 180.00 | 10 |
| 1052 | HPV | 16 | 2 | 19 | B7 | IPGSRPVARL | 1661 | 120.00 | 10 |
| 1053 | HPV | 16 | 2 | 19 | B*5102 | IPGSRPVARL | 1661 | 200.00 | 10 |
| 1054 | HPV | 16 | 2 | 19 | Cw*0401 | IPGSRPVARL | 1661 | 192.00 | 10 |

TABLE 7-continued

| No | Species | Strain type | Frame | ORF | HLA | Seq | Seq ID No. | Score | Length |
|---|---|---|---|---|---|---|---|---|---|
| 1055 | HPV | 16 | 2 | 19 | B*2702 | SRPVARLGLY | 1662 | 200.00 | 10 |
| 1056 | HPV | 16 | 2 | 19 | B*2705 | SRPVARLGLY | 1662 | 1000.00 | 10 |
| 1057 | HPV | 16 | 2 | 19 | A*0201 | GLYSRTTQQV | 1663 | 222.57 | 10 |
| 1058 | HPV | 16 | 2 | 19 | B*2705 | SRTTQQVKVV | 1664 | 180.00 | 10 |
| 1059 | HPV | 16 | 2 | 19 | B*2705 | QQVKVVDPAF | 1665 | 100.00 | 10 |
| 1060 | HPV | 16 | 2 | 19 | B60 | YEGIDVDNTL | 1666 | 176.00 | 10 |
| 1061 | HPV | 16 | 2 | 19 | B*5102 | IAPDPDFLDI | 1667 | 200.00 | 10 |
| 1062 | HPV | 16 | 2 | 19 | B*5103 | IAPDPDFLDI | 1667 | 100.00 | 10 |
| 1063 | HPV | 16 | 2 | 19 | B*5102 | APDPDFLDIV | 1668 | 100.00 | 10 |
| 1064 | HPV | 16 | 2 | 19 | B*5201 | APDPDFLDIV | 1668 | 198.00 | 10 |
| 1065 | HPV | 16 | 2 | 19 | Cw*0401 | DPDFLDIVAL | 1669 | 240.00 | 10 |
| 1066 | HPV | 16 | 2 | 19 | B14 | DIVALHRPAL | 1670 | 135.00 | 10 |
| 1067 | HPV | 16 | 2 | 19 | B*2705 | SRRTGIRYSR | 1671 | 1000.00 | 10 |
| 1068 | HPV | 16 | 2 | 19 | B*2702 | RRTGIRYSRI | 1672 | 180.00 | 10 |
| 1069 | HPV | 16 | 2 | 19 | B*2705 | RRTGIRYSRI | 1672 | 1800.00 | 10 |
| 1070 | HPV | 16 | 2 | 19 | B*2705 | IRYSRIGNKQ | 1673 | 100.00 | 10 |
| 1071 | HPV | 16 | 2 | 19 | B*2705 | SRIGNKQTLR | 1674 | 1000.00 | 10 |
| 1072 | HPV | 16 | 2 | 19 | B*2705 | KQTLRTRSGK | 1675 | 600.00 | 10 |
| 1073 | HPV | 16 | 2 | 19 | B*2705 | TRSGKSIGAK | 1676 | 2000.00 | 10 |
| 1074 | HPV | 16 | 2 | 19 | A*0201 | TRSGKSIGAK | 1676 | 180.37 | 10 |
| 1075 | HPV | 16 | 2 | 19 | B*5102 | VPSTSLSGYI | 1677 | 484.00 | 10 |
| 1076 | HPV | 16 | 2 | 19 | B*5102 | SGYIPANTTI | 1678 | 484.00 | 10 |
| 1077 | HPV | 16 | 2 | 19 | B*5103 | SGYIPANTTI | 1678 | 132.00 | 10 |
| 1078 | HPV | 16 | 2 | 19 | B*5201 | DQAPSLIPIV | 1679 | 240.00 | 10 |
| 1079 | HPV | 16 | 2 | 19 | B*5102 | VPGSPQYTII | 1680 | 440.00 | 10 |
| 1080 | HPV | 16 | 2 | 19 | A*0201 | IIADAGDFYL | 1681 | 653.09 | 10 |
| 1081 | HPV | 16 | 2 | 19 | Cw*0401 | DFYLHPSYYM | 1682 | 100.00 | 10 |
| 1082 | HPV | 16 | 2 | 19 | Cw*0301 | FYLHPSYYML | 1683 | 100.00 | 10 |
| 1083 | HPV | 16 | 2 | 19 | Cw*0401 | FYLHPSYYML | 1683 | 200.00 | 10 |
| 1084 | HPV | 16 | 2 | 19 | A24 | FYLHPSYYML | 1683 | 300.00 | 10 |
| 1085 | HPV | 16 | 2 | 19 | A*0201 | YMLRKRRKRL | 1684 | 262.59 | 10 |
| 1086 | HPV | 16 | 2 | 19 | B14 | YMLRKRRKRL | 1684 | 250.00 | 10 |
| 1087 | HPV | 16 | 2 | 19 | B*2702 | LRKRRKRLPY | 1685 | 200.00 | 10 |
| 1088 | HPV | 16 | 2 | 19 | B*2705 | LRKRRKRLPY | 1685 | 1000.00 | 10 |
| 1089 | HPV | 16 | 2 | 19 | B*2702 | KRRKRLPYFF | 1686 | 600.00 | 10 |
| 1090 | HPV | 16 | 2 | 19 | B*2705 | KRRKRLPYFF | 1686 | 3000.00 | 10 |
| 1091 | HPV | 16 | 2 | 19 | B*2705 | RRKRLPYFFS | 1687 | 600.00 | 10 |
| 1092 | HPV | 16 | 2 | 19 | B*2705 | KRLPYFFSDV | 1688 | 1800.00 | 10 |
| 1093 | HPV | 16 | 2 | 19 | B*5102 | LPYFFSDVSL | 1689 | 500.00 | 10 |
| 1094 | HPV | 16 | 2 | 20 | B*5102 | YGLQTNTI | 1690 | 638.88 | 8 |
| 1095 | HPV | 16 | 2 | 20 | B*2705 | LQTNTIVF | 1691 | 100.00 | 8 |
| 1096 | HPV | 16 | 2 | 20 | B*2705 | YRGTLGQR | 1692 | 1000.00 | 8 |
| 1097 | HPV | 16 | 2 | 20 | B*5102 | RGTLGQRI | 1693 | 117.13 | 8 |
| 1098 | HPV | 16 | 2 | 20 | B*2705 | QRIPMYQC | 1503 | 200.00 | 8 |
| 1099 | HPV | 16 | 2 | 20 | B*2705 | YQCCSKSR | 1504 | 100.00 | 8 |
| 1100 | HPV | 16 | 2 | 20 | B*5201 | YGLQTNTIV | 1694 | 165.00 | 9 |
| 1101 | HPV | 16 | 2 | 20 | B*5102 | YGLQTNTIV | 1694 | 319.44 | 9 |
| 1102 | HPV | 16 | 2 | 20 | B*5801 | QTNTIVFNW | 1695 | 158.40 | 9 |
| 1103 | HPV | 16 | 2 | 20 | B*2705 | LQTTYRGTL | 1696 | 200.00 | 9 |
| 1104 | HPV | 16 | 2 | 20 | B*2705 | YRGTLGQRI | 1697 | 600.00 | 9 |
| 1105 | HPV | 16 | 2 | 20 | B*2705 | QRIPMYQCC | 1505 | 200.00 | 9 |
| 1106 | HPV | 16 | 2 | 20 | B*2705 | QRIPMYQCCS | 1506 | 200.00 | 10 |
| 1107 | HPV | 16 | 2 | 22 | B*2705 | MRAKSLFS | 1510 | 200.00 | 8 |
| 1108 | HPV | 16 | 2 | 23 | B*2705 | MRQRLTYR | 1698 | 1000.00 | 8 |
| 1109 | HPV | 16 | 2 | 23 | B*2705 | MRQRLTYRC | 1699 | 200.00 | 9 |
| 1110 | HPV | 16 | 3 | 1 | B*2705 | LQCFRTHR | 1700 | 100.00 | 8 |
| 1111 | HPV | 16 | 3 | 1 | B*2705 | HRSDPESY | 1701 | 1000.00 | 8 |
| 1112 | HPV | 16 | 3 | 1 | B*5102 | YAQSCKQL | 1702 | 110.00 | 8 |
| 1113 | HPV | 16 | 3 | 1 | B*2705 | AQSCKQLY | 1703 | 100.00 | 8 |
| 1114 | HPV | 16 | 3 | 1 | B*2705 | HRSDPESYH | 1704 | 200.00 | 9 |
| 1115 | HPV | 16 | 3 | 1 | A24 | SYAQSCKQL | 1705 | 200.00 | 9 |
| 1116 | HPV | 16 | 3 | 1 | Cw*0401 | SYAQSCKQL | 1705 | 200.00 | 9 |
| 1117 | HPV | 16 | 3 | 1 | B*2705 | FRTHRSDPES | 1706 | 200.00 | 10 |
| 1118 | HPV | 16 | 3 | 1 | B*2705 | HRSDPESYHS | 1707 | 200.00 | 10 |
| 1119 | HPV | 16 | 3 | 1 | A1 | RSDPESYHSY | 1708 | 375.00 | 10 |
| 1120 | HPV | 16 | 3 | 4 | B*2705 | LRSTAAAL | 1709 | 2000.00 | 8 |
| 1121 | HPV | 16 | 3 | 4 | B*2705 | QRQTVLQH | 1710 | 200.00 | 8 |
| 1122 | HPV | 16 | 3 | 4 | B*2705 | SQMVQWAY | 1711 | 100.00 | 8 |
| 1123 | HPV | 16 | 3 | 4 | B*5102 | WAYDNDIV | 1712 | 550.00 | 8 |
| 1124 | HPV | 16 | 3 | 4 | B*5102 | IAYKYAQL | 1713 | 302.50 | 8 |
| 1125 | HPV | 16 | 3 | 4 | B*2705 | KRAEKKQM | 1714 | 1800.00 | 8 |
| 1126 | HPV | 16 | 3 | 4 | B*2705 | KQIVMFLR | 1715 | 300.00 | 8 |
| 1127 | HPV | 16 | 3 | 4 | B*2705 | LRYQGVEF | 1716 | 5000.00 | 8 |
| 1128 | HPV | 16 | 3 | 4 | B*2705 | KRFLQGIP | 1717 | 300.00 | 8 |
| 1129 | HPV | 16 | 3 | 4 | B*2705 | LQGSVICF | 1718 | 100.00 | 8 |
| 1130 | HPV | 16 | 3 | 4 | B*3901 | SHFWLQPL | 1719 | 180.00 | 8 |

TABLE 7-continued

| No | Species | Strain type | Frame | ORF | HLA | Seq | Seq ID No. | Score | Length |
|---|---|---|---|---|---|---|---|---|---|
| 1131 | HPV | 16 | 3 | 4 | B*2705 | LQPLADAK | 1720 | 200.00 | 8 |
| 1132 | HPV | 16 | 3 | 4 | B*5102 | QPLADAKI | 1721 | 1320.00 | 8 |
| 1133 | HPV | 16 | 3 | 4 | B*2705 | WNYIDDNL | 1722 | 100.00 | 8 |
| 1134 | HPV | 16 | 3 | 4 | B*2705 | LRNALDGN | 1723 | 200.00 | 8 |
| 1135 | HPV | 16 | 3 | 4 | B*5102 | NALDGNLV | 1724 | 363.00 | 8 |
| 1136 | HPV | 16 | 3 | 4 | B*2705 | HRPLVQLK | 1725 | 2000.00 | 8 |
| 1137 | HPV | 16 | 3 | 4 | B*2705 | VQLKCPPL | 1726 | 200.00 | 8 |
| 1138 | HPV | 16 | 3 | 4 | B*2705 | SRWPYLHN | 1727 | 1000.00 | 8 |
| 1139 | HPV | 16 | 3 | 4 | B*5102 | WPYLHNRL | 1728 | 665.50 | 8 |
| 1140 | HPV | 16 | 3 | 4 | B*2705 | NRLVVFTF | 1729 | 1000.00 | 8 |
| 1141 | HPV | 16 | 3 | 4 | B*2705 | SRTWSRLS | 1730 | 200.00 | 8 |
| 1142 | HPV | 16 | 3 | 4 | B*2705 | RTWSRLSL | 1731 | 150.00 | 8 |
| 1143 | HPV | 16 | 3 | 4 | B*2702 | LRSTAAALY | 1732 | 200.00 | 9 |
| 1144 | HPV | 16 | 3 | 4 | B*2705 | LRSTAAALY | 1732 | 1000.00 | 9 |
| 1145 | HPV | 16 | 3 | 4 | B*5801 | RSTAAALYW | 1733 | 264.00 | 9 |
| 1146 | HPV | 16 | 3 | 4 | B*5102 | TGISNISEV | 1734 | 145.20 | 9 |
| 1147 | HPV | 16 | 3 | 4 | B*2705 | QRQTVLQHS | 1735 | 200.00 | 9 |
| 1148 | HPV | 16 | 3 | 4 | B*2705 | RQTVLQHSF | 1736 | 300.00 | 9 |
| 1149 | HPV | 16 | 3 | 4 | B62 | RQTVLQHSF | 1736 | 160.00 | 9 |
| 1150 | HPV | 16 | 3 | 4 | Cw*0401 | SFNDCTFEL | 1737 | 240.00 | 9 |
| 1151 | HPV | 16 | 3 | 4 | B*2705 | VQWAYDNDI | 1738 | 300.00 | 9 |
| 1152 | HPV | 16 | 3 | 4 | A1 | IVDDSEIAY | 1739 | 125.00 | 9 |
| 1153 | HPV | 16 | 3 | 4 | A68.1 | ATMCRHYKR | 1740 | 100.00 | 9 |
| 1154 | HPV | 16 | 3 | 4 | B*2705 | CRHYKRAEK | 1741 | 2000.00 | 9 |
| 1155 | HPV | 16 | 3 | 4 | B*2705 | KRAEKKQMS | 1742 | 600.00 | 9 |
| 1156 | HPV | 16 | 3 | 4 | B*2705 | KQMSMSQWI | 1743 | 180.00 | 9 |
| 1157 | HPV | 16 | 3 | 4 | A68.1 | RVDDGGDWK | 1744 | 120.00 | 9 |
| 1158 | HPV | 16 | 3 | 4 | B*2705 | KQIVMFLRY | 1745 | 300.00 | 9 |
| 1159 | HPV | 16 | 3 | 4 | A*0201 | VMFLRYQGV | 1746 | 473.94 | 9 |
| 1160 | HPV | 16 | 3 | 4 | B62 | FLRYQGVEF | 1747 | 144.00 | 9 |
| 1161 | HPV | 16 | 3 | 4 | B*2702 | LRYQGVEFM | 1748 | 100.00 | 9 |
| 1162 | HPV | 16 | 3 | 4 | B*2705 | LRYQGVEFM | 1748 | 3000.00 | 9 |
| 1163 | HPV | 16 | 3 | 4 | B*2705 | YQGVEFMSF | 1749 | 100.00 | 9 |
| 1164 | HPV | 16 | 3 | 4 | B62 | YQGVEFMSF | 1749 | 160.00 | 9 |
| 1165 | HPV | 16 | 3 | 4 | Cw*0401 | EFMSFLTAL | 1750 | 400.00 | 9 |
| 1166 | HPV | 16 | 3 | 4 | Cw*0401 | SFLTALKRF | 1751 | 220.00 | 9 |
| 1167 | HPV | 16 | 3 | 4 | A*0201 | FLTALKRFL | 1752 | 108.09 | 9 |
| 1168 | HPV | 16 | 3 | 4 | B*2705 | KRFLQGIPK | 1753 | 30000.00 | 9 |
| 1169 | HPV | 16 | 3 | 4 | B*5102 | QGIPKKNCI | 1754 | 240.00 | 9 |
| 1170 | HPV | 16 | 3 | 4 | A3 | SLFGMSLMK | 1755 | 300.00 | 9 |
| 1171 | HPV | 16 | 3 | 4 | B*2705 | SLFGMSLMK | 1755 | 150.00 | 9 |
| 1172 | HPV | 16 | 3 | 4 | Cw*0401 | LFGMSLMKF | 1756 | 220.00 | 9 |
| 1173 | HPV | 16 | 3 | 4 | A*0201 | LQGSVICFV | 1757 | 151.65 | 9 |
| 1174 | HPV | 16 | 3 | 4 | A68.1 | SVICFVNSK | 1758 | 240.00 | 9 |
| 1175 | HPV | 16 | 3 | 4 | Cw*0401 | CFVNSKSHF | 1759 | 110.00 | 9 |
| 1176 | HPV | 16 | 3 | 4 | B*2705 | LRNALDGNL | 1760 | 2000.00 | 9 |
| 1177 | HPV | 16 | 3 | 4 | A68.1 | LVSMDVKHR | 1761 | 300.00 | 9 |
| 1178 | HPV | 16 | 3 | 4 | B*2705 | HRPLVQLKC | 1762 | 200.00 | 9 |
| 1179 | HPV | 16 | 3 | 4 | B*2705 | VQLKCPPLL | 1763 | 200.00 | 9 |
| 1180 | HPV | 16 | 3 | 4 | B*5102 | PPLLITSNI | 1764 | 145.20 | 9 |
| 1181 | HPV | 16 | 3 | 4 | B*2705 | SRWPYLHNR | 1765 | 5000.00 | 9 |
| 1182 | HPV | 16 | 3 | 4 | B*5103 | WPYLHNRLV | 1766 | 132.00 | 9 |
| 1183 | HPV | 16 | 3 | 4 | B*5102 | WPYLHNRLV | 1766 | 1331.00 | 9 |
| 1184 | HPV | 16 | 3 | 4 | B*2705 | KNWKSFFSR | 1767 | 150.00 | 9 |
| 1185 | HPV | 16 | 3 | 4 | Cw*0401 | FFSRTWSRL | 1768 | 240.00 | 9 |
| 1186 | HPV | 16 | 3 | 4 | B14 | SRTWSRLSL | 1769 | 100.00 | 9 |
| 1187 | HPV | 16 | 3 | 4 | B*2705 | SRTWSRLSL | 1769 | 2000.00 | 9 |
| 1188 | HPV | 16 | 3 | 4 | B62 | KLRSTAAALY | 1770 | 120.00 | 10 |
| 1189 | HPV | 16 | 3 | 4 | B*2702 | LRSTAAALYW | 1771 | 100.00 | 10 |
| 1190 | HPV | 16 | 3 | 4 | B*2705 | LRSTAAALYW | 1771 | 200.00 | 10 |
| 1191 | HPV | 16 | 3 | 4 | B*5102 | AALYWKTGI | 1772 | 600.00 | 10 |
| 1192 | HPV | 16 | 3 | 4 | B*5103 | AALYWKTGI | 1772 | 132.00 | 10 |
| 1193 | HPV | 16 | 3 | 4 | B*5102 | TPEWIQRQTV | 1773 | 133.10 | 10 |
| 1194 | HPV | 16 | 3 | 4 | B*2702 | QRQTVLQHSF | 1774 | 200.00 | 10 |
| 1195 | HPV | 16 | 3 | 4 | B*2705 | QRQTVLQHSF | 1774 | 1000.00 | 10 |
| 1196 | HPV | 16 | 3 | 4 | B*2705 | LQHSFNDCTF | 1775 | 100.00 | 10 |
| 1197 | HPV | 16 | 3 | 4 | B*2705 | VQWAYDNDIV | 1776 | 300.00 | 10 |
| 1198 | HPV | 16 | 3 | 4 | B*5201 | VQWAYDNDIV | 1776 | 990.00 | 10 |
| 1199 | HPV | 16 | 3 | 4 | A68.1 | IVDDSEIAYK | 1777 | 120.00 | 10 |
| 1200 | HPV | 16 | 3 | 4 | B60 | SEIAYKYAQL | 1778 | 352.00 | 10 |
| 1201 | HPV | 16 | 3 | 4 | Cw*0301 | SEIAYKYAQL | 1778 | 100.00 | 10 |
| 1202 | HPV | 16 | 3 | 4 | A68.1 | IVKDCATMCR | 1779 | 200.00 | 10 |
| 1203 | HPV | 16 | 3 | 4 | B*2705 | CRHYKRAEKK | 1780 | 2000.00 | 10 |
| 1204 | HPV | 16 | 3 | 4 | Cw*0401 | HYKRAEKKQM | 1781 | 100.00 | 10 |
| 1205 | HPV | 16 | 3 | 4 | B*2705 | KRAEKKQMSM | 1782 | 1800.00 | 10 |
| 1206 | HPV | 16 | 3 | 4 | B*2705 | KQMSMSQWIK | 1783 | 600.00 | 10 |

TABLE 7-continued

| No | Species | Strain type | Frame | ORF | HLA | Seq | Seq ID No. | Score | Length |
|---|---|---|---|---|---|---|---|---|---|
| 1207 | HPV | 16 | 3 | 4 | B*2705 | SQWIKYRCDR | 1784 | 500.00 | 10 |
| 1208 | HPV | 16 | 3 | 4 | B*2705 | DRVDDGGDWK | 1785 | 200.00 | 10 |
| 1209 | HPV | 16 | 3 | 4 | B*3701 | GDWKQIVMFL | 1786 | 300.00 | 10 |
| 1210 | HPV | 16 | 3 | 4 | Cw*0401 | MFLRYQGVEF | 1787 | 100.00 | 10 |
| 1211 | HPV | 16 | 3 | 4 | B*2705 | LRYQGVEFMS | 1788 | 1000.00 | 10 |
| 1212 | HPV | 16 | 3 | 4 | Cw*0401 | RYQGVEFMSF | 1789 | 110.00 | 10 |
| 1213 | HPV | 16 | 3 | 4 | A24 | RYQGVEFMSF | 1789 | 360.00 | 10 |
| 1214 | HPV | 16 | 3 | 4 | A*0201 | YQGVEFMSFL | 1790 | 478.93 | 10 |
| 1215 | HPV | 16 | 3 | 4 | B*2705 | YQGVEFMSFL | 1790 | 200.00 | 10 |
| 1216 | HPV | 16 | 3 | 4 | B*2705 | VEFMSFLTAL | 1791 | 150.00 | 10 |
| 1217 | HPV | 16 | 3 | 4 | B60 | VEFMSFLTAL | 1791 | 160.00 | 10 |
| 1218 | HPV | 16 | 3 | 4 | Cw*0401 | SFLTALKRFL | 1792 | 200.00 | 10 |
| 1219 | HPV | 16 | 3 | 4 | B*5102 | TALKRFLQGI | 1793 | 726.00 | 10 |
| 1220 | HPV | 16 | 3 | 4 | B*5103 | TALKRFLQGI | 1793 | 132.00 | 10 |
| 1221 | HPV | 16 | 3 | 4 | B*2705 | KRFLQGIPKK | 1794 | 30000.00 | 10 |
| 1222 | HPV | 16 | 3 | 4 | Cw*0301 | QGIPKKNCIL | 1795 | 100.00 | 10 |
| 1223 | HPV | 16 | 3 | 4 | B*3501 | IPKKNCILLY | 1796 | 120.00 | 10 |
| 1224 | HPV | 16 | 3 | 4 | A3 | LLYGAANTGK | 1797 | 150.00 | 10 |
| 1225 | HPV | 16 | 3 | 4 | B*2705 | LLYGAANTGK | 1797 | 150.00 | 10 |
| 1226 | HPV | 16 | 3 | 4 | Cw*0401 | LFGMSLMKFL | 1798 | 240.00 | 10 |
| 1227 | HPV | 16 | 3 | 4 | Cw*0401 | KFLQGSVICF | 1799 | 200.00 | 10 |
| 1228 | HPV | 16 | 3 | 4 | A*0201 | FLQGSVICFV | 1800 | 4047.23 | 10 |
| 1229 | HPV | 16 | 3 | 4 | A*0201 | FVNSKSHFWL | 1801 | 274.29 | 10 |
| 1230 | HPV | 16 | 3 | 4 | B*5102 | DATVPCWNYI | 1802 | 220.00 | 10 |
| 1231 | HPV | 16 | 3 | 4 | B*5103 | DATVPCWNYI | 1802 | 121.00 | 10 |
| 1232 | HPV | 16 | 3 | 4 | B*2705 | LRNALDGNLV | 1803 | 600.00 | 10 |
| 1233 | HPV | 16 | 3 | 4 | B*5102 | CPPLLITSNI | 1804 | 484.00 | 10 |
| 1234 | HPV | 16 | 3 | 4 | B*2702 | SRWPYLHNRL | 1805 | 300.00 | 10 |
| 1235 | HPV | 16 | 3 | 4 | B*2705 | SRWPYLHNRL | 1805 | 10000.00 | 10 |
| 1236 | HPV | 16 | 3 | 4 | B*5102 | WPYLHNRLVV | 1806 | 1210.00 | 10 |
| 1237 | HPV | 16 | 3 | 4 | B*5103 | WPYLHNRLVV | 1806 | 145.20 | 10 |
| 1238 | HPV | 16 | 3 | 4 | B*5201 | WPYLHNRLVV | 1806 | 300.00 | 10 |
| 1239 | HPV | 16 | 3 | 4 | A*0201 | YLHNRLVVFT | 1807 | 433.63 | 10 |
| 1240 | HPV | 16 | 3 | 4 | B*2705 | NRLVVFTFPN | 1808 | 200.00 | 10 |
| 1241 | HPV | 16 | 3 | 4 | Cw*0401 | VFTFPNEFPF | 1809 | 100.00 | 10 |
| 1242 | HPV | 16 | 3 | 4 | B*5102 | FPFDENGNPV | 1810 | 2200.00 | 10 |
| 1243 | HPV | 16 | 3 | 4 | B60 | DENGNPVYEL | 1811 | 320.00 | 10 |
| 1244 | HPV | 16 | 3 | 4 | Cw*0401 | SFFSRTWSRL | 1812 | 240.00 | 10 |
| 1245 | HPV | 16 | 3 | 4 | B*2705 | SRTWSRLSLH | 1813 | 200.00 | 10 |
| 1246 | HPV | 16 | 3 | 5 | B*5103 | LACFLLCFV | 1814 | 100.00 | 9 |
| 1247 | HPV | 16 | 3 | 5 | B*5102 | LACFLLCFV | 1814 | 100.00 | 9 |
| 1248 | HPV | 16 | 3 | 5 | Cw*0401 | CFLLCFVCF | 1815 | 100.00 | 9 |
| 1249 | HPV | 16 | 3 | 5 | A*0201 | FLLCFVCFC | 1816 | 4064.58 | 9 |
| 1250 | HPV | 16 | 3 | 5 | A*0201 | LLCFVCFCV | 1817 | 685.78 | 9 |
| 1251 | HPV | 16 | 3 | 5 | A*0201 | FLLCFVCFCV | 1818 | 6865.90 | 10 |
| 1252 | HPV | 16 | 3 | 6 | B*2705 | LRLGVLLY | 1819 | 1000.00 | 8 |
| 1253 | HPV | 16 | 3 | 6 | B*2705 | LRLGVLLYI | 1820 | 600.00 | 9 |
| 1254 | HPV | 16 | 3 | 6 | A*0205 | GVLLYILYL | 1821 | 100.80 | 9 |
| 1255 | HPV | 16 | 3 | 6 | A*0201 | LLYILYLFI | 1822 | 468.22 | 9 |
| 1256 | HPV | 16 | 3 | 6 | A3 | ILYLFIYHY | 1823 | 270.00 | 9 |
| 1257 | HPV | 16 | 3 | 6 | B62 | ILYLFIYHY | 1823 | 104.00 | 9 |
| 1258 | HPV | 16 | 3 | 6 | A24 | LYLFIYHYF | 1824 | 210.00 | 9 |
| 1259 | HPV | 16 | 3 | 6 | Cw*0401 | LYLFIYHYF | 1824 | 100.00 | 9 |
| 1260 | HPV | 16 | 3 | 6 | B14 | LRLGVLLYIL | 1825 | 300.00 | 10 |
| 1261 | HPV | 16 | 3 | 6 | B*2705 | LRLGVLLYIL | 1825 | 2000.00 | 10 |
| 1262 | HPV | 16 | 3 | 6 | B62 | RLGVLLYILY | 1826 | 192.00 | 10 |
| 1263 | HPV | 16 | 3 | 6 | A*0201 | VLLYILYLFI | 1827 | 541.38 | 10 |
| 1264 | HPV | 16 | 3 | 6 | A3 | LLYILYLFIY | 1828 | 270.00 | 10 |
| 1265 | HPV | 16 | 3 | 6 | B62 | ILYLFIYHYF | 1829 | 114.40 | 10 |
| 1266 | HPV | 16 | 3 | 7 | B*2705 | HRLPNFIK | 1830 | 2000.00 | 8 |
| 1267 | HPV | 16 | 3 | 7 | B*5102 | HANRQVHV | 1831 | 121.00 | 8 |
| 1268 | HPV | 16 | 3 | 7 | B*2705 | NRQVHVHL | 1832 | 2000.00 | 8 |
| 1269 | HPV | 16 | 3 | 7 | B8 | YLRLKAKL | 1833 | 160.00 | 8 |
| 1270 | HPV | 16 | 3 | 7 | B*2705 | LRLKAKLL | 1834 | 2000.00 | 8 |
| 1271 | HPV | 16 | 3 | 7 | B*2705 | LQNAQNVHR | 1835 | 100.00 | 9 |
| 1272 | HPV | 16 | 3 | 7 | B*2705 | HRLPNFIKH | 1836 | 200.00 | 9 |
| 1273 | HPV | 16 | 3 | 7 | B7 | ANRQVHVHL | 1837 | 120.00 | 9 |
| 1274 | HPV | 16 | 3 | 7 | B*2705 | NRQVHVHLT | 1838 | 200.00 | 9 |
| 1275 | HPV | 16 | 3 | 7 | B*2705 | RQVHVHLTL | 1839 | 600.00 | 9 |
| 1276 | HPV | 16 | 3 | 7 | B*3901 | VHVHLTLYL | 1840 | 180.00 | 9 |
| 1277 | HPV | 16 | 3 | 7 | A68.1 | HVHLTLYLR | 1841 | 200.00 | 9 |
| 1278 | HPV | 16 | 3 | 7 | B*3901 | VHLTLYLRL | 1842 | 180.00 | 9 |
| 1279 | HPV | 16 | 3 | 7 | Cw*0301 | VHLTLYLRL | 1842 | 100.00 | 9 |
| 1280 | HPV | 16 | 3 | 7 | A24 | LYLRLKAKL | 1843 | 396.00 | 9 |
| 1281 | HPV | 16 | 3 | 7 | Cw*0401 | LYLRLKAKL | 1843 | 264.00 | 9 |
| 1282 | HPV | 16 | 3 | 7 | B8 | YLRLKAKLL | 1844 | 160.00 | 9 |

TABLE 7-continued

| No | Species | Strain type | Frame | ORF | HLA | Seq | Seq ID No. | Score | Length |
|---|---|---|---|---|---|---|---|---|---|
| 1283 | HPV | 16 | 3 | 7 | B14 | LRLKAKLLL | 1845 | 100.00 | 9 |
| 1284 | HPV | 16 | 3 | 7 | B*2705 | LRLKAKLLL | 1845 | 2000.00 | 9 |
| 1285 | HPV | 16 | 3 | 7 | B*2705 | LQNAQNVHRL | 1846 | 200.00 | 10 |
| 1286 | HPV | 16 | 3 | 7 | B*2705 | AQNVHRLPNF | 1847 | 100.00 | 10 |
| 1287 | HPV | 16 | 3 | 7 | A68.1 | NVHRLPNFIK | 1848 | 120.00 | 10 |
| 1288 | HPV | 16 | 3 | 7 | B*2705 | NRQVHVHLTL | 1849 | 2000.00 | 10 |
| 1289 | HPV | 16 | 3 | 7 | B*2705 | RQVHVHLTLY | 1850 | 300.00 | 10 |
| 1290 | HPV | 16 | 3 | 7 | B*2705 | TLYLRLKAKL | 1851 | 150.00 | 10 |
| 1291 | HPV | 16 | 3 | 7 | Cw*0401 | LYLRLKAKLL | 1852 | 200.00 | 10 |
| 1292 | HPV | 16 | 3 | 7 | A24 | LYLRLKAKLL | 1852 | 300.00 | 10 |
| 1293 | HPV | 16 | 3 | 7 | B*2705 | LRLKAKLLLN | 1853 | 200.00 | 10 |
| 1294 | HPV | 16 | 3 | 7 | A*0201 | LLNKYYNMEV | 1854 | 118.24 | 10 |
| 1295 | HPV | 16 | 3 | 7 | Cw*0401 | YYNMEVWVYF | 1855 | 100.00 | 10 |
| 1296 | HPV | 16 | 3 | 7 | A24 | YYNMEVWVYF | 1855 | 210.00 | 10 |
| 1297 | HPV | 16 | 3 | 7 | A*0201 | YNMEVWVYPL | 1856 | 123.10 | 10 |
| 1298 | HPV | 16 | 3 | 8 | B*5102 | QGLPQLQI | 1857 | 290.40 | 8 |
| 1299 | HPV | 16 | 3 | 8 | B*5102 | LPQLQIHL | 1858 | 133.10 | 8 |
| 1300 | HPV | 16 | 3 | 8 | Cw*0401 | LPQLQIHLL | 1859 | 160.00 | 9 |
| 1301 | HPV | 16 | 3 | 8 | B*5102 | LPQLQIHLL | 1859 | 133.10 | 9 |
| 1302 | HPV | 16 | 3 | 8 | B*3901 | FHWEQGLPQL | 1860 | 540.00 | 10 |
| 1303 | HPV | 16 | 3 | 8 | Cw*0301 | QGLPQLQIHL | 1861 | 100.00 | 10 |
| 1304 | HPV | 16 | 3 | 8 | B*5102 | LPQLQIHLLL | 1862 | 110.00 | 10 |
| 1305 | HPV | 16 | 3 | 10 | B*2705 | HQHLYLPF | 1863 | 100.00 | 8 |
| 1306 | HPV | 16 | 3 | 10 | B*5102 | FPQMYQDL | 1864 | 220.00 | 8 |
| 1307 | HPV | 16 | 3 | 10 | B*2705 | QMYQDLVL | 1865 | 250.00 | 8 |
| 1308 | HPV | 16 | 3 | 10 | B*2705 | YQDLVLLL | 1866 | 200.00 | 8 |
| 1309 | HPV | 16 | 3 | 10 | B*2705 | LQLIPHLL | 1867 | 200.00 | 8 |
| 1310 | HPV | 16 | 3 | 10 | B*5102 | FPQMYQDLV | 1868 | 440.00 | 9 |
| 1311 | HPV | 16 | 3 | 10 | A*0201 | QMYQDLVLL | 1869 | 113.55 | 9 |
| 1312 | HPV | 16 | 3 | 10 | B*2705 | QMYQDLVLL | 1869 | 250.00 | 9 |
| 1313 | HPV | 16 | 3 | 10 | A24 | MYQDLVLLL | 1870 | 432.00 | 9 |
| 1314 | HPV | 16 | 3 | 10 | Cw*0401 | MYQDLVLLL | 1870 | 480.00 | 9 |
| 1315 | HPV | 16 | 3 | 10 | A*0201 | LLLQLIPHL | 1871 | 309.05 | 9 |
| 1316 | HPV | 16 | 3 | 10 | B*2705 | LQLIPHLLY | 1872 | 100.00 | 9 |
| 1317 | HPV | 16 | 3 | 10 | B*5102 | LPFPQMYQDL | 1873 | 550.00 | 10 |
| 1318 | HPV | 16 | 3 | 10 | Cw*0301 | LPFPQMYQDL | 1873 | 180.00 | 10 |
| 1319 | HPV | 16 | 3 | 10 | Cw*0401 | LPFPQMYQDL | 1873 | 105.60 | 10 |
| 1320 | HPV | 16 | 3 | 10 | B*5102 | FPQMYQDLVL | 1874 | 220.00 | 10 |
| 1321 | HPV | 16 | 3 | 10 | A*0201 | QMYQDLVLLL | 1875 | 113.55 | 10 |
| 1322 | HPV | 16 | 3 | 10 | B*2705 | QMYQDLVLLL | 1875 | 250.00 | 10 |
| 1323 | HPV | 16 | 3 | 10 | B*2705 | YQDLVLLLQL | 1876 | 200.00 | 10 |
| 1324 | HPV | 16 | 3 | 10 | B*3701 | QDLVLLLQLI | 1877 | 200.00 | 10 |
| 1325 | HPV | 16 | 3 | 10 | A*0201 | VLLLQLIPHL | 1878 | 309.05 | 10 |
| 1326 | HPV | 16 | 3 | 10 | A*0201 | LLLQLIPHLL | 1879 | 134.37 | 10 |
| 1327 | HPV | 16 | 3 | 11 | B*5102 | IPLSLTHL | 1880 | 330.00 | 8 |
| 1328 | HPV | 16 | 3 | 11 | B*2705 | LQKLEGIL | 1881 | 200.00 | 8 |
| 1329 | HPV | 16 | 3 | 11 | B*3901 | LHFHHPLL | 1882 | 180.00 | 8 |
| 1330 | HPV | 16 | 3 | 11 | B*5102 | HPLLVHII | 1883 | 1452.00 | 8 |
| 1331 | HPV | 16 | 3 | 11 | B*2705 | FLWIHLLL | 1884 | 150.00 | 8 |
| 1332 | HPV | 16 | 3 | 11 | A*0201 | LLLHIIIPL | 1885 | 309.05 | 9 |
| 1333 | HPV | 16 | 3 | 11 | B*3901 | LHIIIPLSL | 1886 | 180.00 | 9 |
| 1334 | HPV | 16 | 3 | 11 | B*2705 | HLYCSLQHL | 1887 | 150.00 | 9 |
| 1335 | HPV | 16 | 3 | 11 | B*5102 | HPLLVHIIM | 1888 | 108.90 | 9 |
| 1336 | HPV | 16 | 3 | 11 | A3 | LLVHIIMKK | 1889 | 135.00 | 9 |
| 1337 | HPV | 16 | 3 | 11 | Cw*0401 | KFLWIHLLL | 1890 | 200.00 | 9 |
| 1338 | HPV | 16 | 3 | 11 | A*0201 | FLWIHLLLA | 1891 | 436.26 | 9 |
| 1339 | HPV | 16 | 3 | 11 | B*3901 | IHLLLAQTL | 1892 | 180.00 | 9 |
| 1340 | HPV | 16 | 3 | 11 | A*0201 | LLLLHIIIPL | 1893 | 309.05 | 10 |
| 1341 | HPV | 16 | 3 | 11 | Cw*0301 | IIIPLSLTHL | 1894 | 100.00 | 10 |
| 1342 | HPV | 16 | 3 | 11 | Cw*0301 | LSLTHLYCSL | 1895 | 100.00 | 10 |
| 1343 | HPV | 16 | 3 | 11 | B*3901 | THLYCSLQHL | 1896 | 270.00 | 10 |
| 1344 | HPV | 16 | 3 | 11 | B*2705 | LQKLEGILHF | 1897 | 100.00 | 10 |
| 1345 | HPV | 16 | 3 | 11 | B62 | LQKLEGILHF | 1897 | 576.00 | 10 |
| 1346 | HPV | 16 | 3 | 11 | A*0201 | ILHFHHPLLV | 1898 | 118.24 | 10 |
| 1347 | HPV | 16 | 3 | 12 | B*5102 | LALGTVEL | 1899 | 199.65 | 8 |
| 1348 | HPV | 16 | 3 | 12 | B*5103 | LALGTVELV | 1900 | 132.00 | 9 |
| 1349 | HPV | 16 | 3 | 12 | B*5102 | LALGTVELV | 1900 | 399.30 | 9 |
| 1350 | HPV | 16 | 3 | 12 | A24 | HYVLVVENL | 1901 | 420.00 | 9 |
| 1351 | HPV | 16 | 3 | 12 | Cw*0401 | HYVLVVENL | 1901 | 400.00 | 9 |
| 1352 | HPV | 16 | 3 | 12 | B*5102 | LALGTVELVI | 1902 | 726.00 | 10 |
| 1353 | HPV | 16 | 3 | 12 | B*5103 | LALGTVELVI | 1902 | 145.20 | 10 |
| 1354 | HPV | 16 | 3 | 12 | B*3901 | KHYVLVVENL | 1903 | 270.00 | 10 |
| 1355 | HPV | 16 | 3 | 13 | B*5102 | YPLHLYQV | 1904 | 1452.00 | 8 |
| 1356 | HPV | 16 | 3 | 13 | B*2705 | HLYQVIFL | 1905 | 150.00 | 8 |
| 1357 | HPV | 16 | 3 | 13 | B*2705 | LQIQQFLL | 1906 | 200.00 | 8 |
| 1358 | HPV | 16 | 3 | 13 | B*2705 | QQFLLVVH | 1907 | 100.00 | 8 |

TABLE 7-continued

| No | Species | Strain type | Frame | ORF | HLA | Seq | Seq ID No. | Score | Length |
|---|---|---|---|---|---|---|---|---|---|
| 1359 | HPV | 16 | 3 | 13 | B*5201 | YPLHLYQVI | 1908 | 220.00 | 9 |
| 1360 | HPV | 16 | 3 | 13 | B*5102 | YPLHLYQVI | 1908 | 2904.00 | 9 |
| 1361 | HPV | 16 | 3 | 13 | B*3901 | LHLYQVIFL | 1909 | 270.00 | 9 |
| 1362 | HPV | 16 | 3 | 13 | A24 | LYQVIFLQI | 1910 | 126.00 | 9 |
| 1363 | HPV | 16 | 3 | 13 | Cw*0401 | IFLQIQQFL | 1911 | 200.00 | 9 |
| 1364 | HPV | 16 | 3 | 13 | A*0201 | FLQIQQFLL | 1912 | 569.95 | 9 |
| 1365 | HPV | 16 | 3 | 13 | B*2705 | QQFLLVVHT | 1913 | 100.00 | 9 |
| 1366 | HPV | 16 | 3 | 13 | A*0201 | LLVVHTIFL | 1914 | 199.74 | 9 |
| 1367 | HPV | 16 | 3 | 13 | A24 | LYPLHLYQVI | 1915 | 108.00 | 10 |
| 1368 | HPV | 16 | 3 | 13 | A*0201 | VIFLQIQQFL | 1916 | 101.62 | 10 |
| 1369 | HPV | 16 | 3 | 13 | Cw*0401 | IFLQIQQFLL | 1917 | 200.00 | 10 |
| 1370 | HPV | 16 | 3 | 13 | A*0201 | FLQIQQFLLV | 1918 | 607.88 | 10 |
| 1371 | HPV | 16 | 3 | 13 | B*5201 | LQIQQFLLVV | 1919 | 495.00 | 10 |
| 1372 | HPV | 16 | 3 | 13 | B*2705 | QQFLLVVHTI | 1920 | 300.00 | 10 |
| 1373 | HPV | 16 | 3 | 13 | B*5201 | QQFLLVVHTI | 1920 | 120.00 | 10 |
| 1374 | HPV | 16 | 3 | 13 | Cw*0401 | QFLLVVHTIF | 1921 | 100.00 | 10 |
| 1375 | HPV | 16 | 3 | 13 | A*0201 | FLLVVHTIFL | 1922 | 1999.73 | 10 |
| 1376 | HPV | 16 | 3 | 14 | B*2705 | ARTNIYYH | 1923 | 200.00 | 8 |
| 1377 | HPV | 16 | 3 | 14 | B*2705 | SRLLAVGH | 1924 | 200.00 | 8 |
| 1378 | HPV | 16 | 3 | 14 | B*5102 | KPNNNKIL | 1925 | 121.00 | 8 |
| 1379 | HPV | 16 | 3 | 14 | B*5201 | LQYRVFRI | 1926 | 150.00 | 8 |
| 1380 | HPV | 16 | 3 | 14 | B*2705 | YRVFRIHL | 1927 | 2000.00 | 8 |
| 1381 | HPV | 16 | 3 | 14 | B*5102 | NPDTQRLV | 1928 | 121.00 | 8 |
| 1382 | HPV | 16 | 3 | 14 | B*2705 | QRLVWACV | 1929 | 600.00 | 8 |
| 1383 | HPV | 16 | 3 | 14 | B*5102 | WACVGVEV | 1930 | 121.00 | 8 |
| 1384 | HPV | 16 | 3 | 14 | B*2705 | GRGQPLGV | 1931 | 600.00 | 8 |
| 1385 | HPV | 16 | 3 | 14 | B*2705 | KQTQLCLI | 1932 | 180.00 | 8 |
| 1386 | HPV | 16 | 3 | 14 | B*5102 | SPCTNVAV | 1933 | 242.00 | 8 |
| 1387 | HPV | 16 | 3 | 14 | B*5102 | NPGDCPPL | 1934 | 100.00 | 8 |
| 1388 | HPV | 16 | 3 | 14 | B*5102 | YPDYIKMV | 1935 | 200.00 | 8 |
| 1389 | HPV | 16 | 3 | 14 | B*2705 | LRREQMFV | 1936 | 600.00 | 8 |
| 1390 | HPV | 16 | 3 | 14 | B*2705 | RREQMFVR | 1937 | 3000.00 | 8 |
| 1391 | HPV | 16 | 3 | 14 | B*2705 | QMFVRHLF | 1938 | 125.00 | 8 |
| 1392 | HPV | 16 | 3 | 14 | B*2705 | AQIFNKPY | 1939 | 100.00 | 8 |
| 1393 | HPV | 16 | 3 | 14 | B*2705 | QRAQGHNN | 1940 | 200.00 | 8 |
| 1394 | HPV | 16 | 3 | 14 | B*2705 | TRSTNMSL | 1941 | 2000.00 | 8 |
| 1395 | HPV | 16 | 3 | 14 | B*3901 | RHGEEYDL | 1942 | 180.00 | 8 |
| 1396 | HPV | 16 | 3 | 14 | B*2705 | LQFIFQLC | 1943 | 100.00 | 8 |
| 1397 | HPV | 16 | 3 | 14 | B*2705 | FQLCKITL | 1944 | 200.00 | 8 |
| 1398 | HPV | 16 | 3 | 14 | B*5102 | TADVMTYI | 1945 | 110.00 | 8 |
| 1399 | HPV | 16 | 3 | 14 | B*5102 | QPPPGGTL | 1946 | 110.00 | 8 |
| 1400 | HPV | 16 | 3 | 14 | B*2705 | YRFVTQAI | 1947 | 3000.00 | 8 |
| 1401 | HPV | 16 | 3 | 14 | B*2705 | TQAIACQK | 1948 | 200.00 | 8 |
| 1402 | HPV | 16 | 3 | 14 | B*3501 | APKEDDPL | 1949 | 180.00 | 8 |
| 1403 | HPV | 16 | 3 | 14 | B*5102 | FPLGRKFL | 1950 | 660.00 | 8 |
| 1404 | HPV | 16 | 3 | 14 | B*2705 | GRKFLLQA | 1951 | 200.00 | 8 |
| 1405 | HPV | 16 | 3 | 14 | B*2705 | LQAGLKAK | 1952 | 200.00 | 8 |
| 1406 | HPV | 16 | 3 | 14 | B8 | KAKPKFTL | 1953 | 160.00 | 8 |
| 1407 | HPV | 16 | 3 | 14 | B*2705 | KRKATPTT | 1954 | 600.00 | 8 |
| 1408 | HPV | 16 | 3 | 14 | A*0201 | LMQVTFIYI | 1955 | 133.86 | 9 |
| 1409 | HPV | 16 | 3 | 14 | B*2705 | MQVTFIYIL | 1956 | 200.00 | 9 |
| 1410 | HPV | 16 | 3 | 14 | B*3901 | YHIFFQMSL | 1957 | 180.00 | 9 |
| 1411 | HPV | 16 | 3 | 14 | Cw*0401 | IFFQMSLWL | 1958 | 220.00 | 9 |
| 1412 | HPV | 16 | 3 | 14 | Cw*0401 | LPSEATVYL | 1959 | 105.60 | 9 |
| 1413 | HPV | 16 | 3 | 14 | B*5102 | LPSEATVYL | 1959 | 133.10 | 9 |
| 1414 | HPV | 16 | 3 | 14 | B*5103 | EATVYLPPV | 1960 | 110.00 | 9 |
| 1415 | HPV | 16 | 3 | 14 | B*5102 | EATVYLPPV | 1960 | 100.00 | 9 |
| 1416 | HPV | 16 | 3 | 14 | B*5102 | LPPVPVSKV | 1961 | 400.00 | 9 |
| 1417 | HPV | 16 | 3 | 14 | B*2705 | ARTNIYYHA | 1962 | 200.00 | 9 |
| 1418 | HPV | 16 | 3 | 14 | A24 | YYHAGTSRL | 1963 | 200.00 | 9 |
| 1419 | HPV | 16 | 3 | 14 | Cw*0401 | YYHAGTSRL | 1963 | 300.00 | 9 |
| 1420 | HPV | 16 | 3 | 14 | B*5102 | KPNNNKILV | 1964 | 242.00 | 9 |
| 1421 | HPV | 16 | 3 | 14 | Cw*0301 | ILVPKVSGL | 1965 | 120.00 | 9 |
| 1422 | HPV | 16 | 3 | 14 | B*3501 | VPKVSGLQY | 1966 | 120.00 | 9 |
| 1423 | HPV | 16 | 3 | 14 | A*0201 | GLQYRVFRI | 1967 | 139.17 | 9 |
| 1424 | HPV | 16 | 3 | 14 | A24 | QYRVFRIHL | 1968 | 200.00 | 9 |
| 1425 | HPV | 16 | 3 | 14 | Cw*0401 | QYRVFRIHL | 1968 | 220.00 | 9 |
| 1426 | HPV | 16 | 3 | 14 | B*2705 | FRIHLPDPN | 1969 | 200.00 | 9 |
| 1427 | HPV | 16 | 3 | 14 | Cw*0401 | KFGPPDTSF | 1970 | 110.00 | 9 |
| 1428 | HPV | 16 | 3 | 14 | A24 | FYNPDTQRL | 1971 | 432.00 | 9 |
| 1429 | HPV | 16 | 3 | 14 | Cw*0401 | FYNPDTQRL | 1971 | 240.00 | 9 |
| 1430 | HPV | 16 | 3 | 14 | B60 | VEVGRGQPL | 1972 | 320.00 | 9 |
| 1431 | HPV | 16 | 3 | 14 | B*5103 | SAYAANAGV | 1973 | 330.00 | 9 |
| 1432 | HPV | 16 | 3 | 14 | B*5102 | SAYAANAGV | 1973 | 550.00 | 9 |
| 1433 | HPV | 16 | 3 | 14 | B*5102 | AGVDNRECI | 1974 | 290.40 | 9 |
| 1434 | HPV | 16 | 3 | 14 | B*2702 | NRECISMDY | 1975 | 200.00 | 9 |

TABLE 7-continued

| No | Species | Strain type | Frame | ORF | HLA | Seq | Seq ID No. | Score | Length |
|---|---|---|---|---|---|---|---|---|---|
| 1435 | HPV | 16 | 3 | 14 | B*2705 | NRECISMDY | 1975 | 1000.00 | 9 |
| 1436 | HPV | 16 | 3 | 14 | A24 | DYKQTQLCL | 1976 | 200.00 | 9 |
| 1437 | HPV | 16 | 3 | 14 | Cw*0401 | DYKQTQLCL | 1976 | 240.00 | 9 |
| 1438 | HPV | 16 | 3 | 14 | B*2705 | TQLCLIGCK | 1977 | 200.00 | 9 |
| 1439 | HPV | 16 | 3 | 14 | B*3701 | GDCPPLELI | 1978 | 200.00 | 9 |
| 1440 | HPV | 16 | 3 | 14 | B*5102 | VPLDICTSI | 1979 | 1200.00 | 9 |
| 1441 | HPV | 16 | 3 | 14 | Cw*0301 | CKYPDYIKM | 1980 | 125.00 | 9 |
| 1442 | HPV | 16 | 3 | 14 | Cw*0401 | FFYLRREQM | 1981 | 110.00 | 9 |
| 1443 | HPV | 16 | 3 | 14 | A24 | FYLRREQMF | 1982 | 180.00 | 9 |
| 1444 | HPV | 16 | 3 | 14 | Cw*0401 | FYLRREQMF | 1982 | 110.00 | 9 |
| 1445 | HPV | 16 | 3 | 14 | A*0201 | YLRREQMFV | 1983 | 133.73 | 9 |
| 1446 | HPV | 16 | 3 | 14 | B*2705 | LRREQMFVR | 1984 | 1000.00 | 9 |
| 1447 | HPV | 16 | 3 | 14 | B*2705 | RREQMFVRH | 1985 | 600.00 | 9 |
| 1448 | HPV | 16 | 3 | 14 | B60 | REQMFVRHL | 1986 | 160.00 | 9 |
| 1449 | HPV | 16 | 3 | 14 | B*2705 | NRAGTVGEN | 1987 | 200.00 | 9 |
| 1450 | HPV | 16 | 3 | 14 | B*5103 | RAGTVGENV | 1988 | 121.00 | 9 |
| 1451 | HPV | 16 | 3 | 14 | B*5102 | RAGTVGENV | 1988 | 133.10 | 9 |
| 1452 | HPV | 16 | 3 | 14 | A68.1 | NVPDDLYIK | 1989 | 120.00 | 9 |
| 1453 | HPV | 16 | 3 | 14 | Cw*0401 | YFPTPSGSM | 1990 | 110.00 | 9 |
| 1454 | HPV | 16 | 3 | 14 | B*5102 | FPTPSGSMV | 1991 | 400.00 | 9 |
| 1455 | HPV | 16 | 3 | 14 | B*5103 | RAQGHNNGI | 1992 | 110.00 | 9 |
| 1456 | HPV | 16 | 3 | 14 | B*5102 | RAQGHNNGI | 1992 | 242.00 | 9 |
| 1457 | HPV | 16 | 3 | 14 | A68.1 | FVTVVDTTR | 1993 | 300.00 | 9 |
| 1458 | HPV | 16 | 3 | 14 | B*2705 | TRSTNMSLC | 1994 | 200.00 | 9 |
| 1459 | HPV | 16 | 3 | 14 | B*2705 | LRHGEEYDL | 1995 | 2000.00 | 9 |
| 1460 | HPV | 16 | 3 | 14 | B*2705 | LQFIFQLCK | 1996 | 1000.00 | 9 |
| 1461 | HPV | 16 | 3 | 14 | Cw*0401 | IFQLCKITL | 1997 | 200.00 | 9 |
| 1462 | HPV | 16 | 3 | 14 | B*2705 | LQPPPGGTL | 1998 | 200.00 | 9 |
| 1463 | HPV | 16 | 3 | 14 | B*2702 | YRFVTQAIA | 1999 | 100.00 | 9 |
| 1464 | HPV | 16 | 3 | 14 | B*2705 | YRFVTQAIA | 1999 | 1000.00 | 9 |
| 1465 | HPV | 16 | 3 | 14 | A24 | KYTFWEVNL | 2000 | 400.00 | 9 |
| 1466 | HPV | 16 | 3 | 14 | Cw*0401 | KYTFWEVNL | 2000 | 200.00 | 9 |
| 1467 | HPV | 16 | 3 | 14 | Cw*0401 | KFSADLDQF | 2001 | 200.00 | 9 |
| 1468 | HPV | 16 | 3 | 14 | B62 | DQFPLGRKF | 2002 | 192.00 | 9 |
| 1469 | HPV | 16 | 3 | 14 | Cw*0401 | QFPLGRKFL | 2003 | 200.00 | 9 |
| 1470 | HPV | 16 | 3 | 14 | B*5102 | FPLGRKFLL | 2004 | 660.00 | 9 |
| 1471 | HPV | 16 | 3 | 14 | B*2705 | KRKATPTTS | 2005 | 600.00 | 9 |
| 1472 | HPV | 16 | 3 | 14 | B8 | TAKRKKRKL | 2006 | 320.00 | 9 |
| 1473 | HPV | 16 | 3 | 14 | Cw*0401 | VYHIFFQMSL | 2007 | 330.00 | 10 |
| 1474 | HPV | 16 | 3 | 14 | A24 | VYHIFFQMSL | 2007 | 200.00 | 10 |
| 1475 | HPV | 16 | 3 | 14 | A*0201 | SLWLPSEATV | 2008 | 577.28 | 10 |
| 1476 | HPV | 16 | 3 | 14 | A*0201 | WLPSEATVYL | 2009 | 540.47 | 10 |
| 1477 | HPV | 16 | 3 | 14 | A*0201 | YLPPVPSKV | 2010 | 735.86 | 10 |
| 1478 | HPV | 16 | 3 | 14 | B*5102 | LPPVPVSKVV | 2011 | 242.00 | 10 |
| 1479 | HPV | 16 | 3 | 14 | B*5201 | LPPVPVSKVV | 2011 | 435.60 | 10 |
| 1480 | HPV | 16 | 3 | 14 | A68.1 | VVSTDEYVAR | 2012 | 200.00 | 10 |
| 1481 | HPV | 16 | 3 | 14 | Cw*0401 | IYYHAGTSRL | 2013 | 200.00 | 10 |
| 1482 | HPV | 16 | 3 | 14 | A24 | IYYHAGTSRL | 2013 | 200.00 | 10 |
| 1483 | HPV | 16 | 3 | 14 | Cw*0401 | YYHAGTSRLL | 2014 | 360.00 | 10 |
| 1484 | HPV | 16 | 3 | 14 | A24 | YYHAGTSRLL | 2014 | 200.00 | 10 |
| 1485 | HPV | 16 | 3 | 14 | B*5102 | HAGTSRLLAV | 2015 | 110.00 | 10 |
| 1486 | HPV | 16 | 3 | 14 | B*5103 | HAGTSRLLAV | 2015 | 121.00 | 10 |
| 1487 | HPV | 16 | 3 | 14 | B*2702 | SRLLAVGHPY | 2016 | 200.00 | 10 |
| 1488 | HPV | 16 | 3 | 14 | B*2705 | SRLLAVGHPY | 2016 | 1000.00 | 10 |
| 1489 | HPV | 16 | 3 | 14 | B*5102 | LAVGHPYFPI | 2017 | 660.00 | 10 |
| 1490 | HPV | 16 | 3 | 14 | B*5103 | LAVGHPYFPI | 2017 | 110.00 | 10 |
| 1491 | HPV | 16 | 3 | 14 | A68.1 | AVGHPYFPIK | 2018 | 240.00 | 10 |
| 1492 | HPV | 16 | 3 | 14 | A*0205 | KILVPKVSGL | 2019 | 126.00 | 10 |
| 1493 | HPV | 16 | 3 | 14 | B*5102 | SGLQYRVFRI | 2020 | 528.00 | 10 |
| 1494 | HPV | 16 | 3 | 14 | B*2705 | LQYRVFRIHL | 2021 | 1000.00 | 10 |
| 1495 | HPV | 16 | 3 | 14 | B*2705 | FRIHLPDPNK | 2022 | 2000.00 | 10 |
| 1496 | HPV | 16 | 3 | 14 | Cw*0401 | SFYNPDTQRL | 2023 | 200.00 | 10 |
| 1497 | HPV | 16 | 3 | 14 | B*2705 | QRLVWACVGV | 2024 | 600.00 | 10 |
| 1498 | HPV | 16 | 3 | 14 | B*2705 | GRGQPLGVGI | 2025 | 600.00 | 10 |
| 1499 | HPV | 16 | 3 | 14 | B*5102 | NAGVDNRECI | 2026 | 242.00 | 10 |
| 1500 | HPV | 16 | 3 | 14 | B*5103 | NAGVDNRECI | 2026 | 121.00 | 10 |
| 1501 | HPV | 16 | 3 | 14 | B*2705 | NRECISMDYK | 2027 | 2000.00 | 10 |
| 1502 | HPV | 16 | 3 | 14 | B7 | NPGDCPPLEL | 2028 | 120.00 | 10 |
| 1503 | HPV | 16 | 3 | 14 | B*5102 | NPGDCPPLEL | 2028 | 100.00 | 10 |
| 1504 | HPV | 16 | 3 | 14 | B*5102 | CPPLELINTV | 2029 | 266.20 | 10 |
| 1505 | HPV | 16 | 3 | 14 | B*5102 | PPLELINTVI | 2030 | 145.20 | 10 |
| 1506 | HPV | 16 | 3 | 14 | Cw*0401 | GFGAMDFTTL | 2031 | 200.00 | 10 |
| 1507 | HPV | 16 | 3 | 14 | B*2705 | LQANKSEVPL | 2032 | 200.00 | 10 |
| 1508 | HPV | 16 | 3 | 14 | A1 | VSEPYGDSLF | 2033 | 135.00 | 10 |
| 1509 | HPV | 16 | 3 | 14 | Cw*0401 | LFFYLRREQM | 2034 | 110.00 | 10 |
| 1510 | HPV | 16 | 3 | 14 | Cw*0401 | FFYLRREQMF | 2035 | 110.00 | 10 |

TABLE 7-continued

| No | Species | Strain type | Frame | ORF | HLA | Seq | Seq ID No. | Score | Length |
|---|---|---|---|---|---|---|---|---|---|
| 1511 | HPV | 16 | 3 | 14 | B*2705 | LRREQMFVRH | 2036 | 200.00 | 10 |
| 1512 | HPV | 16 | 3 | 14 | B*2705 | RREQMFVRHL | 2037 | 1800.00 | 10 |
| 1513 | HPV | 16 | 3 | 14 | B*2705 | QMFVRHLFNR | 2038 | 125.00 | 10 |
| 1514 | HPV | 16 | 3 | 14 | B*2705 | VRHLFNRAGT | 2039 | 200.00 | 10 |
| 1515 | HPV | 16 | 3 | 14 | B*2705 | NRAGTVGENV | 2040 | 600.00 | 10 |
| 1516 | HPV | 16 | 3 | 14 | Cw*0401 | NYFPTPSGSM | 2041 | 132.00 | 10 |
| 1517 | HPV | 16 | 3 | 14 | B*2705 | AQIFNKPYWL | 2042 | 200.00 | 10 |
| 1518 | HPV | 16 | 3 | 14 | B*2705 | QRAQGHNNGI | 2043 | 600.00 | 10 |
| 1519 | HPV | 16 | 3 | 14 | B*2705 | TRSTNMSLCA | 2044 | 200.00 | 10 |
| 1520 | HPV | 16 | 3 | 14 | B*2705 | KEYLRHGEEY | 2045 | 225.00 | 10 |
| 1521 | HPV | 16 | 3 | 14 | Cw*0401 | EYDLQFIFQL | 2046 | 600.00 | 10 |
| 1522 | HPV | 16 | 3 | 14 | A24 | EYDLQFIFQL | 2046 | 200.00 | 10 |
| 1523 | HPV | 16 | 3 | 14 | B*2705 | LQFIFQLCKI | 2047 | 300.00 | 10 |
| 1524 | HPV | 16 | 3 | 14 | A*0201 | TLTADVMTYI | 2048 | 131.97 | 10 |
| 1525 | HPV | 16 | 3 | 14 | A*0201 | TILEDWNFGL | 2049 | 258.44 | 10 |
| 1526 | HPV | 16 | 3 | 14 | B*2702 | YRFVTQAIAC | 2050 | 100.00 | 10 |
| 1527 | HPV | 16 | 3 | 14 | B*2705 | YRFVTQAIAC | 2050 | 1000.00 | 10 |
| 1528 | HPV | 16 | 3 | 14 | A68.1 | FVTQAIACQK | 2051 | 120.00 | 10 |
| 1529 | HPV | 16 | 3 | 14 | B*2705 | CQKHTPPAPK | 2052 | 200.00 | 10 |
| 1530 | HPV | 16 | 3 | 14 | Cw*0401 | QFPLGRKFLL | 2053 | 220.00 | 10 |
| 1531 | HPV | 16 | 3 | 14 | B*2705 | GRKFLLQAGL | 2054 | 2000.00 | 10 |
| 1532 | HPV | 16 | 3 | 14 | B*2705 | KRKATPTTSS | 2055 | 600.00 | 10 |
| 1533 | HPV | 16 | 3 | 15 | Cw*0401 | FFTLHYVQL | 2056 | 220.00 | 9 |
| 1534 | HPV | 16 | 3 | 15 | A*0201 | YVQLLNHYV | 2057 | 153.97 | 9 |
| 1535 | HPV | 16 | 3 | 15 | A*0201 | LLNHYVHCV | 2058 | 271.95 | 9 |
| 1536 | HPV | 16 | 3 | 15 | A*0201 | CLPTIPLFFT | 2059 | 546.75 | 10 |
| 1537 | HPV | 16 | 3 | 15 | B*5102 | LPTIPLFFTL | 2060 | 110.00 | 10 |
| 1538 | HPV | 16 | 3 | 15 | B*5102 | IPLFFTLHYV | 2061 | 726.00 | 10 |
| 1539 | HPV | 116 | 3 | 15 | Cw*0401 | LFFTLHYVQL | 2062 | 220.00 | 10 |
| 1540 | HPV | 16 | 3 | 15 | Cw*0401 | FFTLHYVQLL | 2063 | 400.00 | 10 |
| 1541 | HPV | 16 | 3 | 15 | A*0201 | QLLNHYVHCV | 2064 | 591.89 | 10 |
| 1542 | HPV | 16 | 3 | 2 | B*5102 | MGIHMLYV | 2065 | 132.00 | 8 |
| 1543 | HPV | 16 | 3 | 2 | B*5201 | MGIHMLYVI | 2066 | 272.25 | 9 |
| 1544 | HPV | 16 | 3 | 2 | B*5102 | MGIHMLYVI | 2066 | 264.00 | 9 |
| 1545 | HPV | 16 | 3 | 3 | B*2705 | CRGCSGKK | 2067 | 600.00 | 8 |
| 1546 | HPV | 16 | 3 | 3 | A68.1 | MVLCRGCSGK | 2068 | 240.00 | 10 |
| 1547 | HPV | 16 | 3 | 3 | B*2705 | CRGCSGKKNR | 2069 | 300.00 | 10 |
| 1548 | HPV | 16 | 3 | 4 | B*5102 | YGVSFSEL | 2070 | 132.00 | 8 |
| 1549 | HPV | 16 | 3 | 4 | B*2705 | VRPFKSNK | 2071 | 2000.00 | 8 |
| 1550 | HPV | 16 | 3 | 4 | B*5102 | TPSIADSI | 2072 | 400.00 | 8 |
| 1551 | HPV | 16 | 3 | 4 | B*2705 | LQQYCLYL | 2073 | 200.00 | 8 |
| 1552 | HPV | 16 | 3 | 4 | B*2705 | QQYCLYLH | 2074 | 100.00 | 8 |
| 1553 | HPV | 16 | 3 | 4 | B*5102 | LACSWGMV | 2075 | 100.00 | 8 |
| 1554 | HPV | 16 | 3 | 4 | B*2705 | VRYKCGKN | 2076 | 300.00 | 8 |
| 1555 | HPV | 16 | 3 | 4 | B*2705 | NRETIEKL | 2077 | 600.00 | 8 |
| 1556 | HPV | 16 | 3 | 4 | B*2705 | LRSTAAAL | 1709 | 2000.00 | 8 |
| 1557 | HPV | 16 | 3 | 4 | B*2705 | QRQTVLQH | 1710 | 200.00 | 8 |
| 1558 | HPV | 16 | 3 | 4 | B*2705 | SQMVQWAY | 1711 | 100.00 | 8 |
| 1559 | HPV | 16 | 3 | 4 | B*5102 | WAYDNDIV | 1712 | 550.00 | 8 |
| 1560 | HPV | 16 | 3 | 4 | B*5102 | IAYKYAQL | 1713 | 302.50 | 8 |
| 1561 | HPV | 16 | 3 | 4 | B*2705 | KRAEKKQM | 1714 | 1800.00 | 8 |
| 1562 | HPV | 16 | 3 | 4 | B*2705 | KQIVMFLR | 1715 | 300.00 | 8 |
| 1563 | HPV | 16 | 3 | 4 | B*2705 | LRYQGVEF | 1716 | 5000.00 | 8 |
| 1564 | HPV | 16 | 3 | 4 | B*2705 | KRFLQGIP | 1717 | 300.00 | 8 |
| 1565 | HPV | 16 | 3 | 4 | B*2705 | LQGSVICF | 1718 | 100.00 | 8 |
| 1566 | HPV | 16 | 3 | 4 | B*3901 | SHFWLQPL | 1719 | 180.00 | 8 |
| 1567 | HPV | 16 | 3 | 4 | B*2705 | LQPLADAK | 1720 | 200.00 | 8 |
| 1568 | HPV | 16 | 3 | 4 | B*5102 | QPLADAKI | 1721 | 1320.00 | 8 |
| 1569 | HPV | 16 | 3 | 4 | B*2705 | WNYIDDNL | 1722 | 100.00 | 8 |
| 1570 | HPV | 16 | 3 | 4 | B*2705 | LRNALDGN | 1723 | 200.00 | 8 |
| 1571 | HPV | 16 | 3 | 4 | B*5102 | NALDGNLV | 1724 | 363.00 | 8 |
| 1572 | HPV | 16 | 3 | 4 | B*2705 | HRPLVQLK | 1725 | 2000.00 | 8 |
| 1573 | HPV | 16 | 3 | 4 | B*2705 | VQLKCPPL | 1726 | 200.00 | 8 |
| 1574 | HPV | 16 | 3 | 4 | B*2705 | SRWPYLHN | 1727 | 1000.00 | 8 |
| 1575 | HPV | 16 | 3 | 4 | B*5102 | WPYLHNRL | 1728 | 665.50 | 8 |
| 1576 | HPV | 16 | 3 | 4 | B*2705 | NRLVVFTF | 1729 | 1000.00 | 8 |
| 1577 | HPV | 16 | 3 | 4 | B*2705 | SRTWSRLS | 1730 | 200.00 | 8 |
| 1578 | HPV | 16 | 3 | 4 | B*2705 | RTWSRLSL | 1731 | 150.00 | 8 |
| 1579 | HPV | 16 | 3 | 4 | B*2705 | GRHETETPC | 2078 | 200.00 | 9 |
| 1580 | HPV | 16 | 3 | 4 | A1 | ETETPCSQY | 2079 | 112.50 | 9 |
| 1581 | HPV | 16 | 3 | 4 | B*5102 | EGVSERHTI | 2080 | 264.00 | 9 |
| 1582 | HPV | 16 | 3 | 4 | B*2705 | CQTPLTNIL | 2081 | 200.00 | 9 |
| 1583 | HPV | 16 | 3 | 4 | B*5102 | TPLTNILNV | 2082 | 798.60 | 9 |
| 1584 | HPV | 16 | 3 | 4 | A68.1 | NVLKTSNAK | 2083 | 240.00 | 9 |
| 1585 | HPV | 16 | 3 | 4 | A*0201 | AMLAKFKEL | 2084 | 108.46 | 9 |
| 1586 | HPV | 16 | 3 | 4 | Cw*0301 | AMLAKFKEL | 2084 | 120.00 | 9 |

TABLE 7-continued

| No | Species | Strain type | Frame | ORF | HLA | Seq | Seq ID No. | Score | Length |
|---|---|---|---|---|---|---|---|---|---|
| 1587 | HPV | 16 | 3 | 4 | A24 | LYGVSFSEL | 2085 | 264.00 | 9 |
| 1588 | HPV | 16 | 3 | 4 | Cw*0401 | LYGVSFSEL | 2085 | 200.00 | 9 |
| 1589 | HPV | 16 | 3 | 4 | B*5102 | YGVSFSELV | 2086 | 264.00 | 9 |
| 1590 | HPV | 16 | 3 | 4 | A68.1 | GVSFSELVR | 2087 | 300.00 | 9 |
| 1591 | HPV | 16 | 3 | 4 | Cw*0401 | SFSELVRPF | 2088 | 240.00 | 9 |
| 1592 | HPV | 16 | 3 | 4 | A68.1 | LVRPFKSNK | 2089 | 180.00 | 9 |
| 1593 | HPV | 16 | 3 | 4 | B*2705 | VRPFKSNKS | 2090 | 200.00 | 9 |
| 1594 | HPV | 16 | 3 | 4 | B*5103 | AAFGLTPSI | 2091 | 145.20 | 9 |
| 1595 | HPV | 16 | 3 | 4 | B*5102 | AAFGLTPSI | 2091 | 1210.00 | 9 |
| 1596 | HPV | 16 | 3 | 4 | A*0201 | LLQQYCLYL | 2092 | 199.74 | 9 |
| 1597 | HPV | 16 | 3 | 4 | B*2705 | QQYCLYLHI | 2093 | 300.00 | 9 |
| 1598 | HPV | 16 | 3 | 4 | B*5201 | QQYCLYLHI | 2093 | 100.00 | 9 |
| 1599 | HPV | 16 | 3 | 4 | A*0201 | CLYLHIQSL | 2094 | 157.23 | 9 |
| 1600 | HPV | 16 | 3 | 4 | B*2705 | CLYLHIQSL | 2094 | 150.00 | 9 |
| 1601 | HPV | 16 | 3 | 4 | B*5103 | LACSWGMVV | 2095 | 110.00 | 9 |
| 1602 | HPV | 16 | 3 | 4 | B*5102 | LACSWGMVV | 2095 | 100.00 | 9 |
| 1603 | HPV | 16 | 3 | 4 | A68.1 | VVLLLVRYK | 2096 | 240.00 | 9 |
| 1604 | HPV | 16 | 3 | 4 | B*2705 | VRYKCGKNR | 2097 | 1500.00 | 9 |
| 1605 | HPV | 16 | 3 | 4 | B*2705 | NRETIEKLL | 2098 | 600.00 | 9 |
| 1606 | HPV | 16 | 3 | 4 | A68.1 | ETIEKLLSK | 2099 | 180.00 | 9 |
| 1607 | HPV | 16 | 3 | 4 | B60 | IEKLLSKLL | 2100 | 176.00 | 9 |
| 1608 | HPV | 16 | 3 | 4 | A*0201 | KLLSKLLCV | 2101 | 2071.61 | 9 |
| 1609 | HPV | 16 | 3 | 4 | B*2702 | LRSTAAALY | 1732 | 200.00 | 9 |
| 1610 | HPV | 16 | 3 | 4 | B*2705 | LRSTAAALY | 1732 | 1000.00 | 9 |
| 1611 | HPV | 16 | 3 | 4 | B*5801 | RSTAAALYW | 1733 | 264.00 | 9 |
| 1612 | HPV | 16 | 3 | 4 | B*5102 | TGISNISEV | 1734 | 145.20 | 9 |
| 1613 | HPV | 16 | 3 | 4 | B*2705 | QRQTVLQHS | 1735 | 200.00 | 9 |
| 1614 | HPV | 16 | 3 | 4 | B*2705 | RQTVLQHSF | 1736 | 300.00 | 9 |
| 1615 | HPV | 16 | 3 | 4 | B62 | RQTVLQHSF | 1736 | 160.00 | 9 |
| 1616 | HPV | 16 | 3 | 4 | Cw*0401 | SFNDCTFEL | 1737 | 240.00 | 9 |
| 1617 | HPV | 16 | 3 | 4 | B*2705 | VQWAYDNDI | 1738 | 300.00 | 9 |
| 1618 | HPV | 16 | 3 | 4 | A1 | IVDDSEIAY | 1739 | 125.00 | 9 |
| 1619 | HPV | 16 | 3 | 4 | A68.1 | ATMCRHYKR | 1740 | 100.00 | 9 |
| 1620 | HPV | 16 | 3 | 4 | B*2705 | CRHYKRAEK | 1741 | 2000.00 | 9 |
| 1621 | HPV | 16 | 3 | 4 | B*2705 | KRAEKKQMS | 1742 | 600.00 | 9 |
| 1622 | HPV | 16 | 3 | 4 | B*2705 | KQMSMSQWI | 1743 | 180.00 | 9 |
| 1623 | HPV | 16 | 3 | 4 | A68.1 | RVDDGGDWK | 1744 | 120.00 | 9 |
| 1624 | HPV | 16 | 3 | 4 | B*2705 | KQIVMFLRY | 1745 | 300.00 | 9 |
| 1625 | HPV | 16 | 3 | 4 | A*0201 | VMFLRYQGV | 1746 | 473.94 | 9 |
| 1626 | HPV | 16 | 3 | 4 | B62 | FLRYQGVEF | 1747 | 144.00 | 9 |
| 1627 | HPV | 16 | 3 | 4 | B*2702 | LRYQGVEFM | 1748 | 100.00 | 9 |
| 1628 | HPV | 16 | 3 | 4 | B*2705 | LRYQGVEFM | 1748 | 3000.00 | 9 |
| 1629 | HPV | 16 | 3 | 4 | B*2705 | YQGVEFMSF | 1749 | 100.00 | 9 |
| 1630 | HPV | 16 | 3 | 4 | B62 | YQGVEFMSF | 1749 | 160.00 | 9 |
| 1631 | HPV | 16 | 3 | 4 | Cw*0401 | EFMSFLTAL | 1750 | 400.00 | 9 |
| 1632 | HPV | 16 | 3 | 4 | Cw*0401 | SFLTALKRF | 1751 | 220.00 | 9 |
| 1633 | HPV | 16 | 3 | 4 | A*0201 | FLTALKRFL | 1752 | 108.09 | 9 |
| 1634 | HPV | 16 | 3 | 4 | B*2705 | KRFLQGIPK | 1753 | 30000.00 | 9 |
| 1635 | HPV | 16 | 3 | 4 | B*5102 | QGIPKKNCI | 1754 | 240.00 | 9 |
| 1636 | HPV | 16 | 3 | 4 | A3 | SLFGMSLMK | 1755 | 300.00 | 9 |
| 1637 | HPV | 16 | 3 | 4 | B*2705 | SLFGMSLMK | 1755 | 150.00 | 9 |
| 1638 | HPV | 16 | 3 | 4 | Cw*0401 | LFGMSLMKF | 1756 | 220.00 | 9 |
| 1639 | HPV | 16 | 3 | 4 | A*0201 | LQGSVICFV | 1757 | 151.65 | 9 |
| 1640 | HPV | 16 | 3 | 4 | A68.1 | SVICFVNSK | 1758 | 240.00 | 9 |
| 1641 | HPV | 16 | 3 | 4 | Cw*0401 | CFVNSKSHF | 1759 | 110.00 | 9 |
| 1642 | HPV | 16 | 3 | 4 | B*2705 | LRNALDGNL | 1760 | 2000.00 | 9 |
| 1643 | HPV | 16 | 3 | 4 | A68.1 | LVSMDVKHR | 1761 | 300.00 | 9 |
| 1644 | HPV | 16 | 3 | 4 | B*2705 | HRPLVQLKC | 1762 | 200.00 | 9 |
| 1645 | HPV | 16 | 3 | 4 | B*2705 | VQLKCPPLL | 1763 | 200.00 | 9 |
| 1646 | HPV | 16 | 3 | 4 | B*5102 | PPLLITSNI | 1764 | 145.20 | 9 |
| 1647 | HPV | 16 | 3 | 4 | B*2705 | SRWPYLHNR | 1765 | 5000.00 | 9 |
| 1648 | HPV | 16 | 3 | 4 | B*5103 | WPYLHNRLV | 1766 | 132.00 | 9 |
| 1649 | HPV | 16 | 3 | 4 | B*5102 | WPYLHNRLV | 1766 | 1331.00 | 9 |
| 1650 | HPV | 16 | 3 | 4 | B*2705 | KNWKSFFSR | 1767 | 150.00 | 9 |
| 1651 | HPV | 16 | 3 | 4 | Cw*0401 | FFSRTWSRL | 1768 | 240.00 | 9 |
| 1652 | HPV | 16 | 3 | 4 | B14 | SRTWSRLSL | 1769 | 100.00 | 9 |
| 1653 | HPV | 16 | 3 | 4 | B*2705 | SRTWSRLSL | 1769 | 2000.00 | 9 |
| 1654 | HPV | 16 | 3 | 4 | B*2705 | GRHETETPCS | 2102 | 200.00 | 10 |
| 1655 | HPV | 16 | 3 | 4 | B*2705 | ERHTICQTPL | 2103 | 200.00 | 10 |
| 1656 | HPV | 16 | 3 | 4 | B*5102 | TPLTNILNVL | 2104 | 330.00 | 10 |
| 1657 | HPV | 16 | 3 | 4 | Cw*0401 | TPLTNILNVL | 2104 | 160.00 | 10 |
| 1658 | HPV | 16 | 3 | 4 | B7 | AAMLAKFKEL | 2105 | 108.00 | 10 |
| 1659 | HPV | 16 | 3 | 4 | Cw*0301 | AAMLAKFKEL | 2105 | 240.00 | 10 |
| 1660 | HPV | 16 | 3 | 4 | B*5103 | LAKFKELYGV | 2106 | 100.00 | 10 |
| 1661 | HPV | 16 | 3 | 4 | Cw*0401 | KFKELYGVSF | 2107 | 132.00 | 10 |
| 1662 | HPV | 16 | 3 | 4 | Cw*0301 | ELYGVSFSEL | 2108 | 120.00 | 10 |

TABLE 7-continued

| No | Species | Strain type | Frame | ORF | HLA | Seq | Seq ID No. | Score | Length |
|---|---|---|---|---|---|---|---|---|---|
| 1663 | HPV | 16 | 3 | 4 | B*5801 | KSNKSTCCDW | 2109 | 480.00 | 10 |
| 1664 | HPV | 16 | 3 | 4 | B*5102 | IAAFGLTPSI | 2110 | 220.00 | 10 |
| 1665 | HPV | 16 | 3 | 4 | B*5103 | IAAFGLTPSI | 2110 | 110.00 | 10 |
| 1666 | HPV | 16 | 3 | 4 | A*0201 | TLLQQYCLYL | 2111 | 434.72 | 10 |
| 1667 | HPV | 16 | 3 | 4 | A68.1 | MVVLLLVRYK | 2112 | 240.00 | 10 |
| 1668 | HPV | 16 | 3 | 4 | A68.1 | LVRYKCGKNR | 2113 | 200.00 | 10 |
| 1669 | HPV | 16 | 3 | 4 | B*2705 | VRYKCGKNRE | 2114 | 100.00 | 10 |
| 1670 | HPV | 16 | 3 | 4 | B*2705 | NRETIEKLLS | 2115 | 200.00 | 10 |
| 1671 | HPV | 16 | 3 | 4 | B62 | KLRSTAAALY | 1770 | 120.00 | 10 |
| 1672 | HPV | 16 | 3 | 4 | B*2702 | LRSTAAALYW | 1771 | 100.00 | 10 |
| 1673 | HPV | 16 | 3 | 4 | B*2705 | LRSTAAALYW | 1771 | 200.00 | 10 |
| 1674 | HPV | 16 | 3 | 4 | B*5102 | AALYWYKTGI | 1772 | 600.00 | 10 |
| 1675 | HPV | 16 | 3 | 4 | B*5103 | AALYWYKTGI | 1772 | 132.00 | 10 |
| 1676 | HPV | 16 | 3 | 4 | B*5102 | TPEWIQRQTV | 1773 | 133.10 | 10 |
| 1677 | HPV | 16 | 3 | 4 | B*2702 | QRQTVLQHSF | 1774 | 200.00 | 10 |
| 1678 | HPV | 16 | 3 | 4 | B*2705 | QRQTVLQHSF | 1774 | 1000.00 | 10 |
| 1679 | HPV | 16 | 3 | 4 | B*2705 | LQHSFNDCTF | 1775 | 100.00 | 10 |
| 1680 | HPV | 16 | 3 | 4 | B*2705 | VQWAYDNDIV | 1776 | 300.00 | 10 |
| 1681 | HPV | 16 | 3 | 4 | B*5201 | VQWAYDNDIV | 1776 | 990.00 | 10 |
| 1682 | HPV | 16 | 3 | 4 | A68.1 | IVDDSEIAYK | 1777 | 120.00 | 10 |
| 1683 | HPV | 16 | 3 | 4 | B60 | SEIAYKYAQL | 1778 | 352.00 | 10 |
| 1684 | HPV | 16 | 3 | 4 | Cw*0301 | SEIAYKYAQL | 1778 | 100.00 | 10 |
| 1685 | HPV | 16 | 3 | 4 | A68.1 | IVKDCATMCR | 1779 | 200.00 | 10 |
| 1686 | HPV | 16 | 3 | 4 | B*2705 | CRHYKRAEKK | 1780 | 2000.00 | 10 |
| 1687 | HPV | 16 | 3 | 4 | Cw*0401 | HYKRAEKKQM | 1781 | 100.00 | 10 |
| 1688 | HPV | 16 | 3 | 4 | B*2705 | KRAEKKQMSM | 1782 | 1800.00 | 10 |
| 1689 | HPV | 16 | 3 | 4 | B*2705 | KQMSMSQWIK | 1783 | 600.00 | 10 |
| 1690 | HPV | 16 | 3 | 4 | B*2705 | SQWIKYRCDR | 1784 | 500.00 | 10 |
| 1691 | HPV | 16 | 3 | 4 | B*2705 | DRVDDGGDWK | 1785 | 200.00 | 10 |
| 1692 | HPV | 16 | 3 | 4 | B*3701 | GDWKQIVMFL | 1786 | 300.00 | 10 |
| 1693 | HPV | 16 | 3 | 4 | Cw*0401 | MFLRYQGVEF | 1787 | 100.00 | 10 |
| 1694 | HPV | 16 | 3 | 4 | B*2705 | LRYQGVEFMS | 1788 | 1000.00 | 10 |
| 1695 | HPV | 16 | 3 | 4 | Cw*0401 | RYQGVEFMSF | 1789 | 110.00 | 10 |
| 1696 | HPV | 16 | 3 | 4 | A24 | RYQGVEFMSF | 1789 | 360.00 | 10 |
| 1697 | HPV | 16 | 3 | 4 | A*0201 | YQGVEFMSFL | 1790 | 478.93 | 10 |
| 1698 | HPV | 16 | 3 | 4 | B*2705 | YQGVEFMSFL | 1790 | 200.00 | 10 |
| 1699 | HPV | 16 | 3 | 4 | B*2705 | VEFMSFLTAL | 1791 | 150.00 | 10 |
| 1700 | HPV | 16 | 3 | 4 | B60 | VEFMSFLTAL | 1791 | 160.00 | 10 |
| 1701 | HPV | 16 | 3 | 4 | Cw*0401 | SFLTALKRFL | 1792 | 200.00 | 10 |
| 1702 | HPV | 16 | 3 | 4 | B*5102 | TALKRFLQGI | 1793 | 726.00 | 10 |
| 1703 | HPV | 16 | 3 | 4 | B*5103 | TALKRFLQGI | 1793 | 132.00 | 10 |
| 1704 | HPV | 16 | 3 | 4 | B*2705 | KRFLQGIPKK | 1794 | 30000.00 | 10 |
| 1705 | HPV | 16 | 3 | 4 | Cw*0301 | QGIPKKNCIL | 1795 | 100.00 | 10 |
| 1706 | HPV | 16 | 3 | 4 | B*3501 | IPKKNCILLY | 1796 | 120.00 | 10 |
| 1707 | HPV | 16 | 3 | 4 | A3 | LLYGAANTGK | 1797 | 150.00 | 10 |
| 1708 | HPV | 16 | 3 | 4 | B*2705 | LLYGAANTGK | 1797 | 150.00 | 10 |
| 1709 | HPV | 16 | 3 | 4 | Cw*0401 | LFGMSLMKFL | 1798 | 240.00 | 10 |
| 1710 | HPV | 16 | 3 | 4 | Cw*0401 | KFLQGSVICF | 1799 | 200.00 | 10 |
| 1711 | HPV | 16 | 3 | 4 | A*0201 | FLQGSVICFV | 1800 | 4047.23 | 10 |
| 1712 | HPV | 16 | 3 | 4 | A*0201 | FVNSKSHFWL | 1801 | 274.29 | 10 |
| 1713 | HPV | 16 | 3 | 4 | B*5102 | DATVPCWNYI | 1802 | 220.00 | 10 |
| 1714 | HPV | 16 | 3 | 4 | B*5103 | DATVPCWNYI | 1802 | 121.00 | 10 |
| 1715 | HPV | 16 | 3 | 4 | B*2705 | LRNALDGNLV | 1803 | 600.00 | 10 |
| 1716 | HPV | 16 | 3 | 4 | B*5102 | CPPLLITSNI | 1804 | 484.00 | 10 |
| 1717 | HPV | 16 | 3 | 4 | B*2702 | SRWPYLHNRL | 1805 | 300.00 | 10 |
| 1718 | HPV | 16 | 3 | 4 | B*2705 | SRWPYLHNRL | 1805 | 10000.00 | 10 |
| 1719 | HPV | 16 | 3 | 4 | B*5102 | WPYLHNRLVV | 1806 | 1210.00 | 10 |
| 1720 | HPV | 16 | 3 | 4 | B*5103 | WPYLHNRLVV | 1806 | 145.20 | 10 |
| 1721 | HPV | 16 | 3 | 4 | B*5201 | WPYLHNRLVV | 1806 | 300.00 | 10 |
| 1722 | HPV | 16 | 3 | 4 | A*0201 | YLHNRLVVFT | 1807 | 433.63 | 10 |
| 1723 | HPV | 16 | 3 | 4 | B*2705 | NRLVVFTFPN | 1808 | 200.00 | 10 |
| 1724 | HPV | 16 | 3 | 4 | Cw*0401 | VFTFPNEFPF | 1809 | 100.00 | 10 |
| 1725 | HPV | 16 | 3 | 4 | B*5102 | FPFDENGNPV | 1810 | 2200.00 | 10 |
| 1726 | HPV | 16 | 3 | 4 | B60 | DENGNPVYEL | 1811 | 320.00 | 10 |
| 1727 | HPV | 16 | 3 | 4 | Cw*0401 | SFFSRTWSRL | 1812 | 240.00 | 10 |
| 1728 | HPV | 16 | 3 | 4 | B*2705 | SRTWSRLSLH | 1813 | 200.00 | 10 |
| 1729 | HPV | 16 | 3 | 4 | A*0201 | YLLQGQRNGI | 2116 | 177.57 | 10 |
| 1730 | HPV | 16 | 3 | 5 | B*2705 | MQYNALYK | 2117 | 1000.00 | 8 |
| 1731 | HPV | 16 | 3 | 7 | B*2705 | MQYNALYKL | 2118 | 1000.00 | 9 |
| 1732 | HPV | 16 | 3 | 7 | A*0201 | ALYKLDTYI | 2119 | 183.62 | 9 |
| 1733 | HPV | 16 | 3 | 7 | Cw*0301 | YKLDTYIYL | 2120 | 100.00 | 9 |
| 1734 | HPV | 16 | 3 | 7 | B*5102 | NALYKLDTYI | 2121 | 660.00 | 10 |
| 1735 | HPV | 16 | 3 | 7 | B*5103 | NALYKLDTYI | 2121 | 120.00 | 10 |
| 1736 | HPV | 16 | 3 | 7 | Cw*0401 | LYKLDTYIYL | 2122 | 240.00 | 10 |
| 1737 | HPV | 16 | 3 | 7 | A24 | LYKLDTYIYL | 2122 | 200.00 | 10 |
| 1738 | HPV | 16 | 3 | 9 | B*3701 | LDTASTTLL | 2123 | 200.00 | 9 |

TABLE 7-continued

| No | Species | Strain type | Frame | ORF | HLA | Seq | Seq ID No. | Score | Length |
|---|---|---|---|---|---|---|---|---|---|
| 1739 | HPV | 16 | 3 | 9 | B*5103 | LACFLLCFV | 1814 | 100.00 | 9 |
| 1740 | HPV | 16 | 3 | 9 | B*5102 | LACFLLCFV | 1814 | 100.00 | 9 |
| 1741 | HPV | 16 | 3 | 9 | Cw*0401 | CFLLCFVCF | 1815 | 100.00 | 9 |
| 1742 | HPV | 16 | 3 | 9 | A*0201 | FLLCFVCFC | 1816 | 4064.58 | 9 |
| 1743 | HPV | 16 | 3 | 9 | A*0201 | LLCFVCFCV | 1817 | 685.78 | 9 |
| 1744 | HPV | 16 | 3 | 9 | A*0201 | LLACFLLCFV | 2124 | 1495.72 | 10 |
| 1745 | HPV | 16 | 3 | 9 | A*0201 | FLLCFVCFCV | 1818 | 6865.90 | 10 |
| 1746 | HPV | 16 | 3 | 11 | B*2705 | HQHLYLPF | 1863 | 100.00 | 8 |
| 1747 | HPV | 16 | 3 | 11 | B*5102 | FPQMYQDL | 1864 | 220.00 | 8 |
| 1748 | HPV | 16 | 3 | 11 | B*2705 | QMYQDLVL | 1865 | 250.00 | 8 |
| 1749 | HPV | 16 | 3 | 11 | B*2705 | YQDLVLLL | 1866 | 200.00 | 8 |
| 1750 | HPV | 16 | 3 | 11 | B*2705 | LQLIPHLL | 1867 | 200.00 | 8 |
| 1751 | HPV | 16 | 3 | 11 | A*0201 | MLVHQHLYL | 2125 | 199.74 | 9 |
| 1752 | HPV | 16 | 3 | 11 | B*5102 | FPQMYQDLV | 1868 | 440.00 | 9 |
| 1753 | HPV | 16 | 3 | 11 | A*0201 | QMYQDLVLL | 1869 | 113.55 | 9 |
| 1754 | HPV | 16 | 3 | 11 | B*2705 | QMYQDLVLL | 1869 | 250.00 | 9 |
| 1755 | HPV | 16 | 3 | 11 | A24 | MYQDLVLLL | 1870 | 432.00 | 9 |
| 1756 | HPV | 16 | 3 | 11 | Cw*0401 | MYQDLVLLL | 1870 | 480.00 | 9 |
| 1757 | HPV | 16 | 3 | 11 | A*0201 | LLLQLIPHL | 1871 | 309.05 | 9 |
| 1758 | HPV | 16 | 3 | 11 | B*2705 | LQLIPHLLY | 1872 | 100.00 | 9 |
| 1759 | HPV | 16 | 3 | 11 | B*5102 | LPFPQMYQDL | 1873 | 550.00 | 10 |
| 1760 | HPV | 16 | 3 | 11 | Cw*0301 | LPFPQMYQDL | 1873 | 180.00 | 10 |
| 1761 | HPV | 16 | 3 | 11 | Cw*0401 | LPFPQMYQDL | 1873 | 105.60 | 10 |
| 1762 | HPV | 16 | 3 | 11 | B*5102 | FPQMYQDLVL | 1874 | 220.00 | 10 |
| 1763 | HPV | 16 | 3 | 11 | A*0201 | QMYQDLVLLL | 1875 | 113.55 | 10 |
| 1764 | HPV | 16 | 3 | 11 | B*2705 | QMYQDLVLLL | 1875 | 250.00 | 10 |
| 1765 | HPV | 16 | 3 | 11 | B*2705 | YQDLVLLLQL | 1876 | 200.00 | 10 |
| 1766 | HPV | 16 | 3 | 11 | B*3701 | QDLVLLLQLI | 1877 | 200.00 | 10 |
| 1767 | HPV | 16 | 3 | 11 | A*0201 | VLLLQLIPHL | 1878 | 309.05 | 10 |
| 1768 | HPV | 16 | 3 | 11 | A*0201 | LLLQLIPHLL | 1879 | 134.37 | 10 |
| 1769 | HPV | 16 | 3 | 12 | B*2705 | FLWIHLLL | 1884 | 150.00 | 8 |
| 1770 | HPV | 16 | 3 | 12 | Cw*0401 | KFLWIHLLL | 1890 | 200.00 | 9 |
| 1771 | HPV | 16 | 3 | 12 | A*0201 | FLWIHLLLA | 1891 | 436.26 | 9 |
| 1772 | HPV | 16 | 3 | 12 | B*3901 | IHLLLAQTL | 1892 | 180.00 | 9 |
| 1773 | HPV | 16 | 3 | 14 | Cw*0301 | MWIIHYIFL | 2126 | 100.00 | 9 |
| 1774 | HPV | 16 | 3 | 14 | A*0201 | WIIHYIFLV | 2127 | 586.85 | 9 |
| 1775 | HPV | 16 | 3 | 14 | A*0201 | YIFLVMIIV | 2128 | 153.49 | 9 |
| 1776 | HPV | 16 | 3 | 14 | B*5201 | YIFLVMIIV | 2128 | 120.00 | 9 |
| 1777 | HPV | 16 | 3 | 14 | Cw*0401 | IFLVMIIVL | 2129 | 440.00 | 9 |
| 1778 | HPV | 16 | 3 | 14 | A*0201 | FLVMIIVLI | 2130 | 110.38 | 9 |
| 1779 | HPV | 16 | 3 | 14 | A*0205 | YIFLVMIIVL | 2131 | 126.00 | 10 |
| 1780 | HPV | 16 | 3 | 15 | B*2705 | MQPHLLLL | 2132 | 200.00 | 8 |
| 1781 | HPV | 16 | 3 | 15 | B*5102 | QPHLLLLI | 2133 | 440.00 | 8 |
| 1782 | HPV | 16 | 3 | 15 | B*2705 | LQILLQPR | 2134 | 100.00 | 8 |
| 1783 | HPV | 16 | 3 | 15 | B*2705 | LQPRYHLY | 2135 | 100.00 | 8 |
| 1784 | HPV | 16 | 3 | 15 | B*2705 | PRYHLYPL | 2136 | 1000.00 | 8 |
| 1785 | HPV | 16 | 3 | 15 | B*3901 | YHLYPLHL | 2137 | 270.00 | 8 |
| 1786 | HPV | 16 | 3 | 15 | B*5102 | YPLHLYQV | 1904 | 1452.00 | 8 |
| 1787 | HPV | 16 | 3 | 15 | B*2705 | HLYQVIFL | 1905 | 150.00 | 8 |
| 1788 | HPV | 16 | 3 | 15 | B*2705 | LQIQQFLL | 1906 | 200.00 | 8 |
| 1789 | HPV | 16 | 3 | 15 | B*2705 | QQFLLVVH | 1907 | 100.00 | 8 |
| 1790 | HPV | 16 | 3 | 15 | Cw*0401 | QPHLLLLIM | 2138 | 120.00 | 9 |
| 1791 | HPV | 16 | 3 | 15 | A*0201 | LLLLIMDYM | 2139 | 193.70 | 9 |
| 1792 | HPV | 16 | 3 | 15 | A*0201 | LIMDYMIFM | 2140 | 222.85 | 9 |
| 1793 | HPV | 16 | 3 | 15 | B*2705 | MQMTLLQIL | 2141 | 200.00 | 9 |
| 1794 | HPV | 16 | 3 | 15 | B*2705 | LQILLQPRY | 2142 | 100.00 | 9 |
| 1795 | HPV | 16 | 3 | 15 | B62 | LQILLQPRY | 2142 | 160.00 | 9 |
| 1796 | HPV | 16 | 3 | 15 | A*0201 | ILLQPRYHL | 2143 | 134.37 | 9 |
| 1797 | HPV | 16 | 3 | 15 | B7 | QPRYHLYPL | 2144 | 800.00 | 9 |
| 1798 | HPV | 16 | 3 | 15 | Cw*0401 | QPRYHLYPL | 2144 | 176.00 | 9 |
| 1799 | HPV | 16 | 3 | 15 | B*2705 | PRYHLYPLH | 2145 | 100.00 | 9 |
| 1800 | HPV | 16 | 3 | 15 | A24 | RYHLYPLHL | 2146 | 400.00 | 9 |
| 1801 | HPV | 16 | 3 | 15 | Cw*0401 | RYHLYPLHL | 2146 | 330.00 | 9 |
| 1802 | HPV | 16 | 3 | 15 | B*5201 | YPLHLYQVI | 1908 | 220.00 | 9 |
| 1803 | HPV | 16 | 3 | 15 | B*5102 | YPLHLYQVI | 1908 | 2904.00 | 9 |
| 1804 | HPV | 16 | 3 | 15 | B*3901 | LHLYQVIFL | 1909 | 270.00 | 9 |
| 1805 | HPV | 16 | 3 | 15 | A24 | LYQVIFLQI | 1910 | 126.00 | 9 |
| 1806 | HPV | 16 | 3 | 15 | Cw*0401 | IFLQIQQFL | 1911 | 200.00 | 9 |
| 1807 | HPV | 16 | 3 | 15 | A*0201 | FLQIQQFLL | 1912 | 569.95 | 9 |
| 1808 | HPV | 16 | 3 | 15 | B*2705 | QQFLLVVHT | 1913 | 100.00 | 9 |
| 1809 | HPV | 16 | 3 | 15 | A*0201 | LLVVHTIFL | 1914 | 199.74 | 9 |
| 1810 | HPV | 16 | 3 | 15 | B*5201 | MQPHLLLLIM | 2147 | 198.00 | 10 |
| 1811 | HPV | 16 | 3 | 15 | A*0201 | LLIMDYMIFM | 2148 | 106.84 | 10 |
| 1812 | HPV | 16 | 3 | 15 | Cw*0401 | DYMIFMQMTL | 2149 | 220.00 | 10 |
| 1813 | HPV | 16 | 3 | 15 | A24 | DYMIFMQMTL | 2149 | 300.00 | 10 |
| 1814 | HPV | 16 | 3 | 15 | A*0201 | YMIFMQMTLL | 2150 | 163.23 | 10 |

TABLE 7-continued

| No | Species | Strain type | Frame | ORF | HLA | Seq | Seq ID No. | Score | Length |
|---|---|---|---|---|---|---|---|---|---|
| 1815 | HPV | 16 | 3 | 15 | B*2705 | MQMTLLQILL | 2151 | 200.00 | 10 |
| 1816 | HPV | 16 | 3 | 15 | B*2705 | LQPRYHLYPL | 2152 | 200.00 | 10 |
| 1817 | HPV | 16 | 3 | 15 | B*2705 | PRYHLYPLHL | 2153 | 1000.00 | 10 |
| 1818 | HPV | 16 | 3 | 15 | A24 | LYPLHLYQVI | 1915 | 108.00 | 10 |
| 1819 | HPV | 16 | 3 | 15 | A*0201 | VIFLQIQQFL | 1916 | 101.62 | 10 |
| 1820 | HPV | 16 | 3 | 15 | Cw*0401 | IFLQIQQFLL | 1917 | 200.00 | 10 |
| 1821 | HPV | 16 | 3 | 15 | A*0201 | FLQIQQFLLV | 1918 | 607.88 | 10 |
| 1822 | HPV | 16 | 3 | 15 | B*5201 | LQIQQFLLVV | 1919 | 495.00 | 10 |
| 1823 | HPV | 16 | 3 | 15 | B*2705 | QQFLLVVHTI | 1920 | 300.00 | 10 |
| 1824 | HPV | 16 | 3 | 15 | B*5201 | QQFLLVVHTI | 1920 | 120.00 | 10 |
| 1825 | HPV | 16 | 3 | 15 | Cw*0401 | QFLLVVHTIF | 1921 | 100.00 | 10 |
| 1826 | HPV | 16 | 3 | 15 | A*0201 | FLLVVHTIFL | 1922 | 1999.73 | 10 |
| 1827 | HPV | 16 | 3 | 16 | B*2705 | ARTNIYYH | 1923 | 200.00 | 8 |
| 1828 | HPV | 16 | 3 | 16 | B*2705 | SRLLAVGH | 1924 | 200.00 | 8 |
| 1829 | HPV | 16 | 3 | 16 | B*5102 | KPNNNKIL | 1925 | 121.00 | 8 |
| 1830 | HPV | 16 | 3 | 16 | B*5201 | LQYRVFRI | 1926 | 150.00 | 8 |
| 1831 | HPV | 16 | 3 | 16 | B*2705 | YRVFRIHL | 1927 | 2000.00 | 8 |
| 1832 | HPV | 16 | 3 | 16 | B*5102 | NPDTQRLV | 1928 | 121.00 | 8 |
| 1833 | HPV | 16 | 3 | 16 | B*2705 | QRLVWACV | 1929 | 600.00 | 8 |
| 1834 | HPV | 16 | 3 | 16 | B*5102 | WACVGVEV | 1930 | 121.00 | 8 |
| 1835 | HPV | 16 | 3 | 16 | B*2705 | GRGQPLGV | 1931 | 600.00 | 8 |
| 1836 | HPV | 16 | 3 | 16 | B*2705 | KQTQLCLI | 1932 | 180.00 | 8 |
| 1837 | HPV | 16 | 3 | 16 | B*5102 | SPCTNVAV | 1933 | 242.00 | 8 |
| 1838 | HPV | 16 | 3 | 16 | B*5102 | NPGDCPPL | 1934 | 100.00 | 8 |
| 1839 | HPV | 16 | 3 | 16 | B*5102 | YPDYIKMV | 1935 | 200.00 | 8 |
| 1840 | HPV | 16 | 3 | 16 | B*2705 | LRREQMFV | 1936 | 600.00 | 8 |
| 1841 | HPV | 16 | 3 | 16 | B*2705 | RREQMFVR | 1937 | 3000.00 | 8 |
| 1842 | HPV | 16 | 3 | 16 | B*2705 | QMFVRHLF | 1938 | 125.00 | 8 |
| 1843 | HPV | 16 | 3 | 16 | B*2705 | AQIFNKPY | 1939 | 100.00 | 8 |
| 1844 | HPV | 16 | 3 | 16 | B*2705 | QRAQGHNN | 1940 | 100.00 | 8 |
| 1845 | HPV | 16 | 3 | 16 | B*2705 | TRSTNMSL | 1941 | 2000.00 | 8 |
| 1846 | HPV | 16 | 3 | 16 | B*3901 | RHGEEYDL | 1942 | 180.00 | 8 |
| 1847 | HPV | 16 | 3 | 16 | B*2705 | LQFIFQLC | 1943 | 100.00 | 8 |
| 1848 | HPV | 16 | 3 | 16 | B*2705 | FQLCKITL | 1944 | 200.00 | 8 |
| 1849 | HPV | 16 | 3 | 16 | B*5102 | TADVMTYI | 1945 | 110.00 | 8 |
| 1850 | HPV | 16 | 3 | 16 | B*5102 | QPPPGGTL | 1946 | 110.00 | 8 |
| 1851 | HPV | 16 | 3 | 16 | B*2705 | YRFVTQAI | 1947 | 3000.00 | 8 |
| 1852 | HPV | 16 | 3 | 16 | B*2705 | TQAIACQK | 1948 | 200.00 | 8 |
| 1853 | HPV | 16 | 3 | 16 | B*3501 | APKEDDPL | 1949 | 180.00 | 8 |
| 1854 | HPV | 16 | 3 | 16 | B*5102 | FPLGRKFL | 1950 | 660.00 | 8 |
| 1855 | HPV | 16 | 3 | 16 | B*2705 | GRKFLLQA | 1951 | 200.00 | 8 |
| 1856 | HPV | 16 | 3 | 16 | B*2705 | LQAGLKAK | 1952 | 200.00 | 8 |
| 1857 | HPV | 16 | 3 | 16 | B8 | KAKPKFTL | 1953 | 160.00 | 8 |
| 1858 | HPV | 16 | 3 | 16 | B*2705 | KRKATPTT | 1954 | 600.00 | 8 |
| 1859 | HPV | 16 | 3 | 16 | B*2705 | MQVTFIYIL | 1956 | 200.00 | 9 |
| 1860 | HPV | 16 | 3 | 16 | B*3901 | YHIFFQMSL | 1957 | 180.00 | 9 |
| 1861 | HPV | 16 | 3 | 16 | Cw*0401 | IFFQMSLWL | 1958 | 220.00 | 9 |
| 1862 | HPV | 16 | 3 | 16 | Cw*0401 | LPSEATVYL | 1959 | 105.60 | 9 |
| 1863 | HPV | 16 | 3 | 16 | B*5102 | LPSEATVYL | 1959 | 133.10 | 9 |
| 1864 | HPV | 16 | 3 | 16 | B*5103 | EATVYLPPV | 1960 | 110.00 | 9 |
| 1865 | HPV | 16 | 3 | 16 | B*5102 | EATVYLPPV | 1960 | 100.00 | 9 |
| 1866 | HPV | 16 | 3 | 16 | B*5102 | LPPVPVSKV | 1961 | 400.00 | 9 |
| 1867 | HPV | 16 | 3 | 16 | B*2705 | ARTNIYYHA | 1962 | 200.00 | 9 |
| 1868 | HPV | 16 | 3 | 16 | A24 | YYHAGTSRL | 1963 | 200.00 | 9 |
| 1869 | HPV | 16 | 3 | 16 | Cw*0401 | YYHAGTSRL | 1963 | 300.00 | 9 |
| 1870 | HPV | 16 | 3 | 16 | B*5102 | KPNNNKILV | 1964 | 242.00 | 9 |
| 1871 | HPV | 16 | 3 | 16 | Cw*0301 | ILVPKVSGL | 1965 | 120.00 | 9 |
| 1872 | HPV | 16 | 3 | 16 | B*3501 | VPKVSGLQY | 1966 | 120.00 | 9 |
| 1873 | HPV | 16 | 3 | 16 | A*0201 | GLQYRVFRI | 1967 | 139.17 | 9 |
| 1874 | HPV | 16 | 3 | 16 | A24 | QYRVFRIHL | 1968 | 200.00 | 9 |
| 1875 | HPV | 16 | 3 | 16 | Cw*0401 | QYRVFRIHL | 1968 | 220.00 | 9 |
| 1876 | HPV | 16 | 3 | 16 | B*2705 | FRIHLPDPN | 1969 | 200.00 | 9 |
| 1877 | HPV | 16 | 3 | 16 | Cw*0401 | KFGFPDTSF | 1970 | 110.00 | 9 |
| 1878 | HPV | 16 | 3 | 16 | A24 | FYNPDTQRL | 1971 | 432.00 | 9 |
| 1879 | HPV | 16 | 3 | 16 | Cw*0401 | FYNPDTQRL | 1971 | 240.00 | 9 |
| 1880 | HPV | 16 | 3 | 16 | B60 | VEVGRGQPL | 1972 | 320.00 | 9 |
| 1881 | HPV | 16 | 3 | 16 | B*5103 | SAYAANAGV | 1973 | 330.00 | 9 |
| 1882 | HPV | 16 | 3 | 16 | B*5102 | SAYAANAGV | 1973 | 550.00 | 9 |
| 1883 | HPV | 16 | 3 | 16 | B*5102 | AGVDNRECI | 1974 | 290.40 | 9 |
| 1884 | HPV | 16 | 3 | 16 | B*2702 | NRECISMDY | 1975 | 200.00 | 9 |
| 1885 | HPV | 16 | 3 | 16 | B*2705 | NRECISMDY | 1975 | 1000.00 | 9 |
| 1886 | HPV | 16 | 3 | 16 | A24 | DYKQTQLCL | 1976 | 200.00 | 9 |
| 1887 | HPV | 16 | 3 | 16 | Cw*0401 | DYKQTQLCL | 1976 | 240.00 | 9 |
| 1888 | HPV | 16 | 3 | 16 | B*2705 | TQLCLIGCK | 1977 | 200.00 | 9 |
| 1889 | HPV | 16 | 3 | 16 | B*3701 | GDCPPLELI | 1978 | 200.00 | 9 |
| 1890 | HPV | 16 | 3 | 16 | B*5102 | VPLDICTSI | 1979 | 1200.00 | 9 |

TABLE 7-continued

| No | Species | Strain type | Frame | ORF | HLA | Seq | Seq ID No. | Score | Length |
|---|---|---|---|---|---|---|---|---|---|
| 1891 | HPV | 16 | 3 | 16 | Cw*0301 | CKYPDYIKM | 1980 | 125.00 | 9 |
| 1892 | HPV | 16 | 3 | 16 | Cw*0401 | FFYLRREQM | 1981 | 110.00 | 9 |
| 1893 | HPV | 16 | 3 | 16 | A24 | FYLRREQMF | 1982 | 180.00 | 9 |
| 1894 | HPV | 16 | 3 | 16 | Cw*0401 | FYLRREQMF | 1982 | 110.00 | 9 |
| 1895 | HPV | 16 | 3 | 16 | A*0201 | YLRREQMFV | 1983 | 133.73 | 9 |
| 1896 | HPV | 16 | 3 | 16 | B*2705 | LRREQMFVR | 1984 | 1000.00 | 9 |
| 1897 | HPV | 16 | 3 | 16 | B*2705 | RREQMFVRH | 1985 | 600.00 | 9 |
| 1898 | HPV | 16 | 3 | 16 | B60 | REQMFVRHL | 1986 | 160.00 | 9 |
| 1899 | HPV | 16 | 3 | 16 | B*2705 | NRAGTVGEN | 1987 | 200.00 | 9 |
| 1900 | HPV | 16 | 3 | 16 | E*5103 | RAGTVGENV | 1988 | 121.00 | 9 |
| 1901 | HPV | 16 | 3 | 16 | B*5102 | RAGTVGENV | 1988 | 133.10 | 9 |
| 1902 | HPV | 16 | 3 | 16 | A68.1 | NVPDDLYIK | 1989 | 120.00 | 9 |
| 1903 | HPV | 16 | 3 | 16 | Cw*0401 | YFPTPSGSM | 1990 | 110.00 | 9 |
| 1904 | HPV | 16 | 3 | 16 | B*5102 | FPTPSGSMV | 1991 | 400.00 | 9 |
| 1905 | HPV | 16 | 3 | 16 | B*5103 | RAQGHNNGI | 1992 | 110.00 | 9 |
| 1906 | HPV | 16 | 3 | 16 | B*5102 | RAQGHNNGI | 1992 | 242.00 | 9 |
| 1907 | HPV | 16 | 3 | 16 | A68.1 | FVTVVDTTR | 1993 | 300.00 | 9 |
| 1908 | HPV | 16 | 3 | 16 | B*2705 | TRSTNMSLC | 1994 | 200.00 | 9 |
| 1909 | HPV | 16 | 3 | 16 | B*2705 | LRHGEEYDL | 1995 | 2000.00 | 9 |
| 1910 | HPV | 16 | 3 | 16 | B*2705 | LQFIFQLCK | 1996 | 1000.00 | 9 |
| 1911 | HPV | 16 | 3 | 16 | Cw*0401 | IFQLCKITL | 1997 | 200.00 | 9 |
| 1912 | HPV | 16 | 3 | 16 | B*2705 | LQPPPGGTL | 1998 | 200.00 | 9 |
| 1913 | HPV | 16 | 3 | 16 | B*2702 | YRFVTQAIA | 1999 | 100.00 | 9 |
| 1914 | HPV | 16 | 3 | 16 | B*2705 | YRFVTQAIA | 1999 | 1000.00 | 9 |
| 1915 | HPV | 16 | 3 | 16 | A24 | KYTFWEVNL | 2000 | 400.00 | 9 |
| 1916 | HPV | 16 | 3 | 16 | Cw*0401 | KYTFWEVNL | 2000 | 200.00 | 9 |
| 1917 | HPV | 16 | 3 | 16 | Cw*0401 | KFSADLDQF | 2001 | 200.00 | 9 |
| 1918 | HPV | 16 | 3 | 16 | B62 | DQFPLGRKF | 2002 | 192.00 | 9 |
| 1919 | HPV | 16 | 3 | 16 | Cw*0401 | QFPLGRKFL | 2003 | 200.00 | 9 |
| 1920 | HPV | 16 | 3 | 16 | B*5102 | FPLGRKFLL | 2004 | 660.00 | 9 |
| 1921 | HPV | 16 | 3 | 16 | B*2705 | KRKATPTTS | 2005 | 600.00 | 9 |
| 1922 | HPV | 16 | 3 | 16 | B8 | TAKRKKRKL | 2006 | 320.00 | 9 |
| 1923 | HPV | 16 | 3 | 16 | Cw*0401 | VYHIFFQMSL | 2007 | 330.00 | 10 |
| 1924 | HPV | 16 | 3 | 16 | A24 | VYHIFFQMSL | 2007 | 200.00 | 10 |
| 1925 | HPV | 16 | 3 | 16 | A*0201 | SLWLPSEATV | 2008 | 577.28 | 10 |
| 1926 | HPV | 16 | 3 | 16 | A*0201 | WLPSEATVYL | 2009 | 540.47 | 10 |
| 1927 | HPV | 16 | 3 | 16 | A*0201 | YLPPVPVSKV | 2010 | 735.86 | 10 |
| 1928 | HPV | 16 | 3 | 16 | B*5102 | LPPVPVSKVV | 2011 | 242.00 | 10 |
| 1929 | HPV | 16 | 3 | 16 | B*5201 | LPPVPVSKVV | 2011 | 435.60 | 10 |
| 1930 | HPV | 16 | 3 | 16 | A68.1 | VVSTDEYVAR | 2012 | 200.00 | 10 |
| 1931 | HPV | 16 | 3 | 16 | Cw*0401 | IYYHAGTSRL | 2013 | 200.00 | 10 |
| 1932 | HPV | 16 | 3 | 16 | A24 | IYYHAGTSRL | 2013 | 200.00 | 10 |
| 1933 | HPV | 16 | 3 | 16 | Cw*0401 | YYHAGTSRLL | 2014 | 360.00 | 10 |
| 1934 | HPV | 16 | 3 | 16 | A24 | YYHAGTSRLL | 2014 | 200.00 | 10 |
| 1935 | HPV | 16 | 3 | 16 | B*5102 | HAGTSRLLAV | 2015 | 110.00 | 10 |
| 1936 | HPV | 16 | 3 | 16 | B*5103 | HAGTSRLLAV | 2015 | 121.00 | 10 |
| 1937 | HPV | 16 | 3 | 16 | B*2702 | SRLLAVGHPY | 2016 | 200.00 | 10 |
| 1938 | HPV | 16 | 3 | 16 | B*2705 | SRLLAVGHPY | 2016 | 1000.00 | 10 |
| 1939 | HPV | 16 | 3 | 16 | B*5102 | LAVGHPYFPI | 2017 | 660.00 | 10 |
| 1940 | HPV | 16 | 3 | 16 | B*5103 | LAVGHPYFPI | 2017 | 110.00 | 10 |
| 1941 | HPV | 16 | 3 | 16 | A68.1 | AVGHPYFPIK | 2018 | 240.00 | 10 |
| 1942 | HPV | 16 | 3 | 16 | A*0205 | KILVPKVSGL | 2019 | 126.00 | 10 |
| 1943 | HPV | 16 | 3 | 16 | B*5102 | SGLQYRVFRI | 2020 | 528.00 | 10 |
| 1944 | HPV | 16 | 3 | 16 | B*2705 | LQYRVFRIHL | 2021 | 1000.00 | 10 |
| 1945 | HPV | 16 | 3 | 16 | B*2705 | FRIHLPDPNK | 2022 | 2000.00 | 10 |
| 1946 | HPV | 16 | 3 | 16 | Cw*0401 | SFYNPDTQRL | 2023 | 200.00 | 10 |
| 1947 | HPV | 16 | 3 | 16 | B*2705 | QRLVWACVGV | 2024 | 600.00 | 10 |
| 1948 | HPV | 16 | 3 | 16 | B*2705 | GRGQPLGVGI | 2025 | 600.00 | 10 |
| 1949 | HPV | 16 | 3 | 16 | B*5102 | NAGVDNRECI | 2026 | 242.00 | 10 |
| 1950 | HPV | 16 | 3 | 16 | B*5103 | NAGVDNRECI | 2026 | 121.00 | 10 |
| 1951 | HPV | 16 | 3 | 16 | B*2705 | NRECISMDYK | 2027 | 2000.00 | 10 |
| 1952 | HPV | 16 | 3 | 16 | B7 | NPGDCPPLEL | 2028 | 120.00 | 10 |
| 1953 | HPV | 16 | 3 | 16 | B*5102 | NPGDCPPLEL | 2028 | 100.00 | 10 |
| 1954 | HPV | 16 | 3 | 16 | B*5102 | CPPLELINTV | 2029 | 266.20 | 10 |
| 1955 | HPV | 16 | 3 | 16 | B*5102 | PPLELINTVI | 2030 | 145.20 | 10 |
| 1956 | HPV | 16 | 3 | 16 | Cw*0401 | GFGAMDFTTL | 2031 | 200.00 | 10 |
| 1957 | HPV | 16 | 3 | 16 | B*2705 | LQANKSEVPL | 2032 | 200.00 | 10 |
| 1958 | HPV | 16 | 3 | 16 | A1 | VSEPYGDSLF | 2033 | 135.00 | 10 |
| 1959 | HPV | 16 | 3 | 16 | Cw*0401 | LFFYLRREQM | 2034 | 110.00 | 10 |
| 1960 | HPV | 16 | 3 | 16 | Cw*0401 | FFYLRREQMF | 2035 | 110.00 | 10 |
| 1961 | HPV | 16 | 3 | 16 | B*2705 | LRREQMFVRH | 2036 | 200.00 | 10 |
| 1962 | HPV | 16 | 3 | 16 | B*2705 | RREQMFVRHL | 2037 | 1800.00 | 10 |
| 1963 | HPV | 16 | 3 | 16 | B*2705 | QMFVRHLFNR | 2038 | 125.00 | 10 |
| 1964 | HPV | 16 | 3 | 16 | B*2705 | VRHLFNRAGT | 2039 | 200.00 | 10 |
| 1965 | HPV | 16 | 3 | 16 | B*2705 | NRAGTVGENV | 2040 | 600.00 | 10 |
| 1966 | HPV | 16 | 3 | 16 | Cw*0401 | NYFPTPSGSM | 2041 | 132.00 | 10 |

TABLE 7-continued

| No | Species | Strain type | Frame | ORF | HLA | Seq | Seq ID No. | Score | Length |
|---|---|---|---|---|---|---|---|---|---|
| 1967 | HPV | 16 | 3 | 16 | B*2705 | AQIFNKPYWL | 2042 | 200.00 | 10 |
| 1968 | HPV | 16 | 3 | 16 | B*2705 | QRAQGHNNGI | 2043 | 600.00 | 10 |
| 1969 | HPV | 16 | 3 | 16 | B*2705 | TRSTNMSLCA | 2044 | 200.00 | 10 |
| 1970 | HPV | 16 | 3 | 16 | B*2705 | KEYLRHGEEY | 2045 | 225.00 | 10 |
| 1971 | HPV | 16 | 3 | 16 | Cw*0401 | EYDLQFIFQL | 2046 | 600.00 | 10 |
| 1972 | HPV | 16 | 3 | 16 | A24 | EYDLQFIFQL | 2046 | 200.00 | 10 |
| 1973 | HPV | 16 | 3 | 16 | B*2705 | LQFIFQLCKI | 2047 | 300.00 | 10 |
| 1974 | HPV | 16 | 3 | 16 | A*0201 | TLTADVMTYI | 2048 | 131.97 | 10 |
| 1975 | HPV | 16 | 3 | 16 | A*0201 | TILEDWNFGL | 2049 | 258.44 | 10 |
| 1976 | HPV | 16 | 3 | 16 | B*2702 | YRFVTQAIAC | 2050 | 100.00 | 10 |
| 1977 | HPV | 16 | 3 | 16 | B*2705 | YRFVTQAIAC | 2050 | 1000.00 | 10 |
| 1978 | HPV | 16 | 3 | 16 | A68.1 | FVTQAIACQK | 2051 | 120.00 | 10 |
| 1979 | HPV | 16 | 3 | 16 | B*2705 | CQKHTPPAPK | 2052 | 200.00 | 10 |
| 1980 | HPV | 16 | 3 | 16 | Cw*0401 | QFPLGRKFLL | 2053 | 220.00 | 10 |
| 1981 | HPV | 16 | 3 | 16 | B*2705 | GRKFLLQAGL | 2054 | 2000.00 | 10 |
| 1982 | HPV | 16 | 3 | 16 | B*2705 | KRKATPTTSS | 2055 | 600.00 | 10 |
| 1983 | HPV | 16 | 3 | 17 | B*2705 | KLYVCLYV | 2154 | 135.00 | 8 |
| 1984 | HPV | 16 | 3 | 17 | B*2705 | CLYVWYNK | 2155 | 150.00 | 8 |
| 1985 | HPV | 16 | 3 | 17 | A3 | CLYVLVNIK | 2156 | 300.00 | 9 |
| 1986 | HPV | 16 | 3 | 17 | B*2705 | CLYVLVNIK | 2156 | 150.00 | 9 |
| 1987 | HPV | 16 | 3 | 17 | A24 | LYVLVNIKL | 2157 | 462.00 | 9 |
| 1988 | HPV | 16 | 3 | 17 | Cw*0401 | LYVLVNIKL | 2157 | 220.00 | 9 |
| 1989 | HPV | 16 | 3 | 17 | A*0201 | VLVNIKLYV | 2158 | 650.31 | 9 |
| 1990 | HPV | 16 | 3 | 17 | Cw*0301 | VNIKLYVCL | 2159 | 100.00 | 9 |
| 1991 | HPV | 16 | 3 | 17 | B*2705 | CLYVLVNIKL | 2160 | 150.00 | 10 |
| 1992 | HPV | 16 | 3 | 17 | A*0201 | YVLVNIKLYV | 2161 | 569.69 | 10 |
| 1993 | HPV | 16 | 3 | 17 | B*2705 | KLYVCLYVWY | 2162 | 225.00 | 10 |
| 1994 | HPV | 16 | 3 | 17 | A68.1 | YVCLYVWYNK | 2163 | 120.00 | 10 |
| 1995 | HPV | 16 | 3 | 17 | A*0201 | CLYVWYNKHV | 2164 | 222.57 | 10 |
| 1996 | HPV | 16 | 3 | 17 | Cw*0401 | WYNKHVCMCF | 2165 | 100.00 | 10 |
| 1997 | HPV | 16 | 3 | 17 | A24 | WYNKHVCMCF | 2165 | 210.00 | 10 |
| 1998 | HPV | 16 | 3 | 18 | Cw*0301 | FGLHIYKQL | 2166 | 120.00 | 9 |
| 1999 | HPV | 16 | 3 | 18 | B*5102 | FGLHIYKQL | 2166 | 145.20 | 9 |
| 2000 | HPV | 16 | 3 | 18 | A68.1 | KVSHTLFICK | 2167 | 120.00 | 10 |
| 2001 | HPV | 16 | 3 | 18 | B*2705 | VQTDFGLHIY | 2168 | 100.00 | 10 |
| 2002 | HPV | 16 | 3 | 18 | B62 | VQTDFGLHIY | 2168 | 176.00 | 10 |
| 2003 | HPV | 16 | 3 | 18 | A1 | QTDFGLHIYK | 2169 | 125.00 | 10 |
| 2004 | HPV | 16 | 3 | 18 | Cw*0401 | DFGLHIYKQL | 2170 | 200.00 | 10 |
| 2005 | HPV | 16 | 3 | 18 | B*5102 | FGLHIYKQLI | 2171 | 580.80 | 10 |
| 2006 | HPV | 16 | 4 | 1 | B*5102 | LGYKPISI | 2172 | 484.00 | 8 |
| 2007 | HPV | 16 | 4 | 1 | B*5201 | LGYKPISIF | 2173 | 225.00 | 9 |
| 2008 | HPV | 16 | 4 | 2 | B*5102 | GPNQPLCI | 2174 | 440.00 | 8 |
| 2009 | HPV | 16 | 4 | 2 | B*5102 | QPLCIWII | 2175 | 1200.00 | 8 |
| 2010 | HPV | 16 | 4 | 2 | A24 | TYTGPNQPL | 2176 | 240.00 | 9 |
| 2011 | HPV | 16 | 4 | 2 | Cw*0401 | TYTGPNQPL | 2176 | 200.00 | 9 |
| 2012 | HPV | 16 | 4 | 2 | B*5201 | NQPLCIWII | 2177 | 240.00 | 9 |
| 2013 | HPV | 16 | 4 | 2 | B*5102 | GPNQPLCIWI | 2178 | 440.00 | 10 |
| 2014 | HPV | 16 | 4 | 2 | B*2705 | NQPLCIWIIK | 2179 | 200.00 | 10 |
| 2015 | HPV | 16 | 4 | 3 | A*0201 | MVNVYVFV | 2180 | 130.88 | 9 |
| 2016 | HPV | 16 | 4 | 3 | A*0201 | NMVNVYVVFV | 2181 | 635.43 | 10 |
| 2017 | HPV | 16 | 4 | 4 | B*2705 | HQKELLYL | 2182 | 200.00 | 8 |
| 2018 | HPV | 16 | 4 | 4 | B*2705 | LQEYNLIK | 2183 | 200.00 | 8 |
| 2019 | HPV | 16 | 4 | 4 | B*2705 | KEYCMHHQK | 2184 | 450.00 | 9 |
| 2020 | HPV | 16 | 4 | 4 | B*3901 | HHQKELLYL | 2185 | 135.00 | 9 |
| 2021 | HPV | 16 | 4 | 4 | A*0201 | LLYLQEYNL | 2186 | 116.21 | 9 |
| 2022 | HPV | 16 | 4 | 4 | B*2705 | LLYLQEYNL | 2186 | 150.00 | 9 |
| 2023 | HPV | 16 | 4 | 4 | A3 | YLQEYNLIK | 2187 | 180.00 | 9 |
| 2024 | HPV | 16 | 4 | 4 | Cw*0401 | EYCMHHQKEL | 2188 | 220.00 | 10 |
| 2025 | HPV | 16 | 4 | 4 | A24 | EYCMHHQKEL | 2188 | 220.00 | 10 |
| 2026 | HPV | 16 | 4 | 4 | B*3901 | MHHQKELLYL | 2189 | 135.00 | 10 |
| 2027 | HPV | 16 | 4 | 4 | B*0201 | YLQEYNLIKM | 2190 | 215.50 | 10 |
| 2028 | HPV | 16 | 4 | 6 | B*2705 | QLYPKSQDL | 2191 | 150.00 | 9 |
| 2029 | HPV | 16 | 4 | 6 | Cw*0301 | QLYPKSQDL | 2191 | 120.00 | 9 |
| 2030 | HPV | 16 | 4 | 6 | B*5102 | YPKSQDLEL | 2192 | 110.00 | 9 |
| 2031 | HPV | 16 | 4 | 6 | B*2705 | KQLYPKSQDL | 2193 | 600.00 | 10 |
| 2032 | HPV | 16 | 4 | 6 | Cw*0401 | LYPKSQDLEL | 2194 | 200.00 | 10 |
| 2033 | HPV | 16 | 4 | 6 | A24 | LYPKSQDLEL | 2194 | 330.00 | 10 |
| 2034 | HPV | 16 | 4 | 6 | B*3501 | YPKSQDLELY | 2195 | 180.00 | 10 |
| 2035 | HPV | 16 | 4 | 9 | B*2705 | GEWKVQML | 2196 | 150.00 | 8 |
| 2036 | HPV | 16 | 4 | 9 | A*0201 | LIHLGEWKV | 2197 | 121.93 | 9 |
| 2037 | HPV | 16 | 4 | 10 | B*5102 | KGVLQEQV | 2198 | 159.72 | 8 |
| 2038 | HPV | 16 | 4 | 11 | B*2705 | VRLYPTLF | 2199 | 1000.00 | 8 |
| 2039 | HPV | 16 | 4 | 11 | B*5102 | YPTLFQFL | 2200 | 242.00 | 8 |
| 2040 | HPV | 16 | 4 | 11 | B*2705 | FQFLTHQK | 2201 | 1000.00 | 8 |
| 2041 | HPV | 16 | 4 | 11 | B*2705 | HQKIHPYF | 2202 | 100.00 | 8 |
| 2042 | HPV | 16 | 4 | 11 | B*5102 | HPYFHIVI | 2203 | 2200.00 | 8 |

TABLE 7-continued

| No | Species | Strain type | Frame | ORF | HLA | Seq | Seq ID No. | Score | Length |
|---|---|---|---|---|---|---|---|---|---|
| 2043 | HPV | 16 | 4 | 11 | B*5102 | FPMEYTQCV | 2204 | 532.40 | 9 |
| 2044 | HPV | 16 | 4 | 11 | B*2705 | MEYTQCVRL | 2205 | 150.00 | 9 |
| 2045 | HPV | 16 | 4 | 11 | B60 | MEYTQCVRL | 2205 | 352.00 | 9 |
| 2046 | HPV | 16 | 4 | 11 | Cw*0301 | QCVRLYPTL | 2206 | 180.00 | 9 |
| 2047 | HPV | 16 | 4 | 11 | B*2705 | RLYPTLFQF | 2207 | 225.00 | 9 |
| 2048 | HPV | 16 | 4 | 11 | A24 | LYPTLFQFL | 2208 | 518.40 | 9 |
| 2049 | HPV | 16 | 4 | 11 | Cw*0401 | LYPTLFQFL | 2208 | 200.00 | 9 |
| 2050 | HPV | 16 | 4 | 11 | B*2705 | FQFLTHQKI | 2209 | 300.00 | 9 |
| 2051 | HPV | 16 | 4 | 11 | B*5102 | FQFLTHQKI | 2209 | 106.48 | 9 |
| 2052 | HPV | 16 | 4 | 11 | B*5201 | HPYFHIVIF | 2210 | 125.00 | 9 |
| 2053 | HPV | 16 | 4 | 11 | B*2705 | TQCVRLYPTL | 2211 | 200.00 | 10 |
| 2054 | HPV | 16 | 4 | 11 | B*2702 | VRLYPTLFQF | 2212 | 200.00 | 10 |
| 2055 | HPV | 16 | 4 | 11 | B*2705 | VRLYPTLFQF | 2212 | 1000.00 | 10 |
| 2056 | HPV | 16 | 4 | 11 | A*0201 | RLYPTLFQFL | 2213 | 714.36 | 10 |
| 2057 | HPV | 16 | 4 | 11 | B*2705 | RLYPTLFQFL | 2213 | 450.00 | 10 |
| 2058 | HPV | 16 | 4 | 11 | Cw*0301 | RLYPTLFQFL | 2213 | 600.00 | 10 |
| 2059 | HPV | 16 | 4 | 11 | A3 | TLFQFLTHQK | 2214 | 100.00 | 10 |
| 2060 | HPV | 16 | 4 | 11 | B*2705 | TLFQFLTHQK | 2214 | 150.00 | 10 |
| 2061 | HPV | 16 | 4 | 11 | B*5102 | HPYFHIVIFV | 2215 | 1000.00 | 10 |
| 2062 | HPV | 16 | 4 | 11 | B*5103 | HPYFHIVIFV | 2215 | 120.00 | 10 |
| 2063 | HPV | 16 | 4 | 11 | B*5201 | HPYFHIVIFV | 2215 | 150.00 | 10 |
| 2064 | HPV | 16 | 4 | 12 | B*5102 | LPVCMFYKV | 2216 | 1200.00 | 9 |
| 2065 | HPV | 16 | 4 | 13 | A*0201 | LLLSTIVIPI | 2217 | 150.93 | 10 |
| 2066 | HPV | 16 | 4 | 14 | B*5102 | NAVRIGAL | 2218 | 165.00 | 8 |
| 2067 | HPV | 16 | 4 | 14 | B*2705 | VRIGALST | 2219 | 200.00 | 8 |
| 2068 | HPV | 16 | 4 | 14 | B*5102 | GALSTESL | 2220 | 165.00 | 8 |
| 2069 | HPV | 16 | 4 | 14 | B*5102 | FPVSGSDL | 2221 | 660.00 | 8 |
| 2070 | HPV | 16 | 4 | 14 | B*2705 | GRWIVVCV | 2222 | 3000.00 | 8 |
| 2071 | HPV | 16 | 4 | 14 | B*5102 | VPKATALV | 2223 | 110.00 | 8 |
| 2072 | HPV | 16 | 4 | 14 | B*5102 | KATALVWV | 2224 | 100.00 | 8 |
| 2073 | HPV | 16 | 4 | 14 | B*5102 | LAKCCLII | 2225 | 100.00 | 8 |
| 2074 | HPV | 16 | 4 | 14 | Cw*0401 | GFPVSGSDL | 2226 | 200.00 | 9 |
| 2075 | HPV | 16 | 4 | 14 | B*5801 | VSGSDLGRW | 2227 | 105.60 | 9 |
| 2076 | HPV | 16 | 4 | 14 | B*2705 | GRWIVVCVS | 2228 | 1000.00 | 9 |
| 2077 | HPV | 16 | 4 | 14 | A*0201 | WIVVCVSSV | 2229 | 101.18 | 9 |
| 2078 | HPV | 16 | 4 | 14 | A68.1 | VVCVSSVPK | 2230 | 120.00 | 9 |
| 2079 | HPV | 16 | 4 | 14 | Cw*0301 | SSVPKATAL | 2231 | 100.00 | 9 |
| 2080 | HPV | 16 | 4 | 14 | A68.1 | WVAAGWLAK | 2232 | 240.00 | 9 |
| 2081 | HPV | 16 | 4 | 14 | B*5102 | AGWLAKCCL | 2233 | 110.00 | 9 |
| 2082 | HPV | 16 | 4 | 14 | B*2705 | VRIGALSTES | 2234 | 200.00 | 10 |
| 2083 | HPV | 16 | 4 | 14 | A*0201 | NLVVWQGFPV | 2235 | 403.40 | 10 |
| 2084 | HPV | 16 | 4 | 14 | B*5102 | QGFPVSGSDL | 2236 | 100.00 | 10 |
| 2085 | HPV | 16 | 4 | 14 | B*2705 | GRWIVVCVSS | 2237 | 1000.00 | 10 |
| 2086 | HPV | 16 | 4 | 14 | A68.1 | IVVCVSSVPK | 2238 | 240.00 | 10 |
| 2087 | HPV | 16 | 4 | 14 | B*5102 | VPKATALVWV | 2239 | 100.00 | 10 |
| 2088 | HPV | 16 | 4 | 14 | B*5102 | AGWLAKCCLI | 2240 | 440.00 | 10 |
| 2089 | HPV | 16 | 4 | 15 | B*5102 | TPTSTTIL | 2241 | 121.00 | 8 |
| 2090 | HPV | 16 | 4 | 15 | B*5801 | TSTTILTTW | 2242 | 158.40 | 9 |
| 2091 | HPV | 16 | 4 | 15 | A*0201 | ILTTWCFSL | 2243 | 210.63 | 9 |
| 2092 | HPV | 16 | 4 | 15 | B*5102 | TATTPTSTTI | 2244 | 266.20 | 10 |
| 2093 | HPV | 16 | 4 | 15 | B*5103 | TATTPTSTTI | 2244 | 121.00 | 10 |
| 2094 | HPV | 16 | 4 | 15 | Cw*0401 | CFSLMAPFYL | 2245 | 220.00 | 10 |
| 2095 | HPV | 16 | 4 | 16 | Cw*0401 | HFSIAIPAVF | 2246 | 120.00 | 10 |
| 2096 | HPV | 16 | 4 | 18 | B*5103 | SACPAGPSI | 2247 | 110.00 | 9 |
| 2097 | HPV | 16 | 4 | 18 | B*5102 | SACPAGPSI | 2247 | 200.00 | 9 |
| 2098 | HPV | 16 | 4 | 19 | B*5102 | APVGPETL | 2248 | 330.00 | 8 |
| 2099 | HPV | 16 | 4 | 19 | A*0201 | CITVVTFWV | 2249 | 305.07 | 9 |
| 2100 | HPV | 16 | 4 | 2 | B*2705 | MQPNSVEATK | 2250 | 200.00 | 10 |
| 2101 | HPV | 16 | 4 | 2 | B*5801 | NSVEATKWAW | 2251 | 160.00 | 10 |
| 2102 | HPV | 16 | 4 | 2 | A68.1 | SVEATKWAWR | 2252 | 200.00 | 10 |
| 2103 | HPV | 16 | 4 | 3 | B*5102 | LGYKPISI | 2172 | 484.00 | 8 |
| 2104 | HPV | 16 | 4 | 3 | B*5201 | LGYKPISIF | 2173 | 225.00 | 9 |
| 2105 | HPV | 16 | 4 | 8 | B*2705 | IRAYNLRY | 2253 | 300.00 | 8 |
| 2106 | HPV | 16 | 4 | 8 | B*2705 | RRQVDSGL | 2254 | 6000.00 | 8 |
| 2107 | HPV | 16 | 4 | 8 | B*2705 | TRQPKRHL | 2255 | 2000.00 | 8 |
| 2108 | HPV | 16 | 4 | 8 | B*2705 | RQPKRHLK | 2256 | 600.00 | 8 |
| 2109 | HPV | 16 | 4 | 8 | B*2705 | KRHLKKNM | 2257 | 1800.00 | 8 |
| 2110 | HPV | 16 | 4 | 8 | A24 | IYVCACNIF | 2258 | 180.00 | 9 |
| 2111 | HPV | 16 | 4 | 8 | Cw*0401 | IYVCACNIF | 2258 | 110.00 | 9 |
| 2112 | HPV | 16 | 4 | 8 | B14 | LRYWDRRQV | 2259 | 100.00 | 9 |
| 2113 | HPV | 16 | 4 | 8 | B*2705 | LRYWDRRQV | 2259 | 900.00 | 9 |
| 2114 | HPV | 16 | 4 | 8 | B*2705 | DRRQVDSGL | 2260 | 200.00 | 9 |
| 2115 | HPV | 16 | 4 | 8 | B*2705 | RRQVDSGLT | 2261 | 600.00 | 9 |
| 2116 | HPV | 16 | 4 | 8 | B*2705 | RQVDSGLTR | 2262 | 300.00 | 9 |
| 2117 | HPV | 16 | 4 | 8 | B*2705 | TRQPKRHLK | 2263 | 2000.00 | 9 |
| 2118 | HPV | 16 | 4 | 8 | B*2705 | RQPKRHLKK | 2264 | 600.00 | 9 |

TABLE 7-continued

| No | Species | Strain type | Frame | ORF | HLA | Seq | Seq ID No. | Score | Length |
|---|---|---|---|---|---|---|---|---|---|
| 2119 | HPV | 16 | 4 | 8 | B*2705 | KRHLKKNMV | 2265 | 1800.00 | 9 |
| 2120 | HPV | 16 | 4 | 8 | A*0201 | MVNVYVVFV | 2180 | 130.88 | 9 |
| 2121 | HPV | 16 | 4 | 8 | A68.1 | YVCACNIFIR | 2266 | 200.00 | 10 |
| 2122 | HPV | 16 | 4 | 8 | B*2705 | LRYWDRRQVD | 2267 | 100.00 | 10 |
| 2123 | HPV | 16 | 4 | 8 | B*2705 | RRQVDSGLTR | 2268 | 3000.00 | 10 |
| 2124 | HPV | 16 | 4 | 8 | B*2705 | TRQPKRHLKK | 2269 | 2000.00 | 10 |
| 2125 | HPV | 16 | 4 | 8 | B*3501 | QPKRHLKKNM | 2270 | 120.00 | 10 |
| 2126 | HPV | 16 | 4 | 8 | B*2705 | KRHLKKNMVN | 2271 | 600.00 | 10 |
| 2127 | HPV | 16 | 4 | 8 | B62 | HLKKNMVNVY | 2272 | 132.00 | 10 |
| 2128 | HPV | 16 | 4 | 8 | A*0201 | NMVNVYVVFV | 2181 | 635.43 | 10 |
| 2129 | HPV | 16 | 4 | 10 | B*2705 | HQKELLYL | 2182 | 200.00 | 8 |
| 2130 | HPV | 16 | 4 | 10 | B*2705 | LQEYNLIK | 2183 | 200.00 | 8 |
| 2131 | HPV | 16 | 4 | 10 | B*3901 | HHQKELLYL | 2185 | 135.00 | 9 |
| 2132 | HPV | 16 | 4 | 10 | A*0201 | LLYLQEYNL | 2186 | 116.21 | 9 |
| 2133 | HPV | 16 | 4 | 10 | B*2705 | LLYLQEYNL | 2186 | 150.00 | 9 |
| 2134 | HPV | 16 | 4 | 10 | A3 | YLQEYNLIK | 2187 | 180.00 | 9 |
| 2135 | HPV | 16 | 4 | 10 | B*3901 | MHHQKELLYL | 2189 | 135.00 | 10 |
| 2136 | HPV | 16 | 4 | 10 | A*0201 | YLQEYNLIKM | 2190 | 215.50 | 10 |
| 2137 | HPV | 16 | 4 | 11 | B*2705 | QLYPKSQDL | 2191 | 150.00 | 9 |
| 2138 | HPV | 16 | 4 | 11 | Cw*0301 | QLYPKSQDL | 2191 | 120.00 | 9 |
| 2139 | HPV | 16 | 4 | 11 | B*5102 | YPKSQDLEL | 2192 | 110.00 | 9 |
| 2140 | HPV | 16 | 4 | 11 | B*2705 | KQLYPKSQDL | 2193 | 600.00 | 10 |
| 2141 | HPV | 16 | 4 | 11 | Cw*0401 | LYPKSQDLEL | 2194 | 200.00 | 10 |
| 2142 | HPV | 16 | 4 | 11 | A24 | LYPKSQDLEL | 2194 | 330.00 | 10 |
| 2143 | HPV | 16 | 4 | 11 | B*3501 | YPKSQDLELY | 2195 | 180.00 | 10 |
| 2144 | HPV | 16 | 4 | 12 | Cw*0401 | YYPHLYLHM | 2273 | 110.00 | 9 |
| 2145 | HPV | 16 | 4 | 12 | Cw*0301 | MYYPHLYLHM | 2274 | 125.00 | 10 |
| 2146 | HPV | 16 | 4 | 12 | Cw*0401 | MYYPHLYLHM | 2274 | 132.00 | 10 |
| 2147 | HPV | 16 | 4 | 12 | Cw*0401 | LYLHMQDYHM | 2275 | 110.00 | 10 |
| 2148 | HPV | 16 | 4 | 13 | B*2705 | VRLYPTLF | 2199 | 1000.00 | 8 |
| 2149 | HPV | 16 | 4 | 13 | B*5102 | YPTLFQFL | 2200 | 242.00 | 8 |
| 2150 | HPV | 16 | 4 | 13 | B*2705 | FQFLTHQK | 2201 | 1000.00 | 8 |
| 2151 | HPV | 16 | 4 | 13 | B*2705 | HQKIHPYF | 2202 | 100.00 | 8 |
| 2152 | HPV | 16 | 4 | 13 | B*5102 | HPYFHIVI | 2203 | 2200.00 | 8 |
| 2153 | HPV | 16 | 4 | 13 | B*2705 | MEYTQCVRL | 2205 | 150.00 | 9 |
| 2154 | HPV | 16 | 4 | 13 | B60 | MEYTQCVRL | 2205 | 352.00 | 9 |
| 2155 | HPV | 16 | 4 | 13 | Cw*0301 | QCVRLYPTL | 2206 | 180.00 | 9 |
| 2156 | HPV | 16 | 4 | 13 | B*2705 | RLYPTLFQF | 2207 | 225.00 | 9 |
| 2157 | HPV | 16 | 4 | 13 | A24 | LYPTLFQFL | 2208 | 518.40 | 9 |
| 2158 | HPV | 16 | 4 | 13 | Cw*0401 | LYPTLFQFL | 2208 | 200.00 | 9 |
| 2159 | HPV | 16 | 4 | 13 | B*2705 | FQFLTHQKI | 2209 | 300.00 | 9 |
| 2160 | HPV | 16 | 4 | 13 | B*5102 | FQFLTHQKI | 2209 | 106.48 | 9 |
| 2161 | HPV | 16 | 4 | 13 | B*5201 | HPYFHIVIF | 2210 | 125.00 | 9 |
| 2162 | HPV | 16 | 4 | 13 | B*2705 | TQCVRLYPTL | 2211 | 200.00 | 10 |
| 2163 | HPV | 16 | 4 | 13 | B*2702 | VRLYPTLFQF | 2212 | 200.00 | 10 |
| 2164 | HPV | 16 | 4 | 13 | B*2705 | VRLYPTLFQF | 2212 | 1000.00 | 10 |
| 2165 | HPV | 16 | 4 | 13 | A*0201 | RLYPTLFQFL | 2213 | 714.36 | 10 |
| 2166 | HPV | 16 | 4 | 13 | B*2705 | RLYPTLFQFL | 2213 | 450.00 | 10 |
| 2167 | HPV | 16 | 4 | 13 | Cw*0301 | RLYPTLFQFL | 2213 | 600.00 | 10 |
| 2168 | HPV | 16 | 4 | 13 | A3 | TLFQFLTHQK | 2214 | 100.00 | 10 |
| 2169 | HPV | 16 | 4 | 13 | B*2705 | TLFQFLTHQK | 2214 | 150.00 | 10 |
| 2170 | HPV | 16 | 4 | 13 | B*5102 | HPYFHIVIFV | 2215 | 1000.00 | 10 |
| 2171 | HPV | 16 | 4 | 13 | B*5103 | HPYFHIVIFV | 2215 | 120.00 | 10 |
| 2172 | HPV | 16 | 4 | 13 | B*5201 | HPYFHIVIFV | 2215 | 150.00 | 10 |
| 2173 | HPV | 16 | 4 | 14 | B*5102 | LPVCMFYKV | 2216 | 1200.00 | 9 |
| 2174 | HPV | 16 | 4 | 14 | A*0201 | YLPVCMFYKV | 2276 | 607.88 | 10 |
| 2175 | HPV | 16 | 4 | 15 | B*2705 | LQNVCVAL | 2277 | 200.00 | 8 |
| 2176 | HPV | 16 | 4 | 15 | B*2705 | LQNVCVALL | 2278 | 200.00 | 9 |
| 2177 | HPV | 16 | 4 | 15 | B*5102 | VALLSNNSL | 2279 | 181.50 | 9 |
| 2178 | HPV | 16 | 4 | 15 | A*0201 | VLCVLQNVCV | 2280 | 118.24 | 10 |
| 2179 | HPV | 16 | 4 | 15 | B*5102 | VALLSNNSLL | 2281 | 199.65 | 10 |
| 2180 | HPV | 16 | 4 | 15 | B*2705 | KQTNKKKNYI | 2282 | 180.00 | 10 |
| 2181 | HPV | 16 | 4 | 16 | B*2705 | IRPLCELL | 2283 | 2000.00 | 8 |
| 2182 | HPV | 16 | 4 | 16 | B*5102 | NAVRIGAL | 2218 | 165.00 | 8 |
| 2183 | HPV | 16 | 4 | 16 | B*2705 | VRIGALST | 2219 | 200.00 | 8 |
| 2184 | HPV | 16 | 4 | 16 | B*5102 | GALSTESL | 2220 | 165.00 | 8 |
| 2185 | HPV | 16 | 4 | 16 | B*5102 | FPVSGSDL | 2221 | 660.00 | 8 |
| 2186 | HPV | 16 | 4 | 16 | B*2705 | GRWIVVCV | 2222 | 3000.00 | 8 |
| 2187 | HPV | 16 | 4 | 16 | B*5102 | VPKATALV | 2223 | 110.00 | 8 |
| 2188 | HPV | 16 | 4 | 16 | B*5102 | KATALVWV | 2224 | 100.00 | 8 |
| 2189 | HPV | 16 | 4 | 16 | B*5102 | LAKCCLII | 2225 | 100.00 | 8 |
| 2190 | HPV | 16 | 4 | 16 | A68.1 | VVLLLQLIR | 2284 | 400.00 | 9 |
| 2191 | HPV | 16 | 4 | 16 | B*2705 | IRPLCELLN | 2285 | 200.00 | 9 |
| 2192 | HPV | 16 | 4 | 16 | Cw*0401 | GFPVSGSDL | 2226 | 200.00 | 9 |
| 2193 | HPV | 16 | 4 | 16 | B*5801 | VSGSDLGRW | 2227 | 105.60 | 9 |
| 2194 | HPV | 16 | 4 | 16 | B*2705 | GRWIVVCVS | 2228 | 1000.00 | 9 |

TABLE 7-continued

| No | Species | Strain type | Frame | ORF | HLA | Seq | Seq ID No. | Score | Length |
|---|---|---|---|---|---|---|---|---|---|
| 2195 | HPV | 16 | 4 | 16 | A*0201 | WIVVCVSSV | 2229 | 101.18 | 9 |
| 2196 | HPV | 16 | 4 | 16 | A68.1 | VVCVSSVPK | 2230 | 120.00 | 9 |
| 2197 | HPV | 16 | 4 | 16 | Cw*0301 | SSVPKATAL | 2231 | 100.00 | 9 |
| 2198 | HPV | 16 | 4 | 16 | A68.1 | WVAAGWLAK | 2232 | 240.00 | 9 |
| 2199 | HPV | 16 | 4 | 16 | B*5102 | AGWLAKCCL | 2233 | 110.00 | 9 |
| 2200 | HPV | 16 | 4 | 16 | B*5102 | MGVVLLLQLI | 2286 | 264.00 | 10 |
| 2201 | HPV | 16 | 4 | 16 | A68.1 | GVVLLLQLIR | 2287 | 400.00 | 10 |
| 2202 | HPV | 16 | 4 | 16 | B*2705 | LQLIRPLCEL | 2288 | 200.00 | 10 |
| 2203 | HPV | 16 | 4 | 16 | B*2705 | IRPLCELLNA | 2289 | 200.00 | 10 |
| 2204 | HPV | 16 | 4 | 16 | B*5102 | RPLCELLNAV | 2290 | 600.00 | 10 |
| 2205 | HPV | 16 | 4 | 16 | B*2705 | VRIGALSTES | 2234 | 200.00 | 10 |
| 2206 | HPV | 16 | 4 | 16 | A*0201 | NLVVWQGFPV | 2235 | 403.40 | 10 |
| 2207 | HPV | 16 | 4 | 16 | B*5102 | QGFPVSGSDL | 2236 | 100.00 | 10 |
| 2208 | HPV | 16 | 4 | 16 | B*2705 | GRWIVVCVSS | 2237 | 1000.00 | 10 |
| 2209 | HPV | 16 | 4 | 16 | A68.1 | IVVCVSSVPK | 2238 | 240.00 | 10 |
| 2210 | HPV | 16 | 4 | 16 | B*5102 | VPKATALVWV | 2239 | 100.00 | 10 |
| 2211 | HPV | 16 | 4 | 16 | B*5102 | AGWLAKCCLI | 2240 | 440.00 | 10 |
| 2212 | HPV | 16 | 4 | 17 | B*2705 | SRLTSCNV | 2291 | 600.00 | 8 |
| 2213 | HPV | 16 | 4 | 17 | B*5102 | SPSNCTSTV | 2292 | 266.20 | 9 |
| 2214 | HPV | 16 | 4 | 17 | B*5102 | YPCFFIHPV | 2293 | 440.00 | 9 |
| 2215 | HPV | 16 | 4 | 17 | B*5102 | GAVKYTSRL | 2294 | 363.00 | 9 |
| 2216 | HPV | 16 | 4 | 17 | B*2705 | SRLTSCNVH | 2295 | 200.00 | 9 |
| 2217 | HPV | 16 | 4 | 17 | Cw*0401 | HFSLLYCEL | 2296 | 200.00 | 9 |
| 2218 | HPV | 16 | 4 | 17 | A*0201 | SLLYCELYI | 2297 | 212.31 | 9 |
| 2219 | HPV | 16 | 4 | 17 | A*0201 | LLYCELYIV | 2298 | 356.80 | 9 |
| 2220 | HPV | 16 | 4 | 17 | A*0201 | ALFFDTASV | 2299 | 257.34 | 9 |
| 2221 | HPV | 16 | 4 | 17 | B*2702 | SRLTSCNVHF | 2300 | 200.00 | 10 |
| 2222 | HPV | 16 | 4 | 17 | B*2705 | SRLTSCNVHF | 2300 | 1000.00 | 10 |
| 2223 | HPV | 16 | 4 | 17 | B*3901 | VHFSLLYCEL | 2301 | 180.00 | 10 |
| 2224 | HPV | 16 | 4 | 17 | A*0201 | SLLYCELYIV | 2302 | 242.67 | 10 |
| 2225 | HPV | 16 | 4 | 17 | B*5102 | NALFFDTASV | 2303 | 330.00 | 10 |
| 2226 | HPV | 16 | 4 | 17 | B*5103 | NALFFDTASV | 2303 | 132.00 | 10 |
| 2227 | HPV | 16 | 4 | 18 | B*2705 | FRIYKTYY | 2304 | 1000.00 | 8 |
| 2228 | HPV | 16 | 4 | 18 | B*2705 | YRPLQKFH | 2305 | 200.00 | 8 |
| 2229 | HPV | 16 | 4 | 18 | B*2705 | FRIYKTYYR | 2306 | 1000.00 | 9 |
| 2230 | HPV | 16 | 4 | 18 | A24 | IYKTYYRPL | 2307 | 200.00 | 9 |
| 2231 | HPV | 16 | 4 | 18 | Cw*0401 | IYKTYYRPL | 2307 | 200.00 | 9 |
| 2232 | HPV | 16 | 4 | 18 | B*2705 | KTYYRPLQK | 2308 | 150.00 | 9 |
| 2233 | HPV | 16 | 4 | 18 | A24 | TYYRPLQKF | 2309 | 132.00 | 9 |
| 2234 | HPV | 16 | 4 | 18 | Cw*0401 | TYYRPLQKF | 2309 | 220.00 | 9 |
| 2235 | HPV | 16 | 4 | 18 | Cw*0301 | RIYKTYYRPL | 2310 | 100.00 | 10 |
| 2236 | HPV | 16 | 4 | 18 | B*5801 | KTYYRPLQKF | 2311 | 158.40 | 10 |
| 2237 | HPV | 16 | 4 | 20 | B*2705 | NRSSKVRM | 2312 | 180.00 | 8 |
| 2238 | HPV | 16 | 4 | 20 | B*2705 | VRMSTCVL | 2313 | 2000.00 | 8 |
| 2239 | HPV | 16 | 4 | 20 | B*2705 | NRSVESHL | 2314 | 2000.00 | 8 |
| 2240 | HPV | 16 | 4 | 20 | B*2705 | LQQKVTIL | 2315 | 200.00 | 8 |
| 2241 | HPV | 16 | 4 | 20 | A68.1 | SVPINRSSK | 2316 | 120.00 | 9 |
| 2242 | HPV | 16 | 4 | 20 | B*5102 | VPINRSSKV | 2317 | 1320.00 | 9 |
| 2243 | HPV | 16 | 4 | 20 | B7 | KVRMSTCVL | 2318 | 200.00 | 9 |
| 2244 | HPV | 16 | 4 | 20 | B*2705 | VRMSTCVLC | 2319 | 200.00 | 9 |
| 2245 | HPV | 16 | 4 | 20 | A68.1 | SVESHLQQK | 2320 | 120.00 | 9 |
| 2246 | HPV | 16 | 4 | 20 | A68.1 | HTIPSVPINR | 2321 | 150.00 | 10 |
| 2247 | HPV | 16 | 4 | 20 | B*2705 | NRSSKVRMST | 2322 | 200.00 | 10 |
| 2248 | HPV | 16 | 4 | 20 | B*2705 | VRMSTCVLCT | 2323 | 200.00 | 10 |
| 2249 | HPV | 16 | 4 | 20 | B*3901 | SHLQQKVTIL | 2324 | 270.00 | 10 |
| 2250 | HPV | 16 | 4 | 21 | B*5102 | AGFLYVFL | 2325 | 110.00 | 8 |
| 2251 | HPV | 16 | 4 | 21 | B*2705 | DRSTDPLY | 2326 | 100.00 | 8 |
| 2252 | HPV | 16 | 4 | 21 | B*5102 | FAFLQDTV | 2327 | 1210.00 | 8 |
| 2253 | HPV | 16 | 4 | 21 | A*0201 | MITAGFLYV | 2328 | 169.89 | 9 |
| 2254 | HPV | 16 | 4 | 21 | B*5801 | ITAGFLYVF | 2329 | 118.80 | 9 |
| 2255 | HPV | 16 | 4 | 21 | A*0201 | FLYVFLMIC | 2330 | 262.05 | 9 |
| 2256 | HPV | 16 | 4 | 21 | A68.1 | YVFLMICNK | 2331 | 240.00 | 9 |
| 2257 | HPV | 16 | 4 | 21 | B*2705 | DRSTDPLYY | 2332 | 100.00 | 9 |
| 2258 | HPV | 16 | 4 | 21 | A*0201 | GIFAFCPDV | 2333 | 134.46 | 9 |
| 2259 | HPV | 16 | 4 | 21 | Cw*0401 | IFAFCPDVF | 2334 | 100.00 | 9 |
| 2260 | HPV | 16 | 4 | 21 | Cw*0401 | AFCPDVFAF | 2335 | 240.00 | 9 |
| 2261 | HPV | 16 | 4 | 21 | Cw*0401 | AFLQDTVAF | 2336 | 100.00 | 9 |
| 2262 | HPV | 16 | 4 | 21 | B*5102 | AGFLYVFLMI | 2337 | 484.00 | 10 |
| 2263 | HPV | 16 | 4 | 21 | B*5201 | AGFLYVFLMI | 2337 | 180.00 | 10 |
| 2264 | HPV | 16 | 4 | 21 | A*0201 | FLMICNKTYI | 2338 | 976.61 | 10 |
| 2265 | HPV | 16 | 4 | 21 | Cw*0401 | TYIDRSTDPL | 2339 | 240.00 | 10 |
| 2266 | HPV | 16 | 4 | 21 | A24 | TYIDRSTDPL | 2339 | 360.00 | 10 |
| 2267 | HPV | 16 | 4 | 21 | A1 | STDPLYYGIF | 2340 | 125.00 | 10 |
| 2268 | HPV | 16 | 4 | 21 | B*5102 | YGIFAFCPDV | 2341 | 240.00 | 10 |
| 2269 | HPV | 16 | 4 | 21 | Cw*0401 | AFCPDVFAFL | 2342 | 288.00 | 10 |
| 2270 | HPV | 16 | 4 | 23 | B*5102 | NPEKQSHI | 2343 | 242.00 | 8 |

TABLE 7-continued

| No | Species | Strain type | Frame | ORF | HLA | Seq | Seq ID No. | Score | Length |
|---|---|---|---|---|---|---|---|---|---|
| 2271 | HPV | 16 | 4 | 23 | B*2705 | KQSHIPHV | 2344 | 180.00 | 8 |
| 2272 | HPV | 16 | 4 | 23 | B*5102 | IPHVAVTV | 2345 | 200.00 | 8 |
| 2273 | HPV | 16 | 4 | 23 | B*5103 | VACSTHILI | 2346 | 110.00 | 9 |
| 2274 | HPV | 16 | 4 | 23 | B*5102 | VACSTHILI | 2346 | 220.00 | 9 |
| 2275 | HPV | 16 | 4 | 23 | B*2705 | KQSHIPHVAV | 2347 | 180.00 | 10 |
| 2276 | HPV | 16 | 5 | 1 | B*2705 | LRVVSTTV | 2348 | 600.00 | 8 |
| 2277 | HPV | 16 | 5 | 1 | B*5102 | LPQQMPLL | 2349 | 110.00 | 8 |
| 2278 | HPV | 16 | 5 | 1 | B*2705 | LRVVSTTVT | 2350 | 200.00 | 9 |
| 2279 | HPV | 16 | 5 | 1 | B*5801 | VSTTVTNSW | 2351 | 132.00 | 9 |
| 2280 | HPV | 16 | 5 | 1 | Cw*0301 | SWLPQQMPL | 2352 | 120.00 | 9 |
| 2281 | HPV | 16 | 5 | 1 | A*0201 | WLPQQMPLL | 2353 | 226.01 | 9 |
| 2282 | HPV | 16 | 5 | 1 | B*2705 | LRVVSTTVTN | 2354 | 200.00 | 10 |
| 2283 | HPV | 16 | 5 | 1 | Cw*0301 | SWLPQQMPLL | 2355 | 200.00 | 10 |
| 2284 | HPV | 16 | 5 | 2 | B*5102 | FAVDPEPL | 2356 | 300.00 | 8 |
| 2285 | HPV | 16 | 5 | 2 | B*5102 | SPTVPALL | 2357 | 100.00 | 8 |
| 2286 | HPV | 16 | 5 | 2 | Cw*0401 | KFAVDPEPL | 2358 | 200.00 | 9 |
| 2287 | HPV | 16 | 5 | 2 | A1 | AVDPEPLMY | 2359 | 1250.00 | 9 |
| 2288 | HPV | 16 | 5 | 2 | B*2705 | LMYKSSGTF | 2360 | 125.00 | 9 |
| 2289 | HPV | 16 | 5 | 2 | Cw*0401 | TFSPTVPAL | 2361 | 576.00 | 9 |
| 2290 | HPV | 16 | 5 | 2 | B*5102 | VPALLNKCL | 2362 | 133.10 | 9 |
| 2291 | HPV | 16 | 5 | 2 | Cw*0401 | KFAVDPEPLM | 2363 | 100.00 | 10 |
| 2292 | HPV | 16 | 5 | 2 | A1 | AVDPEPLMYK | 2364 | 500.00 | 10 |
| 2293 | HPV | 16 | 5 | 2 | A68.1 | AVDPEPLMYK | 2364 | 180.00 | 10 |
| 2294 | HPV | 16 | 5 | 2 | Cw*0401 | TFSPTVPALL | 2365 | 288.00 | 10 |
| 2295 | HPV | 16 | 5 | 3 | B*5102 | SPYGSDTI | 2366 | 2200.00 | 8 |
| 2296 | HPV | 16 | 5 | 3 | B*5102 | YGSDTILI | 2367 | 193.60 | 8 |
| 2297 | HPV | 16 | 5 | 3 | B*5102 | SPYGSDTIL | 2368 | 550.00 | 9 |
| 2298 | HPV | 16 | 5 | 3 | B*5102 | SPYGSDTILI | 2369 | 2420.00 | 10 |
| 2299 | HPV | 16 | 5 | 3 | B*5103 | SPYGSDTILI | 2369 | 145.20 | 10 |
| 2300 | HPV | 16 | 5 | 4 | B*5102 | NPDTLGTNI | 2370 | 220.00 | 9 |
| 2301 | HPV | 16 | 5 | 4 | A*0201 | ILLLLGFLI | 2371 | 380.61 | 9 |
| 2302 | HPV | 16 | 5 | 4 | A3 | LLLGFLIGK | 2372 | 405.00 | 9 |
| 2303 | HPV | 16 | 5 | 4 | Cw*0401 | NPDTLGTNIL | 2373 | 120.00 | 10 |
| 2304 | HPV | 16 | 5 | 4 | A3 | LLLLGFLIGK | 2374 | 270.00 | 10 |
| 2305 | HPV | 16 | 5 | 5 | B*2705 | YRWVSESG | 2375 | 100.00 | 8 |
| 2306 | HPV | 16 | 5 | 5 | B*2705 | LQYRWVSES | 2376 | 100.00 | 9 |
| 2307 | HPV | 16 | 5 | 5 | B*2702 | YRWVSESGI | 2377 | 300.00 | 9 |
| 2308 | HPV | 16 | 5 | 5 | B*2705 | YRWVSESGI | 2377 | 3000.00 | 9 |
| 2309 | HPV | 16 | 5 | 5 | B*2702 | YRWVSESGII | 2378 | 300.00 | 10 |
| 2310 | HPV | 16 | 5 | 5 | B*2705 | YRWVSESGII | 2378 | 3000.00 | 10 |
| 2311 | HPV | 16 | 5 | 6 | B*2705 | SRCTFCAF | 2379 | 1000.00 | 8 |
| 2312 | HPV | 16 | 5 | 6 | B*5102 | CAFCRTFV | 2380 | 550.00 | 8 |
| 2313 | HPV | 16 | 5 | 6 | B*2705 | CRTFVSHC | 2381 | 200.00 | 8 |
| 2314 | HPV | 16 | 5 | 6 | B*2705 | SRCTFCAFC | 2382 | 200.00 | 9 |
| 2315 | HPV | 16 | 5 | 6 | Cw*0401 | TFCAFCRTF | 2383 | 100.00 | 9 |
| 2316 | HPV | 16 | 5 | 6 | A*0201 | KLGSRCTFCA | 2384 | 100.85 | 10 |
| 2317 | HPV | 16 | 5 | 6 | B*2705 | SRCTFCAFCR | 2385 | 1000.00 | 10 |
| 2318 | HPV | 16 | 5 | 7 | B*2705 | LQYTMYNA | 2386 | 100.00 | 8 |
| 2319 | HPV | 16 | 5 | 7 | B*2702 | LQYTMYNAF | 2387 | 100.00 | 9 |
| 2320 | HPV | 16 | 5 | 7 | B*2705 | LQYTMYNAF | 2387 | 500.00 | 9 |
| 2321 | HPV | 16 | 5 | 9 | B*5102 | NALYCICL | 2388 | 165.00 | 8 |
| 2322 | HPV | 16 | 5 | 9 | B*3901 | LHQTALPL | 2389 | 135.00 | 8 |
| 2323 | HPV | 16 | 5 | 9 | B*2705 | HQTALPLY | 2390 | 100.00 | 8 |
| 2324 | HPV | 16 | 5 | 9 | B*3901 | IHVFLYIL | 2391 | 180.00 | 8 |
| 2325 | HPV | 16 | 5 | 9 | A*0201 | MLLHKYIYV | 2396 | 3609.23 | 9 |
| 2326 | HPV | 16 | 5 | 9 | B*5103 | TALPLYIHV | 2397 | 132.00 | 9 |
| 2327 | HPV | 16 | 5 | 9 | B*5102 | TALPLYIHV | 2397 | 300.00 | 9 |
| 2328 | HPV | 16 | 5 | 9 | B*5102 | LPLYIHVFL | 2398 | 300.00 | 9 |
| 2329 | HPV | 16 | 5 | 9 | A24 | LYIHVFLYI | 2399 | 126.00 | 9 |
| 2330 | HPV | 16 | 5 | 9 | B*3901 | IHVFLYILL | 2400 | 180.00 | 9 |
| 2331 | HPV | 16 | 5 | 9 | Cw*0301 | IHVFLYILL | 2400 | 100.00 | 9 |
| 2332 | HPV | 16 | 5 | 9 | A*0201 | FLYILLVQL | 2401 | 723.25 | 9 |
| 2333 | HPV | 16 | 5 | 9 | A*0205 | FLYILLVQL | 2401 | 126.00 | 9 |
| 2334 | HPV | 16 | 5 | 9 | B*2705 | FLYILLVQL | 2401 | 150.00 | 9 |
| 2335 | HPV | 16 | 5 | 9 | A*0201 | ILLVQLNTL | 2402 | 309.05 | 9 |
| 2336 | HPV | 16 | 5 | 9 | A*0201 | LMLLHKYIYV | 2403 | 2606.66 | 10 |
| 2337 | HPV | 16 | 5 | 9 | Cw*0301 | IYVSSLYNAL | 2404 | 100.00 | 10 |
| 2338 | HPV | 16 | 5 | 9 | Cw*0401 | IYVSSLYNAL | 2404 | 200.00 | 10 |
| 2339 | HPV | 16 | 5 | 9 | A24 | IYVSSLYNAL | 2404 | 432.00 | 10 |
| 2340 | HPV | 16 | 5 | 9 | Cw*0401 | LYNALYCICL | 2405 | 200.00 | 10 |
| 2341 | HPV | 16 | 5 | 9 | A24 | LYNALYCICL | 2405 | 300.00 | 10 |
| 2342 | HPV | 16 | 5 | 9 | A*0201 | ALPLYIHVFL | 2406 | 117.49 | 10 |
| 2343 | HPV | 16 | 5 | 9 | Cw*0401 | LYIHVFLYIL | 2407 | 400.00 | 10 |
| 2344 | HPV | 16 | 5 | 9 | A24 | LYIHVFLYIL | 2407 | 300.00 | 10 |
| 2345 | HPV | 16 | 5 | 9 | Cw*0401 | VFLYILLVQL | 2408 | 400.00 | 10 |
| 2346 | HPV | 16 | 5 | 9 | A*0201 | YILLVQLNTL | 2409 | 114.98 | 10 |

TABLE 7-continued

| No | Species | Strain type | Frame | ORF | HLA | Seq | Seq ID No. | Score | Length |
|---|---|---|---|---|---|---|---|---|---|
| 2347 | HPV | 16 | 5 | 9 | A*0205 | YILLVQLNTL | 2409 | 126.00 | 10 |
| 2348 | HPV | 16 | 5 | 10 | B*5102 | CPDTHLNV | 2410 | 110.00 | 8 |
| 2349 | HPV | 16 | 5 | 10 | B*2705 | FQFLSLSS | 2411 | 100.00 | 8 |
| 2350 | HPV | 16 | 5 | 10 | A24 | LYYHFHNVL | 2412 | 240.00 | 9 |
| 2351 | HPV | 16 | 5 | 10 | Cw*0401 | LYYHFHNVL | 2412 | 200.00 | 9 |
| 2352 | HPV | 16 | 5 | 10 | B60 | LEKKDFQFL | 2413 | 160.00 | 9 |
| 2353 | HPV | 16 | 5 | 10 | B*2702 | FQFLSLSSY | 2414 | 100.00 | 9 |
| 2354 | HPV | 16 | 5 | 10 | B*2705 | FQFLSLSSY | 2414 | 500.00 | 9 |
| 2355 | HPV | 16 | 5 | 10 | Cw*0401 | YYHFHNVLVF | 2415 | 300.00 | 10 |
| 2356 | HPV | 16 | 5 | 10 | A24 | YYHFHNVLVF | 2415 | 100.00 | 10 |
| 2357 | HPV | 16 | 5 | 10 | A3 | KLNLDHVLEK | 2416 | 360.00 | 10 |
| 2358 | HPV | 16 | 5 | 10 | B*2705 | FQFLSLSSYT | 2417 | 100.00 | 10 |
| 2359 | HPV | 16 | 5 | 10 | B*5102 | FPFSSNGNSL | 2418 | 1100.00 | 10 |
| 2360 | HPV | 16 | 5 | 10 | A68.1 | NVNTTNLLCK | 2419 | 120.00 | 10 |
| 2361 | HPV | 16 | 5 | 11 | B*2705 | HQSQHVDL | 2420 | 200.00 | 8 |
| 2362 | HPV | 16 | 5 | 11 | B*2705 | SQHVDLLL | 2421 | 200.00 | 8 |
| 2363 | HPV | 16 | 5 | 11 | B*3901 | QHVDLLLL | 2422 | 540.00 | 8 |
| 2364 | HPV | 16 | 5 | 11 | B*5102 | IAAFALLV | 2423 | 100.00 | 8 |
| 2365 | HPV | 16 | 5 | 11 | B*3901 | WHIVCLSL | 2424 | 270.00 | 8 |
| 2366 | HPV | 16 | 5 | 11 | B*5102 | TPSPPLPL | 2425 | 100.00 | 8 |
| 2367 | HPV | 16 | 5 | 11 | B*5102 | LGVSPNAAI | 2426 | 264.00 | 9 |
| 2368 | HPV | 16 | 5 | 11 | B*5102 | AAIHQSQHV | 2427 | 110.00 | 9 |
| 2369 | HPV | 16 | 5 | 11 | B*5103 | AAIHQSQHV | 2427 | 399.30 | 9 |
| 2370 | HPV | 16 | 5 | 11 | B*2705 | HQSQHVDLL | 2428 | 200.00 | 9 |
| 2371 | HPV | 16 | 5 | 11 | B*2705 | SQHVDLLLL | 2429 | 200.00 | 9 |
| 2372 | HPV | 16 | 5 | 11 | B*5102 | NGLTNSEKL | 2430 | 159.72 | 9 |
| 2373 | HPV | 16 | 5 | 11 | Cw*0301 | EKLTPYNSL | 2431 | 100.00 | 9 |
| 2374 | HPV | 16 | 5 | 11 | B*5102 | FANIAAFAL | 2432 | 100.00 | 9 |
| 2375 | HPV | 16 | 5 | 11 | Cw*0301 | ANIAAFALL | 2433 | 100.00 | 9 |
| 2376 | HPV | 16 | 5 | 11 | A*0201 | LLVFSTFKI | 2434 | 102.87 | 9 |
| 2377 | HPV | 16 | 5 | 11 | B7 | TPSPPLPLL | 2435 | 120.00 | 9 |
| 2378 | HPV | 16 | 5 | 11 | Cw*0401 | TPSPPLPLL | 2435 | 192.00 | 9 |
| 2379 | HPV | 16 | 5 | 11 | B*5102 | TPSPPLPLL | 2435 | 100.00 | 9 |
| 2380 | HPV | 16 | 5 | 11 | B*5102 | NAAIHQSQHV | 2436 | 121.00 | 10 |
| 2381 | HPV | 16 | 5 | 11 | B*5103 | NAAIHQSQHV | 2436 | 110.00 | 10 |
| 2382 | HPV | 16 | 5 | 11 | B*3901 | IHQSQHVDLL | 2437 | 135.00 | 10 |
| 2383 | HPV | 16 | 5 | 11 | B*2705 | HQSQHVDLLL | 2438 | 200.00 | 10 |
| 2384 | HPV | 16 | 5 | 11 | B60 | SEKLTPYNSL | 2439 | 160.00 | 10 |
| 2385 | HPV | 16 | 5 | 11 | Cw*0401 | NFANIAAFAL | 2440 | 220.00 | 10 |
| 2386 | HPV | 16 | 5 | 11 | B*5102 | FANIAAFALL | 2441 | 100.00 | 10 |
| 2387 | HPV | 16 | 5 | 11 | Cw*0401 | AFALLVFSTF | 2442 | 100.00 | 10 |
| 2388 | HPV | 16 | 5 | 11 | A*0201 | ALLVFSTFKI | 2443 | 223.89 | 10 |
| 2389 | HPV | 16 | 5 | 11 | A*0201 | LVFSTFKIFV | 2444 | 800.05 | 10 |
| 2390 | HPV | 16 | 5 | 11 | A*0201 | KIFVSGVWHI | 2445 | 320.45 | 10 |
| 2391 | HPV | 16 | 5 | 12 | B*5102 | QPPPLPPL | 2446 | 100.00 | 8 |
| 2392 | HPV | 16 | 5 | 12 | B*2705 | LQPPPLPPL | 2447 | 200.00 | 9 |
| 2393 | HPV | 16 | 5 | 12 | B*2705 | LQPPPLPPLY | 2448 | 100.00 | 10 |
| 2394 | HPV | 16 | 5 | 12 | B62 | LQPPPLPPLY | 2448 | 192.00 | 10 |
| 2395 | HPV | 16 | 5 | 13 | B*5102 | AALLCFSI | 2449 | 660.00 | 8 |
| 2396 | HPV | 16 | 5 | 13 | B*5102 | IAFNLGLI | 2450 | 1100.00 | 8 |
| 2397 | HPV | 16 | 5 | 13 | B*5102 | SGLPNTFV | 2451 | 145.20 | 8 |
| 2398 | HPV | 16 | 5 | 13 | B*5102 | EPVLHLYV | 2452 | 660.00 | 8 |
| 2399 | HPV | 16 | 5 | 13 | B*3901 | LHLYVVLL | 2453 | 270.00 | 8 |
| 2400 | HPV | 16 | 5 | 13 | B*5103 | FAALLCFSI | 2454 | 110.00 | 9 |
| 2401 | HPV | 16 | 5 | 13 | B*5102 | FAALLCFSI | 2454 | 440.00 | 9 |
| 2402 | HPV | 16 | 5 | 13 | A*0201 | ALLCFSIHI | 2455 | 146.69 | 9 |
| 2403 | HPV | 16 | 5 | 13 | B*3901 | IHIAFNLGL | 2456 | 180.00 | 9 |
| 2404 | HPV | 16 | 5 | 13 | B*5102 | IAFNLGLIL | 2457 | 275.00 | 9 |
| 2405 | HPV | 16 | 5 | 13 | Cw*0401 | AFNLGLILL | 2458 | 400.00 | 9 |
| 2406 | HPV | 16 | 5 | 13 | Cw*0401 | HPLISLSGL | 2459 | 160.00 | 9 |
| 2407 | HPV | 16 | 5 | 13 | B*5102 | HPLISLSGL | 2459 | 300.00 | 9 |
| 2408 | HPV | 16 | 5 | 13 | B62 | SLSGLPNTF | 2460 | 105.60 | 9 |
| 2409 | HPV | 16 | 5 | 13 | Cw*0301 | SGLPNTFVL | 2461 | 120.00 | 9 |
| 2410 | HPV | 16 | 5 | 13 | A*0201 | FVLEPVLHL | 2462 | 300.01 | 9 |
| 2411 | HPV | 16 | 5 | 13 | A*0205 | FVLEPVLHL | 2462 | 756.00 | 9 |
| 2412 | HPV | 16 | 5 | 13 | A1 | VLEPVLHLY | 2463 | 450.00 | 9 |
| 2413 | HPV | 16 | 5 | 13 | B*5102 | EPVLHLYVV | 2464 | 660.00 | 9 |
| 2414 | HPV | 16 | 5 | 13 | B*5102 | AALLCFSIHI | 2465 | 660.00 | 10 |
| 2415 | HPV | 16 | 5 | 13 | B*5103 | AALLCFSIHI | 2465 | 132.00 | 10 |
| 2416 | HPV | 16 | 5 | 13 | Cw*0401 | CFSIHIAFNL | 2466 | 200.00 | 10 |
| 2417 | HPV | 16 | 5 | 13 | B*5102 | IAFNLGLILL | 2467 | 302.50 | 10 |
| 2418 | HPV | 16 | 5 | 13 | B*3901 | THPLISLSGL | 2468 | 135.00 | 10 |
| 2419 | HPV | 16 | 5 | 13 | B*5801 | ISLSGLPNTF | 2469 | 108.90 | 10 |
| 2420 | HPV | 16 | 5 | 13 | A*0201 | SLSGLPNTFV | 2470 | 382.54 | 10 |
| 2421 | HPV | 16 | 5 | 13 | B*5102 | LPNTFVLEPV | 2471 | 266.20 | 10 |
| 2422 | HPV | 16 | 5 | 13 | Cw*0401 | TFVLEPVLHL | 2472 | 440.00 | 10 |

TABLE 7-continued

| No | Species | Strain type | Frame | ORF | HLA | Seq | Seq ID No. | Score | Length |
|---|---|---|---|---|---|---|---|---|---|
| 2423 | HPV | 16 | 5 | 13 | B*5102 | EPVLHLYVVL | 2473 | 330.00 | 10 |
| 2424 | HPV | 16 | 5 | 13 | Cw*0301 | EPVLHLYVVL | 2473 | 100.00 | 10 |
| 2425 | HPV | 16 | 5 | 14 | B*5102 | LPVLNNHYHL | 2474 | 363.00 | 10 |
| 2426 | HPV | 16 | 5 | 16 | B*3901 | IHYIPYPL | 2475 | 180.00 | 8 |
| 2427 | HPV | 16 | 5 | 16 | B*5102 | YPLPHWYL | 2476 | 600.00 | 8 |
| 2428 | HPV | 16 | 5 | 16 | Cw*0401 | LFFFPLQPL | 2477 | 400.00 | 9 |
| 2429 | HPV | 16 | 5 | 16 | B*5102 | FPLQPLHKT | 2478 | 132.00 | 9 |
| 2430 | HPV | 16 | 5 | 16 | B*5102 | FPLQPLHKTI | 2479 | 3194.40 | 10 |
| 2431 | HPV | 16 | 5 | 16 | B*2705 | LQPLHKTIHY | 2480 | 100.00 | 10 |
| 2432 | HPV | 16 | 5 | 16 | B*5102 | QPLHKTIHYI | 2481 | 1756.92 | 10 |
| 2433 | HPV | 16 | 5 | 16 | B7 | IPYPLPHWYL | 2482 | 120.00 | 10 |
| 2434 | HPV | 16 | 5 | 16 | B*5102 | IPYPLPHWYL | 2482 | 550.00 | 10 |
| 2435 | HPV | 16 | 5 | 16 | Cw*0301 | IPYPLPHWYL | 2482 | 100.00 | 10 |
| 2436 | HPV | 16 | 5 | 17 | B*2705 | HLFHPPPL | 2483 | 150.00 | 8 |
| 2437 | HPV | 16 | 5 | 17 | B*5102 | PPLSCHLI | 2484 | 120.00 | 8 |
| 2438 | HPV | 16 | 5 | 17 | B*2705 | SRDQLSLV | 2485 | 600.00 | 8 |
| 2439 | HPV | 16 | 5 | 17 | B*3901 | DHLFHPPPL | 2486 | 180.00 | 9 |
| 2440 | HPV | 16 | 5 | 17 | Cw*0401 | HPPPLSCHL | 2487 | 105.60 | 9 |
| 2441 | HPV | 16 | 5 | 17 | B*5102 | HPPPLSCHL | 2487 | 100.00 | 9 |
| 2442 | HPV | 16 | 5 | 17 | B*2705 | SRDQLSLVA | 2488 | 200.00 | 9 |
| 2443 | HPV | 16 | 5 | 17 | A*0201 | SLVANLTYI | 2489 | 131.97 | 9 |
| 2444 | HPV | 16 | 5 | 17 | B*5102 | HPPPLSCHLI | 2490 | 400.00 | 10 |
| 2445 | HPV | 16 | 5 | 17 | B*2705 | SRDQLSLVAN | 2491 | 200.00 | 10 |
| 2446 | HPV | 16 | 5 | 19 | B*5102 | FGYALSFI | 2492 | 800.00 | 8 |
| 2447 | HPV | 16 | 5 | 19 | A*0205 | WVLKHCSSL | 2493 | 126.00 | 9 |
| 2448 | HPV | 16 | 5 | 19 | B*5102 | YALSFIHEL | 2494 | 330.00 | 9 |
| 2449 | HPV | 16 | 5 | 19 | A*0205 | WVLKHCSSLL | 2495 | 126.00 | 10 |
| 2450 | HPV | 16 | 5 | 19 | B62 | ILTGFGSTDF | 2496 | 149.76 | 10 |
| 2451 | HPV | 16 | 5 | 19 | B*3701 | TDFGYALSFI | 2497 | 200.00 | 10 |
| 2452 | HPV | 16 | 5 | 19 | Cw*0401 | GYALSFIHEL | 2498 | 400.00 | 10 |
| 2453 | HPV | 16 | 5 | 19 | A24 | GYALSFIHEL | 2498 | 220.00 | 10 |
| 2454 | HPV | 16 | 5 | 19 | B*5102 | YALSFIHELL | 2499 | 330.00 | 10 |
| 2455 | HPV | 16 | 5 | 1 | B*5103 | CAVLQMNNV | 2500 | 121.00 | 9 |
| 2456 | HPV | 16 | 5 | 1 | B*5102 | CAVLQMNNV | 2500 | 363.00 | 9 |
| 2457 | HPV | 16 | 5 | 2 | B*5102 | KALAHSDL | 2501 | 150.00 | 8 |
| 2458 | HPV | 16 | 5 | 2 | A*0201 | ALAHSDLFYM | 2502 | 364.50 | 10 |
| 2459 | HPV | 16 | 5 | 3 | B*2705 | CRSGKQGF | 2503 | 1000.00 | 8 |
| 2460 | HPV | 16 | 5 | 3 | B*2705 | KQETYKFK | 2504 | 600.00 | 8 |
| 2461 | HPV | 16 | 5 | 3 | B*2705 | KQGFGTHGK | 2505 | 600.00 | 9 |
| 2462 | HPV | 16 | 5 | 3 | A68.1 | MVGKQCRSGK | 2506 | 240.00 | 10 |
| 2463 | HPV | 16 | 5 | 3 | B*2705 | KQCRSGKQGF | 2507 | 300.00 | 10 |
| 2464 | HPV | 16 | 5 | 3 | B*2705 | CRSGKQGFGT | 2508 | 200.00 | 10 |
| 2465 | HPV | 16 | 5 | 6 | B*5102 | AAHNDIFV | 2509 | 121.00 | 8 |
| 2466 | HPV | 16 | 5 | 6 | B*3901 | AHNDIFVL | 2510 | 180.00 | 8 |
| 2467 | HPV | 16 | 5 | 6 | B*2705 | LRVVSTTV | 2348 | 600.00 | 8 |
| 2468 | HPV | 16 | 5 | 6 | B*5102 | LPQQMPLL | 2349 | 110.00 | 8 |
| 2469 | HPV | 16 | 5 | 6 | B*5103 | MAAHNDIFV | 2511 | 110.00 | 9 |
| 2470 | HPV | 16 | 5 | 6 | B*5102 | MAAHNDIFV | 2511 | 121.00 | 9 |
| 2471 | HPV | 16 | 5 | 6 | B*2705 | LRVVSTTVT | 2350 | 200.00 | 9 |
| 2472 | HPV | 16 | 5 | 6 | B*5801 | VSTTVTNSW | 2351 | 132.00 | 9 |
| 2473 | HPV | 16 | 5 | 6 | Cw*0301 | SWLPQQMPL | 2352 | 120.00 | 9 |
| 2474 | HPV | 16 | 5 | 6 | A*0201 | WLPQQMPLL | 2353 | 226.01 | 9 |
| 2475 | HPV | 16 | 5 | 6 | A*0201 | FVLRVVSTTV | 2512 | 103.58 | 10 |
| 2476 | HPV | 16 | 5 | 6 | B*2705 | LRVVSTTVTN | 2354 | 200.00 | 10 |
| 2477 | HPV | 16 | 5 | 6 | Cw*0301 | SWLPQQMPLL | 2355 | 200.00 | 10 |
| 2478 | HPV | 16 | 5 | 7 | B*5102 | SPTVPALL | 2357 | 100.00 | 8 |
| 2479 | HPV | 16 | 5 | 7 | Cw*0401 | TFSPTVPAL | 2361 | 576.00 | 9 |
| 2480 | HPV | 16 | 5 | 7 | B*5102 | VPALLNKCL | 2362 | 133.10 | 9 |
| 2481 | HPV | 16 | 5 | 7 | Cw*0401 | TFSPTVPALL | 2365 | 288.00 | 10 |
| 2482 | HPV | 16 | 5 | 8 | B*2705 | VRATYSSV | 2513 | 600.00 | 8 |
| 2483 | HPV | 16 | 5 | 8 | B*2705 | VRATYSSVL | 2514 | 2000.00 | 9 |
| 2484 | HPV | 16 | 5 | 8 | A24 | TYSSVLTTL | 2515 | 280.00 | 9 |
| 2485 | HPV | 16 | 5 | 8 | Cw*0401 | TYSSVLTTL | 2515 | 400.00 | 9 |
| 2486 | HPV | 16 | 5 | 8 | B7 | FVRATYSSVL | 2516 | 200.00 | 10 |
| 2487 | HPV | 16 | 5 | 8 | B*2705 | VRATYSSVLT | 2517 | 200.00 | 10 |
| 2488 | HPV | 16 | 5 | 9 | B*2705 | YRFSTTST | 2518 | 1000.00 | 8 |
| 2489 | HPV | 16 | 5 | 9 | A*0201 | YLSTYRFST | 2519 | 198.82 | 9 |
| 2490 | HPV | 16 | 5 | 10 | B*2705 | CRCWRLQY | 2520 | 1000.00 | 8 |
| 2491 | HPV | 16 | 5 | 10 | B*2705 | WRLQYRWV | 2521 | 600.00 | 8 |
| 2492 | HPV | 16 | 5 | 10 | B*2705 | YRWVSESG | 2375 | 100.00 | 8 |
| 2493 | HPV | 16 | 5 | 10 | B*2705 | CRCWRLQYR | 2522 | 1000.00 | 9 |
| 2494 | HPV | 16 | 5 | 10 | B*2705 | WRLQYRWVS | 2523 | 200.00 | 9 |
| 2495 | HPV | 16 | 5 | 10 | B*2705 | LQYRWVSES | 2376 | 100.00 | 9 |
| 2496 | HPV | 16 | 5 | 10 | B*2702 | YRWVSESGI | 2377 | 300.00 | 9 |
| 2497 | HPV | 16 | 5 | 10 | B*2705 | YRWVSESGI | 2377 | 3000.00 | 9 |
| 2498 | HPV | 16 | 5 | 10 | B*2702 | CRCWRLQYRW | 2524 | 100.00 | 10 |

TABLE 7-continued

| No | Species | Strain type | Frame | ORF | HLA | Seq | Seq ID No. | Score | Length |
|---|---|---|---|---|---|---|---|---|---|
| 2499 | HPV | 16 | 5 | 10 | B*2705 | CRCWRLQYRW | 2524 | 200.00 | 10 |
| 2500 | HPV | 16 | 5 | 10 | B*2702 | YRWVSESGII | 2378 | 300.00 | 10 |
| 2501 | HPV | 16 | 5 | 10 | B*2705 | YRWVSESGII | 2378 | 3000.00 | 10 |
| 2502 | HPV | 16 | 5 | 11 | B*5102 | LPQLLMLL | 2525 | 110.00 | 8 |
| 2503 | HPV | 16 | 5 | 11 | B*5102 | NALYCICL | 2388 | 165.00 | 8 |
| 2504 | HPV | 16 | 5 | 11 | B*3901 | LHQTALPL | 2389 | 135.00 | 8 |
| 2505 | HPV | 16 | 5 | 11 | B*2705 | HQTALPLY | 2390 | 100.00 | 8 |
| 2506 | HPV | 16 | 5 | 11 | B*3901 | IHVFLYIL | 2391 | 180.00 | 8 |
| 2507 | HPV | 16 | 5 | 11 | B*3901 | NHNSQLDPL | 2392 | 135.00 | 9 |
| 2508 | HPV | 16 | 5 | 11 | A*0205 | SQLDPLPQL | 2393 | 100.80 | 9 |
| 2509 | HPV | 16 | 5 | 11 | B*2705 | SQLDPLPQL | 2393 | 200.00 | 9 |
| 2510 | HPV | 16 | 5 | 11 | Cw*0301 | DPLPQLLML | 2394 | 100.00 | 9 |
| 2511 | HPV | 16 | 5 | 11 | Cw*0401 | DPLPQLLML | 2394 | 192.00 | 9 |
| 2512 | HPV | 16 | 5 | 11 | B*5102 | DPLPQLLML | 2394 | 330.00 | 9 |
| 2513 | HPV | 16 | 5 | 11 | A*0201 | LLMLLHKYI | 2395 | 360.92 | 9 |
| 2514 | HPV | 16 | 5 | 11 | A*0201 | MLLHKYIYV | 2396 | 3609.23 | 9 |
| 2515 | HPV | 16 | 5 | 11 | B*5103 | TALPLYTHV | 2397 | 132.00 | 9 |
| 2516 | HPV | 16 | 5 | 11 | B*5102 | TALPLYIHV | 2397 | 300.00 | 9 |
| 2517 | HPV | 16 | 5 | 11 | B*5102 | LPLYIHVFL | 2398 | 300.00 | 9 |
| 2518 | HPV | 16 | 5 | 11 | A24 | LYIHVFLYI | 2399 | 126.00 | 9 |
| 2519 | HPV | 16 | 5 | 11 | B*3901 | IHVFLYILL | 2400 | 180.00 | 9 |
| 2520 | HPV | 16 | 5 | 11 | Cw*0301 | IHVFLYILL | 2400 | 100.00 | 9 |
| 2521 | HPV | 16 | 5 | 11 | A*0201 | FLYILLVQL | 2401 | 723.25 | 9 |
| 2522 | HPV | 16 | 5 | 11 | A*0205 | FLYILLVQL | 2401 | 126.00 | 9 |
| 2523 | HPV | 16 | 5 | 11 | B*2705 | FLYILLVQL | 2401 | 150.00 | 9 |
| 2524 | HPV | 16 | 5 | 11 | A*0201 | ILLVQLNTL | 2402 | 309.05 | 9 |
| 2525 | HPV | 16 | 5 | 11 | B*2705 | SQLDPLPQLL | 2526 | 200.00 | 10 |
| 2526 | HPV | 16 | 5 | 11 | B*3701 | LDPLPQLLML | 2527 | 200.00 | 10 |
| 2527 | HPV | 16 | 5 | 11 | B*5102 | DPLPQLLMLL | 2528 | 300.00 | 10 |
| 2528 | HPV | 16 | 5 | 11 | Cw*0301 | DPLPQLLMLL | 2528 | 120.00 | 10 |
| 2529 | HPV | 16 | 5 | 11 | Cw*0401 | DPLPQLLMLL | 2528 | 192.00 | 10 |
| 2530 | HPV | 16 | 5 | 11 | A*0201 | QLLMLLHKYI | 2529 | 212.31 | 10 |
| 2531 | HPV | 16 | 5 | 11 | A*0201 | LMLLHKYIYV | 2403 | 2606.66 | 10 |
| 2532 | HPV | 16 | 5 | 11 | Cw*0301 | IYVSSLYNAL | 2404 | 100.00 | 10 |
| 2533 | HPV | 16 | 5 | 11 | Cw*0401 | IYVSSLYNAL | 2404 | 200.00 | 10 |
| 2534 | HPV | 16 | 5 | 11 | A24 | IYVSSLYNAL | 2404 | 432.00 | 10 |
| 2535 | HPV | 16 | 5 | 11 | Cw*0401 | LYNALYCICL | 2405 | 200.00 | 10 |
| 2536 | HPV | 16 | 5 | 11 | A24 | LYNALYCICL | 2405 | 300.00 | 10 |
| 2537 | HPV | 16 | 5 | 11 | A*0201 | ALPLYIHVFL | 2406 | 117.49 | 10 |
| 2538 | HPV | 16 | 5 | 11 | Cw*0401 | LYIHVFLYIL | 2407 | 400.00 | 10 |
| 2539 | HPV | 16 | 5 | 11 | A24 | LYIHVFLYIL | 2407 | 300.00 | 10 |
| 2540 | HPV | 16 | 5 | 11 | Cw*0401 | VFLYILLVQL | 2408 | 400.00 | 10 |
| 2541 | HPV | 16 | 5 | 11 | A*0201 | YILLVQLNTL | 2409 | 114.98 | 10 |
| 2542 | HPV | 16 | 5 | 11 | A*0205 | YILLVQLNTL | 2409 | 126.00 | 10 |
| 2543 | HPV | 16 | 5 | 12 | B*2705 | VQLLVMLY | 2530 | 100.00 | 8 |
| 2544 | HPV | 16 | 5 | 12 | B*2705 | IQPVLAPL | 2531 | 200.00 | 8 |
| 2545 | HPV | 16 | 5 | 12 | A24 | HYYIVSYIL | 2532 | 280.00 | 9 |
| 2546 | HPV | 16 | 5 | 12 | Cw*0401 | HYYIVSYIL | 2532 | 200.00 | 9 |
| 2547 | HPV | 16 | 5 | 12 | A24 | YYIVSYILF | 2533 | 150.00 | 9 |
| 2548 | HPV | 16 | 5 | 12 | Cw*0401 | YYIVSYILF | 2533 | 100.00 | 9 |
| 2549 | HPV | 16 | 5 | 12 | A*0201 | YIVSYILFL | 2534 | 170.92 | 9 |
| 2550 | HPV | 16 | 5 | 12 | Cw*0301 | VSYILFLTL | 2535 | 120.00 | 9 |
| 2551 | HPV | 16 | 5 | 12 | A*0201 | ILFLTLVAV | 2536 | 1006.21 | 9 |
| 2552 | HPV | 16 | 5 | 12 | B*5102 | VAVQLLVML | 2537 | 165.00 | 9 |
| 2553 | HPV | 16 | 5 | 12 | A*0201 | QLLVMLYSL | 2538 | 181.79 | 9 |
| 2554 | HPV | 16 | 5 | 12 | A*0201 | MLYSLIQPV | 2539 | 870.23 | 9 |
| 2555 | HPV | 16 | 5 | 12 | A24 | LYSLIQPVL | 2540 | 280.00 | 9 |
| 2556 | HPV | 16 | 5 | 12 | Cw*0401 | LYSLIQPVL | 2540 | 200.00 | 9 |
| 2557 | HPV | 16 | 5 | 12 | B*3901 | FHYYIVSYIL | 2541 | 180.00 | 10 |
| 2558 | HPV | 16 | 5 | 12 | Cw*0401 | HYYIVSYILF | 2542 | 100.00 | 10 |
| 2559 | HPV | 16 | 5 | 12 | A24 | HYYIVSYILF | 2542 | 100.00 | 10 |
| 2560 | HPV | 16 | 5 | 12 | Cw*0401 | YYIVSYILFL | 2543 | 400.00 | 10 |
| 2561 | HPV | 16 | 5 | 12 | A24 | YYIVSYILFL | 2543 | 300.00 | 10 |
| 2562 | HPV | 16 | 5 | 12 | A*0201 | YILFLTLVAV | 2544 | 374.37 | 10 |
| 2563 | HPV | 16 | 5 | 12 | Cw*0401 | LFLTLVAVQL | 2545 | 200.00 | 10 |
| 2564 | HPV | 16 | 5 | 12 | A*0201 | FLTLVAVQLL | 2546 | 226.01 | 10 |
| 2565 | HPV | 16 | 5 | 12 | B*2705 | VQLLVMLYSL | 2547 | 200.00 | 10 |
| 2566 | HPV | 16 | 5 | 12 | A*0201 | VMLYSLIQPV | 2548 | 726.71 | 10 |
| 2567 | HPV | 16 | 5 | 12 | B*2705 | MLYSLIQPVL | 2549 | 150.00 | 10 |
| 2568 | HPV | 16 | 5 | 13 | B*5102 | NGLCFTSI | 2550 | 264.00 | 8 |
| 2569 | HPV | 16 | 5 | 13 | B*3901 | GHFSCTNGL | 2551 | 180.00 | 9 |
| 2570 | HPV | 16 | 5 | 13 | Cw*0401 | CFTSIETKF | 2552 | 110.00 | 9 |
| 2571 | HPV | 16 | 5 | 13 | B*5102 | FPSNAFLKL | 2553 | 440.00 | 9 |
| 2572 | HPV | 16 | 5 | 13 | Cw*0401 | HFSCTNGLCF | 2554 | 100.00 | 10 |
| 2573 | HPV | 16 | 5 | 13 | Cw*0401 | KFPSNAFLKL | 2555 | 242.00 | 10 |
| 2574 | HPV | 16 | 5 | 14 | B*2705 | MQFFLGMPC | 2556 | 100.00 | 9 |

TABLE 7-continued

| No | Species | Strain type | Frame | ORF | HLA | Seq | Seq ID No. | Score | Length |
|---|---|---|---|---|---|---|---|---|---|
| 2575 | HPV | 16 | 5 | 14 | B*2705 | MQFFLGMPCK | 2557 | 1000.00 | 10 |
| 2576 | HPV | 16 | 5 | 14 | Cw*0401 | FFLGMPCKNL | 2558 | 200.00 | 10 |
| 2577 | HPV | 16 | 5 | 14 | B*5102 | MPCKNLFNAV | 2559 | 220.00 | 10 |
| 2578 | HPV | 16 | 5 | 15 | B*2705 | KQYCCNSV | 2560 | 900.00 | 8 |
| 2579 | HPV | 16 | 5 | 15 | B*2705 | HQSQHVDL | 2420 | 200.00 | 8 |
| 2580 | HPV | 16 | 5 | 15 | B*2705 | SQHVDLLL | 2421 | 200.00 | 8 |
| 2581 | HPV | 16 | 5 | 15 | B*3901 | QHVDLLLL | 2422 | 540.00 | 8 |
| 2582 | HPV | 16 | 5 | 15 | B*5102 | IAAFALLV | 2423 | 100.00 | 8 |
| 2583 | HPV | 16 | 5 | 15 | B*3901 | WHIVCLSL | 2424 | 270.00 | 8 |
| 2584 | HPV | 16 | 5 | 15 | B*5102 | TPSPPLPL | 2425 | 100.00 | 8 |
| 2585 | HPV | 16 | 5 | 15 | B*2702 | KQYCCNSVF | 2561 | 300.00 | 9 |
| 2586 | HPV | 16 | 5 | 15 | B*2705 | KQYCCNSVF | 2561 | 1500.00 | 9 |
| 2587 | HPV | 16 | 5 | 15 | B*5201 | KQYCCNSVF | 2561 | 275.00 | 9 |
| 2588 | HPV | 16 | 5 | 15 | A*0201 | FILSAILGV | 2562 | 374.37 | 9 |
| 2589 | HPV | 16 | 5 | 15 | B*5102 | LGVSPNAAI | 2426 | 264.00 | 9 |
| 2590 | HPV | 16 | 5 | 15 | B*5103 | AAIHQSQHV | 2427 | 110.00 | 9 |
| 2591 | HPV | 16 | 5 | 15 | B*5102 | AAIHQSQHV | 2427 | 399.30 | 9 |
| 2592 | HPV | 16 | 5 | 15 | B*2705 | HQSQHVDLL | 2428 | 200.00 | 9 |
| 2593 | HPV | 16 | 5 | 15 | B*2705 | SQHVDLLLL | 2429 | 200.00 | 9 |
| 2594 | HPV | 16 | 5 | 15 | B*5102 | NGLTNSEKL | 2430 | 159.72 | 9 |
| 2595 | HPV | 16 | 5 | 15 | Cw*0301 | EKLTPYNSL | 2431 | 100.00 | 9 |
| 2596 | HPV | 16 | 5 | 15 | B*5102 | FANIAAFAL | 2432 | 100.00 | 9 |
| 2597 | HPV | 16 | 5 | 15 | Cw*0301 | ANIAAFALL | 2563 | 100.00 | 9 |
| 2598 | HPV | 16 | 5 | 15 | A*0201 | LLVFSTFKI | 2434 | 102.87 | 9 |
| 2599 | HPV | 16 | 5 | 15 | B7 | TPSPPLPLL | 2435 | 120.00 | 9 |
| 2600 | HPV | 16 | 5 | 15 | Cw*0401 | TPSPPLPLL | 2435 | 192.00 | 9 |
| 2601 | HPV | 16 | 5 | 15 | B*5102 | TPSPPLPLL | 2435 | 100.00 | 9 |
| 2602 | HPV | 16 | 5 | 15 | B*2705 | KQYCCNSVFI | 2564 | 900.00 | 10 |
| 2603 | HPV | 16 | 5 | 15 | B*5201 | KQYCCNSVFI | 2564 | 165.00 | 10 |
| 2604 | HPV | 16 | 5 | 15 | Cw*0401 | QYCCNSVFIL | 2565 | 400.00 | 10 |
| 2605 | HPV | 16 | 5 | 15 | A24 | QYCCNSVFIL | 2565 | 200.00 | 10 |
| 2606 | HPV | 16 | 5 | 15 | B*5102 | NAAIHQSQHV | 2436 | 121.00 | 10 |
| 2607 | HPV | 16 | 5 | 15 | B*5103 | NAAIHQSQHV | 2436 | 110.00 | 10 |
| 2608 | HPV | 16 | 5 | 15 | B*3901 | IHQSQHVDLL | 2437 | 135.00 | 10 |
| 2609 | HPV | 16 | 5 | 15 | B*2705 | HQSQHVDLLL | 2438 | 200.00 | 10 |
| 2610 | HPV | 16 | 5 | 15 | B60 | SEKLTPYNSL | 2439 | 160.00 | 10 |
| 2611 | HPV | 16 | 5 | 15 | Cw*0401 | NFANIAAFAL | 2440 | 220.00 | 10 |
| 2612 | HPV | 16 | 5 | 15 | B*5102 | FANIAAFALL | 2441 | 100.00 | 10 |
| 2613 | HPV | 16 | 5 | 15 | Cw*0401 | AFALLVFSTF | 2442 | 100.00 | 10 |
| 2614 | HPV | 16 | 5 | 15 | A*0201 | ALLVFSTFKI | 2443 | 223.89 | 10 |
| 2615 | HPV | 16 | 5 | 15 | A*0201 | LVFSTFKIFV | 2444 | 800.05 | 10 |
| 2616 | HPV | 16 | 5 | 15 | A*0201 | KIFVSGVWHI | 2445 | 320.45 | 10 |
| 2617 | HPV | 16 | 5 | 16 | B*2705 | NRWGTQFL | 2566 | 10000.00 | 8 |
| 2618 | HPV | 16 | 5 | 16 | B*2705 | TQFLVCPL | 2567 | 1000.00 | 8 |
| 2619 | HPV | 16 | 5 | 16 | B*2702 | NRWGTQFLV | 2568 | 100.00 | 9 |
| 2620 | HPV | 16 | 5 | 16 | B*2705 | NRWGTQFLV | 2568 | 3000.00 | 9 |
| 2621 | HPV | 16 | 5 | 16 | B*2705 | TQFLVCPLT | 2569 | 100.00 | 9 |
| 2622 | HPV | 16 | 5 | 16 | A*0201 | FLVCPLTGL | 2570 | 226.01 | 9 |
| 2623 | HPV | 16 | 5 | 16 | Cw*0301 | TGLPKYECL | 2571 | 500.00 | 9 |
| 2624 | HPV | 16 | 5 | 16 | B*5102 | LPKYECLRV | 2572 | 200.00 | 9 |
| 2625 | HPV | 16 | 5 | 16 | A24 | KYECLRVCF | 2573 | 360.00 | 9 |
| 2626 | HPV | 16 | 5 | 16 | Cw*0401 | KYECLRVCF | 2573 | 100.00 | 9 |
| 2627 | HPV | 16 | 5 | 16 | B60 | SENRWGTQFL | 2574 | 160.00 | 10 |
| 2628 | HPV | 16 | 5 | 16 | B*2702 | NRWGTQFLVC | 2575 | 100.00 | 10 |
| 2629 | HPV | 16 | 5 | 16 | B*2705 | NRWGTQFLVC | 2575 | 1000.00 | 10 |
| 2630 | HPV | 16 | 5 | 16 | Cw*0401 | QFLVCPLTGL | 2576 | 400.00 | 10 |
| 2631 | HPV | 16 | 5 | 16 | A68.1 | LVCPLTGLPK | 2577 | 180.00 | 10 |
| 2632 | HPV | 16 | 5 | 17 | B*2705 | LLFVQMSL | 2578 | 150.00 | 8 |
| 2633 | HPV | 16 | 5 | 17 | B*2705 | VQMSLLFF | 2579 | 100.00 | 8 |
| 2634 | HPV | 16 | 5 | 17 | B*2705 | FRTQWLLT | 2580 | 200.00 | 8 |
| 2635 | HPV | 16 | 5 | 17 | B*2705 | TQWLLTVN | 2581 | 100.00 | 8 |
| 2636 | HPV | 16 | 5 | 17 | A*0201 | LLFVQMSLL | 2582 | 309.05 | 9 |
| 2637 | HPV | 16 | 5 | 17 | B*2705 | LLFVQMSLL | 2582 | 150.00 | 9 |
| 2638 | HPV | 16 | 5 | 17 | Cw*0401 | LFVQMSLLF | 2583 | 110.00 | 9 |
| 2639 | HPV | 16 | 5 | 17 | B*2705 | VQMSLLFFR | 2584 | 100.00 | 9 |
| 2640 | HPV | 16 | 5 | 17 | A*0201 | LLFFRTQWL | 2585 | 739.03 | 9 |
| 2641 | HPV | 16 | 5 | 17 | B*2705 | LLFFRTQWL | 2585 | 150.00 | 9 |
| 2642 | HPV | 16 | 5 | 17 | Cw*0401 | LFFRTQWLL | 2586 | 240.00 | 9 |
| 2643 | HPV | 16 | 5 | 17 | B*2705 | FRTQWLLTV | 2587 | 600.00 | 9 |
| 2644 | HPV | 16 | 5 | 17 | B*2705 | TQWLLTVNT | 2588 | 100.00 | 9 |
| 2645 | HPV | 16 | 5 | 17 | A*0201 | SLLFVQMSLL | 2589 | 181.79 | 10 |
| 2646 | HPV | 16 | 5 | 17 | Cw*0401 | LFVQMSLLFF | 2590 | 200.00 | 10 |
| 2647 | HPV | 16 | 5 | 17 | A68.1 | FVQMSLLFFR | 2591 | 200.00 | 10 |
| 2648 | HPV | 16 | 5 | 17 | B*5801 | MSLLFFRTQW | 2592 | 120.00 | 10 |
| 2649 | HPV | 16 | 5 | 17 | A*0201 | SLLFFRTQWL | 2593 | 434.72 | 10 |
| 2650 | HPV | 16 | 5 | 17 | A*0201 | LLFFRTQWLL | 2594 | 1007.77 | 10 |

TABLE 7-continued

| No | Species | Strain type | Frame | ORF | HLA | Seq | Seq ID No. | Score | Length |
|---|---|---|---|---|---|---|---|---|---|
| 2651 | HPV | 16 | 5 | 17 | B*2705 | LLFFRTQWLL | 2594 | 150.00 | 10 |
| 2652 | HPV | 16 | 5 | 17 | B*2705 | FRTQWLLTVN | 2595 | 200.00 | 10 |
| 2653 | HPV | 16 | 5 | 18 | A*0201 | ILTNFRIKL | 2596 | 138.00 | 9 |
| 2654 | HPV | 16 | 5 | 20 | B*5102 | FGYALSFI | 2492 | 800.00 | 8 |
| 2655 | HPV | 16 | 5 | 20 | B*5102 | YALSFIHEL | 2494 | 330.00 | 9 |
| 2656 | HPV | 16 | 5 | 20 | B62 | ILTGFGSTDF | 2496 | 149.76 | 10 |
| 2657 | HPV | 16 | 5 | 20 | B*3701 | TDFGYALSFI | 2497 | 200.00 | 10 |
| 2658 | HPV | 16 | 5 | 20 | Cw*0401 | GYALSFIHEL | 2498 | 400.00 | 10 |
| 2659 | HPV | 16 | 5 | 20 | A24 | GYALSFIHEL | 2498 | 220.00 | 10 |
| 2660 | HPV | 16 | 5 | 20 | B*5102 | YALSFIHELL | 2499 | 330.00 | 10 |
| 2661 | HPV | 16 | 6 | 1 | B*2705 | LQNIVYIK | 2597 | 200.00 | 8 |
| 2662 | HPV | 16 | 6 | 1 | B*2705 | KQDVANIV | 2598 | 180.00 | 8 |
| 2663 | HPV | 16 | 6 | 1 | B*5103 | LALQNIVYI | 2599 | 175.69 | 9 |
| 2664 | HPV | 16 | 6 | 1 | B*5102 | LALQNIVYI | 2599 | 878.46 | 9 |
| 2665 | HPV | 16 | 6 | 1 | A3 | ALQNIVYIK | 2600 | 270.00 | 9 |
| 2666 | HPV | 16 | 6 | 1 | B*2705 | KQKQDVANI | 2601 | 180.00 | 9 |
| 2667 | HPV | 16 | 6 | 1 | B*2705 | KQDVANIVY | 2602 | 300.00 | 9 |
| 2668 | HPV | 16 | 6 | 1 | B*2705 | KQKQDVANIV | 2603 | 180.00 | 10 |
| 2669 | HPV | 16 | 6 | 1 | B*5201 | KQKQDVANIV | 2603 | 200.00 | 10 |
| 2670 | HPV | 16 | 6 | 1 | B*2705 | KQDVANIVYI | 2604 | 180.00 | 10 |
| 2671 | HPV | 16 | 6 | 2 | B*2705 | KTFPLNLL | 2605 | 150.00 | 8 |
| 2672 | HPV | 16 | 6 | 2 | A68.1 | LVVKICVLK | 2606 | 240.00 | 9 |
| 2673 | HPV | 16 | 6 | 2 | B*2705 | LQKTFPLNL | 2607 | 200.00 | 9 |
| 2674 | HPV | 16 | 6 | 2 | B*2705 | LQKTFPLNLL | 2608 | 200.00 | 10 |
| 2675 | HPV | 16 | 6 | 2 | B*2705 | KTFPLNLLPK | 2609 | 150.00 | 10 |
| 2676 | HPV | 16 | 6 | 2 | B*5102 | FPLNLLPKKC | 2610 | 145.20 | 10 |
| 2677 | HPV | 16 | 6 | 3 | B*2705 | LQTYKYLL | 2611 | 200.00 | 8 |
| 2678 | HPV | 16 | 6 | 3 | Cw*0401 | VFDKQLPGL | 2612 | 600.00 | 9 |
| 2679 | HPV | 16 | 6 | 3 | B*2705 | KQLPGLQTY | 2613 | 300.00 | 9 |
| 2680 | HPV | 16 | 6 | 3 | B62 | KQLPGLQTY | 2613 | 211.20 | 9 |
| 2681 | HPV | 16 | 6 | 3 | A24 | TYKYLLVCL | 2614 | 240.00 | 9 |
| 2682 | HPV | 16 | 6 | 3 | Cw*0401 | TYKYLLVCL | 2614 | 400.00 | 9 |
| 2683 | HPV | 16 | 6 | 3 | B60 | LEVYVFDKQL | 2615 | 352.00 | 10 |
| 2684 | HPV | 16 | 6 | 3 | A*0201 | YVFDKQLPGL | 2616 | 300.01 | 10 |
| 2685 | HPV | 16 | 6 | 3 | A*0205 | YVFDKQLPGL | 2616 | 756.00 | 10 |
| 2686 | HPV | 16 | 6 | 3 | B*2705 | KQLPGLQTYK | 2617 | 600.00 | 10 |
| 2687 | HPV | 16 | 6 | 3 | B*5102 | LPGLQTYKYL | 2618 | 146.41 | 10 |
| 2688 | HPV | 16 | 6 | 3 | A*0201 | GLQTYKYLLV | 2619 | 104.33 | 10 |
| 2689 | HPV | 16 | 6 | 3 | Cw*0401 | TYKYLLVCLL | 2620 | 400.00 | 10 |
| 2690 | HPV | 16 | 6 | 3 | A24 | TYKYLLVCLL | 2620 | 240.00 | 10 |
| 2691 | HPV | 16 | 6 | 3 | A*0201 | YLLVCLLGEV | 2621 | 353.95 | 10 |
| 2692 | HPV | 16 | 6 | 3 | A68.1 | VVDQNSSPPK | 2622 | 120.00 | 10 |
| 2693 | HPV | 16 | 6 | 4 | B*2705 | RLFCTVEK | 2623 | 450.00 | 8 |
| 2694 | HPV | 16 | 6 | 4 | B*2705 | LRLFCTVEK | 2624 | 2000.00 | 9 |
| 2695 | HPV | 16 | 6 | 6 | B*3901 | QHWYMGIL | 2625 | 180.00 | 8 |
| 2696 | HPV | 16 | 6 | 6 | B*5102 | MGILCPSV | 2626 | 132.00 | 8 |
| 2697 | HPV | 16 | 6 | 6 | A*0201 | LMVDNHLDL | 2627 | 107.54 | 9 |
| 2698 | HPV | 16 | 6 | 6 | B*2705 | LQHWYMGIL | 2628 | 200.00 | 9 |
| 2699 | HPV | 16 | 6 | 6 | A*0201 | YMGILCPSV | 2629 | 231.07 | 9 |
| 2700 | HPV | 16 | 6 | 6 | A*0201 | LMVDNHLDLL | 2630 | 121.19 | 10 |
| 2701 | HPV | 16 | 6 | 8 | B*2705 | MRCQENQT | 2631 | 200.00 | 8 |
| 2702 | HPV | 16 | 6 | 8 | B*2702 | MRCQENQTY | 2632 | 200.00 | 9 |
| 2703 | HPV | 16 | 6 | 8 | B*2705 | MRCQENQTY | 2632 | 1000.00 | 9 |
| 2704 | HPV | 16 | 6 | 8 | A24 | TYWGQVNVF | 2633 | 120.00 | 9 |
| 2705 | HPV | 16 | 6 | 8 | Cw*0401 | TYWGQVNVF | 2633 | 200.00 | 9 |
| 2706 | HPV | 16 | 6 | 8 | B*2702 | MRCQENQTYW | 2634 | 100.00 | 10 |
| 2707 | HPV | 16 | 6 | 8 | B*2705 | MRCQENQTYW | 2634 | 200.00 | 10 |
| 2708 | HPV | 16 | 6 | 9 | B*2705 | LQVVWMFL | 2635 | 200.00 | 8 |
| 2709 | HPV | 16 | 6 | 9 | B*2705 | VQHIHPCL | 2636 | 200.00 | 8 |
| 2710 | HPV | 16 | 6 | 9 | Cw*0401 | MFLHDNICL | 2637 | 200.00 | 9 |
| 2711 | HPV | 16 | 6 | 9 | A*0201 | FLHDNICLC | 2638 | 215.50 | 9 |
| 2712 | HPV | 16 | 6 | 9 | A*0201 | WMFLHDNICL | 2639 | 262.59 | 10 |
| 2713 | HPV | 16 | 6 | 9 | B*2705 | WMFLHDNICL | 2639 | 250.00 | 10 |
| 2714 | HPV | 16 | 6 | 9 | A*0201 | FLHDNICLCV | 2640 | 1311.75 | 10 |
| 2715 | HPV | 16 | 6 | 11 | B*5102 | AGLCKATI | 2641 | 240.00 | 8 |
| 2716 | HPV | 16 | 6 | 11 | B*5102 | YAGLSYVI | 2642 | 440.00 | 8 |
| 2717 | HPV | 16 | 6 | 11 | B*2705 | VRLYNPRR | 2643 | 300.00 | 8 |
| 2718 | HPV | 16 | 6 | 11 | B*2705 | GRDPGMGV | 2644 | 600.00 | 8 |
| 2719 | HPV | 16 | 6 | 11 | B*5102 | DPGMGVLL | 2645 | 110.00 | 8 |
| 2720 | HPV | 16 | 6 | 11 | B*5102 | MGVLLVTV | 2646 | 132.00 | 8 |
| 2721 | HPV | 16 | 6 | 11 | A*0201 | YLMPVRLEV | 2647 | 1183.78 | 9 |
| 2722 | HPV | 16 | 6 | 11 | B14 | VRLEVNAGL | 2648 | 100.00 | 9 |
| 2723 | HPV | 16 | 6 | 11 | B*2705 | VRLEVNAGL | 2648 | 2000.00 | 9 |
| 2724 | HPV | 16 | 6 | 11 | B*5103 | NAGLCKATI | 2649 | 121.00 | 9 |
| 2725 | HPV | 16 | 6 | 11 | B*5102 | NAGLCKATI | 2649 | 242.00 | 9 |
| 2726 | HPV | 16 | 6 | 11 | A3 | GLCKATISK | 2650 | 120.00 | 9 |

TABLE 7-continued

| No | Species | Strain type | Frame | ORF | HLA | Seq | Seq ID No. | Score | Length |
|---|---|---|---|---|---|---|---|---|---|
| 2727 | HPV | 16 | 6 | 11 | B*5102 | GAILILLSL | 2651 | 165.00 | 9 |
| 2728 | HPV | 16 | 6 | 11 | B62 | ILLSLLEKY | 2652 | 104.00 | 9 |
| 2729 | HPV | 16 | 6 | 11 | A*0201 | SLLEKYNVL | 2653 | 199.30 | 9 |
| 2730 | HPV | 16 | 6 | 11 | A*0205 | SLLEKYNVL | 2653 | 126.00 | 9 |
| 2731 | HPV | 16 | 6 | 11 | Cw*0301 | SLLEKYNVL | 2653 | 150.00 | 9 |
| 2732 | HPV | 16 | 6 | 11 | A24 | KYNVLSTSI | 2654 | 180.00 | 9 |
| 2733 | HPV | 16 | 6 | 11 | Cw*0301 | TSIPSYAGL | 2655 | 500.00 | 9 |
| 2734 | HPV | 16 | 6 | 11 | A*0201 | GLSYVISLV | 2656 | 159.97 | 9 |
| 2735 | HPV | 16 | 6 | 11 | A68.1 | TTLTCCVVR | 2657 | 100.00 | 9 |
| 2736 | HPV | 16 | 6 | 11 | A68.1 | CVVRLYNPR | 2658 | 400.00 | 9 |
| 2737 | HPV | 16 | 6 | 11 | A68.1 | VVRLYNPRR | 2659 | 200.00 | 9 |
| 2738 | HPV | 16 | 6 | 11 | B*2705 | GRDPGMGVL | 2660 | 2000.00 | 9 |
| 2739 | HPV | 16 | 6 | 11 | B*3701 | RDPGMGVLL | 2661 | 200.00 | 9 |
| 2740 | HPV | 16 | 6 | 11 | B*5102 | DPGMGVLLV | 2662 | 220.00 | 9 |
| 2741 | HPV | 16 | 6 | 11 | A*0201 | GMGVLLVTV | 2663 | 115.53 | 9 |
| 2742 | HPV | 16 | 6 | 11 | A*0201 | LLVTVLGFV | 2664 | 194.44 | 9 |
| 2743 | HPV | 16 | 6 | 11 | B*5102 | LGFVLTINV | 2665 | 220.00 | 9 |
| 2744 | HPV | 16 | 6 | 11 | B*2705 | VRLEVNAGLC | 2666 | 200.00 | 10 |
| 2745 | HPV | 16 | 6 | 11 | B*5102 | GAILILLSLL | 2667 | 165.00 | 10 |
| 2746 | HPV | 16 | 6 | 11 | A*0201 | LLSLLEKYNV | 2668 | 118.24 | 10 |
| 2747 | HPV | 16 | 6 | 11 | Cw*0301 | LSLLEKYNVL | 2669 | 100.00 | 10 |
| 2748 | HPV | 16 | 6 | 11 | B*5102 | IPSYAGLSYV | 2670 | 242.00 | 10 |
| 2749 | HPV | 16 | 6 | 11 | B*5102 | YAGLSYVISL | 2671 | 110.00 | 10 |
| 2750 | HPV | 16 | 6 | 11 | B*5102 | AGLSYVISLV | 2672 | 145.20 | 10 |
| 2751 | HPV | 16 | 6 | 11 | A68.1 | CVVRLYNPRR | 2673 | 400.00 | 10 |
| 2752 | HPV | 16 | 6 | 11 | B*2705 | RRATGRDPGM | 2674 | 1800.00 | 10 |
| 2753 | HPV | 16 | 6 | 11 | B*2705 | GRDPGMGVLL | 2675 | 2000.00 | 10 |
| 2754 | HPV | 16 | 6 | 11 | A*0201 | VLLVTVLGFV | 2676 | 719.44 | 10 |
| 2755 | HPV | 16 | 6 | 11 | A*0201 | VLGFVLTINV | 2677 | 118.24 | 10 |
| 2756 | HPV | 16 | 6 | 12 | B*2705 | SRLCFFGA | 2678 | 200.00 | 8 |
| 2757 | HPV | 16 | 6 | 12 | B*2705 | GQVLPNNF | 2679 | 100.00 | 8 |
| 2758 | HPV | 16 | 6 | 12 | B*2705 | FRRGYFVA | 2680 | 200.00 | 8 |
| 2759 | HPV | 16 | 6 | 12 | B*2705 | RRGYFVAA | 2681 | 600.00 | 8 |
| 2760 | HPV | 16 | 6 | 12 | Cw*0401 | FFGAQGDGF | 2682 | 100.00 | 9 |
| 2761 | HPV | 16 | 6 | 12 | B*2705 | GRGGVVGQV | 2683 | 600.00 | 9 |
| 2762 | HPV | 16 | 6 | 12 | B*2705 | GQVLPNNFR | 2679 | 100.00 | 9 |
| 2763 | HPV | 16 | 6 | 12 | A68.1 | QVLPNNFRR | 2684 | 600.00 | 9 |
| 2764 | HPV | 16 | 6 | 12 | B*2705 | FRRGYFVAA | 2685 | 200.00 | 9 |
| 2765 | HPV | 16 | 6 | 12 | B*2705 | RRGYFVAAK | 2686 | 6000.00 | 9 |
| 2766 | HPV | 16 | 6 | 12 | A68.1 | FVAAKHRCR | 2687 | 400.00 | 9 |
| 2767 | HPV | 16 | 6 | 12 | Cw*0401 | CFFGAQGDGF | 2688 | 100.00 | 10 |
| 2768 | HPV | 16 | 6 | 12 | B*2705 | AQGDGFGMGR | 2689 | 100.00 | 10 |
| 2769 | HPV | 16 | 6 | 12 | B*5102 | DGFGMGRGGV | 2690 | 242.00 | 10 |
| 2770 | HPV | 16 | 6 | 12 | B*2705 | GRGGVVGQVL | 2691 | 2000.00 | 10 |
| 2771 | HPV | 16 | 6 | 12 | B*2705 | GQVLPNNFRR | 2692 | 100.00 | 10 |
| 2772 | HPV | 16 | 6 | 12 | B*2705 | FRRGYFVAAK | 2693 | 2000.00 | 10 |
| 2773 | HPV | 16 | 6 | 12 | B*2705 | RRGYFVAAKH | 2694 | 600.00 | 10 |
| 2774 | HPV | 16 | 6 | 13 | B*2705 | TRMNFPYF | 2695 | 1000.00 | 8 |
| 2775 | HPV | 16 | 6 | 13 | B*5102 | FPYFIFTI | 2696 | 4000.00 | 8 |
| 2776 | HPV | 16 | 6 | 13 | B*2705 | TRMNFPYFI | 2697 | 600.00 | 9 |
| 2777 | HPV | 16 | 6 | 13 | B*5201 | FPYFIFTIF | 2698 | 250.00 | 9 |
| 2778 | HPV | 16 | 6 | 13 | A*0201 | FIFTIFFCI | 2699 | 269.06 | 9 |
| 2779 | HPV | 16 | 6 | 13 | Cw*0401 | IFFCIIFKL | 2700 | 440.00 | 9 |
| 2780 | HPV | 16 | 6 | 13 | B*2702 | TRMNFPYFIF | 2701 | 200.00 | 10 |
| 2781 | HPV | 16 | 6 | 13 | B*2705 | TRMNFPYFIF | 2701 | 1000.00 | 10 |
| 2782 | HPV | 16 | 6 | 13 | Cw*0401 | NFPYFIFTIF | 2702 | 100.00 | 10 |
| 2783 | HPV | 16 | 6 | 13 | Cw*0401 | IFTIFFCIIF | 2703 | 100.00 | 10 |
| 2784 | HPV | 16 | 6 | 13 | A*0201 | TIFFCIIFKL | 2704 | 144.98 | 10 |
| 2785 | HPV | 16 | 6 | 14 | Cw*0401 | HFHCISMFF | 2705 | 150.00 | 9 |
| 2786 | HPV | 16 | 6 | 14 | B*5801 | ISMFFYTSCW | 2706 | 120.00 | 10 |
| 2787 | HPV | 16 | 6 | 15 | B*2705 | FRFRQMET | 2707 | 1000.00 | 8 |
| 2788 | HPV | 16 | 6 | 15 | B*2702 | FRFRQMETH | 2708 | 100.00 | 9 |
| 2789 | HPV | 16 | 6 | 15 | B*2705 | FRFRQMETH | 2708 | 1000.00 | 9 |
| 2790 | HPV | 16 | 6 | 18 | B*5102 | NPLQFLPV | 2709 | 660.00 | 8 |
| 2791 | HPV | 16 | 6 | 18 | B*2705 | LQFLPVNY | 2710 | 500.00 | 8 |
| 2792 | HPV | 16 | 6 | 18 | A*0205 | LVYNVYTLL | 2711 | 142.80 | 9 |
| 2793 | HPV | 16 | 6 | 18 | Cw*0301 | LVYNVYTLL | 2711 | 100.00 | 9 |
| 2794 | HPV | 16 | 6 | 18 | A24 | VYTLLHNPL | 2712 | 288.00 | 9 |
| 2795 | HPV | 16 | 6 | 18 | Cw*0401 | VYTLLHNPL | 2712 | 200.00 | 9 |
| 2796 | HPV | 16 | 6 | 18 | A*0201 | LLHNPLQFL | 2713 | 459.40 | 9 |
| 2797 | HPV | 16 | 6 | 18 | B*2702 | LQFLPVNYF | 2714 | 100.00 | 9 |
| 2798 | HPV | 16 | 6 | 18 | B*2705 | LQFLPVNYF | 2714 | 500.00 | 9 |
| 2799 | HPV | 16 | 6 | 18 | Cw*0301 | QFLPVNYFL | 2715 | 100.00 | 9 |
| 2800 | HPV | 16 | 6 | 18 | Cw*0401 | QFLPVNYFL | 2715 | 240.00 | 9 |
| 2801 | HPV | 16 | 6 | 18 | Cw*0301 | LLVYNVYTLL | 2716 | 100.00 | 10 |
| 2802 | HPV | 16 | 6 | 18 | A*0201 | TLLHNPLQFL | 2717 | 999.87 | 10 |

TABLE 7-continued

| No | Species | Strain type | Frame | ORF | HLA | Seq | Seq ID No. | Score | Length |
|---|---|---|---|---|---|---|---|---|---|
| 2803 | HPV | 16 | 6 | 18 | B*2705 | LQFLPVNYFL | 2718 | 1000.00 | 10 |
| 2804 | HPV | 16 | 6 | 18 | B*5201 | LQFLPVNYFL | 2718 | 130.68 | 10 |
| 2805 | HPV | 16 | 6 | 19 | B*2705 | MQFHYRLL | 2719 | 1000.00 | 8 |
| 2806 | HPV | 16 | 6 | 19 | B*2705 | YRLLCHYR | 2720 | 1000.00 | 8 |
| 2807 | HPV | 16 | 6 | 19 | B*2705 | YRRPIVPS | 2721 | 200.00 | 8 |
| 2808 | HPV | 16 | 6 | 19 | B*2705 | RRPIVPSV | 2722 | 1800.00 | 8 |
| 2809 | HPV | 16 | 6 | 19 | B*5102 | RPIVPSVI | 2723 | 1200.00 | 8 |
| 2810 | HPV | 16 | 6 | 19 | A24 | IYMQFHYRL | 2724 | 300.00 | 9 |
| 2811 | HPV | 16 | 6 | 19 | Cw*0401 | IYMQFHYRL | 2724 | 200.00 | 9 |
| 2812 | HPV | 16 | 6 | 19 | B*2705 | MQFHYRLLC | 2725 | 100.00 | 9 |
| 2813 | HPV | 16 | 6 | 19 | B*2705 | YRLLCHYRR | 2726 | 1000.00 | 9 |
| 2814 | HPV | 16 | 6 | 19 | B*2705 | YRRPIVPSV | 2727 | 600.00 | 9 |
| 2815 | HPV | 16 | 6 | 19 | B*2702 | RRPIVPSVI | 2728 | 180.00 | 9 |
| 2816 | HPV | 16 | 6 | 19 | B*2705 | RRPIVPSVI | 2728 | 1800.00 | 9 |
| 2817 | HPV | 16 | 6 | 19 | B*5201 | RPIVPSVII | 2729 | 132.00 | 9 |
| 2818 | HPV | 16 | 6 | 19 | B*5102 | RPIVPSVII | 2729 | 1200.00 | 9 |
| 2819 | HPV | 16 | 6 | 19 | Cw*0301 | IYMQFHYRLL | 2730 | 100.00 | 10 |
| 2820 | HPV | 16 | 6 | 19 | Cw*0401 | IYMQFHYRLL | 2730 | 220.00 | 10 |
| 2821 | HPV | 16 | 6 | 19 | A24 | IYMQFHYRLL | 2730 | 300.00 | 10 |
| 2822 | HPV | 16 | 6 | 19 | B*2705 | MQFHYRLLCH | 2731 | 100.00 | 10 |
| 2823 | HPV | 16 | 6 | 19 | B*2705 | YRRPIVPSVI | 2732 | 600.00 | 10 |
| 2824 | HPV | 16 | 6 | 19 | B*2702 | RRPIVPSVII | 2733 | 180.00 | 10 |
| 2825 | HPV | 16 | 6 | 19 | B*2705 | RRPIVPSVII | 2733 | 1800.00 | 10 |
| 2826 | HPV | 16 | 6 | 20 | Cw*0401 | VFVSILACL | 2734 | 480.00 | 9 |
| 2827 | HPV | 16 | 6 | 20 | A*0205 | FVFVSILACL | 2735 | 252.00 | 10 |
| 2828 | HPV | 16 | 6 | 21 | B*5102 | EALSSYTL | 2736 | 150.00 | 8 |
| 2829 | HPV | 16 | 6 | 21 | Cw*0401 | LFYTNIMLL | 2737 | 400.00 | 9 |
| 2830 | HPV | 16 | 6 | 21 | A24 | FYTNIMLLL | 2738 | 280.00 | 9 |
| 2831 | HPV | 16 | 6 | 21 | Cw*0401 | FYTNIMLLL | 2738 | 240.00 | 9 |
| 2832 | HPV | 16 | 6 | 21 | Cw*0301 | MLLLYYAIL | 2739 | 100.00 | 9 |
| 2833 | HPV | 16 | 6 | 21 | A24 | LYYAILEAL | 2740 | 280.00 | 9 |
| 2834 | HPV | 16 | 6 | 21 | Cw*0401 | LYYAILEAL | 2740 | 400.00 | 9 |
| 2835 | HPV | 16 | 6 | 21 | B60 | LEALSSYTL | 2741 | 640.00 | 9 |
| 2836 | HPV | 16 | 6 | 21 | Cw*0401 | LFYTNIMLLL | 2742 | 240.00 | 10 |
| 2837 | HPV | 16 | 6 | 21 | Cw*0301 | IMLLLYYAIL | 2743 | 100.00 | 10 |
| 2838 | HPV | 16 | 6 | 21 | A*0201 | LLYYAILEAL | 2744 | 130.97 | 10 |
| 2839 | HPV | 16 | 6 | 21 | B*2705 | LLYYAILEAL | 2744 | 150.00 | 10 |
| 2840 | HPV | 16 | 6 | 23 | B*2705 | QRMCCLCF | 2745 | 1000.00 | 8 |
| 2841 | HPV | 16 | 6 | 23 | A3 | MLFCFLCSK | 2746 | 450.00 | 9 |
| 2842 | HPV | 16 | 6 | 23 | B*2705 | MLFCFLCSK | 2746 | 150.00 | 9 |
| 2843 | HPV | 16 | 6 | 23 | Cw*0401 | CFLCSKQRM | 2747 | 100.00 | 9 |
| 2844 | HPV | 16 | 6 | 23 | B*2705 | KQRMCCLCF | 2748 | 300.00 | 9 |
| 2845 | HPV | 16 | 6 | 23 | B62 | KQRMCCLCF | 2748 | 288.00 | 9 |
| 2846 | HPV | 16 | 6 | 23 | B*2705 | QRMCCLCFC | 2749 | 200.00 | 9 |
| 2847 | HPV | 16 | 6 | 23 | B*2705 | RMCCLCFCL | 2750 | 150.00 | 9 |
| 2848 | HPV | 16 | 6 | 23 | Cw*0401 | LYCISMLFCF | 2751 | 220.00 | 10 |
| 2849 | HPV | 16 | 6 | 23 | A24 | LYCISMLFCF | 2751 | 100.00 | 10 |
| 2850 | HPV | 16 | 6 | 23 | Cw*0301 | YCISMLFCFL | 2752 | 100.00 | 10 |
| 2851 | HPV | 16 | 6 | 23 | A3 | SMLFCFLCSK | 2753 | 135.00 | 10 |
| 2852 | HPV | 16 | 6 | 23 | B*2705 | QRMCCLCFCL | 2754 | 2000.00 | 10 |
| 2853 | HPV | 16 | 6 | 24 | B*2705 | LRTDGAHN | 2755 | 200.00 | 8 |
| 2854 | HPV | 16 | 6 | 24 | B*2705 | LRTDGAHNS | 2756 | 200.00 | 9 |
| 2855 | HPV | 16 | 6 | 25 | B*2705 | HRPVHRPL | 2757 | 2000.00 | 8 |
| 2856 | HPV | 16 | 6 | 25 | B*5102 | RPVHRPLI | 2758 | 1320.00 | 8 |
| 2857 | HPV | 16 | 6 | 25 | B*2705 | HRPLILWN | 2759 | 200.00 | 8 |
| 2858 | HPV | 16 | 6 | 25 | B*5102 | RPLILWNL | 2760 | 300.00 | 8 |
| 2859 | HPV | 16 | 6 | 25 | B*2705 | ILWNLCFL | 2761 | 150.00 | 8 |
| 2860 | HPV | 16 | 6 | 25 | B*2705 | SRCLCFSS | 2762 | 200.00 | 8 |
| 2861 | HPV | 16 | 6 | 25 | B14 | HRPVHRPLI | 2763 | 120.00 | 9 |
| 2862 | HPV | 16 | 6 | 25 | B*2705 | HRPVHRPLI | 2763 | 600.00 | 9 |
| 2863 | HPV | 16 | 6 | 25 | B*5102 | RPVHRPLIL | 2764 | 330.00 | 9 |
| 2864 | HPV | 16 | 6 | 25 | B14 | HRPLILWNL | 2765 | 120.00 | 9 |
| 2865 | HPV | 16 | 6 | 25 | B*2705 | HRPLILWNL | 2765 | 2000.00 | 9 |
| 2866 | HPV | 16 | 6 | 25 | A*0201 | LILWNLCFL | 2766 | 233.72 | 9 |
| 2867 | HPV | 16 | 6 | 25 | Cw*0401 | CFLSRCLCF | 2767 | 110.00 | 9 |
| 2868 | HPV | 16 | 6 | 25 | Cw*0401 | CFSSGHSGF | 2768 | 100.00 | 9 |
| 2869 | HPV | 16 | 6 | 25 | B*2705 | QQDIHRPVHR | 2769 | 100.00 | 10 |
| 2870 | HPV | 16 | 6 | 25 | B14 | HRPVHRPLIL | 2770 | 400.00 | 10 |
| 2871 | HPV | 16 | 6 | 25 | B*2705 | HRPVHRPLIL | 2770 | 2000.00 | 10 |
| 2872 | HPV | 16 | 6 | 25 | B*2705 | HRPLILWNLC | 2771 | 200.00 | 10 |
| 2873 | HPV | 16 | 6 | 25 | A3 | ILWNLCFLSR | 2772 | 120.00 | 10 |
| 2874 | HPV | 16 | 6 | 25 | B*2705 | SRCLCFSSGH | 2773 | 200.00 | 10 |
| 2875 | HPV | 16 | 6 | 1 | B*2705 | NRDLARMA | 2774 | 200.00 | 8 |
| 2876 | HPV | 16 | 6 | 1 | B*2705 | ARMASRKR | 2775 | 300.00 | 8 |
| 2877 | HPV | 16 | 6 | 1 | B*2705 | SRKRTSLN | 2776 | 200.00 | 8 |
| 2878 | HPV | 16 | 6 | 1 | B*2705 | KRTSLNHS | 2777 | 600.00 | 8 |

TABLE 7-continued

| No | Species | Strain type | Frame | ORF | HLA | Seq | Seq ID No. | Score | Length |
|---|---|---|---|---|---|---|---|---|---|
| 2879 | HPV | 16 | 6 | 1 | B*2705 | GQENRDLAR | 2778 | 100.00 | 9 |
| 2880 | HPV | 16 | 6 | 1 | B*2705 | NRDLARMAS | 2779 | 200.00 | 9 |
| 2881 | HPV | 16 | 6 | 1 | B*2705 | SRKRTSLNH | 2780 | 200.00 | 9 |
| 2882 | HPV | 16 | 6 | 1 | B*2705 | KRTSLNHSC | 2781 | 600.00 | 9 |
| 2883 | HPV | 16 | 6 | 1 | B*2705 | NRDLARMASR | 2782 | 1000.00 | 10 |
| 2884 | HPV | 16 | 6 | 1 | B*2705 | RMASRKRTSL | 2783 | 150.00 | 10 |
| 2885 | HPV | 16 | 6 | 1 | B*2705 | SRKRTSLNHS | 2784 | 200.00 | 10 |
| 2886 | HPV | 16 | 6 | 2 | B*5102 | MGLALQNI | 2785 | 264.00 | 8 |
| 2887 | HPV | 16 | 6 | 2 | B*2705 | LQNIVYIK | 2597 | 200.00 | 8 |
| 2888 | HPV | 16 | 6 | 2 | B*2705 | KQDVANIV | 2598 | 180.00 | 8 |
| 2889 | HPV | 16 | 6 | 2 | B*5201 | MGLALQNIV | 2786 | 360.00 | 9 |
| 2890 | HPV | 16 | 6 | 2 | B*5102 | MGLALQNIV | 2786 | 132.00 | 9 |
| 2891 | HPV | 16 | 6 | 2 | B*5103 | LALQNIVYI | 2599 | 175.69 | 9 |
| 2892 | HPV | 16 | 6 | 2 | B*5102 | LALQNIVYI | 2599 | 878.46 | 9 |
| 2893 | HPV | 16 | 6 | 2 | A3 | ALQNIVYIK | 2600 | 270.00 | 9 |
| 2894 | HPV | 16 | 6 | 2 | B*2705 | KQKQDVANI | 2601 | 180.00 | 9 |
| 2895 | HPV | 16 | 6 | 2 | B*2705 | KQDVANIVY | 2602 | 300.00 | 9 |
| 2896 | HPV | 16 | 6 | 2 | A*0201 | GLALQNIVYI | 2787 | 131.97 | 10 |
| 2897 | HPV | 16 | 6 | 2 | B*2705 | KQKQDVANIV | 2603 | 180.00 | 10 |
| 2898 | HPV | 16 | 6 | 2 | B*5201 | KQKQDVANIV | 2603 | 200.00 | 10 |
| 2899 | HPV | 16 | 6 | 2 | B*2705 | KQDVANIVYI | 2604 | 180.00 | 10 |
| 2900 | HPV | 16 | 6 | 3 | B*2705 | TQAFKNTY | 2788 | 100.00 | 8 |
| 2901 | HPV | 16 | 6 | 3 | B*2705 | TRVYYTIH | 2789 | 200.00 | 8 |
| 2902 | HPV | 16 | 6 | 3 | A68.1 | DTIVTQAFK | 2790 | 180.00 | 9 |
| 2903 | HPV | 16 | 6 | 3 | B*2705 | TRVYYTIHT | 2791 | 200.00 | 9 |
| 2904 | HPV | 16 | 6 | 3 | B*3801 | LHDTIVTQAF | 2792 | 117.00 | 10 |
| 2905 | HPV | 16 | 6 | 3 | B*2705 | TQAFKNTYTR | 2793 | 100.00 | 10 |
| 2906 | HPV | 16 | 6 | 3 | B*5102 | QAFKNTYTRV | 2794 | 1210.00 | 10 |
| 2907 | HPV | 16 | 6 | 3 | B*5103 | QAFKNTYTRV | 2794 | 120.00 | 10 |
| 2908 | HPV | 16 | 6 | 3 | B*2705 | TRVYYTIHTN | 2795 | 200.00 | 10 |
| 2909 | HPV | 16 | 6 | 4 | Cw*0401 | MYKYPVELHF | 2796 | 110.00 | 10 |
| 2910 | HPV | 16 | 6 | 4 | A24 | MYKYPVELHF | 2796 | 140.00 | 10 |
| 2911 | HPV | 16 | 6 | 5 | B*3901 | QHWYMGIL | 2625 | 180.00 | 8 |
| 2912 | HPV | 16 | 6 | 5 | B*5102 | MGILCPSV | 2626 | 132.00 | 8 |
| 2913 | HPV | 16 | 6 | 5 | B*2705 | LQHWYMGIL | 2628 | 200.00 | 9 |
| 2914 | HPV | 16 | 6 | 5 | A*0201 | YMGILCPSV | 2629 | 231.07 | 9 |
| 2915 | HPV | 16 | 6 | 6 | B*3901 | DHDLPQHL | 2797 | 270.00 | 8 |
| 2916 | HPV | 16 | 6 | 6 | B*2705 | HRPKPAAV | 2798 | 600.00 | 8 |
| 2917 | HPV | 16 | 6 | 6 | B*3501 | RPKPAAVY | 2799 | 240.00 | 8 |
| 2918 | HPV | 16 | 6 | 6 | B*2705 | MRCQENQT | 2630 | 200.00 | 8 |
| 2919 | HPV | 16 | 6 | 6 | B*2702 | HRPKPAAVY | 2800 | 200.00 | 9 |
| 2920 | HPV | 16 | 6 | 6 | B*2705 | HRPKPAAVY | 2800 | 1000.00 | 9 |
| 2921 | HPV | 16 | 6 | 6 | Cw*0401 | RPKPAAVYL | 2801 | 105.60 | 9 |
| 2922 | HPV | 16 | 6 | 6 | B*3501 | RPKPAAVYL | 2801 | 120.00 | 9 |
| 2923 | HPV | 16 | 6 | 6 | Cw*0702 | KPAAVYLDY | 2802 | 115.20 | 9 |
| 2924 | HPV | 16 | 6 | 6 | A68.1 | AVYLDYKMR | 2803 | 200.00 | 9 |
| 2925 | HPV | 16 | 6 | 6 | B*2702 | MRCQENQTY | 2632 | 200.00 | 9 |
| 2926 | HPV | 16 | 6 | 6 | B*2705 | MRCQENQTY | 2632 | 1000.00 | 9 |
| 2927 | HPV | 16 | 6 | 6 | A24 | TYWGQVNVF | 2632 | 120.00 | 9 |
| 2928 | HPV | 16 | 6 | 6 | Cw*0401 | TYWGQVNVF | 2632 | 200.00 | 9 |
| 2929 | HPV | 16 | 6 | 6 | B*2705 | HRPKPAAVYL | 2804 | 2000.00 | 10 |
| 2930 | HPV | 16 | 6 | 6 | B*2702 | MRCQENQTYW | 2634 | 100.00 | 10 |
| 2931 | HPV | 16 | 6 | 6 | B*2705 | MRCQENQTYW | 2634 | 200.00 | 10 |
| 2932 | HPV | 16 | 6 | 7 | B*2705 | VQHIHPCL | 2636 | 200.00 | 8 |
| 2933 | HPV | 16 | 6 | 7 | Cw*0401 | MFLHDNICL | 2637 | 200.00 | 9 |
| 2934 | HPV | 16 | 6 | 7 | A*0201 | FLHDNICLC | 2638 | 215.50 | 9 |
| 2935 | HPV | 16 | 6 | 7 | A*0201 | FLHDNICLCV | 2640 | 1311.75 | 10 |
| 2936 | HPV | 16 | 6 | 8 | B*5102 | YAPPKGIV | 2805 | 200.00 | 8 |
| 2937 | HPV | 16 | 6 | 8 | B*5102 | APPKGIVV | 2806 | 266.20 | 8 |
| 2938 | HPV | 16 | 6 | 8 | B*5103 | YAPPKGIVV | 2807 | 100.00 | 9 |
| 2939 | HPV | 16 | 6 | 8 | B*5102 | YAPPKGIVV | 2807 | 200.00 | 9 |
| 2940 | HPV | 16 | 6 | 8 | B*5102 | KGIVVFAGI | 2808 | 264.00 | 9 |
| 2941 | HPV | 16 | 6 | 9 | B*5102 | AGLCKATI | 2641 | 240.00 | 8 |
| 2942 | HPV | 16 | 6 | 9 | B*5102 | YAGLSYVI | 2642 | 440.00 | 8 |
| 2943 | HPV | 16 | 6 | 9 | B*2705 | VRLYNPRR | 2643 | 300.00 | 8 |
| 2944 | HPV | 16 | 6 | 9 | B*2705 | GRDPGMGV | 2644 | 600.00 | 8 |
| 2945 | HPV | 16 | 6 | 9 | B*5102 | DPGMGVLL | 2645 | 110.00 | 8 |
| 2946 | HPV | 16 | 6 | 9 | B*5102 | MGVLLVTV | 2646 | 132.00 | 8 |
| 2947 | HPV | 16 | 6 | 9 | B14 | VRLEVNAGL | 2648 | 100.00 | 9 |
| 2948 | HPV | 16 | 6 | 9 | B*2705 | VRLEVNAGL | 2648 | 2000.00 | 9 |
| 2949 | HPV | 16 | 6 | 9 | B*5103 | NAGLCKATI | 2649 | 121.00 | 9 |
| 2950 | HPV | 16 | 6 | 9 | B*5102 | NAGLCKATI | 2649 | 242.00 | 9 |
| 2951 | HPV | 16 | 6 | 9 | A3 | GLCKATISK | 2650 | 120.00 | 9 |
| 2952 | HPV | 16 | 6 | 9 | B*5102 | GAILILLSL | 2651 | 165.00 | 9 |
| 2953 | HPV | 16 | 6 | 9 | B62 | ILLSLLEKY | 2652 | 104.00 | 9 |
| 2954 | HPV | 16 | 6 | 9 | A*0201 | SLLEKYNVL | 2653 | 199.30 | 9 |

TABLE 7-continued

| No | Species | Strain type | Frame | ORF | HLA | Seq | Seq ID No. | Score | Length |
|---|---|---|---|---|---|---|---|---|---|
| 2955 | HPV | 16 | 6 | 9 | A*0205 | SLLEKYNVL | 2653 | 126.00 | 9 |
| 2956 | HPV | 16 | 6 | 9 | Cw*0301 | SLLEKYNVL | 2653 | 150.00 | 9 |
| 2957 | HPV | 16 | 6 | 9 | A24 | KYNVLSTSI | 2654 | 180.00 | 9 |
| 2958 | HPV | 16 | 6 | 9 | Cw*0301 | TSIPSYAGL | 2655 | 500.00 | 9 |
| 2959 | HPV | 16 | 6 | 9 | A*0201 | GLSYVISLV | 2656 | 159.97 | 9 |
| 2960 | HPV | 16 | 6 | 9 | A68.1 | TTLTCCVVR | 2657 | 100.00 | 9 |
| 2961 | HPV | 16 | 6 | 9 | A68.1 | CVVRLYNPR | 2658 | 400.00 | 9 |
| 2962 | HPV | 16 | 6 | 9 | A68.1 | VVRLYNPRR | 2659 | 200.00 | 9 |
| 2963 | HPV | 16 | 6 | 9 | B*2705 | GRDPGMGVL | 2660 | 2000.00 | 9 |
| 2964 | HPV | 16 | 6 | 9 | B*3701 | RDPGMGVLL | 2661 | 200.00 | 9 |
| 2965 | HPV | 16 | 6 | 9 | B*5102 | DPGMGVLLV | 2662 | 220.00 | 9 |
| 2966 | HPV | 16 | 6 | 9 | A*0201 | GMGVLLVTV | 2663 | 115.53 | 9 |
| 2967 | HPV | 16 | 6 | 9 | A*0201 | LLVTVLGFV | 2664 | 194.44 | 9 |
| 2968 | HPV | 16 | 6 | 9 | B*5102 | LGFVLTINV | 2665 | 220.00 | 9 |
| 2969 | HPV | 16 | 6 | 9 | B*2705 | VRLEVNAGLC | 2666 | 200.00 | 10 |
| 2970 | HPV | 16 | 6 | 9 | B*5102 | GAILILLSLL | 2667 | 165.00 | 10 |
| 2971 | HPV | 16 | 6 | 9 | A*0201 | LLSLLEKYNV | 2668 | 118.24 | 10 |
| 2972 | HPV | 16 | 6 | 9 | Cw*0301 | LSLLEKYNVL | 2669 | 100.00 | 10 |
| 2973 | HPV | 16 | 6 | 9 | B*5102 | IPSYAGLSYV | 2670 | 242.00 | 10 |
| 2974 | HPV | 16 | 6 | 9 | B*5102 | YAGLSYVISL | 2671 | 110.00 | 10 |
| 2975 | HPV | 16 | 6 | 9 | B*5102 | AGLSYVISLV | 2672 | 145.20 | 10 |
| 2976 | HPV | 16 | 6 | 9 | A68.1 | CVVRLYNPRR | 2673 | 400.00 | 10 |
| 2977 | HPV | 16 | 6 | 9 | B*2705 | RRATGRDPGM | 2674 | 1800.00 | 10 |
| 2978 | HPV | 16 | 6 | 9 | B*2705 | GRDPGMGVLL | 2675 | 2000.00 | 10 |
| 2979 | HPV | 16 | 6 | 9 | A*0201 | VLLVTVLGFV | 2676 | 719.44 | 10 |
| 2980 | HPV | 16 | 6 | 9 | A*0201 | VLGFVLTINV | 2677 | 118.24 | 10 |
| 2981 | HPV | 16 | 6 | 10 | B*5102 | APASIKLV | 2809 | 200.00 | 8 |
| 2982 | HPV | 16 | 6 | 10 | B*5102 | GGLTGASV | 2810 | 145.20 | 8 |
| 2983 | HPV | 16 | 6 | 10 | B*5102 | GASVSVAV | 2811 | 100.00 | 8 |
| 2984 | HPV | 16 | 6 | 10 | B*5102 | GGLVPNGI | 2812 | 264.00 | 8 |
| 2985 | HPV | 16 | 6 | 10 | B*5102 | VPNGIYPV | 2813 | 220.00 | 8 |
| 2986 | HPV | 16 | 6 | 10 | B*5102 | RPPVPDPV | 2814 | 200.00 | 8 |
| 2987 | HPV | 16 | 6 | 10 | B*5102 | NPPKNTPI | 2815 | 532.40 | 8 |
| 2988 | HPV | 16 | 6 | 10 | B*5102 | VPACLHVL | 2816 | 100.00 | 8 |
| 2989 | HPV | 16 | 6 | 10 | A68.1 | DVGAPASIK | 2817 | 720.00 | 9 |
| 2990 | HPV | 16 | 6 | 10 | B*5103 | GAPASIKLV | 2818 | 110.00 | 9 |
| 2991 | HPV | 16 | 6 | 10 | B*5102 | GAPASIKLV | 2818 | 121.00 | 9 |
| 2992 | HPV | 16 | 6 | 10 | B*2705 | VRPPVPDPV | 2819 | 600.00 | 9 |
| 2993 | HPV | 16 | 6 | 10 | B*5102 | PPVPDPVPI | 2820 | 120.00 | 9 |
| 2994 | HPV | 16 | 6 | 10 | B*5102 | NPPKNTPIL | 2821 | 133.10 | 9 |
| 2995 | HPV | 16 | 6 | 10 | B*5102 | TPILPYCNI | 2822 | 1320.00 | 9 |
| 2996 | HPV | 16 | 6 | 10 | B*5102 | SAIVLPSTL | 2823 | 165.00 | 9 |
| 2997 | HPV | 16 | 6 | 10 | B*5102 | LGIMSGGHV | 2824 | 120.00 | 9 |
| 2998 | HPV | 16 | 6 | 10 | B*5102 | GGLTGASVSV | 2825 | 132.00 | 10 |
| 2999 | HPV | 16 | 6 | 10 | A*0201 | GLVPNGIYPV | 2826 | 159.97 | 10 |
| 3000 | HPV | 16 | 6 | 10 | A68.1 | LVPNGIYPVR | 2827 | 200.00 | 10 |
| 3001 | HPV | 16 | 6 | 10 | B*5102 | NGIYPVRPPV | 2828 | 132.00 | 10 |
| 3002 | HPV | 16 | 6 | 10 | B*5102 | RPPVPDPVPI | 2829 | 400.00 | 10 |
| 3003 | HPV | 16 | 6 | 10 | B*5102 | IPNPPKNTPI | 2830 | 440.00 | 10 |
| 3004 | HPV | 16 | 6 | 10 | B*5102 | LPYCNICSAI | 2831 | 2000.00 | 10 |
| 3005 | HPV | 16 | 6 | 10 | B*5103 | LPYCNICSAI | 2831 | 120.00 | 10 |
| 3006 | HPV | 16 | 6 | 10 | B*3901 | GHVPACLHVL | 2832 | 270.00 | 10 |
| 3007 | HPV | 16 | 6 | 10 | Cw*0301 | GHVPACLHVL | 2832 | 100.00 | 10 |
| 3008 | HPV | 16 | 6 | 11 | B*2705 | MQYQDLSY | 2833 | 500.00 | 8 |
| 3009 | HPV | 16 | 6 | 11 | B*2705 | SRHCNSFW | 2834 | 200.00 | 8 |
| 3010 | HPV | 16 | 6 | 11 | B*2705 | LRQKLVTL | 2835 | 2000.00 | 8 |
| 3011 | HPV | 16 | 6 | 11 | B*2705 | RRHCSIQC | 2836 | 600.00 | 8 |
| 3012 | HPV | 16 | 6 | 11 | B*2705 | IQCTMLFK | 2837 | 200.00 | 8 |
| 3013 | HPV | 16 | 6 | 11 | A*0201 | MLWMQYQDL | 2838 | 452.14 | 9 |
| 3014 | HPV | 16 | 6 | 11 | B*2705 | MLWMQYQDL | 2838 | 150.00 | 9 |
| 3015 | HPV | 16 | 6 | 11 | B*2705 | MQYQDLSYR | 2839 | 500.00 | 9 |
| 3016 | HPV | 16 | 6 | 11 | B*5801 | KSSRHCNSF | 2840 | 132.00 | 9 |
| 3017 | HPV | 16 | 6 | 11 | B*2702 | SRHCNSFWY | 2841 | 200.00 | 9 |
| 3018 | HPV | 16 | 6 | 11 | B*2705 | SRHCNSFWY | 2841 | 1000.00 | 9 |
| 3019 | HPV | 16 | 6 | 11 | A24 | WYFNLRQKL | 2842 | 316.80 | 9 |
| 3020 | HPV | 16 | 6 | 11 | Cw*0401 | WYFNLRQKL | 2842 | 220.00 | 9 |
| 3021 | HPV | 16 | 6 | 11 | B8 | NLRQKLVTL | 2843 | 160.00 | 9 |
| 3022 | HPV | 16 | 6 | 11 | B*2705 | RQKLVTLPF | 2844 | 300.00 | 9 |
| 3023 | HPV | 16 | 6 | 11 | B62 | RQKLVTLPF | 2844 | 576.00 | 9 |
| 3024 | HPV | 16 | 6 | 11 | A*0201 | KLVTLPFTI | 2845 | 211.79 | 9 |
| 3025 | HPV | 16 | 6 | 11 | B*5102 | LPFTIICKC | 2846 | 121.00 | 9 |
| 3026 | HPV | 16 | 6 | 11 | Cw*0401 | MFYIMSCPM | 2847 | 110.00 | 9 |
| 3027 | HPV | 16 | 6 | 11 | B*5102 | MPCRRHCSI | 2848 | 440.00 | 9 |
| 3028 | HPV | 16 | 6 | 11 | B*2705 | CRRHCSIQC | 2849 | 200.00 | 9 |
| 3029 | HPV | 16 | 6 | 11 | B*2705 | RRHCSIQCT | 2850 | 600.00 | 9 |
| 3030 | HPV | 16 | 6 | 11 | B*2705 | MQYQDLSYRH | 2851 | 100.00 | 10 |

TABLE 7-continued

| No | Species | Strain type | Frame | ORF | HLA | Seq | Seq ID No. | Score | Length |
|---|---|---|---|---|---|---|---|---|---|
| 3031 | HPV | 16 | 6 | 11 | B*2705 | YRHKSSRHCN | 2852 | 200.00 | 10 |
| 3032 | HPV | 16 | 6 | 11 | B*5801 | KSSRHCNSFW | 2853 | 240.00 | 10 |
| 3033 | HPV | 16 | 6 | 11 | B*2702 | SRHCNSFWYF | 2854 | 200.00 | 10 |
| 3034 | HPV | 16 | 6 | 11 | B*2705 | SRHCNSFWYF | 2854 | 1000.00 | 10 |
| 3035 | HPV | 16 | 6 | 11 | B*2702 | LRQKLVTLPF | 2855 | 200.00 | 10 |
| 3036 | HPV | 16 | 6 | 11 | B*2705 | LRQKLVTLPF | 2855 | 1000.00 | 10 |
| 3037 | HPV | 16 | 6 | 11 | B*2705 | CRRHCSIQCT | 2856 | 200.00 | 10 |
| 3038 | HPV | 16 | 6 | 11 | B*2705 | RRHCSIQCTM | 2857 | 1800.00 | 10 |
| 3039 | HPV | 16 | 6 | 12 | B*5102 | YGCSVTITV | 2858 | 106.48 | 9 |
| 3040 | HPV | 16 | 6 | 13 | B*2705 | GQVLPNNF | 2679 | 100.00 | 8 |
| 3041 | HPV | 16 | 6 | 13 | B*2705 | FRRGYFVA | 2680 | 200.00 | 8 |
| 3042 | HPV | 16 | 6 | 13 | B*2705 | RRGYFVAA | 2681 | 600.00 | 8 |
| 3043 | HPV | 16 | 6 | 13 | B*2705 | GRGGVVGQV | 2683 | 600.00 | 9 |
| 3044 | HPV | 16 | 6 | 13 | B*2705 | GQVLPNNFR | 2679 | 100.00 | 9 |
| 3045 | HPV | 16 | 6 | 13 | A68.1 | QVLPNNFRR | 2684 | 600.00 | 9 |
| 3046 | HPV | 16 | 6 | 13 | B*2705 | FRRGYFVAA | 2685 | 200.00 | 9 |
| 3047 | HPV | 16 | 6 | 13 | B*2705 | RRGYFVAAK | 2686 | 6000.00 | 9 |
| 3048 | HPV | 16 | 6 | 13 | A68.1 | FVAAKHRCR | 2687 | 400.00 | 9 |
| 3049 | HPV | 16 | 6 | 13 | B*2705 | GRGGVVGQVL | 2691 | 2000.00 | 10 |
| 3050 | HPV | 16 | 6 | 13 | B*2705 | GQVLPNNFRR | 2692 | 100.00 | 10 |
| 3051 | HPV | 16 | 6 | 13 | B*2705 | FRRGYFVAAK | 2693 | 2000.00 | 10 |
| 3052 | HPV | 16 | 6 | 13 | B*2705 | RRGYFVAAKH | 2694 | 600.00 | 10 |
| 3053 | HPV | 16 | 6 | 14 | B*5102 | FPYFIFTI | 2696 | 4000.00 | 8 |
| 3054 | HPV | 16 | 6 | 14 | B*5201 | FPYFIFTIF | 2698 | 250.00 | 9 |
| 3055 | HPV | 16 | 6 | 14 | A*0201 | FIFTIFFCI | 2699 | 269.06 | 9 |
| 3056 | HPV | 16 | 6 | 14 | Cw*0401 | IFFCIIFKL | 2700 | 440.00 | 9 |
| 3057 | HPV | 16 | 6 | 14 | Cw*0401 | NFPYFIFTIF | 2702 | 100.00 | 10 |
| 3058 | HPV | 16 | 6 | 14 | Cw*0401 | IFTIFFCIIF | 2703 | 100.00 | 10 |
| 3059 | HPV | 16 | 6 | 14 | A*0201 | TIFFCIIFKL | 2704 | 144.98 | 10 |
| 3060 | HPV | 16 | 6 | 15 | B*5102 | IAYVSIKL | 2859 | 302.50 | 8 |
| 3061 | HPV | 16 | 6 | 15 | B*5102 | CPVCIMHCI | 2860 | 1200.00 | 9 |
| 3062 | HPV | 16 | 6 | 15 | A*0201 | CIMHCIAYV | 2861 | 447.61 | 9 |
| 3063 | HPV | 16 | 6 | 15 | A24 | AYVSIKLHF | 2862 | 210.00 | 9 |
| 3064 | HPV | 16 | 6 | 15 | Cw*0401 | AYVSIKLHF | 2862 | 110.00 | 9 |
| 3065 | HPV | 16 | 6 | 15 | Cw*0401 | HFHCISMFF | 2705 | 150.00 | 9 |
| 3066 | HPV | 16 | 6 | 15 | B*5801 | ISMFFYTSCW | 2706 | 120.00 | 10 |
| 3067 | HPV | 16 | 6 | 16 | Cw*0401 | MFKSHFSGL | 2863 | 220.00 | 9 |
| 3068 | HPV | 16 | 6 | 17 | B*5102 | EGILVVPMV | 2864 | 145.20 | 9 |
| 3069 | HPV | 16 | 6 | 17 | A*0201 | ILVVPMVYA | 2865 | 106.84 | 9 |
| 3070 | HPV | 16 | 6 | 17 | Cw*0301 | LVVPMVYAL | 2866 | 100.00 | 9 |
| 3071 | HPV | 16 | 6 | 18 | B*3901 | MHFLNCHL | 2867 | 180.00 | 8 |
| 3072 | HPV | 16 | 6 | 18 | B*3901 | CHLCSSNRAL | 2868 | 180.00 | 10 |
| 3073 | HPV | 16 | 6 | 20 | B*2705 | MQFHYRLL | 2719 | 1000.00 | 8 |
| 3074 | HPV | 16 | 6 | 20 | B*2705 | YRLLCHYR | 2720 | 1000.00 | 8 |
| 3075 | HPV | 16 | 6 | 20 | B*2705 | YRRPIVPS | 2721 | 200.00 | 8 |
| 3076 | HPV | 16 | 6 | 20 | B*2705 | RRPIVPSV | 2722 | 1800.00 | 8 |
| 3077 | HPV | 16 | 6 | 20 | B*5102 | RPIVPSVI | 2723 | 1200.00 | 8 |
| 3078 | HPV | 16 | 6 | 20 | B*2705 | MQFHYRLLC | 2725 | 100.00 | 9 |
| 3079 | HPV | 16 | 6 | 20 | B*2705 | YRLLCHYRR | 2726 | 1000.00 | 9 |
| 3080 | HPV | 16 | 6 | 20 | B*2705 | YRRPIVPSV | 2727 | 600.00 | 9 |
| 3081 | HPV | 16 | 6 | 20 | B*2702 | RRPIVPSVI | 2728 | 180.00 | 9 |
| 3082 | HPV | 16 | 6 | 20 | B*2705 | RRPIVPSVI | 2728 | 1800.00 | 9 |
| 3083 | HPV | 16 | 6 | 20 | B*5201 | RPIVPSVII | 2729 | 132.00 | 9 |
| 3084 | HPV | 16 | 6 | 20 | B*5102 | RPIVPSVII | 2729 | 1200.00 | 9 |
| 3085 | HPV | 16 | 6 | 20 | B*2705 | MQFHYRLLCH | 2731 | 100.00 | 10 |
| 3086 | HPV | 16 | 6 | 20 | B*2705 | YRRPIVPSVI | 2732 | 600.00 | 10 |
| 3087 | HPV | 16 | 6 | 20 | B*2702 | RRPIVPSVII | 2733 | 180.00 | 10 |
| 3088 | HPV | 16 | 6 | 20 | B*2705 | RRPIVPSVII | 2733 | 1800.00 | 10 |
| 3089 | HPV | 16 | 6 | 21 | B*5102 | EALSSYTL | 2736 | 150.00 | 8 |
| 3090 | HPV | 16 | 6 | 21 | Cw*0301 | MLLLYYAIL | 2739 | 100.00 | 9 |
| 3091 | HPV | 16 | 6 | 21 | A24 | LYYAILEAL | 2740 | 280.00 | 9 |
| 3092 | HPV | 16 | 6 | 21 | Cw*0401 | LYYAILEAL | 2740 | 400.00 | 9 |
| 3093 | HPV | 16 | 6 | 21 | B60 | LEALSSYTL | 2741 | 640.00 | 9 |
| 3094 | HPV | 16 | 6 | 21 | A*0201 | LLYYAILEAL | 2744 | 130.97 | 10 |
| 3095 | HPV | 16 | 6 | 21 | B*2705 | LLYYAILEAL | 2744 | 150.00 | 10 |
| 3096 | HPV | 16 | 6 | 22 | Cw*0301 | VIVFLYCQL | 2869 | 100.00 | 9 |
| 3097 | HPV | 16 | 6 | 22 | A*0201 | FLYCQLYWV | 2870 | 12951.14 | 9 |
| 3098 | HPV | 16 | 6 | 22 | Cw*0301 | VVIVFLYCQL | 2871 | 100.00 | 10 |
| 3099 | HPV | 16 | 6 | 23 | B*2705 | QQYTNRNT | 2872 | 100.00 | 8 |
| 3100 | HPV | 16 | 6 | 23 | B*2705 | NRNTLIYY | 2873 | 1000.00 | 8 |
| 3101 | HPV | 16 | 6 | 23 | B*2705 | QQYTNRNTL | 2874 | 1000.00 | 9 |
| 3102 | HPV | 16 | 6 | 23 | B*2702 | NRNTLIYYF | 2875 | 200.00 | 9 |
| 3103 | HPV | 16 | 6 | 23 | B*2705 | NRNTLIYYF | 2875 | 1000.00 | 9 |
| 3104 | HPV | 16 | 6 | 23 | B*2705 | MQQYTNRNTL | 2876 | 200.00 | 10 |
| 3105 | HPV | 16 | 6 | 23 | B*2705 | QQYTNRNTLI | 2877 | 300.00 | 10 |
| 3106 | HPV | 16 | 6 | 25 | B*2705 | FQSHGALL | 2878 | 200.00 | 8 |

TABLE 7-continued

| No | Species | Strain type | Frame | ORF | HLA | Seq | Seq ID No. | Score | Length |
|---|---|---|---|---|---|---|---|---|---|
| 3107 | HPV | 16 | 6 | 25 | B*2705 | TRCLRFQI | 2879 | 600.00 | 8 |
| 3108 | HPV | 16 | 6 | 25 | B*2705 | LRFQIISF | 2880 | 5000.00 | 8 |
| 3109 | HPV | 16 | 6 | 25 | B*2705 | LQLYFVFL | 2881 | 200.00 | 8 |
| 3110 | HPV | 16 | 6 | 25 | Cw*0401 | VFQSHGALL | 2882 | 264.00 | 9 |
| 3111 | HPV | 16 | 6 | 25 | B*2705 | LQYCHTRCL | 2883 | 300.00 | 9 |
| 3112 | HPV | 16 | 6 | 25 | B*2705 | TRCLRFQII | 2884 | 600.00 | 9 |
| 3113 | HPV | 16 | 6 | 25 | B62 | CLRFQIISF | 2885 | 144.00 | 9 |
| 3114 | HPV | 16 | 6 | 25 | B14 | LRFQIISFL | 2886 | 300.00 | 9 |
| 3115 | HPV | 16 | 6 | 25 | B*2702 | LRFQIISFL | 2886 | 300.00 | 9 |
| 3116 | HPV | 16 | 6 | 25 | B*2705 | LRFQIISFL | 2886 | 10000.00 | 9 |
| 3117 | HPV | 16 | 6 | 25 | B*2705 | FQIISFLQL | 2887 | 200.00 | 9 |
| 3118 | HPV | 16 | 6 | 25 | Cw*0301 | FQIISFLQL | 2887 | 100.00 | 9 |
| 3119 | HPV | 16 | 6 | 25 | Cw*0401 | SFLQLYFVF | 2888 | 100.00 | 9 |
| 3120 | HPV | 16 | 6 | 25 | A*0201 | FLQLYFVFL | 2889 | 1026.89 | 9 |
| 3121 | HPV | 16 | 6 | 25 | B*2705 | LQLYFVFLY | 2890 | 100.00 | 9 |
| 3122 | HPV | 16 | 6 | 25 | B62 | LQLYFVFLY | 2890 | 160.00 | 9 |
| 3123 | HPV | 16 | 6 | 25 | A*0201 | QLYFVFLYI | 2891 | 348.87 | 9 |
| 3124 | HPV | 16 | 6 | 25 | B*5102 | LPVTSAEFPL | 2892 | 330.00 | 10 |
| 3125 | HPV | 16 | 6 | 25 | B*5102 | FPLQYCHTRC | 2893 | 132.00 | 10 |
| 3126 | HPV | 16 | 6 | 25 | B*2705 | LQYCHTRCLR | 2894 | 500.00 | 10 |
| 3127 | HPV | 16 | 6 | 25 | Cw*0401 | QYCHTRCLRF | 2895 | 110.00 | 10 |
| 3128 | HPV | 16 | 6 | 25 | A24 | QYCHTRCLRF | 2895 | 100.00 | 10 |
| 3129 | HPV | 16 | 6 | 25 | B*2705 | TRCLRFQIIS | 2896 | 200.00 | 10 |
| 3130 | HPV | 16 | 6 | 25 | B*2705 | LRFQIISFLQ | 2897 | 100.00 | 10 |
| 3131 | HPV | 16 | 6 | 25 | Cw*0401 | RFQIISFLQL | 2898 | 200.00 | 10 |
| 3132 | HPV | 16 | 6 | 25 | B*2705 | FQIISFLQLY | 2899 | 100.00 | 10 |
| 3133 | HPV | 16 | 6 | 25 | B62 | FQIISFLQLY | 2899 | 160.00 | 10 |
| 3134 | HPV | 16 | 6 | 25 | A*0201 | IISFLQLYFV | 2900 | 205.66 | 10 |
| 3135 | HPV | 16 | 6 | 25 | Cw*0301 | SFLQLYFVFL | 2901 | 100.00 | 10 |
| 3136 | HPV | 16 | 6 | 25 | Cw*0401 | SFLQLYFVFL | 2901 | 200.00 | 10 |
| 3137 | HPV | 16 | 6 | 25 | A3 | FLQLYFVFLY | 2902 | 108.00 | 10 |
| 3138 | HPV | 16 | 6 | 26 | B*2705 | QRMCCLCF | 2745 | 1000.00 | 8 |
| 3139 | HPV | 16 | 6 | 26 | A3 | MLFCFLCSK | 2746 | 450.00 | 9 |
| 3140 | HPV | 16 | 6 | 26 | B*2705 | MLFCFLCSK | 2746 | 150.00 | 9 |
| 3141 | HPV | 16 | 6 | 26 | Cw*0401 | CFLCSKQRM | 2747 | 100.00 | 9 |
| 3142 | HPV | 16 | 6 | 26 | B*2705 | KQRMCCLCF | 2748 | 300.00 | 9 |
| 3143 | HPV | 16 | 6 | 26 | B62 | KQRMCCLCF | 2748 | 288.00 | 9 |
| 3144 | HPV | 16 | 6 | 26 | B*2705 | QRMCCLCFC | 2749 | 200.00 | 9 |
| 3145 | HPV | 16 | 6 | 26 | B*2705 | RMCCLCFCL | 2750 | 150.00 | 9 |
| 3146 | HPV | 16 | 6 | 26 | B*2705 | QRMCCLCFCL | 2754 | 2000.00 | 10 |
| 3147 | HPV | 16 | 6 | 27 | B*2705 | VRFCLSSW | 2903 | 1000.00 | 8 |
| 3148 | HPV | 16 | 6 | 27 | B*2702 | VRFCLSSWT | 2904 | 100.00 | 9 |
| 3149 | HPV | 16 | 6 | 27 | B*2705 | VRFCLSSWT | 2904 | 1000.00 | 9 |
| 3150 | HPV | 16 | 6 | 27 | B*2702 | VRFCLSSWTI | 2905 | 300.00 | 10 |
| 3151 | HPV | 16 | 6 | 27 | B*2705 | VRFCLSSWTI | 2905 | 3000.00 | 10 |
| 3152 | HPV | 16 | 6 | 27 | A*0201 | CLSSWTIYFI | 2906 | 131.97 | 10 |
| 3153 | HPV | 16 | 6 | 28 | B*2705 | HRPVHRPL | 2757 | 2000.00 | 8 |
| 3154 | HPV | 16 | 6 | 28 | B*5102 | RPVHRPLI | 2758 | 1320.00 | 8 |
| 3155 | HPV | 16 | 6 | 28 | B*2705 | HRPLILWN | 2759 | 200.00 | 8 |
| 3156 | HPV | 16 | 6 | 28 | B*5102 | RPLILWNL | 2760 | 300.00 | 8 |
| 3157 | HPV | 16 | 6 | 28 | B*2705 | ILWNLCFL | 2761 | 150.00 | 8 |
| 3158 | HPV | 16 | 6 | 28 | B*2705 | SRCLCFSS | 2762 | 200.00 | 8 |
| 3159 | HPV | 16 | 6 | 28 | B*2702 | CRCISMHDY | 2907 | 200.00 | 9 |
| 3160 | HPV | 16 | 6 | 28 | B*2705 | CRCISMHDY | 2907 | 1000.00 | 9 |
| 3161 | HPV | 16 | 6 | 28 | B*3901 | MHDYSWVSL | 2908 | 270.00 | 9 |
| 3162 | HPV | 16 | 6 | 28 | B14 | HRPVHRPLI | 2763 | 120.00 | 9 |
| 3163 | HPV | 16 | 6 | 28 | B*2705 | HRPVHRPLI | 2763 | 600.00 | 9 |
| 3164 | HPV | 16 | 6 | 28 | B*5102 | RPVHRPLIL | 2764 | 330.00 | 9 |
| 3165 | HPV | 16 | 6 | 28 | B14 | HRPLILWNL | 2765 | 120.00 | 9 |
| 3166 | HPV | 16 | 6 | 28 | B*2705 | HRPLILWNL | 2765 | 2000.00 | 9 |
| 3167 | HPV | 16 | 6 | 28 | A*0201 | LILWNLCFL | 2766 | 233.72 | 9 |
| 3168 | HPV | 16 | 6 | 28 | Cw*0401 | CFLSRCLCF | 2767 | 110.00 | 9 |
| 3169 | HPV | 16 | 6 | 28 | Cw*0401 | CFSSGHSGF | 2768 | 100.00 | 9 |
| 3170 | HPV | 16 | 6 | 28 | B*2705 | CRCISMHDYS | 2909 | 200.00 | 10 |
| 3171 | HPV | 16 | 6 | 28 | A*0201 | SMHDYSWVSL | 2910 | 107.54 | 10 |
| 3172 | HPV | 16 | 6 | 28 | Cw*0401 | DYSWVSLRVL | 2911 | 400.00 | 10 |
| 3173 | HPV | 16 | 6 | 28 | A24 | DYSWVSLRVL | 2911 | 200.00 | 10 |
| 3174 | HPV | 16 | 6 | 28 | B*2705 | QQDIHRPVHR | 2769 | 100.00 | 10 |
| 3175 | HPV | 16 | 6 | 28 | B14 | HRPVHRPLIL | 2770 | 400.00 | 10 |
| 3176 | HPV | 16 | 6 | 28 | B*2705 | HRPVHRPLIL | 2770 | 2000.00 | 10 |
| 3177 | HPV | 16 | 6 | 28 | B*2705 | HRPLILWNLC | 2771 | 200.00 | 10 |
| 3178 | HPV | 16 | 6 | 28 | A3 | ILWNLCFLSR | 2772 | 120.00 | 10 |
| 3179 | HPV | 16 | 6 | 28 | B*2705 | SRCLCFSSGH | 2773 | 200.00 | 10 |
| 3180 | HPV | 16 | 6 | 29 | B*2705 | SRKAKSYT | 2912 | 200.00 | 8 |
| 3181 | HPV | 16 | 6 | 29 | B*2705 | SRRSNCCL | 2913 | 2000.00 | 8 |
| 3182 | HPV | 16 | 6 | 29 | B*2705 | LQYTHSNI | 2914 | 300.00 | 8 |

TABLE 7-continued

| No | Species | Strain type | Frame | ORF | HLA | Seq | Seq ID No. | Score | Length |
|---|---|---|---|---|---|---|---|---|---|
| 3183 | HPV | 16 | 6 | 29 | B*2705 | SRKAKSYTS | 2915 | 200.00 | 9 |
| 3184 | HPV | 16 | 6 | 29 | B*2702 | RRSNCCLQY | 2916 | 600.00 | 9 |
| 3185 | HPV | 16 | 6 | 29 | B*2705 | RRSNCCLQY | 2916 | 3000.00 | 9 |
| 3186 | HPV | 16 | 6 | 29 | B*2705 | LQYTHSNII | 2917 | 300.00 | 9 |
| 3187 | HPV | 16 | 6 | 29 | B*5201 | LQYTHSNII | 2917 | 825.00 | 9 |
| 3188 | HPV | 16 | 6 | 29 | B*2705 | SRKAKSYTSR | 2918 | 1000.00 | 10 |
| 3189 | HPV | 16 | 6 | 29 | B*2702 | SRRSNCCLQY | 2919 | 200.00 | 10 |
| 3190 | HPV | 16 | 6 | 29 | B*2705 | SRRSNCCLQY | 2919 | 1000.00 | 10 |
| 3191 | HPV | 16 | 6 | 29 | B*2705 | RRSNCCLQYT | 2920 | 600.00 | 10 |
| 3192 | HPV | 16 | 6 | 29 | B*2705 | LQYTHSNIIS | 2921 | 100.00 | 10 |

4. Influenza

Vaccination of mice with ncORF derived peptides from influenza A virus in combination with KLK/o-d(IC)$_{13}$. Specific T-cell response is measured 7 days after vaccination, and animals are subsequently challenged with a lethal dose of mouse adapted influenza A virus (x31). Survival is monitored for 15 days.

Materials

Mice C57B1/6 (Harlan-Winkelmann, Germany)

Peptides p82 (GLCTLVAML—SEQ ID NO: 1038)
  Control peptide derived from EBV; HLA-A*0201; AA start 280
  p1574 (IASNENMETM—SEQ ID NO: 1039) Control peptide derived from Influenza nucleoprotein, AA start 365
  p1569 (TMLYNKMEF—SEQ ID NO: 1040) Flu ncORF derived peptide from segment 1, frame 1, ORF 1, AA start 569
  p1600 (SSIAAQDAL—SEQ ID NO: 1041) Flu ncORF derived peptide from segment 3, frame 6, ORF 2, AA start 83
  P1664 (VTILNLALL—SEQ ID NO: 1042) Flu ncORF derived peptide from segment 4, frame 5, ORF 6, AA start 9
  Dose: 100 µg/peptide/mouse o-d(IC)$_{13}$ ODN 5'ICI CIC ICI CIC ICI CIC ICI CIC—SEQ ID NO: 1043
(=ODN1a) IC3'
  was synthesized by Purimex Nucleic Acids Technology, Göttingen
  Dose: 5 nmol/mouse KLK KLKLLLLLKLK—COOH—SEQ ID NO: 1044
  was synthesized by MPS (Multiple Peptide System, USA)
  Dose: 127 nmol/mouse Formulation 270 mM Sorbit/10 mM Hepes Influenza A x31, mouse adapted influenza A virus, virus rec. virus derived from A/Pr/8/34 (seg 1, 2, 3, 5, 7, 8) and A/Aichi/2/68 (seg 4, 6)

Experimental Setup (15 Mice/Group)
1. p1574+KLK+o-d(IC)$_{13}$
2. p1569+KLK+o-d(IC)$_{13}$
3. p1600+KLK+o-d(IC)$_{13}$
4. p1664+KLK+o-d(IC)$_{13}$
5. p1600+p1569+KLK+o-d(IC)$_{13}$ On day 0 mice were injected s.c. into both hind footpads with a total amount of 100 µl vaccine/mouse (50 µl/foot) containing the above listed compounds. On day 7, unseparated splenocytes from 5 mice were stimulated in 96-well ELIspot plates in order to enumerate the number of peptide-specific IFN-γ producing cells for each experimental group.

Remaining 10 mice were challenged with mouse adapted x31 influenza A virus (5* 10E5 pfu). Survival was monitored for 15 days.

Results ELIspot (FIG. 5a)

Spleen cells of groups 1 and 3 (peptides p1574 and p1600) do not show any specific spots after restimulation with the respective peptides. Groups 2 and 4 (p1569 and p1664) specifically release IFN-γ after restimulation. Group 5 was vaccinated with two individual peptides (not as a mix, p1600 and p1569). Upon restimulation with either the mix of both peptides or p1569, specific cytokine release is detected. In contrast, upon restimulation with p1600 alone, no IFN-γ spots are detectable. This is consistent with group 3 (p1600 alone).

Results Challenge (FIG. 5b)

FIG. 5b shows the survival rate of challenged mice with a lethal dose of mice adapted influenza A virus x31. Group 1 (p1574, reported protective epitope for H2-Db) protects 30% of all challenged mice. Peptide p1569 does not at all provide protection (0%). In contrast, peptides p1600 and p1664 do protect 50% and 62% of challenged animals, respectively. When animals are vaccinated with two different peptides (group 5, peptides p1600 and 1569) up to 70% of animals are protected.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07528223B2). An electronic copy of the "Sequence Listing" will also be available from the USPTO upon request and payment of the fee set forth in 37 CFR 1.19(b)(3).

The invention claimed is:

1. An isolated polypeptide encoded by an alternative reading frame of an influenza virus, wherein said polypeptide comprises the sequence VTILNLALL (SEQ ID NO: 1042) and starts with a methionine amino acid residue, or a fragment of said polypeptide comprising the sequence VTILNLALL (SEQ ID NO: 1042).

2. The polypeptide or fragment of claim 1, further defined as comprising at least one cytotoxic T lymphocyte (CTL-) epitope.

3. The polypeptide or fragment of claim 1, wherein the CTL-epitope is further defined as an HLA allele.

4. The polypeptide or fragment of claim 3, wherein the HLA allele is an A0201, A1, A24, A3, A31, B3501, B4403, B7, or B8 allele.

5. The polypeptide or fragment of claim 4, where in the HLA allele is an A0201 allele.

6. The polypeptide or fragment of claim 1, further defined as comprising at least one T helper cell epitope.

7. The polypeptide or fragment of claim 6, wherein the T helper cell epitope is for an HLA allele, the HLA allele further defined as DP, DQ, or DR.

8. The polypeptide or fragment of claim 1, further defined as a polypeptide comprising a fragment with a score of 50 or more.

9. The polypeptide or fragment of claim 8, further defined as a polypeptide comprising a fragment with a score of more than 200.

10. The polypeptide or fragment of claim 9, further defined as a polypeptide comprising a fragment with a score of more than 500.

11. The polypeptide or fragment of claim 1, further defined as conjugated to a carrier.

12. The polypeptide or fragment of claim 11, wherein the carrier is defined as a immunomodulating substance.

13. The polypeptide or fragment of claim 12, wherein the immunomodulating substance is a polycationic substance.

14. The polypeptide or fragment of claim 13, wherein the polycationic substance is a polycationic polypeptide.

15. The polypeptide or fragment of claim 12, wherein the immunomodulating substance is an immunomodulating nucleic acid.

16. The polypeptide or fragment of claim 15, wherein the immunomodulating nucleic acid is a deoxyinosine- and/or deoxyuridine containing oligodeoxynucleotide.

17. The polypeptide or fragment of claim 1, further defined as comprising at least one T cell epitope.

18. The polypeptide or fragment of claim 1, further defined as encoded by an alternative reading frame which reads on the complementary strand as the functional reading frame of said influenza virus.

19. The polypeptide or fragment of claim 1, further defined as comprising a tail consisting of two to seven amino acids, the amino acids defined as selected from F, I, L, A, Y, W or C, at at least one of its N- or C-terminus.

20. The polypeptide or fragment of claim 1, further defined as comprising a tail consisting of two to seven amino acids, the amino acids defined as selected from E or D, at at least one of its N- or C-terminus.

21. The polypeptide or fragment of claim 20, further defined as comprised in a pharmaceutical composition.

22. A pharmaceutical composition comprising one or more polypeptide encoded by an alternative reading frame of an influenza virus, wherein said polypeptide comprises the sequence VTILNLALL (SEQ ID NO: 1042) and starts with a methionine amino acid residue, or a fragment of said polypeptide comprising the sequence VTILNLALL (SEQ ID NO: 1042).

23. The pharmaceutical composition of 22, further defined as comprising an immunomodulating substance.

24. The pharmaceutical composition of claim 23, wherein the immunomodulating substance is a polycationic substance.

25. The pharmaceutical composition of claim 24, wherein the polycationic substance is a polycationic polypeptide.

26. The pharmaceutical composition of claim 23, wherein the immunomodulating substance is an immunomodulating nucleic acid.

27. The pharmaceutical composition of claim 26, wherein the immunomodulating nucleic acid is a deoxyinosine- and/or deoxyuridine containing oligodeoxynucleotide.

28. The pharmaceutical composition of claim 22, further defined as comprising a structural or functional polypeptide of an influenza virus or a fragment thereof.

29. The pharmaceutical composition of claim 28, further defined as comprising an antigenic determinant.

30. The pharmaceutical composition of claim 22, further defined as comprising, per administerable dose, 1 ng to 1 g of one or more polypeptide encoded by an alternative reading frame of an influenza virus, wherein said polypeptide comprises the sequence VTILNLALL (SEQ ID NO: 1042) and starts with a methionine amino acid residue, or a fragment of said polypeptide comprising the sequence VTILNLALL (SEQ ID NO: 1042).

31. The pharmaceutical composition of claim 30, further defined as comprising, per administerable dose, 100 ng to 10 mg of the one or more polypeptide encoded by an alternative reading frame of an influenza virus or fragment thereof.

32. The pharmaceutical composition of claim 31, further defined as comprising, per administerable dose, 10 μg to 1 mg of the one or more polypeptide encoded by an alternative reading frame of an influenza virus or fragment thereof.

33. The pharmaceutical composition of claim 22, further defined as a vaccine.

34. The pharmaceutical composition of claim 22, further defined as comprising at least one immunopotentiating cytokine, anti-inflammatory substance, or antimicrobial substance.

35. The pharmaceutical composition of claim 22, further defined as comprising a polycationic polymer.

36. The pharmaceutical composition of claim 35, wherein the polycationic polymer is further defined as a polycationic polypeptide further defined as polyarginine or polylysine.

37. The pharmaceutical composition of claim 22, further defined as comprising an antimicrobial peptide.

38. The pharmaceutical composition of claim 37, wherein the antimicrobial peptide is further defined as a cathelicidin-derived antimicrobial peptide.

39. The pharmaceutical composition of claim 22, further defined as comprising a growth hormone.

40. The pharmaceutical composition of claim 39, wherein the growth hormone is further defined as a human growth hormone.

41. The pharmaceutical composition of claim 22, further defined as comprising at least one pharmaceutically acceptable carrier, buffer substance, or stabilizer.

* * * * *

UNITED STATES PATENT AND TRADEMARK OFFICE
CERTIFICATE OF CORRECTION

| | |
|---|---|
| PATENT NO. | : 7,528,223 B2 |
| APPLICATION NO. | : 10/512790 |
| DATED | : May 5, 2009 |
| INVENTOR(S) | : Frank Mattner et al. |

It is certified that error appears in the above-identified patent and that said Letters Patent is hereby corrected as shown below:

On title page, item (56) References Cited - U.S. Patent Documents, insert --5,683,864    11/97   Houghton et al. ...... 435/5--.

Signed and Sealed this

Fourteenth Day of July, 2009

JOHN DOLL
*Acting Director of the United States Patent and Trademark Office*